US012735397B2

(12) United States Patent
Martin et al.

(10) Patent No.: US 12,735,397 B2
(45) Date of Patent: Sep. 15, 2026

(54) IL-17A MODULATORS

(71) Applicant: SANOFI, Paris (FR)

(72) Inventors: Barrie Phillip Martin, Manchester (GB); Jan-Christoph Westermann, Manchester (GB); Oliver Thomas Kern, Manchester (GB); Arthur Jonathan Holmes, Manchester (GB); Bohdan Waszkowycz, Manchester (GB); Angus Morrison, Lanarkshire (GB); Michael Kiczun, Lanarkshire (GB); Mounir Al Masri, Lanarkshire (GB); Alasdair Smith, Lanarkshire (GB); Anthony Huxley, Egham (GB)

(73) Assignee: SANOFI, Paris (FR)

( * ) Notice: Subject to any disclaimer, the term of this patent is extended or adjusted under 35 U.S.C. 154(b) by 723 days.

(21) Appl. No.: 17/926,864

(22) PCT Filed: May 25, 2021

(86) PCT No.: PCT/EP2021/063934
§ 371 (c)(1),
(2) Date: Nov. 21, 2022

(87) PCT Pub. No.: WO2021/239743
PCT Pub. Date: Dec. 2, 2021

(65) Prior Publication Data

US 2023/0227427 A1 Jul. 20, 2023

(30) Foreign Application Priority Data

May 27, 2020 (GB) ...................................... 2007931
Oct. 26, 2020 (GB) ...................................... 2016934
Feb. 4, 2021 (GB) ...................................... 2101577
Mar. 16, 2021 (GB) ...................................... 2103642

(51) Int. Cl.

| | |
|---|---|
| ***C07D 401/12*** | (2006.01) |
| ***C07D 231/14*** | (2006.01) |
| ***C07D 401/14*** | (2006.01) |
| ***C07D 403/12*** | (2006.01) |
| ***C07D 405/12*** | (2006.01) |
| ***C07D 413/12*** | (2006.01) |
| ***C07D 413/14*** | (2006.01) |
| ***C07D 417/14*** | (2006.01) |
| ***C07D 471/04*** | (2006.01) |
| ***C07D 487/04*** | (2006.01) |

(52) U.S. Cl.
CPC ......... *C07D 401/12* (2013.01); *C07D 231/14* (2013.01); *C07D 401/14* (2013.01); *C07D 403/12* (2013.01); *C07D 405/12* (2013.01); *C07D 413/12* (2013.01); *C07D 413/14* (2013.01); *C07D 417/14* (2013.01); *C07D 471/04* (2013.01); *C07D 487/04* (2013.01)

(58) Field of Classification Search
CPC ..... A61P 11/06; C07D 231/14; C07D 401/12; C07D 401/14; C07D 403/04; C07D 403/12; C07D 405/12; C07D 413/12; C07D 413/14; C07D 417/14; C07D 471/04; C07D 487/04
See application file for complete search history.

(56) References Cited

U.S. PATENT DOCUMENTS

| | | | | |
|---|---|---|---|---|
| 9,365,520 | B2 | 6/2016 | Yamamoto et al. | |
| 11,377,425 | B1 * | 7/2022 | Dack .................... | C07D 403/12 |
| 11,831,049 | B2 | 11/2023 | Shim et al. | |
| 2008/0269467 | A1 | 10/2008 | Allan | |
| 2017/0107240 | A1 | 4/2017 | Yamamoto et al. | |
| 2020/0138797 | A1 | 5/2020 | Brace et al. | |

(Continued)

FOREIGN PATENT DOCUMENTS

| | | |
|---|---|---|
| CN | 113164448 A | 7/2021 |
| EA | 031262 B1 | 12/2018 |

(Continued)

OTHER PUBLICATIONS

Machine Translation of WO2014208751 (Year: 2014).*
Ahmed Ali, M. et al. (2018, e-pub. Sep. 15, 2017). "Interleukin-17 as a Predictor of Sepsis in Polytrauma Patients: A Prospective Cohort Study," European of Trauma and Emergency Surgery 44:621-626.
Amadi-Obi, A. et al. (Jun. 2007, e-pub. May 13, 2007). "TH17 Cells Contribute to Uveitis and Scleritis and Are Expanded by IL-2 and Inhibited by IL-27/STAT1," Nature Medicine 13(6):711-718.
Bartlett, H.S. et al. (Jan. 2015). "Targeting the IL-17-TH17 Pathway," Nat. Rev. Drug Discovery 14(1):11-12.

(Continued)

*Primary Examiner* — Jeffrey H Murray
*Assistant Examiner* — Daniel John Burkett
(74) *Attorney, Agent, or Firm* — MORRISON & FOERSTER LLP

(57) ABSTRACT

The present invention relates to compounds that are IL-17A modulators. The compounds have the structural Formula I as shown below, wherein $X^1$, $X^2$, $X^3$, $X^4$, Y, $R^1$, $R^2$, $R^3$, and $R^4$ are as defined herein. The present invention also relates to processes for the preparation of these compounds, to pharmaceutical compositions comprising them, and to their use in the treatment of diseases or disorders associated with modulation of IL-17A activity.

(I)

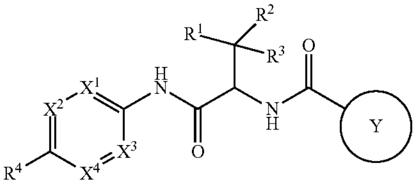

15 Claims, No Drawings

(56) References Cited

U.S. PATENT DOCUMENTS

| | | | | |
|---|---|---|---|---|
| 2020/0247785 | A1 | 8/2020 | Fatheree et al. | |
| 2021/0230481 | A1 | 7/2021 | Chen et al. | |
| 2023/0286943 | A1* | 9/2023 | Martin | C07D 417/14 |

FOREIGN PATENT DOCUMENTS

| | | | | |
|---|---|---|---|---|
| EP | 3018123 | B1 | 5/2023 | |
| JP | 2009114071 | A | 5/2009 | |
| JP | 2016123333 | A | 7/2016 | |
| JP | 2016152772 | A | 8/2016 | |
| JP | 2021533227 | A | 12/2021 | |
| JP | 2021535563 | A | 12/2021 | |
| JP | 2022512201 | A | 2/2022 | |
| JP | 2022514079 | A | 2/2022 | |
| TW | 202039473 | A | 11/2020 | |
| WO | 00/77027 | A2 | 12/2000 | |
| WO | 2009089036 | A2 | 7/2009 | |
| WO | 2010062858 | A1 | 6/2010 | |
| WO | 2011163452 | A2 | 12/2011 | |
| WO | 2013100027 | A1 | 7/2013 | |
| WO | 2013116682 | A1 | 8/2013 | |
| WO | 2014066726 | A2 | 5/2014 | |
| WO | WO-2014208751 | A1 * | 12/2014 | A23L 1/22657 |
| WO | 2015002230 | A1 | 1/2015 | |
| WO | 2018229079 | A1 | 12/2018 | |
| WO | 2019138017 | A1 | 7/2019 | |
| WO | 2020011731 | A1 | 1/2020 | |
| WO | 2020120140 | A1 | 6/2020 | |
| WO | 2020120141 | A1 | 6/2020 | |
| WO | 2020127685 | A1 | 6/2020 | |
| WO | 2020146194 | A1 | 7/2020 | |
| WO | 2020163554 | A1 | 8/2020 | |
| WO | 2020182666 | A1 | 9/2020 | |

OTHER PUBLICATIONS

Caproni, M. et al. (2009, e-pub. Sep. 2, 2008). "Serum Levels of IL-17 and IL-22 Are Reduced by Etanercept, but Not by Acitretin, in Patients With Psoriasis: A Randomized-Controlled Trial," Journal of Clinical Immunology 29:210-214.

Chen, W. C. et al. (2013, e-pub. Apr. 1, 2013). "Interleukin-17-Producing Cell Infiltration in the Breast Cancer Tumour Microenvironment Is a Poor Prognostic Factor," Histopathology 63(2):225-233.

Chen, X. Q. et al. (2010, e-pub. Jan. 28, 2010). "Plasma IL-17A Is Increased in New-Onset SLE Patients and Associated With Disease Activity," Journal of Clinical Immunology 30:221-225.

Coimbra, S. et al. (Jul. 21, 2014). "Brodalumab: An Evidence-Based Review of Its Potential in the Treatment of Moderate-To-Severe Psoriasis," Core Evidence 9:89-97.

Cristiano, C. et al. (2019). "Neutralization of IL-17 Rescues Amyloid-ß-Induced Neuroinflammation and Memory Impairment," British Journal of Pharmacology 176(18):3544-3557.

Cua, D. J. et al. (Jul. 2010, e-pub. Jun. 25, 2010). "Innate IL-17-Producing Cells: The Sentinels of the Immune System," Nature Reviews Immunology 10(7):479-489.

De Paiva, C. S. et al. (Dec. 14, 2009). "Essential Role for C-Jun N-Terminal Kinase 2 in Corneal Epithelial Response to Desiccating Stress," Archives of Ophthalmology 127(12):1625-1631.

Deady, L. W. (1977, e-pub. Apr. 1, 2009). "Ring Nitrogen Oxidation of Amino Substituted Nitrogen Heterocycles with m-Chloroperbenzoic Acid," Synthetic Communications 7(8):509-514.

Deodhar, A. et al. (Apr. 2019). "Efficacy and Safety of Ixekizumab in the Treatment of Radiographic Axial Spondyloarthritis: Sixteen-Week Results From a Phase III Randomized, Double-Blind, Placebo-Controlled Trial in Patients With Prior Inadequate Response to or Intolerance of Tumor Necrosis Factor Inhibitors," Arthritis Rheumatol 71(4):599-611.

Ding, Q. et al. (Nov. 7, 2017, e-pub. Oct. 4, 2017). "Role of IL-17 in LPS-Induced Acute Lung Injury: An In Vivo Study," Oncotarget 8(55):93704-93711.

Duthaler, R. O. (1994). "Recent Developments in the Stereoselective Synthesis of α-Aminoacids," Tetrahedron 50(6):1539-1650.

El Malki, K. et al. (2013, e-pub. Sep. 6, 2012). "An Alternative Pathway of Imiquimod-Induced Psoriasis-Like Skin Inflammation in the Absence of Interleukin-17 Receptor a Signaling," Journal of Investigative Dermatology 133(2):441-451.

Gaffen, S.L. (Aug. 2009, e-pub. Jul. 3, 2009). "Structure and Signalling in the IL-17 Receptor Family," Nature Reviews 9:556-567.

Gaffen, S.L. (Oct. 8, 2004). "Biology of Recently Discovered Cytokines: Interleukin-17—a Unique Inflammatory Cytokine with Roles in Bone Biology and Arthritis," Arthritis Res Ther 6(6):240-247.

Galano Carvalho, D. F. et al. (2017, e-pub. Jan. 25, 2017). "High IL-17 Expression Is Associated With an Unfavorable Prognosis in Thyroid Cancer," Oncology Letters 13(3):1925-1931.

Geoghegan, K. F. et al. (2013, e-pub. Oct. 13, 2012). "Unexpected Mucin-Type O-Glycosylation and Host-Specific N-Glycosylation of Human Recombinant Interleukin-17A Expressed in a Human Kidney Cell Line," Protein Expression and Purification 87(1):27-34.

Gordon, K. B. et al. (Jul. 28, 2016, e-pub. Jun. 8, 2016). "Phase 3 Trials of Ixekizumab in Moderate-To-Severe Plaque Psoriasis," New England Journal of Medicine 375(4):345-356.

Gottlieb, A. et al. (Jan. 2017, e-pub. Oct. 1, 2016). "Secukinumab Shows Significant Efficacy in Palmoplantar Psoriasis: Results From Gesture, a Randomized Controlled Trial," Journal of the American Academy of Dermatology 76(1):70-80.

Guilloteau, K. et al. (2010). "Skin Inflammation Induced by the Synergistic Action of IL-17A, IL-22, Oncostatin M, IL-1α, and TNF-A Recapitulates Some Features of Psoriasis," The Journal of Immunology 184(9):5263-5270.

Havrdova, E. et al. (Jul. 2016; e-pub. May 3, 2016). "Activity of Secukinumab, an Anti-IL-17A Antibody, on Brain Lesions in RRMS: Results From a Randomized, Proof-of-Concept Study," J. Neurol. 263(7):1287-1295.

He, S. et al. (Oct. 28, 2011). "Distribution and Clinical Significance of Th17 Cells in the Tumor Microenvironment and Peripheral Blood of Pancreatic Cancer Patients," International Journal of Molecular Sciences 12(11):7424-7437.

Jin, W. et al. (2013, e-pub. Jan. 25, 2019). "IL-17 Cytokines in Immunity and Inflammation," Emerging Microbes & Infections 2(1):1-5.

Johansen, C. et al. (2009). "Characterization of the Interleukin-17 Isoforms and Receptors in Lesional Psoriatic Skin," British Journal of Dermatology 160(2):319-324.

Kang, M. H. et al. (2011, e-pub. Jun. 20, 2011). "Interleukin-17 in Various Ocular Surface Inflammatory Diseases," Journal of Korean Medical Science 26(7):938-944.

Kolls, J. K. et al. (Oct. 2004). "Interleukin-17 Family Members and Inflammation," Immunity 21(4):467-476.

Langley, R. G. et al. (Jul. 24, 2014, e-pub. Jul. 9, 2014). "Secukinumab in Plaque Psoriasis—Results of Two Phase 3 Trials," New England Journal of Medicine 371(4):326-338.

Le Gouvello, S. et al. (2008). "High Prevalence of Foxp3 and IL17 in MMR-Proficient Colorectal Carcinomas," Gut 57(6):772-779, 27 pages.

Lebwohl, M. et al. (Oct. 1, 2015). "Phase 3 Studies Comparing Brodalumab With Ustekinumab in Psoriasis," New England Journal of Medicine 373(14):1318-1328.

Lee, M. H. et al. (Jan. 3, 2018). "Interleukin 17 and Peripheral IL-17-Expressing T Cells Are Negatively Correlated With the Overall Survival of Head and Neck Cancer Patients," Oncotarget 9(11):9825-9837.

Lemancewicz, D. et al. (Jan. 1, 2012). "The Role of Interleukin-17A and Interleukin-17E in Multiple Myeloma Patients," Med Sci Monit 18(1):BR54-59.

Lønnberg, A. S. et al. (Sep. 15, 2014, e-pub. Dec. 18, 2022). "Targeting of Interleukin-17 in the Treatment of Psoriasis," Clinical, Cosmetic and Investigational Dermatology 7:251-259.

Mease, P. et al. (2018, e-pub. Mar. 17, 2018). "Secukinumab Improves Active Psoriatic Arthritis Symptoms and Inhibits Radio-

(56) References Cited

OTHER PUBLICATIONS graphic Progression: Primary Results From the Randomised, Double-Blind, Phase III Future 5 Study," Annals of the Rheumatic Diseases 77(6):890-897.
Meng, X. et al. (Jan. 2018). "Expression of Th17/Treg Related Molecules in Gastric Cancer Tissues," The Turkish Journal of Gastroenterology 29(1):45-51.
Menter, A. et al. (2017). "Efficacy of Ixekizumab Compared to Etanercept and Placebo in Patients With Moderate-To-Severe Plaque Psoriasis and Non-Pustular Palmoplantar Involvement: Results From Three Phase 3 Trials (Uncover-1, Uncover-2 and Uncover-3)," Journal of the European Academy of Dermatology and Venereology 31(10):1686-1692.
Moseley, T. A. et al. (2003). "Interleukin-17 Family and IL-17 Receptors," Cytokine & Growth Factor Reviews 14(2):155-174.
Najera, C. et al. (2007, e-pub. Oct. 4, 2007). "Catalytic Asymmetric Synthesis of α-Amino Acids," Chemical Reviews 107(11):4584-4671.
Nash, P. et al. (Jun. 10, 2017, e-pub. May 24, 2017). "Ixekizumab for the Treatment of Patients With Active Psoriatic Arthritis and an Inadequate Response to Tumour Necrosis Factor Inhibitors: Results From the 24-Week Randomised, Double-Blind, Placebo-Controlled Period of the Spirit-P2 Phase 3 Trial," The Lancet 389(10086):2317-2327.
Onishi, R. M. et al. (2010). "Interleukin-17 and Its Target Genes: Mechanisms of Interleukin-17 Function in Disease," Immunology 129(3):311-321.
Ortega, C. et al. (Aug. 2009). "IL-17-Producing CD8+ T Lymphocytes From Psoriasis Skin Plaques Are Cytotoxic Effector Cells That Secrete Th17-Related Cytokines," Journal of Leukocyte Biology 86(2):435-443.
Pacha, O. et al. (Jun. 2020, e-pub. May 1, 2020). "Covid-19: A Case for Inhibiting IL-17?" Nature Reviews Immunology 20(6):345-346, 2 pages.
Pan, B. et al. (Nov. 3, 2015). "Interleukin-17 Promotes Angiogenesis by Stimulating VEGF Production of Cancer Cells via the STAT3/GIV Signaling Pathway in Non-Small-Cell Lung Cancer," Scientific Reports 5(1):16053, 13 pages.
Paul, C. et al. (2014). "Secukinumab Improves Hand, Foot and Nail Lesions in Moderate-To-Severe Plaque Psoriasis: Subanalysis of a Randomized, Double-Blind, Placebo-Controlled, Regimen-Finding Phase 2 Trial," Journal of the European Academy of Dermatology and Venereology 28(12):1670-1675.
Pavelka, K. et al. (2017, e-pub. Dec. 22, 2017). "Efficacy, Safety, and Tolerability of Secukinumab in Patients With Active Ankylosing Spondylitis: A Randomized, Double-Blind Phase 3 Study, Measure 3," Arthritis Research & Therapy 19(285):1-10.
Punt, S. et al. (Feb. 2015). "The Correlations Between IL-17 vs. Th17 Cells and Cancer Patient Survival: A Systematic Review," Oncolmmunol 4(2):e984547, 10 pages.
Santibanez, J. F. et al. (2018). "Novel Patents Targeting Interleukin-17A; Implications in Cancer and Inflammation," Recent Patents on Anti-cancer Drug Discovery 13(2):133-144, 12 pages.
Skepner, J. et al. (2014, e-pub. Feb. 10, 2014). "Pharmacologic Inhibition of RORγt Regulates Th17 Signature Gene Expression and Suppresses Cutaneous Inflammation In Vivo," The Journal of Immunology 192(6):2564-2575.
Storelli, E. et al. (Jan. 24, 2019). "Do Th17 Lymphocytes and IL-17 Contribute to Parkinson's Disease? A Systematic Review of Available Evidence," Frontiers in Neurology 10(13):1-15.
Takahashi, H. et al. (2009). "Serum Cytokines and Growth Factor Levels in Japanese Patients With Psoriasis," Clinical and Experimental Dermatology 35(6):645-649.
Tesmer, L. A. et al. (Jun. 2008, e-pub. Mar. 12, 2012). "Th17 Cells in Human Disease," Immunological Reviews 223(1):87-113, 41 pages.
Tseng, J. Y. et al. (Jun. 1, 2014, e-pub. Mar. 27, 2014). "Interleukin-17A Modulates Circulating Tumor Cells in Tumor Draining Vein of Colorectal Cancers and Affects MetastasesIL-17A Modulates Change of CTCs and Affects Metastases," Clinical Cancer Research 20(11):1-13.
Tu, J. F. et al. (Apr. 2016). "Mast Cells Comprise the Major of Interleukin 17-Producing Cells and Predict a Poor Prognosis in Hepatocellular Carcinoma," Medicine 95(13):e3220, 7 pages.
Van Der Fits, L. et al. (2009). "Imiquimod-Induced Psoriasis-Like Skin Inflammation in Mice Is Mediated via the IL-23/IL-17 Axis," The Journal of Immunology 182(9):5836-5845.
Wang, Y. et al. (2009). "Laser Microdissection-Based Analysis of Cytokine Balance in the Kidneys of Patients With Lupus Nephritis," Clinical & Experimental Immunology 159(1):1-10.
Welte, T. et al. (2015). "Interleukin-17 Could Promote Breast Cancer Progression at Several Stages of the Disease," Mediators of Inflammation 2015(Article ID 804347):7 pages.
Williams, R. M. et al. (1992). "Asymmetric Synthesis of Arylglycines," Chemical Reviews 92(5):889-917.
Wilson, N. J. et al. (Sep. 2007, e-pub. Aug. 5, 2007). "Development, Cytokine Profile and Function of Human Interleukin 17-Producing Helper T Cells," Nature Immunology 8(9):950-957.
Xu, C. et al. (2014, e-pub. Apr. 14, 2014). "Serum Interleukin-17 as a Diagnostic and Prognostic Marker for Non-Small Cell Lung Cancer," Biomarkers 19(4):287-290.
Yamada, Y. et al. (2012, e-pub. Aug. 9, 2012). "Prevalence and Clinical Relevance of Th17 Cells in Patients With Gastric Cancer," Journal of Surgical Research 178(2):685-691.
Yilmaz, S. B. et al. (2012, e-pub. Mar. 20, 2012). "Serum and Tissue Levels of IL-17 in Different Clinical Subtypes of Psoriasis," Archives of Dermatological Research 304:465-469.
Zaba, L. C. et al. (Dec. 24, 2007). "Amelioration of Epidermal Hyperplasia by TNF Inhibition Is Associated With Reduced Th17 Responses," The Journal of Experimental Medicine 204(13):3183-3194.
Zhang, L. et al. (2010, e-pub. Dec. 16, 2009). "Increased Th17 Cells Are Accompanied by Foxp3+ Treg Cell Accumulation and Correlated With Psoriasis Disease Severity," Clinical immunology 135(1):108-117.
Zhou, P. et al. (2010). "The Role of T-Helper 17 (Th17) Cells in Patients With Medulloblastoma," Journal of International Medical Research 38(2):611-619.

* cited by examiner

IL-17A MODULATORS

CROSS REFERENCE TO RELATED APPLICATIONS

This application is a national stage application under 35 U.S.C. § 371 of International Application No. PCT/EP2021/063934, filed internationally on May 25, 2021, which claims priority of Great Britain Application No. 2007931.5, filed May 27, 2020; Great Britain Application No. 2016934.8, filed Oct. 26, 2020; Great Britain Application No. 2101577.1, filed Feb. 4, 2021; and Great Britain Application No. 2103642.1, filed Mar. 16, 2021, the disclosures of each of which are hereby incorporated by reference in their entirety.

INTRODUCTION

The present invention relates to therapeutic compounds. More specifically, the present invention relates to compounds that are modulators of IL-17A activity. The present invention also relates to processes for the preparation of these compounds, to pharmaceutical compositions comprising them, and to their use in the treatment of diseases or disorders associated with IL-17A activity.

BACKGROUND OF THE INVENTION

The interleukin-17 cytokine family consists of six members (termed IL-17A through IL-17F) of which IL-17A (also known as CTLA-8) is the primary effector cytokine of the T-helper-17 (Th17) cell lineage.

IL-17A is a variably glycosylated, disulfide linked, homodimeric glycoprotein of 34-38 kDa which shares in the order of 50% homology with its closest family member IL-17F, both of which can be secreted either as homodimers or the heterodimer IL-17AF [K. F. Geoghegan et al., Protein Expression and Purification 2013, 87, 27-34; J. K. Kolls and A. Lindén/Immunity 2004, 21, 467-476].

Activation of naïve CD4+ T-cells in response to cytokines such as IL-6, transforming growth factor β (TGF-β), IL-23, STAT3, and RORγt leads to their differentiation to TH17 cells and expression of pro-inflammatory mediators such as IL-17A. Furthermore, a variety of cell types from the innate and adaptive immune systems have been identified as sources of IL-17A. These include mast cells, neutrophilic granulocytes, NK cells, NKT cells, CD8+ T cells, δγ T-cells, macrophages, and type 3-innate lymphoid cells [D. J. Cua and C. M. Tato, Nat Rev Immunol 2010, 10, 479-489; W. Jin and C. Dong, Emerging Microbes & Infections 2013, 2, e60].

Cytokines IL-17A, IL-17F and IL-17AF bind to common heteromeric receptor complexes IL-17RA and IL-17RC, albeit with different affinities, and although various cell types have been reported to express the IL-17RA subunit, the highest responses to IL-17A come from epithelial cells, endothelial cells, keratinocytes, and fibroblasts [T. A. Moseley et al./Cytokine Growth Factor Reviews. 2003, 14, 155-174; S. L. Gaffen/Nature Rev Immunol 2009, 9, 556-567; R. M. Onishi and S. L. Gaffen/Immunology 2010, 129, 311-321].

Binding of IL-17A to its receptor activates various signal transduction pathways such as nuclear factor (NF)-κB, phosphoinositide 3-kinase (PI3K), activator protein (AP1), CCAAT/enhancer-binding protein (C/EBP), and mitogen-activated protein kinase (MAPK) leading to pro-inflammatory gene expression and the secretion of various pro-inflammatory cytokines including IL-1β, IL-6, IL-8, TNFα, G-CSF, PGE2, and IFN-γ as well as numerous chemokines and other effectors [S. L. Gaffen, Arthritis Research & Therapy 2004, 6, 240-247; S. L. Gaffe, Nature Rev Immunol 2009, 9, 556-567; R. M. Onishi and S. L. Gaffen, Immunology 2010, 129, 311-321]. The attraction and activation of cells of the innate immune system to the site of inflammation completes the induction of an inflammatory loop which may also be mediated cooperatively with other cytokines such as TNFα, IFN-γ, and IL-1β [S. L. Gaffen, Arthritis Research & Therapy 2004, 6, 240-247].

These IL-17 mediated biological processes have been implicated in the pathology of many human diseases with an immune component or autoimmune pathology, such as psoriasis, ankylosing spondylitis, axial spondyloarthritis, psoriatic arthritis, eczema, enthesitis-related arthritis, asthma (including severe asthma), chronic obstructive pulmonary disease (COPD), cystic fibrosis, pulmonary fibrosis, ulcerative colitis, Crohn's disease, atopic dermatitis, contact dermatitis, dermatomyositis, myocarditis, uveitis, exophtalmos, autoimmune thyroiditis, Peyronie's disease, coeliac disease, gall bladder disease, Pilonidal disease, peritonitis, multiple sclerosis, Guillan-Bar Syndrome, irritable bowel syndrome, inflammatory bowel disease, Castleman's disease, pelvic inflammatory disease, systemic onset juvenille idiopathic arthritis (JIA), rheumatoid arthritis, giant cell arteritis, graft versus host disease, discoid lupus erythematosus, systemic lupus erythematosus, lupus nephritis, vasculitis, insulin dependent diabetes type I, autoimmune diabetes, Necrobiosis Lipoidica Diabeticorum, Pyoderma Gangrenosum, Hidradenitis Suppurativa, Papulopustular Rosacea, Lichen Planus, heart disease including ischaemic diseases such as myocardial infarction as well as atherosclerosis, intravascular coagulaton, bone resorption, osteroporosis, peridontitis, hypochlorhydria, pain (particularly pain associated with inflammation), and also in cancer (Bartlett, H S; Million, R P (2015) Nat. Rev. Drug Discovery 14:11-12; Santibanez, J F; Bjelica, S (2018) Recent Pat Anticancer Drug Discov. 13(2):133-144). In addition, due to the emerging role of neuroinflammation in neurodegeneration, IL-17 has also been implicated in the progression of neurodegenerative disorders such as Alzheimer's disease (Cristiano et al (2019) Br J Pharmacol. 176(18):3544-3557) and Parkinson's disease (Storelli et al, (2019) Front Neurol. 24; 10:13). Furthermore, due to IL-17A's key regulatory roles in host defense pathological conditions of relevance also include viral, bacterial, fungal and parasitic infections. An association between serum levels of IL-17 at the time of admission to the intensive care unit and the development of sepsis has also been observed suggesting increased IL-17 may increase the susceptibility for septic complications and endotoxic shock associated with infection [Ahmed et al., Eur J Trauma Emerg Surg 2018, 44(4):621-626]. Its role in sepsis has also been suggested to extend to patients with sepsis-induced Acute Respiratory Distress Syndrome (ARDS) and acute lung injury [Ding et al., Oncotarget 2017, 8(55):93704-93711]. Very recently inhibition of IL-17 has also been suggested to be used to prevent acute respiratory distress syndrome (ARDS) in coronavirus disease 2019 (COVID-19) [Pacha, Sallman & Evans, Nat Rev Immunol 2020, 1:1-2].

Pre-clinical studies have demonstrated that IL-17A (as well as IL-17F and IL-17C) is elevated in psoriatic skin [N. J. Wilson et al., Nat Immunol 2007, 8, 950-957; L. C. Zaba et al., J Exp Med 2007, 204, 3183-3194; C. Ortega et al, J Leukocyte Biol 2009, 86, 435-443; C. Johansen et al., Br J Dermatol 2009, 160, 319-324]. Th17 cells in the peripheral circulation and lesional skin of patients with psoriasis have also been shown to positively correlate with disease severity as measured by the Psoriasis Area and Severity Index (PASI) score [L. Zhang et al., Clin Immunol 2010, 135, 108-117]. Serum IL-17A levels are also significantly correlated with PASI score [H. Takahashi et al., Clin Exp Dermatol 2010, 35, 645-649; S. B. Yilmaz et al. Arch Dermatol Res 2012, 304, 465-469; M. Caproni et al., J Clin Immunol 2009, 29, 210-214].

Animal model studies supported the hypothesis that targeting the IL-17A pathway would be an effective treatment for psoriasis [L. van der Fits et al., J Immunol 2009, 182, 5836-5845; K. El Malki et al., J Investig Dermatol 2013, 133, 441-451; J. Skepner et al., J Immunol 2014, 192, 2564-2575] and clinical results with antibodies to IL-17A or IL-17RA delivered the ultimate validation with excellent efficacy being observed [R. G. Langley et al., N Engl J Med 2014, 371, 326-338; K. B. Gordon et al., N Engl J Med 2016, 375, 345-356; A. S. Lonnberg et al., Clin Cosmet Investig Dermatol 2014, 7, 251-259; S. Coimbra et al., Core Evid 2014, 9, 89-97; M. Lebwohl et al., N Engl J Med 2015, 373, 1318-1328].

Elevated levels of IL-17A or IL-17F have been reported in a number of other diseases including Rheumatoid Arthritis (RA), Psoriatic Arthritis (PsA), Ankylosing Spondylitis (AS), Systemic Lupus Erythematosus (SLE), Inflammatory Bowel Disease (IBD), Multiple Sclerosis (MS), bone erosion, intraperitoneal abscesses, allograft rejection, angiogenesis, atherosclerosis, and asthma [e.g. S. L. Gaffen, Arthritis Research & Therapy 2004, 6, 240-247; L. A. Tesmer et al., Immunol Rev 2008, 223, 87-113; US Publ No 20080269467].

The anti-IL-17A therapeutic antibodies Secukinumab and Ixekizumab have shown evidence of positive effects in treating palmoplantar and nail psoriasis; [A. Gottlieb et al., J Am Acad Dermatol 2016, 76, 70-80; A. Menter et al., J Eur Acad Dermatol Venereol 2017, 31, 1686-1692; C. Paul et al., J Eur Acad Dermatol Venereol 2014, 28, 1670-1675]; PsA [P. Mease et al., Ann Rheum Dis 2018, 77, 890-897; P. Nash et al., Lancet 2017, 389, 2317-2327] and AS [K. Pavelka et al., Arthritis Res Ther 2017, 19, 285; A. Deodhar et al., Arthritis Rheumatol 2018, doi:10.1002/art.40753]. A proof of concept study with Secukinumab in MS has also shown encouraging signs of efficacy [E. Havdrova et al., J Neurol 2016, 263, 1287-1295].

IL-17A expression has been shown to be increased in SLE patients and correlated with disease severity [Y. Wang et al., Clin Exp Immunol 2009, 159, 1-10; X. Q. Chen et al., J Clin Immunol 2010, 30, 221-225].

In addition, IL-17A has been associated with ocular surface disorders such as DES [PCT publications WO2009089036, WO2010062858 and WO2011163452; C. S. De Paiva et al., Mucosal Immunol 2009, 2, 243-253] and Th17 cells have been shown to be elevated in active uveitis and scleritis [A. Amadi-Obi et al., Nat Med 2007, 13, 711-718]. IL-17A levels in tears were associated with clinical severity of dry eye in patients with a range of systemic autoimmune or inflammatory diseases including Sjögren's syndrome, Stevens-Johnson syndrome (SJS), SLE, filamentary keratitis, DES, Meibomian gland dysfunction (MGD), and Graft-versus-Host disease (GVHD) [M. H. Kang et al., J Korean Med Sci 2011, 26, 938-944].

Several studies have demonstrated that IL-17A is overexpressed in patients with a range of cancers including gastric carcinoma, medulloblastoma, multiple myeloma, colorectal carcinoma, Non-Small-Cell Lung Cancer (NSCLC), breast cancer, hepatocellular carcinoma (HCC), and thyroid cancer [X. Meng et al., Turk J Gastroenterol 2018, 29, 45-51; P. Zhou et al., J Int Med Res 2010, 38, 611-619; D. Lemancewicz et al., Med Sci Monit 2012, 18, BR 54-59; S. Le Gouvello et al., Gut 2008, 57, 772-779; B. Pan et al., Sci Rep 2015, 5, 16053; T. Welte and X. H-F. Zhang, Mediators Inflammation 2015, 804347; J-F. Tu et al., Medicine (Baltimore) 2016, 95, e3220; D. F. G. Carvalho et al., Oncol Lett 2017, 13, 1925-1931]. Increased levels of IL-17A have been shown to correlate with poor prognosis in several cancer types including malignant thyroid tumor, breast cancer, pancreatic carcinoma, gastric cancer, NSCLC, colorectal cancer, and head and neck cancer [S. Punt et al., OncoImmunol 2015, 4, e984547; D. F. G. Carvalho et al., Oncol Lett 2017, 13, 1925-1931; W-C. Chen et al., Histopathology 2013, 63, 225-233; C. Xu et al., Biomarkers 2014, 19, 287-290; Y. Yamada et al., J Surg Res 2012, 178, 685-691; S. He et al., Int J Mol Sci 2011, 12, 7424-7437; J-Y. Tseng et al., Clin Cancer Res 2014, 20, 2885-2897; M-H. Lee et al., Oncotarget 2018, 9, 9825-9837].

Taken together, modulation of the IL-17A pathway, in particular modulation of IL-17A activity through inhibition of its interaction with the receptor IL-17RA, may be considered a target for the treatment of conditions relating to the immune system and inflammation, cancer and neurodegenerative disorders.

WO 2013/116682, WO 2014/066726 and WO 2018/229079 describe classes of chemical compounds that are stated to modulate the activity of IL-17 and to be useful in the treatment of medical conditions, including inflammatory disease.

Nevertheless, there is an ongoing need for compounds capable of attenuating IL-17A activity.

SUMMARY OF THE INVENTION

In one aspect, the present invention provides a compound, or a pharmaceutically acceptable salt thereof as defined herein.

In another aspect, the present invention provides a pharmaceutical composition comprising a compound of the invention as defined herein, or a pharmaceutically acceptable salt thereof, and one or more pharmaceutically acceptable excipients.

In another aspect, the present invention relates to a compound of the invention as defined herein, or a pharmaceutically acceptable salt thereof, or a pharmaceutical composition as defined herein, for use in therapy.

In another aspect, the present invention relates to a compound of the invention as defined herein, or a pharmaceutically acceptable salt thereof, or a pharmaceutical composition as defined herein, for use in the treatment of diseases or disorders associated with IL-17A activity.

In another aspect, the present invention relates to the use of a compound of the invention as defined herein, or a pharmaceutically acceptable salt thereof, in the manufacture of a medicament for use in the treatment of diseases or disorders associated with IL-17A activity.

In another aspect, the present invention relates to a method of treating a disease or disorder associated with IL-17A activity, said method comprising administering to a subject in need of such treatment a therapeutically effective amount of a compound of the invention as defined herein, or a pharmaceutically acceptable salt thereof, or a pharmaceutical composition as defined herein.

Examples of diseases or disorders associated with IL-17A activity include diseases with an immune component or autoimmune pathology (such as psoriasis, ankylosing spondylitis, psoriatic arthritis, and rheumatoid arthritis), cancer and neurodegenerative disorders.

In another aspect, the present invention provides a compound, or a pharmaceutically acceptable salt thereof, or a pharmaceutical composition as defined herein, for use in the treatment of diseases with an immune component or autoimmune pathology (such as psoriasis, ankylosing spondylitis, psoriatic arthritis, and rheumatoid arthritis), cancer, and neurodegenerative disorders.

In another aspect, the present invention provides the use of a compound, or a pharmaceutically acceptable salt, in the manufacture of a medicament for use in the treatment of diseases with an immune component or autoimmune pathology (such as psoriasis, ankylosing spondylitis, psoriatic arthritis, and rheumatoid arthritis), cancer, and neurodegenerative disorders.

In another aspect, the present invention provides a method of treating diseases with an immune component or autoimmune pathology (such as psoriasis, ankylosing spondylitis, psoriatic arthritis, and rheumatoid arthritis), cancer, and neurodegenerative disorders, said method comprising administering to a subject in need of such treatment a therapeutically effective amount of a compound, or a pharmaceutically acceptable salt thereof, or a pharmaceutical composition as defined herein.

The present invention further provides a method of synthesising a compound, or a pharmaceutically acceptable salt thereof, as defined herein.

In another aspect, the present invention provides a compound, or a pharmaceutically acceptable salt thereof, obtainable by, or obtained by, or directly obtained by a method of synthesis as defined herein.

In another aspect, the present invention provides novel intermediates as defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" refers to aliphatic hydrocarbon groups and includes both straight and branched chain alkyl groups. References to individual alkyl groups such as "propyl" are specific for the straight chain version only and references to individual branched chain alkyl groups such as "isopropyl" are specific for the branched chain version only. For example, "$C_{1-6}$alkyl" includes $C_{1-4}$alkyl, $C_{1-3}$alkyl, propyl, isopropyl and t-butyl. A similar convention applies to other radicals, for example "phenyl$C_{1-6}$alkyl" includes phenyl$C_{1-4}$alkyl, benzyl, 1-phenylethyl and 2-phenylethyl.

The term "alkylene" includes both straight and branched chain divalent alkyl groups. For example, "$C_{1-4}$alkylene" includes methylene ($-CH_2-$), ethylene ($-CH_2CH_2-$), propylene and butylene.

The term "alkoxy" includes both straight and branched chain alkyl groups singularly bonded to oxygen. For example, "$C_{1-4}$alkoxy" includes methoxy, ethoxy, isopropoxy and t-butoxy.

The term "$C_{m-n}$" used as a prefix, refers to any group having m to n carbon atoms.

"Cycloalkyl" means a hydrocarbon ring containing from 3 to 8 carbon atoms, for example, cyclopropyl, cyclobutyl, cyclopentyl, cyclohexyl, cycloheptyl or bicycle[2.2.2]octane, bicycle[2.1.1]hexane, bicycle[1.1.1]pentane and bicyclo[2.2.1]heptyl.

The term "halo" refers to fluoro, chloro, bromo and iodo.

The term "haloalkyl" or "haloalkoxy" is used herein to refer to an alkyl or alkoxy group respectively in which one or more hydrogen atoms have been replaced by halogen (e.g. fluorine) atoms. Examples of haloalkyl and haloalkoxy groups include fluoroalkyl and fluoroalkoxy groups such as $-CHF_2$, $-CH_2CF_3$, or perfluoroalkyl/alkoxy groups such as $-CF_3$, $-CF_2CF_3$ or $-OCF_3$.

The term "carbocyclyl", "carbocyclic" or "carbocycle" means a non-aromatic saturated or partially saturated monocyclic, or a fused, bridged, or spiro bicyclic carbocyclic ring system(s). Monocyclic carbocyclic rings contain from about 3 to 12 (suitably from 3 to 7) ring atoms. Bicyclic carbocycles contain from 7 to 17 carbon atoms in the rings, suitably 7 to 12 carbon atoms, in the rings. Bicyclic carbocyclic rings may be fused, spiro, or bridged ring systems.

The term "heterocyclyl", "heterocyclic" or "heterocycle" means a non-aromatic saturated or partially unsaturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or $SO_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (═O) or thioxo (═S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. Partially unsaturated heterocyclyl rings contain at least one double bond, such as 1 or 2 double bonds. Examples of partially unsaturated heterocyclyl rings include 1,6-dihydropyridinyl, 1,6-dihydropyridazinyl and 2,3-dihydropyrrolyl. As the skilled person would appreciate, any heterocycle may be linked to another group via any suitable atom, such as via a carbon or nitrogen atom. Suitably, the term "heterocyclyl", "heterocyclic" or "heterocycle" will refer to 4, 5, 6 or 7 membered monocyclic rings as defined above.

By "bridged ring systems" is meant ring systems in which two rings share more than two atoms, see for example Advanced Organic Chemistry, by Jerry March, 4th Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4]octane, 2-oxa-6-azaspiro[3.4]octane, 2-azaspiro[3.3]heptanes and 2-oxa-6-azaspiro[3.3]heptanes.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five. Heteroaryl groups containing nitrogen atoms may be present as the corresponding N-oxides. Particular examples of such heteroaryl groups are pyridine N-oxides. Suitably, the term "heteroaryl" or "heteroaromatic" will refer to 5 or 6 membered monocyclic heteroaryl rings as defined above.

Non-limiting examples of heteroaryl groups include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, and imidazo[1,2-b][1,2,4]triazinyl groups.

Non-limiting examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl, and tetrazolyl groups.

Non-limiting examples of six membered heteroaryl groups include but are not limited to pyridyl, pyrazinyl, pyridazinyl, pyrimidinyl and triazinyl groups.

A bicyclic heteroaryl group may be, for example, a group selected from:

- a benzene ring fused to a 5- or 6-membered ring containing 1, 2 or 3 ring heteroatoms;
- a pyridine ring fused to a 5- or 6-membered ring containing 1, 2 or 3 ring heteroatoms;
- a pyrimidine ring fused to a 5- or 6-membered ring containing 1 or 2 ring heteroatoms;
- a pyrrole ring fused to a 5- or 6-membered ring containing 1, 2 or 3 ring heteroatoms;
- a pyrazole ring fused to a 5- or 6-membered ring containing 1 or 2 ring heteroatoms;
- a pyrazine ring fused to a 5- or 6-membered ring containing 1 or 2 ring heteroatoms;
- an imidazole ring fused to a 5- or 6-membered ring containing 1 or 2 ring heteroatoms;
- an oxazole ring fused to a 5- or 6-membered ring containing 1 or 2 ring heteroatoms;
- an isoxazole ring fused to a 5- or 6-membered ring containing 1 or 2 ring heteroatoms;
- a thiazole ring fused to a 5- or 6-membered ring containing 1 or 2 ring heteroatoms;
- an isothiazole ring fused to a 5- or 6-membered ring containing 1 or 2 ring heteroatoms;
- a thiophene ring fused to a 5- or 6-membered ring containing 1, 2 or 3 ring heteroatoms;
- a furan ring fused to a 5- or 6-membered ring containing 1, 2 or 3 ring heteroatoms;
- a cyclohexyl ring fused to a 5- or 6-membered heteroaromatic ring containing 1, 2 or 3 ring heteroatoms; and
- a cyclopentyl ring fused to a 5- or 6-membered heteroaromatic ring containing 1, 2 or 3 ring heteroatoms.

Particular non-limiting examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular non-limiting examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl, and pteridinyl groups.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In an embodiment, an aryl is phenyl or naphthyl, especially phenyl.

This specification also makes use of several composite terms to describe groups comprising more than one functionality. Such terms will be understood by a person skilled in the art. For example heterocyclyl$C_{1-4}$alkyl comprises $C_{1-4}$alkyl substituted by heterocyclyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups. It is understood that where there are multiple substituents, the substituents chosen may be the same or different.

Where numerical ranges are given, it is understood that the ranges are inclusive of the endpoints.

The phrase "compound of the invention" means those compounds which are disclosed herein, both generically and specifically.

Compounds of the Invention

In a first aspect, the present invention provides a compound of Formula I:

(I)

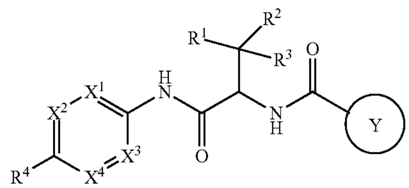

wherein:

$X^1$, $X^2$, $X^3$ and $X^4$ are each independently $CR^5$ or N;

Y is aryl or heteroaryl, each of which is optionally substituted by one or more substituents independently selected from halo, $C_{1-4}$alkyl, $C_{1-4}$alkoxy, $C_{1-3}$alkylene-$C_{1-4}$alkoxy, $C_{1-3}$alkylene-$N(C_{1-3}alkyl)_2$, and $C_{1-4}$haloalkyl; and wherein when Y is a 5- or 6-membered heteroaryl ring, said ring is optionally fused to a 5- or 6-membered cycloalkyl or heterocyclyl ring, each of which is optionally substituted by one or more substituents independently selected from halo, $C_{1-4}$alkyl, $C_{1-4}$alkoxy, $C_{1-3}$alkylene-$C_{1-4}$alkoxy, $C_{1-3}$alkylene-$N(C_{1-3}alkyl)_2$, and $C_{1-4}$haloalkyl;

$R^1$ and $R^2$:

(A) are both phenyl optionally substituted with one or more substituents independently selected from halo, $C_{1-4}$alkyl, $C_{1-4}$alkoxy, and $C_{1-4}$haloalkyl, and wherein the phenyl groups are optionally linked by a bond or a $C_{1-2}$alkylene moiety; OR (B) together with the carbon atom to which they are attached form a 4- to 10-membered cycloalkyl, or 4- to 10-membered heterocyclyl ring, wherein the cycloalkyl or heterocyclyl ring:

a. is optionally substituted with one or more substituents independently selected from halo, $C_{1-4}$alkyl, $C_{1-4}$alkoxy, $C_{1-4}$haloalkyl, and $C_{1-4}$haloalkoxy;

b. optionally comprises one or two C═C double bonds;

c. is optionally bridged by a $C_{1-3}$alkylene group connecting two carbon atoms of the ring; and d. is optionally spiro-attached to one or more independently selected $C_{3-6}$cycloalkyl groups;

$R^3$ is hydrogen, fluoro, or $C_{1-4}$alkyl;

$R^4$ is:

(A) a 5- to 10-membered heteroaryl, a $C_{3-7}$cycloalkyl, or a 3- to 12-membered heterocyclyl ring, each of which is optionally substituted by one or more substituents independently selected from hydroxy, halo, $C_{1-4}$alkyl, $C_{1-4}$alkoxy, $C_{1-4}$haloalkyl, cyano, $NR^6R^7$, $C(O)NR^3R^9$, $CO_2R^{10}$, $C_{1-3}$alkylene-$R^{11}$, $C_{3-7}$cycloalkyl, and heterocyclyl, wherein said $C_{3-7}$cycloalkyl and heterocyclyl substituents are optionally substituted with one or more substituents independently selected from hydroxy, halo, $C_{1-4}$alkyl, $C_{1-4}$alkoxy, $C_{1-4}$haloalkyl, cyano, $NR^6R^7$, $C(O)NR^3R^9$ and $CO_2R^{10}$;

(B) $C_{1-6}$alkyl optionally substituted with hydroxy, halo, $C_{1-4}$alkoxy, cyano, $NR^6R^7$, $C(O)NR^8R^9$ or $CO_2R^{10}$;

(C) 5- to 6-membered heteroaryl ring, said ring being fused to a 5- or 6-membered cycloalkyl or heterocyclyl ring, each of which is optionally substituted by one or more substituents independently selected from hydroxy, halo, oxo, $C_{1-4}$alkyl, $C_{1-4}$alkoxy, $C_{1-4}$haloalkyl, cyano, $NR^6R^7$, $C(O)NR^8R^9$, $CO_2R^{10}$, $C_{1-3}$alkylene-$R^{11}$, $C_{3-7}$cycloalkyl, and heterocyclyl;

(D) a 5- or 6-membered cycloalkyl or a 5- or 6-membered heterocyclyl ring, said ring being fused to a phenyl or 5- to 6-membered heteroaryl ring, each of which rings is optionally substituted by one or more substituents independently selected from hydroxy, halo, oxo, $C_{1-4}$alkyl, $C_{1-4}$alkoxy, $C_{1-4}$haloalkyl, cyano, $NR^6R^7$, $C(O)NR^8R^9$, $CO_2R^{10}$, $C_{1-3}$alkylene-$R^{11}$, $C_{3-7}$cycloalkyl, and heterocyclyl; or (E) a partially unsaturated heterocyclic ring, optionally fused to a 5- to 6-membered heteroaryl ring and optionally substituted with one or more substituents independently selected from hydroxy, halo, oxo, $C_{1-4}$alkyl, $C_{1-4}$alkoxy, $C_{1-4}$haloalkyl, cyano, $NR^6R^7$, $C(O)NR^8R^9$, $CO_2R^{10}$, $C_{1-3}$alkylene-$R^{11}$, $C_{3-7}$cycloalkyl, and heterocyclyl;

$R^5$ is hydrogen, halo, $C_{1-4}$alkyl, $C_{1-4}$alkoxy, $C_{1-4}$haloalkyl or cyano;

$R^{11}$ is hydroxy, halo, $C_{1-4}$alkoxy, cyano, $NR^{12}R^{13}$, $C(O)R^{14}$, aryl, or heteroaryl;

$R^{14}$ is hydroxy, $C_{1-4}$alkyl, $C_{1-4}$alkoxy, or $NR^{15}R^{16}$;

$R^6$, $R^7$, $R^8$, $R^9$, $R^{10}$, $R^{12}$ and $R^{13}$ are independently selected from hydrogen and $C_{1-4}$alkyl;

$R^{15}$ and $R^{16}$ are independently selected from hydrogen and $C_{1-4}$alkyl; or $R^{15}$ and $R^{16}$ taken together with the nitrogen atom to which they are attached form a 3- to 7-membered heterocyclyl ring, the ring optionally containing a further heteroatom chosen from O, S and N and being optionally substituted with $C_{1-4}$alkyl;

or a pharmaceutically acceptable salt thereof.

Compounds according to Formula (I) may exist as a mixture of stereoisomers. Preferably, compounds according to Formula (I) have the following structure:

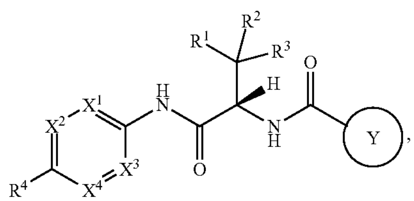

wherein $X^1$, $X^2$, $X^3$, $X^4$, Y, $R^1$, $R^2$, $R^3$ and $R^4$ are as defined hereinbefore or hereinafter.

Particular compounds of the invention include, for example, compounds of the Formula I, or pharmaceutically acceptable salts thereof, wherein, unless otherwise stated, each of $X^1$, $X^2$, $X^3$, $X^4$, Y, $R^1$, $R^2$, $R^3$, $R^4$, $R^5$, $R^{11}$, $R^{14}$, $R^{15}$, and $R^{16}$ has any of the meanings defined hereinbefore or in any of paragraphs (1) to (78) hereinafter. For the avoidance of doubt, the invention encompasses combinations of two or more substituent definitions as described in paragraphs (1) to (78):

(1) $X^1$, $X^2$, $X^3$ and $X^4$ are each independently CH or N;

(2) Two of $X^1$, $X^2$, $X^3$ and $X^4$ are $CR^5$ and two are N;

(3) $X^2$ and $X^4$ are N and $X^1$ and $X^3$ are $CR^5$;

(4) $X^2$ and $X^4$ are N and $X^1$ and $X^3$ are CH;

(5) Three of $X^1$, $X^2$, $X^3$ and $X^4$ are $CR^5$ and the other is N;

(6) $X^1$ is N and $X^2$, $X^3$ and $X^4$ are $CR^5$;

(7) $X^1$ is N and $X^2$, $X^3$ and $X^4$ are CH;

(8) $X^2$ is N and $X^1$, $X^3$ and $X^4$ are $CR^5$;

(9) $X^2$ is N and $X^1$, $X^3$ and $X^4$ are CH;

(10) $X^1$, $X^2$, $X^3$ and $X^4$ are all $CR^5$;

(11) $X^1$, $X^2$, $X^3$ and $X^4$ are all CH;

(12) Y is aryl or heteroaryl, each of which is optionally substituted by one or more substituents independently selected from halo, $C_{1-4}$alkyl, $C_{1-4}$alkoxy, $C_{1-3}$alkylene-$C_{1-4}$alkoxy, $C_{1-3}$alkylene-N($C_{1-3}$alkyl)$_2$, and $C_{1-4}$haloalkyl;

(13) Y is phenyl optionally substituted by one or more substituents independently selected from halo, $C_{1-2}$alkyl, $C_{1-2}$alkoxy, $C_{1-2}$alkylene-$C_{1-2}$alkoxy, and $C_{1-2}$haloalkyl;

(14) Y is a heteroaryl ring optionally substituted by one or more substituents independently selected from halo, $C_{1-3}$alkyl, $C_{1-2}$alkoxy, $C_{1-2}$alkylene-$C_{1-2}$alkoxy, and $C_{1-2}$haloalkyl;

(15) Y is a 5- to 6-membered heteroaryl ring optionally substituted by one or more substituents independently selected from chloro, fluoro, methyl, and difluoromethyl;

(16) Y is a 5- to 6-membered heteroaryl ring substituted in a position ortho to the NHC(O)— moiety by methyl or ethyl (such as methyl);

(17) Y is a 5- or 6-membered heteroaryl ring fused to a 5- or 6-membered cycloalkyl or heterocyclyl ring, each of which is optionally substituted by one or more substituents independently selected from halo, $C_{1-2}$alkyl, $C_{1-2}$alkoxy, $C_{1-2}$alkylene-$C_{1-2}$alkoxy, $C_{1-2}$alkylene-N ($C_{1-3}$alkyl)$_2$, and $C_{1-2}$haloalkyl;

(18) Y is a 5-membered heteroaryl ring fused to a 5- or 6-membered heterocyclyl ring, each of which is optionally substituted by one or more substituents independently selected from halo, $C_{1-2}$alkyl, $C_{1-2}$alkoxy, $C_{1-2}$alkylene-$C_{1-2}$alkoxy, and $C_{1-2}$haloalkyl;

(19) Y is pyrazolyl, pyrrolyl, isoxazolyl, oxadiazolyl or triazolyl, substituted by one or more substituents independently selected from chloro, fluoro, methyl, and difluoromethyl;

(20) Y is:

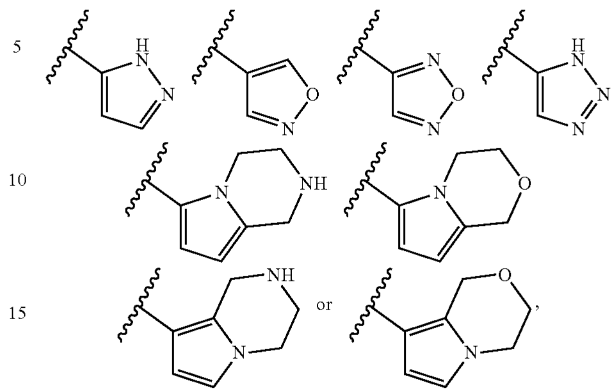

wherein ∿∿∿ is the point of attachment to the rest of the compound of Formula I and Y is optionally substituted by one or more substituents independently selected from halo, $C_{1-3}$alkyl, $C_{1-2}$alkoxy, $C_{1-2}$alkylene-$C_{1-2}$alkoxy, $C_{1-2}$alkylene-N($C_{1-3}$ alkyl)$_2$, and $C_{1-2}$haloalkyl;

(21) Y is pyrazolyl, substituted by one or more substituents independently selected from chloro, fluoro, methyl, ethyl, isopropyl, and difluoromethyl;

(22) Y is:

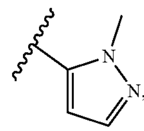 [SMILES: *c1ccnn1C]

wherein ∿∿∿ is the point of attachment to the rest of the compound of Formula I;

(23) $R^1$ and $R^2$ are both phenyl optionally substituted with one or more substituents independently selected from halo, $C_{1-2}$alkyl, $C_{1-2}$alkoxy, and $C_{1-2}$haloalkyl, and wherein the phenyl groups are optionally linked by a bond or a $C_{1-2}$alkylene moiety;

(24) $R^1$ and $R^2$ are both phenyl optionally substituted with one or more substituents independently selected from halo, methyl, and methoxy, and wherein the phenyl groups are optionally linked by a bond or a $C_{1-2}$alkylene moiety;

(25) $R^1$ and $R^2$ are both phenyl optionally substituted with one or more substituents independently selected from halo, methyl, and methoxy;

(26) $R^1$ and $R^2$ are both phenyl optionally substituted with one or more substituents independently selected from fluoro and methyl;

(27) $R^1$ and $R^2$ are both phenyl optionally substituted with one or more substituents independently selected from halo, $C_{1-2}$alkyl, $C_{1-2}$alkoxy, and $C_{1-2}$haloalkyl, and wherein the phenyl groups are linked by a bond;

(28) $R^1$ and $R^2$ together with the carbon atom to which they are attached form a 4- to 10-membered cycloalkyl ring or a a 4- to 10-membered heterocyclyl ring (such as 1,3-dioxanyl or 1,4-dioxanyl), wherein the cycloalkyl or heterocyclyl ring:

a. is optionally substituted with one or more substituents independently selected from halo, $C_{1-2}$alkyl, $C_{1-2}$alkoxy, and $C_{1-2}$haloalkyl;

b. optionally comprises one or two C═C double bonds;

c. is optionally bridged by a $C_{1-3}$alkylene group connecting two carbon atoms of the ring; and d. is optionally spiro-attached to one or more independently selected $C_{3-8}$cycloalkyl groups;

(29) $R^1$ and $R^2$ together with the carbon atom to which they are attached form a 4- to 8-membered cycloalkyl ring, wherein the cycloalkyl ring:

a. is optionally substituted with one or more substituents independently selected from halo, $C_{1-2}$alkyl, $C_{1-2}$alkoxy, and $C_{1-2}$haloalkyl;

b. optionally comprises one or two C═C double bonds;

c. is optionally bridged by a $C_{1-3}$alkylene group connecting two carbon atoms of the ring; and d. is optionally spiro-attached to one or more independently selected $C_{3-8}$cycloalkyl groups;

(30) $R^1$ and $R^2$ together with the carbon atom to which they are attached form a 4- to 8-membered cycloalkyl ring, wherein the cycloalkyl ring:

a. is optionally substituted with one or more substituents independently selected from fluoro, methyl, trifluoromethyl, and methoxy;

b. optionally comprises one or two C═C double bonds;

c. is optionally bridged by a $C_{1-3}$alkylene group connecting two carbon atoms of the ring; and d. is optionally spiro-attached to one or more independently selected $C_{3-8}$cycloalkyl groups;

(31) $R^1$ and $R^2$ together with the carbon atom to which they are attached form a 5- to 8-membered cycloalkyl ring, wherein the cycloalkyl ring:

a. is substituted with one or more substituents independently selected from fluoro, trifluoromethyl, and methyl;

b. optionally comprises one or two C═C double bonds;

c. is optionally bridged by a $C_{1-3}$alkylene group connecting two carbon atoms of the ring; and d. is optionally spiro-attached to one or two $C_{3-5}$cycloalkyl groups (such as one or two cyclopropyl groups);

(32) $R^1$ and $R^2$ together with the carbon atom to which they are attached form a 5- to 8-membered cycloalkyl ring, wherein the cycloalkyl ring:

a. is substituted with a methyl substituent;

b. optionally comprises one or two C═C double bonds;

c. is optionally bridged by a $C_{1-3}$alkylene group connecting two carbon atoms of the ring; and d. is optionally spiro-attached to a $C_{3-5}$cycloalkyl group;

(33) $R^1$ and $R^2$ together with the carbon atom to which they are attached form a cyclohexyl ring, wherein the cyclohexyl ring:

a. is substituted with one or more substituents independently selected from fluoro, trifluoromethyl, and methyl;

b. optionally comprises one or two C═C double bonds;

c. is optionally bridged by a $C_{1-3}$alkylene group connecting two carbon atoms of the ring; and d. is optionally spiro-attached to a $C_{3-5}$cycloalkyl group;

(34) $R^1$ and $R^2$ together with the carbon atom to which they are attached form a group selected from:

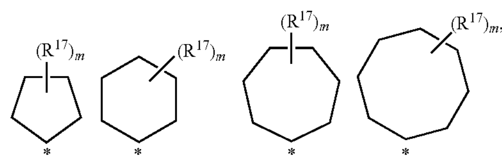

wherein * is the carbon atom to which $R^1$ and $R^2$ are attached, each occurrence of $R^{17}$ is independently selected from halo, $C_{1-2}$alkyl, $C_{1-2}$alkoxy, $C_{1-2}$haloalkyl, and $C_{1-2}$haloalkoxy, and m is 0, 1, 2 or 3;

(35) $R^1$ and $R^2$ together with the carbon atom to which they are attached form a group selected from:

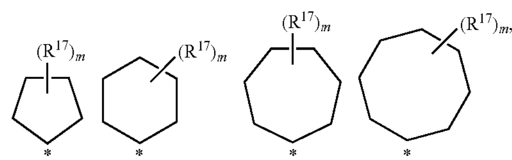

wherein * is the carbon atom to which $R^1$ and $R^2$ are attached, each occurrence of $R^{17}$ is independently selected from fluoro, methyl, trifluoromethyl, and methoxy, and m is 0, 1 or 2;

(36) $R^1$ and $R^2$ together with the carbon atom to which they are attached form a group selected from:

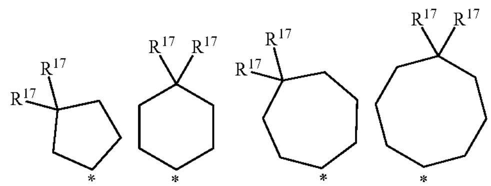

wherein * is the carbon atom to which $R^1$ and $R^2$ are attached, and each occurrence of $R^{17}$ is independently selected from hydrogen, fluoro, methyl, trifluoromethyl, and methoxy;

(37) $R^1$ and $R^2$ together with the carbon atom to which they are attached form the following:

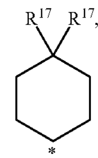

wherein * is the carbon atom to which $R^1$ and $R^2$ are attached, and each $R^{17}$ is independently selected from hydrogen, fluoro, methyl, and trifluoromethyl;

(38) $R^3$ is hydrogen, fluoro, or methyl;

(39) $R^3$ is hydrogen;

(40) $R^3$ is methyl;

(41) $R^4$ is:

(A) a 5- to 10-membered heteroaryl or $C_{3-7}$cycloalkyl ring, each of which is optionally substituted by one or more substituents independently selected from hydroxy, halo, $C_{1-4}$alkyl, $C_{1-4}$alkoxy, $C_{1-4}$haloalkyl, cyano, $NR^6R^7$, $C(O)NR^3R^9$, $CO_2R^{10}$, $C_{1-3}$alkylene-$R^{11}$, $C_{3-7}$cycloalkyl, and heterocyclyl, wherein said $C_{3-7}$cycloalkyl and heterocyclyl substituents are optionally substituted with one or more substituents independently selected from hydroxy, halo, $C_{1-4}$alkyl, $C_{1-4}$alkoxy, $C_{1-4}$haloalkyl, cyano, $NR^6R^7$, $C(O)NR^3R^9$, and $CO_2R^{10}$;

(B) $C_{1-6}$-alkyl optionally substituted with hydroxy, halo, $C_{1-4}$alkoxy, cyano, $NR^6R^7$ or $CO_2R^{10}$;

(C) 5- to 6-membered heteroaryl ring, said ring being fused to a 5- or 6-membered cycloalkyl or heterocyclyl ring, each of which is optionally substituted by one or more substituents independently selected from hydroxy, halo, oxo, $C_{1-4}$alkyl, $C_{1-4}$alkoxy, $C_{1-4}$haloalkyl, cyano, $NR^6R^7$, $C(O)NR^3R^9$, $CO_2R^{10}$, $C_{1-3}$alkylene-$R^{11}$, $C_{3-7}$cycloalkyl, and heterocyclyl;

(D) a 5- or 6-membered cycloalkyl or a 5- or 6-membered heterocyclyl ring, said ring being fused to a phenyl or 5- to 6-membered heteroaryl ring, each of which rings is optionally substituted by one or more substituents independently selected from hydroxy, halo, oxo, $C_{1-4}$alkyl, $C_{1-4}$alkoxy, $C_{1-4}$haloalkyl, cyano, $NR^6R^7$, $C(O)NR^3R^9$, $CO_2R^{10}$, $C_{1-3}$alkylene-$R^{11}$, $C_{3-7}$cycloalkyl, and heterocyclyl; or (E) a partially unsaturated heterocyclic ring, optionally fused to a 5- to 6-membered heteroaryl ring and optionally substituted with one or more substituents independently selected from hydroxy, halo, oxo, $C_{1-4}$alkyl, $C_{1-4}$alkoxy, $C_{1-4}$haloalkyl, cyano, $NR^6R^7$, $C(O)NR^3R^9$, $CO_2R^{10}$, $C_{1-3}$alkylene-$R^{11}$, $C_{3-7}$cycloalkyl, and heterocyclyl;

(42) $R^4$ is:

(A) a 5- to 10-membered heteroaryl ring optionally substituted by one or more substituents independently selected from hydroxy, halo, $C_{1-4}$alkyl, $C_{1-4}$alkoxy, $C_{1-4}$haloalkyl, cyano, $NR^6R^7$, $C(O)NR^3R^9$, $CO_2R^{10}$, $C_{1-3}$alkylene-$R^{11}$, $C_{3-7}$cycloalkyl, and heterocyclyl;

(C) 5- to 6-membered heteroaryl ring, said ring being fused to a 5- or 6-membered cycloalkyl or heterocyclyl ring, each of which is optionally substituted by one or more substituents independently selected from hydroxy, halo, oxo, $C_{1-4}$alkyl, $C_{1-4}$alkoxy, $C_{1-4}$haloalkyl, cyano, $NR^6R^7$, $C(O)NR^3R^9$, $CO_2R^{10}$, $C_{1-3}$alkylene-$R^{11}$, $C_{3-7}$cycloalkyl, and heterocyclyl;

(D) a 5- or 6-membered cycloalkyl or a 5- or 6-membered heterocyclyl ring, said ring being fused to a phenyl or 5- to 6-membered heteroaryl ring, each of which rings is optionally substituted by one or more substituents independently selected from hydroxy, halo, oxo, $C_{1-4}$alkyl, $C_{1-4}$alkoxy, $C_{1-4}$haloalkyl, cyano, $NR^6R^7$, $C(O)NR^3R^9$, $CO_2R^{10}$, $C_{1-3}$alkylene-$R^{11}$, $C_{3-7}$cycloalkyl, and heterocyclyl; or (E) a partially unsaturated heterocyclic ring, optionally fused to a 5- to 6-membered heteroaryl ring and optionally substituted with one or more substituents independently selected from hydroxy, halo, oxo, $C_{1-4}$alkyl, $C_{1-4}$alkoxy, $C_{1-4}$haloalkyl, cyano, $NR^6R^7$, $C(O)NR^3R^9$, $CO_2R^{10}$, $C_{1-3}$alkylene-$R^{11}$, $C_{3-7}$cycloalkyl, and heterocyclyl;

(43) $R^4$ is:

(A) a 5- to 10-membered heteroaryl, optionally substituted by one or more substituents independently selected from hydroxy, halo, $C_{1-4}$alkyl, $C_{1-4}$alkoxy, $C_{1-4}$haloalkyl, cyano, $NR^6R^7$, $C(O)NR^3R^9$, $CO_2R^{10}$, $C_{1-3}$alkylene-$R^{11}$, and $C_{3-7}$cycloalkyl;

(C) 5- to 6-membered heteroaryl ring, said ring being fused to a 5- or 6-membered cycloalkyl or heterocyclyl ring, each of which is optionally substituted by one or more substituents independently selected from hydroxy, halo, oxo, $C_{1-4}$alkyl, $C_{1-4}$alkoxy, $C_{1-4}$haloalkyl, cyano, $NR^6R^7$, $C(O)NR^8R^9$, $CO_2R^{10}$, and $C_{1-3}$alkylene-$R^{11}$; or (E) a partially unsaturated heterocyclic ring, optionally fused to a 5- to 6-membered heteroaryl ring and optionally substituted with one or more substituents independently selected from hydroxy, halo, oxo, $C_{1-4}$alkyl, $C_{1-4}$alkoxy, $C_{1-4}$haloalkyl, cyano, $NR^6R^7$, $C(O)NR^3R^9$, $CO_2R^{10'}$ and $C_{1-3}$alkylene-$R^{11}$;

(44) $R^4$ is:

(A) a 5- to 10-membered heteroaryl, optionally substituted by one or more substituents independently selected from hydroxy, halo, $C_{1-4}$alkyl, $C_{1-4}$alkoxy, $C_{1-4}$haloalkyl, cyano, $NR^6R^7$, $C(O)NR^3R^9$, $CO_2R^{10}$, $C_{1-3}$alkylene-$R^{11}$, and $C_{3-7}$cycloalkyl; or (E) a partially unsaturated heterocyclic ring, optionally fused to a 5- to 6-membered heteroaryl ring and optionally substituted with one or more substituents independently selected from hydroxy, halo, oxo, $C_{1-4}$alkyl, $C_{1-4}$alkoxy, $C_{1-4}$haloalkyl, cyano, $NR^6R^7$, $C(O)NR^3R^9$, $CO_2R^{10}$, and $C_{1-3}$alkylene-$R^{11}$;

(45) $R^4$ is a 5- to 10-membered heteroaryl, $C_{3-7}$cycloalkyl, or 3- to 12-membered heterocyclyl ring, each of which is optionally substituted by one or more substituents independently selected from hydroxy, halo, $C_{1-4}$alkyl, $C_{1-4}$alkoxy, $C_{1-2}$fluoroalkyl, cyano, $NR^6R^7$, $C(O)NR^3R^9$, and $C_{1-3}$alkylene-$R^{11}$;

(46) $R^4$ is a 6- to 10-membered heteroaryl, $C_{3-7}$cycloalkyl, or 3- to 7-membered heterocyclyl ring, each of which is optionally substituted by one or more substituents independently selected from hydroxy, halo, $C_{1-4}$alkyl, $C_{1-4}$alkoxy, $C_{1-2}$fluoroalkyl, cyano, $NR^6R^7$, $C(O)NR^3R^9$, and $C_{1-3}$alkylene-$R^{11}$;

(47) $R^4$ is a 5- to 10-membered heteroaryl ring, optionally substituted by one or more substituents independently selected from halo, $C_{1-4}$alkyl, $C_{1-2}$alkoxy, $C_{1-2}$fluoroalkyl, cyano, $NR^6R^7$, $C_{1-3}$alkylene-$R^{11}$, and $C_{3-7}$cycloalkyl;

(48) $R^4$ is a 5- to 6-membered monocyclic heteroaryl ring or a 9- to 10-membered bicyclic heteroaryl ring, optionally substituted by one or more substituents independently selected from fluoro, chloro, methyl, methoxy, trifluoromethoxy, cyano, $NR^6R^7$, $CH_2$—$R^{11}$, and cyclopropyl;

(49) $R^4$ is a 6- to 10-membered heteroaryl ring, optionally substituted by one or more substituents independently selected from halo, $C_{1-4}$alkyl, $C_{1-2}$alkoxy, $C_{1-2}$fluoroalkyl, cyano, $NR^6R^7$, and $C_{1-3}$alkylene-$R^{11}$;

(50) $R^4$ is a $C_{3-7}$cycloalkyl ring, optionally substituted by one or more substituents independently selected from hydroxy, halo, $C_{1-2}$alkyl, $C_{1-2}$alkoxy, cyano, $NR^6R^7$, $C(O)NR^3R^9$, and $C_{1-3}$alkylene-$R^{11}$;

(51) $R^4$ is a $C_{3-5}$cycloalkyl ring, optionally substituted by one or more substituents independently selected from hydroxy, fluoro, methyl, methoxy, cyano, $NR^6R^7$, and $C(O)NR^3R^9$;

(52) $R^4$ is a 3- to 7-membered heterocyclyl ring, optionally substituted by one or more substituents independently selected from hydroxy, halo, $C_{1-2}$alkyl, $C_{1-2}$alkoxy, $C_{1-2}$fluoroalkyl, cyano, $NR^6R^7$, $C(O)NR^3R^9$, and $C_{1-3}$alkylene-$R^{11}$;

(53) $R^4$ is a 3- to 7-membered heterocyclyl ring, optionally substituted by one or more substituents independently selected from hydroxy, methyl, methoxy, cyano, $NR^6R^7$, and $C(O)NR^3R^9$;

(54) $R^4$ is $C_{1-6}$alkyl optionally substituted with hydroxy, halo, $C_{1-2}$alkoxy, cyano, $NR^6R^7$, $C(O)NR^3R^9$ or $CO_2R^{10}$;

(55) $R^4$ is $C_{2-5}$alkyl optionally substituted with hydroxy, fluoro, $NR^6R^7$ or $CO_2R^{10}$;

(56) $R^4$ is a 5- to 6-membered heteroaryl ring, said ring being fused to a 5- or 6-membered cycloalkyl or heterocyclyl ring, each of which is optionally substituted by one or more substituents independently selected from halo, oxo, $C_{1-2}$alkyl, $C_{1-2}$alkoxy, $C_{1-2}$haloalkyl, and cyano;

(57) $R^4$ is a 5- to 6-membered heteroaryl ring, said ring being fused to a 5-membered cycloalkyl or heterocyclyl ring, each of which is optionally substituted by one or more substituents independently selected from chloro, fluoro, methyl, methoxy and cyano;

(58) $R^4$ is a 5- or 6-membered cycloalkyl or a 5- or 6-membered heterocyclyl ring, said ring being fused to a phenyl or 5- to 6-membered heteroaryl ring, each of which rings is optionally substituted by one or more substituents independently selected from halo, oxo, $C_{1-2}$alkyl, $C_{1-2}$alkoxy, $C_{1-2}$haloalkyl, and cyano;

(59) $R^4$ is a partially unsaturated heterocyclic ring, optionally fused to a 5- to 6-membered heteroaryl ring and optionally substituted with one or more substituents independently selected from hydroxy, halo, oxo, $C_{1-2}$alkyl, $C_{1-2}$alkoxy, $C_{1-2}$haloalkyl, and cyano;

(60) $R^4$ is a partially unsaturated heterocyclic ring optionally substituted with one or more substituents independently selected from fluoro, oxo, and $C_{1-2}$alkyl;

(61) $R^4$ is a partially unsaturated heterocyclic ring optionally substituted with one or more substituents independently selected from oxo and methyl;

(62) $R^4$ is a partially unsaturated 6-membered N-containing heterocyclic ring substituted with one or more substituents independently selected from oxo and methyl;

(63) $R^4$ is a partially unsaturated heterocyclic ring, fused to a 5- to 6-membered heteroaryl ring and optionally substituted with one or more substituents independently selected from fluoro, oxo, and $C_{1-2}$alkyl;

(64) $R^4$ is a partially unsaturated heterocyclic ring, fused to a 5- to 6-membered heteroaryl ring and optionally substituted with one or more substituents independently selected from oxo and methyl;

(65) $R^4$ is a partially unsaturated 6-membered N-containing heterocyclic ring, fused to a 5-membered N-containing heteroaryl ring and optionally substituted with one or more substituents independently selected from oxo and methyl;

(66) $R^4$ is selected from one of the following groups:

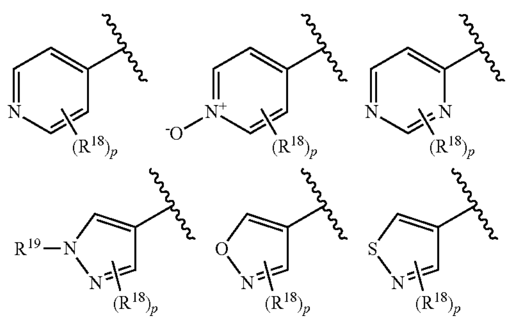

-continued

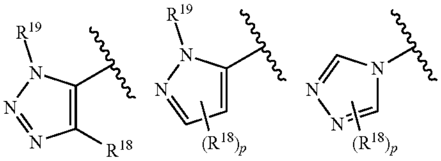

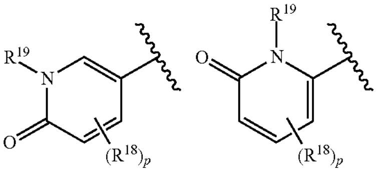

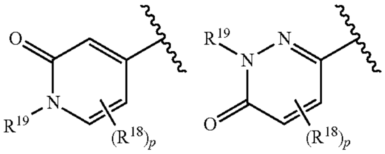

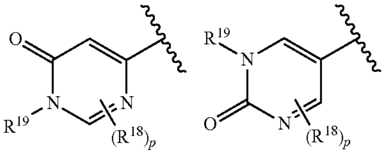

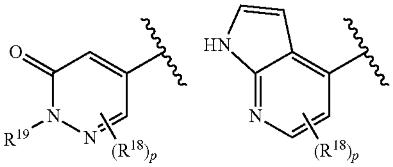

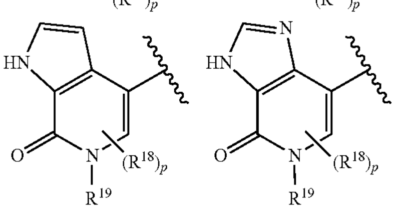

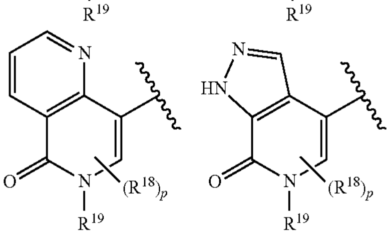

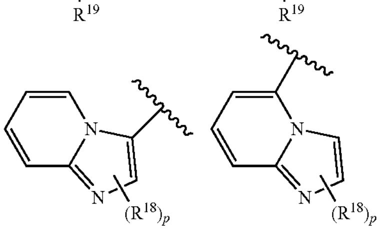

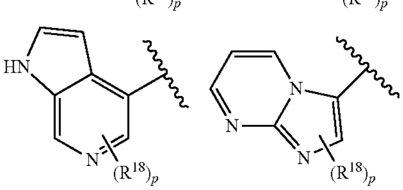

-continued

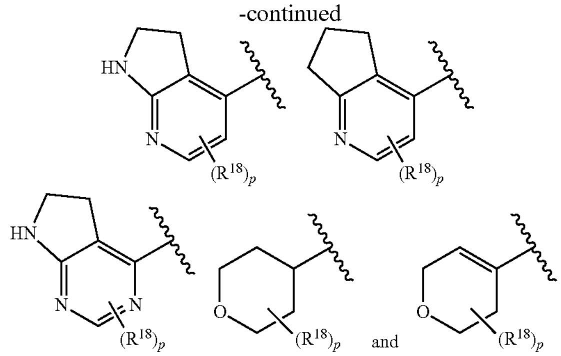

and , wherein:

is the point of attachment to the rest of the compound of Formula I;

$R^{13}$ is independently selected from hydroxy, halo, $C_{1-4}$alkyl, $C_{1-4}$alkoxy, $C_{1-4}$haloalkyl, cyano, $NR^6R^7$, $C_{1-3}$alkylene-$R^{11}$, and $C_{3-7}$cycloalkyl;

$R^{19}$ is independently selected from hydrogen, $C_{1-4}$alkyl, $C_{1-3}$alkylene-$R^{11}$, and $C_{3-7}$cycloalkyl; and p is 0, 1 or 2;

wherein when $R^4$ is a bicyclic group and p is 1 or 2, then each $R^{18}$ substituent may be present on either ring of the bicyclic group;

(67) $R^4$ is selected from one of the following groups:

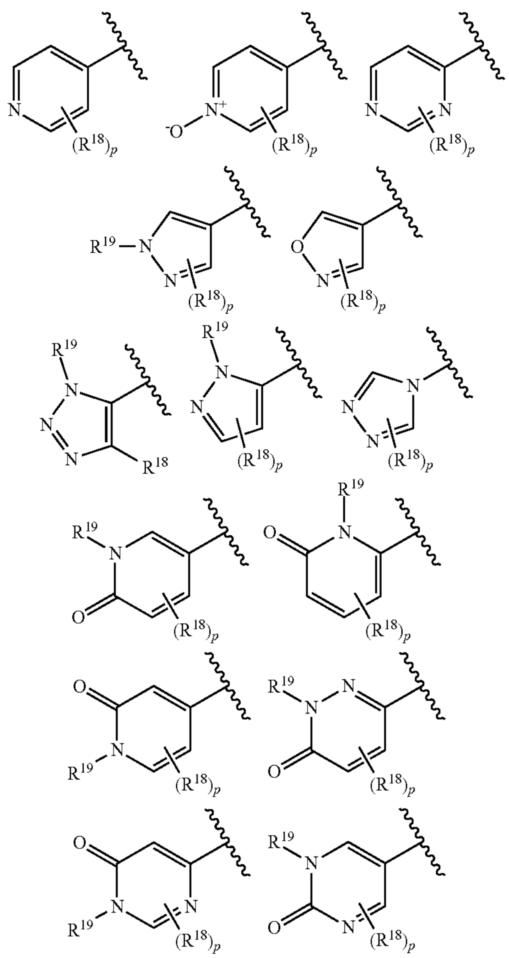

-continued

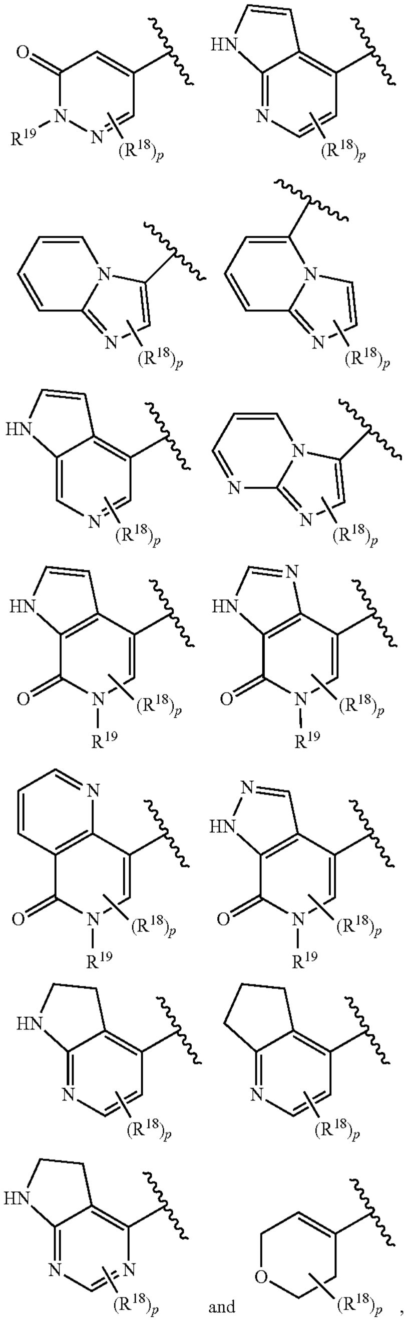

and , wherein is the point of attachment to the rest of the compound of Formula I;

$R^{18}$ is independently selected from hydroxy, halo, $C_{1-4}$alkyl, $C_{1-4}$alkoxy, $C_{1-4}$haloalkyl, cyano, $NR^6R^7$, $C_{1-3}$alkylene-$R^{11}$, and $C_{3-7}$cycloalkyl; $R^{19}$ is independently selected from hydrogen, $C_{1-4}$alkyl, $C_{1-3}$alkylene-$R^{11}$, and $C_{3-7}$cycloalkyl; and p is 0, 1 or 2;

wherein when $R^4$ is a bicyclic group and p is 1 or 2, then each $R^{18}$ substituent may be present on either ring of the bicyclic group;

(68) $R^4$ is selected from one of the following groups:

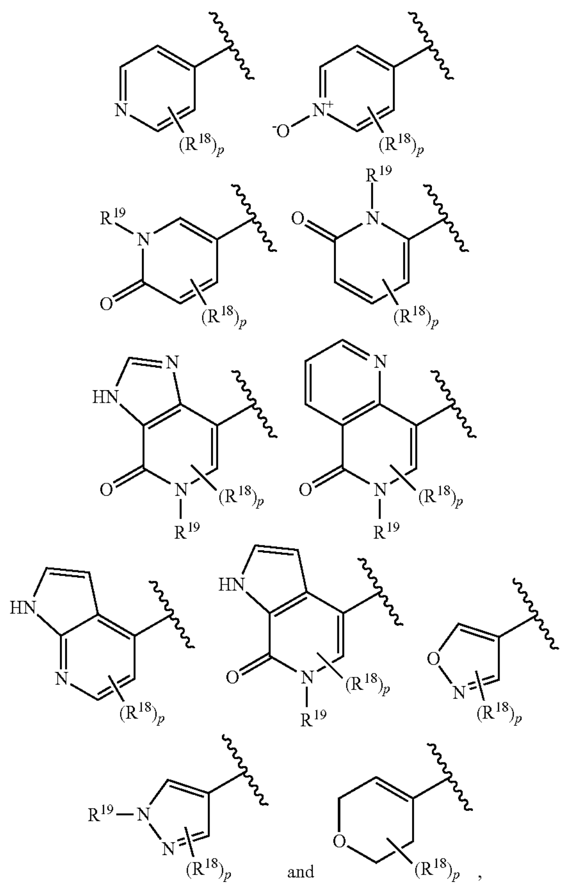

wherein:

⌇ is the point of attachment to the rest of the compound of Formula I;

$R^{18}$ is independently selected from hydroxy, fluoro, chloro, methyl, methoxy, $CF_3$, $NR^6R^7$, $C_{1-3}$alkylene-$R^{11}$, and cyclopropyl;

$R^{19}$ is independently selected from hydrogen, methyl, and cyclopropyl; and p is 0, 1 or 2;

wherein when $R^4$ is a bicyclic group and p is 1 or 2, then each $R^{18}$ substituent may be present on either ring of the bicyclic group;

(69) $R^5$ is hydrogen, fluoro, chloro, methyl, methoxy, trifluoromethyl, or cyano;

(70) $R^5$ is hydrogen, fluoro, chloro or methyl;

(71) $R^5$ is hydrogen;

(72) $R^5$ is fluoro;

(73) $R^{11}$ is hydroxy, halo, methoxy, cyano, $NR^{12}R^{13}$, $C(O)R^{14}$ or aryl;

(74) $R^{11}$ is hydroxy, methoxy, cyano, $NR^{12}R^{13}$, $C(O)R^{14}$ or phenyl;

(75) $R^{14}$ is hydroxy, methoxy or $NR^{15}R^{16}$;

(76) $R^{14}$ is $NR^{15}R^{16}$;

(77) $R^{15}$ and $R^{16}$ taken together with the nitrogen atom to which they are attached form a 3- to 7-membered heterocyclyl ring, the ring optionally containing a further heteroatom chosen from O, S or N and being optionally substituted with $C_{1-4}$alkyl;

(78) $R^{15}$ and $R^{16}$ taken together with the nitrogen atom to which they are attached form a 5- to 6-membered heterocyclyl ring, the ring optionally containing a further heteroatom chosen from O, S or N and being optionally substituted with methyl.

Suitably, $X^1$ to $X^4$ are as defined in any one of paragraphs (1) to (11) above. In an embodiment, $X^1$ to $X^4$ are as defined in any one of paragraphs (6) to (7) and (10) to (11) above. In a further embodiment, $X^1$ to $X^4$ are as defined in paragraph (11) above. In a further embodiment, $X^1$ to $X^4$ are as defined in paragraph (7) above.

Suitably, Y is as defined in any one of paragraphs (12) to (22) above. In an embodiment, Y is as defined in any one of paragraphs (19) to (22) above. In a further embodiment, Y is as defined in paragraph (22) above.

Suitably, $R^1$ and $R^2$ are as defined in any one of paragraphs (23) to (37) above. In an embodiment, $R^1$ and $R^2$ are as defined in any one of paragraphs (26) and (34) to (37) above. Preferably, $R^1$ and $R^2$ are as defined in paragraph (37) above.

Suitably, $R^3$ is as defined in any one of paragraphs (38) to (40) above. Preferably, $R^3$ is as defined in paragraph (39) above.

Suitably, $R^4$ is as defined in any one of paragraphs (41) to (68) above. In an embodiment, $R^4$ is as defined in any one of paragraphs (67) to (68) above. Preferably, $R^4$ is as defined in paragraph (68) above.

Suitably, $R^5$ is as defined in any one of paragraphs (69) to (72) above. Preferably, $R^5$ is as defined in paragraph (71) above.

Suitably, $R^{11}$ is as defined in any one of paragraphs (73) to (74) above. Preferably, $R^{11}$ is as defined in paragraph (74) above.

Suitably, $R^{14}$ is as defined in any one of paragraphs (75) to (76) above. Preferably, $R^{14}$ is as defined in paragraph (76) above.

Suitably, $R^{15}$ and $R^{16}$ are as defined in any one of paragraphs (77) to (78) above. Preferably, $R^{15}$ and $R^{16}$ are as defined in paragraph (78) above.

In a further group of compounds, the compounds have one of the structural Formulae IA, IB, IC or ID shown below:

(IA)

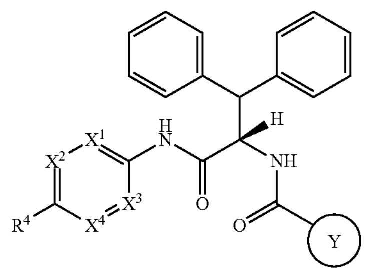

(IB)

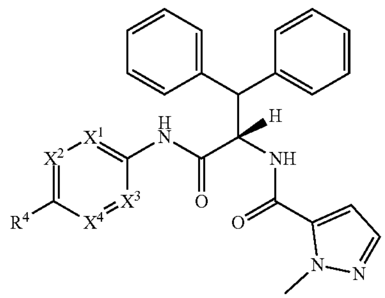

-continued (IC)

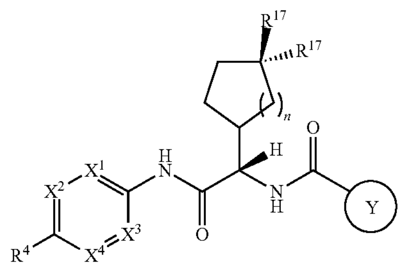

(ID)

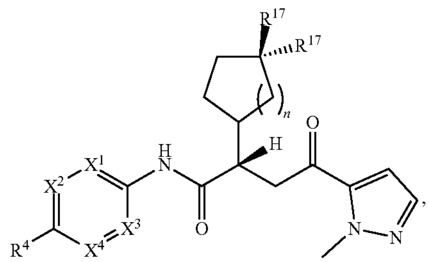

wherein $X^1$ to $X^4$, Y and $R^4$ are as defined hereinabove; each $R^{17}$ is independently selected from hydrogen, halo (such as fluoro), $C_{1-2}$alkyl (such as methyl), $C_{1-2}$alkoxy and $C_{1-2}$haloalkyl; and n is 1, 2, 3 or 4.

In a further group of compounds, the compounds have one of the structural Formulae IA, IB, IC or ID above, wherein $X^1$ to $X^4$ are as defined in any one of paragraphs (1) to (11) above; Y is as defined in any one of paragraphs (12) to (22) above; $R^4$ is as defined in any one of paragraphs (41) to (68) above; each $R^{17}$ is independently selected from hydrogen, halo (such as fluoro), $C_{1-2}$alkyl (such as methyl), $C_{1-2}$alkoxy, and $C_{1-2}$haloalkyl; and n is 1, 2, 3 or 4.

In a further group of compounds, the compounds have the structural Formula IA shown above, wherein $X^1$ to $X^4$ are as defined in any one of paragraphs (6) to (7) or (10) to (11) above; Y is as defined in any one of paragraphs (19) to (22) above; and $R^4$ is as defined in any one of paragraphs (67) to (68) above. In a further group of compounds, the compounds have the structural Formula IA shown above, wherein $X^1$ to $X^4$ are as defined in paragraph (11) above; Y is as defined in paragraph (22) above; and $R^4$ is as defined in paragraph (68) above.

In a further group of compounds, the compounds have the structural Formula IB shown above, wherein $X^1$ to $X^4$ are as defined in any one of paragraphs (6) to (7) or (10) to (11) above; and $R^4$ is as defined in any one of paragraphs (67) to (68) above. In a further group of compounds, the compounds have the structural Formula IA shown above, wherein $X^1$ to $X^4$ are as defined in paragraph (11) above; and $R^4$ is as defined in paragraph (68) above.

In a further group of compounds, the compounds have the structural Formula IC shown above, wherein $X^1$ to $X^4$ are as defined in any one of paragraphs (6) to (7) or (10) to (11) above; Y is as defined in any one of paragraphs (19) to (22) above; $R^4$ is as defined in any one of paragraphs (67) to (68) above; each $R^{17}$ is independently selected from hydrogen, fluoro, methyl, methoxy, and $C_{1-2}$haloalkyl; and n is 1, 2, 3 or 4. In a further group of compounds, the compounds have the structural Formula IC shown above, wherein $X^1$ to $X^4$ are as defined in paragraph (11) above; Y is as defined in paragraph (22) above; $R^4$ is as defined in paragraph (68) above; each $R^{17}$ is independently selected from hydrogen, fluoro, methyl, and trifluoromethyl; and n is 1, 2, 3 or 4.

In a further group of compounds, the compounds have the structural Formula ID shown above, wherein $X^1$ to $X^4$ are as defined in any one of paragraphs (6) to (7) or (10) to (11) above; $R^4$ is as defined in any one of paragraphs (67) to (68) above; each $R^{17}$ is independently selected from hydrogen, fluoro, methyl, methoxy, and $C_{1-2}$haloalkyl; and n is 1, 2, 3 or 4. In a further group of compounds, the compounds have the structural Formula ID shown above, wherein $X^1$ to $X^4$ are as defined in paragraph (11) above; $R^4$ is as defined in paragraph (68) above; each $R^{17}$ is independently selected from hydrogen, fluoro, methyl, and trifluoromethyl; and n is 1, 2, 3 or 4.

In a further group of compounds, the compounds have one of the structural Formulae IE, IF, IG, IH, IJ, IK, IL or IM shown below:

(IE)

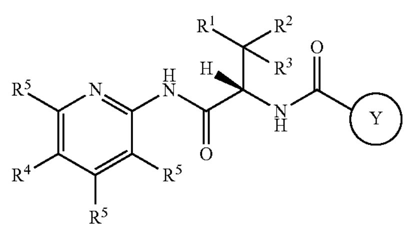

(IF)

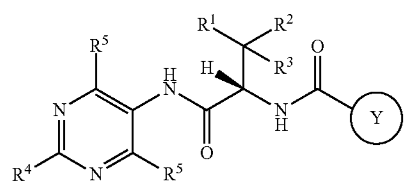

(IG)

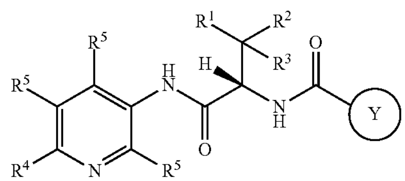

(IH)

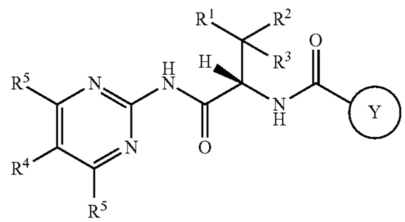

(IJ)

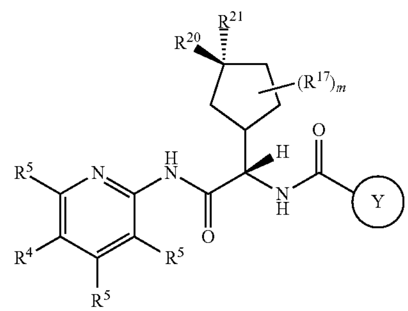

-continued (IK)

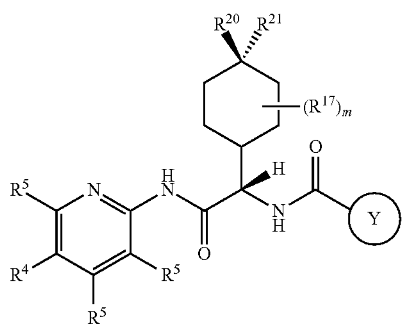

(IL)

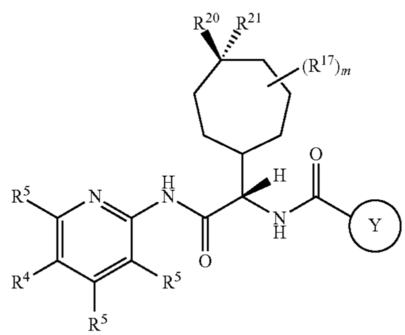

(IM)

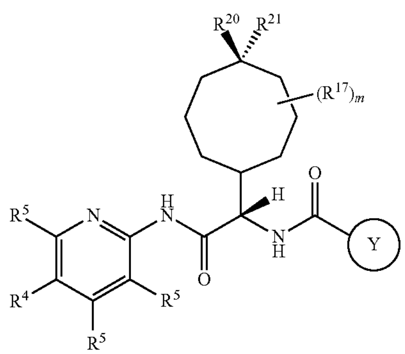

wherein Y, $R^1$, $R^2$, $R^3$, $R^4$, and $R^5$ are as defined hereinabove; each $R^{17}$ is independently selected from halo, $C_{1-4}$alkyl, $C_{1-4}$alkoxy, $C_{1-4}$haloalkyl, and $C_{1-4}$haloalkoxy; $R^{20}$ and $R^{21}$ are independently selected from hydrogen, halo, $C_{1-4}$alkyl, $C_{1-4}$alkoxy, $C_{1-4}$haloalkyl, and $C_{1-4}$haloalkoxy; and m is 0 to 4.

In a further group of compounds, the compounds have one of the structural Formulae IE, IF, IG, IH, IJ, IK, IL or IM, wherein Y is as defined in any one of paragraphs (12) to (22) above; $R^1$ and $R^2$ are as defined in any one of paragraphs (23) to (37) above; $R^3$ is as defined in any one of paragraphs (38) to (40) above; $R^4$ is as defined in any one of paragraphs (41) to (68) above; each $R^5$ is independently as defined in any one of paragraphs (69) to (72) above; each $R^{17}$ is independently selected from halo, $C_{1-4}$alkyl, $C_{1-4}$alkoxy, $C_{1-4}$haloalkyl, and $C_{1-4}$haloalkoxy; $R^{20}$ and $R^{21}$ are independently selected from hydrogen, halo, $C_{1-4}$alkyl, $C_{1-4}$alkoxy, $C_{1-4}$haloalkyl, and $C_{1-4}$haloalkoxy; and m is 0 to 4.

In a further group of compounds, the compounds have the structural Formulae IE, IF, IG or IH shown above, wherein Y is as defined in any one of paragraphs (19) to (22) above; $R^1$ and $R^2$ are as defined in any one of paragraphs (31) to (37) above; $R^3$ is as defined in any one of paragraphs (38) to (40) above; $R^4$ is as defined in any one of paragraphs (67) to (68) above; and each $R^5$ is independently as defined in any one of paragraphs (70) to (71) above. In a further group of compounds, the compounds have the structural Formulae Formulae IE, IF, IG or IH shown above, wherein Y is as defined in paragraph (22) above; $R^1$ and $R^2$ are as defined in paragraph (37) above; $R^3$ is as defined in paragraph (39) above; $R^4$ is as defined in paragraph (68) above; and each $R^5$ is as defined in paragraph (71) above.

In a further group of compounds, the compounds have the structural Formulae IJ, IK, IL or IM shown above, wherein Y is as defined in any one of paragraphs (19) to (22) above; $R^4$ is as defined in any one of paragraphs (67) to (68) above; each $R^5$ is independently as defined in any one of paragraphs (70) to (71) above; each $R^{17}$ is independently selected from fluoro, methyl, methoxy, and $C_{1-2}$haloalkyl; $R^{20}$ and $R^{21}$ are independently selected from hydrogen, fluoro, methyl, ethyl, methoxy, $C_{1-2}$haloalkyl, and $C_{1-2}$haloalkoxy; and m is 0 to 4. In a further group of compounds, the compounds have the structural Formulae IJ, IK, IL or IM shown above, wherein Y is as defined in paragraph (22) above; $R^4$ is as defined in paragraph (68) above; each $R^5$ is as defined in paragraph (71) above; each $R^{17}$ is independently selected from fluoro, methyl, methoxy, and $C_{1-2}$haloalkyl; $R^{20}$ and $R^{21}$ are independently selected from hydrogen, fluoro, methyl, ethyl, methoxy, and $C_{1-2}$haloalkyl (such as trifluoromethyl); and m is 0 to 3.

Particular compounds of the present invention include any one of the following:

(S)—N-(1-((4-(2,3-dimethylpyridin-4-yl)phenyl)amino)-1-oxo-3,3-diphenylpropan-2-yl)-1-methyl-1H-pyrazole-5-carboxamide (Example 1);

(S)—N-(1-((4-(3-chloropyridin-4-yl)phenyl)amino)-1-oxo-3,3-diphenylpropan-2-yl)-1-methyl-1H-pyrazole-5-carboxamide (Example 2);

(S)—N-(1-((4-(3-methoxypyridin-4-yl)phenyl)amino)-1-oxo-3,3-diphenylpropan-2-yl)-1-methyl-1H-pyrazole-5-carboxamide (Example 3);

(S)-1-methyl-N-(1-((4-(3-methylpyridin-4-yl)phenyl)amino)-1-oxo-3,3-diphenylpropan-2-yl)-1H-pyrazole-5-carboxamide (Example 4);

(S)-1-methyl-N-(1-oxo-3,3-diphenyl-1-((4-(3-(trifluoromethyl)pyridin-4-yl)phenyl)amino)propan-2-yl)-1H-pyrazole-5-carboxamide (Example 5);

(S)—N-(1-((4-(3,5-dimethylpyridin-4-yl)phenyl)amino)-1-oxo-3,3-diphenylpropan-2-yl)-1-methyl-1H-pyrazole-5-carboxamide (Example 6);

(S)-1-methyl-N-(1-((4-(3-(methylamino)pyridin-4-yl)phenyl)amino)-1-oxo-3,3-diphenylpropan-2-yl)-1H-pyrazole-5-carboxamide (Example 7);

(S)—N-(1-((4-(3-(dimethylamino)pyridin-4-yl)phenyl)amino)-1-oxo-3,3-diphenylpropan-2-yl)-1-methyl-1H-pyrazole-5-carboxamide (Example 8);

(S)—N-(1-((4-(3,5-dimethoxypyridin-4-yl)phenyl)amino)-1-oxo-3,3-diphenylpropan-2-yl)-1-methyl-1H-pyrazole-5-carboxamide (Example 9);

(S)—N-(1-((4-(3-fluoro-5-methoxypyridin-4-yl)phenyl)amino)-1-oxo-3,3-diphenylpropan-2-yl)-1-methyl-1H-pyrazole-5-carboxamide (Example 10);

(S)-1-methyl-N-(1-((4-(2-methyl-6-oxo-1,6-dihydropyridin-3-yl)phenyl)amino)-1-oxo-3,3-diphenylpropan-2-yl)-1H-pyrazole-5-carboxamide (Example 11);

(S)—N-(1-((4-(1,4-dimethyl-6-oxo-1,6-dihydropyridin-3-yl)phenyl)amino)-1-oxo-3,3-diphenylpropan-2-yl)-1-methyl-1H-pyrazole-5-carboxamide (Example 12);

(S)—N-(1-((4-(1,2-dimethyl-6-oxo-1,6-dihydropyridin-3-yl)phenyl)amino)-1-oxo-3,3-diphenylpropan-2-yl)-1-methyl-1H-pyrazole-5-carboxamide (Example 13);

(S)—N-(1-((4-(3,5-dimethylpyridin-4-yl)-3-fluorophenyl)amino)-1-oxo-3,3-diphenylpropan-2-yl)-1-methyl-1H-pyrazole-5-carboxamide (Example 14);

(S)—N-(1-((3-fluoro-4-(3-methylpyridin-4-yl)phenyl)amino)-1-oxo-3,3-diphenylpropan-2-yl)-1-methyl-1H-pyrazole-5-carboxamide (Example 15);

(S)—N-(1-((4-(1,2-dimethyl-6-oxo-1,6-dihydropyridin-3-yl)-3-fluorophenyl)amino)-1-oxo-3,3-diphenylpropan-2-yl)-1-methyl-1H-pyrazole-5-carboxamide (Example 16);

(S)—N-(1-((4-(1,4-dimethyl-6-oxo-1,6-dihydropyridin-3-yl)-3-fluorophenyl)amino)-1-oxo-3,3-diphenylpropan-2-yl)-1-methyl-1H-pyrazole-5-carboxamide (Example 17);

N-((2S)-1-((3-fluoro-4-(3-fluoro-5-methoxypyridin-4-yl)phenyl)amino)-1-oxo-3,3-diphenylpropan-2-yl)-1-methyl-1H-pyrazole-5-carboxamide (Example 18);

(S)—N-(1,1-bis(4-fluorophenyl)-3-((4-(3-methoxypyridin-4-yl)phenyl)amino)-3-oxopropan-2-yl)-1-methyl-1H-pyrazole-5-carboxamide (Example 19);

(S)—N-(1-((4-(3-methoxypyridin-4-yl)-3-methylphenyl)amino)-1-oxo-3,3-diphenylpropan-2-yl)-1-methyl-1H-pyrazole-5-carboxamide (Example 20);

(S)—N-(1-((4-(1H-pyrrolo[2,3-b]pyridin-4-yl)phenyl)amino)-1-oxo-3,3-diphenylpropan-2-yl)-1-methyl-1H-pyrazole-5-carboxamide (Example 21);

(S)—N-(1-((4-(2,3-dihydro-1H-pyrrolo[2,3-b]pyridin-4-yl)phenyl)amino)-1-oxo-3,3-diphenylpropan-2-yl)-1-methyl-1H-pyrazole-5-carboxamide (Example 22);

(S)—N-(1-((2-fluoro-4-(3-methoxypyridin-4-yl)phenyl)amino)-1-oxo-3,3-diphenylpropan-2-yl)-1-methyl-1H-pyrazole-5-carboxamide (Example 23);

(S)—N-(1-((3-fluoro-4-(3-methoxypyridin-4-yl)phenyl)amino)-1-oxo-3,3-diphenylpropan-2-yl)-1-methyl-1H-pyrazole-5-carboxamide (Example 24);

(S)-3-methoxy-4-(4-(2-(1-methyl-1H-pyrazole-5-carboxamido)-3,3-diphenylpropanamido)phenyl)pyridine 1-oxide (Example 25);

(S)-3,5-dimethyl-4-(4-(2-(1-methyl-1H-pyrazole-5-carboxamido)-3,3-diphenylpropanamido)phenyl)pyridine 1-oxide (Example 26);

(S)-3,5-dimethoxy-4-(4-(2-(1-methyl-1H-pyrazole-5-carboxamido)-3,3-diphenylpropanamido)phenyl)pyridine 1-oxide (Example 27);

(S)-3-fluoro-5-methoxy-4-(4-(2-(1-methyl-1H-pyrazole-5-carboxamido)-3,3-diphenylpropanamido)phenyl)pyridine 1-oxide (Example 28);

(S)—N-(1-((4-(1,2-dimethyl-6-oxo-1,6-dihydropyridin-3-yl)-3,5-difluorophenyl)amino)-1-oxo-3,3-diphenylpropan-2-yl)-1-methyl-1H-pyrazole-5-carboxamide (Example 29);

(S)—N-(1-((3,5-difluoro-4-(3-methoxypyridin-4-yl)phenyl)amino)-1-oxo-3,3-diphenylpropan-2-yl)-1-methyl-1H-pyrazole-5-carboxamide (Example 30);

(S)—N-(1-((4-(1-benzyl-3,5-dimethyl-1H-pyrazol-4-yl)phenyl)amino)-1-oxo-3,3-diphenylpropan-2-yl)-1-methyl-1H-pyrazole-5-carboxamide (Example 31);

(S)—N-(1-((4-(3,5-dimethyl-1H-pyrazol-4-yl)phenyl)amino)-1-oxo-3,3-diphenylpropan-2-yl)-1-methyl-1H-pyrazole-5-carboxamide (Example 32);

N—((S)-2-((4-(1,2-dimethyl-6-oxo-1,6-dihydropyridin-3-yl)phenyl)amino)-1-((1r,4S)-4-methylcyclohexyl)-2-oxoethyl)-1-methyl-1H-pyrazole-5-carboxamide (Example 33);

(S)-1-ethyl-N-(1-((3-fluoro-4-(6-oxo-1,6-dihydropyridazin-3-yl)phenyl)amino)-1-oxo-3,3-diphenylpropan-2-yl)-1H-pyrazole-5-carboxamide (Example 34);

(S)—N-(1-((3-fluoro-4-(2-oxo-1,2-dihydropyridin-4-yl)phenyl)amino)-1-oxo-3,3-diphenylpropan-2-yl)-1-methyl-1H-pyrazole-5-carboxamide (Example 35);

(S)—N-(1-((4-(3-fluoropyridin-4-yl)phenyl)amino)-1-oxo-3,3-diphenylpropan-2-yl)-1-methyl-1H-pyrazole-5-carboxamide (Example 36);

(S)—N-(1-((4-(2,5-dimethylpyrimidin-4-yl)phenyl)amino)-1-oxo-3,3-diphenylpropan-2-yl)-1-methyl-1H-pyrazole-5-carboxamide (Example 37);

(S)—N-(1-((4-(2,5-dimethylpyridin-4-yl)phenyl)amino)-1-oxo-3,3-diphenylpropan-2-yl)-1-methyl-1H-pyrazole-5-carboxamide (Example 38);

(S)—N-(1-((4-(imidazo[1,2-a]pyridin-3-yl)phenyl)amino)-1-oxo-3,3-diphenylpropan-2-yl)-1-methyl-1H-pyrazole-5-carboxamide (Example 39);

(S)—N-(1-((4-(6,7-dihydro-5H-pyrrolo[2,3-d]pyrimidin-4-yl)phenyl)amino)-1-oxo-3,3-diphenylpropan-2-yl)-1-methyl-1H-pyrazole-5-carboxamide (Example 40);

(S)—N-(1-((4-(imidazo[1,2-a]pyrimidin-3-yl)phenyl)amino)-1-oxo-3,3-diphenylpropan-2-yl)-1-methyl-1H-pyrazole-5-carboxamide (Example 41);

(S)—N-(1-((4-(3-(hydroxymethyl)pyridin-4-yl)phenyl)amino)-1-oxo-3,3-diphenylpropan-2-yl)-1-methyl-1H-pyrazole-5-carboxamide (Example 42);

(S)—N-(1-((4-(3-cyanopyridin-4-yl)phenyl)amino)-1-oxo-3,3-diphenylpropan-2-yl)-1-methyl-1H-pyrazole-5-carboxamide (Example 43);

(S)—N-(1-((4-(6,7-dihydro-5H-cyclopenta[b]pyridin-4-yl)phenyl)amino)-1-oxo-3,3-diphenylpropan-2-yl)-1-methyl-1H-pyrazole-5-carboxamide (Example 44);

(S)-1-methyl-N-(1-((3-methyl-4-(pyridin-4-yl)phenyl)amino)-1-oxo-3,3-diphenylpropan-2-yl)-1H-pyrazole-5-carboxamide (Example 45);

(S)-1-(difluoromethyl)-N-(1-((4-(3-methoxypyridin-4-yl)phenyl)amino)-1-oxo-3,3-diphenylpropan-2-yl)-1H-pyrazole-5-carboxamide (Example 46);

(S)—N-(1-((3-methoxy-4-(3-methoxypyridin-4-yl)phenyl)amino)-1-oxo-3,3-diphenylpropan-2-yl)-1-methyl-1H-pyrazole-5-carboxamide (Example 47);

(S)—N-(1-((3-fluoro-4-(1-methyl-6-oxo-1,6-dihydropyridazin-3-yl)phenyl)amino)-1-oxo-3,3-diphenylpropan-2-yl)-1-methyl-1H-pyrazole-5-carboxamide (Example 48);

(S)-1-methyl-N-(1-oxo-1-((4-(6-oxo-1,6-dihydropyridin-3-yl)phenyl)amino)-3,3-diphenylpropan-2-yl)-1H-pyrazole-5-carboxamide (Example 49);

(S)-1-methyl-N-(1-((4-(4-methyl-6-oxo-1,6-dihydropyridin-3-yl)phenyl)amino)-1-oxo-3,3-diphenylpropan-2-yl)-1H-pyrazole-5-carboxamide (Example 50);

(S)-1-methyl-N-(1-((4-(1-methyl-6-oxo-1,6-dihydropyridin-3-yl)phenyl)amino)-1-oxo-3,3-diphenylpropan-2-yl)-1H-pyrazole-5-carboxamide (Example 51);

(S)-1-methyl-N-(1-oxo-1-((4-(7-oxo-6,7-dihydro-1H-pyrrolo[2,3-c]pyridin-4-yl)phenyl)amino)-3,3-diphenylpropan-2-yl)-1H-pyrazole-5-carboxamide (Example 52);

(S)—N-(1-((4-(3-(hydroxymethyl)pyridin-4-yl)-3-methoxyphenyl)amino)-1-oxo-3,3-diphenylpropan-2-yl)-1-methyl-1H-pyrazole-5-carboxamide (Example 53);

(S)—N-(1-((4-(1,2-dimethyl-6-oxo-1,6-dihydropyridin-3-yl)-3-(trifluoromethyl)phenyl)amino)-1-oxo-3,3-diphenylpropan-2-yl)-1-methyl-1H-pyrazole-5-carboxamide (Example 54);

(S)—N-(1-((3-chloro-4-(3,5-dimethylpyridin-4-yl)phenyl)amino)-1-oxo-3,3-diphenylpropan-2-yl)-1-methyl-1H-pyrazole-5-carboxamide (Example 55);

(S)—N-(1-((4-(2,5-dimethylpyridin-4-yl)-3-fluorophenyl)amino)-1-oxo-3,3-diphenylpropan-2-yl)-1-methyl-1H-pyrazole-5-carboxamide (Example 56);
(S)—N-(1-((4-(2,3-dimethylpyridin-4-yl)-3-fluorophenyl)amino)-1-oxo-3,3-diphenylpropan-2-yl)-1-methyl-1H-pyrazole-5-carboxamide (Example 57);
(S)—N-(1-((3-fluoro-4-(6-oxo-1,6-dihydropyridazin-3-yl)phenyl)amino)-1-oxo-3,3-diphenylpropan-2-yl)-1-methyl-1H-pyrazole-5-carboxamide (Example 58);
(S)-1-ethyl-N-(1-((3-fluoro-4-(3-methyl-1H-pyrazol-4-yl)phenyl)amino)-1-oxo-3,3-diphenylpropan-2-yl)-1H-pyrazole-5-carboxamide (Example 59);
(S)—N-(1-((4-(3,5-dimethylisoxazol-4-yl)-3-fluorophenyl)amino)-1-oxo-3,3-diphenylpropan-2-yl)-1-methyl-1H-pyrazole-5-carboxamide (Example 60);
(S)—N-(1-((4-(3,5-dimethylisoxazol-4-yl)-3-fluorophenyl)amino)-1-oxo-3,3-diphenylpropan-2-yl)-1-ethyl-1H-pyrazole-5-carboxamide (Example 61);
(S)—N-(1-((3-fluoro-4-(1H-pyrazol-4-yl)phenyl)amino)-1-oxo-3,3-diphenylpropan-2-yl)-1-methyl-1H-pyrazole-5-carboxamide (Example 62);
(S)—N-(1-((3-fluoro-4-(1-methyl-2-oxo-1,2-dihydropyrimidin-5-yl)phenyl)amino)-1-oxo-3,3-diphenylpropan-2-yl)-1-methyl-1H-pyrazole-5-carboxamide (Example 63);
(S)—N-(1-((3-fluoro-4-(2-oxo-1,2-dihydropyrimidin-5-yl)phenyl)amino)-1-oxo-3,3-diphenylpropan-2-yl)-1-methyl-1H-pyrazole-5-carboxamide (Example 64);
(S)—N-(1-((3-fluoro-4-(3-methyl-1H-pyrazol-4-yl)phenyl)amino)-1-oxo-3,3-diphenylpropan-2-yl)-1-methyl-1H-pyrazole-5-carboxamide (Example 65);
(S)—N-(1-((3-fluoro-4-(5-oxo-5,6-dihydro-1,6-naphthyridin-8-yl)phenyl)amino)-1-oxo-3,3-diphenylpropan-2-yl)-1-methyl-1H-pyrazole-5-carboxamide (Example 66);
(S)-1-ethyl-N-(1-((3-fluoro-4-(6-oxo-1,6-dihydropyridazin-4-yl)phenyl)amino)-1-oxo-3,3-diphenylpropan-2-yl)-1H-pyrazole-5-carboxamide (Example 67);
(S)—N-(1-((3-fluoro-4-(7-oxo-6,7-dihydro-1H-pyrrolo[2,3-c]pyridin-4-yl)phenyl)amino)-1-oxo-3,3-diphenylpropan-2-yl)-1-methyl-1H-pyrazole-5-carboxamide (Example 68);
(S)—N-(1-((3-fluoro-4-(4-oxo-4,5-dihydro-3H-imidazo[4,5-c]pyridin-7-yl)phenyl)amino)-1-oxo-3,3-diphenylpropan-2-yl)-1-methyl-1H-pyrazole-5-carboxamide (Example 69);
(S)—N-(1-((3-fluoro-4-(6-oxo-1,6-dihydropyridazin-4-yl)phenyl)amino)-1-oxo-3,3-diphenylpropan-2-yl)-1-methyl-1H-pyrazole-5-carboxamide (Example 70);
(S)—N-(1-((3-fluoro-4-(1-methyl-6-oxo-1,6-dihydropyridin-2-yl)phenyl)amino)-1-oxo-3,3-diphenylpropan-2-yl)-1-methyl-1H-pyrazole-5-carboxamide (Example 71);
(S)—N-(1-((1',2'-dimethyl-6'-oxo-1',6'-dihydro-[3,3'-bipyridin]-6-yl)amino)-1-oxo-3,3-diphenylpropan-2-yl)-1-methyl-1H-pyrazole-5-carboxamide (Example 72);
(S)—N-(1-((3',5'-dimethyl-[3,4'-bipyridin]-6-yl)amino)-1-oxo-3,3-diphenylpropan-2-yl)-1-methyl-1H-pyrazole-5-carboxamide (Example 73);
(S)-1-methyl-N-(1-((4-(5-methyl-1H-pyrazol-4-yl)phenyl)amino)-1-oxo-3,3-diphenylpropan-2-yl)-1H-pyrazole-5-carboxamide (Example 74);
(S)—N-(1-((3-fluoro-4-(6-methyl-7-oxo-6,7-dihydro-1H-pyrazolo[3,4-c]pyridin-4-yl)phenyl)amino)-1-oxo-3,3-diphenylpropan-2-yl)-1-methyl-1H-pyrazole-5-carboxamide (Example 75);
(S)—N-(1-((4-(7-methoxy-1H-pyrrolo[2,3-c]pyridin-4-yl)phenyl)amino)-1-oxo-3,3-diphenylpropan-2-yl)-1-methyl-1H-pyrazole-5-carboxamide (Example 76);
(S)—N-(1-((3-fluoro-4-(6-oxo-1,6-dihydropyridin-2-yl)phenyl)amino)-1-oxo-3,3-diphenylpropan-2-yl)-1-methyl-1H-pyrazole-5-carboxamide (Example 77);
(S)-1-methyl-N-(1-oxo-1-((4-(3-(2-oxo-2-(pyrrolidin-1-yl)ethyl)pyridin-4-yl)phenyl)amino)-3,3-diphenylpropan-2-yl)-1H-pyrazole-5-carboxamide (Example 78);
(S)-4-(4-(2-(1-methyl-1H-pyrazole-5-carboxamido)-3,3-diphenylpropanamido)phenyl)-3-(2-oxo-2-(pyrrolidin-1-yl)ethyl)pyridine 1-oxide (Example 79);
(S)—N-(1-((3-fluoro-4-(6-oxo-1,6-dihydropyrimidin-4-yl)phenyl)amino)-1-oxo-3,3-diphenylpropan-2-yl)-1-methyl-1H-pyrazole-5-carboxamide (Example 80);
(S)—N-(1-((4-(3,6-dihydro-2H-pyran-4-yl)phenyl)amino)-1-oxo-3,3-diphenylpropan-2-yl)-1-methyl-1H-pyrazole-5-carboxamide (Example 81);
N-(1-(9H-fluoren-9-yl)-2-((4-(3-methoxypyridin-4-yl)phenyl)amino)-2-oxoethyl)-1-methyl-1H-pyrazole-5-carboxamide (Example 82);
N—((S)-2-((4-(1,2-dimethyl-6-oxo-1,6-dihydropyridin-3-yl)-3-fluorophenyl)amino)-1-((1r,4S)-4-methylcyclohexyl)-2-oxoethyl)-1-methyl-1H-pyrazole-5-carboxamide (Example 83);
N—((S)-2-((4-(3,5-dimethyl-1H-pyrazol-4-yl)phenyl)amino)-1-((1r,4S)-4-methylcyclohexyl)-2-oxoethyl)-1-methyl-1H-pyrazole-5-carboxamide (Example 84);
1-methyl-N—((S)-1-((1 r,4S)-4-methylcyclohexyl)-2-oxo-2-((4-(7-oxo-6,7-dihydro-1H-pyrrolo[2,3-c]pyridin-4-yl)phenyl)amino)ethyl)-1H-pyrazole-5-carboxamide (Example 85);
1-methyl-N—((S)-1-((1 r,4S)-4-methylcyclohexyl)-2-oxo-2-((4-(3-(2-oxo-2-(pyrrolidin-1-yl)ethyl)pyridin-4-yl)phenyl)amino)ethyl)-1H-pyrazole-5-carboxamide (Example 86);
1-methyl-N—((S)-1-((1 r,4S)-4-methylcyclohexyl)-2-oxo-2-((4-(2-oxo-1,2-dihydropyridin-4-yl)phenyl)amino)ethyl)-1H-pyrazole-5-carboxamide (Example 87);
N—((S)-2-((4-(imidazo[1,2-a]pyridin-5-yl)phenyl)amino)-1-((1r,4S)-4-methylcyclohexyl)-2-oxoethyl)-1-methyl-1H-pyrazole-5-carboxamide (Example 88);
N—((S)-2-((1',2'-dimethyl-6'-oxo-1',6'-dihydro-[3,3'-bipyridin]-6-yl)amino)-1-((1r,4S)-4-methylcyclohexyl)-2-oxoethyl)-1-methyl-1H-pyrazole-5-carboxamide (Example 89);
N—((S)-2-((3',5'-dimethyl-[3,4'-bipyridin]-6-yl)amino)-1-((1 r,4S)-4-methylcyclohexyl)-2-oxoethyl)-1-methyl-1H-pyrazole-5-carboxamide (Example 90);
N—((S)-2-((1',2'-dimethyl-6'-oxo-1',6'-dihydro-[3,3'-bipyridin]-6-yl)amino)-1-((1r,4S)-4-methylcyclohexyl)-2-oxoethyl)-1-ethyl-1H-pyrazole-5-carboxamide (Example 91);
N—((S)-2-((3',5'-dimethyl-[3,4'-bipyridin]-6-yl)amino)-1-((1r,4S)-4-methylcyclohexyl)-2-oxoethyl)-1-ethyl-1H-pyrazole-5-carboxamide (Example 92);
1-methyl-N—((S)-1-((1 r,4S)-4-methylcyclohexyl)-2-oxo-2-((4-(tetrahydro-2H-pyran-4-yl)phenyl)amino)ethyl)-1H-pyrazole-5-carboxamide (Example 93);
N—((S)-2-((4-(4-hydroxytetrahydro-2H-pyran-4-yl)phenyl)amino)-1-((1r,4S)-4-methylcyclohexyl)-2-oxoethyl)-1-methyl-1H-pyrazole-5-carboxamide (Example 94);
N—((S)-2-((4-(3,6-dihydro-2H-pyran-4-yl)phenyl)amino)-1-((1r,4S)-4-methylcyclohexyl)-2-oxoethyl)-1-methyl-1H-pyrazole-5-carboxamide (Example 95);

N—((S)-2-((4-(3,5-dimethylisoxazol-4-yl)phenyl)amino)-1-((1r,4S)-4-methylcyclohexyl)-2-oxoethyl)-1-methyl-1H-pyrazole-5-carboxamide (Example 96);

N—((S)-2-((5-(3,5-dimethylisoxazol-4-yl)pyridin-2-yl)amino)-1-((1r,4S)-4-methylcyclohexyl)-2-oxoethyl)-1-methyl-1H-pyrazole-5-carboxamide (Example 97);

N-(1-(4,4-difluorocyclohexyl)-2-((4-(3,5-dimethylpyridin-4-yl)phenyl)amino)-2-oxoethyl)-1-methyl-1H-pyrazole-5-carboxamide (Example 98);

N—((S)-2-((5-(3,5-dimethyl-1H-pyrazol-4-yl)pyridin-2-yl)amino)-1-((1r,4S)-4-methylcyclohexyl)-2-oxoethyl)-1-methyl-1H-pyrazole-5-carboxamide (Example 99);

N-(1-(4,4-dimethylcyclohexyl)-2-((4-(3,5-dimethylpyridin-4-yl)phenyl)amino)-2-oxoethyl)-1-methyl-1H-pyrazole-5-carboxamide (Example 100);

N-(1-(4,4-difluorocyclohexyl)-2-((4-(1,2-dimethyl-6-oxo-1,6-dihydropyridin-3-yl)phenyl)amino)-2-oxoethyl)-1-methyl-1H-pyrazole-5-carboxamide (Example 101);

N-(2-((4-(1,2-dimethyl-6-oxo-1,6-dihydropyridin-3-yl)phenyl)amino)-1-(4,4-dimethylcyclohexyl)-2-oxoethyl)-1-methyl-1H-pyrazole-5-carboxamide (Example 102);

N-(1-cyclooctyl-2-((4-(3,5-dimethylpyridin-4-yl)phenyl)amino)-2-oxoethyl)-1-methyl-1H-pyrazole-5-carboxamide (Example 103);

N-(1-cyclooctyl-2-((4-(3,5-dimethyl-1H-pyrazol-4-yl)phenyl)amino)-2-oxoethyl)-1-methyl-1H-pyrazole-5-carboxamide (Example 104);

N-(1-Cyclooctyl-2-((5-(3,5-dimethylisoxazol-4-yl)pyridin-2-yl)amino)-2-oxoethyl)-1-methyl-1H-pyrazole-5-carboxamide (Example 105);

N—((S)-2-((5-(1,4-dimethyl-1H-pyrazol-5-yl)pyridin-2-yl)amino)-1-((1r,4S)-4-methylcyclohexyl)-2-oxoethyl)-1-methyl-1H-pyrazole-5-carboxamide (Example 106);

N-(1-cyclooctyl-2-((4-(1,2-dimethyl-6-oxo-1,6-dihydropyridin-3-yl)phenyl)amino)-2-oxoethyl)-1-methyl-1H-pyrazole-5-carboxamide (Example 107);

(S)—N-(1-Cyclohexyl-2-((5-(3,5-dimethylisoxazol-4-yl)pyridin-2-yl)amino)-2-oxoethyl)-1-isopropyl-1H-pyrazole-5-carboxamide (Example 108);

N—((S)-2-((5-(3,5-Dimethylisoxazol-4-yl)pyridin-2-yl)amino)-1-((1r,4S)-4-methylcyclohexyl)-2-oxoethyl)-1-ethyl-1H-pyrazole-5-carboxamide (Example 109);

N—((S)-2-((5-(3,5-dimethylisoxazol-4-yl)pyridin-2-yl)amino)-1-((1r,4S)-4-methylcyclohexyl)-2-oxoethyl)-1-isopropyl-1H-pyrazole-5-carboxamide (Example 110);

N—((S)-2-((5-(3,5-dimethylisoxazol-4-yl)pyridin-2-yl)amino)-1-((1r,4S)-4-methylcyclohexyl)-2-oxoethyl)-3-ethylisoxazole-4-carboxamide (Example 111);

N—((S)-2-((5-(3,5-dimethylisoxazol-4-yl)pyridin-2-yl)amino)-1-((1r,4S)-4-methylcyclohexyl)-2-oxoethyl)-3-methylisoxazole-4-carboxamide (Example 112);

N-(1-Cyclooctyl-2-((5-(1,4-dimethyl-1H-pyrazol-5-yl)pyridin-2-yl)amino)-2-oxoethyl)-1-methyl-1H-pyrazole-5-carboxamide (Example 113);

(S)—N-(1-Cyclohexyl-2-((5-(3,5-dimethylisoxazol-4-yl)pyridin-2-yl)amino)-2-oxoethyl)-3-ethylisoxazole-4-carboxamide (Example 114);

(S)—N-(1-Cycloheptyl-2-((5-(3,5-dimethylisoxazol-4-yl)pyridin-2-yl)amino)-2-oxoethyl)-1-methyl-1H-pyrazole-5-carboxamide (Example 115);

(S)—N-(1-Cycloheptyl-2-((5-(3,5-dimethylisoxazol-4-yl)pyridin-2-yl)amino)-2-oxoethyl)-3-methylisoxazole-4-carboxamide (Example 116);

(S)—N-(1-Cycloheptyl-2-((5-(3,5-dimethylisoxazol-4-yl)pyridin-2-yl)amino)-2-oxoethyl)-1-methyl-1H-1,2,3-triazole-5-carboxamide (Example 117);

(S)—N-(1-Cyclohexyl-2-((5-(3,5-dimethylisoxazol-4-yl)pyridin-2-yl)amino)-2-oxoethyl)-1-ethyl-1H-pyrazole-5-carboxamide (Example 118);

(S)—N-(1-Cyclohexyl-2-((4-(1,2-dimethyl-6-oxo-1,6-dihydropyridin-3-yl)phenyl)amino)-2-oxoethyl)-1-methyl-1H-pyrazole-5-carboxamide (Example 119);

N—((S)-2-((5-(3,5-Dimethylisoxazol-4-yl)pyridin-2-yl)amino)-1-((1r,4S)-4-methylcyclohexyl)-2-oxoethyl)-4-methyl-1,2,5-oxadiazole-3-carboxamide (Example 120);

(S)—N-(1-Cyclohexyl-2-((5-(3,5-dimethylisoxazol-4-yl)pyridin-2-yl)amino)-2-oxoethyl)-3-methylisoxazole-4-carboxamide (Example 121);

(S)—N-(1-Cycloheptyl-2-((5-(3,5-dimethylisoxazol-4-yl)pyridin-2-yl)amino)-2-oxoethyl)-1-ethyl-1H-pyrazole-5-carboxamide (Example 122);

(S)—N-(1-Cycloheptyl-2-((5-(3,5-dimethylisoxazol-4-yl)pyridin-2-yl)amino)-2-oxoethyl)-1-isopropyl-1H-pyrazole-5-carboxamide (Example 123);

(S)—N-(1-Cycloheptyl-2-((5-(3,5-dimethylisoxazol-4-yl)pyridin-2-yl)amino)-2-oxoethyl)-3-ethylisoxazole-4-carboxamide (Example 124);

N—((S)-2-((5-(1,4-dimethyl-1H-1,2,3-triazol-5-yl)pyridin-2-yl)amino)-1-((1r,4S)-4-methylcyclohexyl)-2-oxoethyl)-1-methyl-1H-pyrazole-5-carboxamide (Example 125);

N—((S)-2-((5-(1,4-Dimethyl-1H-pyrazol-5-yl)pyridin-2-yl)amino)-1-((1r,4S)-4-methylcyclohexyl)-2-oxoethyl)-1-ethyl-1H-pyrazole-5-carboxamide (Example 126);

N—((S)-2-((5-(1,4-Dimethyl-1H-pyrazol-5-yl)pyridin-2-yl)amino)-1-((1r,4S)-4-methylcyclohexyl)-2-oxoethyl)-3-ethylisoxazole-4-carboxamide (Example 127);

(S)—N-(1-Cycloheptyl-2-((5-(3,5-dimethylisoxazol-4-yl)pyridin-2-yl)amino)-2-oxoethyl)-4-methyl-1,2,5-oxadiazole-3-carboxamide (Example 128);

(S)—N-(1-Cyclohexyl-2-((5-(3,5-dimethylisoxazol-4-yl)pyridin-2-yl)amino)-2-oxoethyl)-1-methyl-1H-pyrazole-5-carboxamide (Example 129);

(S)—N-(1-Cyclohexyl-2-((5-(3,5-dimethylisoxazol-4-yl)pyridin-2-yl)amino)-2-oxoethyl)-1,2,3,4-tetrahydropyrrolo[1,2-a]pyrazine-6-carboxamide (Example 130);

N—((S)-2-((5-(1,4-Dimethyl-1H-pyrazol-5-yl)pyridin-2-yl)amino)-1-((1r,4S)-4-methylcyclohexyl)-2-oxoethyl)-3-methylisoxazole-4-carboxamide (Example 131);

(S)—N-(1-Cycloheptyl-2-((5-(1,4-dimethyl-1H-pyrazol-5-yl)pyridin-2-yl)amino)-2-oxoethyl)-1-methyl-1H-pyrazole-5-carboxamide (Example 132);

(S)—N-(1-Cycloheptyl-2-((5-(1,4-dimethyl-1H-pyrazol-5-yl)pyridin-2-yl)amino)-2-oxoethyl)-1-methyl-1H-1,2,3-triazole-5-carboxamide (Example 133);

(S)—N-(1-Cycloheptyl-2-((5-(1,4-dimethyl-1H-pyrazol-5-yl)pyridin-2-yl)amino)-2-oxoethyl)-4-methyl-1,2,5-oxadiazole-3-carboxamide (Example 134);

N—((S)-2-((2-(3,5-dimethylisoxazol-4-yl)pyrimidin-5-yl)amino)-1-((1r,4S)-4-methylcyclohexyl)-2-oxoethyl)-1-methyl-1H-pyrazole-5-carboxamide (Example 135);

(S)—N-(1-Cycloheptyl-2-((5-(1,4-dimethyl-1H-pyrazol-5-yl)pyridin-2-yl)amino)-2-oxoethyl)-3-methylisoxazole-4-carboxamide (Example 136);

(S)—N-(1-Cycloheptyl-2-((5-(1,4-dimethyl-1H-pyrazol-5-yl)pyridin-2-yl)amino)-2-oxoethyl)-3-(methoxymethyl)isoxazole-4-carboxamide (Example 137);

N—((S)-2-((6-(3,5-dimethylisoxazol-4-yl)pyridin-3-yl)amino)-1-((1r,4S)-4-methylcyclohexyl)-2-oxoethyl)-1-methyl-1H-pyrazole-5-carboxamide (Example 138);

6-((S)-2-(1-Ethyl-1H-pyrazole-5-carboxamido)-2-((1r,4S)-4-methylcyclohexyl)acetamido)-3',5'-dimethyl-[3,4'-bipyridine] 1'-oxide (Example 139);

3-ethyl-N—((S)-1-((1r,4S)-4-methylcyclohexyl)-2-((5-(5-methylpyrimidin-4-yl)pyridin-2-yl)amino)-2-oxoethyl) isoxazole-4-carboxamide (Example 140);

(S)—N-(1-cycloheptyl-2-((5-(1,4-dimethyl-1H-pyrazol-5-yl)pyridin-2-yl)amino)-2-oxoethyl)-1-ethyl-1H-1,2,3-triazole-5-carboxamide (Example 141);

N—((S)-2-((5-(3-(methoxymethyl)-5-methylisoxazol-4-yl) pyridin-2-yl)amino)-1-((1r,4S)-4-methylcyclohexyl)-2-oxoethyl)-1-methyl-1H-pyrazole-5-carboxamide (Example 142);

(S)—N-(1-cycloheptyl-2-((5-(3,5-dimethyl-4H-1,2,4-triazol-4-yl)pyridin-2-yl)amino)-2-oxoethyl)-1-methyl-1H-pyrazole-5-carboxamide (Example 143);

(S)—N-(1-(4,4-difluorocyclohexyl)-2-((5-(1,4-dimethyl-1H-pyrazol-5-yl)pyridin-2-yl)amino)-2-oxoethyl)-3-ethylisoxazole-4-carboxamide (Example 144);

N—((S)-2-((6-(1,4-dimethyl-1H-pyrazol-5-yl)pyridin-3-yl) amino)-1-((1r,4S)-4-methylcyclohexyl)-2-oxoethyl)-1-methyl-1H-pyrazole-5-carboxamide (Example 145);

1-methyl-N—((S)-2-((4-methyl-5-(1-methyl-1H-pyrazol-5-yl)pyridin-2-yl)amino)-1-((1r,4S)-4-methylcyclohexyl)-2-oxoethyl)-1H-pyrazole-5-carboxamide (Example 146);

N—((S)-2-((2-(1,4-dimethyl-1H-pyrazol-5-yl)pyrimidin-5-yl)amino)-1-((1r,4S)-4-methylcyclohexyl)-2-oxoethyl)-1-ethyl-1H-pyrazole-5-carboxamide (Example 147);

(S)—N-(1-cycloheptyl-2-((5-(1,4-dimethyl-1H-1,2,3-triazol-5-yl)pyridin-2-yl)amino)-2-oxoethyl)-1-methyl-1H-pyrazole-5-carboxamide (Example 148);

(S)—N-(1-cycloheptyl-2-((5-(1,4-dimethyl-1H-1,2,3-triazol-5-yl)pyridin-2-yl)amino)-2-oxoethyl)-1-ethyl-1H-pyrazole-5-carboxamide (Example 149);

(S)—N-(1-cycloheptyl-2-((5-(5-(methoxymethyl)-3-methylisoxazol-4-yl)pyridin-2-yl)amino)-2-oxoethyl)-1-methyl-1H-pyrazole-5-carboxamide (Example 150);

N—((S)-2-((3'-methoxy-2'-methyl-[3,4'-bipyridin]-6-yl) amino)-1-((1r,4S)-4-methylcyclohexyl)-2-oxoethyl)-1-methyl-1H-pyrazole-5-carboxamide (Example 151);

N—((S)-2-((2',3'-dimethyl-[3,4'-bipyridin]-6-yl)amino)-1-((1r,4S)-4-methylcyclohexyl)-2-oxoethyl)-1-methyl-1H-pyrazole-5-carboxamide (Example 152);

N—((S)-2-((2',5'-dimethyl-[3,4'-bipyridin]-6-yl)amino)-1-((1r,4S)-4-methylcyclohexyl)-2-oxoethyl)-1-methyl-1H-pyrazole-5-carboxamide (Example 153);

N—((S)-2-((6-(1,4-dimethyl-1H-pyrazol-5-yl)pyridin-3-yl) amino)-1-((1r,4S)-4-methylcyclohexyl)-2-oxoethyl)-1-ethyl-1H-pyrazole-5-carboxamide (Example 154);

N—((S)-2-((6-(1,4-dimethyl-1H-pyrazol-5-yl)pyridin-3-yl) amino)-1-((1r,4S)-4-methylcyclohexyl)-2-oxoethyl)-3-ethylisoxazole-4-carboxamide (Example 155);

N—((S)-2-((2-(1,4-dimethyl-1H-pyrazol-5-yl)pyrimidin-5-yl)amino)-1-((1r,4S)-4-methylcyclohexyl)-2-oxoethyl)-1-methyl-1H-pyrazole-5-carboxamide (Example 156);

(S)—N-(1-cycloheptyl-2-((5-(1-ethyl-4-methyl-1H-1,2,3-triazol-5-yl)pyridin-2-yl)amino)-2-oxoethyl)-1-methyl-1H-pyrazole-5-carboxamide (Example 157);

(S)—N-(1-cycloheptyl-2-((5-(3,5-dimethylisoxazol-4-yl) pyrazin-2-yl)amino)-2-oxoethyl)-1-methyl-1H-pyrazole-5-carboxamide (Example 158);

N—((S)-2-((5-(1,4-dimethyl-1H-1,2,3-triazol-5-yl)pyridin-2-yl)amino)-1-((1r,4S)-4-methylcyclohexyl)-2-oxoethyl)-1-ethyl-1H-pyrazole-5-carboxamide (Example 159);

N—((S)-2-((5-(1,4-dimethyl-1H-1,2,3-triazol-5-yl)pyridin-2-yl)amino)-1-((1r,4S)-4-methylcyclohexyl)-2-oxoethyl)-3-methylisoxazole-4-carboxamide (Example 160);

(S)—N-(1-cycloheptyl-2-((5-(1-cyclopropyl-4-methyl-1H-1,2,3-triazol-5-yl)pyridin-2-yl)amino)-2-oxoethyl)-1-methyl-1H-pyrazole-5-carboxamide (Example 161);

(S)—N-(1-cycloheptyl-2-((5-(3,5-dimethylisoxazol-4-yl)-3-fluoropyridin-2-yl)amino)-2-oxoethyl)-1-methyl-1H-pyrazole-5-carboxamide (Example 162);

(S)—N-(1-cycloheptyl-2-((5-(3,5-dimethylisoxazol-4-yl)-3-fluoropyridin-2-yl)amino)-2-oxoethyl)-1-ethyl-1H-pyrazole-5-carboxamide (Example 163);

(S)—N-(1-cycloheptyl-2-((5-(3,5-dimethylisoxazol-4-yl)-3-fluoropyridin-2-yl)amino)-2-oxoethyl)-3-ethylisoxazole-4-carboxamide (Example 164);

(S)—N-(1-cycloheptyl-2-((5-(1,4-dimethyl-1H-pyrazol-5-yl)pyrimidin-2-yl)amino)-2-oxoethyl)-1-methyl-1H-pyrazole-5-carboxamide (Example 165);

(S)—N-(1-cycloheptyl-2-((5-(4-hydroxy-1-methyl-1H-pyrazol-5-yl)pyridin-2-yl)amino)-2-oxoethyl)-1-methyl-1H-pyrazole-5-carboxamide (Example 166);

N—((S)-2-((5-(1,4-dimethyl-1H-pyrazol-5-yl)pyridin-2-yl) amino)-1-((1r,4S)-4-methylcyclohexyl)-2-oxoethyl)-1-methyl-1H-1,2,3-triazole-5-carboxamide (Example 167);

N—((S)-2-((5-(1,4-dimethyl-1H-pyrazol-5-yl)pyridin-2-yl) amino)-1-((1r,4S)-4-methylcyclohexyl)-2-oxoethyl)-1-ethyl-1H-1,2,3-triazole-5-carboxamide (Example 168);

(S)—N-(1-cycloheptyl-2-((6-(3,5-dimethylisoxazol-4-yl) pyridin-3-yl)amino)-2-oxoethyl)-1-ethyl-1H-pyrazole-5-carboxamide (Example 169);

(S)—N-(1-cycloheptyl-2-((6-(3,5-dimethylisoxazol-4-yl) pyridin-3-yl)amino)-2-oxoethyl)-3-methylisoxazole-4-carboxamide (Example 170);

(S)—N-(1-cycloheptyl-2-((6-(3,5-dimethylisoxazol-4-yl) pyridin-3-yl)amino)-2-oxoethyl)-3-ethylisoxazole-4-carboxamide (Example 171);

(S)—N-(1-cycloheptyl-2-((6-(3,5-dimethylisoxazol-4-yl) pyridin-3-yl)amino)-2-oxoethyl)-1-methyl-1H-pyrazole-5-carboxamide (Example 172);

(S)—N-(1-cycloheptyl-2-((5-(4-cyclopropyl-1-methyl-1H-1,2,3-triazol-5-yl)pyridin-2-yl)amino)-2-oxoethyl)-1-methyl-1H-pyrazole-5-carboxamide (Example 173);

(S)—N-(2-((5-(4-chloro-1-methyl-1H-pyrazol-5-yl)pyridin-2-yl)amino)-1-cycloheptyl-2-oxoethyl)-1-methyl-1H-pyrazole-5-carboxamide (Example 174);

(S)—N-(2-((5-(4-chloro-1-methyl-1H-pyrazol-5-yl)pyridin-2-yl)amino)-1-cycloheptyl-2-oxoethyl)-3-ethylisoxazole-4-carboxamide (Example 175);

(S)—N-(2-((5-(4-chloro-1-methyl-1H-pyrazol-5-yl)pyridin-2-yl)amino)-1-cycloheptyl-2-oxoethyl)-1-ethyl-1H-pyrazole-5-carboxamide (Example 176);

(S)—N-(1-cyclohexyl-2-((5-(1,4-dimethyl-1H-pyrazol-5-yl)pyridin-2-yl)amino)-2-oxoethyl)-1-methyl-1H-pyrazole-5-carboxamide (Example 177);

(S)—N-(1-cyclohexyl-2-((5-(1,4-dimethyl-1H-pyrazol-5-yl)pyridin-2-yl)amino)-2-oxoethyl)-3-ethylisoxazole-4-carboxamide (Example 178);

N—((S)-2-((6-(1,4-dimethyl-1H-pyrazol-5-yl)-5-fluoropyridin-3-yl)amino)-1-((1r,4S)-4-methylcyclohexyl)-2-oxoethyl)-1-methyl-1H-pyrazole-5-carboxamide (Example 179);

N—((S)-2-((6-(1,4-dimethyl-1H-pyrazol-5-yl)-5-fluoropyridin-3-yl)amino)-1-((1r,4S)-4-methylcyclohexyl)-2-oxoethyl)-3-ethylisoxazole-4-carboxamide (Example 180);

(S)—N-(1-cyclohexyl-2-((5-(1,4-dimethyl-1H-pyrazol-5-yl)pyridin-2-yl)amino)-2-oxoethyl)-3-methylisoxazole-4-carboxamide (Example 181);

(S)—N-(1-cycloheptyl-2-((5-(4-(hydroxymethyl)-1-methyl-1H-pyrazol-5-yl)pyridin-2-yl)amino)-2-oxoethyl)-1-methyl-1H-pyrazole-5-carboxamide (Example 182);

(S)—N-(1-cyclopentyl-2-((5-(1,4-dimethyl-1H-pyrazol-5-yl)pyridin-2-yl)amino)-2-oxoethyl)-1-methyl-1H-pyrazole-5-carboxamide (Example 183);

N-(1-(bicyclo[2.2.1]heptan-2-yl)-2-((5-(1,4-dimethyl-1H-pyrazol-5-yl)pyridin-2-yl)amino)-2-oxoethyl)-1-methyl-1H-pyrazole-5-carboxamide (Example 184);

N-(2-((5-(1,4-dimethyl-1H-pyrazol-5-yl)pyridin-2-yl)amino)-2-oxo-1-((1r,4r)-4-(trifluoromethyl)cyclohexyl)ethyl)-1-methyl-1H-pyrazole-5-carboxamide (Example 185);

N-(2-((5-(1,4-dimethyl-1H-pyrazol-5-yl)pyridin-2-yl)amino)-2-oxo-1-((1r,4r)-4-(trifluoromethyl)cyclohexyl)ethyl)-1-ethyl-1H-pyrazole-5-carboxamide (Example 186);

N-(2-((5-(1,4-dimethyl-1H-pyrazol-5-yl)pyridin-2-yl)amino)-2-oxo-1-((1r,4r)-4-(trifluoromethyl)cyclohexyl)ethyl)-3-ethylisoxazole-4-carboxamide (Example 187);

N—((S)-2-((5-(1,4-dimethyl-1H-1,2,3-triazol-5-yl)pyridin-2-yl)amino)-1-((1r,4S)-4-methylcyclohexyl)-2-oxoethyl)-3-ethylisoxazole-4-carboxamide (Example 188);

N—((S)-2-((6-(1,4-dimethyl-1H-pyrazol-5-yl)-5-fluoropyridin-3-yl)amino)-1-((1r,4S)-4-methylcyclohexyl)-2-oxoethyl)-1-ethyl-1H-pyrazole-5-carboxamide (Example 189);

(S)—N-(1-cycloheptyl-2-((5-(1-(2-(dimethylamino)-2-oxoethyl)-4-methyl-1H-1,2,3-triazol-5-yl)pyridin-2-yl)amino)-2-oxoethyl)-1-methyl-1H-pyrazole-5-carboxamide (Example 190);

N—((S)-2-((5-(1,4-dimethyl-1H-pyrazol-5-yl)pyridin-2-yl)amino)-1-((1r,4S)-4-methylcyclohexyl)-2-oxoethyl)-3-isopropylisoxazole-4-carboxamide (Example 191);

3-(tert-butyl)-N—((S)-2-((5-(1,4-dimethyl-1H-pyrazol-5-yl)pyridin-2-yl)amino)-1-((1r,4S)-4-methylcyclohexyl)-2-oxoethyl)isoxazole-4-carboxamide (Example 192);

N—((S)-2-((5-(4-cyano-1-methyl-1H-pyrazol-5-yl)pyridin-2-yl)amino)-1-((1r,4S)-4-methylcyclohexyl)-2-oxoethyl)-1-methyl-1H-pyrazole-5-carboxamide (Example 193);

N—((S)-2-((5-(1,4-dimethyl-1H-pyrazol-5-yl)pyridin-2-yl)amino)-1-((1r,4S)-4-methylcyclohexyl)-2-oxoethyl)-3-(trifluoromethyl)isoxazole-4-carboxamide (Example 194);

(S)—N-(1-cycloheptyl-2-oxo-2-((5-(1,3,4-trimethyl-1H-pyrazol-5-yl)pyridin-2-yl)amino)ethyl)-1-methyl-1H-pyrazole-5-carboxamide (Example 195);

N—((S)-2-((5-(3,5-dimethylisothiazol-4-yl)pyridin-2-yl)amino)-1-((1r,4S)-4-methylcyclohexyl)-2-oxoethyl)-1-methyl-1H-pyrazole-5-carboxamide (Example 196);

N—((S)-2-((5-(3,5-dimethylisothiazol-4-yl)pyridin-2-yl)amino)-1-((1r,4S)-4-methylcyclohexyl)-2-oxoethyl)-1-methyl-1H-1,2,3-triazole-5-carboxamide (Example 197);

(S)—N-(1-cycloheptyl-2-((5-(4-(hydroxymethyl)-1-methyl-1H-pyrazol-5-yl)pyridin-2-yl)amino)-2-oxoethyl)-1-ethyl-1H-pyrazole-5-carboxamide (Example 198);

N—((S)-2-((5-(4-chloro-1-methyl-1H-pyrazol-5-yl)pyridin-2-yl)amino)-1-((1r,4S)-4-methylcyclohexyl)-2-oxoethyl)-1-ethyl-1H-pyrazole-5-carboxamide (Example 199);

N—((S)-2-((5-(4-chloro-1-methyl-1H-pyrazol-5-yl)pyridin-2-yl)amino)-1-((1r,4S)-4-methylcyclohexyl)-2-oxoethyl)-1-methyl-1H-1,2,3-triazole-5-carboxamide (Example 200);

N—((S)-2-((5-(4-chloro-1-methyl-1H-pyrazol-5-yl)pyridin-2-yl)amino)-1-((1r,4S)-4-methylcyclohexyl)-2-oxoethyl)-3-ethylisoxazole-4-carboxamide (Example 201);

(S)—N-(1-cycloheptyl-2-((5-(4-(hydroxymethyl)-1-methyl-1H-pyrazol-5-yl)pyridin-2-yl)amino)-2-oxoethyl)-3-ethylisoxazole-4-carboxamide (Example 202);

N—((S)-2-((6-(3,5-dimethylisoxazol-4-yl)pyridin-3-yl)amino)-1-((1r,4S)-4-methylcyclohexyl)-2-oxoethyl)-3-ethylisoxazole-4-carboxamide (Example 203);

N—((S)-2-((6-(1,4-dimethyl-1H-pyrazol-5-yl)pyridin-3-yl)amino)-1-((1r,4S)-4-methylcyclohexyl)-2-oxoethyl)-1-isopropyl-1H-pyrazole-5-carboxamide (Example 204);

1-ethyl-N—((S)-2-((5-(4-(hydroxymethyl)-1-methyl-1H-pyrazol-5-yl)pyridin-2-yl)amino)-1-((1r,4S)-4-methylcyclohexyl)-2-oxoethyl)-1H-pyrazole-5-carboxamide (Example 205);

N—((S)-2-((6-(3,5-dimethylisoxazol-4-yl)pyridin-3-yl)amino)-1-((1r,4S)-4-methylcyclohexyl)-2-oxoethyl)-1-isopropyl-1H-pyrazole-5-carboxamide (Example 206);

(S)—N-(1-cyclohexyl-2-((6-(3,5-dimethyl-1H-pyrazol-4-yl)pyridin-3-yl)amino)-2-oxoethyl)-1-methyl-1H-pyrazole-5-carboxamide (Example 207);

(S)—N-(1-cycloheptyl-2-((6-(3,5-dimethyl-1H-pyrazol-4-yl)pyridin-3-yl)amino)-2-oxoethyl)-1-ethyl-1H-pyrazole-5-carboxamide (Example 208);

(S)—N-(1-cycloheptyl-2-((6-(3,5-dimethyl-1H-pyrazol-4-yl)pyridin-3-yl)amino)-2-oxoethyl)-1-methyl-1H-1,2,3-triazole-5-carboxamide (Example 209);

(S)—N-(1-cycloheptyl-2-((6-(3,5-dimethyl-1H-pyrazol-4-yl)pyridin-3-yl)amino)-2-oxoethyl)-3-ethylisoxazole-4-carboxamide (Example 210);

N—((S)-2-((6-(3,5-dimethyl-1H-pyrazol-4-yl)pyridin-3-yl)amino)-1-((1r,4S)-4-methylcyclohexyl)-2-oxoethyl)-1-methyl-1H-pyrazole-5-carboxamide (Example 211);

N—((S)-2-((6-(3,5-dimethyl-1H-pyrazol-4-yl)pyridin-3-yl)amino)-1-((1r,4S)-4-methylcyclohexyl)-2-oxoethyl)-1-ethyl-1H-pyrazole-5-carboxamide (Example 212);

N—((S)-2-((6-(3,5-dimethyl-1H-pyrazol-4-yl)pyridin-3-yl)amino)-1-((1r,4S)-4-methylcyclohexyl)-2-oxoethyl)-3-ethylisoxazole-4-carboxamide (Example 213);

(S)—N-(1-cycloheptyl-2-oxo-2-((1',2',4'-trimethyl-6'-oxo-1',6'-dihydro-[3,3'-bipyridin]-6-yl)amino)ethyl)-1-methyl-1H-pyrazole-5-carboxamide (Example 214);

1-methyl-N—((S)-1-((1r,4S)-4-methylcyclohexyl)-2-oxo-2-((1',2',4'-trimethyl-6'-oxo-',6'-dihydro-[3,3'-bipyridin]-6-yl)amino)ethyl)-1H-pyrazole-5-carboxamide (Example 215);

(S)—N-(1-cycloheptyl-2-oxo-2-((5-(1,3,5-trimethyl-1H-pyrazol-4-yl)pyridin-2-yl)amino)ethyl)-1-methyl-1H-pyrazole-5-carboxamide (Example 216);

1-methyl-N—((S)-1-((1r,4S)-4-methylcyclohexyl)-2-oxo-2-((5-(1,3,5-trimethyl-1H-pyrazol-4-yl)pyridin-2-yl)amino)ethyl)-1H-pyrazole-5-carboxamide (Example 217);

(S)—N-(1-cycloheptyl-2-((6-(3,5-dimethyl-1H-pyrazol-4-yl)pyridin-3-yl)amino)-2-oxoethyl)-1-methyl-1H-pyrazole-5-carboxamide (Example 218);

1-methyl-N—((S)-2-((5-(1-methyl-4-(trifluoromethyl)-1H-pyrazol-5-yl)pyridin-2-yl)amino)-1-((1r,4S)-4-methylcyclohexyl)-2-oxoethyl)-1H-pyrazole-5-carboxamide (Example 219); or N-(2-((5-(1,4-dimethyl-1H-pyrazol-5-yl)pyridin-2-yl)amino)-1-(dispiro[$2.1.2^5.2^3$]nonan-4-yl)-2-oxoethyl)-1-methyl-1H-pyrazole-5-carboxamide (Example 220);

or a pharmaceutically acceptable salt thereof.

The various functional groups and substituents making up the compounds of the present invention are typically chosen such that the molecular weight of the compound does not exceed 1000. More usually, the molecular weight of the compound will be less than 750, for example less than 700, or less than 650, or less than 600.

Suitable or preferred features of any compounds of the present invention may also be suitable features of any other aspect.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds that have the same molecular Formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof.

The present invention also encompasses compounds of the invention as defined herein which comprise one or more isotopic substitutions. For example, H may be in any isotopic form, including 1H, 2H (D) and 3H (T); C may be in any isotopic form including 12C, 13C, and 14C; and O may be in any isotopic form, including 16O and 18O; and the like.

It is also to be understood that certain compounds of the invention may exist in solvated as well as unsolvated forms such as, for example, hydrated forms. It is to be understood that the invention encompasses all such solvated forms.

It is also to be understood that certain compounds of the invention may exhibit polymorphism, and that the invention encompasses all such forms.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

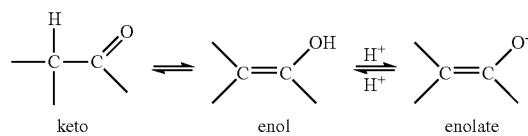

Compounds of the invention containing an amine function may also form N-oxides. A reference herein to a compound of the Formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example Advanced Organic Chemistry, by Jerry March, 4th Edition, Wiley Interscience, pages. More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the Formula I as defined hereinbefore when made available by organic synthesis and when made available within the human or animal body by way of cleavage of a pro-drug thereof. Accordingly, the present invention includes those compounds of the Formula I that are produced by organic synthetic means and also such compounds that are produced in the human or animal body by way of metabolism of a precursor compound, that is a compound of the Formula I may be a synthetically-produced compound or a metabolically-produced compound.

Synthesis

In the description of the synthetic methods described below and in the referenced synthetic methods that are used to prepare the starting materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples. Alternatively, necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, "Protecting groups in Organic Synthesis ($3^{rd}$ Ed), John Wiley & Sons, NY (1999)", T. Greene & P. Wuts. Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively, an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3 \cdot OEt_2$. A suitable alternative protecting group for a primary amino group is, for example, a phthaloyl group which may be removed by treatment with an alkylamine, for example dimethylaminopropylamine, or with hydrazine.

The person skilled in the art will recognise that the compounds of the invention may be prepared, in known manner, in a variety of ways. Compounds of Formula I can be prepared by the methods given below, by the methods given in the experimental, or by analogous methods. The routes described are merely illustrative of some of the methods that can be employed for the synthesis of compounds of Formula I and the person skilled in the art will appreciate that the order of the reaction steps is not limited to those described.

It will also be appreciated that the assignment of nucleophile and electrophile is not limited to that described herein and in some cases it may be appropriate for the assignment to be reversed. Different approaches to synthetic chemistry strategy are described in "Organic Synthesis: The Disconnection Approach", $2^{nd}$ edition, S. Warren and P. Wyatt (2008).

A compound of Formula I, or a pharmaceutically acceptable salt thereof, wherein $R^1$, $R^2$, $R^3$, $R^4$, $X^1$, $X^2$, $X^3$, $X^4$, and Y are as previously defined, may be prepared by reacting a carboxylic acid or a suitably reactive derivative of a carboxylic acid of Formula III, wherein $R^1$, $R^2$, $R^3$, and Y are as previously defined in Formula I, with an amine of Formula II, wherein $R^4$, $X^1$, $X^2$, $X^3$, and $X^4$ are as previously defined in Formula I (Scheme A, step i).

Alternatively, a compound of Formula I, or a pharmaceutically acceptable salt thereof, wherein $R^1$, $R^2$, $R^3$, $R^4$, $X^1$, $X^2$, $X^3$, $X^4$, and Y are as previously defined, may be prepared by reacting an amine of Formula IV, wherein $R^1$, $R^2$, $R^3$, $R^4$, $X^1$, $X^2$, $X^3$, and $X^4$ are as previously defined in Formula I, with a carboxylic acid or a suitably reactive derivative of a carboxylic acid of Formula V, wherein Y is as previously defined in Formula I (Scheme A, step ii).

Scheme A

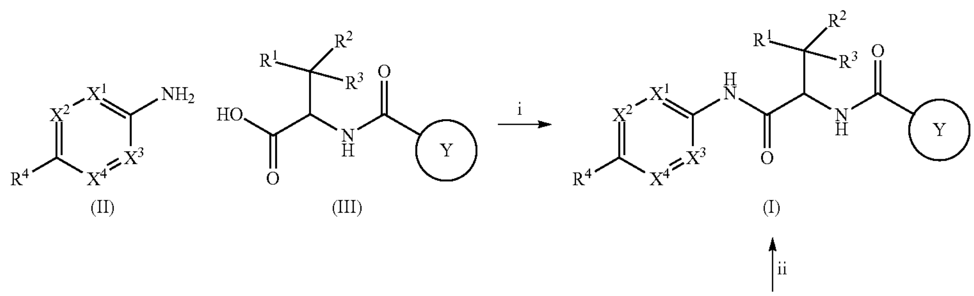

(II) (III) (I)

-continued

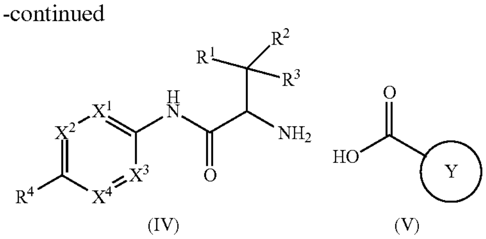

(IV) (V)

A compound of Formula III may be prepared by reacting a suitably protected amine of Formula VI, wherein $R^1$, $R^2$ and $R^3$ are as previously defined in Formula I, with a carboxylic acid or a suitably reactive derivative of a carboxylic acid of Formula V, wherein Y is as previously defined in Formula I (Scheme B, step i).

A compound of Formula IV may be prepared by reacting a suitably protected carboxylic acid or a suitably protected, reactive derivative of a carboxylic acid of Formula VI, wherein $R^1$, $R^2$ and $R^3$ are as previously defined in Formula I, with an amine of Formula II, wherein $R^4$, $X^1$, $X^2$, $X^3$ and $X^4$ are as previously defined in Formula I (Scheme B, step ii).

Scheme B

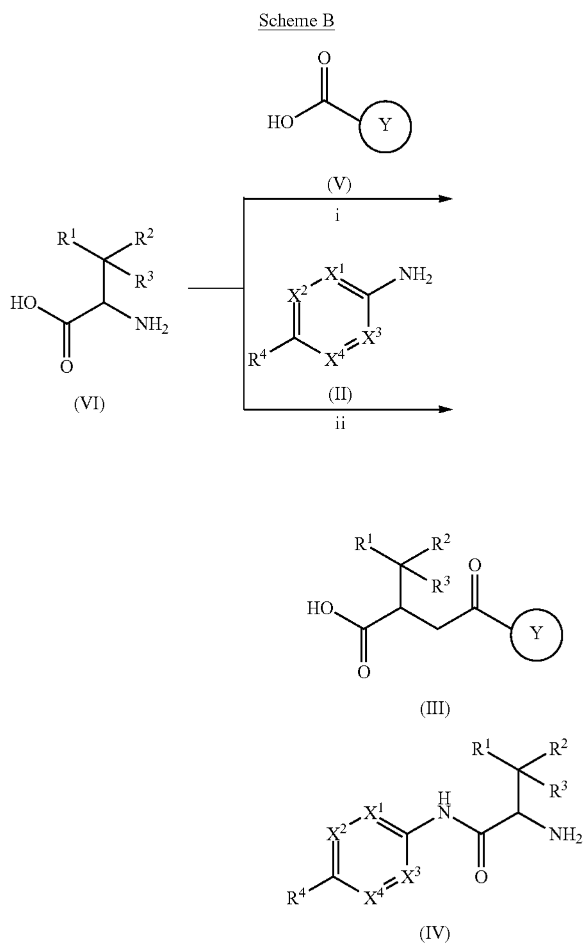

(V) (VI) (II) (III) (IV)

Suitably reactive derivatives of carboxylic acids of Formula III, Formula V and Formula VI include, for example: an acyl halide formed by the reaction of the acid and an inorganic acid chloride such as thionyl chloride; a mixed anhydride, formed by the reaction of the acid and a chloroformate such as isobutyl chloroformate; an ester, formed by reaction with an alcohol in the presence of acid or base; an activated ester, formed by the reaction of the acid with a phenol such as pentafluorophenyl trifluoroacetate or with an alcohol such as N-hydroxybenzotriazole; or the product of the reaction of the acid and an amide-coupling agent such as dicyclohexylcarbodiimide. Where carboxylic acids of Formula III and Formula V are converted to esters, for example by the reaction of an acyl chloride with an organic alcohol, such as methanol, this may be reacted with suitable amines in the presence of an organometallic activating agent, for example a Grignard reagent such as isopropylmagnesium bromide. Typically, a carboxylic acid of Formula III and an amine of Formula II, or a carboxylic acid of Formula V and an amine of Formula IV, or a suitably protected carboxylic acid of Formula VI and an amine of Formula II, in a suitable solvent such as DMF, ethyl acetate or MeCN, in the presence of a non-nucleophilic base such as triethylamine, 2,4,6-trimethylpyridine or N,N-diisopropylethylamine, are treated with an amide-coupling agent such as HATU or T3P®.

It will be appreciated by those skilled in the art that the conversion of amino acids of Formula VI to compounds of Formula III and Formula IV will require a suitable synthetic strategy which may require multiple steps. Those skilled in the art will be able to identify such synthetic strategies which may include the selection, preparation and removal of suitable protecting groups.

Natural and non-natural amino acids of Formula VI and their derivatives, wherein $R^1$, $R^2$ and $R^3$ are as defined in Formula I, are either commercially available or may be prepared by methods known to those skilled in the art. For reviews of the synthesis of amino acids, see (a) C. Najera and J. M. Sansano, Chem Rev, 2007, 107, 4584; (b) R. M. Williams and J. A. Hendrix, Chem Rev, 1992, 92, 889; and (c) R. O. Duthaler, Tetrahedron, 1994, 50, 1539.

Carboxylic acids of Formula V or their derivatives, wherein Y is as defined in Formula I, are either commercially available or may be prepared by methods known to those skilled in the art. Compounds of Formula V may be prepared by: acid or base catalysed hydrolysis of an ester, an amide or a nitrile, such as the hydrolysis of a methyl ester with sodium hydroxide; transition metal catalysed oxidation of an aldehyde or alcohol; treatment of an organolithium or Grignard reagent with carbon dioxide; or transition metal catalysed carbonylation of an aryl halide in the presence of water. Transition metal catalysed carbonylation of an aryl halide in the presence of an amine of Formula VI or Formula IV, may form a compound of Formula III or Formula I directly.

Scheme C

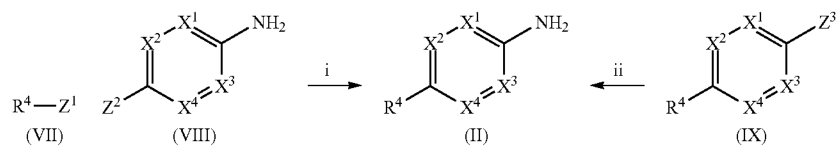

(VII) (VIII) (II) (IX)

Amines of Formula II, wherein $R^4$, $X^1$, $X^2$, $X^3$ and $X^4$ are as previously defined in Formula I, are either commercially available or may be prepared by methods known to those skilled in the art.

Compounds of Formula II may be prepared from compounds of Formula VII, wherein $R^4$ is as defined in Formula I, and Formula VIII, wherein $X^1$, $X^2$, $X^3$ and $X^4$ are as defined in Formula I, and where $Z^1$ and $Z^2$ are functional groups that facilitate the formation of the bond between $R^4$ and the phenyl/heteroaryl ring and which are displaced/eliminated during the bond-forming reaction (Scheme C, step i). Such bond-forming reactions, conditions and suitable $Z^1$ and $Z^2$ functional groups are known to those skilled in the art. For example, where $R^4$ is heteroaryl, a suitable bond-forming reaction may be the Suzuki reaction and either $Z^1$ or $Z^2$ is a boronic acid or boronic ester, and the other is a halide. Typically, compounds of Formula VII and Formula VIII in which one of $Z^1$ or $Z^2$ is a boronic acid or boronic ester and the other is a halide are combined and reacted together in a solvent or solvent mixture such as 1,4-dioxane/water, ethanol/water or toluene in the presence of a base such as potassium carbonate, sodium carbonate or potassium phosphate and a catalyst such as Pd(dppf)$Cl_2$ or XPhos Pd $G_2$.

Amines of Formula II may also be prepared from compounds of Formula IX, wherein $R^4$, $X^1$, $X^2$, $X^3$ and $X^4$ are as previously defined in Formula I and $Z^3$ is a functional group that can be converted via known methods to an amine (Scheme C, step ii). Examples of known methods include; reduction, wherein $Z^3$ is, for example, an azide or nitro; rearrangement, wherein $Z^3$ is, for example, a primary amide (Hoffmann rearrangement), a carboxylic acid (Schmidt rearrangement), or an acyl azide (Curtius rearrangement); or C—N bond forming, wherein $Z^3$ is H or halide, for example, nitration followed by reduction or amination (eg. Buchwald-Hartwig reaction).

Compounds of Formula IX, wherein $R^4$, $X^1$, $X^2$, $X^3$ and $X^4$ are as previously defined in Formula I is as described herein, are either commercially available or may be prepared by methods known to those skilled in the art.

Pharmaceutical Compositions

The compounds of the invention will normally, but not necessarily, be formulated into pharmaceutical compositions prior to administration to a patient. Therefore, according to a further aspect of the invention there is provided a pharmaceutical composition which comprises a compound of the invention as defined herein, or a pharmaceutically acceptable salt thereof, and one or more pharmaceutically acceptable excipients, diluents or carriers.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The compositions of the invention may be in a form suitable for oral use (for example as tablets, capsules, caplets, pills, troches, powders, syrups, elixirs, suspensions, solutions, emulsions, sachets, and cachets), for topical use (for example as creams, ointments, lotions, solutions, pastes, sprays, foams, and gels), for transdermal administration (for example via transdermal patches), for administration by inhalation (for example as a dry powders, aerosols, suspensions, and solutions), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

As used herein, "pharmaceutically acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient, and interactions which would result in pharmaceutical compositions that are not pharmaceutically acceptable, are avoided. In addition, each excipient must of course be of sufficiently high purity to render it pharmaceutically acceptable.

The pharmaceutical compositions of the invention are prepared using techniques and methods known to those skilled in the art. Some of the methods commonly used in the art are described in Remington's Pharmaceutical Sciences (Mack Publishing Company).

An effective amount of a compound of the present invention for use in therapy of proliferative disease is an amount sufficient to symptomatically relieve in a warm-blooded animal, particularly a human, the symptoms of the proliferative disease, to slow the progression of the proliferative disease, or to reduce in patients with symptoms of the proliferative disease the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the Formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, from 0.1 mg/kg to 75 mg/kg body weight is received, given if required in divided doses. In general, lower doses will be administered when a parenteral route is employed. Thus, for example, for intravenous or intraperitoneal administration, a dose in the range, for example, from 0.1 mg/kg to 30 mg/kg body weight will generally be used. Similarly, for administration by inhalation, a dose in the range, for example, from 0.05 mg/kg to 25 mg/kg body weight will be used. Oral administration may also be suitable, particularly in tablet form. Typically, unit dosage forms will contain about from 0.5 mg to 0.5 g of a compound of this invention.

Routes of Administration

The compounds of the invention or pharmaceutical composition comprising the active compound may be administered to a subject by any convenient route of administration, whether systemically/peripherally or topically (i.e. at the site of desired action).

Routes of administration include, but are not limited to, oral (e.g, by ingestion); buccal; sublingual; transdermal (including, e.g., by a patch, plaster, etc.); transmucosal (including, e.g., by a gum, film etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Therapeutic Uses and Applications

The compounds of the present invention, being high affinity binders to human IL-17A and potent modulators of human IL-17A activity, are therefore beneficial as therapeutic compounds in the treatment or prevention of human ailments occurring as a result of IL-17A activity.

The compounds of the present invention, being high affinity binders to human IL-17A and potent modulators of human IL-17A activity, may be beneficial as pharmacological standards for use in the development of new biological tests and in the search for new pharmacological agents. Thus, the compounds of the present invention may be useful as radioligands in assays for detecting pharmacologically active compounds.

Thus, in one aspect, the present invention relates to a compound of the invention as defined herein, or a pharmaceutically acceptable salt or solvate thereof, or a pharmaceutical composition as defined herein, for use in therapy.

In another aspect, the present invention relates to a compound of the invention as defined herein, or a pharmaceutically acceptable salt or solvate thereof, or a pharmaceutical composition as defined herein, for use in the treatment of diseases or disorders mediated by IL-17A activity.

In another aspect, the present invention relates to the use of a compound of the invention as defined herein, or a pharmaceutically acceptable salt or solvate thereof, in the manufacture of a medicament for use in the treatment of diseases or disorders mediated by IL-17A activity.

In another aspect, the present invention relates to a method of treating a disease or disorder in which IL-17A activity is implicated, said method comprising administering to a subject in need of such treatment a therapeutically effective amount of a compound of the invention as defined herein, or a pharmaceutically acceptable salt or solvate thereof, or a pharmaceutical composition as defined herein.

Examples of particular diseases or disorders that the compounds of Formula (I) and their pharmaceutically acceptable salts may be used to treat include, but are not limited to, any one of the following: acute lung injury, Alzheimer's Disease, ankylosing spondylitis, axial spondyloarthritis and other spondyloarthropathies, arthritis, asthma (including severe asthma), atopic dermatitis, autoimmune diabetes other autoimmune disorders, autoimmune thyroiditis, bone resorption, cancer (both solid tumours such as melanomas, sarcomas, squamous cell carcinomas, transitional call cancers, ovarian cancers and hematologic malignancies and in particular acute myelogenous leukaemia, chronic lymphocytic leukemia, gastric cancer and colon cancer), Castleman's disease, contact dermatitis, Crohn's Disease, chronic myelogenous leukemia, chronic obstructive pulmonary disease (COPD), coeliac disease, cystic fibrosis, dermatomyositis, discoid lupus erythematosus, eczema, enthesitis-related arthritis, endotoxic shock associated with infection, exophthalmos, fibrosing disorders including pulmonary fibrosis, gall bladder disease, giant cell arteritis, graft-versus-host disease, heart disease including ischaemic diseases such as myocardial infarction as well as atherosclerosis, hepatoblastomas, hypochlorhydia, immune mediated inflammatory disorders of the central and peripheral nervous system such as multiple sclerosis and Guillain-Barr syndrome, infections (viral, bacterial, fungal and parasitic), inflammatory bowel disease, intravascular coagulation, irritable bowel syndrome, liver fibrosis, lyme arthritis, meningoencephalitis, myocarditis, meningoencephalitis, osteoporosis, pancreatitis, Parkinson's disease, pelvic inflammatory disease, pain (particularly pain associated with inflammation), periodontitis, peritonitis, Peyronie's Disease, Pilonidal disease, psoriasis, psoriatic arthritis (PsA), renal fibrosis, rheumatoid arthritis, scleroderma or systemic sclerosis, stroke, surgical adhesions, systemic lupus erythematosus (SLE), systemic onset juvenile idiopathic arthritis (JIA), trauma (surgery), transplant rejection, Type I diabetes, ulcerative colitis, uveitis, and vasculitis.

Modulators of IL-17 activity may be administered to inhibit or reduce the severity of ocular inflammatory disorders (WO 2009/089036), for example ocular surface inflammatory disorders including Dry Eye Syndrome (DES). Consequently, the compounds in accordance with the present invention are useful in the treatment or prevention of an IL-17-mediated ocular inflammatory disorder, for example an IL-17-mediated ocular surface inflammatory disorder including Dry Eye Syndrome. Ocular surface inflammatory disorders include Dry Eye Syndrome, penetrating keratoplasty, corneal transplantation, lamellar or partial thickness transplantation, selective endothelial transplantation, corneal neovascularization, keratoprosthesis surgery, corneal ocular surface inflammatory disorders, conjunctival scarring disorders, ocular autoimmune disorders, Pemphigoid syndrome, Stevens-Johnson syndrome, ocular allergy, severe allergic (atopic) eye disease, conjunctivitis, and microbial keratitis. Particular categories of Dry Eye Syndrome include keratoconjunctivitis sicca (KCS), Sjogren syndrome, Sjogren syndrome-associated keratoconjunctivitis sicca, non-Sjogren syndrome-associated keratoconjunctivitis sicca, keratitis sicca, sicca syndrome, xerophthalmia, tear film disorder, decreased tear production, aqueous tear deficiency (ATD), meibomian gland dysfunction, and evaporative loss.

Combination Therapies

The compounds of the invention may be administered alone as a monotherapy or may administered in combination with one or more additional therapeutic agents. The selection of the one or more additional therapeutic agents will of course vary depending on the disease or condition to be treated and its severity.

It is commonplace to use combination therapies to treat certain medical conditions.

According to a particular aspect of the invention there is provided a combination suitable for use in the treatment of a disease or condition in which IL-17 activity is implicated, comprising a compound of the invention as defined hereinbefore, or a pharmaceutically acceptable salt thereof, and another therapeutic agent.

According to this aspect of the invention there is provided a combination suitable for use in the prevention or treatment of acute lung injury, Alzheimer's Disease, ankylosing spondylitis, axial spondyloarthritis and other spondyloarthropathies, arthritis, asthma (including severe asthma), atopic dermatitis, autoimmune diabetes other autoimmune disorders, autoimmune thyroiditis, bone resorption, cancer (both solid tumours such as melanomas, sarcomas, squamous cell carcinomas, transitional call cancers, ovarian cancers and hematologic malignancies and in particular acute myelogenous leukaemia, chronic lymphocytic leukemia, gastric cancer and colon cancer), Castleman's disease, contact dermatitis, Crohn's Disease, chronic myelogenous leukemia, chronic obstructive pulmonary disease (COPD), coeliac disease, cystic fibrosis, dermatomyositis, discoid lupus erythematosus, eczema, enthesitis-related arthritis, endotoxic shock associated with infection, exophthalmos, fibrosing disorders including pulmonary fibrosis, gall bladder disease, giant cell arteritis, graft-versus-host disease, heart disease including ischaemic diseases such as myocardial infarction as well as atherosclerosis, hepatoblastomas, hypochlorhydia, immune mediated inflammatory disorders of the central and peripheral nervous system such as multiple sclerosis and Guillain-Barr syndrome, infections (viral, bacterial, fungal and parasitic), inflammatory bowel disease, intravascular coagulation, irritable bowel syndrome, liver fibrosis, lyme arthritis, meningoencephalitis, myocarditis, meningoencephalitis, osteoporosis, pancreatitis, Parkinson's disease, pelvic inflammatory disease, pain (particularly pain associated with inflammation), periodontitis, peritonitis, Peyronie's Disease, Pilonidal disease, psoriasis, psoriatic arthritis (PsA), renal fibrosis, rheumatoid arthritis, scleroderma or systemic sclerosis, stroke, surgical adhesions, systemic lupus erythematosus (SLE), systemic onset juvenile idiopathic arthritis (JIA), trauma (surgery), transplant rejection, Type I diabetes, ulcerative colitis, uveitis, vasculitis, Dry Eye Syndrome, penetrating keratoplasty, corneal transplantation, lamellar or partial thickness transplantation, selective endothelial transplantation, corneal neovascularization, keratoprosthesis surgery, corneal ocular surface inflammatory disorders, conjunctival scarring disorders, ocular autoimmune disorders, Pemphigoid syndrome, Stevens-Johnson syndrome, ocular allergy, severe allergic (atopic) eye disease, conjunctivitis, and microbial keratitis, the combination comprising a compound of the invention as defined hereinbefore, or a pharmaceutically acceptable salt thereof, and one or more additional therapeutic agents.

Examples of these additional therapeutic agents may include but are not limited to corticosteroids (topical or systemically administered), Vitamin D analogues, Anthralin, retinoids, calcineurin inhibitors, salicylic acid, methotrexate, cyclosporine, leflunomide, sulfasalazine, azathioprine, etanercept (Enbrel), infliximab (Remicade), adalimumab (Humira), ustekinumab (Stelara), golimumab (Simponi), guselkumab, PDE inhibitors (such as apremilast), thioguanine, hydroxyurea, dimethyl fumarate, JAK inhibitors including TYK2 inhibitors (such as Ruxolitinib, Tofacitinib, Oclacitinib, Baricitinib, Filgotinib, Cerdulatinib, Gandotinib, Lestaurtinib, Momelotinib, Pacritinib, PF-04965842, Upadacitinib, Peficitinib, Fedratinib, BMS-986165), and NSAIDs (such as naproxen, indomethacin).

In a further aspect of the invention there is provided a compound of the invention or a pharmaceutically acceptable salt thereof, in combination with one or more additional therapeutic agents.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt thereof in combination with one or more additional therapeutic agents in association with a pharmaceutically acceptable diluent or carrier.

The one or more additional therapeutic agents may comprise a further compound of the present invention. Therefore, in an embodiment, there is provided a pharmaceutical composition which comprises two compounds of the invention, or pharmaceutically acceptable salts thereof, in association with a pharmaceutically acceptable diluent or carrier.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention.

Such combination treatment may be achieved by way of the simultaneous, sequential or separate dosing of the individual components of the treatment. In one embodiment, the individual compounds will be administered simultaneously in a combined pharmaceutical formulation.

Such combination therapies employ the compounds of this invention within the dosage range described herein and the other pharmaceutically active agent within approved dosage ranges or the dosage such as described in the relevant publication reference.

General Procedures:

Methods for preparing the compounds of this invention are illustrated in the following Examples. Starting materials are made according to procedures known in the art or as illustrated herein or are available commercially. Commercial reagents were used without further purification. Where no reaction temperature is included, the reaction was performed at ambient (or room) temperature which is typically from 17-27° C.

A person skilled in the art will appreciate that reaction temperatures, reaction times and reagent quantities may be varied from those stated herein.

Compounds names have been generated using ChemDraw Professional Version 20.0.0.41.

Where compounds described in the invention are characterized by $^1H$ NMR spectroscopy, spectra were recorded on JEOL ECX300 (300 MHz), JEOL ECX400 (400 MHz) or BrukerAvance III Ultra shield 400 (400 MHz) instruments. Where no temperature is included, the spectra were recorded at ambient temperature. Chemical shift values are expressed in parts per million (ppm). The following abbreviations are used for the multiplicity of the NMR signals: s=singlet, b=broad, t=triplet, q=quartet, m=multiplet, d=doublet.

Where compounds described in the invention are characterized by LCMS data, retention time and molecular weight were determined using the conditions listed below.

Method 1: Waters Acquity UPLC H-Class system (Quaternary pump with PDA (210-350 nm) and QDa mass detector). Column: XBridge C18, 2.5 μm, 2.1×50 mm (Flow 0.8 mL/min). Run Time: 1.30 min. Conditions: 10 mM ammonium bicarbonate pH10 [eluent C], MeCN [eluent B]. Gradient: 2-98% B in 0.80 min, hold at 98% B to 1.30 min.

Method 2: Waters Acquity UPLC H-Class system (Quaternary pump with PDA (210-350 nm) and QDa mass detector). Column: XBridge C18, 2.5 μm, 2.1×50 mm (Flow 0.8 mL/min). Run Time: 1.40 min. Conditions: 10 mM ammonium bicarbonate pH10 [eluent C], MeCN [eluent B]. Gradient: 2-98% B in 1.20 min, hold at 98% B to 1.40 min.

Method 3: Waters Acquity UPLC H-Class system (Quaternary pump with PDA (210-350 nm) and QDa mass detector). Column: BEH C18, 1.7 μm, 2.1×50 mm (Flow 0.8 mL/min). Run Time: 4.60 min. Conditions: water [eluent A], MeCN [eluent B], 2% ammonia in water [eluent C; 5% throughout]. Gradient: 2-95% B with A and 5% C in 4.0 mins, hold at 95% B 5% C to 4.60 min, column temp 40° C.

Method 4: Waters Acquity UPLC H-Class system (Quaternary pump with PDA (210-350 nm) and QDa mass detector). Column: BEH C18, 1.7 μm, 2.1×50 mm (Flow 0.8 mL/min). Run Time: 1.40 min. Conditions: water [eluent A], MeCN [eluent B], 2% ammonia in water [eluent C; 5% throughout]. Gradient: 2-95% B with A and 5% C in 1.2 mins, hold at 95% B 5% C to 1.40 min, column temp 40° C.

Method 5: Waters Acquity UPLC H-Class system (Quaternary pump with PDA (210-350 nm) and QDa mass detector). Column: XBridge C18, 2.5 μm, 2.1×50 mm (Flow 0.8 mL/min). Run Time: 4.60 min. Conditions: 10 mM ammonium bicarbonate pH10 [eluent C], MeCN [eluent B]. Gradient: 2-98% B in 4.0 min, hold at 98% B to 4.60 min.

Method 6: Waters Acquity UPLC system (Binary pump with PDA (210-350 nm) and QDa_mass detector). Column: Acquity UPLC CSH C18, 1.7 μm, 2.1×50 mm (Flow 0.8 mL/min). Run Time: 4.6 min. Conditions: Water+0.1% formic acid [eluent A], MeCN+0.1% formic acid [eluent B]. Gradient: 2-98% B in 4.0 min, hold at 98% B to 4.60 min, column temp 40° C.

Method 7: Waters Acquity UPLC H-Class system (Quaternary pump with PDA (210-350 nm) and SQD mass detector). Column: XBridge C18, 2.5 μm, 2.1×50 mm (Flow 0.8 mL/min). Run Time: 5.00 min. Conditions: 2% ammonia in water [eluent D], MeCN [eluent C], water [eluent A]. Gradient: 2-95% C in A with 5% D in 4.50 min, hold at 95% C to 5.00 min, column temp 40° C.

Method 8: Waters Acquity UPLC system (Binary pump with PDA (210-350 nm) and QDa_mass detector). Column: Acquity UPLC CSH C18, 1.7 μm, 2.1×50 mm (Flow 0.8 mL/min). Run Time: 1.4 min. Conditions: Water+0.1% formic acid [eluent A], MeCN+0.1% formic acid [eluent B]. Gradient: 2-98% B in 1.2 min, hold at 98% B to 1.40 min, column temp 40° C.

Method 9: Waters Acquity UPLC H-Class system (Quaternary pump with PDA (210-350 nm) and SQD mass detector). Column: CSH C18, 1.7 μm, 2.1×50 mm (Flow 0.7 mL/min). Run Time: 5.00 min. Conditions: Water+0.1% formic acid [eluent A], MeCN+0.1% formic acid [eluent B]. Gradient: 2-95% B in 4.50 min, hold at 95% B to 5.00 min.

Method 10: Waters Acquity UPLC system (Binary pump with PDA (210-350 nm) and QDa mass detector). Column: XBridge BEH C18, 2.5 μm, 2.1×50 mm (Flow 0.8 mL/min). Run Time: 4.80 min. Conditions: 10 mM ammonium bicarbonate pH10 [eluent A], MeCN [eluent B]. Gradient: 2-98% B in 4.0 min, hold at 98% B to 4.70 min.

Method 11: Waters Acquity UPLC H-Class system (Quaternary pump with PDA (210-350 nm) and SQD mass detector). Column: XBridge BEH C18, 1.7 μm, 2.1×50 mm (Flow 0.8 mL/min). Conditions: water [eluent A], MeCN [eluent B], 2% ammonia in water [eluent C; 5% throughout]. Gradient: 5-95% B in 4.50 min, hold at 95% B to 5.00 min, column temp. 40° C.

Method 12: Waters Acquity UPLC H-Class system (Quaternary pump with PDA (210-350 nm) and SQD mass detector). Column: XBridge BEH C18, 1.7 μm, 2.1×50 mm (Flow 0.8 mL/min). Conditions: water [eluent A], MeCN [eluent B], 2% ammonia in water [eluent C; 5% throughout]. Gradient: 2-95% B in 4.0 min, hold at 95% B to 4.60 min, column temp. 40° C.

Method 13: Waters Acquity UPLC H-Class system (Quaternary pump with PDA (210-350 nm) and SQD mass detector). Column: CSH C18, 1.7 μm, 2.1×50 mm (Flow 0.8 mL/min). Conditions: water [eluent A], MeCN [eluent B], 2% formic acid in water [eluent D; 5% throughout]. Gradient: 2-95% B in 4.0 min, hold at 95% B to 4.60 min, column temp. 40° C.

Method 14: Agilent 6140 Series Quadrupole Mass Spectrometer with a multimode source (monitored at 254 nm). Column: Phenomenex Luna® C18 (2)-HST column, 2.5 μm, 50×2.0 mm (Flow 1.0 mL/min). Conditions: mobile phase A contained 0.1% formic acid in 18 MO water; mobile phase B contained 0.1% formic acid in acetonitrile. Gradient: 1-100% B in 3.75 min.

Method 15: Agilent 6140 Series Quadrupole Mass Spectrometer with a multimode source (monitored at 254 nm). Column: Phenomenex Luna® C18 (2)-HST column, 2.5 μm, 50×2.0 mm (Flow 1.0 mL/min). Conditions: mobile phase A contained 0.1% formic acid in 18 MO water; mobile phase B contained 0.1% formic acid in acetonitrile. Gradient: 1-100% B in 5.5 min.

Method 16: Agilent 6140 Series Quadrupole Mass Spectrometer with a multimode source (monitored at 254 nm). Column: Phenomenex Luna® C18 (2)-HST column, 2.5 μm, 50×2.0 mm (Flow 1.0 mL/min). Conditions: mobile phase A contained 5 mM ammonium acetate in 18 MO water; mobile phase B contained 5 mM ammonium acetate in 18 MO water/5 mM ammonium acetate in acetonitrile (9:1). Gradient: 5-100% B in 3.5 min.

Method 17: Waters Acquity UPLC H-Class system (Quaternary pump with PDA (210-350 nm) and QDa mass detector). Column: Acquity UPLC CSH C18, 1.7 μm, 2.1×50 mm (Flow 0.8 mL/min). Conditions: Water+0.1% formic acid [eluent A], MeCN+0.1% formic acid [eluent B]. Gradient: 2-95% B in 4.0 min, hold at 95% B to 4.60 min, column temp 40° C.

Method 18: Waters Acquity UPLC H-Class system (Quaternary pump with PDA (210-350 nm) and SQD mass detector). Column: XBridge BEH C18, 1.7 μm, 2.1×50 mm (Flow 0.8 mL/min). Conditions: water [eluent A], MeCN

[eluent B], 2% ammonia in water [eluent C; 5% throughout]. 2-95% B over 4.5 min, hold at 95% B to 5.00 min, column temp. 40° C.

Method 19: Agilent 6140 Series Quadrupole Mass Spectrometer with a multimode source (monitored at 254 nm). Column: Phenomenex Kinetix® C18 100 Å, 1.7 μm, 50×2.1 mm. Conditions: mobile phase A contained 0.1% formic acid in 18 Mo water and mobile phase B contained 0.1% formic acid in HPLC grade acetonitrile (Flow 0.8 ml/min). Gradient: 5-95% B in 5 min.

Method 20: Waters Acquity UPLC H-Class system (Quaternary pump with PDA (210-350 nm) and QDa mass detector). Column: BEH C18, 1.7 μm, 2.1×50 mm (Flow 0.8 mL/min). Run Time: 1.40 min. Conditions: water [eluent A], MeCN [eluent B], 2% ammonia in water [eluent C; 5% throughout]. Gradient: 50-95% B with A and 5% C in 1.2 mins, hold at 95% B 5% C to 1.40 min, column temp. 40° C.

Method 21: Waters Acquity UPLC H-Class system (Quaternary pump with PDA (210-350 nm) and SQD mass detector). Column: Acquity UPLC CSH C18, 1.7 μm, 2.1×50 mm (Flow 0.8 mL/min). Conditions: water [eluent A], MeCN [eluent B], 2% formic acid in water [eluent D; 5% throughout]. Gradient: 2-20% B in 3.0 min, to 95% B at 4.0 min, hold at 95% B to 4.60 min, column temp. 40° C.

Method 22: Waters Acquity UPLC H-Class system (Quaternary pump with PDA (210-350 nm) and QDa mass detector). Column: BEH C18, 1.7 μm, 2.1×50 mm (Flow 0.8 mL/min). Run Time: 1.40 min. Conditions: water [eluent A], MeCN [eluent B], 2% ammonia in water [eluent C; 5% throughout]. Gradient: 2-50% B with A and 5% C in 1.0 min, to 95% B at 1.8 min, hold at 95% B 5% C to 2.0 min, column temp. 40° C.

Method 23: Waters Acquity UPLC H-Class system (Quaternary pump with PDA (210-350 nm) and SQD mass detector). Column: Acquity UPLC CSH C18, 1.7 μm, 2.1×50 mm (Flow 0.8 mL/min). Conditions: water [eluent A], MeCN [eluent B], 2% formic acid in water [eluent D; 5% throughout]. Gradient: 2-20% B in 1.0 min, to 95% B at 1.8 min, hold at 95% B to 2.0 min, column temp. 40° C.

Method 24: Waters Acquity UPLC H-Class system (Quaternary pump with PDA (210-350 nm) and SQD mass detector). Column: XBridge C18, 2.5 μm, 2.1×50 mm (Flow 0.8 mL/min). Run Time: 1.80 min. Conditions: 10 mM ammonium bicarbonate pH10 [eluent A], MeCN [eluent B]. Gradient: 2-50% B in 1.00 min, hold at 98% B to 1.80 min, column temp. 40° C.

Method 25: Agilent 1260. Column: XSelect CSH C18, 130 Å, 2.5 μm, 4.6×30 mm. Conditions: 0.1% Formic acid [eluent A], MeCN [eluent B] (Flow 2.5 mL/min). Gradient: 5-95% B in 4 min, column temp 40° C.

Method 26: Agilent 1260 (Binary Pump, HiP Sampler, Column Compartment, DAD:260+/−90 nm, G6150 MSD: ESI); Column: Cortecs C18, 2.6 μm, 30×2.1 mm. Conditions: 0.1% $NH_3$ in water [eluent A], MeCN [eluent B] (Flow 1.35 mL/min). Gradient: 5-100% B in 2.5 min, hold at 100% B to 3 min, column temp 40° C.

Method 27: Agilent 1260 (Quaternary Pump, HiP Sampler, Column Compartment, DAD:260+/−90 nm, G6150 MSD: ESI); Column: Cortecs C18, 2.6 μm, 30×2.1 mm. Conditions: 0.1% Formic in water [eluent A], MeCN [eluent B] (Flow 1.35 mL/min). Gradient: 5-100% B in 2.5 min, hold at 100% B to 3 min, column temp 40° C.

Method 28: Agilent 1260 (Waters Acquity PDA 210-400 nm and Waters Acquity QDa detector). Column: Waters BEH C18 column, 1.7 μm, 30×2.1 mm. Conditions: 0.1% $NH_3$ in water [eluent A], MeCN [eluent B] (Flow 0.77 mL/min). Gradient: 2-100% B in 3 min, column temp 40° C.

Method 29: Agilent 1260 (Agilent VWD or DAD detector at 254 nm and Agilent MSD detector) Column: X-Bridge BEH C18, 130 Å, 2.5 μm, 4.6×30 mm. Conditions: 0.1% $NH_3$ in water [eluent A], MeCN [eluent B] (Flow 2.5 mL/min). Gradient: 5-95% B in 4 min, column temp 40° C.

Preparative HPLC was performed using a variety of preparative systems with variable wavelength UV detection or Mass Directed AutoPrep (MDAP) systems as listed below:

Method 1: Waters Fractionlynx preparative HPLC system (2545 pump, 2998 UV/VIS detector, 2767 liquid handler) with Waters 3100 mass detector. Column: Waters XBridge OBD C18 column, XSelect CSH C18 (5 μm, 19×150 mm) or as specified. Conditions: eluents chosen from MeOH, MeCN with modifiers chosen from formic acid (0.1%) and ammonia hydroxide (0.1%) as specified. Gradient as specified.

Method 2: Waters HPLC (Waters 2767 Sample Manager, Waters 2545 Binary Gradient Module, Waters Systems Fluidics Organiser, Waters 515 ACD pump, Waters 2998 Photodiode Array Detector), using a Waters XBridge Prep OBD C18, 5 μm, 19 mm×50 mm i.d. column and a flow rate of 20 mL/minute. Basic reverse phase HPLC (water/acetonitrile/0.005 M ammonia solution) using a standard gradient of 10% acetonitrile/90% water to 95% acetontrile/5% water. UV detection e.g. 254 nM is used for the collection of fractions from HPLC.

Method 3: Waters HPLC (Waters 2767 Sample Manager, Waters 2545 Binary Gradient Module, Waters Systems Fluidics Organiser, Waters 515 ACD pump, Waters 2998 Photodiode Array Detector), using a Waters XBridge Prep OBD C18, 5 μm, 19 mm×50 mm i.d. column and a flow rate of 20 mL/minute. Acidic reverse phase HPLC (water/acetonitrile/0.1% formic acid) using a standard gradient of 5% acetonitrile/95% water to 95% acetonitrile/5% water. UV detection e.g. 254 nM is used for the collection of fractions from HPLC.

Method 4: Waters HPLC (Waters 2767 Sample Manager, Waters 2545 Binary Gradient Module, Waters Systems Fluidics Organiser, Waters 515 ACD pump, Waters 2998 Photodiode Array Detector), using a Waters XBridge Prep OBD C18, 5 μm, 19 mm×50 mm i.d. column and a flow rate of 20 ml/minute. Acidic reverse phase HPLC (water/acetonitrile/0.1% trifluoroacetic acid) using a standard gradient of 5% acetonitrile/95% water to 95% acetonitrile/5% water. UV detection e.g. 254 nM is used for the collection of fractions from HPLC.

Method 5: Waters HPLC (Waters 2767 Sample Manager, Waters 2545 Binary Gradient Module, Waters Systems Fluidics Organiser, Waters 515 ACD pump, Waters 2998 Photodiode Array Detector), using Waters X-Select CSH C18 ODB prep column, 130 Å, 5 μm, 30 mm×100 mm, flow rate 40 mL min-1 eluting with a 0.1% formic acid in water-MeCN gradient over 12.5 mins. At-column dilution pump gives 2 mL min−1 MeCN over the entire method, which is included in the following MeCN percentages. Gradient information: 0.0-0.5 min, 25% MeCN; 0.5-10.5 min, ramped from 25% MeCN to 55% MeCN; 10.5-10.6 min, ramped from 55% MeCN to 100% MeCN; 10.6-12.5 min, held at 100% MeCN. UV detection across all wavelengths with PDA as well as a QDA and ELS detector.

Method 6: Waters HPLC (Waters 2767 Sample Manager, Waters 2545 Binary Gradient Module, Waters Systems Fluidics Organiser, Waters 515 ACD pump, Waters 2998 Photodiode Array Detector), using Waters XBridge BEH C18 ODB prep column, 130 Å, 5 µm, 30 mm×100 mm, flow rate 40 mL min-1 eluting with a 0.3% ammonia in water-MeCN gradient over 12.5 mins. At-column dilution pump gives 2 mL min-1 MeCN over the entire method, which is included in the following MeCN percentages. Gradient information: 0.0-0.5 min, 30% MeCN; 0.5-10.5 min, ramped from 30% MeCN to 60% MeCN; 10.5-10.6 min, ramped from 60% MeCN to 100% MeCN; 10.6-12.5 min, held at 100% MeCN. UV detection across all wavelengths with PDA as well as a QDA and ELS detector.

Preparative Supercritical fluid chromatography (SFC) was carried out on a Waters Investigator SFC comprising of a Waters 05962 fluid delivery module, Waters 07419 autosampler, Waters 2489 UV/Vis detector Waters 08005 column oven, Waters 279002192 heat exchanger, Waters ABPR-20A back pressure regulator and Waters 08127 fraction collection module. The general method used liquid $CO_2$ (Airproducts) and the appropriate modifier as stated. UV detection was at 254 nM.

Abbreviations

| | |
|---|---|
| Boc Anhydride | Di-tert-butyl dicarbonate |
| BTFFH | Fluoro-N,N,N',N'-bis(tetramethylene)formamidinium hexafluorophosphate |
| CPME | Cyclopentyl methyl ether |
| DCM | Dichloromethane |
| DIPEA | N,N-Diisopropylethylamine |
| DMA | Dimethylacetamide |
| DMAP | 4-(Dimethylamino)pyridine |
| DMF | N,N-Dimethylformamide |
| DMSO | Dimethylsulfoxide |
| EDCl | N-(3-Dimethylaminopropyl)-N'-ethylcarbodiimide hydrochloride |
| EDTA | Ethylenediaminetetraacetic acid |
| EEDQ | Ethyl 2-ethoxy-2H-quinoline-1-carboxylate |
| EtOAc | Ethyl acetate |
| h | Hour(s) |
| HATU | N-[(Dimethylamino)-1H-1,2,3-triazolo-[4,5-b]pyridin-1-ylmethylene]-N-methylmethanaminium hexafluorophosphate N-oxide |
| HCl | Hydrogen chloride |
| HPLC | High Performance Liquid Chromatography |
| IIDQ | Isobutyl 1,2-dihydro-2-isobutoxy-1-quinolinecarboxylate |
| IPA | Isopropyl alcohol |
| LCMS | Liquid Chromatography Mass Spectrometry |
| $LiAlH_4$ | Lithium Aluminium Hydride |
| mCPBA | 3-Chloroperbenzoic acid |
| MDAP | Mass Directed Auto Purification |
| MeCN | Acetonitrile |
| MeOH | Methanol |
| $MgSO_4$ | Magnesium sulfate |
| min | Minute(s) |
| $NaHCO_3$ | Sodium bicarbonate |
| NaOH | Sodium hydroxide |
| $Na_2SO_4$ | Sodium sulfate |
| NBS | N-bromosuccinimide |
| $NH_4HCO_3$ | Ammonium bicarbonate |
| $NH_4Cl$ | Ammonium chloride |
| NMR | Nuclear Magnetic Resonance |
| Pd-170 | Chloro(crotyl)(2-dicyclohexylphosphino-2'4',6'-triisopropyl-1,1'-biphenyl)palladium(II) |
| $Pd(dppf)Cl_2$ | 1,1'-bis(diphenylphosphino)ferrocenepalladium(II) dichloride |
| PEPPSI ™-IPr | [1,3-Bis(2,6-Diisopropylphenyl)imidazol-2-ylidene](3-chloropyridyl)palladium(II) dichloride |
| rt | Room Temperature (i.e. ambient temperature) |
| s | Second(s) |
| SFC | Supercritical fluid chromatography |
| T3P ® | Propylphosphonic anhydride solution |
| TCFH | N,N,N',N'-tetramethylchloroformamidinium hexafluorophosphate |
| TFA | Trifluoroacetic acid |
| THF | Tetrahydrofuran |
| XantPhos | 4,5-Bis(diphenylphosphino)-9,9-dimethylxanthene |
| XantPhos Pd G3 | [(4,5-Bis(diphenylphosphino)-9,9-dimethylxanthene)-2-(2'-amino-1,1'-biphenyl)]palladium(II) methanesulfonate |
| XPhos Pd G2 | Chloro(2-dicyclohexylphosphino-2',4',6'-triisopropyl-1,1'-biphenyl)[2-(2'-amino-1,1'-biphenyl)]palladium(II) |

Intermediate 1.1: 4-(2,3-dimethylpyridin-4-yl)aniline

A suspension of 4-bromo-2,3-dimethyl-pyridine (3.3 g, 18 mmol, CAS: 259807-91-5), 4-(4,4,5,5-tetramethyl-1,3,2-dioxaborolan-2-yl)aniline (3.9 g, 18 mmol, CAS: 214360-73-3), potassium carbonate (6.1 g, 44 mmol) and Pd(dppf)$Cl_2$ (1.3 g, 1.8 mmol) in 1,4-dioxane (20 mL) and water (3 mL) was heated at 70° C. for 15 h. The reaction mixture was filtered through a pad of Celite® and concentrated in vacuo. The crude product was purified by flash column chromatography (eluting 100% EtOAc) to provide the title compound (2.6 g). LCMS (Method 1): 0.64 min, 199.1 $[M+H]^+$ Intermediate 1.2: 4-(3-chloropyridin-4-yl)aniline The title compound (0.18 g) was prepared from 3-chloro-4-iodo-pyridine (0.25 g, 1.0 mmol, CAS: 77332-79-7), 4-(4,4,5,5-tetramethyl-1,3,2-dioxaborolan-2-yl)aniline (0.23 g, 1.0 mmol, CAS: 214360-73-3), Pd(dppf)$Cl_2$ (0.85 g, 1.0 mmol) and sodium carbonate (0.33 g, 3.1 mmol) in accordance with the procedure described for Intermediate 1.1 heating at 80° C. for 4 h. The crude product was purified by flash column chromatography (eluting 50% EtOAc in heptanes). LCMS (Method 2): 0.63 min, 205.1 $[M+H]^+$ Intermediate 1.3: 4-(3-methoxypyridin-4-yl)aniline To a solution of (3-methoxy-4-pyridyl)boronic acid (0.7 g, 4.6 mmol, CAS: 1008506-24-8), 4-iodoaniline (1.0 g, 4.6 mmol, CAS: 540-37-4) and potassium phosphate (2.9 g, 13 mmol) in water (7 mL) and ethanol (7 mL) was added XPhos Pd G2 (1.8 g, 0.23 mmol) and the reaction heated to 80° C. for 6 h. The reaction mixture was diluted with water and the crude product extracted into EtOAc. The combined organics were washed with water, brine, dried over $Na_2SO_4$, filtered and concentrated in vacuo. The crude product was purified by flash column chromatography (eluting 50% EtOAc in heptanes) to provide the title compound (0.25 g). LCMS (Method 2): 0.54 min, 201.1 $[M+H]^+$ Intermediate 1.4: 4-(3-methylpyridin-4-yl)aniline The title compound (61 mg) was prepared from 4-chloro-3-methylpyridine hydrochloride (0.20 g, 1.2 mmol, CAS: 19524-08-4), 4-aminophenylboronic acid hydrochloride (0.17 g, 1.2 mmol, CAS: 80460-73-7), Pd(dppf)$Cl_2$ (0.10 g, 0.12 mmol) and sodium carbonate (0.39 g, 3.7 mmol) in accordance with the procedure described for Intermediate 1.1, heating at 80° C. for 3 h. The crude product was purified by flash column chromatography (eluting 60-80% EtOAc in heptanes). LCMS (Method 2): 0.57 min, 185.1 $[M+H]^+$ Intermediate 1.5: 4-(3-(trifluoromethyl)pyridin-4-yl)aniline The title compound (75 mg) was prepared from 4-chloro-3-(trifluoromethyl)pyridine hydrochloride (0.20 g, 0.92 mmol, CAS: 732306-24-0), 4-aminophenylboronic acid hydrochloride (0.17 g, 1.0 mmol, CAS: 80460-73-7), Pd(dppf)$Cl_2$ (34 mg, 0.05 mmol) and sodium carbonate (0.39 g, 3.7 mmol) in accordance with the procedure described for Intermediate 1.1, heating at 80° C. for 6 h. The crude product was purified by flash column chromatography (eluting 50% EtOAc in heptanes). LCMS (Method 2): 0.71 min, 239.1 $[M+H]^+$ Intermediate 1.6: 4-(3,5-dimethylpyridin-4-yl)aniline To a stirred suspension of 4-chloro-3,5-dimethyl-pyridine (0.40 g, 2.8 mmol, CAS: 143798-73-6), 4-aminophenylboronic acid hydrochloride (0.59 g, 3.4 mmol, CAS: 80460-73-7) and sodium carbonate (0.96 g, 9.0 mmol) in degassed water (8 mL) and 1,4-dioxane (8 mL) was added Pd(dppf) $Cl_2$ (0.21 g, 0.28 mmol) and then heated by microwave irradiation at 120° C. for 2 h. The reaction mixture was filtered through a pad of Celite® and rinsed with EtOAc. The filtrate was washed with brine, dried over $MgSO_4$, filtered and concentrated in vacuo. The crude product was purified by flash column chromatography (eluting 10-30% EtOAc in DCM) to provide the title compound (0.15 g). LCMS (Method 3): 1.42 min, 199.1 $[M+H]^+$ Intermediate 1.7: 4-(4-aminophenyl)-N-methylpyridin-3-amine Intermediate 1.7a: methyl (E)-N-(4-iodopyridin-3-yl)formimidate A suspension of 4-iodopyridin-3-amine (2.0 g, 9.1 mmol, CAS: 105752-11-2) in trimethyl orthoformate (20 mL, 182 mmol) and TFA (0.04 mL, 0.52 mmol) was heated at reflux for 2 h. The reaction mixture was concentrated in vacuo to provide the title compound (2.4 g) which was used without further purification. LCMS (Method 2): 0.66 min, 262.9 $[M+H]^+$ Intermediate 1.7b: 4-iodo-N-methylpyridin-3-amine To a suspension of Intermediate 1.7a (2.6 g, 9.9 mmol) in anhydrous THF (20 mL) was added dropwise $LiAlH_4$ (5.2 mL, 5.2 mmol, 1 M in THF) at −5° C. under argon. The reaction was stirred at −5° C. for 30 min, then warmed to 0° C. and quenched with saturated aqueous $NH_4Cl$. The mixture was diluted with EtOAc, filtered through a pad of Celite®, rinsed with EtOAc and the filtrate dried over $MgSO_4$, filtered and concentrated in vacuo. The crude product was purified by flash column chromatography (eluting 50% EtOAc in heptanes) to provide the title compound (0.58 g). LCMS (Method 2): 0.60 min, 234.9 $[M+H]^+$ Intermediate 1.7: 4-(4-aminophenyl)-N-methylpyridin-3-amine The title compound (0.14 g) was prepared from Intermediate 1.7b (0.15 g, 0.64 mmol), 4-(4,4,5,5-tetramethyl-1,3,2-dioxaborolan-2-yl)aniline (0.15 g, 0.71 mmol, CAS: 214360-73-3), Pd(dppf)$Cl_2$ (47 mg, 0.06 mmol) and potassium carbonate (0.22 g, 1.6 mmol) in accordance with the procedure described for Intermediate 1.1, heating at 70° C. for 16 h. The crude product was purified by flash column chromatography (eluting 100% EtOAc) and by reverse phase column chromatography on the Biotage Isolera One™ (30 g C18 column, eluting 0-40% MeCN in pH10 0.1 M $NH_4HCO_3$ buffer solution). LCMS (Method 2): 0.50 min, 200.1 $[M+H]^+$ Intermediate 1.8: 4-(4-aminophenyl)-N,N-dimethylpyridin-3-amine Intermediate 1.8a: 4-iodo-N,N-dimethylpyridin-3-amine To a solution of 4-iodopyridin-3-amine (0.5 g, 2.3 mmol, CAS: 105752-11-2) in anhydrous DMF (40 mL) was added sodium hydride (60% dispersion in mineral oil, 0.27 g, 6.8 mmol) at rt under argon. The mixture was stirred at rt for 30 min then cooled to 0° C., iodomethane (0.42 mL, 6.8 mmol) was added dropwise over 10 min at 0° C. and the reaction was stirred at 0° C. for 3 h. The mixture was quenched with 2 M aqueous NaOH and extracted into EtOAc. The combined organics were washed with water, dried over $MgSO_4$, filtered and concentrated in vacuo. The crude product was purified by flash column chromatography (eluting 20% EtOAc in hexanes) to provide the title compound (0.35 g). LCMS (Method 2): 0.70 min, 248.9 $[M+H]^+$ Intermediate 1.8: 4-(4-aminophenyl)-N,N-dimethylpyridin-3-amine The title compound (75 mg) was prepared from Intermediate 1.8a (0.15 g, 0.60 mmol), 4-(4,4,5,5-tetramethyl-1,3,2-dioxaborolan-2-yl)aniline (0.13 g, 0.60 mmol, CAS: 214360-73-3), Pd(dppf)$Cl_2$ (44 mg, 0.06 mmol) and potassium carbonate (0.21 g, 1.5 mmol) in accordance with the procedure described for Intermediate 1.1, heating at 70° C. for 16 h. The crude product was purified by reverse phase column chromatography on the Biotage Isolera One™ (30 g C18 column, eluting 0-40% MeCN in pH10 0.1 M $NH_4HCO_3$ buffer solution) and by flash column chromatography (eluting 90% EtOAc in hexanes). LCMS (Method 2): 0.63 min, 214.1 $[M+H]^+$ Intermediate 1.9: 4-(3,5-dimethoxypyridin-4-yl)aniline The title compound (0.18 g) was prepared from 4-bromo-3,5-dimethoxy-pyridine (0.20 g, 0.92 mmol, CAS: 1033610-45-5), 4-(4,4,5,5-tetramethyl-1,3,2-dioxaborolan-2-yl)aniline (0.22 g, 1.0 mmol, CAS: 214360-73-3), Pd(dppf)$Cl_2$ (0.10 g, 0.14 mmol) and potassium carbonate (0.32 g, 2.3 mmol) in accordance with the procedure described for Intermediate 1.1, heating at 90° C. for 16 h. The crude product was purified by flash column chromatography (eluting 100% EtOAc). LCMS (Method 2): 0.52 min, 231.1 $[M+H]^+$ Intermediate 1.10: 4-(3-fluoro-5-methoxypyridin-4-yl)aniline The title compound (0.17 g) was prepared from 4-bromo-3-fluoro-5-methoxy-pyridine (0.20 g, 0.97 mmol, CAS: 1256825-73-6), 4-(4,4,5,5-tetramethyl-1,3,2-dioxaborolan-2-yl)aniline (0.23 g, 1.1 mmol, CAS: 214360-73-3), Pd(dppf)$Cl_2$ (71 mg, 0.10 mmol) and potassium carbonate (0.33 g, 2.4 mmol) in accordance with the procedure described for Intermediate 1.1, heating at 80° C. for 16 h. The crude product was purified by flash column chromatography (eluting 60% EtOAc in hexanes). LCMS (Method 2): 0.58 min, 219.1 $[M+H]^+$ Intermediate 1.11: 5-(4-aminophenyl)-6-methylpyridin-2(1H)-one The title compound (0.14 g) was prepared from 5-bromo-6-methyl-pyridin-2-ol (0.50 g, 2.6 mmol, CAS: 54923-31-8), 4-(4,4,5,5-tetramethyl-1,3,2-dioxaborolan-2-yl)aniline (0.63 g, 3.0 mmol, CAS: 214360-73-3), Pd(dppf)$Cl_2$ (97 mg, 0.13 mmol) and sodium carbonate (0.85 g, 8.0 mmol) in accordance with the procedure described for Intermediate 1.1, heating at 80° C. for 20 h. The crude product was purified by flash column chromatography (eluting 50-100% EtOAc in heptanes). LCMS (Method 2): 0.38 min, 201.1 $[M+H]^+$ Intermediate 1.12: 5-(4-aminophenyl)-1,4-dimethylpyridin-2(1H)-one Intermediate 1.12a: 5-bromo-1,4-dimethylpyridin-2(1H)-one To a suspension of 5-bromo-4-methyl-pyridin-2-ol (0.15 g, 0.80 mmol, CAS: 164513-38-6) in acetone (10 mL) was added potassium carbonate (0.52 g, 3.8 mmol) followed by iodomethane (0.22 mL, 3.6 mmol). The resulting mixture was stirred at rt for 6 h. The precipitate was removed by filtration, rinsed with acetone, and the liquors concentrated to dryness in vacuo. The crude product was purified by flash column chromatography (eluting 0-15% MeOH in EtOAc) to give the title compound (0.20 g). LCMS (Method 4): 0.48 min, 204.0 $[M+H]^+$ Intermediate 1.12: 5-(4-aminophenyl)-1,4-dimethylpyridin-2(1H)-one The title compound (0.11 g) was prepared from Intermediate 1.12a (0.20 g, 0.97 mmol), 4-(4,4,5,5-tetramethyl-1,3,2-dioxaborolan-2-yl)aniline (0.23 g, 1.1 mmol, CAS: 214360-73-3), Pd(dppf)$Cl_2$ (79 mg, 0.10 mmol) and sodium carbonate (0.31 g, 2.9 mmol) in accordance with the procedure described for Intermediate 1.1, heating at 80° C. for 4 h. The crude product was purified by flash column chromatography on the Biotage Isolera One™ (30 g ZIP sphere silica column, eluting 40-100% EtOAc in heptanes). LCMS (Method 4): 0.42 min, 215.1 $[M+H]^+$ Intermediate 1.13: 5-(4-aminophenyl)-1,6-dimethylpyridin-2(1H)-one Intermediate 1.13a: 5-bromo-1,6-dimethylpyridin-2(1H)-one To a suspension of 5-bromo-6-methyl-pyridin-2-ol (0.5 g, 2.7 mmol, CAS: 54923-31-8) in acetone (33 mL) was added potassium carbonate (1.7 g, 13 mmol) followed by iodomethane (0.74 mL, 12 mmol) and the resulting mixture stirred at rt for 6 h. The precipitate was removed by filtration, rinsed with acetone, and the liquors concentrated to dryness in vacuo. The crude product was purified by flash column chromatography on the Biotage Isolera One™ (30 g ZIP sphere silica column, eluting 60-100% EtOAc in heptanes, followed by 0-10% MeOH in EtOAc) to give the title compound (0.37 g). LCMS (Method 4): 0.52 min, 203.9 $[M+H]^+$ Intermediate 1.13: 5-(4-aminophenyl)-1,6-dimethylpyridin-2(1H)-one The title compound (0.13 g) was prepared from Intermediate 1.13a (0.17 g, 0.79 mmol), 4-(4,4,5,5-tetramethyl-1,3,2-dioxaborolan-2-yl)aniline (0.41 g, 1.9 mmol, CAS: 214360-73-3), XPhos Pd G2 (12 mg, 0.02 mmol) and potassium carbonate (0.31 g, 4.7 mmol) in accordance with the procedure described for Intermediate 1.3, heating at 85° C. for 1 h. The crude product was purified by flash column chromatography on the Biotage Isolera One™ (30 g ZIP sphere silica column, eluting 40-100% EtOAc in heptanes followed by 0-10% MeOH in EtOAc). LCMS (Method 4): 0.50 min, 215.1 $[M+H]^+$ Intermediate 1.14: 4-(3,5-dimethylpyridin-4-yl)-3-fluoroaniline The title compound (0.1 g) was prepared from 4-chloro-3,5-dimethyl-pyridine (0.20 g, 1.4 mmol, CAS: 143798-73-6), 3-fluoro-4-(4,4,5,5-tetramethyl-1,3,2-dioxaborolan-2-yl) aniline (0.37 g, 1.6 mmol, CAS: 819057-45-9), $Pd(dppf)Cl_2$ (51 mg, 0.07 mmol) and sodium carbonate (0.45 g, 4.2 mmol) in accordance with the procedure described for Intermediate 1.6, and heated by microwave irradiation at 120° C. for 1 h. The crude product was purified by flash column chromatography (eluting 50-100% EtOAc in heptanes). LCMS (Method 4): 0.66 min, 217.1 [M+H]+

Intermediate 1.15: 3-fluoro-4-(3-methylpyridin-4-yl)aniline

The title compound (0.17 g) was prepared from 4-chloro-3-methyl-pyridine hydrochloride (0.25 g, 1.5 mmol, CAS: 19524-08-4), 3-fluoro-4-(4,4,5,5-tetramethyl-1,3,2-dioxaborolan-2-yl)aniline (0.36 g, 1.5 mmol, CAS: 819057-45-9), $Pd(dppf)Cl_2$ (111.5 mg, 0.15 mmol) and sodium carbonate (0.57 g, 5.4 mmol) in accordance with the procedure described for Intermediate 1.6, and heated by microwave irradiation at 120° C. for 1 h. The crude product was purified by flash column chromatography on silica gel (eluting 70% EtOAc in heptanes). LCMS (Method 4): 0.62 min, 203.0 $[M+H]^+$ Intermediate 1.16: 5-(4-amino-2-fluorophenyl)-1,6-dimethylpyridin-2(1H)-one The title compound (0.16 g) was prepared from Intermediate 1.13a (0.23 g, 1.14 mmol), 3-fluoro-4-(4,4,5,5-tetramethyl-1,3,2-dioxaborolan-2-yl)aniline (0.27 g, 1.14 mmol, CAS: 819057-45-9), $Pd(dppf)Cl_2$ (83 mg, 0.11 mmol) and sodium carbonate (0.30 g, 2.9 mmol) in accordance with the procedure described for Intermediate 1.1, heating at 80° C. for 5 h. The crude product was purified by flash column chromatography (eluting 2% MeOH in EtOAc). LCMS (Method 3): 1.07 min, 233.1 $[M+H]^+$ Intermediate 1.17: 5-(4-amino-2-fluorophenyl)-1,4-dimethylpyridin-2(1H)-one The title compound (0.19 g) was prepared from Intermediate 1.12a (0.28 g, 1.4 mmol), 3-fluoro-4-(4,4,5,5-tetramethyl-1,3,2-dioxaborolan-2-yl)aniline (0.33 g, 1.4 mmol, CAS: 819057-45-9), $Pd(dppf)Cl_2$ (0.10 g, 0.14 mmol) and sodium carbonate (0.37 g, 3.5 mmol) in accordance with the procedure described for Intermediate 1.1, heating at 80° C. for 5 h. The crude product was purified by flash column chromatography on silica gel (eluting 2% MeOH in EtOAc). LCMS (Method 4): 0.49 min, 233.1 $[M+H]^+$ Intermediate 1.18: 3-fluoro-4-(3-fluoro-5-methoxypyridin-4-yl)aniline The title compound (0.26 g) was prepared from 4-bromo-3-fluoro-5-methoxy-pyridine (0.24 g, 1.1 mmol, CAS: 1256825-73-6), 3-fluoro-4-(4,4,5,5-tetramethyl-1,3,2-dioxaborolan-2-yl)aniline (0.30 g, 1.3 mmol, CAS: 819057-45-9), $Pd(dppf)Cl_2$ (83 mg, 0.11 mmol) and potassium carbonate (0.39 g, 2.9 mmol) in accordance with the procedure described for Intermediate 1.1, heating at 85° C. for 16 h. The crude product was purified by flash column chromatography (eluting 50% EtOAc in heptanes). LCMS (Method 4): 0.69 min, 237.0 $[M+H]^+$ Intermediate 1.20: 4-(3-methoxypyridin-4-yl)-3-methylaniline Intermediate 1.20a: N-(4-(3-methoxypyridin-4-yl)-3-methylphenyl)acetamide The title compound (0.27 g) was prepared from N-(4-bromo-3-methyl-phenyl)acetamide (0.23 g, 0.99 mmol, CAS: 90914-81-1), (3-methoxy-4-pyridyl)boronic acid (0.15 g, 0.99 mmol, CAS: 1008506-24-8), $Pd(dppf)Cl_2$ (0.81 g, 0.10 mmol) and sodium carbonate (0.31 g, 3.0 mmol) in accordance with the procedure described for Intermediate 1.1, heating at 80° C. for 3 h. The crude product was purified by flash column chromatography on the Biotage Isolera One™ (30 g ZIP sphere silica column, eluting 40-100% EtOAc in heptanes). LCMS (Method 2): 0.54 min, 257.1 $[M+H]^+$ Intermediate 1.20: 4-(3-methoxypyridin-4-yl)-3-methylaniline A solution of Intermediate 1.20a (0.25 g, 0.98 mmol) in MeOH (15 mL) and sodium hydroxide (2 M aqueous; 2.5 mL, 4.9 mmol) was stirred at 80° C. for 4 h. The mixture was diluted with water and extracted into EtOAc. The combined organics were dried over $MgSO_4$, filtered and concentrated in vacuo to give the title compound (130 mg) which was used without further purification. LCMS (Method 2): 0.56 min, 215.1 $[M+H]^+$ Intermediate 1.21: 4-(1H-pyrrolo[2,3-b]pyridin-4-yl)aniline The title compound (0.53 g) was prepared from 4-bromo-1H-pyrrolo[2,3-b]pyridine (0.50 g, 2.5 mmol, CAS: 348640-06-2), 4-(4,4,5,5-tetramethyl-1,3,2-dioxaborolan-2-yl)aniline (0.61 g, 2.8 mmol, CAS: 214360-73-3), $Pd(dppf)Cl_2$ (93 mg, 0.13 mmol) and sodium carbonate (0.81 g, 7.6 mmol) in accordance with the procedure described for Intermediate 1.1, heating at 80° C. for 2 h. The crude product was purified by flash column chromatography (eluting 66% EtOAc in heptanes). LCMS (Method 2): 0.54 min, 210.1 $[M+H]^+$ Intermediate 1.22: 4-(2,3-dihydro-1H-pyrrolo[2,3-b]pyridin-4-yl)aniline To a stirred solution of Intermediate 1.21 (0.1 g, 0.48 mmol) in THF (2 mL) at rt under an atmosphere of argon, was added borane dimethyl sulfide complex (0.27 mL, 2.9 mmol) dropwise and the mixture stirred in a sealed tube at 80° C. for 16 h. The reaction was quenched at 0° C. with MeOH followed by water and ethanolamine, then heated at reflux for 2 min. The mixture was extracted with EtOAc, the combined organics were washed with saturated aqueous $NaHCO_3$, brine, dried over $Na_2SO_4$, filtered and concentrated in vacuo. The crude product was purified by reverse phase column chromatography on the Biotage Isolera One™ (16 g C18 column, eluting 25-50% MeCN in pH10 0.1 M $NH_4HCO_3$ buffer solution) to afford the title compound (35 mg). LCMS (Method 5): 1.05 min, 212.1 $[M+H]^+$ Intermediate 1.23: 2-fluoro-4-(3-methoxypyridin-4-yl)aniline The title compound (0.16 g) was prepared from (3-methoxy-4-pyridyl)boronic acid (0.25 g, 1.6 mmol, CAS: 1008506-24-8), 2-fluoro-4-iodo-aniline (0.39 g, 1.7 mmol, CAS: 29632-74-4), XPhos Pd G2 (76 mg, 0.10 mmol) and potassium phosphate (1.0 g, 4.9 mmol) in accordance with the procedure described for Intermediate 1.3. The crude product was purified by flash column chromatography (eluting 50% EtOAc in hexanes). LCMS (Method 2): 0.59 min, 219.1 $[M+H]^+$ Intermediate 1.24: 3-fluoro-4-(3-methoxypyridin-4-yl)aniline The title compound (0.15 g) was prepared from (3-methoxy-4-pyridyl)boronic acid (0.25 g, 1.6 mmol, CAS: 1008506-24-8), 3-fluoro-4-iodo-aniline (0.39 g, 1.7 mmol, CAS: 656-66-6), XPhos Pd G2 (76 mg, 0.10 mmol) and potassium phosphate (1.0 g, 4.9 mmol) in accordance with the procedure described for Intermediate 1.3. The crude product was purified by flash column chromatography (eluting 60% EtOAc in hexanes). LCMS (Method 2): 0.57 min, 219.1 $[M+H]^+$ Intermediate 1.29: 5-(4-amino-2,6-difluorophenyl)-1,6-dimethylpyridin-2(1H)-one Intermediate 1.29a: 3,5-difluoro-4-(4,4,5,5-tetramethyl-1,3,2-dioxaborolan-2-yl)aniline To a solution of 4-bromo-3,5-difluoro-aniline (1.1 g, 5.3 mmol, CAS: 203302-95-8), triethylamine (3.0 mL, 21 mmol), and XPhos Pd G2 (42 mg, 0.06 mmol) in degassed anhydrous toluene (33 mL) at rt was added 4,4,5,5-tetramethyl-1,3,2-dioxaborolane (2.3 mL, 16 mmol) dropwise and the reaction mixture was stirred at 100° C. for 4 h. The mixture was filtered through Celite®, washed with EtOAc, diluted with water and extracted into EtOAc. The combined organics were washed with water, brine, dried over $MgSO_4$, filtered and concentrated in vacuo. The crude product was purified by flash column chromatography on the Biotage Isolera One™ (120 g ZIP sphere silica column, eluting 0-45% EtOAc in heptanes) to provide the title compound (0.86 g). LCMS (Method 3): 1.14 min, 254.0 $[M-H]^-$ Intermediate 1.29: 5-(4-amino-2,6-difluorophenyl)-1,6-dimethylpyridin-2(1H)-one To a solution of Intermediate 1.13a (0.1 g, 0.49 mmol) and Intermediate 1.29a (0.15 g, 0.59 mmol) in a mixture of degassed 1,4-dioxane (3 mL) and degassed potassium phosphate (2 M aqueous; 0.74 mL, 1.5 mmol) at rt and under argon, was added XPhos Pd G2 (20 mg, 0.02 mmol). The reaction mixture was heated to 45° C. and additional quantities of Intermediate 1.29a (3×35 mg, 0.42 mmol) were added portion-wise over 3 h. The reaction mixture was filtered through Celite® and washed with EtOAc. The filtrate was diluted with water and the crude product extracted into EtOAc. The combined organics were washed with water, brine, dried over $MgSO_4$, filtered and concentrated in vacuo and the crude product was purified by flash column chromatography on the Biotage Isolera One™ (45 g ZIP sphere silica column, eluting 20-100% EtOAc in heptanes) to provide the title compound (0.10 g). LCMS (Method 3): 1.19 min, 251.0 $[M+H]^+$ Intermediate 1.30: 3,5-difluoro-4-(3-methoxypyridin-4-yl)aniline The title compound (0.11 g) was prepared from (3-methoxy-4-pyridyl)boronic acid (0.17 g, 1.1 mmol, CAS: 1008506-24-8), 4-bromo-3,5-difluoro-aniline (0.27 g, 1.3 mmol, CAS: 203302-95-8), XPhos Pd G2 (85 mg, 0.11 mmol) and potassium phosphate (2 M aqueous; 1.8 mL, 3.2 mmol) in accordance with the procedure described for Intermediate 1.29. The crude product was purified by flash column chromatography (eluting 40-100% EtOAc in heptanes). LCMS (Method 3): 1.47 min, 237.1 $[M+H]^+$ Intermediate 1.31: 4-(1-benzyl-3,5-dimethyl-1H-pyrazol-4-yl)aniline hydrochloride Intermediate 1.31a: tert-butyl (4-(3,5-dimethyl-1H-pyrazol-4-yl)phenyl)carbamate hydrochloride The title compound (0.27 g) was prepared from tert-butyl (4-(4,4,5,5-tetramethyl-1,3,2-dioxaborolan-2-yl)phenyl)carbamate (0.44 g, 1.4 mmol, CAS: 330793-01-6]), 4-bromo-3,5-dimethyl-1H-pyrazole (0.20 g, 1.1 mmol, CAS: 3398-16-1), XPhos Pd G2 (9 mg, 0.01 mmol) and potassium carbonate (1.8 M aqueous; 1.9 mL, 3.4 mmol) in accordance with the procedure described for Intermediate 1.3 and with heating by microwave irradiation. The crude product was purified flash column chromatography on the Biotage Isolera One™ (30 g ZIP sphere silica column, eluting 20-100% EtOAc in heptanes). LCMS (Method 4): 0.84 min, 288.2 $[M+H]^+$ Intermediate 1.31b: tert-butyl (4-(1-benzyl-3,5-dimethyl-1H-pyrazol-4-yl)phenyl)carbamate To a solution of Intermediate 1.31a (0.27 g, 0.83 mmol) and potassium carbonate (0.29 g, 2.1 mmol) in acetone (20 mL) was added bromomethylbenzene (0.10 mL, 0.83 mmol) and the reaction heated at 55° C. for 3 days. The solvent was concentrated in vacuo and the crude product purified by flash column chromatography on the Biotage Isolera One™ (30 g ZIP sphere silica column, eluting 30-100% EtOAc in heptanes) to give the title compound (0.11 g). LCMS (Method 4): 1.06 min, 378.3 $[M+H]^+$ Intermediate 1.31: 4-(1-benzyl-3,5-dimethyl-1H-pyrazol-4-yl)aniline hydrochloride A solution of Intermediate 1.31b (0.11 g, 0.25 mmol) in HCl (3 M in 1,4-dioxane; 4.0 mL, 0.25 mmol) was stirred at rt for 2 h. The solvent was concentrated in vacuo to give the title compound (78 mg). The crude product was used without further purification. LCMS (Method 4): 0.82 min, 278.2 $[M+H]^+$ Intermediate 1.34: 6-(4-amino-2-fluorophenyl)pyridazin-3(2H)-one The title compound (0.13 g) was prepared from 3-fluoro-4-(4,4,5,5-tetramethyl-1,3,2-dioxaborolan-2-yl)aniline (0.18 g, 0.77 mmol, CAS: 819057-45-9), 3-chloro-1H-pyridazin-6-one (0.1 g, 0.77 mmol, CAS: 19064-67-6), XPhos Pd G2 (12 mg, 0.02 mmol) and a solution of tripotassium phosphate (1.8 M aqueous, 1.28 mL, 2.3 mmol) in accordance with the procedure described for Intermediate 1.3. The crude product was purified by flash column chromatography (eluting 20-100% EtOAc in heptanes, followed by 10% MeOH in DCM). LCMS (Method 4): 0.38 min, 206.2 $[M+H]^+$ Intermediate 1.35: 4-(4-amino-2-fluorophenyl)pyridin-2(1H)-one The title compound (0.29 g) was prepared from 3-fluoro-4-(4,4,5,5-tetramethyl-1,3,2-dioxaborolan-2-yl)aniline (0.3 g, 1.3 mmol, CAS: 819057-45-9), 4-bromo-1H-pyridin-2-one (0.2 g, 1.2 mmol, CAS: 36953-37-4), Pd(dppf)$Cl_2$ (84 mg, 0.11 mmol) and sodium carbonate (0.31 mg, 2.9 mmol) in accordance with the procedure described for Intermediate 1.6, heating at 80° C. for 4 h. The crude product was purified by flash column chromatography (eluting 5% MeOH in EtOAc). LCMS (Method 4): 0.39 min, 205.0 $[M+H]^+$ Intermediate 1.37: 4-(2,5-dimethylpyrimidin-4-yl)aniline The title compound (0.24 g) was prepared from 4-(4,4,5,5-tetramethyl-1,3,2-dioxaborolan-2-yl)aniline (0.31 g, 1.4 mmol, CAS: 214360-73-3), 4-chloro-2,5-dimethyl-pyrimidine (0.2 g, 1.4 mmol, CAS: 75712-74-2), Pd(dppf)$Cl_2$ (0.12 mg, 0.14 mmol) and sodium carbonate (0.45 g, 4.2 mmol) in accordance with the procedure described for Intermediate 1.6, heating at 80° C. for 4 h. The crude product was purified by flash column chromatography (eluting 40-50% EtOAc in heptanes). LCMS (Method 2): 0.49 min, 200.1 $[M+H]^+$ Intermediate 1.40: 4-(6,7-dihydro-5H-pyrrolo[2,3-d]pyrimidin-4-yl)aniline The title compound (0.25 g) was prepared from 4-(4,4,5,5-tetramethyl-1,3,2-dioxaborolan-2-yl)aniline (0.28 g, 1.3 mmol CAS: 214360-73-3), 4-chloro-6,7-dihydro-5H-pyrrolo[2,3-d]pyrimidine (0.2 g, 1.3 mmol, CAS: 16372-08-0), Pd(dppf)$Cl_2$ (0.11 g, 0.13 mmol) and sodium carbonate (0.41 g, 3.9 mmol) in accordance with the procedure described for Intermediate 1.6, heating at 80° C. for 3 h. The crude product was purified by flash column chromatography (eluting 50% EtOAc in heptanes). LCMS (Method 2): 0.40 min, 213.1 $[M+H]^+$ Intermediate 1.41: 4-(imidazo[1,2-a]pyrimidin-3-yl)aniline The title compound (0.21 g) was prepared from 4-(4,4,5,5-tetramethyl-1,3,2-dioxaborolan-2-yl)aniline (0.33 g, 1.5 mmol, CAS: 214360-73-3), 3-bromoimidazo[1.2-a]pyrimidine (0.3 g, 1.5 mmol, CAS: 6840-45-5), Pd(dppf)$Cl_2$ (62 mg, 0.08 mmol) and sodium carbonate (1 M aqueous, 4.5 mL, 4.5 mmol) in accordance with the procedure described for Intermediate 1.6, heating at 60° C. for 2 h. The crude product was purified by flash column chromatography (eluting 5% MeOH in EtOAc). LCMS (Method 2): 0.39 min, 211.1 $[M+H]^+$ Intermediate 1.42: (4-(4-aminophenyl)pyridin-3-yl)methanol hydrochloride Intermediate 1.42a: tert-butyl N—[4-(3-formyl-4-pyridyl)phenyl]carbamate The title compound (0.4 g) was prepared from 4-chloropyridine-3-carbaldehyde (0.2 g, 1.4 mmol, CAS: 114077-82-6]), tert-butyl N—[4-(4,4,5,5-tetramethyl-1,3,2-dioxaborolan-2-yl)phenyl]carbamate (0.45 g, 1.4 mmol), Pd(dppf)$Cl_2$ (0.12 mg, 0.14 mmol) and sodium carbonate (0.45 g, 4.3 mmol) in accordance with the procedure described for Intermediate 1.6, heating at 80° C. for 4 h. The crude product was purified by flash column chromatography on the Biotage Isolera One™ (30 g ZIP sphere silica column, eluting 40-100% EtOAc in heptanes). LCMS (Method 2): 0.82 min, 299.1 $[M+H]^+$ Intermediate 1.42b: tert-butyl N—[4-[3-(hydroxymethyl)-4-pyridyl]phenyl]carbamate To a solution of Intermediate 1.42a (0.2 g, 0.67 mmol) in MeOH (3 mL) was added sodium borohydride (51 mg, 1.4 mmol) and the reaction stirred at rt for 1.5 h. The reaction was diluted with water and extracted into EtOAc. The combined organics were dried over $MgSO_4$, filtered and concentrated in vacuo to give the title compound (0.16 g) which was used without further purification. LCMS (Method 2): 0.70 min, 301.1 $[M+H]^+$ Intermediate 1.42: (4-(4-aminophenyl)pyridin-3-yl)methanol hydrochloride Intermediate 1.42b (0.16 g, 0.54 mmol) was mixed with HCl (3 M in 1,4 dioxane, 4 mL, 0.54 mmol) and the reaction stirred at rt for 2 h. The reaction mixture was concentrated in vacuo to provide the title compound (0.13 g) which was used without further purification. LCMS (Method 2): 0.40 min, 201.1 $[M+H]^+$ Intermediate 1.44: 4-(6,7-dihydro-5H-cyclopenta[b]pyridin-4-yl)aniline The title compound (65 mg) was prepared from 4-(4,4,5,5-tetramethyl-1,3,2-dioxaborolan-2-yl)aniline (0.18 g, 0.81 mmol, CAS: 214360-73-3), 4-chloro-6,7-dihydro-5H-cyclopenta[b]pyridine (0.13 g, 0.81 mmol, CAS: 54664-55-0), Pd(dppf)$Cl_2$ (66 mg, 0.08 mmol) and sodium carbonate (0.26 g, 2.4 mmol) in accordance with the procedure described for Intermediate 1.6, heating at 80° C. for 5 h. The crude product was purified by flash column chromatography (eluting 50-100% EtOAc in heptanes). LCMS (Method 2): 0.62 min, 211.1 $[M+H]^+$ Intermediate 1.47: 3-methoxy-4-(3-methoxypyridin-4-yl)aniline The title compound (32 mg) was prepared from (3-methoxy-4-pyridyl)boronic acid (0.13 g, 0.82 mmol, CAS: 1008506-24-8), 4-bromo-3-methoxy-aniline (0.17 g, 0.82 mmol CAS: 19056-40-7), Pd(dppf)$Cl_2$ (66 mg, 0.08 mmol) and sodium carbonate (0.26 g, 2.5 mmol) in accordance with the procedure described for Intermediate 1.6, heating at 80° C. for 16 h. The crude product was purified by flash column chromatography on the Biotage Isolera One™ (30 g ZIP sphere silica column, eluting 40-100% EtOAc in heptanes). LCMS (Method 2): 0.52 min, 231.1 $[M+H]^+$ Intermediate 1.48: 6-(4-amino-2-fluorophenyl)-2-methylpyridazin-3(2H)-one The title compound (0.15 g) was prepared from (3-fluoro-4-(4,4,5,5-tetramethyl-1,3,2-dioxaborolan-2-yl)aniline (0.18 g, 0.77 mmol, CAS: 819057-45-9), 6-chloro-2-methyl-pyridazin-3-one (0.11 g, 0.77 mmol CAS: 10071-38-2), XPhos Pd G2 (12 mg, 0.02 mmol) and a solution of tripotassium phosphate (1.8 M aqueous, 1.3 mL, 2.3 mmol) in accordance with the procedure described for Intermediate 1.3. The crude product was purified by flash column chromatography (eluting 50-100% EtOAc in heptanes). LCMS (Method 4): 0.48 min, 220.0 $[M+H]^+$ Intermediate 1.51: 5-(4-aminophenyl)-1-methylpyridin-2(1H)-one The title compound (0.18 g) was prepared from 4-(4,4,5,5-tetramethyl-1,3,2-dioxaborolan-2-yl)aniline (0.26 g, 1.2 mmol, CAS: 214360-73-3), 5-bromo-1-methyl-pyridin-2-one (0.2 g, 1 mmol, CAS: 81971-39-3), Pd(dppf)$Cl_2$ (87 mg, 0.11 mmol) and sodium carbonate (0.34 g, 3.2 mmol) in accordance with the procedure described for Intermediate 1.6. The crude product was purified by flash column chromatography on the Biotage Isolera One™ (30 g ZIP sphere silica column, eluting 60-100% EtOAc in heptanes then 7% MeOH in EtOAc). LCMS (Method 24): 0.64 min, 201.1 $[M+H]^+$ Intermediate 1.52: 4-(4-aminophenyl)-1,6-dihydro-7H-pyrrolo[2,3-c]pyridin-7-one To a stirred suspension of 4-(4,4,5,5-tetramethyl-1,3,2-dioxaborolan-2-yl)aniline (0.2 mg, 0.89 mmol, CAS: 214360-73-3) and 4-bromo-1,6-dihydropyrrolo[2,3-c]pyridin-7-one (0.19 mg, 0.89 mmol, CAS: 1361481-62-0) in degassed ethanol (24 mL) and a solution of tripotassium phosphate (1.8 M aqueous, 1.5 mL, 2.7 mmol) were added XPhos (85 mg, 0.18 mmol) and XPhos Pd G2 (70 mg, 0.09 mmol) and the reaction mixture heated by microwave irradiation at 100° C. for 1 h. The solvent was removed in vacuo and the residue triturated with toluene. The crude product was purified twice by flash column chromatography (eluting 5-10% MeOH in DCM) to give the title compound (0.13 g). LCMS (Method 4): 0.44 min, 226.07 $[M+H]^+$ Intermediate 1.53: 4-(4-amino-2-methoxyphenyl)pyridin-3-yl)methanol dihydrochloride tert-Butyl N—[4-[3-(hydroxymethyl)-4-pyridyl]-3-methoxy-phenyl]carbamate (0.1 mg, 0.17 mmol, CAS: 1622889-96-6) was dispersed in HCl (3 M in CPME, 2.3 mL, 6.9 mmol), under an atmosphere of argon, and stirred at rt for 2 h. The reaction mixture was concentrated in vacuo to provide the title compound (52 mg) which was used without further purification. LCMS (Method 2): 0.42 min, 231.1 $[M+H]^+$ Intermediate 1.54: 5-(4-amino-2-(trifluoromethyl) phenyl)-1,6-dimethylpyridin-2(1H)-one The title compound (0.11 g) was prepared from 4-(4,4,5,5-tetramethyl-1,3,2-dioxaborolan-2-yl)-3-(trifluoromethyl) aniline (0.18 g, 0.63 mmol, CAS: 1259285-61-4), 5-bromo-1,6-dimethyl-pyridin-2-one (0.13 mg, 0.63 mmol, CAS: 889865-54-7), XPhos Pd G2 (12 mg, 0.02 mmol) and a solution of tripotassium phosphate (1.8 M aqueous, 1 mL, 1.9 mmol) in accordance with the procedure described for Intermediate 1.3, heating at 100° C. for 1.5 h. The crude product was purified by flash column chromatography (eluting 100% EtOAc). LCMS (Method 3): 1.38 min, 283.1 $[M+H]^+$ Intermediate 1.55: 3-chloro-4-(3,5-dimethylpyridin-4-yl)aniline The title compound (96 mg) was prepared from 3-chloro-4-(4,4,5,5-tetramethyl-1,3,2-dioxaborolan-2-yl)aniline (0.34 g, 1.3 mmol, CAS: 877160-63-9), 4-chloro-3,5-dimethyl-pyridine (0.17 g, 1.2 mmol, CAS: 143798-73-6), XPhos Pd G2 (95 mg, 0.12 mmol) and a solution of tripotassium phosphate (1.8 M aqueous, 1.8 mL, 3.6 mmol) in accordance with the procedure described for Intermediate 1.3. The crude product was purified by flash column chromatography on the Biotage Isolera One™ (80 g ZIP sphere silica column eluting 5-70% EtOAc in DCM). LCMS (Method 4): 0.74 min; 233.1 $[M+H]^+$ Intermediate 1.56: 4-(2,5-dimethylpyridin-4-yl)-3-fluoroaniline The title compound (0.29 g) was prepared from 3-fluoro-4-(4,4,5,5-tetramethyl-1,3,2-dioxaborolan-2-yl)aniline (0.36 g, 1.5 mmol, CAS: 819057-45-9), of 4-chloro-2,5-dimethyl-pyridine (0.22 g, 1.5 mmol, CAS: 22282-80-0), XPhos Pd G2 (12 mg, 0.02 mmol) and a solution of potassium carbonate (1.8 M aqueous, 2.5 mL, 4.5 mmol) in accordance with the procedure described for Intermediate 1.3. The crude product was purified by flash column chromatography (eluting 90% EtOAc in heptanes). LCMS (Method 3): 1.64 min, 217.1 $[M+H]^+$ Intermediate 1.57: 4-(2,3-dimethylpyridin-4-yl)-3-fluoroaniline The title compound (0.18 g) was prepared from 4-bromo-2,3-dimethyl-pyridine (0.25 g, 1.3 mmol, CAS: 259807-91-5), 3-fluoro-4-(4,4,5,5-tetramethyl-1,3,2-dioxaborolan-2-yl) aniline (0.32 g, 1.3 mmol, CAS: 819057-45-9), Pd(dppf)$Cl_2$ (98 mg, 0.13 mmol) and potassium carbonate (0.46 g, 3.4 mmol) in accordance with the procedure described for Intermediate 1.1, heating at 80° C. for 16 h. The crude product was purified by flash column chromatography (eluting 90% EtOAc in heptanes). LCMS (Method 4): 0.68 min, 217.1 $[M+H]^+$ Intermediate 1.59: 4-(1-benzyl-3-methyl-1H-pyrazol-4-yl)-3-fluoroaniline The title compound (0.5 g) was prepared as a mixture of regioisomers with 4-(1-benzyl-5-methyl-1H-pyrazol-4-yl)-3-fluoroaniline from a mixture of 1-benzyl-4-bromo-5-methyl-1H-pyrazole (CAS: 916080-12-1) and 1-benzyl-4-bromo-3-methyl-1H-pyrazole (0.5 g, 2.2 mmol, CAS: 137968-32-2) and 3-fluoro-4-(4,4,5,5-tetramethyl-1,3,2-dioxaborolan-2-yl)aniline (0.5 g, 2.2 mmol, CAS: 819057-45-9), XPhos Pd G2 (35 mg, 0.04 mmol) and potassium phosphate (2 M aqueous; 3.7 mL, 6.6 mmol) in accordance with the procedure described for Intermediate 1.3. The crude product was purified by flash column chromatography on the Biotage Isolera One™ (25 g SiliCycle silica column, eluting 50-100% EtOAc in heptanes). LCMS (Method 4): 0.83 min, 282.1 $[M+H]^+$ Intermediate 1.60: 4-(3,5-dimethylisoxazol-4-yl)-3-fluoroaniline The title compound (0.15 g) was prepared from 3-fluoro-4-(4,4,5,5-tetramethyl-1,3,2-dioxaborolan-2-yl)aniline (0.77 g, 3.2 mmol, CAS: 819057-45-9), 4-bromo-3,5-dimethyl-isoxazole (0.38 mL, 3.2 mmol, CAS: 10558-25-5), XPhos Pd G2 (51 mg, 0.06 mmol) and a solution of tripotassium phosphate (1.8 M aqueous, 5.4 mL, 9.6 mmol) in accordance with the procedure described for Intermediate 1.3, heating at 100° C. for 2 h. The crude product was purified by flash column chromatography (eluting 30-50% EtOAc in heptanes) and reverse phase column chromatography on the Biotage Isolera One™ (60 g C18 column, eluting 0-50% MeCN containing 0.1% formic solution in water containing 0.1% formic acid). LCMS (Method 3): 1.52 min, 207.0 $[M+H]^+$ Intermediate 1.62: 4-(1-benzyl-1H-pyrazol-4-yl)-3-fluoroaniline The title compound (0.22 g) was prepared from 1-benzyl-4-bromo-pyrazole (0.4 g, 1.7 mmol, CAS: 50877-41-3) and 3-fluoro-4-(4,4,5,5-tetramethyl-1,3,2-dioxaborolan-2-yl)aniline (0.4 g, 1.7 mmol, CAS: 819057-45-9), XPhos Pd G2 (27 mg, 0.03 mmol) and a solution of tripotassium phosphate (1.8 M aqueous, 2.8 mL, 5.1 mmol) in accordance with the procedure described for Intermediate 1.3, heating at 90° C. for 1 h. The crude product was purified by flash column chromatography on the Biotage Isolera One™ (12 g ZIP Sphere silica column, eluting 30-100% EtOAc in heptanes). LCMS (Method 4): 0.80 min, 268.1 $[M+H]^+$ Intermediate 1.63: 5-(4-amino-2-fluorophenyl)-1-methylpyrimidin-2(1H)-one The title compound (0.1 g) was prepared from 5-bromo-1-methyl-pyrimidin-2-one (0.25 g, 1.3 mmol, CAS: 14248-01-2) and 3-fluoro-4-(4,4,5,5-tetramethyl-1,3,2-dioxaborolan-2-yl)aniline (0.4 g, 1.7 mmol, CAS: 819057-45-9), XPhos Pd G2 (20 mg, 0.03 mmol) and a solution of tripotassium phosphate (1.8 M aqueous, 2.1 mL, 3.9 mmol) in accordance with the procedure described for Intermediate 1.3, heating by microwave radiation at 120° C. for 1 h. The crude product was purified by flash column chromatography on the Biotage Isolera One™ (45 g ZIP sphere silica column, eluting 0-15% MeOH in DCM). LCMS (Method 21): 0.93 min, 220.3 $[M+H]^+$ Intermediate 1.64: 5-(4-amino-2-fluorophenyl)pyrimidin-2(1H)-one The title compound (0.26 g) was prepared from 5-bromo-1H-pyrimidin-2-one (0.4 g, 2.3 mmol, CAS: 38353-06-9) and 3-fluoro-4-(4,4,5,5-tetramethyl-1,3,2-dioxaborolan-2-yl)aniline (0.7 g, 3 mmol, CAS: 819057-45-9), XPhos Pd G2 (36 mg, 0.05 mmol) and a solution of tripotassium phosphate (1.8 M aqueous, 3.8 mL, 6.9 mmol) in accordance with the procedure described for Intermediate 1.3, heating by microwave radiation at 120° C. for 1 h. The crude product was purified by flash column chromatography on the Biotage Isolera One™ (80 g ZIP sphere silica column, eluting 0-20% MeOH in DCM). LCMS (Method 21): 0.66 min, 206.0 $[M+H]^+$ Intermediate 1.66: 8-(4-amino-2-fluorophenyl)-1,6-naphthyridin-5(6H)-one The title compound (0.52 g) was prepared from 8-bromo-6H-1,6-naphthyridin-5-one (0.11 g, 4.9 mmol, CAS: 155057-97-9) and 3-fluoro-4-(4,4,5,5-tetramethyl-1,3,2-dioxaborolan-2-yl)aniline (0.12 g 5.1 mmol, CAS: 819057-45-9), XPhos Pd G2 (77 mg, 0.1 mmol) and a solution of tripotassium phosphate (1.8 M aqueous, 8.1 mL, 15 mmol) in accordance with the procedure described for Intermediate 1.3, heating at 100° C. for 2 h. The crude product was purified by flash column chromatography (eluting 33-100% EtOAc in heptanes then 10-50% MeOH in DCM with 5% triethylamine), then triturated with heptanes. LCMS (Method 3): 0.88 min, 256.0 $[M+H]^+$ Intermediate 1.67: 5-(4-amino-2-fluorophenyl)pyridazin-3(2H)-one The title compound (0.24 g) was prepared from 4-iodo-1H-pyridazin-6-one (0.5 g, 2.3 mmol, CAS: 825633-94-1) and 3-fluoro-4-(4,4,5,5-tetramethyl-1,3,2-dioxaborolan-2-yl)aniline (0.59 g, 2.5 mmol, CAS: 819057-45-9), XPhos Pd G2 (35 mg, 0.05 mmol) and a solution of tripotassium phosphate (1.8 M aqueous, 3.8 mL, 6.8 mmol) in accordance with the procedure described for Intermediate 1.3, heating at 100° C. for 20 h. The crude product was purified by flash column chromatography (eluting 0-10% MeOH in EtOAc), then triturated with heptanes. LCMS (Method 13): 0.79 min, 206.0 $[M+H]^+$ Intermediate 1.68: 3-fluoro-4-(7-methoxy-1H-pyrrolo[2,3-c]pyridin-4-yl)aniline The title compound (0.6 mg) was prepared from 4-bromo-7-methoxy-1H-pyrrolo[2,3-c]pyridine (0.5 mg, 2.2 mmol, CAS: 425380-37-6) and 3-fluoro-4-(4,4,5,5-tetramethyl-1,3,2-dioxaborolan-2-yl)aniline (0.52 g, 2.2 mmol, CAS: 819057-45-9), XPhos Pd G2 (0.17 g, 0.22 mmol) and potassium phosphate (1.8M aqueous; 3.7 mL, 6.6 mmol) in accordance with the procedure described for Intermediate 1.3. The crude product was purified by flash column chromatography on silica gel (eluting 40% EtOAc in heptanes). LCMS (Method 4): 0.69 min, 258.0 $[M+H]^+$ Intermediate 1.69: 7-(4-amino-2-fluorophenyl)-3,5-dihydro-4H-imidazo[4,5-c]pyridin-4-one The title compound (0.26 g) was prepared from 7-bromo-3,5-dihydroimidazo[4,5-c]pyridin-4-one (0.42 g, 2.0 mmol, CAS: 163452-70-8) and 3-fluoro-4-(4,4,5,5-tetramethyl-1,3,2-dioxaborolan-2-yl)aniline (0.51 g, 2.2 mmol, CAS: 819057-45-9), XPhos Pd G2 (62 mg, 0.08 mmol) and a solution of tripotassium phosphate (1.8 M aqueous, 3.3 mL, 5.9 mmol) in accordance with the procedure described for Intermediate 1.3, heating by microwave irradiation at 120° C. for 1 h. The crude product was purified by flash column chromatography (eluting 10-20% MeOH in DCM with 5% $Et_3N$). LCMS (Method 21): 0.63 min, 245.0 $[M+H]^+$ Intermediate 1.71: 6-(4-amino-2-fluorophenyl)-1-methylpyridin-2(1H)-one The title compound (0.19 g) was prepared from 6-bromo-1-methyl-pyridin-2-one (0.19 g, 1.0 mmol, CAS: 163452-70-8) and 3-fluoro-4-(4,4,5,5-tetramethyl-1,3,2-dioxaborolan-2-yl)aniline (0.24 g, 1.0 mmol, CAS: 819057-45-9), XPhos Pd G2 (32 mg, 0.04 mmol) and a solution of tripotassium phosphate (1.8 M aqueous, 1.7 mL, 3.0 mmol) in accordance with the procedure described for Intermediate 1.3, heating by microwave irradiation at 85° C. for 1 h. The crude product was purified by flash column chromatography Biotage Isolera One™ (25 g SiliCycle silica column, eluting 40-100% EtOAc in heptanes). LCMS (Method 4): 0.49 min, 219.1 $[M+H]^+$ Intermediate 1.72: 6'-amino-1,2-dimethyl-[3,3'-bipyridin]-6(1H)-one The title compound (0.23 g) was prepared from 5-(4,4,5,5-tetramethyl-1,3,2-dioxaborolan-2-yl)pyridin-2-amine (0.25 g, 1.1 mmol, CAS: 827614-64-2), 5-bromo-1,6-dimethyl-pyridin-2-one (0.3 g, 1.1 mmol, CAS: 889865-54-7), XPhos Pd G2 (18 mg, 0.02 mmol) and a solution of tripotassium phosphate (1.8 M aqueous, 1.9 mL, 3.3 mmol) in accordance with the procedure described for Intermediate 1.3, heating by microwave irradiation at 85° C. for 1 h. The crude product was purified by reverse phase column chromatography on the Biotage Isolera One™ (30 g C18 column, eluting 1-40% MeCN MeCN/0.1% ammonia in $H_2O$/0.1% ammonia solution). LCMS (Method 4): 0.36 min, 216.1 $[M+H]^+$ Intermediate 1.73: 3',5'-dimethyl-[3,4'-bipyridin]-6-amine The title compound (0.22 g) was prepared from 5-(4,4,5,5-tetramethyl-1,3,2-dioxaborolan-2-yl)pyridin-2-amine (0.25 g, 1.1 mmol, CAS: 827614-64-2), 4-chloro-3,5-dimethyl-pyridine (0.16 g, 1.1 mmol, CAS: 143798-73-6), XPhos Pd G2 (18 mg, 0.02 mmol) and a solution of potassium carbonate (1.8 M aqueous, 1.9 mL, 3.4 mmol) in accordance with the procedure described for Intermediate 1.3, heating by microwave irradiation at 85° C. for 2 h. The crude product was purified by reverse phase column chromatography on the Biotage Isolera One™ (30 g C18 column, eluting 10-70% MeCN/0.1% ammonia in $H_2O$/0.1% ammonia solution). LCMS (Method 4): 0.49 min, 200.1 $[M+H]^+$ Intermediate 1.74: 4-(1-benzyl-5-methyl-1H-pyrazol-4-yl)aniline The title compound (0.57 g) was prepared as a mixture of regioisomers with 4-(1-benzyl-3-methyl-1H-pyrazol-4-yl) aniline from a mixture of 1-benzyl-4-bromo-5-methyl-1H-pyrazole (CAS: 916080-12-1) and 1-benzyl-4-bromo-3-methyl-1H-pyrazole (0.54 g, 2.2 mmol, CAS: 137968-32-2) and 4-(4,4,5,5-tetramethyl-1,3,2-dioxaborolan-2-yl)aniline (0.57 g, 2.6 mmol, CAS: 214360-73-3), XPhos Pd G2 (34 mg, 0.04 mmol) and a solution of tripotassium phosphate (1.8 M aqueous, 3.6 mL, 6.5 mmol) in accordance with the procedure described for Intermediate 1.3, heating by microwave irradiation at 85° C. for 1 h. The crude product was purified by flash column chromatography on the Biotage Isolera One™ (25 g SiliCycle silica column, eluting 30-100% EtOAc in heptanes). LCMS (Method 4): 0.75 min, 264.1 $[M+H]^+$, 0.77 min, 264.1 $[M+H]^+$ Intermediate 1.75: 4-(4-amino-2-fluorophenyl)-6-methyl-1,6-dihydro-7H-pyrazolo[3,4-c]pyridin-7-one The title compound (0.14 g) was prepared from 3-fluoro-4-(4,4,5,5-tetramethyl-1,3,2-dioxaborolan-2-yl)aniline (0.32 g, 1.4 mmol, CAS: 819057-45-9), 4-bromo-6-methyl-1H-pyrazolo[3,4-c]pyridin-7-one (0.28 g, 1.3 mmol, CAS: 1446236-51-6), XPhos Pd G2 (48 mg, 0.06 mmol) and a solution of tripotassium phosphate (1.8 M aqueous, 2.1 mL, 3.7 mmol) in accordance with the procedure described for Intermediate 1.3, heating by microwave irradiation at 120° C. for 1.5 h. The crude product was purified flash column chromatography on the Biotage Isolera One™ (40 g ZIP sphere silica column, eluting 25-100% EtOAc in heptanes). LCMS (Method 3): 0.98 min, 259.1 $[M+H]^+$ Intermediate 1.76: 4-(7-methoxy-1H-pyrrolo[2,3-c]pyridin-4-yl)aniline The title compound (0.21 g) was prepared from 4-(4,4,5,5-tetramethyl-1,3,2-dioxaborolan-2-yl)aniline (0.19 g, 0.88 mmol, CAS: 214360-73-3) and 4-bromo-7-methoxy-1H-pyrrolo[2,3-c]pyridine (0.2 g, 0.88 mmol, CAS: 425380-37-6), XPhos Pd G2 (14 mg, 0.02 mmol) and a solution of tripotassium phosphate (1.8 M aqueous, 1.5 mL, 2.6 mmol) in accordance with the procedure described for Intermediate 1.3, heating by microwave irradiation at 100° C. for 30 min. The crude product was purified flash column chromatography on the Biotage Isolera One™ (25 g ZIP sphere silica column, eluting 50-100% EtOAc in heptanes). LCMS (Method 4): 0.61 min, 240.1 $[M+H]^+$ Intermediate 1.77: 6-(4-amino-2-fluorophenyl)-1-benzylpyridin-2(1H)-one Intermediate 1.77a: 1-benzyl-6-chloro-pyridin-2-one To a solution of 6-chloropyridin-2-ol (0.2 g, 1.5 mmol, CAS: 16879-02-0) and potassium carbonate (0.53 g, 3.9 mmol) in acetone (15 mL) was added bromomethylbenzene (0.18 mL, 1.5 mmol, CAS: 100-39-0) and the reaction heated to 55° C. for 24 h. The mixture was filtered, and the filtrate concentrated in vacuo. The crude product was purified by flash column chromatography on the Biotage Isolera One™ (25 g SiliCycle silica column, eluting 40-100% EtOAc in heptanes) to give the title compound (0.2 g). $^1H$ NMR (400 MHz, DMSO-$d_6$) δ: 7.74 (t, 1H), 7.43 (d, 2H), 7.33 (td, 3H), 7.07 (d, 1H), 6.86 (d, 1H), 5.28 (s, 2H).

Intermediate 1.77: 6-(4-amino-2-fluorophenyl)-1-benzylpyridin-2(1H)-one

The title compound (0.2 g) was prepared from Intermediate 1.77a (0.2 g, 0.93 mmol) and 3-fluoro-4-(4,4,5,5-tetramethyl-1,3,2-dioxaborolan-2-yl)aniline (0.2 g, 0.93 mmol, CAS: 819057-45-9), XPhos Pd G2 (15 mg, 0.02 mmol) and a solution of tripotassium phosphate (1.8 M aqueous, 1.6 mL, 2.8 mmol) in accordance with the procedure described for Intermediate 1.3, heating by microwave irradiation at 85° C. for 1 h. The crude product was purified flash column chromatography on the Biotage Isolera One™ (25 g SiliCycle silica column, eluting 40-100% EtOAc in heptanes). LCMS (Method 4): 1.06 min, 295.1 $[M+H]^+$ Intermediate 1.78: 2-(4-(4-aminophenyl)pyridin-3-yl)-1-(pyrrolidin-1-yl)ethan-1-one Intermediate 1.78a: 2-(4-chloro-3-pyridyl)-1-pyrrolidin-1-yl-ethanone To a stirred solution of 2-(4-chloro-3-pyridyl)acetic acid hydrochloride (0.52 g, 2.5 mmol, CAS: 1803562-33-5), triethylamine (1.05 mL, 7.54 mmol) and pyrrolidine (0.31 mL, 3.8 mmol, CAS: 123-75-1) in MeCN (10 mL) and EtOAc (15 mL) at 0° C. was added T3P® (50% w/w in EtOAc; 3.2 mL, 5.0 mmol). The reaction mixture stirred at rt for 3 h then diluted with saturated aqueous $NaHCO_3$ and extracted into EtOAc. The combined organics were washed with brine, dried over $MgSO_4$, filtered and concentrated in vacuo to give the title compound (0.38 g) which was used without further purification. LCMS (Method 22): 0.70 min, 189.1 $[M-Cl]^+$ Intermediate 1.78: 2-(4-(4-aminophenyl)pyridin-3-yl)-1-(pyrrolidin-1-yl)ethan-1-one The title compound (0.2 g) was prepared from Intermediate 1.78a (0.34 g, 1.6 mmol) and 4-(4,4,5,5-tetramethyl-1,3,2-dioxaborolan-2-yl)aniline (0.41 g, 1.9 mmol, CAS: 214360-73-3), XPhos Pd G2 (123 mg, 0.15 mmol) and a solution of potassium carbonate (2 M aqueous, 3.1 mL, 6.3 mmol) in accordance with the procedure described for Intermediate 1.3, heating at 100° C. for 2 h. The crude product was purified flash column chromatography on the Biotage Isolera One™ (40 g SiliCycle silica column, eluting 0-20% MeOH in EtOAc). LCMS (Method 22): 0.66 min, 282.1 $[M+H]^+$ Intermediate 1.80: 6-(4-amino-2-fluorophenyl)pyrimidin-4(3H)-one The title compound (0.2 g) was prepared from 3-fluoro-4-(4,4,5,5-tetramethyl-1,3,2-dioxaborolan-2-yl)aniline (1.1 g, 4.6 mmol, CAS: 819057-45-9) and 4-chloro-1H-pyrimidin-6-one (0.5 g, 3.8 mmol, CAS: 4765-77-9), XPhos Pd G2 (90 mg, 0.11 mmol) and a solution of tripotassium phosphate (1.8 M aqueous, 6.4 mL, 11.5 mmol) in accordance with the procedure described for Intermediate 1.3, heating by microwave irradiation at 85° C. for 1 h. The crude product was purified flash column chromatography (eluting 0-10% MeOH in EtOAc). LCMS (Method 23) 0.73 min, 206 $[M+H]^+$ Intermediate 1.84: 4-(1-(4-methoxybenzyl)-3,5-dimethyl-1H-pyrazol-4-yl)aniline The title compound (1.1 g) was prepared from 4-(4,4,5,5-tetramethyl-1,3,2-dioxaborolan-2-yl)aniline (2.2 g, 10.2 mmol, CAS: 214360-73-3), 4-bromo-1-(4-methoxybenzyl)-3,5-dimethyl-1H-pyrazole (3 g, 10.2 mmol, CAS: 1457073-32-3), Xphos Pd G2 (0.24 mg, 0.31 mmol), tripotassium phosphate (4.2 g, 31 mmol) in accordance with the procedure described for Intermediate 1.3, heating by microwave irradiation at 80° C. for 1 h. The crude product was purified by flash column chromatography on the Biotage Isolera One™ (100 g silica column, eluting 0-100% EtOAc in heptanes). $^1H$ NMR (400 MHz, MeOD) δ: 7.11-7.03 (m, 2H), 7.03-6.95 (m, 2H), 6.93-6.84 (m, 2H), 6.82-6.74 (m, 2H), 5.21 (s, 2H), 3.77 (s, 3H), 2.16 (d, 6H).

Intermediate 1.87: 4-(4-aminophenyl)pyridin-2(1H)-one

The title compound (80 mg) was prepared from 4-(4,4,5,5-tetramethyl-1,3,2-dioxaborolan-2-yl)aniline (0.28 g, 1.3 mmol, CAS: 214360-73-3), 4-bromo-1H-pyridin-2-one (0.2 g, 1.2 mmol, CAS: 36953-37-4), Pd(dppf)$Cl_2$ (84 mg, 0.11 mmol) and sodium carbonate (0.30 g, 2.9 mmol) in accordance with the procedure described for Intermediate 1.6, heating at 80° C. for 2 h. The crude product was purified by flash column chromatography (eluting 5% MeOH in EtOAc followed by 5% MeOH in DCM). LCMS (Method 4): 0.36 min, 187.1 $[M+H]^+$ Intermediate 1.88: 4-(imidazo[1,2-a]pyridin-5-yl)aniline The title compound (61 mg) was prepared from 4-(4,4,5,5-tetramethyl-1,3,2-dioxaborolan-2-yl)aniline (0.33 g, 1.5 mmol, CAS: 214360-73-3), 5-bromoimidazo[1,2-a]pyridine (0.25 g, 1.3 mmol, CAS: 69214-09-1), XPhos Pd G2 (20 mg, 0.03 mmol) and a solution of tripotassium phosphate (1.8 M aqueous, 2.1 mL, 3.8 mmol) in accordance with the procedure described for Intermediate 1.3, heating by microwave irradiation at 85° C. for 1 h. The crude product was purified by flash column chromatography on the Biotage Isolera One™ (25 g SiliCycle silica column, eluting 40-100% EtOAc in heptanes). LCMS (Method 4): 0.56 min, 210.1 $[M+H]^+$ Intermediate 1.99: 5-(1-(4-methoxybenzyl)-3,5-dimethyl-1H-pyrazol-4-yl)pyridin-2-amine Intermediate 1.99a: 4-bromo-1-[(4-methoxyphenyl)methyl]-3,5-dimethyl-pyrazole To a solution of 4-bromo-3,5-dimethyl-1H-pyrazole (0.5 g, 2.9 mmol, CAS: 3398-16-1) and potassium carbonate (0.39 g, 2.9 mmol) in acetone (10 mL) was added 1-(bromomethyl)-4-methoxy-benzene (0.57 g, 2.9 mmol, CAS: 2746-25-0). The mixture was heated at 55° C. for 18 h. The reaction mixture was concentrated in vacuo. The residue was partitioned between EtOAc and brine. The organics were dried over $Na_2SO_4$, filtered and concentrated in vacuo. The crude product was purified by flash column chromatography on the Biotage Isolera One™ (12 g silica column, eluting 0-30% EtOAc in heptanes) to give the title compound (0.53 g). $^1H$ NMR (400 MHz, $CDCl_3$) δ: 7.08-7.01 (m, 2H), 6.87-6.81 (m, 2H), 5.16 (s, 2H), 3.78 (s, 3H), 2.23 (s, 3H), 2.15 (s, 3H).

Intermediate 1.99b: tert-butyl N—[5-[1-[(4-methoxyphenyl)methyl]-3,5-dimethyl-pyrazol-4-yl]-2-pyridyl]carbamate The title compound (0.61 g) was prepared from Intermediate 1.99a (0.49 g, 1.7 mmol), tert-butyl N—[5-(4,4,5,5-tetramethyl-1,3,2-dioxaborolan-2-yl)-2-pyridyl]carbamate (0.53 g, 1.7 mmol, CAS: 910462-31-6), XPhos Pd G2 (26 mg, 0.03 mmol) and a solution of tripotassium phosphate (1.8 M aqueous, 2.8 mL, 5.0 mmol) in accordance with the procedure described for Intermediate 1.3, heating at reflux for 19 h. The crude product was purified by flash column chromatography (eluting 0-80% EtOAc in heptanes). LCMS (Method 14): 1.88 min, 409.2 $[M+H]^+$ Intermediate 1.99: 5-(1-(4-methoxybenzyl)-3,5-dimethyl-1H-pyrazol-4-yl)pyridin-2-amine To a solution of Intermediate 1.99b (0.6 g, 1.5 mmol) in 1,4-dioxane (4 mL) was added HCl (4 M in 1,4 dioxane; 0.54 mL, 2.2 mmol). The reaction mixture was stirred at rt for 20 h then an additional portion of HCl (4 M in 1,4 dioxane; 2.4 mL, 9.6 mmol) was added and the mixture stirred at rt for a further 2.5 h. The reaction mixture was concentrated in vacuo and the residue dissolved in DCM and washed with saturated aqueous $NaHCO_3$ and brine. The combined organics were concentrated in vacuo. The crude product was purified by flash column chromatography (20-100% EtOAc in heptanes) to provide the title compound (0.27 g). $^1H$ NMR (400 MHz, $CDCl_3$) δ: 7.89 (dd, 1H), 7.29-7.20 (m, 1H), 7.08-7.00 (m, 2H), 6.83-6.75 (m, 2H), 6.48 (dd, 1H), 5.13 (s, 2H), 4.34 (s, 2H), 3.72 (s, 3H), 2.17 (s, 3H), 2.07 (s, 3H).

Intermediate 1.104: tert-butyl 4-(4-aminophenyl)-3,5-dimethyl-1H-pyrazole-1-carboxylate The title compound (70 mg) was prepared from tert-butyl 4-bromo-3,5-dimethyl-pyrazole-1-carboxylate (0.2 g, 0.73 mmol, CAS: 1040276-87-6), 4-(4,4,5,5-tetramethyl-1,3,2-dioxaborolan-2-yl)aniline (0.16 g, 0.73 mmol, CAS: 214360-73-3), potassium carbonate (0.4 g, 2.9 mmol), and Xphos Pd G2 (57 mg, 0.07 mmol) in accordance with the procedure described for Intermediate 1.3, heating at 85° C. for 1 h. The crude product was purified by flash column chromatography on the Biotage Isolera One™ (40 g silica cartilage, eluting 0-10% MeOH in DCM). $^1$H NMR (400 MHz, $CDCl_3$) δ: 7.04-6.95 (m, 2H), 6.77-6.70 (m, 2H), 3.49 (s, 2H), 2.42 (s, 3H), 2.23 (s, 3H), 1.66 (s, 9H).

Intermediate 1.106: 5-(1,4-dimethyl-1H-pyrazol-5-yl)pyridin-2-amine

The title compound (0.35 g) was prepared from 5-iodopyridin-2-amine (1.1 g, 5 mmol, CAS: 20511-12-0), 1,4-dimethyl-5-(4,4,5,5-tetramethyl-1,3,2-dioxaborolan-2-yl)pyrazole (1.1 g, 5 mmol, CAS: 1047644-76-7), XPhos Pd G2 (79 mg, 0.1 mmol) and a solution of tripotassium phosphate (1.8 M aqueous, 8.3 mL, 15 mmol) in accordance with the procedure described for Intermediate 1.3, heating at reflux for 20 h. The crude product was purified flash column chromatography on the Biotage Isolera One™ (40 g silica column, eluting 0-10% MeOH in DCM). LCMS (Method 14): 1.06 min, 189.2 $[M+H]^+$ Intermediate 1.125: 5-(1,4-dimethyl-1H-1,2,3-triazol-5-yl)pyridin-2-amine To a solution of tert-butyl N-(5-iodo-2-pyridyl)carbamate (0.9 g, 2.8 mmol, CAS: 375853-79-5) in 1,4-dioxane (14 mL) was added tributyl-(3,5-dimethyltriazol-4-yl)stannane (2.2 g, 5.6 mmol, CAS: 1047637-17-1), triethylamine (1.2 mL, 8.4 mmol) and copper(I) iodide (80 mg, 0.42 mmol). The reaction mixture was degassed with argon for 5 min then tetrakis(triphenylphosphine)palladium(0) (0.33 g, 0.28 mmol) was added and the reaction heated at 120° C. for 20 h. The reaction was concentrated in vacuo and the residue portioned between EtOAc and water. The organics were washed with brine then dried over $Na_2SO_4$, filtered and concentrated in vacuo. The crude product was purified by flash column chromatography on the Biotage Isolera One™ (100 g silica column, 0-100% EtOAc in heptanes) to afford the title compound (0.3 g). $^1$H NMR (400 MHz, MeOD) δ: 8.28 (dd, 1H), 8.05 (dd, 1H), 7.82 (dd, 1H), 3.97 (s, 3H), 2.28 (s, 3H), 1.55 (s, 9H).

Intermediate 1.125a: 2-chloro-5-(1,4-dimethyl-1H-1,2,3-triazol-5-yl)pyridine

To a solution of 5-bromo-2-chloro-pyridine (4.6 g, 24 mmol, CAS: 53939-30-3) in DMA (100 mL) was added 1,4-dimethyl-1H-1,2,3-triazole (4.6 g, 48 mmol, CAS: 60166-43-0), 2,2-dimethylpropanoic acid (0.73 g, 7.2 mmol), $K_2CO_3$ (6.6 g, 48 mmol) and PEPPSI™-IPr catalyst (0.33 g, 0.28 mmol). The mixture was heated at 120° C. for 20 h. The reaction was concentrated in vacuo and the residue partitioned between EtOAc and water. The aqueous was extracted with EtOAc then the combined organics were washed with brine, dried over $Na_2SO_4$, filtered and concentrated in vacuo. The crude product was purified by flash column chromatography on the Biotage Isolera One™ (340 g silica column, 0-70% EtOAc in heptanes) to afford the title compound (1.6 g). $^1$H NMR (400 MHz, $CDCl_3$) δ: 8.39 (dd, 1H), 7.63 (dd, 1H), 7.51 (dd, 1H), 3.97 (s, 3H), 2.33 (s, 3H).

Intermediate 1.138: 6-(3,5-dimethylisoxazol-4-yl)pyridin-3-amine

The title compound (0.18 g) was prepared from 2-chloropyridin-5-amine (1 g, 7.8 mmol, CAS: 5350-93-6), (3,5-dimethylisoxazol-4-yl)boronic acid (3.8 mg, 27 mmol, CAS: 16114-47-9), Pd(dppf)$Cl_2$ (0.57 g, 0.78 mmol) and sodium carbonate (3.3 g, 31 mmol) in accordance with the procedure described for Intermediate 1.6, heating by microwave irradiation at 145° C. for 3 h. The crude product was purified by reverse phase column chromatography on the Biotage Isolera One™ (50 g C18 column, eluting 5-100% MeCN in water buffer with 0.005 M $NH_4OH$). LCMS (Method 14): 1.21 min, 190.2 $[M+H]^+$ Intermediate 1.140: 5-(5-methylpyrimidin-4-yl)pyridin-2-amine The title compound (0.24 g) was prepared from 4-chloro-5-methyl-pyrimidine (0.25 g, 2.0 mmol, CAS: 51957-32-5), 5-(4,4,5,5-tetramethyl-1,3,2-dioxaborolan-2-yl)pyridin-2-amine (0.43 mg, 2.0 mmol, CAS: 827614-64-2), Pd(dppf)$Cl_2$ (0.14 g, 0.19 mmol) and sodium carbonate (0.62 mg, 5.8 mmol) in accordance with the procedure described for Intermediate 1.6, heating at 80° C. for 3 h. The crude product was purified by flash column chromatography on the Biotage Isolera One™ (20 g silica column, eluting 0-7% MeOH in DCM) and flash column chromatography on the Biotage Isolera One™ (4 g silica column, 0-7% MeOH in DCM). $^1$H NMR (400 MHz, $CDCl_3$) δ: 9.10 (s, 1H), 8.59 (s, 1H), 8.47 (dd, 1H), 7.88 (dd, 1H), 6.64 (dd, 1H), 4.75 (s, 2H), 2.47 (d, 3H).

Intermediate 1.142: 5-(3-(methoxymethyl)-5-methylisoxazol-4-yl)pyridin-2-amine

The title compound (0.2 g) was prepared from 4-bromo-3-(methoxymethyl)-5-methyl-isoxazole (0.57 g, 2.76 mmol, CAS: 1000894-06-3), 5-(4,4,5,5-tetramethyl-1,3,2-dioxaborolan-2-yl)pyridin-2-amine (0.67 g, 3.0 mmol, CAS: 827614-64-2), Pd(dppf)$Cl_2$ (0.23 g, 0.28 mmol) and potassium carbonate (1.1 g, 8.3 mmol) in accordance with the procedure described for Intermediate 1.1, heating at 120° C. for 1 h. The crude product was purified by flash column chromatography on the Biotage Isolera One™ (40 g silica column, eluting 0-100% EtOAc in heptanes). LCMS (Method 14): 1.18 min, 220.2 $[M+H]^+$ Intermediate 1.143: 2-chloro-5-(3,5-dimethyl-4H-1,2,4-triazol-4-yl)pyridine Intermediate 1.143a: 5-(3,5-dimethyl-4H-1,2,4-triazol-4-yl)-2-methoxypyridine A solution of dimethylacetamide dimethyl acetal (0.18 g, 13.3 mmol, CAS: 18871-66-4), acetohydrazide (0.98 g, 13.3 mmol, CAS: 1068-57-1) in acetonitrile (5 mL) was heated to 50° C. for 30 min before the addition of 6-methoxypyridin-3-amine (0.15 g, 12.1 mmol, CAS: 6628-77-9), acetic acid (7.5 mL) and acetonitrile (2.5 mL). The reaction was heated to 120° C. for 20 h then concentrated in vacuo. The crude product was triturated with diethyl ether to afford the title compound (0.72 g). LCMS (Method 14): 1.24 min, 205.2 $[M+H]^+$ Intermediate 1.143b: 5-(3,5-dimethyl-4H-1,2,4-triazol-4-yl)pyridin-2(1H)-one To a solution of Intermediate 1.143a (0.68 g, 3.3 mmol) in acetic acid (7.7 mL) was added HBr (48% aqueous; 7.5 mL, 66 mmol). The reaction mixture was heated to 80° C. for 6 h then concentrated in vacuo. The residue was azeotroped from a mixture of EtOAc and heptanes (1:1). The crude product was triturated with diethyl ether to afford the title compound (0.65 g). $^1$H NMR (400 MHz, MeOD) δ: 8.05 (d, 1H), 7.73 (dd, 1H), 6.75 (d, 1H), 2.53 (s, 6H).

Intermediate 1.143: 2-chloro-5-(3,5-dimethyl-4H-1,2,4-triazol-4-yl)pyridine

Phosphorus oxychloride (2.5 mL, 26 mmol) was added to Intermediate 1.143b (0.5 g, 2.6 mmol) and the reaction was heated at reflux for 20 h. The mixture was concentrated in vacuo then a mixture of MeOH/$H_2O$ (1:1) was added slowly. The crude product was purified by flash column chromatography on the Biotage Isolera One™ (20 g silica column, eluting 0-10% MeOH in DCM) to afford the title compound (0.41 g). LCMS (Method 14): 1.22 min, 209.2 $[M+H]^+$ Intermediate 1.145: 6-(1,4-dimethyl-1H-pyrazol-5-yl)pyridin-3-amine The title compound (0.91 g) was prepared from 1,4-dimethyl-5-(4,4,5,5-tetramethyl-1,3,2-dioxaborolan-2-yl) pyrazole (0.13 g, 5.5 mmol, CAS: 1047644-76-7), 6-chloropyridin-3-amine (0.71 g, 5.5 mmol, CAS: 5350-93-6), XPhos Pd G2 (87 mg, 0.11 mmol) and tripotassium phosphate (2.5 M aqueous; 6.6 mL, 16.6 mmol) in accordance with the procedure described for Intermediate 1.3 and heating at reflux for 24 h. The crude product was purified flash column chromatography on the Biotage Isolera One™ (20 g silica column, eluting 10% MeOH in DCM). LCMS (Method 14): 1.22 min, 189.2 $[M+H]^+$ Intermediate 1.146: 4-methyl-5-(1-methyl-1H-pyrazol-5-yl)pyridin-2-amine The title compound (0.85 g) was prepared from 1-methyl-5-(4,4,5,5-tetramethyl-1,3,2-dioxaborolan-2-yl)pyrazole (1.7 g, 8 mmol, CAS: 847818-74-0), 5-bromo-4-methyl-pyridin-2-amine (1 g, 5.3 mmol, CAS: 98198-48-2), Pd(dppf)$Cl_2$ (0.19 mg, 0.27 mmol) and sodium carbonate (2.3 g, 21 mmol) in accordance with the procedure described for Intermediate 1.6, heating at 120° C. for 16 h. The crude product was purified by flash column chromatography on the Biotage Isolera One™ (12 g silica column, eluting 0-10% MeOH in DCM). LCMS (Method 19): 0.52 min, 189.2 $[M+H]^+$ Intermediate 1.147: 2-(1,4-dimethyl-1H-pyrazol-5-yl)pyrimidin-5-amine The title compound (0.66 g) was prepared from 2-chloropyrimidin-5-amine (603 mg, 4.66 mmol, CAS: 56621-90-0), 1,4-dimethyl-5-(4,4,5,5-tetramethyl-1,3,2-dioxaborolan-2-yl)pyrazole (1.0 g, 4.7 mmol, CAS: 1047644-76-7), XPhos Pd G2 (73 mg, 0.09 mmol) and tripotassium phosphate (2.5 M aqueous; 5.6 mL, 16.6 mmol) in accordance with the procedure described for Intermediate 1.3, heating at reflux for 24 h. The crude product was purified by flash column chromatography on the Biotage Isolera One™ (20 g silica column, eluting 10% MeOH in DCM). LCMS (Method 19): 1.25 min, 190.2 $[M+H]^+$ Intermediate 1.150: 5-(5-(methoxymethyl)-3-methylisoxazol-4-yl)pyridin-2-amine Intermediate 1.150a: 4-bromo-5-(methoxymethyl)-3-methylisoxazole 5-(methoxymethyl)-3-methyl-isoxazole (1.1 g, 8.3 mmol, CAS: 13999-31-0) was dissolved in DMF (13 mL) and NBS (1.8 g, 9.9 mmol) was added in one portion. The reaction was heated at 55° C. under argon for 20 h. The reaction was cooled to rt then diluted with diethyl ether and washed with water and brine. The organics were dried over $Na_2SO_4$, filtered and concentrated in vacuo to provide the title compound (1.7 g). $^1$H NMR (400 MHz, MeOD) δ: 4.53 (s, 2H), 3.37 (s, 3H), 2.28 (s, 3H).

Intermediate 1.150: 5-(5-(methoxymethyl)-3-methylisoxazol-4-yl)pyridin-2-amine

The title compound (0.22 g) was prepared from Intermediate 1.150a (1.6 g, 7.8 mmol), 5-(4,4,5,5-tetramethyl-1,3,2-dioxaborolan-2-yl)pyridin-2-amine (1.9 g, 8.5 mmol, CAS: 827614-64-2), Pd(dppf)$Cl_2$ (0.63 g, 0.78 mmol) and potassium carbonate (3.2 g, 23 mmol) in accordance with the procedure described for Intermediate 1.1, heating at 120° C. for 1 h. The crude product was purified by flash column chromatography on the Biotage Isolera One™ (40 g silica column, eluting 0-100% EtOAc in heptanes). $^1$H NMR (400 MHz, MeOD) δ: 7.91 (dd, 1H), 7.49 (dd, 1H), 6.67 (dd, 1H), 4.45 (s, 2H), 3.36 (s, 3H), 2.28 (s, 3H)

Intermediate 1.151: 3'-methoxy-2'-methyl-[3,4'-bipyridin]-6-amine

The title compound (0.2 g) was prepared from 4-chloro-3-methoxy-2-methyl-pyridine (0.50 g, 3.2 mmol, CAS: 107512-34-5) 5-(4,4,5,5-tetramethyl-1,3,2-dioxaborolan-2-yl)pyridin-2-amine (0.7 g, 3.2 mmol, CAS: 827614-64-2), Pd(dppf)$Cl_2$ (0.23 g, 0.32 mmol) and sodium carbonate (1.0 g, 9.5 mmol) in accordance with the procedure described for Intermediate 1.6, heating at 80° C. for 3 h. The crude product was purified by flash column chromatography on the Biotage Isolera One™ (10 g silica column, eluting 0-5% MeOH in DCM). $^1$H NMR (400 MHz, $CDCl_3$) δ: 8.23 (s, 1H), 8.18 (d, 1H), 7.70 (dd, 1H), 7.21 (d, 1H), 6.53 (d, 1H), 6.24 (s, 2H), 3.43 (s, 3H), 2.45 (s, 3H).

Intermediate 1.152: 2',3'-dimethyl-[3,4'-bipyridin]-6-amine

The title compound (0.5 g) was prepared from 4-bromo-2,3-dimethyl-pyridine (0.50 g, 2.7 mmol, CAS: 259807-91-5), 5-(4,4,5,5-tetramethyl-1,3,2-dioxaborolan-2-yl)pyridin-2-amine (0.59 g, 2.7 mmol, CAS: 827614-64-2), Pd(dppf)$Cl_2$ (0.2 g, 0.27 mmol) and sodium carbonate (0.85 g, 8.1 mmol) in accordance with the procedure described for Intermediate 1.6, heating at 80° C. for 3 h. The crude product was purified by flash column chromatography on the Biotage Isolera One™ (10 g silica column, eluting 0-5%

MeOH in DCM). $^1$H NMR (400 MHz, $CDCl_3$) δ: 8.33 (d, 1H), 8.04 (dd, 1H), 7.40 (dd, 1H), 6.97 (d, 1H), 6.58 (dd, 1H), 4.59 (br s, 2H), 2.58 (s, 3H), 2.22 (s, 3H).

Intermediate 1.153: 2',5'-dimethyl-[3,4'-bipyridin]-6-amine

The title compound (0.17 g) was prepared from 4-chloro-2,5-dimethyl-pyridine (0.50 g, 3.5 mmol, CAS: 22282-80-0), 5-(4,4,5,5-tetramethyl-1,3,2-dioxaborolan-2-yl)pyridin-2-amine (0.78 g, 3.5 mmol, CAS: 827614-64-2), Pd(dppf)$Cl_2$ (0.26 g, 0.35 mmol) and sodium carbonate (1.1 g, 10.6 mmol) in accordance with the procedure described for Intermediate 1.6, heating at 80° C. for 20 h. The crude product was purified by flash column chromatography on the Biotage Isolera One™ (10 g silica column, eluting 0-5% MeOH in DCM) and an SCX cartridge (5 g, washed with MeOH and eluted with 2 M methanolic ammonia). $^1$H NMR (400 MHz, DMSO-$d_6$) δ: 8.29 (s, 1H), 7.96 (d, 1H), 7.47 (dd, 1H), 7.07 (s, 1H), 6.52 (dd, 1H), 6.15 (br s, 2H), 2.43 (s, 3H), 2.22 (s, 3H).

Intermediate 1.157: 2-chloro-5-(1-ethyl-4-methyl-1H-1,2,3-triazol-5-yl)pyridine

Intermediate 1.157a: 1-ethyl-4-methyl-1H-1,2,3-triazole

A solution of 1,1-dimethoxypropan-2-one (1 g, 8.5 mmol, CAS: 6342-56-9) and 4-methylbenzenesulfonohydrazide (1.6 g, 8.5 mmol, CAS: 1576-35-8) in MeOH (2 mL) was stirred at rt for 10 min. Ethanamine (4.7 mL, 9.3 mmol) and $Et_3N$ (1.3 mL, 9.3 mmol) were added and the mixture heated by microwave irradiation at 140° C. for 5 min. The mixture was concentrated in vacuo and the residue dissolved in DCM and $H_2O$. The phases were separated and the aqueous layer extracted with DCM. The combined organics were washed with brine, dried over $Na_2SO_4$, filtered and concentrated in vacuo to give the title compound (0.99 g) which was used without further purification. $^1$H NMR (400 MHz, $CDCl_3$) δ: 7.30 (s, 1H), 4.38 (qt, 2H), 2.38-2.33 (m, 3H), 1.54 (tt, 3H).

Intermediate 1.157: 2-chloro-5-(1-ethyl-4-methyl-1H-1,2,3-triazol-5-yl)pyridine

The title compound (0.27 g) was prepared from Intermediate 1.157a (0.98 g, 8.8 mmol), 5-bromo-2-chloro-pyridine (0.85 g, 4.4 mmol, CAS: 53939-30-3), PEPPSI™ Pr catalyst (60 mg, 0.09 mmol), 2,2-dimethylpropanoic acid (0.14 g, 1.3 mmol) and potassium carbonate (1.2 g, 8.8 mmol) in accordance with the procedure described for Intermediate 1.125a, heating at 130° C. for 2 h. The crude product was purified by flash column chromatography on the Biotage Isolera One™ (10 g silica column, eluting 0-70% EtOAc in heptanes) and reverse phase preparative HPLC (Method 2). LCMS (Method 14): 1.55 min, 223.6 $[M+H]^+$ Intermediate 1.158: 4-(5-chloropyrazin-2-yl)-3,5-dimethylisoxazole The title compound (0.52 g) was prepared from 2-bromo-5-chloro-pyrazine (1 g, 5.2 mmol, CAS: 912773-21-8), (3,5-dimethylisoxazol-4-yl)boronic acid (1.1 g, 7.8 mmol, CAS: 16114-47-9), Pd(dppf)$Cl_2$ (0.19 mg, 0.26 mmol) and sodium carbonate (2.2 g, 21 mmol) in accordance with the procedure described for Intermediate 1.6, heating at 120° C. for 16 h. The crude product was purified by flash column chromatography on the Biotage Isolera One™ (12 g silica column, eluting 0-10% MeOH in DCM). LCMS (Method 19): 2.09 min, 210.2 $[M+H]^+$ Intermediate 1.161: 2-chloro-5-(1-cyclopropyl-4-methyl-1H-1,2,3-triazol-5-yl)pyridine The title compound (0.26 g) was prepared from 1-cyclopropyl-4-methyl-triazole (1.1 g, 8.8 mmol, CAS: 2370890-05-2), 5-bromo-2-chloro-pyridine (0.85 g, 4.4 mmol, CAS: 53939-30-3), PEPPSI™ Pr catalyst (60 mg, 0.09 mmol), 2,2-dimethylpropanoic acid (0.14 g, 1.3 mmol) and potassium carbonate (1.2 g, 8.8 mmol) in accordance with the procedure described for Intermediate 1.125a, heating at 130° C. for 2 h. The crude product was purified by flash column chromatography on the Biotage Isolera One™ (10 g silica column eluting 0-70% EtOAc in heptanes) and reverse phase preparative HPLC (Method 2). LCMS (Method 14): 1.55 min, 223.6 $[M+H]^+$ Intermediate 1.162: 5-(3,5-dimethylisoxazol-4-yl)-3-fluoropyridin-2-amine The title compound (0.56 g) was prepared from 5-bromo-3-fluoro-pyridin-2-amine (1.0 g, 5.2 mmol, CAS: 748812-37-5), (3,5-dimethylisoxazol-4-yl)boronic acid (0.89 g, 6.3 mmol, CAS: 16114-47-9), Pd(dppf)$Cl_2$ (0.19 g, 0.26 mmol) and sodium carbonate (0.22 g, 21 mmol) in accordance with the procedure described for Intermediate 1.6, heating at 80° C. for 16 h. The crude product was purified by flash column chromatography on the Biotage Isolera One™ (25 g silica column, eluting 0-2% MeOH in DCM). LCMS (Method 14): 1.26 min, 208.2 $[M+H]^+$ Intermediate 1.165: 2-chloro-5-(1,4-dimethyl-1H-pyrazol-5-yl)pyrimidine The title compound (0.16 g) was prepared from 5-bromo-2-chloro-pyrimidine (0.25 g, 1.3 mmol, CAS: 32779-36-5), 1,4-dimethyl-5-(4,4,5,5-tetramethyl-1,3,2-dioxaborolan-2-yl)pyrazole (0.34 g, 1.5 mmol, CAS: 1047644-76-7), tetrakis(triphenylphosphine)palladium(0) (0.15 g, 0.13 mmol) and potassium carbonate (0.36 g, 2.6 mmol) in accordance with the procedure described for Intermediate 1.125. The crude product was purified by flash column chromatography on the Biotage Isolera One™ (12 g silica column, eluting 0-2% MeOH in DCM). LCMS (Method 14): 1.51 min, 209.2 $[M+H]^+$ Intermediate 1.173: 5-(4-cyclopropyl-1-methyl-1H-1,2,3-triazol-5-yl)pyridin-2-amine Intermediate 1.173a: 1-cyclopropyl-2,2-diethoxy-ethanone A solution of 2,2-diethoxy-N-methoxy-N-methyl-acetamide (3.35 g, 17.5 mmol, CAS: 1378705-69-1) in anhydrous THF (80 mL) was cooled to −78° C. under argon. A solution of bromo(cyclopropyl)magnesium (1 M in MeTHF; 21 mL, 21 mmol, CAS: 23719-80-4) was added slowly and mixture was stirred at −78° C. for 3 h. The reaction was quenched with the addition of saturated aqueous $NH_4Cl$ and extracted with EtOAc. The combined organics were dried over $Na_2SO_4$, filtered and concentrated in vacuo to provide the title compound (3.0 g). $^1$H NMR (400 MHz, $CDCl_3$) δ:

4.71 (s, 1H), 3.76-3.54 (m, 4H), 2.41-2.33 (m, 1H), 1.30-1.20 (m, 6H), 1.09-1.04 (m, 2H), 1.01-0.91 (m, 2H).

Intermediate 1.173b: 4-cyclopropyl-1-methyl-1H-1,2,3-triazole

To a stirred solution of Intermediate 1.173a (2 g, 11.6 mmol) in MeOH (25 mL) was added 4-methylbenzenesulfonohydrazide (2.8 g, 15.1 mmol, CAS: 1576-35-8) and the mixture stirred at rt for 1 h. A further portion of 4-methylbenzenesulfonohydrazide (0.64 g, 3.4 mmol) was added and mixture was stirred at rt for 1 h. Methanamine (1.3 mL, 15.1 mmol) and triethylamine (2.1 mL, 15.1 mmol) were then added and the mixture stirred for 5 min at rt and then heated by microwave irradiation at 140° C. for 5 min. The mixture was concentrated in vacuo and the residue was dissolved in water and DCM. The aqueous layer was extracted with DCM and the combined organics were, dried over $Na_2SO_4$, filtered and concentrated in vacuo. The crude product was purified by flash column chromatography on the Biotage Isolera One™ (40 g silica column, 2-65% EtOAc in heptanes) to provide the title product (0.66 g). $^1H$ NMR (400 MHz, $CDCl_3$) δ: 7.20 (s, 1H), 4.02 (s, 3H), 1.97-1.89 (m, 1H), 0.96-0.90 (m, 2H), 0.84-0.79 (m, 2H).

Intermediate 1.173: 5-(4-cyclopropyl-1-methyl-1H-1,2,3-triazol-5-yl)pyridin-2-amine To a solution of Intermediate 1.173b (0.3 g, 2.4 mmol) in toluene (6.1 mL) was added 5-bromo-2-chloro-pyridine (1.4 g, 7.3 mmol, CAS: 53939-30-3), palladium(II) acetate (55 mg, 0.24 mmol), potassium carbonate (0.67 g, 4.9 mmol) and triphenylphosphine (0.13 g, 0.49 mmol) under argon. The reaction mixture was stirred at 120° C. for 40 h. Further portions of palladium(II) acetate (55 mg, 0.24 mmol), triphenylphosphine (0.13 g, 0.49 mmol), potassium carbonate (0.34 g, 2.5 mmol) and 5-bromo-2-chloro-pyridine (0.47 g, 2.4 mmol) were added and the reaction mixture was stirred at 120° C. for 72 h. The reaction mixture was diluted with EtOAc and water and the aqueous layer was extracted with EtOAc. The combined organics were washed with brine, dried over $Na_2SO_4$, filtered and concentrated in vacuo. The crude product was purified by flash column chromatography on the Biotage Isolera One™ (12 g silica column, 2-80% EtOAc in heptanes) to provide the title compound (0.22 g). $^1H$ NMR (400 MHz, $CDCl_3$) δ: 8.48 (dd, 1H), 7.73 (dd, 1H), 7.52 (dd, 1H), 3.96 (s, 3H), 1.77-1.66 (tt, 1H), 1.07-1.00 (m, 2H), 0.97-0.87 (m, 2H).

Intermediate 1.174: 5-(4-chloro-1-methyl-1H-pyrazol-5-yl)pyridin-2-amine

The title compound (1.1 g) was prepared from 4-chloro-1-methyl-5-(4,4,5,5-tetramethyl-1,3,2-dioxaborolan-2-yl) pyrazole (2.3 g, 9.5 mmol, CAS: 1430057-83-2), 5-bromopyridin-2-amine (1.1 g, 6.40 mmol, CAS: 1072-97-5), XPhos Pd G2 (0.25 g, 0.32 mmol) and tripotassium phosphate (0.5 M aqueous; 25 mL, 13 mmol) in accordance with the procedure described for Intermediate 1.3 and heating to 60° C. for 18 h. The crude product was purified flash column chromatography (eluting 0-5% MeOH in DCM). $^1H$ NMR (400 MHz, $CDCl_3$) δ: 8.04 (dd, 1H), 7.46-7.39 (m, 2H), 6.56 (dd, 1H), 4.71 (s, 2H), 3.73 (s, 3H).

Intermediate 1.179: 6-(1,4-dimethyl-1H-pyrazol-5-yl)-5-fluoropyridin-3-amine

The title compound (1 g) was prepared from 6-bromo-5-fluoro-pyridin-3-amine (1 g, 5.2 mmol, CAS: 1256276-41-1), 1,4-dimethyl-5-(4,4,5,5-tetramethyl-1,3,2-dioxaborolan-2-yl)pyrazole (1.7 g, 7.9 mmol, CAS: 1047644-76-7), $Pd(dppf)Cl_2$ (0.38 g, 0.52 mmol) and sodium carbonate (2.2 g, 21 mmol) in accordance with the procedure described for Intermediate 1.6, and heated by microwave irradiation at 120° C. for 1 h. The crude product was purified by flash column chromatography on the Biotage Isolera One™ (20 g silica column, eluting 20-100% EtOAc in heptanes). $^1H$ NMR (400 MHz, $CDCl_3$) δ: 8.05 (s, 1H), 7.37 (s, 1H), 6.86-6.74 (m, 1H), 3.82 (s, 3H), 2.01 (d, 3H).

Intermediate 1.190: 2-(5-(6-chloropyridin-3-yl)-4-methyl-1H-1,2,3-triazol-1-yl)-N,N-dimethylacetamide Intermediate 1.190a: N,N-dimethyl-2-(4-methyl-1H-1,2,3-triazol-1-yl)acetamide To a solution of 2-(4-methyltriazol-1-yl)acetic acid (0.11 g, 8.1 mmol, CAS: 887405-58-5) and N-methylmethanamine (2 M in THF; 12 mL, 24 mmol) in DMF (25 mL) was added T3P® (50% w/w solution in EtOAc; 7.2 mL, 12 mmol). The reaction was stirred at rt for 20 h, then concentrated in vacuo. The residue was diluted with DCM and washed with aqueous saturated $NaHCO_3$. The aqueous layer was extracted with DCM and the combined organics washed with water, dried over $Na_2SO_4$, and concentrated in vacuo. The crude product was purified by flash column chromatography on the Biotage Isolera One™ (40 g silica column, eluting 0-10% MeOH in DCM) to provide the title compound (0.7 g). LCMS (Method 14): 1.01 min, 169.2 $[M+H]^+$ Intermediate 1.190: 2-(5-(6-chloropyridin-3-yl)-4-methyl-1H-1,2,3-triazol-1-yl)-N,N-dimethylacetamide A solution of Intermediate 1.190a (0.64 g, 3.1 mmol), 5-bromo-2-chloro-pyridine (0.59 g, 3.1 mmol, CAS: 53939-30-3), 2,2-dimethylpropanoic acid (94 mg, 0.92 mmol), palladium(II) acetate (69 mg, 0.31 mmol), and potassium carbonate (0.85 g, 6.1 mmol) in DMA (12 mL) was heated by microwave irradiation at 120° C. for 1 h. The reaction mixture was cooled to rt, diluted with EtOAc, and quenched with aqueous saturated $NH_4Cl$. The layers were separated, and the aqueous layer was extracted with EtOAc. The combined organics were washed with brine, dried over $Na_2SO_4$, and concentrated in vacuo. The crude product was purified by flash column chromatography on the Biotage Isolera One™ (20 g silica column, eluting 0-100% EtOAc in heptanes then 0-10% MeOH in DCM) to provide the title compound (71 mg). $^1H$ NMR (400 MHz, $CDCl_3$) δ: 8.40 (dd, 1H), 7.80 (dd, 1H), 7.46 (dd, 1H), 5.05 (s, 2H), 3.07 (s, 3H), 2.96 (s, 3H), 2.33 (s, 3H).

Intermediate 1.193: 5-(6-aminopyridin-3-yl)-1-methyl-1H-pyrazole-4-carbonitrile

The title compound (0.21 g) was prepared from 5-(4,4,5,5-tetramethyl-1,3,2-dioxaborolan-2-yl)pyridin-2-amine (0.53 g, 2.4 mmol, CAS: 827614-64-2), 5-bromo-1-methyl-pyrazole-4-carbonitrile (0.3 g, 1.6 mmol, CAS: 1269293-80-2), $Pd(dppf)Cl_2$ (0.12 g, 0.16 mmol) and sodium carbonate (0.68 g, 6.5 mmol) in accordance with the procedure described for Intermediate 1.6, and heated by microwave irradiation at 120° C. for 1 h. The crude product was purified by flash column chromatography on the Biotage Isolera One™ (20 g silica column, eluting 0-100% EtOAc in heptanes then 0-10% MeOH in DCM). LCMS (Method 14): 0.78 min, 200.2 [M+H]+

Intermediate 1.195: 5-(1,3,4-trimethyl-1H-pyrazol-5-yl)pyridin-2-amine

Split over 3 separate batches, a mixture of 2,4,5-trimethyl-4H-pyrazol-3-one hydrochloride (1.5 g, 9.2 mmol, CAS: 1285259-23-5), N-phenyl-bis(trifluoromethanesulfonimide) (3.5 g, 9.7 mmol) and sodium carbonate (2.9 g, 27.6 mmol) in THF (33 mL) were heated by microwave irradiation at 110° C. for 6 min. The mixture was cooled to rt, then 5-(4,4,5,5-tetramethyl-1,3,2-dioxaborolan-2-yl)pyridin-2-amine (3.1 g, 14 mmol, CAS: 827614-64-2), Pd(dppf)$Cl_2$ (0.34 g, 0.46 mmol) and water (15 mL) were added and the mixture heated microwave irradiation at 110° C. for 45 min. The batches were combined, and the mixture filtered through a pad of celite. The solvent was concentrated in vacuo, and the crude product was purified by flash column chromatography (eluting 0-5% MeOH in DCM) to provide the title compound (1.4 g). LCMS (Method 14): 0.97 min, 203.2 $[M+H]^+$ Intermediate 1.196: 5-(3,5-dimethylisothiazol-4-yl)pyridin-2-amine The title compound (0.14 g) was prepared from 4-iodo-3,5-dimethyl-isothiazole (0.2 g, 0.82 mmol, CAS: 113234-27-8), 5-(4,4,5,5-tetramethyl-1,3,2-dioxaborolan-2-yl)pyridin-2-amine (0.18 g, 0.82 mmol, CAS: 827614-64-2), Pd(dppf)$Cl_2$ (59 mg, 0.08 mmol) and potassium carbonate (0.34 g, 2.5 mmol) in accordance with the procedure described for Intermediate 1.1, heating at 100° C. for 18 h. The crude product was purified by flash column chromatography on the Biotage Isolera One™ (40 g silica column, eluting 2-10% MeOH in DCM). $^1$H NMR (400 MHz, $CDCl_3$) δ: 7.94 (s, 1H), 7.32 (dd, 1H), 6.61 (d, 1H), 4.60 (s, 2H), 2.39 (s, 3H), 2.33 (s, 3H).

Intermediate 1.207: 6-(3,5-dimethyl-1-((2-(trimethylsilyl)ethoxy)methyl)-1H-pyrazol-4-yl)pyridin-3-amine To a stirred solution of 6-chloropyridin-3-amine (0.1 g, 0.8 mmol, CAS: 5350-93-6) and 2-[[3,5-dimethyl-4-(4,4,5,5-tetramethyl-1,3,2-dioxaborolan-2-yl)pyrazol-1-yl]methoxy]ethyl-trimethyl-silane (0.58 g, 1.4 mmol, CAS: 1000801-22-8) in 1,4-dioxane (4 mL) was added water (1 mL), Pd-170 (26 mg, 0.04 mmol) and potassium carbonate (0.24 g, 1.7 mmol). The reaction mixture was stirred at 90° C. for 2 h. The reaction mixture was cooled to rt, diluted with brine, and extracted with EtOAc. The combined organics were passed through a phase separator and concentrated in vacuo. The crude product was purified by flash column chromatography on the Teledyne ISCO CombiFlash® (12 g silica column, eluting 0-100% 3:1 EtOAc:EtOH in isohexane) to provide the title compound as a brown oil (0.21 g). LCMS (Method 28): 1.42 min, 319.5 $[M+H]^+$ Intermediate 1.214: 6'-amino-1,2,4-trimethyl-[3,3'-bipyridin]-6(1H)-one The title compound (90 mg) was prepared from 5-bromo-1,4,6-trimethyl-pyridin-2-one (0.1 g, 0.48 mmol, CAS: 1380389-40-1), (6-amino-3-pyridyl)boronic acid (0.1 g, 0.73 mmol, CAS: 851524-96-4), Pd-170 (20 mg, 0.03 mmol) and potassium carbonate (0.13 g, 0.96 mmol) in accordance with the procedure described for Intermediate 1.207. The crude product was purified by flash column chromatography on the Teledyne ISCO CombiFlash® (12 g silica column, eluting 0-10% MeOH in DCM). LCMS (Method 29): 0.44 min, 230.2 $[M+H]^+$ Intermediate 1.216: 5-(1,3,5-trimethyl-1H-pyrazol-4-yl)pyridin-2-amine The title compound (79 mg) was prepared from 4-bromo-1,3,5-trimethyl-pyrazole (0.1 g, 0.55 mmol, CAS: 15801-69-1), (6-amino-3-pyridyl)boronic acid (0.11 g, 0.83 mmol, CAS: 851524-96-4), Pd-170 (22 mg, 0.03 mmol) and potassium carbonate (0.15 g, 1.1 mmol) in accordance with the procedure described for Intermediate 1.207. The crude product was purified by flash column chromatography on the Teledyne ISCO CombiFlash® (12 g silica column, eluting 0-10% MeOH in DCM). LCMS (Method 26): 0.53 min, 203.2 $[M+H]^+$ Intermediate 1.219: 5-(1-methyl-4-(trifluoromethyl)-1H-pyrazol-5-yl)pyridin-2-amine The title compound (0.45 g) was prepared from 5-iodo-1-methyl-4-(trifluoromethyl)-1H-pyrazole (0.75 g, 2.7 mmol, CAS: 2137730-49-3), 5-(4,4,5,5-tetramethyl-1,3,2-dioxaborolan-2-yl)pyridin-2-amine (0.82 g, 3.3 mmol, CAS: 827614-64-2), Pd(dppf)$Cl_2$ (0.2 g, 0.27 mmol) and potassium carbonate (1.1 g, 8.2 mmol) in accordance with the procedure described for Intermediate 1.1, heating at 80° C. for 18 h. The crude product was purified by flash column chromatography on the Biotage Isolera One™ (50 g silica column, eluting 2-4% MeOH in DCM) then by an SCX cartridge (10 g, washed with MeOH and eluted with 2 M methanolic ammonia). LCMS (Method 14): 1.18 min, 243.2 $[M+H]^+$ Intermediate 2.1: tert-butyl (S)-(1-((4-(2,3-dimethylpyridin-4-yl)phenyl)amino)-1-oxo-3,3-diphenylpropan-2-yl)carbamate To a stirred solution of (S)-2-((tert-butoxycarbonyl)amino)-3,3-diphenylpropanoic acid (0.20 g, 0.59 mmol, CAS: 138662-63-2) and Intermediate 1.1 (0.12 g, 0.59 mmol) in EtOAc (5 mL) at rt was added triethylamine (0.16 mL, 1.2 mmol) and T3P® (50% w/w solution in EtOAc; 1.1 mL, 1.8 mmol) and the reaction mixture stirred for 2 h. The reaction mixture was diluted with saturated aqueous $NaHCO_3$ and extracted into EtOAc. The combined organics were washed with water, brine, dried over $Na_2SO_4$, filtered and concentrated in vacuo. The crude product was purified by flash column chromatography (eluting 75-100% EtOAc in heptanes) to provide the title compound (0.15 g). LCMS (Method 2): 1.02 min, 522.3 $[M+H]^+$ Intermediate 1.219: 5-(1-methyl-4-(trifluoromethyl)-1H-pyrazol-5-yl)pyridin-2-amine The title compound (0.45 g) was prepared from 5-iodo-1-methyl-4-(trifluoromethyl)-1H-pyrazole (0.75 g, 2.7 mmol, CAS: 2137730-49-3), 5-(4,4,5,5-tetramethyl-1,3,2-dioxaborolan-2-yl)pyridin-2-amine (0.82 g, 3.3 mmol, CAS: 827614-64-2), Pd(dppf)$Cl_2$ (0.2 g, 0.27 mmol) and potassium carbonate (1.1 g, 8.2 mmol) in accordance with the procedure described for Intermediate 1.1, heating at 80° C. for 18 h. The crude product was purified by flash column chromatography on the Biotage Isolera One™ (50 g silica column, eluting 2-4% MeOH in DCM) then by an SCX cartridge (10 g, washed with MeOH and eluted with 2 M methanolic ammonia). LCMS (Method 14): 1.18 min, 243.2 $[M+H]^+$ Intermediate 2.2: tert-butyl (S)-(1-((4-(3-chloropyridin-4-yl)phenyl)amino)-1-oxo-3,3-diphenylpropan-2-yl)carbamate The title compound (0.48 g) was prepared from Intermediate 1.2 (0.18 g, 0.89 mmol), (S)-2-((tert-butoxycarbonyl)amino)-3,3-diphenylpropanoic acid (0.18 g, 0.89 mmol, CAS: 138662-63-2), T3P® (50% w/w solution in EtOAc; 1.7 mL, 2.7 mmol), and triethylamine (0.31 mL, 2.22 mmol) in accordance with the procedure described for Intermediate 2.1 and used without further purification. LCMS (Method 2): 1.02 min, 528.2 $[M+H]^+$ Intermediate 2.3: tert-butyl (S)-(1-((4-(3-methoxypyridin-4-yl)phenyl)amino)-1-oxo-3,3-diphenylpropan-2-yl)carbamate The title compound (0.57 g) was prepared from Intermediate 1.3 (0.25 g, 1.3 mmol), (S)-2-((tert-butoxycarbonyl)amino)-3,3-diphenylpropanoic acid (0.43 g, 1.25 mmol, CAS: 138662-63-2), T3P® (50% w/w solution in EtOAc; 2.4 mL, 3.8 mmol) and triethylamine (0.35 mL, 2.5 mmol) in accordance with the procedure described for Intermediate 2.1. The crude product was purified by flash column chromatography (eluting 50% EtOAc in heptanes). LCMS (Method 2): 0.98 min, 524.3 $[M+H]^+$ Intermediate 2.4: tert-butyl (S)-(1-((4-(3-methylpyridin-4-yl)phenyl)amino)-1-oxo-3,3-diphenylpropan-2-yl)carbamate The title compound (0.21 g) was prepared from Intermediate 1.4 (61 mg, 0.33 mmol), (S)-2-((tert-butoxycarbonyl)amino)-3,3-diphenylpropanoic acid (0.11 g, 0.82 mmol, CAS: 138662-63-2), T3P® (50% w/w solution in EtOAc; 0.21 mL, 0.33 mmol) and triethylamine (0.11 mL, 0.82 mmol) in accordance with the procedure described for Intermediate 2.1 and used without further purification. LCMS (Method 2): 1.00 min, 508.3 $[M+H]^+$ Intermediate 2.5: tert-butyl (S)-(1-oxo-3,3-diphenyl-1-((4-(3-(trifluoromethyl)pyridin-4-yl)phenyl)amino)propan-2-yl)carbamate The title compound (0.16 g) was prepared from Intermediate 1.5 (75 mg, 0.31 mmol), (S)-2-((tert-butoxycarbonyl)amino)-3,3-diphenylpropanoic acid (0.11 g, 0.31 mmol, CAS: 138662-63-2), T3P® (50% w/w solution in EtOAc; 0.6 mL, 0.94 mmol) and triethylamine (0.09 mL, 0.63 mmol) in accordance with the procedure described for Intermediate 2.1 and used without further purification. LCMS (Method 2): 1.06 min, 562.3 $[M+H]^+$ Intermediate 2.6: tert-butyl (S)-(1-((4-(3,5-dimethylpyridin-4-yl)phenyl)amino)-1-oxo-3,3-diphenylpropan-2-yl)carbamate The title compound (0.27 g) was prepared from Intermediate 1.6 (0.15 g, 0.76 mmol), (S)-2-((tert-butoxycarbonyl)amino)-3,3-diphenylpropanoic acid (0.26 g, 0.76 mmol, CAS: 138662-63-2), T3P® (50% w/w solution in EtOAc; 1.4 mL, 2.3 mmol) and triethylamine (0.32 mL, 2.27 mmol) in accordance with the procedure described for Intermediate 2.1. The crude product was purified by flash column chromatography (eluting 60-70% EtOAc in heptanes). LCMS (Method 3): 2.72 min, 522.3 $[M+H]^+$ Intermediate 2.7: tert-butyl (S)-(1-((4-(3-(methylamino)pyridin-4-yl)phenyl)amino)-1-oxo-3,3-diphenylpropan-2-yl)carbamate The title compound (0.16 g) was prepared from Intermediate 1.7 (0.14 g, 0.35 mmol), (S)-2-((tert-butoxycarbonyl)amino)-3,3-diphenylpropanoic acid (0.12 g, 0.35 mmol, CAS: 138662-63-2), T3P® (50% w/w solution in EtOAc; 1.3 mL, 1.1 mmol) and triethylamine (0.15 mL, 1.05 mmol) in accordance with the procedure described for Intermediate 2.1, with reagents added at 0° C. and the mixture stirred at rt for 3 h. The crude product was purified by reverse phase column chromatography on the Biotage Isolera One™ (30 g C18 column, eluting 30-80% MeCN in pH10 0.1 M $NH_4HCO_3$ buffer solution). LCMS (Method 2): 0.96 min, 523.3 $[M+H]^+$ Intermediate 2.8: tert-butyl (S)-(1-((4-(3-(dimethylamino)pyridin-4-yl)phenyl)amino)-1-oxo-3,3-diphenylpropan-2-yl)carbamate The title compound (0.14 g) was prepared from Intermediate 1.8 (75 mg, 0.35 mmol), (S)-2-((tert-butoxycarbonyl)amino)-3,3-diphenylpropanoic acid (0.13 g, 0.37 mmol, CAS: 138662-63-2), T3P® (50% w/w solution in EtOAc; 1.3 mL, 1.1 mmol) and triethylamine (0.17 mL, 1.23 mmol) in accordance with the procedure described for Intermediate 2.1, with reagents added at 0° C. and the mixture stirred at rt for 1.5 h. The crude product was purified by reverse phase column chromatography on the Biotage Isolera One™ (30 g C18 column, eluting 30-80% MeCN in pH10 0.1 M $NH_4HCO_3$ buffer solution). LCMS (Method 2): 1.02 min, 537.3 [M+H]+

Intermediate 2.9: tert-butyl (S)-(1-((4-(3,5-dimethoxypyridin-4-yl)phenyl)amino)-1-oxo-3,3-diphenylpropan-2-yl)carbamate The title compound (0.16 g) was prepared from Intermediate 1.9 (0.10 g, 0.44 mmol), (S)-2-((tert-butoxycarbonyl)amino)-3,3-diphenylpropanoic acid (0.15 g, 0.44 mmol, CAS: 138662-63-2), T3P® (50% w/w solution in EtOAc; 0.84 mL, 1.3 mmol) and triethylamine (0.21 mL, 1.54 mmol) in accordance with the procedure described for Intermediate 2.1. The crude product was purified by flash column chromatography (eluting 5% MeOH in DCM). LCMS (Method 2): 0.97 min, 554.3 [M+H]+

Intermediate 2.10: tert-butyl (S)-(1-((4-(3-fluoro-5-methoxypyridin-4-yl)phenyl)amino)-1-oxo-3,3-diphenylpropan-2-yl)carbamate The title compound (98 mg) was prepared from Intermediate 1.10 (90 mg, 0.41 mmol), (S)-2-((tert-butoxycarbonyl)amino)-3,3-diphenylpropanoic acid (0.14 g, 0.41 mmol, CAS: 138662-63-2), T3P® (50% w/w solution in EtOAc; 0.79 mL, 1.2 mmol) and triethylamine (0.2 mL, 1.4 mmol) in accordance with the procedure described for Intermediate 2.1, with reagents added at 0° C. and the mixture stirred at rt for 2 h. The crude product was purified by flash column chromatography (eluting 40% EtOAc in hexanes). LCMS (Method 2): 1.00 min, 542.3 $[M+H]^+$ Intermediate 2.11: tert-butyl (S)-(1-((4-(2-methyl-6-oxo-1,6-dihydropyridin-3-yl)phenyl)amino)-1-oxo-3,3-diphenylpropan-2-yl)carbamate The title compound (0.20 g) was prepared from Intermediate 1.11 (0.12 g, 0.57 mmol), (S)-2-((tert-butoxycarbonyl)amino)-3,3-diphenylpropanoic acid (0.20 g, 0.57 mmol, CAS: 138662-63-2), T3P® (50% w/w solution in EtOAc; 1.1 mL, 1.7 mmol) and triethylamine (0.28 mL, 2.0 mmol) in accordance with the procedure described for Intermediate 2.1. The crude product was purified by flash column chromatography (eluting 1% MeOH in EtOAc). LCMS (Method 2): 0.86 min, 524.3 $[M+H]^+$ Intermediate 2.12: tert-butyl (S)-(1-((4-(1,4-dimethyl-6-oxo-1,6-dihydropyridin-3-yl)phenyl)amino)-1-oxo-3,3-diphenylpropan-2-yl)carbamate The title compound (0.28 g) was prepared from Intermediate 1.12 (0.11 g, 0.53 mmol), (S)-2-((tert-butoxycarbonyl)amino)-3,3-diphenylpropanoic acid (0.18 g, 0.53 mmol, CAS: 138662-63-2), T3P® (50% w/w solution in EtOAc; 1.0 mL, 1.6 mmol) and triethylamine (0.18 mL, 1.32 mmol) in accordance with the procedure described for Intermediate 2.1 and used without further purification. LCMS (Method 4): 0.91 min, 538.3 $[M+H]^+$ Intermediate 2.13: tert-butyl (S)-(1-((4-(1,2-dimethyl-6-oxo-1,6-dihydropyridin-3-yl)phenyl)amino)-1-oxo-3,3-diphenylpropan-2-yl)carbamate The title compound (0.29 g) was prepared from Intermediate 1.13 (0.15 g, 0.70 mmol), (S)-2-((tert-butoxycarbonyl)amino)-3,3-diphenylpropanoic acid (0.24 g, 0.70 mmol, CAS: 138662-63-2), T3P® (50% w/w solution in EtOAc; 1.3 mL, 2.1 mmol) and triethylamine (0.24 mL, 1.75 mmol) in accordance with the procedure described for Intermediate 2.1. The crude product was purified by flash column chromatography on the Biotage Isolera One™ (30 g ZIP sphere silica column, eluting 40-100% EtOAc in heptanes followed by 5% MeOH in EtOAc). LCMS (Method 4): 0.94 min, 538.3 $[M+H]^+$ Intermediate 2.14: tert-butyl (S)-(1-((4-(3,5-dimethylpyridin-4-yl)-3-fluorophenyl)amino)-1-oxo-3,3-diphenylpropan-2-yl)carbamate The title compound (0.11 g) was prepared from Intermediate 1.14 (0.10 g, 0.44 mmol), (S)-2-((tert-butoxycarbonyl)amino)-3,3-diphenylpropanoic acid (0.15 g, 0.44 mmol, CAS: 138662-63-2), T3P® (50% w/w solution in EtOAc; 0.84 mL, 1.3 mmol) and triethylamine (0.18 mL, 1.32 mmol) in accordance with the procedure described for Intermediate 2.1. The crude product was purified by flash column chromatography on the Biotage Isolera One™ (10 g silica column, eluting 20-80% EtOAc in heptanes). LCMS (Method 4): 1.04 min, 540.3 $[M+H]^+$ Intermediate 2.15: tert-butyl (S)-(1-((3-fluoro-4-(3-methylpyridin-4-yl)phenyl)amino)-1-oxo-3,3-diphenylpropan-2-yl)carbamate The title compound (0.20 g) was prepared from Intermediate 1.15 (0.16 g, 0.79 mmol), (S)-2-((tert-butoxycarbonyl)amino)-3,3-diphenylpropanoic acid (0.27 g, 0.79 mmol, CAS: 138662-63-2), T3P® (50% w/w solution in EtOAc; 1.5 mL, 2.4 mmol) and triethylamine (0.33 mL, 2.37 mmol) in accordance with the procedure described for Intermediate 2.1. The crude product was purified by flash column chromatography (eluting 70% EtOAc in heptanes). LCMS (Method 3): 2.71 min, 526.3 $[M+H]^+$ Intermediate 2.16: tert-butyl (S)-(1-((4-(1,2-dimethyl-6-oxo-1,6-dihydropyridin-3-yl)-3-fluorophenyl)amino)-1-oxo-3,3-diphenylpropan-2-yl)carbamate The title compound (0.12 g) was prepared from Intermediate 1.16 (0.16 g, 0.69 mmol), (S)-2-((tert-butoxycarbonyl)amino)-3,3-diphenylpropanoic acid (0.24 g, 0.69 mmol, CAS: 138662-63-2), T3P® (50% w/w solution in EtOAc; 1.3 mL, 2.1 mmol) and triethylamine (0.29 mL, 2.07 mmol) in accordance with the procedure described for Intermediate 2.1. The crude product was purified by flash column chromatography (eluting 1% MeOH in EtOAc). LCMS (Method 3): 2.49 min, 556.3 $[M+H]^+$ Intermediate 2.17: tert-butyl (S)-(1-((4-(1,4-dimethyl-6-oxo-1,6-dihydropyridin-3-yl)-3-fluorophenyl)amino)-1-oxo-3,3-diphenylpropan-2-yl)carbamate The title compound (0.16 g) was prepared from Intermediate 1.17 (0.19 g, 0.81 mmol), (S)-2-((tert-butoxycarbonyl)amino)-3,3-diphenylpropanoic acid (0.28 g, 0.81 mmol, CAS: 138662-63-2), T3P® (50% w/w solution in EtOAc; 1.6 mL, 2.4 mmol) and triethylamine (0.34 mL, 2.43 mmol) in accordance with the procedure described for Intermediate 2.1. The crude product was purified by flash column chromatography (eluting 1% MeOH in EtOAc). LCMS (Method 4): 0.92 min, 556.3 $[M+H]^+$ Intermediate 2.18: tert-butyl ((2S)-1-((3-fluoro-4-(3-fluoro-5-methoxypyridin-4-yl)phenyl)amino)-1-oxo-3,3-diphenylpropan-2-yl)carbamate The title compound (0.10 g) was prepared from Intermediate 1.18 (0.26 g, 1.1 mmol), (S)-2-((tert-butoxycarbonyl)amino)-3,3-diphenylpropanoic acid (0.38 g, 1.1 mmol, CAS: 138662-63-2) T3P® (50% w/w solution in EtOAc; 2.1 mL, 3.3 mmol) and triethylamine (0.46 mL, 3.3 mmol) in accordance with the procedure described for Intermediate 2.1. The crude product was purified by flash column chromatography (eluting 40% EtOAc in heptanes). LCMS (Method 3): 2.78 min, 560.3 $[M+H]^+$ Intermediate 2.19: tert-butyl (S)-(1,1-bis(4-fluorophenyl)-3-((4-(3-methoxypyridin-4-yl)phenyl)amino)-3-oxopropan-2-yl)carbamate To a stirred solution of Intermediate 1.3 (0.10 g, 0.50 mmol) and (2S)-2-(tert-butoxycarbonylamino)-3,3-bis(4-fluorophenyl)propanoic acid (0.19 g, 0.50 mmol, CAS: 481055-29-2) and triethylamine (0.14 mL, 1.0 mmol) in EtOAc (4 mL) at rt was added HATU (0.20 g, 0.52 mmol) and the reaction stirred at rt for 2 h. The reaction mixture was diluted with saturated aqueous $NaHCO_3$ and extracted into EtOAc. The combined organics were washed with brine, dried over $Na_2SO_4$, filtered and concentrated in vacuo. The crude product was purified by flash column chromatography (eluting 100% EtOAc) to provide the title compound (0.28 g). LCMS (Method 2): 0.98 min, 560.3 $[M+H]^+$ Intermediate 2.29: tert-butyl (S)-(1-((4-(1,2-dimethyl-6-oxo-1,6-dihydropyridin-3-yl)-3,5-difluorophenyl)amino)-1-oxo-3,3-diphenylpropan-2-yl)carbamate To a solution of Intermediate 1.29 (0.10 g, 0.41 mmol), (S)-2-((tert-butoxycarbonyl)amino)-3,3-diphenyl-propanoic acid (0.15 g, 0.45 mmol, CAS: 138662-63-2), triethylamine (0.23 mL, 1.6 mmol), and DMAP (10 mg, 0.08 mmol) in MeCN (4 mL) at rt was added T3P® (50% w/w solution in EtOAc; 1.0 mL, 1.6 mmol) and the reaction mixture stirred for 18 h. The mixture was diluted with saturated aqueous $NaHCO_3$ and the crude product extracted into EtOAc. The combined organics were washed with brine, dried over $MgSO_4$, filtered and concentrated in vacuo. The crude product was purified by reverse phase column chromatography on the Biotage Isolera One™ (30 g C18 column, eluting 20-80% 0.1% ammonia in MeCN in 0.1% ammonia aqueous solution) to provide the title compound (36 mg). LCMS (Method 3): 2.55 min, 574.2 $[M+H]^+$ Intermediate 2.30: tert-butyl (S)-(1-((3,5-difluoro-4-(3-methoxypyridin-4-yl)phenyl)amino)-1-oxo-3,3-diphenylpropan-2-yl)carbamate The title compound (0.14 g) was prepared from Intermediate 1.30 (0.11 g, 0.47 mmol), (S)-2-((tert-butoxycarbonyl)amino)-3,3-diphenylpropanoic acid (0.17 g, 0.49 mmol, CAS: 138662-63-2) and T3P® (50% w/w solution in EtOAc; 0.42 mL, 0.70 mmol) in accordance with the procedure described for Intermediate 2.1. The crude product was purified by flash chromatography (eluting 50-100% EtOAc in heptanes). LCMS (Method 4): 1.04 min, 560.3 $[M+H]^+$ Intermediate 2.31: tert-butyl (S)-(1-((4-(1-benzyl-3,5-dimethyl-1H-pyrazol-4-yl)phenyl)amino)-1-oxo-3,3-diphenylpropan-2-yl)carbamate The title compound (0.14 g) was prepared from Intermediate 1.31 (78 mg, 0.25 mmol), (S)-2-((tert-butoxycarbonyl)amino)-3,3-diphenylpropanoic acid (85 mg, 0.25 mmol, CAS: 138662-63-2), triethylamine (0.09 mL, 0.62 mmol) and HATU (0.11 g, 0.30 mmol) in accordance with the procedure described for Intermediate 2.19. The crude product was purified by flash column chromatography on the Biotage Isolera One™ (10 g ZIP sphere silica column, eluting 30-100% EtOAc in heptanes). LCMS (Method 4): 1.11 min, 601.4 $[M+H]^+$ Intermediate 2.33: tert-butyl ((S)-2-((4-(1,2-dimethyl-6-oxo-1,6-dihydropyridin-3-yl)phenyl)amino)-1-((1r,4S)-4-methylcyclohexyl)-2-oxoethyl)carbamate The title compound (73 mg) was prepared from Intermediate 1.13 (95 mg, 0.44 mmol), (S)-2-((tert-butoxycarbonyl)amino)-2-((1r,4S)-4-methylcyclohexyl)acetic acid (120 mg, 0.44 mmol, CAS: 1187224-06-1; prepared according to the method described in WO2020/011731) and T3P® (50% w/w solution in EtOAc; 0.73 mL, 1.2 mmol) in accordance with the procedure described for Intermediate 2.1. The crude product was purified by flash column chromatography (eluting 10% methanol in EtOAc). LCMS (Method 4): 0.98 min, 468.3 $[M+H]^+$ Intermediate 2.34: tert-butyl (S)-(1-((3-fluoro-4-(6-oxo-1,6-dihydropyridazin-3-yl)phenyl)amino)-1-oxo-3,3-diphenylpropan-2-yl)carbamate To a solution of Intermediate 2.34 (0.13 g, 0.62 mmol), (2S)-2-(tert-butoxycarbonylamino)-3,3-diphenyl-propanoic acid (0.47 g, 1.4 mmol, CAS: 138662-63-2), DMAP (31 mg, 0.12 mmol) in DCM (3 mL) and MeCN (1.5 mL), was added EDCl (299 mg, 1.56 mmol) and the reaction mixture stirred at rt under argon for 21 h. Additional (2S)-2-(tert-butoxycarbonylamino)-3,3-diphenyl-propanoic acid (0.23 g, 0.69 mmol) and EDCl (0.13 g, 0.69 mmol) were added and the reaction mixture stirred at rt for 3 h. The reaction mixture was diluted with saturated aqueous $NaHCO_3$ and extracted into EtOAc. The organics were washed with brine, dried over $Na_2SO_4$, filtered and concentrated in vacuo. The crude product was purified by flash column chromatography (eluting 50-100% EtOAc in heptanes) to provide the title compound (0.19 g). LCMS (Method 4): 0.89 min, 429.2 $[M-Boc+H]^+$ Intermediate 2.35: tert-butyl (S)-(1-((3-fluoro-4-(2-oxo-1,2-dihydropyridin-4-yl)phenyl)amino)-1-oxo-3,3-diphenylpropan-2-yl)carbamate The title compound (0.19 g) was prepared from Intermediate 1.35 (215 mg, 1.05 mmol), (S)-2-((tert-butoxycarbonyl)amino)-3,3-diphenylpropanoic acid (0.36 g, 1.1 mmol, CAS: 138662-63-2), triethylamine (0.16 mL, 1.2 mmol) and HATU (0.44 g, 1.2 mmol) in accordance with the procedure described for Intermediate 2.19, except in DMF/EtOAc (1:2) solvent mixture. The crude product was purified by flash column chromatography (eluting 5% MeOH in EtOAc). LCMS (Method 3): 2.30 min, 528.2 $[M+H]^+$ Intermediate 2.36: tert-butyl (S)-(1-((4-(3-fluoropyridin-4-yl)phenyl)amino)-1-oxo-3,3-diphenylpropan-2-yl)carbamate The title compound (0.45 g) was prepared from 4-(3-fluoropyridin-4-yl)aniline (0.35 g, 1.8 mmol, CAS: 928322-47-8), (S)-2-((tert-butoxycarbonyl)amino)-3,3-diphenylpropanoic acid (0.66 g, 1.8 mmol, CAS: 138662-63-2) and T3P® (50% w/w solution in EtOAc; 3.5 mL, 5.5 mmol) in accordance with the procedure described for Intermediate 2.1. The crude product was purified by flash column chromatography (eluting 50% EtOAc in heptanes). LCMS (Method 1): 1.01 min, 512.3 $[M+H]^+$ Intermediate 2.37: tert-butyl (S)-(1-((4-(2,5-dimethylpyrimidin-4-yl)phenyl)amino)-1-oxo-3,3-diphenylpropan-2-yl)carbamate The title compound (0.45 g) was prepared from Intermediate 1.37 (0.1 g, 0.5 mmol), (S)-2-((tert-butoxycarbonyl)amino)-3,3-diphenylpropanoic acid (0.17 g, 0.5 mmol, CAS: 138662-63-2) and T3P® (50% w/w solution in EtOAc; 0.91 mL, 1.5 mmol) in accordance with the procedure described for Intermediate 2.1. The crude product was used directly without further purification. LCMS (Method 2): 0.97 min, 523.3 $[M+H]^+$ Intermediate 2.38: tert-butyl (S)-(1-((4-(2,5-dimethylpyridin-4-yl)phenyl)amino)-1-oxo-3,3-diphenylpropan-2-yl)carbamate The title compound (46 mg) was prepared from 4-(2,5-dimethylpyridin-4-yl)aniline (52 mg, 0.26 mmol, CAS: 71153-40-7), (S)-2-((tert-butoxycarbonyl)amino)-3,3-diphenylpropanoic acid (90 mg, 0.26 mmol, CAS: 138662-63-2) and T3P® (50% w/w solution in EtOAc; 0.5 mL, 0.79 mmol) in accordance with the procedure described for Intermediate 2.1. The crude product was purified by flash column chromatography (eluting 50% EtOAc in heptanes). LCMS (Method 8): 0.65 min, 521.9 $[M+H]^+$ Intermediate 2.42: tert-butyl (S)-(1-((4-(3-(hydroxymethyl)pyridin-4-yl)phenyl)amino)-1-oxo-3,3-diphenylpropan-2-yl)carbamate The title compound (0.34 g) was prepared from Intermediate 1.42 (0.28 g, 1.2 mmol), (S)-2-((tert-butoxycarbonyl)amino)-3,3-diphenylpropanoic acid (0.4 g, 1.2 mmol, CAS: 138662-63-2), triethylamine (0.4 mL, 2.9 mmol) and HATU (0.53 g, 1.4 mmol) in accordance with the procedure described for Intermediate 2.19. The crude product was purified by flash column chromatography on the Biotage Isolera One™ (30 g ZIP sphere silica column, eluting 40-100% EtOAc in heptanes). LCMS (Method 2): 0.88 min, 524.3 $[M+H]^+$ Intermediate 2.43: tert-butyl (S)-(1-((4-(3-cyanopyridin-4-yl)phenyl)amino)-1-oxo-3,3-diphenylpropan-2-yl)carbamate The title compound (66 mg) was prepared from 4-(4-aminophenyl)nicotinonitrile (25 mg, 0.13 mmol, CAS: 2090576-40-0), (S)-2-((tert-butoxycarbonyl)amino)-3,3-diphenylpropanoic acid (44 mg, 0.13 mmol, CAS: 138662-63-2), triethylamine (0.04 mL, 0.32 mmol) and T3P® (50% w/w solution in EtOAc; 0.24 mL, 0.38 mmol) in accordance with the procedure described for Intermediate 2.1. The crude product was purified by flash column chromatography on the Biotage Isolera One™ (30 g ZIP sphere silica column, eluting 40-100% EtOAc in heptanes). LCMS (Method 2): 0.97 min, 419.2 $[M-Boc+H]^+$ Intermediate 2.47: tert-butyl (S)-(1-((3-methoxy-4-(3-methoxypyridin-4-yl)phenyl)amino)-1-oxo-3,3-diphenylpropan-2-yl)carbamate The title compound (75 mg) was prepared from Intermediate 1.47 (68 mg, 0.29 mmol), (S)-2-((tert-butoxycarbonyl)amino)-3,3-diphenylpropanoic acid (98 mg, 0.29 mmol, CAS: 138662-63-2), triethylamine (0.1 mL, 0.71 mmol) and T3P® (50% w/w solution in EtOAc; 0.55 mL, 0.86 mmol) in accordance with the procedure described for Intermediate 2.1. The crude product was used directly without further purification. LCMS (Method 2): 0.96 min, 554.3 $[M+H]^+$ Intermediate 2.48: tert-butyl (S)-(1-((3-fluoro-4-(1-methyl-6-oxo-1,6-dihydropyridazin-3-yl)phenyl)amino)-1-oxo-3,3-diphenylpropan-2-yl)carbamate The title compound (0.21 g) was prepared from Intermediate 1.48 (0.15 g, 0.67 mmol), (S)-2-((tert-butoxycarbonyl)amino)-3,3-diphenylpropanoic acid (0.24 g, 0.70 mmol, CAS: 138662-63-2), triethylamine (0.28 mL, 2.0 mmol) and T3P® (50% w/w solution in EtOAc; 0.59 mL, 1.0 mmol) in accordance with the procedure described for Intermediate 2.1. The crude product was purified by flash column chromatography (eluting 50% EtOAc in heptanes). LCMS (Method 4): 0.96 min, 543.2 $[M+H]^+$ Intermediate 2.49: tert-butyl (S)-(1-oxo-1-((4-(6-oxo-1,6-dihydropyridin-3-yl)phenyl)amino)-3,3-diphenylpropan-2-yl)carbamate The title compound (52 mg) was prepared from 5-(4-aminophenyl)pyridin-2(1H)-one (87 mg, 0.47 mmol, CAS: 1159819-58-5), (S)-2-((tert-butoxycarbonyl)amino)-3,3-diphenylpropanoic acid (0.16 g, 0.47 mmol, CAS: 138662-63-2), triethylamine (0.04 mL, 0.32 mmol) and T3P® (50% w/w solution in EtOAc; 0.89 mL, 1.4 mmol) in accordance with the procedure described for Intermediate 2.1. The crude product was purified by flash column chromatography on the Biotage Isolera One™ (30 g ZIP sphere silica column, eluting 40-100% EtOAc in heptanes then 5% MeOH in EtOAc). LCMS (Method 2): 0.84 min, 510.3 $[M+H]^+$ Intermediate 2.50: tert-butyl (S)-(1-((4-(4-methyl-6-oxo-1,6-dihydropyridin-3-yl)phenyl)amino)-1-oxo-3,3-diphenylpropan-2-yl)carbamate The title compound (35 mg) was prepared from 5-(4-aminophenyl)-4-methylpyridin-2(1H)-one (0.1 g, 0.51 mmol, CAS: 1258623-31-2), (S)-2-((tert-butoxycarbonyl)amino)-3,3-diphenylpropanoic acid (0.18 g, 0.51 mmol, CAS: 138662-63-2), triethylamine (0.18 mL, 1.3 mmol) and T3P® (50% w/w solution in EtOAc; 0.98 mL, 1.5 mmol) in accordance with the procedure described for Intermediate 2.1. The crude product was purified by flash column chromatography on the Biotage Isolera One™ (30 g ZIP sphere silica column, eluting 60-100% EtOAc in heptanes then 7% MeOH in EtOAc). LCMS (Method 2): 0.86 min, 524.9 [M+H]+

Intermediate 2.51: tert-butyl (S)-(1-((4-(1-methyl-6-oxo-1,6-dihydropyridin-3-yl)phenyl)amino)-1-oxo-3,3-diphenylpropan-2-yl)carbamate The title compound (0.46 g) was prepared from Intermediate 1.51 (0.18 g, 0.91 mmol), (S)-2-((tert-butoxycarbonyl)amino)-3,3-diphenylpropanoic acid (0.31 g, 0.91 mmol, CAS: 138662-63-2), triethylamine (0.32 mL, 2.3 mmol) and T3P® (50% w/w solution in EtOAc; 1.74 mL, 2.7 mmol) in accordance with the procedure described for Intermediate 2.1. The crude product was used directly. LCMS (Method 2): 0.88 min, 524.3 $[M+H]^+$ Intermediate 2.52: tert-butyl (S)-(1-oxo-1-((4-(7-oxo-6,7-dihydro-1H-pyrrolo[2,3-c]pyridin-4-yl)phenyl)amino)-3,3-diphenylpropan-2-yl)carbamate The title compound (0.13 mg) was prepared from Intermediate 1.52 (0.1 g, 0.44 mmol), (S)-2-((tert-butoxycarbonyl)amino)-3,3-diphenylpropanoic acid (0.18 mg, 0.53 mmol, CAS: 138662-63-2), triethylamine (0.21 mL, 1.5 mmol) and HATU (0.2 g, 0.53 mmol) in accordance with the procedure described for Intermediate 2.19, except using DMF instead of EtOAc as solvent. The crude product was purified by flash column chromatography (eluting 4% MeOH in EtOAc). LCMS (Method 3): 2.38 min, 549.3 $[M+H]^+$ Intermediate 2.53: tert-butyl (S)-(1-((4-(3-(hydroxymethyl)pyridin-4-yl)-3-methoxyphenyl) amino)-1-oxo-3,3-diphenylpropan-2-yl)carbamate The title compound (38 mg) was prepared from Intermediate 1.53 (51 mg, 0.17 mmol), (S)-2-((tert-butoxycarbonyl) amino)-3,3-diphenylpropanoic acid (68 mg, 0.20 mmol, CAS: 138662-63-2), DIPEA (0.12 mL, 0.67 mmol) and HATU (76 mg, 0.20 mmol) in accordance with the procedure described for Intermediate 2.19, except in EtOAc/MeCN (2:1) solvent mixture. The crude product was purified by flash column chromatography (eluting 10% MeOH in DCM). LCMS (Method 2): 0.88 min, 554.3 $[M+H]^+$ Intermediate 2.54: tert-butyl (S)-(1-((4-(1,2-dimethyl-6-oxo-1,6-dihydropyridin-3-yl)-3-(trifluoromethyl)phenyl)amino)-1-oxo-3,3-diphenylpropan-2-yl)carbamate The title compound (56 mg) was prepared from Intermediate 1.54 (0.1 g, 0.38 mmol), (S)-2-((tert-butoxycarbonyl) amino)-3,3-diphenylpropanoic acid (0.14 g, 0.39 mmol, CAS: 138662-63-2), triethylamine (0.28 mL, 2.0 mmol) and T3P® (50% w/w solution in EtOAc; 0.59 mL, 2.0 mmol) in accordance with the procedure described for Intermediate 2.1. The crude product was purified by flash column chromatography (eluting 100% EtOAc). LCMS (Method 4): 0.99 min, 606.3 $[M+H]^+$ Intermediate 2.55: tert-butyl (S)-(1-((3-chloro-4-(3,5-dimethylpyridin-4-yl)phenyl)amino)-1-oxo-3,3-diphenylpropan-2-yl)carbamate The title compound (65 mg) was prepared from Intermediate 1.55 (0.11 g, 0.47 mmol), (S)-2-((tert-butoxycarbonyl) amino)-3,3-diphenylpropanoic acid (0.16 g, 0.47 mmol, CAS: 138662-63-2), triethylamine (0.2 mL, 1.4 mmol) and T3P® (50% w/w solution in EtOAc; 0.9 mL, 1.4 mmol) in accordance with the procedure described for Intermediate 2.1. The crude product was purified by flash column chromatography on the Biotage Isolera One™ (30 g ZIP sphere silica column, eluting 0-50% EtOAc in heptanes). LCMS (Method 4): 1.08 min, 556.3 $[M+H]^+$ Intermediate 2.56: tert-butyl (S)-(1-((4-(2,5-dimethylpyridin-4-yl)-3-fluorophenyl)amino)-1-oxo-3,3-diphenylpropan-2-yl)carbamate The title compound (0.1 g) was prepared from Intermediate 1.56 (0.15 g, 0.69 mmol), (S)-2-((tert-butoxycarbonyl) amino)-3,3-diphenylpropanoic acid (0.24 g, 0.69 mmol, CAS: 138662-63-2), triethylamine (0.29 mL, 2.1 mmol) and T3P® (50% w/w solution in EtOAc; 1.3 mL, 2.1 mmol) in accordance with the procedure described for Intermediate 2.1. The crude product was purified by flash column chromatography (eluting 50% EtOAc in heptanes). LCMS (Method 4): 1.06 min, 540.3 $[M+H]^+$ Intermediate 2.57: tert-butyl (S)-(1-((4-(2,3-dimethylpyridin-4-yl)-3-fluorophenyl)amino)-1-oxo-3,3-diphenylpropan-2-yl)carbamate The title compound (0.12 g) was prepared from Intermediate 1.57 (0.11 g, 0.51 mmol), (S)-2-((tert-butoxycarbonyl) amino)-3,3-diphenylpropanoic acid (0.17 g, 0.51 mmol, CAS: 138662-63-2), triethylamine (0.21 mL, 1.5 mmol) and T3P® (50% w/w solution in EtOAc; 0.97 mL, 1.5 mmol) in accordance with the procedure described for Intermediate 2.1. The crude product was purified by flash column chromatography (eluting 70% EtOAc in heptanes). LCMS (Method 3): 2.80 min, 540.3 $[M+H]^+$ Intermediate 2.59: tert-butyl (S)-(1-((4-(1-benzyl-5-methyl-1H-pyrazol-4-yl)-3-fluorophenyl)amino)-1-oxo-3,3-diphenylpropan-2-yl)carbamate The title compound (0.28 g) was prepared as a mixture of regioisomers with tert-butyl (S)-(1-((4-(1-benzyl-3-methyl-1H-pyrazol-4-yl)-3-fluorophenyl)amino)-1-oxo-3,3-diphenylpropan-2-yl)carbamate from Intermediate 1.59 (0.25 mg, 0.89 mmol), (S)-2-((tert-butoxycarbonyl)amino)-3,3-diphenylpropanoic acid (0.3 g, 0.88 mmol, CAS: 138662-63-2) and T3P® (50% w/w solution in EtOAc; 1.7 mL, 2.7 mmol) in accordance with the procedure described for Intermediate 2.1. The crude product was purified by flash column chromatography on the Biotage Isolera One™ (25 g SiliCycle silica column, eluting 40-100% EtOAc in heptanes). LCMS (Method 4): 1.12 min, 605.3 $[M+H]^+$ Intermediate 2.60: tert-butyl (S)-(1-((4-(3,5-dimethylisoxazol-4-yl)-3-fluorophenyl)amino)-1-oxo-3,3-diphenylpropan-2-yl)carbamate The title compound (0.22 g) was prepared from Intermediate 1.60 (0.15 g, 0.75 mmol), (S)-2-((tert-butoxycarbonyl) amino)-3,3-diphenylpropanoic acid (0.27 g, 0.79 mmol, CAS: 138662-63-2), triethylamine (0.31 mL, 2.2 mmol) and T3P® (50% w/w solution in EtOAc; 1.3 mL, 2.2 mmol) in accordance with the procedure described for Intermediate 2.1. The crude product was purified by flash column chromatography (eluting 25% EtOAc in heptanes). LCMS (Method 4): 1.08 min, 430.2 $[M-Boc+H]^+$ Intermediate 2.62: tert-butyl (S)-(1-((4-(1-benzyl-1H-pyrazol-4-yl)-3-fluorophenyl)amino)-1-oxo-3,3-diphenylpropan-2-yl)carbamate The title compound (65 mg) was prepared from Intermediate 1.62 (240 mg, 0.83 mmol), (S)-2-((tert-butoxycarbonyl)amino)-3,3-diphenylpropanoic acid (282 mg, 0.83 mmol, CAS: 138662-63-2), triethylamine (0.35 mL, 2.48 mmol) and T3P® (50% w/w solution in EtOAc; 1.58 mL, 2.48 mmol) in accordance with the procedure described for Intermediate 2.1. The crude product was purified by flash column chromatography on the Biotage Isolera One™ (25 g ZIP sphere silica column, eluting 40-100% EtOAc in heptanes). LCMS (Method 4): 1.11 min, 591.3 $[M+H]^+$ Intermediate 2.63: tert-butyl (S)-(1-((3-fluoro-4-(1-methyl-2-oxo-1,2-dihydropyrimidin-5-yl)phenyl) amino)-1-oxo-3,3-diphenylpropan-2-yl)carbamate The title compound (64 mg) was prepared from Intermediate 2.63 (95 mg, 0.43 mmol), (2S)-2-(tert-butoxycarbonylamino)-3,3-diphenyl-propanoic acid (0.52 g, 1.5 mmol, CAS: 138662-63-2), DMAP (11 mg, 0.09 mmol) and EDCl (0.29 g, 1.5 mmol) in accordance with the procedure described for Intermediate 2.34. The crude product was purified by reverse phase chromatography on the Biotage Isolera One™ (60 g 018 column, eluting 15-65% MeCN in 0.1% pH10 0.1 M $NH_4HCO_3$ buffer solution). LCMS (Method 3): 2.27 min, 543.2 $[M+H]^+$ Intermediate 2.64: tert-butyl (S)-(1-((3-fluoro-4-(2-oxo-1,2-dihydropyrimidin-5-yl)phenyl)amino)-1-oxo-3,3-diphenylpropan-2-yl)carbamate The title compound (0.14 g) was prepared from Intermediate 1.64 (0.26 g, 1.3 mmol), (S)-2-((tert-butoxycarbonyl)amino)-3,3-diphenylpropanoic acid (0.48 g, 1.4 mmol, CAS: 138662-63-2), triethylamine (0.53 mL, 3.8 mmol) and T3P® (50% w/w solution in EtOAc; 2.3 mL, 3.8 mmol) in accordance with the procedure described for Intermediate 2.1. The crude product was purified by flash column chromatography on the Biotage Isolera One™ (80 g ZIP sphere silica column, eluting 0-10% MeOH in DCM). LCMS (Method 3): 1.72 min, 529.2 $[M+H]^+$ Intermediate 2.66: tert-butyl (S)-(1-((3-fluoro-4-(5-oxo-5,6-dihydro-1,6-naphthyridin-8-yl)phenyl)amino)-1-oxo-3,3-diphenylpropan-2-yl)carbamate The title compound (88 mg) was prepared from Intermediate 1.66 (0.47 g, 1.9 mmol), (S)-2-((tert-butoxycarbonyl)amino)-3,3-diphenylpropanoic acid (0.66 g, 1.9 mmol, CAS: 138662-63-2), triethylamine (0.77 mL, 5.5 mmol) and T3P® (50% w/w solution in EtOAc; 3.3 mL, 5.5 mmol) in accordance with the procedure described for Intermediate 2.1. The crude product was purified by flash column chromatography on the Biotage Isolera One™ (45 g ZIP sphere silica column, eluting 50-100% EtOAc in heptanes). LCMS (Method 4): 0.93 min, 579.3 $[M+H]^+$ Intermediate 2.67: tert-butyl (S)-(1-((3-fluoro-4-(6-oxo-1,6-dihydropyridazin-4-yl)phenyl)amino)-1-oxo-3,3-diphenylpropan-2-yl)carbamate To a solution of (S)-2-((tert-butoxycarbonyl)amino)-3,3-diphenylpropanoic acid (0.48 g, 1.4 mmol, CAS: 138662-63-2) and DIPEA (0.83 mL, 4.8 mmol) in 1,2-dichloroethane (4.2 mL) was added BTFFH (0.51 g, 1.6 mmol) and the reaction mixture stirred at rt under argon for 1 h. Intermediate 1.67 (0.22 g, 1.1 mmol) was added and the reaction mixture heated at 80° C. for 6 h. The reaction mixture was diluted with water and brine and three times extracted into DCM. The combined organics were dried over $Na_2SO_4$, filtered and concentrated in vacuo. The crude product was purified by flash column chromatography (eluting 100% EtOAc) then by automated reverse phase column chromatography on the Biotage Isolera One™ (60 g C18 column, eluting 0-80% 0.1% ammonia/MeCN in pH11 0.1% ammonia/$H_2O$) to provide the title compound (0.23 g). LCMS (Method 4): 0.88 min, 529.2 $[M+H]^+$ Intermediate 2.68: tert-butyl (S)-(1-((3-fluoro-4-(7-methoxy-1H-pyrrolo[2,3-c]pyridin-4-yl)phenyl)amino)-1-oxo-3,3-diphenylpropan-2-yl)carbamate The title compound (0.43 g) was prepared from Intermediate 1.68 (0.56 g, 2.2 mmol), (S)-2-((tert-butoxycarbonyl)amino)-3,3-diphenylpropanoic acid (0.74 g, 2.2 mmol, CAS: 138662-63-2), triethylamine (0.91 mL, 6.53 mmol) and T3P® (50% w/w solution in EtOAc; 4.2 mL, 6.5 mmol) in accordance with the procedure described for Intermediate 2.1. The crude product was purified by flash column chromatography (eluting 45% ethyl acetate in heptanes). LCMS (Method 4): 1.03 min, 581.3 $[M+H]^+$ Intermediate 2.69: tert-butyl (S)-(1-((3-fluoro-4-(4-oxo-4,5-dihydro-3H-imidazo[4,5-c]pyridin-7-yl)phenyl)amino)-1-oxo-3,3-diphenylpropan-2-yl)carbamate The title compound (0.14 g) was prepared from Intermediate 1.69 (0.24 g, 0.96 mmol), (S)-2-((tert-butoxycarbonyl)amino)-3,3-diphenylpropanoic acid (0.35 g, 1.0 mmol, CAS: 138662-63-2), triethylamine (0.4 mL, 2.9 mmol) and T3P® (50% w/w solution in EtOAc; 1.7 mL, 2.9 mmol) in accordance with the procedure described for Intermediate 2.1. The crude product was purified by automated reverse phase column chromatography on the Biotage Isolera One™ (60 g C18 column, eluting 0-95% MeCN containing 0.1% formic acid in water containing 0.1% formic acid). LCMS (Method 13): 2.10 min, 568.2 $[M+H]^+$ Intermediate 2.71: tert-butyl (S)-(1-((3-fluoro-4-(5-oxo-5,6-dihydro-1,6-naphthyridin-8-yl)phenyl)amino)-1-oxo-3,3-diphenylpropan-2-yl)carbamate The title compound (98 mg) was prepared from Intermediate 1.71 (0.19 g, 0.86 mmol), (S)-2-((tert-butoxycarbonyl)amino)-3,3-diphenylpropanoic acid (0.29 g, 0.86 mmol, CAS: 138662-63-2), triethylamine (0.36 mL, 2.6 mmol) and T3P® (50% w/w solution in EtOAc; 1.64 mL, 2.6 mmol) in accordance with the procedure described for Intermediate 2.1. The crude product was purified by flash column chromatography on the Biotage Isolera One™ (30 g ZIP sphere silica column, eluting 40-100% EtOAc in heptanes). LCMS (Method 4): 0.94 min, 542.2 $[M+H]^+$ Intermediate 2.72: tert-butyl (S)-(1-((1',2'-dimethyl-6'-oxo-1',6'-dihydro-[3,3'-bipyridin]-6-yl)amino)-1-oxo-3,3-diphenylpropan-2-yl)carbamate The title compound (20 mg) was prepared from Intermediate 1.72 (39 mg, 0.18 mmol), (S)-2-((tert-butoxycarbonyl)amino)-3,3-diphenylpropanoic acid (80 mg, 0.24 mmol, CAS: 138662-63-2), DIPEA (0.14 mL, 0.82 mmol) and BTFFH (86 mg, 0.27 mmol) in accordance with the procedure described for Intermediate 2.67. The crude product was purified by automated reverse phase column chromatography on the Biotage Isolera One™ (30 g C18 column, 0.1% ammonia/MeCN in pH11 0.1% ammonia/$H_2O$). LCMS (Method 4): 0.90 min, 539.2 $[M+H]^+$ Intermediate 2.73: tert-butyl (S)-(1-((3',5'-dimethyl-[3,4'-bipyridin]-6-yl)amino)-1-oxo-3,3-diphenylpropan-2-yl)carbamate The title compound (0.18 g) was prepared from Intermediate 1.73 (0.23 g, 1.1 mmol), (S)-2-((tert-butoxycarbonyl)amino)-3,3-diphenylpropanoic acid (0.5 g, 1.5 mmol, CAS: 138662-63-2), DIPEA (0.89 mL, 5.1 mmol) and BTFFH (0.54 g, 1.7 mmol) in accordance with the procedure described for Intermediate 2.67. The crude product was purified by automated reverse phase column chromatography on the Biotage Isolera One™ (30 g ZIP sphere silica column, eluting 40-100% EtOAc in heptanes). LCMS (Method 4): 1.01 min, 523.2 $[M+H]^+$ Intermediate 2.74: tert-butyl (S)-(1-((4-(1-benzyl-5-methyl-1H-pyrazol-4-yl)phenyl)amino)-1-oxo-3,3-diphenylpropan-2-yl)carbamate The title compound (0.67 g) was prepared from Intermediate 1.74 (0.57 g, 2.2 mmol), (S)-2-((tert-butoxycarbonyl)amino)-3,3-diphenylpropanoic acid (0.74 g, 2.2 mmol, CAS: 138662-63-2), triethylamine (0.9 mL, 6.5 mmol) and T3P® (50% w/w solution in EtOAc; 4.1 mL, 6.5 mmol) in accordance with the procedure described for Intermediate 2.1. The crude product was purified by flash column chromatography on the Biotage Isolera One™ (30 g ZIP sphere silica column, eluting 40-100% EtOAc in heptanes). LCMS (Method 4): 1.08 min, 587.3 $[M+H]^+$ Intermediate 2.75: tert-butyl (S)-(1-((3-fluoro-4-(6-methyl-7-oxo-6,7-dihydro-1H-pyrazolo[3,4-c]pyridin-4-yl)phenyl)amino)-1-oxo-3,3-diphenylpropan-2-yl)carbamate The title compound (83 mg) was prepared from Intermediate 1.75 (0.1 g, 0.39 mmol), (S)-2-((tert-butoxycarbonyl)amino)-3,3-diphenylpropanoic acid (0.14 g, 0.41 mmol, CAS: 138662-63-2), triethylamine (0.17 mL, 1.2 mmol) and HATU (0.22 g, 0.56 mmol) in accordance with the procedure described for Intermediate 2.19, except using DMF as solvent. The crude product was purified by flash column chromatography on the Biotage Isolera One™ (25 g ZIP sphere silica column, eluting 50-100% EtOAc in heptanes). LCMS (Method 4): 0.92 min, 582.3 $[M+H]^+$ Intermediate 2.76: tert-butyl (S)-(1-((4-(7-methoxy-1H-pyrrolo[2,3-c]pyridin-4-yl)phenyl)amino)-1-oxo-3,3-diphenylpropan-2-yl)carbamate The title compound (0.2 g) was prepared from Intermediate 1.76 (0.21 g, 0.84 mmol), (S)-2-((tert-butoxycarbonyl)amino)-3,3-diphenylpropanoic acid (0.29 g, 0.84 mmol, CAS: 138662-63-2), triethylamine (0.35 mL, 2.5 mmol) and T3P® (50% w/w solution in EtOAc; 1.6 mL, 2.5 mmol) in accordance with the procedure described for Intermediate 2.1. The crude product was purified by flash column chromatography on the Biotage Isolera One™ (25 g ZIP sphere silica column, eluting 40-100% EtOAc in heptanes). LCMS (Method 4): 1.01 min, 563.3 $[M+H]^+$ Intermediate 2.77: tert-butyl (S)-(1-((4-(1-benzyl-6-oxo-1,6-dihydropyridin-2-yl)-3-fluorophenyl)amino)-1-oxo-3,3-diphenylpropan-2-yl)carbamate The title compound (86 mg) was prepared from Intermediate 1.77 (0.18 g, 0.57 mmol), (S)-2-((tert-butoxycarbonyl)amino)-3,3-diphenylpropanoic acid (0.19 g, 0.57 mmol, CAS: 138662-63-2), triethylamine (0.24 mL, 1.7 mmol) and T3P® (50% w/w solution in EtOAc; 1.1 mL, 1.7 mmol) in accordance with the procedure described for Intermediate 2.1. The crude product was purified by flash column chromatography on the Biotage Isolera One™ (30 g ZIP sphere silica column, eluting 30-100% EtOAc in heptanes). LCMS (Method 20): 1.01 min, 618.3 $[M+H]^+$ Intermediate 2.78: tert-butyl (S)-(1-oxo-1-((4-(3-(2-oxo-2-(pyrrolidin-1-yl)ethyl)pyridin-4-yl)phenyl)amino)-3,3-diphenylpropan-2-yl)carbamate The title compound (61 mg) was prepared from Intermediate 1.78 (89 mg, 0.32 mmol), (S)-2-((tert-butoxycarbonyl)amino)-3,3-diphenylpropanoic acid (0.11 g, 0.33 mmol, CAS: 138662-63-2), triethylamine (0.13 mL, 0.95 mmol) and T3P® (50% w/w solution in EtOAc; 0.6 mL, 0.95 mmol) in accordance with the procedure described for Intermediate 2.1. The crude product was purified by flash column chromatography on the Biotage Isolera One™ (12 g ZIP sphere silica column, eluting 0-20% MeOH in EtOAc). LCMS (Method 4): 1.18 min, 605.4 $[M+H]^+$ Intermediate 2.80: tert-butyl (S)-(1-((3-fluoro-4-(6-oxo-1,6-dihydropyrimidin-4-yl)phenyl)amino)-1-oxo-3,3-diphenylpropan-2-yl)carbamate The title compound (75 mg) was prepared from Intermediate 1.80 (80 mg, 0.39 mmol), (S)-2-((tert-butoxycarbonyl)amino)-3,3-diphenylpropanoic acid (0.13 g, 0.39 mmol, CAS: 138662-63-2), DIPEA (0.15 g, 1.2 mmol) and BTFFH (0.19 g, 0.58 mmol) in accordance with the procedure described for Intermediate 2.67. The crude product was purified by automated reverse phase column chromatography on the Biotage Isolera One™ (30 g C18 column, eluting 10-50% 0.1% ammonia/MeCN in pH11 0.1% ammonia/$H_2O$). LCMS (Method 3): 1.65 min, 529.2 $[M+H]^+$ Intermediate 2.81: tert-butyl (S)-(1-((4-(3,6-dihydro-2H-pyran-4-yl)phenyl)amino)-1-oxo-3,3-diphenylpropan-2-yl)carbamate The title compound (0.23 g) was prepared from 4-(3,6-dihydro-2H-pyran-4-yl)aniline (0.1 g, 0.57 mmol, CAS: 1039053-21-8), (S)-2-((tert-butoxycarbonyl)amino)-3,3-diphenylpropanoic acid (0.2 g, 0.57 mmol, CAS: 138662-63-2), triethylamine (0.24 mL, 1.7 mmol) and T3P® (50% w/w solution in EtOAc; 1.1 mL, 1.7 mmol) in accordance with the procedure described for Intermediate 2.1. The crude product was used directly without further purification. LCMS (Method 4): 1.04 min, 399.3 $[M\text{-}Boc+H]^+$ Intermediate 2.83: tert-butyl ((S)-2-((4-(1,2-dimethyl-6-oxo-1,6-dihydropyridin-3-yl)-3-fluorophenyl)amino)-1-((1r,4S)-4-methylcyclohexyl)-2-oxoethyl)carbamate The title compound (71 mg) was prepared from Intermediate 1.16 (0.4 g, 1.7 mmol) and (S)-2-((tert-butoxycarbonyl)amino)-2-((1r,4S)-4-methylcyclohexyl)acetic acid (0.27 g, 0.98 mmol, CAS: 1187224-06-1), triethylamine (0.54 mL, 3.9 mmol) and T3P® (50% w/w solution in EtOAc; 2.5 mL, 3.9 mmol) in accordance with the procedure described for Intermediate 2.1. The crude product was purified by automated reverse phase column chromatography on the Biotage Isolera One™ (60 g C18 column, 0.1% ammonia/MeCN in pH11 0.1% ammonia/$H_2O$). LCMS (Method 4): 1.06 min, 486.2 $[M+H]^+$ Intermediate 2.84: tert-butyl ((S)-2-((4-(1-(4-methoxybenzyl)-3,5-dimethyl-1H-pyrazol-4-yl)phenyl)amino)-1-((1r,4S)-4-methylcyclohexyl)-2-oxoethyl)carbamate The title compound (0.6 g) was prepared from Intermediate 1.84 (0.35 g, 1.1 mmol), (S)-2-((tert-butoxycarbonyl)amino)-2-((1r,4S)-4-methylcyclohexyl)acetic acid (0.31 g, 1.1 mmol, CAS: 1187224-06-1), HATU (0.52 mg, 1.4 mmol) and triethylamine (0.48 mL, 3.4 mmol) in accordance with the procedure described for Intermediate 2.19, except in EtOAc/MeCN (2:1) solvent mixture. The crude product was purified by flash column chromatography on the Biotage Isolera One™ (20 g ZIP sphere silica column, eluting 20-100% EtOAc in heptanes). LCMS (Method 16): 3.12 min, 561.2 [M+H]$^+$ Intermediate 2.85: tert-butyl ((S)-1-((1r,4S)-4-methylcyclohexyl)-2-oxo-2-((4-(7-oxo-6,7-dihydro-1H-pyrrolo[2,3-c]pyridin-4-yl)phenyl)amino)ethyl)carbamate The title compound (0.12 g) was prepared from Intermediate 1.52 (86 mg, 0.38 mmol) and (S)-2-((tert-butoxycarbonyl)amino)-2-((1r,4S)-4-methylcyclohexyl)acetic acid (0.1 g, 0.38 mmol, CAS: 1187224-06-1), HATU (0.52 g, 1.4 mmol) and triethylamine (0.48 mL, 3.4 mmol) in accordance with the procedure described for Intermediate 2.19, except in DMF as solvent. The crude product was purified by flash column chromatography (eluting 5% MeOH in DCM). LCMS (Method 3): 2.39 min, 479.3 [M+H]$^+$ Intermediate 2.86: tert-butyl ((S)-1-((1r,4S)-4-methylcyclohexyl)-2-oxo-2-((4-(3-(2-oxo-2-(pyrrolidin-1-yl)ethyl)pyridin-4-yl)phenyl)amino)ethyl)carbamate The title compound (98 mg) was prepared from Intermediate 1.78 (83 mg, 0.29 mmol), (S)-2-((tert-butoxycarbonyl)amino)-2-((1r,4S)-4-methylcyclohexyl)acetic acid (81 mg, 0.29 mmol, CAS: 1187224-06-1), triethylamine (0.12 mL, 0.89 mmol) and T3P® (50% w/w solution in EtOAc; 0.53 mL, 0.89 mmol) in accordance with the procedure described for Intermediate 2.1. The crude product was purified by flash column chromatography (eluting 10-20% MeOH in EtOAc). LCMS (Method 4): 0.97 min, 535.3 [M+H]$^+$ Intermediate 2.87: tert-butyl ((S)-1-((1r,4S)-4-methylcyclohexyl)-2-oxo-2-((4-(2-oxo-1,2-dihydropyridin-4-yl)phenyl)amino)ethyl)carbamate The title compound (49 mg) was prepared from Intermediate 1.87 (60 mg, 0.32 mmol) and (S)-2-((tert-butoxycarbonyl)amino)-2-((1r,4S)-4-methylcyclohexyl)acetic acid (87 mg, 0.32 mmol, CAS: 1187224-06-1), HATU (0.14 g, 0.35 mmol) and triethylamine (0.09 mL, 0.64 mmol) in accordance with the procedure described for Intermediate 2.19, except in DMF as solvent. The crude product was purified by flash column chromatography (eluting 5% MeOH in DCM). LCMS (Method 3): 2.26 min, 440.3 [M+H]$^+$ Intermediate 2.88: tert-butyl ((S)-2-((4-(imidazo[1,2-a]pyridin-5-yl)phenyl)amino)-1-((1r,4S)-4-methylcyclohexyl)-2-oxoethyl)carbamate The title compound (49 mg) was prepared from Intermediate 1.88 (56 mg, 0.24 mmol) and (S)-2-((tert-butoxycarbonyl)amino)-2-((1r,4S)-4-methylcyclohexyl)acetic acid (64 mg, 0.24 mmol, CAS: 1187224-06-1), triethylamine (0.12 mL, 0.89 mmol) and T3P® (50% w/w solution in EtOAc; 0.53 mL, 0.89 mmol) in accordance with the procedure described for Intermediate 2.1. The crude product was purified by flash column chromatography on the Biotage Isolera One™ (25 g Silicycle silica column, eluting 30-100% EtOAc in heptanes). LCMS (Method 4): 1.03 min, 463.3 [M+H]$^+$ Intermediate 2.89: tert-butyl ((S)-2-((1',2'-dimethyl-6'-oxo-1',6'-dihydro-[3,3'-bipyridin]-6-yl)amino)-1-((1r,4S)-4-methylcyclohexyl)-2-oxoethyl)carbamate The title compound (18 mg) was prepared from Intermediate 1.72 (78 mg, 0.36 mmol), (S)-2-((tert-butoxycarbonyl)amino)-2-((1r,4S)-4-methylcyclohexyl)acetic acid (0.13 g, 0.47 mmol, CAS: 1187224-06-1), DIPEA (0.28 mL, 1.6 mmol) and BTFFH (0.17 g, 0.54 mmol) in accordance with the procedure described for Intermediate 2.67. The crude product was purified by automated reverse phase column chromatography on the Biotage Isolera One™ (30 g C18 column, eluting 5-85% MeCN 0.1% ammonia/MeCN in pH11 0.1% ammonia/$H_2O$). LCMS (Method 4): 0.95 min, 469.3 [M+H]$^+$ Intermediate 2.90: tert-butyl ((S)-2-((3',5'-dimethyl-[3,4'-bipyridin]-6-yl)amino)-1-((1r,4S)-4-methylcyclohexyl)-2-oxoethyl)carbamate The title compound (60 mg) was prepared from Intermediate 1.73 (0.11 g, 0.55 mmol), (S)-2-((tert-butoxycarbonyl)amino)-2-((1r,4S)-4-methylcyclohexyl)acetic acid (0.18 g, 0.66 mmol, CAS: 1187224-06-1), DIPEA (0.43 mL, 2.5 mmol) and BTFFH (0.21 g, 0.66 mmol) in accordance with the procedure described for Intermediate 2.67. The crude product was purified by MDAP (Method 1: 20-90% MeCN in 0.1% $NH_4OH$). LCMS (Method 4): 1.07 min, 453.3 [M+H]$^+$ Intermediate 2.93: tert-butyl ((S)-1-((1r,4S)-4-methylcyclohexyl)-2-oxo-2-((4-(tetrahydro-2H-pyran-4-yl)phenyl)amino)ethyl)carbamate The title compound (0.13 g) was prepared from 4-(tetrahydro-2H-pyran-4-yl)aniline (64 mg, 0.36 mmol, CAS: 62071-40-3), (S)-2-((tert-butoxycarbonyl)amino)-2-((1r,4S)-4-methylcyclohexyl)acetic acid (98 mg, 0.36 mmol, CAS: 1187224-06-1), HATU (0.15 g, 0.40 mmol) and triethylamine (0.1 mL, 0.72 mmol) in accordance with the procedure described for Intermediate 2.19, except in EtOAc/MeCN (2:1) solvent mixture. The crude product was used directly. LCMS (Method 12) 2.83 min, 331.2 [M-Boc+H]$^+$ Intermediate 2.94: tert-butyl ((S)-2-((4-(4-hydroxytetrahydro-2H-pyran-4-yl)phenyl)amino)-1-((1r,4S)-4-methylcyclohexyl)-2-oxoethyl)carbamate The title compound (93 mg) was prepared from 4-(4-aminophenyl)tetrahydro-2H-pyran-4-ol (51 mg, 0.26 mmol, CAS: 1002726-77-3) and (S)-2-((tert-butoxycarbonyl)amino)-2-((1r,4S)-4-methylcyclohexyl)acetic acid (72 mg, 0.26 mmol, CAS: 1187224-06-1), triethylamine (0.11 mL, 0.79 mmol) and T3P® (50% w/w solution in EtOAc; 0.5 mL, 0.79 mmol) in accordance with the procedure described for Intermediate 2.1. The crude product was used directly without further purification. LCMS (Method 4): 0.94 min, 347.0 [M-Boc+H]$^+$ Intermediate 2.95: tert-butyl ((S)-2-((4-(3,6-dihydro-2H-pyran-4-yl)phenyl)amino)-1-((1r,4S)-4-methylcyclohexyl)-2-oxoethyl)carbamate The title compound (65 mg) was prepared from Intermediate 1.81 (0.1 g, 0.57 mmol) and (S)-2-((tert-butoxycarbonyl)amino)-2-((1r,4S)-4-methylcyclohexyl)acetic acid (0.16 g, 0.57 mmol, CAS: 1187224-06-1), triethylamine (0.24 mL, 1.7 mmol) and T3P® (50% w/w solution in EtOAc; 1.1 mL, 1.7 mmol) in accordance with the procedure described for Intermediate 2.1. The crude product was purified by flash column chromatography on the Biotage Isolera One™ (25 g Silicycle silica column, eluting, 10-100% EtOAc in heptanes). LCMS (Method 4): 1.10 min, 329.2 [M-Boc+H]$^+$ Intermediate 2.96: tert-butyl ((S)-2-((4-(3,5-dimethylisoxazol-4-yl)phenyl)amino)-1-((1r,4S)-4-methylcyclohexyl)-2-oxoethyl)carbamate The title compound (84 mg) was prepared from 4-(3,5-dimethylisoxazol-4-yl)aniline (55 mg, 0.29 mmol, CAS: 2155-99-9) and (S)-2-((tert-butoxycarbonyl)amino)-2-((1r, 4S)-4-methylcyclohexyl)acetic acid (76 mg, 0.28 mmol, CAS: 1187224-06-1), triethylamine (0.12 mL, 0.84 mmol) and T3P® (50% w/w solution in EtOAc; 0.5 mL, 0.84 mmol) in accordance with the procedure described for Intermediate 2.1. The crude product was purified by flash column chromatography on the Biotage Isolera One™ (4 g silica column, eluting, 0-25% EtOAc in heptanes). $^1$H NMR (400 MHz, $CDCl_3$) δ: 8.19 (s, 1H), 7.62-7.55 (m, 2H), 7.17 (d, 2H), 5.14 (s, 1H), 4.02 (t, 1H), 2.37 (s, 3H), 2.24 (s, 3H), 1.84 (d, 5H), 1.46 (s, 9H), 1.34-1.27 (m, 1H), 1.21-1.04 (m, 2H), 1.00-0.90 (m, 2H), 0.88 (d, 3H).

Intermediate 2.97: tert-butyl ((S)-2-((5-(3,5-dimethylisoxazol-4-yl)pyridin-2-yl)amino)-1-((1r,4S)-4-methylcyclohexyl)-2-oxoethyl)carbamate To a solution of 5-(3,5-dimethylisoxazol-4-yl)pyridin-2-amine (59 mg, 0.3 mmol, CAS: 1177269-12-3) and (S)-2-((tert-butoxycarbonyl)amino)-2-((1r,4S)-4-methylcyclohexyl)acetic acid (85 mg, 0.3 mmol, CAS: 1187224-06-1) in tetrahydrofuran (3 mL) was added EEDQ (84 mg, 0.35 mmol) under an atmosphere of argon. The mixture was stirred for 64 h, concentrated in vacuo before partitioning between EtOAc and saturated $NaHCO_3$. The organics were washed with brine, dried over $Na_2SO_4$, filtered and concentrated in vacuo. The crude product was purified by flash column chromatography (5 g silica column, eluting 0%-50% EtOAc in heptanes) to provide the title compound (23 mg). LCMS (Method 14): 2.02 min, 443.3 [M+H]$^+$ Intermediate 2.99: tert-butyl ((S)-2-((5-(1-(4-methoxybenzyl)-3,5-dimethyl-1H-pyrazol-4-yl)pyridin-2-yl)amino)-1-((1r,4S)-4-methylcyclohexyl)-2-oxoethyl)carbamate The title compound (39 mg) was prepared from Intermediate 1.99 (50 mg, 0.16 mmol) and (S)-2-((tert-butoxycarbonyl)amino)-2-((1r,4S)-4-methylcyclohexyl)acetic acid (53 mg, 0.19 mmol, CAS: 1187224-06-1) and EEDQ (60 mg, 0.24 mmol) in accordance with the procedure described for Intermediate 2.97. An additional portion of EEDQ (60 mg, 0.24 mmol) was added and the mixture stirred for a further 24 h before work up. The crude product was purified by flash column chromatography (4 g silica column, eluting, 0-25% EtOAc in heptanes). LCMS (Method 14): 2.09 min, 562.2 [M+H]$^+$ Intermediate 2.106: tert-butyl ((S)-2-((5-(1,4-dimethyl-1H-pyrazol-5-yl)pyridin-2-yl)amino)-1-((1r, 4S)-4-methylcyclohexyl)-2-oxoethyl)carbamate The title compound (19 mg) was prepared from Intermediate 1.106 (65 mg, 0.35 mmol) and (S)-2-((tert-butoxycarbonyl)amino)-2-((1r,4S)-4-methylcyclohexyl)acetic acid (0.11 g, 0.41 mmol, CAS: 1187224-06-1) and EEDQ (0.13 g, 0.52 mmol) in accordance with the procedure described for Intermediate 2.97. The crude product was purified by flash column chromatography (5 g silica column, eluting, 20-80% EtOAc in heptanes). LCMS (Method 14): 1.99 min, 442.2 [M+H]$^+$ Intermediate 2.108: tert-butyl (S)-(1-cyclohexyl-2-((5-(3,5-dimethylisoxazol-4-yl)pyridin-2-yl)amino)-2-oxoethyl)carbamate The title compound (67 mg) was prepared from 5-(3,5-dimethylisoxazol-4-yl)pyridin-2-amine (0.11 g, 0.58 mmol, CAS: 1177269-12-3), and (2S)-2-(tert-butoxycarbonylamino)-2-cyclohexyl-acetic acid (0.15 g, 0.58 mmol, CAS: 109183-71-3) in accordance with the procedure described for Intermediate 2.97 except using IIDQ (0.35 g, 1.2 mmol) and DIPEA (0.41 mL, 2.3 mmol) with heating at 90° C. for 16 h. The crude product was purified by flash column chromatography on the Biotage Isolera One™ (12 g silica column, eluting, 0-100% EtOAc in heptanes). LCMS (Method 14): 1.99 min, 429.2 [M+H]$^+$ Intermediate 2.115: tert-butyl (S)-(1-cycloheptyl-2-((5-(3,5-dimethylisoxazol-4-yl)pyridin-2-yl)amino)-2-oxoethyl)carbamate The title compound (0.2 g) was prepared from 5-(3,5-dimethylisoxazol-4-yl)pyridin-2-amine (0.43 g, 2.2 mmol, CAS: 1177269-12-3) and (2S)-2-(tert-butoxycarbonylamino)-2-cycloheptyl-acetic acid (0.61 g, 2.2 mmol, CAS: 1228542-19-5) and EEDQ (0.61 g, 2.5 mmol) in accordance with the procedure described for Intermediate 2.97. The crude product was purified by flash column chromatography on the Biotage Isolera One™ (40 g silica column, eluting, 0-3% MeOH in DCM). LCMS (Method 14): 2.00 min, 443.2 [M+H]$^+$ Intermediate 2.119: tert-butyl (S)-(1-cyclohexyl-2-((4-(1,2-dimethyl-6-oxo-1,6-dihydropyridin-3-yl)phenyl)amino)-2-oxoethyl)carbamate The title compound (0.28 g) was prepared from Intermediate 1.119 (0.18 g, 0.86 mmol), (2S)-2-(tert-butoxycarbonylamino)-2-cyclohexyl-acetic acid (0.2 g, 0.78 mmol, CAS: 109183-71-3), DIPEA (0.2 g, 1.6 mmol) and HATU (0.4 g, 1.1 mmol) in accordance with the procedure described for Intermediate 2.19, except in DMF as solvent. The crude product was used directly. LCMS: (Method 14) 1.75 min, 454.2 [M+H]$^+$ Intermediate 2.125: tert-butyl ((S)-2-((5-(1,4-dimethyl-1H-1,2,3-triazol-5-yl)pyridin-2-yl)amino)-1-((1r,4S)-4-methylcyclohexyl)-2-oxoethyl)carbamate To a stirred solution of Intermediate 1.125 (0.12 g, 0.62 mmol) and (S)-2-((tert-butoxycarbonyl)amino)-2-((1r,4S)-4-methylcyclohexyl)acetic acid (0.15 g, 0.56 mmol, CAS: 1187224-06-1) in anhydrous DMF (0.77 mL) was added DIPEA (0.15 g, 1.1 mmol) and HATU (0.3 g, 0.79 mmol) under an atmosphere of argon. The mixture was heated at 50° C. for 44 h. The reaction mixture was diluted with MeOH (1 mL) then purified by reverse phase column chromatography on the Biotage Isolera One™ (30 g KP-C18_HS Biotage SNAP cartridge, eluting 5-100%

MeCN in water buffer with 0.005 M $NH_4OH$) to provide the title compound (35 mg). LCMS: (Method 14) 1.83 min, 443.3 $[M+H]^+$.

Alternative route to Intermediate 2.125: tert-butyl ((S)-2-((5-(1,4-dimethyl-1H-1,2,3-triazol-5-yl)pyridin-2-yl)amino)-1-((1r,4S)-4-methylcyclohexyl)-2-oxoethyl)carbamate Intermediate 2.125a: tert-butyl ((S)-2-amino-1-((1r,4S)-4-methylcyclohexyl)-2-oxoethyl)carbamate To a solution of (S)-2-((tert-butoxycarbonyl)amino)-2-((1r,4S)-4-methylcyclohexyl)acetic acid (1 g, 3.7 mmol, CAS: 1187224-06-1) in anhydrous DMF (5 mL) was added DIPEA (3.2 mL, 18.4 mmol) then ammonium chloride (0.99 g, 18.4 mmol). The mixture was stirred at ambient temperature for 20 h. The mixture was partitioned between EtOAc and water. The aqueous layer was extracted with EtOAc and combined organics dried over $Na_2SO_4$, filtered and concentrated in vacuo. The crude product was triturated in DCM to provide the title compound (0.85 g). $^1H$ NMR (400 MHz, DMSO-$d_6$) δ: 7.25 (s, 1H), 6.97 (s, 1H), 6.50 (d, 1H), 3.77-3.68 (m, 1H), 1.69-1.44 (m, 5H), 1.38 (s, 9H), 1.27-1.21 (m, 1H), 1.07-0.92 (m, 2H), 0.90-0.75 (m, 5H).

Intermediate 2.125: tert-butyl ((S)-2-((5-(1,4-dimethyl-1H-1,2,3-triazol-5-yl)pyridin-2-yl)amino)-1-((1r,4S)-4-methylcyclohexyl)-2-oxoethyl)carbamate To a suspension of Intermediate 1.125a (0.3 g, 1.5 mmol) and Intermediate 2.125a (0.27 g, 1.0 mmol) in degassed anhydrous 1,4-dioxane (14 mL) was added Xantphos (58 mg, 0.1 mmol) and $Cs_2CO_3$ (0.98 g, 3 mmol). The mixture was degassed with argon for 5 min before addition of tris(dibenzylideneacetone)dipalladium(0) (46 mg, 0.05 mmol) and degassing for 5 min. The vial was sealed and the reaction mixture heated to 100° C. for 18 h. The mixture was diluted with EtOAc and water and the aqueous phase extracted with EtOAc. The combined organics were dried over $Na_2SO_4$, filtered, and concentrated in vacuo. The crude product was purified by flash column chromatography on the Biotage Isolera One™ (20 g silica, 30-100% EtOAc in heptanes) to give the title compound (0.12 g). $^1H$ NMR (400 MHz, MeOD) δ: 8.39 (dd, 1H), 8.32 (dd, 1H), 7.88 (dd, 1H), 4.09 (d, 1H), 3.98 (s, 3H), 2.29 (s, 3H), 1.84-1.65 (m, 5H), 1.45 (s, 9H), 1.36-1.10 (m, 3H), 1.03-0.81 (m, 5H).

Intermediate 2.132: tert-butyl (S)-(1-cycloheptyl-2-((5-(1,4-dimethyl-1H-pyrazol-5-yl)pyridin-2-yl)amino)-2-oxoethyl)carbamate To a solution of Intermediate 1.106 (0.62 g, 3.3 mmol), (2S)-2-(tert-butoxycarbonylamino)-2-cycloheptyl-acetic acid (0.4 g, 1.6 mmol, CAS: 1228542-19-5) and DIPEA (0.4 g, 3.1 mmol) in anhydrous DMF (2.6 mL) was added HATU (0.83 mg, 2.2 mmol) under an atmosphere of argon. The mixture was heated at 50° C. for 24 h. The mixture was partitioned between EtOAc and water and the aqueous extracted with EtOAc. The combined organics were washed with brine, dried over $Na_2SO_4$, filtered and concentrated in vacuo. The crude product was purified by flash column chromatography on the Biotage Isolera One™ (40 g silica column, eluting, 0-50% EtOAc in heptanes) to provide the title compound (0.28 g). LCMS: (Method 14): 1.85 min, 442.2 $[M+H]^+$ Intermediate 2.135: tert-butyl ((S)-2-((2-(3,5-dimethylisoxazol-4-yl)pyrimidin-5-yl)amino)-1-((1r,4S)-4-methylcyclohexyl)-2-oxoethyl)carbamate The title compound (0.24 g) was prepared from 2-(3,5-dimethylisoxazol-4-yl)pyrimidin-5-amine (0.2 g, 1 mmol, CAS: 1094246-50-0), (S)-2-((tert-butoxycarbonyl)amino)-2-((1r,4S)-4-methylcyclohexyl)acetic acid (0.15 g, 0.55 mmol, CAS: 1187224-06-1), DIPEA (0.14 g, 1.1 mmol) and HATU (0.29 g, 0.77 mmol) in accordance with the procedure described for Intermediate 2.132. The crude product was purified by flash column chromatography on the Biotage Isolera One™ (10 g silica column, eluting, 30% EtOAc in heptanes). LCMS: (Method 14): 1.88 min, 444.2 $[M+H]^+$ Intermediate 2.138: tert-butyl ((S)-2-((6-(3,5-dimethylisoxazol-4-yl)pyridin-3-yl)amino)-1-((1r,4S)-4-methylcyclohexyl)-2-oxoethyl)carbamate The title compound (0.13 g) was prepared from Intermediate 1.138 (0.18 g, 0.95 mmol), (S)-2-((tert-butoxycarbonyl)amino)-2-((1r,4S)-4-methylcyclohexyl)acetic acid (0.15 mg, 0.55 mmol, CAS: 1187224-06-1), DIPEA (0.14 g, 1.1 mmol) and HATU (0.29 g, 0.77 mmol) in accordance with the procedure described for Intermediate 2.132. The crude product was purified by flash column chromatography on the Biotage Isolera One™ (10 g silica column eluting, 30% EtOAc in heptanes). LCMS (Method 14): 1.93 min, 443.2 $[M+H]^+$ Intermediate 2.140: tert-butyl ((S)-1-((1r,4S)-4-methylcyclohexyl)-2-((5-(5-methylpyrimidin-4-yl)pyridin-2-yl)amino)-2-oxoethyl)carbamate The title compound (0.14 g) was prepared from Intermediate 1.140 (0.24 g, 1.2 mmol), (S)-2-((tert-butoxycarbonyl)amino)-2-((1r,4S)-4-methylcyclohexyl)acetic acid (0.17 g, 0.62 mmol, CAS: 1187224-06-1), DIPEA (0.16 g, 1.2 mmol) and HATU (0.33 g, 0.87 mmol) in accordance with the procedure described for Intermediate 2.132. The crude product was purified by flash column chromatography on the Biotage Isolera One™ (20 g silica column eluting, 0-3% MeOH in DCM). LCMS (Method 14): 1.88 min, 440.2 $[M+H]^+$ Intermediate 2.142: tert-butyl ((S)-2-((5-(3-(methoxymethyl)-5-methylisoxazol-4-yl)pyridin-2-yl)amino)-1-((1r,4S)-4-methylcyclohexyl)-2-oxoethyl)carbamate The title compound (0.12 g) was prepared from Intermediate 1.142 (0.2 g, 0.9 mmol), (S)-2-((tert-butoxycarbonyl)amino)-2-((1r,4S)-4-methylcyclohexyl)acetic acid (0.16 g, 0.6 mmol, CAS: 1187224-06-1), DIPEA (0.17 g, 1.2 mmol) and HATU (0.32 g, 0.84 mmol) in accordance with the procedure described for Intermediate 2.132. The crude product was purified by flash column chromatography on the Biotage Isolera One™ (20 g silica column eluting, 0-50% EtOAc in heptane). LCMS (Method 14): 1.99 min, 473.2 $[M+H]^+$ Intermediate 2.143a: tert-butyl (S)-(2-amino-1-cycloheptyl-2-oxoethyl)carbamate To a solution of (2S)-2-(tert-butoxycarbonylamino)-2-cycloheptyl-acetic acid (0.25 g, 0.92 mmol, CAS: 1228542-19-5) in anhydrous THF (11 mL) was added DIPEA (0.36 g, 2.76 mmol) at 0° C. followed by dropwise addition of isobutyl chloroformate (0.18 g, 1.3 mmol). The mixture was stirred at 0° C. for 30 min before dropwise addition of ammonium hydroxide solution (30%, 0.22 g, 1.8 mmol). The mixture was stirred at rt for 16 h. The mixture was concentrated in vacuo then partitioned between EtOAc and water. The aqueous layer was extracted with EtOAc and combined organics dried over $Na_2SO_4$, filtered and concentrated in vacuo. The crude product was triturated in diethyl ether to provide the title compound (75 mg). $^1H$ NMR (400 MHz, DMSO-$d_6$) δ: 7.25 (s, 1H), 6.97 (s, 1H), 6.48 (d, 1H), 3.78-3.69 (m, 1H), 1.74-1.46 (m, 20H).

Intermediate 2.143: tert-butyl (S)-(1-cycloheptyl-2-((5-(3,5-dimethyl-4H-1,2,4-triazol-4-yl)pyridin-2-yl)amino)-2-oxoethyl)carbamate To a suspension of Intermediate 1.143 (35 mg, 0.17 mmol), Intermediate 2.143a (30 mg, 0.11 mmol) in degassed anhydrous 1,4-dioxane (1.4 mL) was added Xantphos (6.4 mg, 11 μmol) and $Cs_2CO_3$ (109 mg, 0.33 mmol). The mixture was degassed with argon for 5 min before addition of tris(dibenzylideneacetone)dipalladium(0) (5.1 mg, 6 μmol) and degassing for 5 min. The vial was sealed and the reaction mixture heated at 100° C. for 18 h. The mixture was diluted with EtOAc and water and the aqueous phase extracted with EtOAc. The combined organics dried over $Na_2SO_4$, filtered, and concentrated in vacuo. The crude product was purified by flash column chromatography on the Biotage Isolera One™ (4 g silica column, eluting 0-10% MeOH in DCM) to provide the title compound (40 mg). LCMS (Method 19): 2.36 min, 443.2 $[M+H]^+$ Intermediate 2.144: tert-butyl (S)-(1-(4,4-difluorocyclohexyl)-2-((5-(1,4-dimethyl-1H-pyrazol-5-yl)pyridin-2-yl)amino)-2-oxoethyl)carbamate The title compound (0.29 g) was prepared from Intermediate 1.106 (0.39 g, 2.1 mmol), (2S)-2-(tert-butoxycarbonylamino)-2-(4,4-difluorocyclohexyl)acetic acid (0.17 g, 0.62 mmol, CAS: 394735-65-0), DIPEA (0.26 g, 2.1 mmol) and HATU (0.55 g, 1.4 mmol) in accordance with the procedure described for Intermediate 2.132. The crude product was purified by flash column chromatography on the Biotage Isolera One™ (10 g silica column, eluting 0-2% MeOH in DCM) then by SCX cartridge (washed with MeOH and eluted with 2 M methanolic ammonia). LCMS (Method 14): 2.56 min, 464.2 $[M+H]^+$ Intermediate 2.145: tert-butyl ((S)-2-((6-(1,4-dimethyl-1H-pyrazol-5-yl)pyridin-3-yl)amino)-1-((1r,4S)-4-methylcyclohexyl)-2-oxoethyl)carbamate The title compound (0.34 g) was prepared from Intermediate 1.145 (0.31 g, 1.7 mmol), (S)-2-((tert-butoxycarbonyl)amino)-2-((1r,4S)-4-methylcyclohexyl)acetic acid (0.22 g, 0.81 mmol, CAS: 1187224-06-1), DIPEA (0.21 g, 1.6 mmol) and HATU (0.46 g, 1.2 mmol) in accordance with the procedure described for Intermediate 2.132. The crude product was purified by flash column chromatography on the Biotage Isolera One™ (10 g silica column, eluting 100% EtOAc in heptane). LCMS (Method 19): 2.73 min, 442.2 $[M+H]^+$ Intermediate 2.146: tert-butyl ((S)-2-((4-methyl-5-(1-methyl-1H-pyrazol-5-yl)pyridin-2-yl)amino)-1-((1r,4S)-4-methylcyclohexyl)-2-oxoethyl)carbamate The title compound (0.23 g) was prepared from Intermediate 1.146 (0.21 g, 1.1 mmol), (S)-2-((tert-butoxycarbonyl)amino)-2-((1r,4S)-4-methylcyclohexyl)acetic acid (0.2 g, 0.74 mmol, CAS: 1187224-06-1), DIPEA (0.19 g, 1.5 mmol) and HATU (0.39 g, 1.0 mmol) in accordance with the procedure described for Intermediate 2.132. The crude product was purified by flash column chromatography on the Biotage Isolera One™ (12 g silica column, eluting 0-12% MeOH in DCM). LCMS (Method 14): 1.92 min, 442.2 $[M+H]^+$ Intermediate 2.147: tert-butyl ((S)-2-((2-(1,4-dimethyl-1H-pyrazol-5-yl)pyrimidin-5-yl)amino)-1-((1r,4S)-4-methylcyclohexyl)-2-oxoethyl)carbamate The title compound (0.50 g) was prepared from Intermediate 1.147 (0.49 g, 2.6 mmol), (S)-2-((tert-butoxycarbonyl)amino)-2-((1r,4S)-4-methylcyclohexyl)acetic acid (0.35 g, 1.3 mmol, CAS: 1187224-06-1), DIPEA (0.45 mL, 2.6 mmol) and HATU (0.69 g, 1.8 mmol) in accordance with the procedure described for Intermediate 2.132. The crude product was purified by flash column chromatography on the Biotage Isolera One™ (12 g silica column, eluting 100% EtOAc in heptanes). LCMS (Method 19): 2.82 min, 443.2 $[M+H]^+$ Intermediate 2.148: tert-butyl (S)-(1-cycloheptyl-2-((5-(1,4-dimethyl-1H-1,2,3-triazol-5-yl)pyridin-2-yl)amino)-2-oxoethyl)carbamate The title compound (0.18 g) was prepared from Intermediate 1.125a (0.3 g, 1.5 mmol), Intermediate 2.143a (0.27 g, 1.0 mmol), Xantphos (58 mg, 0.10 mmol), $Cs_2CO_3$ (976 mg, 3.00 mmol) and tris(dibenzylideneacetone)dipalladium(0) (46 mg, 0.05 mmol) in accordance with the procedure described for Intermediate 2.143. The crude product was purified by flash column chromatography on the Biotage Isolera One™ (20 g silica, 50-100% EtOAc in heptanes). LCMS (Method 19): 1.62 min, 443.2 $[M+H]^+$ Intermediate 2.150: tert-butyl (S)-(1-cycloheptyl-2-((5-(5-(methoxymethyl)-3-methylisoxazol-4-yl)pyridin-2-yl)amino)-2-oxoethyl)carbamate The title compound (90 mg) was prepared from Intermediate 1.150 (0.13 g, 0.61 mmol), (2S)-2-(tert-butoxycarbonylamino)-2-cycloheptyl-acetic acid (0.11 g, 0.41 mmol, CAS: 1228542-19-5), DIPEA (0.14 mL, 0.81 mmol) and HATU (0.21 g, 0.57 mmol) in accordance with the procedure described for Intermediate 2.132. The crude product was purified by flash column chromatography on the Biotage Isolera One™ (12 g silica column, eluting 0-60% EtOAc in heptanes). LCMS (Method 19): 2.89 min, 473.2 $[M+H]^+$ Intermediate 2.151: tert-butyl ((S)-2-((3'-methoxy-2'-methyl-[3,4'-bipyridin]-6-yl)amino)-1-((1r,4S)-4-methylcyclohexyl)-2-oxoethyl)carbamate The title compound (0.11 g) was prepared from Intermediate 1.151 (0.18 g, 0.83 mmol), (S)-2-((tert-butoxycarbonyl)amino)-2-((1r,4S)-4-methylcyclohexyl)acetic acid (0.15 g, 0.55 mmol, CAS: 1187224-06-1), DIPEA (0.19 mL, 1.1 mmol) and HATU (0.29 g, 0.77 mmol) in accordance with the procedure described for Intermediate 2.132. The crude product was purified by flash column chromatography on the Biotage Isolera One™ (10 g silica column, eluting 0-2% MeOH in DCM) then SCX cartridge (washed with MeOH and eluted with 2 M methanolic ammonia). LCMS (Method 19): 2.40 min, 469.2 [M+H]$^+$ Intermediate 2.152: tert-butyl ((S)-2-((2',3'-dimethyl-[3,4'-bipyridin]-6-yl)amino)-1-((1r,4S)-4-methylcyclohexyl)-2-oxoethyl)carbamate The title compound (0.19 g) was prepared from Intermediate 1.152 (0.26 g, 1.3 mmol), (S)-2-((tert-butoxycarbonyl)amino)-2-((1r,4S)-4-methylcyclohexyl)acetic acid (0.18 g, 0.65 mmol, CAS: 1187224-06-1), DIPEA (0.17 g, 1.3 mmol) and HATU (0.34 g, 0.9 mmol) in accordance with the procedure described for Intermediate 2.132. The crude product was purified by flash column chromatography on the Biotage Isolera One™ (10 g silica column, eluting 0-2% MeOH in DCM) then then SCX cartridge (washed with MeOH and eluted with 2 M methanolic ammonia). LCMS (Method 14): 1.54 min, 453.2 [M+H]$^+$ Intermediate 2.153: tert-butyl ((S)-2-((2',5'-dimethyl-[3,4'-bipyridin]-6-yl)amino)-1-((1r,4S)-4-methylcyclohexyl)-2-oxoethyl)carbamate The title compound (102 mg) was prepared from Intermediate 1.153 (171 mg, 0.86 mmol), (S)-2-((tert-butoxycarbonyl)amino)-2-((1r,4S)-4-methylcyclohexyl)acetic acid (155 mg, 0.57 mmol, CAS: 1187224-06-1), DIPEA (0.3 mL, 1.71 mmol) and HATU (304 mg, 0.80 mmol) in accordance with the procedure described for Intermediate 2.132. The crude product was purified by flash column chromatography on the Biotage Isolera One™ (4 g silica column eluting, 0-10% MeOH in DCM) then by ion exchange (SCX eluting with MeOH then with 2 M ammonia in MeOH). LCMS (Method 14): 1.57 min, 453.2 [M+H]$^+$ Intermediate 2.157: tert-butyl (S)-(1-cycloheptyl-2-((5-(1-ethyl-4-methyl-1H-1,2,3-triazol-5-yl)pyridin-2-yl)amino)-2-oxoethyl)carbamate The title compound (31 mg) was prepared from Intermediate 1.157 (0.27 g, 1.2 mmol), Intermediate 2.143a (0.22 g, 0.81 mmol), Xantphos Pd G3 (39 mg, 0.04 mmol) and $Cs_2CO_3$ (0.8 g, 2.4 mmol) in accordance with the procedure described for Intermediate 2.143. The crude product was purified by flash column chromatography on the Biotage Isolera One™ (20 g silica column, eluting 0-100% EtOAc in heptanes). LCMS (Method 14): 1.87 min, 457.2 [M+H]$^+$ Intermediate 2.158: tert-butyl (S)-(1-cycloheptyl-2-((5-(1-ethyl-4-methyl-1H-1,2,3-triazol-5-yl)pyridin-2-yl)amino)-2-oxoethyl)carbamate The title compound (31 mg) was prepared from Intermediate 1.158 (0.2 g, 0.96 mmol), Intermediate 2.143a (0.2 g, 0.74 mmol), Xantphos Pd G3 (70 mg, 0.07 mmol) and $Cs_2CO_3$ (0.72 g, 2.2 mmol) in accordance with the procedure described for Intermediate 2.143. The crude product was used directly. LCMS (Method 14): 1.87 min, 457.2 [M+H]$^+$ Intermediate 2.161: tert-butyl (S)-(1-cycloheptyl-2-((5-(1-cyclopropyl-4-methyl-1H-1,2,3-triazol-5-yl)pyridin-2-yl)amino)-2-oxoethyl)carbamate The title compound (18 mg) was prepared from Intermediate 1.161 (0.15 g, 0.67 mmol), Intermediate 2.143a (0.14 g, 0.52 mmol), Xantphos Pd G3 (49 mg, 0.05 mmol) and $Cs_2CO_3$ (0.5 g, 1.5 mmol) in accordance with the procedure described for Intermediate 2.143. The crude product was purified by flash column chromatography on the Biotage Isolera One™ (10 g silica, 0-100% EtOAc in heptanes). LCMS (Method 14): 1.98 min, 469.2 [M+H]$^+$ Intermediate 2.162: tert-butyl (S)-(1-cycloheptyl-2-((5-(3,5-dimethylisoxazol-4-yl)-3-fluoropyridin-2-yl)amino)-2-oxoethyl)carbamate The title compound (23 mg) was prepared from Intermediate 1.162 (0.34 g, 1.7 mmol), (2S)-2-(tert-butoxycarbonylamino)-2-cycloheptyl-acetic acid (0.3 g, 1.1 mmol, CAS: 1228542-19-5), DIPEA (0.39 mL, 2.2 mmol) and HATU (0.5 g, 1.3 mmol) in accordance with the procedure described for Intermediate 2.132. Additional portions of (2S)-2-(tert-butoxycarbonylamino)-2-cycloheptyl-acetic acid (0.3 g, 1.1 mmol, CAS: 1228542-19-5), HATU (0.5 g, 1.3 mmol) and DIPEA (0.39 mL, 2.2 mmol) were added, and the reaction was stirred at 50° C. for a further 24 h. The crude product was purified by flash column chromatography on the Biotage Isolera One™ (10 g silica column, eluting 0-30% EtOAc in heptanes). LCMS (Method 14): 1.97 min, 461.2 [M+H]$^+$ Intermediate 2.165: tert-butyl (S)-(1-cycloheptyl-2-((5-(1,4-dimethyl-1H-pyrazol-5-yl)pyrimidin-2-yl)amino)-2-oxoethyl)carbamate The title compound (59 mg) was prepared from Intermediate 1.165 (0.14 g, 0.67 mmol), Intermediate 2.143a (0.12 g, 0.44 mmol), Xantphos (26 mg, 0.044 mmol), $Cs_2CO_3$ (0.43 g, 1.3 mmol) and tris(dibenzylideneacetone)dipalladium(0) (20 mg, 0.022 mmol) in accordance with the procedure described for Intermediate 2.143. The crude product was purified by flash column chromatography on the Biotage Isolera One™ (12 g silica, 0-3% MeOH in DCM). LCMS (Method 14): 1.86 min, 443.2 [M+H]$^+$ Intermediate 2.166: tert-butyl (S)-(1-cycloheptyl-2-((5-(4-hydroxy-1-methyl-1H-pyrazol-5-yl)pyridin-2-yl)amino)-2-oxoethyl)carbamate The title compound (30 mg) was prepared from 5-(4-benzyloxy-2-methyl-pyrazol-3-yl)pyridin-2-amine (35 mg, 0.12 mmol, CAS: 2151907-63-8), (2S)-2-(tert-butoxycarbonylamino)-2-cycloheptyl-acetic acid (50 mg, 0.18 mmol, CAS: 1228542-19-5), DIPEA (0.06 mL, 0.37 mmol) and HATU (77 mg, 0.2 mmol) in accordance with the procedure described for Intermediate 2.132. The crude product was purified by flash column chromatography on the Biotage Isolera One™ (4 g silica column, eluting 0-50% EtOAc in heptanes). LCMS (Method 14): 2.13 min, 534.2 [M+H]$^+$ Intermediate 2.169: tert-butyl (S)-(1-cycloheptyl-2-((6-(3,5-dimethylisoxazol-4-yl)pyridin-3-yl)amino)-2-oxoethyl)carbamate The title compound (0.48 g) was prepared from Intermediate 1.138 (0.42 g, 2.2 mmol), (2S)-2-(tert-butoxycarbonylamino)-2-cycloheptyl-acetic acid (0.3 g, 1.1 mmol, CAS: 1228542-19-5), DIPEA (0.39 mL, 2.2 mmol) and HATU (0.63 g, 1.7 mmol) in accordance with the procedure described for Intermediate 2.132. The crude product was purified by flash column chromatography on the Biotage Isolera One™ (20 g silica column, eluting 0-100% EtOAc in heptanes). LCMS (Method 14): 2.00 min, 443.2 [M+H]$^+$ Intermediate 2.173: tert-butyl (S)-(1-cycloheptyl-2-((5-(4-cyclopropyl-1-methyl-1H-1,2,3-triazol-5-yl)pyridin-2-yl)amino)-2-oxoethyl)carbamate The title compound (51 mg) was prepared from Intermediate 1.173 (88 mg, 0.33 mmol), Intermediate 2.143a (80 mg, 0.3 mmol), Xantphos (17 mg, 0.03 mmol), $Cs_2CO_3$ (0.29 g, 0.89 mmol) and tris(dibenzylideneacetone)dipalladium(0) (14 mg, 0.015 mmol) in accordance with the procedure described for Intermediate 2.143. Additional portions of tris(dibenzylideneacetone)dipalladium(0) (14 mg, 0.015 mmol), Xantphos (17 mg, 0.03 mmol) and $Cs_2CO_3$ (0.29 g, 0.89 mmol) were added and mixture was stirred for at 100° C. for 18 h. The crude product was purified by flash column chromatography on the Biotage Isolera One™ (20 g silica column, eluting 2-80% EtOAc in heptanes). LCMS (Method 19): 2.81 min, 469.2 $[M+H]^+$ Intermediate 2.174: tert-butyl (S)-(2-((5-(4-chloro-1-methyl-1H-pyrazol-5-yl)pyridin-2-yl)amino)-1-cycloheptyl-2-oxoethyl)carbamate The title compound (0.72 g) was prepared from Intermediate 1.174 (1.1 g, 5.3 mmol), (2S)-2-(tert-butoxycarbonylamino)-2-cycloheptyl-acetic acid (0.8 g, 2.9 mmol, CAS: 1228542-19-5), DIPEA (1.0 mL, 5.9 mmol) and HATU (1.6 g, 4.2 mmol) in accordance with the procedure described for Intermediate 2.132. The crude product was purified by flash column chromatography on the Biotage Isolera One™ (100 g silica column, eluting 0-100% EtOAc in heptanes). LCMS (Method 19): 2.96 min, 462.2 $[M+H]^+$ Intermediate 2.177: tert-butyl (S)-(1-cyclohexyl-2-((5-(1,4-dimethyl-1H-pyrazol-5-yl)pyridin-2-yl)amino)-2-oxoethyl)carbamate The title compound (0.5 g) was prepared from Intermediate 1.106 (0.79 g, 4.2 mmol), (2S)-2-(tert-butoxycarbonylamino)-2-cyclohexyl-acetic acid (0.54 g, 2.1 mmol, CAS: 109183-71-3), DIPEA (0.73 mL, 4.2 mmol) and HATU (1.1 g, 2.9 mmol) in accordance with the procedure described for Intermediate 2.132. The crude product was purified by flash column chromatography on the Biotage Isolera One™ (100 g silica column, eluting 100% EtOAc). $^1H$ NMR (400 MHz, $CDCl_3$) δ: 8.65 (s, 1H), 8.37 (dd, 1H), 8.25 (dd, 1H), 7.67 (dd, 1H), 7.40 (d, 1H), 5.08 (s, 1H), 4.12 (m, 1H), 3.77 (s, 3H), 2.01 (d, 3H), 1.77 (s, 3H), 1.66 (s, 2H), 1.47 (s, 9H), 1.26-1.18 (m, 3H), 1.18-1.01 (m, 3H).

Intermediate 2.179: tert-butyl ((S)-2-((6-(1,4-dimethyl-1H-pyrazol-5-yl)-5-fluoropyridin-3-yl)amino)-1-((1r,4S)-4-methylcyclohexyl)-2-oxoethyl)carbamate The title compound (0.49 g) was prepared from Intermediate 1.179 (0.79 g, 3.7 mmol), (S)-2-((tert-butoxycarbonyl)amino)-2-((1r,4S)-4-methylcyclohexyl)acetic acid (0.5 g, 1.8 mmol, CAS: 1187224-06-1), DIPEA (0.64 mL, 3.7 mmol) and HATU (1.1 g, 2.8 mmol) in accordance with the procedure described for Intermediate 2.132. The crude product was purified by flash column chromatography on the Biotage Isolera One™ (20 g silica column, eluting 0-100% EtOAc in heptanes). LCMS (Method 14): 2.02 min, 460.2 $[M+H]^+$ Intermediate 2.182: tert-butyl (S)-(2-((5-(4-(((tert-butyldimethylsilyl)oxy)methyl)-1-methyl-1H-pyrazol-5-yl)pyridin-2-yl)amino)-1-cycloheptyl-2-oxoethyl)carbamate Intermediate 2.182a: tert-butyl (S)-(1-cycloheptyl-2-oxo-2-((5-(4,4,5,5-tetramethyl-1,3,2-dioxaborolan-2-yl)pyridin-2-yl)amino)ethyl)carbamate The title compound (0.59 g) was prepared from 5-(4,4,5,5-tetramethyl-1,3,2-dioxaborolan-2-yl)pyridin-2-amine (0.81 g, 3.7 mmol, CAS: 827614-64-2), (2S)-2-(tert-butoxycarbonylamino)-2-cycloheptyl-acetic acid (0.5 g, 1.8 mmol, CAS: 1228542-19-5), DIPEA (0.64 mL, 3.7 mmol) and HATU (2 g, 2.6 mmol) in accordance with the procedure described for Intermediate 2.132. The crude product was purified by flash column chromatography on the Biotage Isolera One™ (40 g silica column, eluting 2-80% EtOAc in heptanes). LCMS (Method 15): 2.36 min, 392.2 $[M-C_6H_{14}+H]^+$ Intermediate 2.182b: 5-bromo-4-(((tert-butyldimethylsilyl)oxy)methyl)-1-methyl-1H-pyrazole To a solution of (5-bromo-1-methyl-1H-pyrazol-4-yl)methanol (0.38 g, 2 mmol, CAS: 1415638-13-9) in DMF (15 mL) was added tert-butyldimethylsilyl chloride (0.36 g, 2.4 mmol) followed by imidazole (0.34 g, 5 mmol). The mixture was stirred at rt for 18 h. The reaction mixture was diluted with EtOAc and washed with brine. The organic layer was dried over $Na_2SO_4$, filtered and concentrated in vacuo. The crude product was purified by flash column chromatography on the Biotage Isolera One™ (20 g silica column, eluting 2-40% EtOAc in heptanes) to provide the title compound (0.54 g). $^1H$ NMR (400 MHz, $CDCl_3$) δ: 7.50 (s, 1H), 4.52 (s, 2H), 3.86 (s, 3H), 0.91 (s, 9H), 0.09 (s, 6H)

Intermediate 2.182: tert-butyl (S)-(2-((5-(4-(((tert-butyldimethylsilyl)oxy)methyl)-1-methyl-1H-pyrazol-5-yl)pyridin-2-yl)amino)-1-cycloheptyl-2-oxoethyl)carbamate The title compound (0.11 g) was prepared from Intermediate 2.182a (0.12 mg, 0.24 mmol), Intermediate 2.182b (89 mg, 0.29 mmol), $Pd(dppf)Cl_2$ (20 mg, 0.02 mmol) and potassium carbonate (0.1 g, 0.73 mmol) in accordance with the procedure described for Intermediate 1.1, heating at 100° C. for 18 h. The crude product was purified by flash column chromatography on the Biotage Isolera One™ (20 g silica column, eluting 2-70% EtOAc in heptanes). LCMS (Method 15): 3.47 min, 572.2 $[M+H]^+$ Intermediate 2.183: tert-butyl (S)-(1-cyclopentyl-2-((5-(1,4-dimethyl-1H-pyrazol-5-yl)pyridin-2-yl)amino)-2-oxoethyl)carbamate The title compound (48 mg) was prepared from Intermediate 1.106 (0.1 g, 0.53 mmol), (2S)-2-(tert-butoxycarbonylamino)-2-cyclopentyl-acetic acid (0.14 g, 0.56 mmol, CAS: 109183-72-4), DIPEA (0.19 mL, 1.1 mmol) and HATU (0.3 g, 0.8 mmol) in accordance with the procedure described for Intermediate 2.132. The crude product was purified by flash column chromatography on the Teledyne ISCO CombiFlash® (12 g silica column, eluting 0-100% EtOAc in isohexane). LCMS (Method 25): 2.26 min, 414.3 $[M+H]^+$ Intermediate 2.184: tert-butyl (1-(bicyclo[2.2.1]heptan-2-yl)-2-((5-(1,4-dimethyl-1H-pyrazol-5-yl)pyridin-2-yl)amino)-2-oxoethyl)carbamate The title compound (60 mg) was prepared from Intermediate 1.106 (77 mg, 0.41 mmol), 2-(tert-butoxycarbonylamino)-2-norbornan-2-yl-acetic acid (0.1 g, 0.37 mmol, CAS: 182292-11-1), DIPEA (0.13 mL, 0.74 mmol) and HATU (0.21 g, 0.56 mmol) in accordance with the procedure described for Intermediate 2.132. The crude product was purified by flash column chromatography on the Teledyne ISCO CombiFlash® (12 g silica column, eluting 0-100% EtOAc in isohexane). LCMS (Method 26): 1.50 min, 440.20 $[M+H]^+$ Intermediate 2.185: tert-butyl (2-((5-(1,4-dimethyl-1H-pyrazol-5-yl)pyridin-2-yl)amino)-2-oxo-1-((1r,4r)-4-(trifluoromethyl)cyclohexyl)ethyl)carbamate Intermediate 2.185a: 5-((1r,4r)-4-(trifluoromethyl)cyclohexyl)imidazolidine-2,4-dione A solution of trans-4-(trifluoromethyl)cyclohexane-1-carbaldehyde (0.93 g, 5.2 mmol, CAS: 133261-34-4), sodium cyanide (0.51 g, 10.3 mmol) and ammonium carbonate (1.5 g, 15.5 mmol) in MeOH (3 mL) then water (3 mL) was degassed with argon and heated at 60° C. for 48 h. The reaction mixture was cooled to rt and carefully quenched with HCl (1 M aqueous; 8 mL). HCl (5 M aqueous) were added carefully until the pH was ~4-5. The mixture was filtered and the solids washed with water to give the title compound (0.73 g). LCMS (Method 19): 1.82 min, 249.2 $[M-H]^-$ Intermediate 2.185b: 2-((1r,4r)-4-(trifluoromethyl)cyclohexyl)-2-ureidoacetic acid A solution of Intermediate 2.185a (0.73 g, 2.9 mmol) in sodium hydroxide (5 M aqueous; 3.8 mL, 18.9 mmol) was heated at reflux for 18 h. The reaction cooled to rt, and the pH adjusted to ~5-6 by dropwise addition of HCl (5 M aqueous). The mixture was filtered, and the solids triturated with diethyl ether to provide the title compound (0.3 g). LCMS (Method 14): 1.46 min, 269.2 $[M+H]^+$ Intermediate 2.185c: 2-((tert-butoxycarbonyl)amino)-2-((1r,4r)-4-(trifluoromethyl)cyclohexyl)acetic acid To a suspension of Intermediate 2.185b (0.3 g, 1.1 mmol) in water (3.4 mL) was added sodium hydroxide (6 M aqueous; 0.56 mL, 3.4 mmol). The mixture was heated at 110° C. for 48 h. A further portion of sodium hydroxide (134 mg, 3.4 mmol) was added, and the mixture heated at 110° C. for a further 72 h. The reaction was acidified to pH 6 by dropwise addition of HCl (5 M aqueous). Sodium carbonate (0.36 g, 3.4 mmol) was added to the mixture followed by THF (4 mL) and Boc anhydride (0.37 g, 1.7 mmol). The reaction mixture was stirred at rt for 18 h. The reaction was adjusted to pH 5 with HCl (1 M aqueous) and diluted with water before extraction with EtOAc. The aqueous phase was acidified to pH 1 and extracted with EtOAc. The combined organics were dried over $Na_2SO_4$, filtered, and concentrated in vacuo. The residue was triturated with heptanes to provide the title compound (0.22 g). LCMS (Method 14): 1.83 min, 324.0 $[M-H]^-$ Intermediate 2.185: tert-butyl (2-((5-(1,4-dimethyl-1H-pyrazol-5-yl)pyridin-2-yl)amino)-2-oxo-1-((1r,4r)-4-(trifluoromethyl)cyclohexyl)ethyl)carbamate The title compound (0.22 g) was prepared from Intermediate 1.106 (0.25 g, 1.3 mmol), Intermediate 2.185c (0.22 g, 0.66 mmol), DIPEA (72 mg, 1.3 mmol) and HATU (0.35 g, 0.93 mmol) in accordance with the procedure described for Intermediate 2.132. The crude product was purified by flash column chromatography on the Biotage Isolera One™ (40 g silica column, eluting 0-1.5% MeOH in DCM). LCMS (Method 14): 1.96 min, 496.2 $[M+H]^+$ Intermediate 2.190: tert-butyl (S)-(1-cycloheptyl-2-((5-(1-(2-(dimethylamino)-2-oxoethyl)-4-methyl-1H-1,2,3-triazol-5-yl)pyridin-2-yl)amino)-2-oxoethyl)carbamate The title compound (55 mg) was prepared from Intermediate 1.190 (0.11 g, 0.38 mmol), Intermediate 2.143a (68 mg, 0.25 mmol), XantPhos (15 mg, 0.03 mmol), $Cs_2CO_3$ (0.25 g, 0.75 mmol) and tris(dibenzylideneacetone)dipalladium(0) (12 mg, 0.01 mmol) in accordance with the procedure described for Intermediate 2.143. The crude product was purified by flash column chromatography on the Biotage Isolera One™ (10 g silica, 0-100% EtOAc in heptanes). $^1H$ NMR (400 MHz, $CDCl_3$) δ: 8.87 (s, 1H), 8.37 (dd, 1H), 8.30 (dd, 1H), 7.80 (dd, 1H), 5.03 (s, 2H), 4.21 (s, 1H), 3.05 (s, 3H), 2.96 (s, 4H), 2.32 (s, 3H), 2.17 (d, 1H), 1.83-1.65 (m, 4H), 1.60 (d, 2H), 1.47 (s, 15H).

Intermediate 2.193: tert-butyl ((S)-2-((5-(4-cyano-1-methyl-1H-pyrazol-5-yl)pyridin-2-yl)amino)-1-((1r,4S)-4-methylcyclohexyl)-2-oxoethyl)carbamate The title compound (70 mg) was prepared from Intermediate 1.193 (0.21 g, 1.0 mmol), (S)-2-((tert-butoxycarbonyl)amino)-2-((1r,4S)-4-methylcyclohexyl)acetic acid (0.14 g, 0.51 mmol, CAS: 1187224-06-1), DIPEA (0.18 mL, 1.0 mmol) and HATU (0.29 g, 0.77 mmol) in accordance with the procedure described for Intermediate 2.132. The crude product was purified by flash column chromatography on the Biotage Isolera One™ (20 g silica column, eluting 0-100% EtOAc in heptanes). LCMS (Method 14): 1.99 min, 453.2 $[M+H]^+$ Intermediate 2.195: tert-butyl (S)-(1-cycloheptyl-2-oxo-2-((5-(1,3,4-trimethyl-1H-pyrazol-5-yl)pyridin-2-yl)amino)ethyl)carbamate The title compound (70 mg) was prepared from Intermediate 1.195 (0.85 g, 4.2 mmol), (2S)-2-(tert-butoxycarbonylamino)-2-cycloheptyl-acetic acid (0.67 g, 2.5 mmol, CAS: 1228542-19-5), DIPEA (0.86 mL, 4.9 mmol)) and HATU (0.32 g, 3.5 mmol) in accordance with the procedure described for Intermediate 2.132. The crude product was purified by flash column chromatography (eluting 20-100% EtOAc in heptanes). LCMS (Method 14): 2.07 min, 456.2 $[M+H]^+$ Intermediate 2.196: tert-butyl ((S)-2-((5-(3,5-dimethylisothiazol-4-yl)pyridin-2-yl)amino)-1-((1r,4S)-4-methylcyclohexyl)-2-oxoethyl)carbamate The title compound (0.11 g) was prepared from Intermediate 1.196 (0.14 g, 0.66 mmol), (S)-2-((tert-butoxycarbonyl)amino)-2-((1r,4S)-4-methylcyclohexyl)acetic acid (0.1 g, 0.37 mmol, CAS: 1187224-06-1), DIPEA (0.13 mL, 0.74 mmol) and HATU (0.2 g, 0.52 mmol) in accordance with the procedure described for Intermediate 2.132. The crude product was purified by flash column chromatography on the Biotage Isolera One™ (20 g silica column, eluting 20-100% EtOAc in heptanes). LCMS (Method 15): 3.09 min, 459.2 $[M+H]^+$ Intermediate 2.199: tert-butyl ((S)-2-((5-(4-chloro-1-methyl-1H-pyrazol-5-yl)pyridin-2-yl)amino)-1-((1r,4S)-4-methylcyclohexyl)-2-oxoethyl)carbamate The title compound (0.48 g) was prepared from Intermediate 1.174 (0.46 g, 2.1 mmol), (S)-2-((tert-butoxycarbonyl)amino)-2-((1r,4S)-4-methylcyclohexyl)acetic acid (0.4 g, 1.4 mmol, CAS: 1187224-06-1), DIPEA (0.49 mL, 2.8 mmol) and HATU (0.75 g, 2.0 mmol) in accordance with the procedure described for Intermediate 2.132. The crude product was purified by flash column chromatography on the Biotage Isolera One™ (40 g, silica column, eluting 10-50% EtOAc in heptanes). LCMS (Method 15): 3.04 min, 462.2 $[M+H]^+$ Intermediate 2.205: tert-butyl ((S)-2-((5-(4-(((tert-butyldimethylsilyl)oxy)methyl)-1-methyl-1H-pyrazol-5-yl)pyridin-2-yl)amino)-1-((1r,4S)-4-methylcyclohexyl)-2-oxoethyl)carbamate Intermediate 2.205a: tert-butyl ((S)-1-((1r,4S)-4-methylcyclohexyl)-2-oxo-2-((5-(4,4,5,5-tetramethyl-1,3,2-dioxaborolan-2-yl)pyridin-2-yl)amino)ethyl) carbamate The title compound (0.69 g) was prepared from 5-(4,4,5,5-tetramethyl-1,3,2-dioxaborolan-2-yl)pyridin-2-amine (0.8 g, 3.7 mmol CAS: 827614-64-2), (S)-2-((tert-butoxycarbonyl)amino)-2-((1r,4S)-4-methylcyclohexyl)acetic acid (0.5 g, 1.8 mmol, CAS: 1187224-06-1), DIPEA (0.64 mL, 3.7 mmol) and HATU (0.98 g, 2.6 mmol) in accordance with the procedure described for Intermediate 2.132. The crude product was purified by flash column chromatography on the Biotage Isolera One™ (25 g silica column, eluting 2-100% EtOAc in heptanes). LCMS (Method 15): 2.41 min, 392.2 $[M+H]^+$ for boronic acid Intermediate 2.205: tert-butyl ((S)-2-((5-(4-(((tert-butyldimethylsilyl)oxy)methyl)-1-methyl-1H-pyrazol-5-yl)pyridin-2-yl)amino)-1-((1r,4S)-4-methylcyclohexyl)-2-oxoethyl)carbamate The title compound (0.27 g) was prepared from Intermediate 2.205a (0.32 g, 0.67 mmol), Intermediate 2.182b (0.27 g, 0.87 mmol), $Pd(dppf)Cl_2$ (49 mg, 0.07 mmol) and potassium carbonate (0.28 g, 2.0 mmol) in accordance with the procedure described for Intermediate 1.1, heating at 110° C. for 18 h. The crude product was purified by flash column chromatography on the Biotage Isolera One™ (50 g silica column, eluting 2-70% EtOAc in heptanes).] LCMS (Method 15): 3.49 min, 572.2 $[M+H]^+$ Intermediate 2.207: tert-butyl (S)-(1-cyclohexyl-2-((6-(3,5-dimethyl-1-((2-(trimethylsilyl)ethoxy)methyl)-1H-pyrazol-4-yl)pyridin-3-yl)amino)-2-oxoethyl)carbamate The title compound (37 mg) was prepared from Intermediate 1.207 (0.15 g, 0.43 mmol), (2S)-2-(tert-butoxycarbonylamino)-2-cyclohexyl-acetic acid (0.14 g, 0.52 mmol, CAS: 109183-71-3), DIPEA (0.24 mL, 1.4 mmol) and HATU (0.2 g, 0.51 mmol) in accordance with the procedure described for Intermediate 2.132. The crude product was purified by flash column chromatography on the Teledyne ISCO CombiFlash® (12 g silica column, eluting 0-100% 3:1 EtOAc:EtOH in isohexane). LCMS (Method 28): 2.04 min, 558.5 $[M+H]^+$ Intermediate 2.208: tert-butyl (S)-(1-cycloheptyl-2-((6-(3,5-dimethyl-1-((2-(trimethylsilyl)ethoxy)methyl)-1H-pyrazol-4-yl)pyridin-3-yl)amino)-2-oxoethyl)carbamate The title compound (0.9 g) was prepared from Intermediate 1.207 (0.55 g, 1.5 mmol), (2S)-2-(tert-butoxycarbonylamino)-2-cycloheptyl-acetic acid (0.57 g, 2.1 mmol, CAS: 1228542-19-5), DIPEA (0.8 mL, 4.6 mmol) and HATU (0.8 g, 2.1 mmol) in accordance with the procedure described for Intermediate 2.132. The crude product was purified by flash column chromatography on the Teledyne ISCO CombiFlash® (24 g silica column, eluting 0-100% 3:1 EtOAc:EtOH in isohexane). LCMS (Method 28): 2.14 min, 572.4 $[M+H]^+$ Intermediate 2.211: tert-butyl ((S)-2-((6-(3,5-dimethyl-1-((2-(trimethylsilyl)ethoxy)methyl)-1H-pyrazol-4-yl)pyridin-3-yl)amino)-1-((1r,4S)-4-methylcyclohexyl)-2-oxoethyl)carbamate The title compound (0.36 g) was prepared from Intermediate 1.207 (0.22 g, 0.59 mmol), (S)-2-((tert-butoxycarbonyl)amino)-2-((1r,4S)-4-methylcyclohexyl)acetic acid (0.2 g, 0.74 mmol, CAS: 1187224-06-1), DIPEA (0.32 mL, 1.8 mmol) and HATU (0.29 g, 0.76 mmol) in accordance with the procedure described for Intermediate 2.132. Additional portions of (S)-2-((tert-butoxycarbonyl)amino)-2-((1r,4S)-4-methylcyclohexyl)acetic acid (40 mg, 0.15 mmol, CAS: 1187224-06-1) and HATU (56 mg, 0.15 mmol) were added, and the mixture stirred at 50° C. for a further 3 h. The crude product was purified by flash column chromatography on the Teledyne ISCO CombiFlash® (24 g silica column, eluting 0-100% 3:1 EtOAc:EtOH in isohexane). LCMS (Method 26): 1.95 min, 572.4 $[M+H]^+$ Intermediate 2.214: tert-butyl (S)-(1-cycloheptyl-2-oxo-2-((1',2',4'-trimethyl-6'-oxo-1',6'-dihydro-[3,3'-bipyridin]-6-yl)amino)ethyl)carbamate The title compound (0.36 g) was prepared from Intermediate 1.214 (30 mg, 0.13 mmol), (2S)-2-(tert-butoxycarbonylamino)-2-cycloheptyl-acetic acid (0.12 g, 0.43 mmol, CAS: 1228542-19-5), DIPEA (0.14 mL, 0.8 mmol) and HATU (0.22 g, 0.59 mmol) in accordance with the procedure described for Intermediate 2.132. The crude product was purified by flash column chromatography on the Teledyne ISCO CombiFlash® (12 g silica column, eluting 0-100% EtOAc in isohexane). LCMS (Method 28): 1.63 min, 483.3 $[M+H]^+$ Intermediate 2.215: tert-butyl ((S)-1-((1r,4S)-4-methylcyclohexyl)-2-oxo-2-((1',2',4'-trimethyl-6'-oxo-1',6'-dihydro-[3,3'-bipyridin]-6-yl)amino)ethyl) carbamate The title compound (30 mg) was prepared from Intermediate 1.214 (90 mg, 0.39 mmol), (S)-2-((tert-butoxycarbonyl)amino)-2-((1r,4S)-4-methylcyclohexyl)acetic acid (32 mg, 0.12 mmol, CAS: 1187224-06-1), DIPEA (0.04 mL, 0.23 mmol) and HATU (68 mg, 0.18 mmol) in accordance with the procedure described for Intermediate 2.132. The crude product was purified by flash column chromatography on the Teledyne ISCO CombiFlash® (12 g silica column, eluting 0-100% EtOAc in isohexane). LCMS (Method 28): 1.64 min, 483.3 $[M+H]^+$ Intermediate 2.216: tert-butyl (S)-(1-cycloheptyl-2-oxo-2-((5-(1,3,5-trimethyl-1H-pyrazol-4-yl)pyridin-2-yl)amino)ethyl)carbamate The title compound (30 mg) was prepared from Intermediate 1.216 (79 mg, 0.38 mmol), (2S)-2-(tert-butoxycarbonylamino)-2-cycloheptyl-acetic acid (0.1 g, 0.38 mmol, CAS: 1228542-19-5), DIPEA (0.13 mL, 0.75 mmol) and HATU (0.17 g, 0.46 mmol) in accordance with the procedure described for Intermediate 2.132. The crude product was purified by flash column chromatography on the Teledyne ISCO CombiFlash® (12 g silica column, eluting 0-100% EtOAc in isohexane). LCMS (Method 27): 1.54 min, 456.2 $[M+H]^+$ Intermediate 2.217: tert-butyl ((S)-1-((1r,4S)-4-methylcyclohexyl)-2-oxo-2-((5-(1,3,5-trimethyl-1H-pyrazol-4-yl)pyridin-2-yl)amino)ethyl)carbamate The title compound (30 mg) was prepared from Intermediate 1.216 (46 mg, 0.23 mmol), (S)-2-((tert-butoxycarbonyl)amino)-2-((1r,4S)-4-methylcyclohexyl)acetic acid (62 mg, 0.23 mmol, CAS: 1187224-06-1), DIPEA (0.08 mL, 0.46 mmol) and HATU (95 mg, 0.25 mmol) in accordance with the procedure described for Intermediate 2.132. The crude product used without further purification. LCMS (Method 27): 1.55 min, 456.2 $[M+H]^+$ Intermediate 2.219: tert-butyl ((S)-2-((5-(1-methyl-4-(trifluoromethyl)-1H-pyrazol-5-yl)pyridin-2-yl)amino)-1-((1r,4S)-4-methylcyclohexyl)-2-oxoethyl)carbamate The title compound (0.22 g) was prepared from Intermediate 1.219 (0.46 g, 1.9 mmol), (S)-2-((tert-butoxycarbonyl)amino)-2-((1r,4S)-4-methylcyclohexyl)acetic acid (0.26 g, 0.94 mmol, CAS: 1187224-06-1), DIPEA (0.33 mL, 1.9 mmol) and HATU (0.54 g, 1.4 mmol) in accordance with the procedure described for Intermediate 2.132. The crude product was purified by flash column chromatography on the Biotage Isolera One™ (50 g silica column, eluting 0-3% MeOH in DCM) and flash column chromatography on the Biotage Isolera One™ (50 g silica column, eluting 0-30% EtOAc in heptanes). LCMS (Method 14): 2.11 min, 496.2 $[M+H]^+$ Intermediate 2.220: tert-butyl (2-((5-(1,4-dimethyl-1H-pyrazol-5-yl)pyridin-2-yl)amino)-1-(dispiro[2.1.2$^5$.2$^3$]nonan-4-yl)-2-oxoethyl)carbamate Intermediate 2.220a: 4-(methoxymethylene)dispiro[2.1.2$^5$.2$^3$]nonane To a solution of (methoxymethyl)triphenylphosphonium chloride (1.9 g, 5.5 mmol) in THF (6 mL) at 0° C. was slowly added n-butyl lithium (2.5 M in hexanes; 2.2 mL, 5.5 mmol). The mixture was stirred for 20 min before the addition of dispiro[2.1.2$^5$.2$^3$]nonan-4-one (0.5 g, 3.7 mmol, CAS: 1004-54-2) in tetrahydrofuran (4 mL). The mixture was heated at 60° C. for 20 h then cooled to rt and quenched with water and DCM. The layers were separated, and the aqueous layers extracted with DCM. The combined organics were passed through a phase separation cartridge then concentrated in vacuo. The crude product was purified by flash column chromatography on the Biotage Isolera One™ (10 g silica column, eluting 100% DCM) to provide the title compound as an impure mixture which was subject to the same reaction conditions as described below.

To a solution of (methoxymethyl)triphenylphosphonium chloride (1.3 g, 3.7 mmol) in THF (4 mL) at 0° C. was slowly added n-butyl lithium (2.5 M in hexanes; 1.5 mL, 3.7 mmol). The mixture was stirred for 20 min before the addition of the crude mixture as a solution in tetrahydrofuran (2 mL). The mixture was heated at 60° C. for 20 h then cooled to rt and quenched with water and DCM. The layers were separated, and the aqueous layers extracted with DCM. The combined organics were passed through a phase separation cartridge then concentrated in vacuo. The crude product was purified by flash column chromatography on the Biotage Isolera One™ (10 g silica column, eluting 100% DCM) to provide the title compound (0.56 g). $^1$H NMR (400 MHz, $CDCl_3$) δ: 5.32 (s, 1H), 3.40 (s, 3H), 1.74 (d, 4H), 1.38 (q, 2H), 0.76-0.68 (m, 2H), 0.65 (q, 2H), 0.62-0.56 (m, 2H).

Intermediate 2.220b: dispiro[2.1.2$^5$.2$^3$]nonane-4-carbaldehyde

To a solution of Intermediate 2.220a (70 mg, 0.43 mmol) in THF (0.5 mL) was added HCl (5 M aqueous; 0.5 mL, 2.5 mmol) in water (0.5 mL) and the mixture was stirred at rt for 2 h. The mixture was extracted with DCM, passed through a phase separation cartridge and concentrated in vacuo to provide the title compound (67 mg) which was used without further purification. $^1$H NMR (400 MHz, $CDCl_3$) δ 9.45 (d, 1H), 3.51 (t, 2H), 2.60 (tt, 2H), 2.39 (ddt, 2H), 1.88-1.79 (m, 3H), 0.78-0.70 (m, 2H), 0.48-0.44 (m, 2H).

Intermediate 2.220c: 5-(dispiro[2.1.2$^5$.2$^3$]nonan-4-yl)imidazolidine-2,4-dione A mixture of Intermediate 2.220b (0.2 g, 1.3 mmol), ammonium carbonate (0.37 mg, 3.9 mmol), sodium cyanide (95 mg, 1.9 mmol) in MeOH (5 mL) and water (5 mL) was added to a microwave vial. The vial was sealed and the mixture heated to 60° C. for 2 days. The mixture was cooled to rt then acidified to pH 3 with HCl (1 M aqueous). The volatiles were concentrated in vacuo and the aqueous residue extracted with DCM. The organics were passed through a phase separation cartridge and concentrated in vacuo. The crude product was triturated with DCM to provide the title compound (35 mg). LCMS (Method 14): 1.50 min, 221.2 $[M+H]^+$ Intermediate 2.220d: 2-((tert-butoxycarbonyl)amino)-2-(dispiro[2.1.2$^5$.2$^3$]nonan-4-yl)acetic acid A solution of Intermediate 2.220c (0.5 g, 2.3 mmol) in NaOH (5 M aqueous; 25 mL, 125 mmol) and water (25 mL) was heated at reflux for 3 days. The mixture cooled to rt then acidified to pH 3 with HCl (12 M aqueous). Potassium carbonate was added to adjust the pH ~8, then THF (150 mL) was added followed by Boc Anhydride (1.4 g, 6.8 mmol) and the mixture stirred at rt for 18 h. The mixture was diluted with EtOAc, the layers separated and the aqueous layer extracted with EtOAc. The combined organics were dried over $Na_2SO_4$, filtered and concentrated in vacuo. The crude product was purified by flash column chromatography on the Biotage Isolera One™ (40 g silica column, eluting 0-10% MeOH in DCM) to provide the title compound (0.27 g). LCMS (Method 14): 2.11 min, 1.89 min, 294.2 $[M-H]^-$ Intermediate 2.220: tert-butyl (2-((5-(1,4-dimethyl-1H-pyrazol-5-yl)pyridin-2-yl)amino)-1-(dispiro[2.1.2$^5$.2$^3$]nonan-4-yl)-2-oxoethyl)carbamate The title compound (0.22 g) was prepared from Intermediate 1.106 (45 mg, 0.24 mmol), Intermediate 2.220d (47 mg, 0.16 mmol), DIPEA (0.06 mL, 0.32 mmol) and HATU (85 mg, 0.22 mmol) in accordance with the procedure described for Intermediate 2.132. The crude product was purified by flash column chromatography on the Biotage Isolera One™ (10 g silica column, eluting 0-10% MeOH in DCM). LCMS (Method 14): 2.05 min, 466.2 $[M+H]^+$ Intermediate 3.1: (S)-2-amino-N-(4-(2,3-dimethylpyridin-4-yl)phenyl)-3,3-diphenylpropanamide dihydrochloride A solution of Intermediate 2.1 (0.15 g, 0.28 mmol) in HCl (3 M in CPME; 2 mL) was stirred at rt for 2 h. The reaction mixture was concentrated in vacuo to provide the title compound (0.14 g) which was used without further purification. LCMS (Method 2): 0.86 min, 422.3 $[M+H]^+$ Intermediate 3.2: (S)-2-amino-N-(4-(3-chloropyridin-4-yl)phenyl)-3,3-diphenylpropanamide dihydrochloride A solution of Intermediate 2.2 (0.47 g, 0.89 mmol) in HCl (3 M in 1,4-dioxane; 10 mL) was stirred at rt for 2 h. The reaction mixture was concentrated in vacuo to provide the title compound (0.41 g) which was used without further purification. LCMS (Method 2): 0.87 min, 428.2 $[M+H]^+$ Intermediate 3.3: (S)-2-amino-N-(4-(3-methoxypyridin-4-yl)phenyl)-3,3-diphenylpropanamide dihydrochloride A solution of Intermediate 2.3 (0.57 g, 1.1 mmol) in HCl (4 M in 1,4-dioxane; 1.4 mL) was stirred at rt for 18 h. The reaction mixture was concentrated in vacuo to provide the title compound (0.44 g) which was used without further purification. LCMS (Method 2): 0.81 min, 424.3 $[M+H]^+$ Intermediate 3.4: (S)-2-amino-N-(4-(3-methylpyridin-4-yl)phenyl)-3,3-diphenylpropanamide dihydrochloride A solution of Intermediate 2.4 (0.17 g, 0.33 mmol) in HCl (3 M in 1,4-dioxane; 4.0 mL) was stirred at rt for 2 h. The reaction mixture was concentrated in vacuo to provide the title compound (0.15 g) which was used without further purification. LCMS (Method 2): 0.83 min, 408.3 $[M+H]^+$ Intermediate 3.5: (S)-2-amino-3,3-diphenyl-N-(4-(3-(trifluoromethyl)pyridin-4-yl)phenyl)propanamide dihydrochloride A solution of Intermediate 2.5 (0.16 g, 0.22 mmol) in HCl (3 M in CPME; 0.73 mL) was stirred at rt for 2 h. The reaction mixture was concentrated in vacuo to provide the title compound (0.12 g) which was used without further purification. LCMS (Method 2): 0.92 min, 462.2 $[M+H]^+$ Intermediate 3.6: (S)-2-amino-N-(4-(3,5-dimethylpyridin-4-yl)phenyl)-3,3-diphenylpropanamide dihydrochloride A solution of Intermediate 2.6 (0.26 g, 0.51 mmol) in HCl (3 M in CPME; 15 mL) was stirred at rt for 24 h. The reaction mixture was concentrated in vacuo to provide the title compound (0.25 g) which was used without further purification. LCMS (Method 3): 2.21 min, 422.3 $[M+H]^+$ Intermediate 3.7: (S)-2-amino-N-(4-(3-(methylamino)pyridin-4-yl)phenyl)-3,3-diphenylpropanamide trihydrochloride A solution of Intermediate 2.7 (0.15 g, 0.29 mmol) in HCl (3 M in CPME; 3 mL) was stirred at rt for 5 h. The reaction mixture was concentrated in vacuo to provide the title compound (0.15 g) which was used without further purification. LCMS (Method 2): 0.79 min, 423.3 $[M+H]^+$ Intermediate 3.8: (S)-2-amino-N-(4-(3-(dimethylamino)pyridin-4-yl)phenyl)-3,3-diphenylpropanamide trihydrochloride A solution of Intermediate 2.8 (0.14 g, 0.26 mmol) in HCl (3 M in CPME; 3 mL) was stirred at rt for 4 h. The reaction mixture was concentrated in vacuo to provide the title compound (0.14 g) which was used without further purification. LCMS (Method 2): 0.86 min, 437.3 $[M+H]^+$ Intermediate 3.9: (S)-2-amino-N-(4-(3,5-dimethoxypyridin-4-yl)phenyl)-3,3-diphenylpropanamide dihydrochloride A solution of Intermediate 2.9 (0.16 g, 0.29 mmol) in HCl (3 M in CPME; 5 mL) was stirred at rt for 24 h. The reaction mixture was concentrated in vacuo to provide the title compound (0.16 g) which was used without further purification. LCMS (Method 2): 0.80 min, 454.2 $[M+H]^+$ Intermediate 3.10: (S)-2-amino-N-(4-(3-fluoro-5-methoxypyridin-4-yl)phenyl)-3,3-diphenylpropanamide dihydrochloride A solution of Intermediate 2.10 (98 mg, 0.18 mmol) in HCl (3 M in CPME; 5 mL) was stirred at rt for 24 h. The reaction mixture was concentrated in vacuo to provide the title compound (80 mg) which was used without further purification. LCMS (Method 2): 0.84 min, 442.2 $[M+H]^+$ Intermediate 3.11: (S)-2-amino-N-(4-(2-methyl-6-oxo-1,6-dihydropyridin-3-yl)phenyl)-3,3-diphenylpropanamide hydrochloride A solution of Intermediate 2.11 (0.14 g, 0.26 mmol) in HCl (3 M in CPME; 6 mL) was stirred at rt for 4 h. The reaction mixture was concentrated in vacuo to provide the title compound (89 mg) which was used without further purification. LCMS (Method 2): 0.68 min, 424.3 $[M+H]^+$ Intermediate 3.12: (S)-2-amino-N-(4-(1,4-dimethyl-6-oxo-1,6-dihydropyridin-3-yl)phenyl)-3,3-diphenylpropanamide hydrochloride A solution of Intermediate 2.12 (0.28 g, 0.53 mmol) in HCl (3 M in 1,4-dioxane; 7 mL) was stirred at rt for 2 h. The reaction mixture was concentrated in vacuo to provide the title compound (0.25 g) which was used without further purification. LCMS (Method 4): 0.73 min, 438.3 [M+H]$^+$ Intermediate 3.13: (S)-2-amino-N-(4-(1,2-dimethyl-6-oxo-1,6-dihydropyridin-3-yl)phenyl)-3,3-diphenylpropanamide A solution of Intermediate 2.13 (0.29 g, 0.55 mmol) in HCl (3 M in 1,4-dioxane; 8 mL) was stirred at rt for 2 h. The reaction mixture was concentrated in vacuo to provide the title compound (0.26 g) which was used without further purification. LCMS (Method 4): 0.80 min, 438.2 [M+H]$^+$ Intermediate 3.14: (S)-2-amino-N-(4-(3,5-dimethylpyridin-4-yl)-3-fluorophenyl)-3,3-diphenylpropanamide dihydrochloride A solution of Intermediate 2.14 (0.11 g, 0.18 mmol) in HCl (4 M in 1,4-dioxane; 0.46 mL) was stirred at rt for 18 h. The reaction mixture was concentrated in vacuo to provide the title compound (0.10 g) which was used without further purification. LCMS (Method 4): 0.89 min, 440.3 [M+H]$^+$ Intermediate 3.15: (S)-2-amino-N-(3-fluoro-4-(3-methylpyridin-4-yl)phenyl)-3,3-diphenylpropanamide dihydrochloride A solution of Intermediate 2.15 (0.20 g, 0.38 mmol) in HCl (3 M in CPME; 15 mL) was stirred at rt for 24 h. The reaction mixture was concentrated in vacuo to provide the title compound (0.19 g) which was used without further purification. LCMS (Method 3): 2.24 min, 426.2 [M+H]$^+$ Intermediate 3.16: (S)-2-amino-N-(4-(1,2-dimethyl-6-oxo-1,6-dihydropyridin-3-yl)-3-fluorophenyl)-3,3-diphenylpropanamide hydrochloride A solution of Intermediate 2.16 (0.20 g, 0.38 mmol) in HCl (3 M in CPME; 15 mL) was stirred at rt for 24 h. The reaction mixture was concentrated in vacuo to provide the title compound (0.10 g) which was used without further purification. LCMS (Method 3): 1.85 min, 456.3 [M+H]$^+$ Intermediate 3.17: (S)-2-amino-N-(4-(1,4-dimethyl-6-oxo-1,6-dihydropyridin-3-yl)-3-fluorophenyl)-3,3-diphenylpropanamide hydrochloride A solution of Intermediate 2.17 (0.16 g, 0.29 mmol) in HCl (3 M in CPME; 15 mL) was stirred at rt for 24 h. The reaction mixture was concentrated in vacuo to provide the title compound (0.14 g) which was used without further purification. LCMS (Method 4): 0.76 min, 456.3 [M+H]$^+$ Intermediate 3.18: (S)-2-amino-N-(3-fluoro-4-(3-fluoro-5-methoxypyridin-4-yl)phenyl)-3,3-diphenylpropanamide dihydrochloride A solution of Intermediate 2.18 (0.10 g, 0.19 mmol) in HCl (3 M in CPME; 15 mL) was stirred at rt for 16 h. The reaction mixture was concentrated in vacuo to provide the title compound (95 mg) which was used without further purification. LCMS (Method 4): 0.89 min, 460.2 [M+H]$^+$ Intermediate 3.19: (S)-2-amino-3,3-bis(4-fluorophenyl)-N-(4-(3-methoxypyridin-4-yl)phenyl)propanamide dihydrochloride A solution of Intermediate 2.19 (0.28 g, 0.47 mmol) in HCl (3 M in CPME; 0.94 mL) was stirred at rt for 5 h. The reaction mixture was concentrated in vacuo to provide the title compound (0.24 g). LCMS (Method 2): 0.82 min, 460.2 [M+H]$^+$ Intermediate 3.29: (S)-2-amino-N-(4-(1,2-dimethyl-6-oxo-1,6-dihydropyridin-3-yl)-3,5-difluorophenyl)-3,3-diphenylpropanamide hydrochloride A solution of Intermediate 2.29 (36 mg, 0.06 mmol) in HCl (4 M in 1,4-dioxane; 1.0 mL) was stirred at rt for 18 h. The reaction mixture was concentrated in vacuo to provide the title compound (36 mg). LCMS (Method 4): 0.82 min, 474.2 [M+H]$^+$ Intermediate 3.30: (S)-2-amino-N-(3,5-difluoro-4-(3-methoxypyridin-4-yl)phenyl)-3,3-diphenylpropanamide dihydrochloride A solution of Intermediate 2.30 (0.13 g, 0.23 mmol) in HCl (3 M in CPME; 1.6 mL) was stirred at rt for 4 h. The reaction mixture was concentrated in vacuo to provide the title compound (0.12 g). LCMS (Method 4): 0.90 min, 460.2 [M+H]$^+$ Intermediate 3.31: (S)-2-amino-N-(4-(1-benzyl-3,5-dimethyl-1H-pyrazol-4-yl)phenyl)-3,3-diphenylpropanamide hydrochloride A solution of Intermediate 2.31 (0.14 g, 0.24 mmol) in HCl (3 M in 1,4-dioxane; 4 mL) was stirred at rt for 2 h. The reaction mixture was concentrated in vacuo to provide the title compound (0.13 g). LCMS (Method 4): 1.00 min, 501.3 [M+H]$^+$ Intermediate 3.33: (S)-2-amino-N-(4-(1,2-dimethyl-6-oxo-1,6-dihydropyridin-3-yl)phenyl)-2-((1r,4S)-4-methylcyclohexyl)acetamide hydrochloride A solution of Intermediate 2.33 (73 mg, 0.16 mmol) in HCl (4 M in 1,4-dioxane; 2 mL) was stirred at rt for 2 h. The reaction mixture was concentrated in vacuo to provide the title compound (0.11 g). LCMS (Method 4): 0.76 min, 368.2 [M+H]$^+$ Intermediate 3.34: (S)-2-amino-N-(3-fluoro-4-(6-oxo-1,6-dihydropyridazin-3-yl)phenyl)-3,3-diphenylpropanamide hydrochloride A solution of Intermediate 2.34 (0.19 g, 0.27 mmol) in HCl (4 M in 1,4-dioxane; 2.4 mL) was stirred at rt for 2 h. The reaction mixture was concentrated in vacuo to provide the title compound (0.17 g). LCMS (Method 4): 0.72 min, 429.2 [M+H]$^+$ Intermediate 3.35: (S)-2-amino-N-(3-fluoro-4-(2-oxo-1,2-dihydropyridin-4-yl)phenyl)-3,3-diphenylpropanamide hydrochloride A suspension of Intermediate 2.35 (0.19 mg, 0.35 mmol) in HCl (3 M in in CPME; 15 mL) was stirred at rt for 48 h. The reaction mixture was filtered and the filtrate concentrated in vacuo to provide the title compound (0.15 g). LCMS (Method 12): 1.79 min, 428.18 [M+H]$^+$ Intermediate 3.36: (S)-2-amino-N-(4-(3-fluoropyridin-4-yl)phenyl)-3,3-diphenylpropanamide dihydrochloride A solution of Intermediate 2.36 (0.4 g, 0.79 mmol) in HCl (3 M in CPME; 2.6 mL, 7.8 mmol) and MeOH (3 mL) was stirred at rt for 4 h. The reaction mixture was concentrated in vacuo. The residue was triturated with diethyl ether to provide the title product (0.26 g). LCMS (Method 14): 0.85 min, 412.2 [M+H]$^+$ Intermediate 3.37: (S)-2-amino-N-(4-(2,5-dimethylpyrimidin-4-yl)phenyl)-3,3-diphenylpropanamide dihydrochloride A solution of Intermediate 2.37 (0.26 g, 0.5 mmol) in HCl (3 M in 1,4-dioxane; 4 mL) was stirred at rt for 2 h. The reaction mixture was concentrated in vacuo to provide the title compound (0.23 g). LCMS (Method 8): 0.78 min, 423.3 [M+H]$^+$ Intermediate 3.38: (S)-2-amino-N-(4-(2,5-dimethylpyridin-4-yl)phenyl)-3,3-diphenylpropanamide dihydrochloride A solution of Intermediate 2.38 (46 mg, 0.09 mmol) in HCl (3 M in 1,4-dioxane; 4 mL) was stirred at rt for 2 h. The reaction mixture was concentrated in vacuo to provide the title compound (40 mg). LCMS (Method 9): 0.87 min, 422.6 [M+H]$^+$ Intermediate 3.42: (S)-2-amino-N-(4-(3-(hydroxymethyl)pyridin-4-yl)phenyl)-3,3-diphenylpropanamide dihydrochloride A solution of Intermediate 2.42 (0.34 g, 0.65 mmol) in HCl (3 M in 1,4-dioxane; 5 mL) was stirred at rt for 2 h. The reaction mixture was concentrated in vacuo to provide the title compound (0.28 mg). LCMS (Method 2): 0.70 min, 424.2 [M+H]$^+$ Intermediate 3.43: (S)-2-amino-N-(4-(3-cyanopyridin-4-yl)phenyl)-3,3-diphenylpropanamide dihydrochloride A solution of Intermediate 2.43 (66 mg, 0.13 mmol) in HCl (3 M in 1,4-dioxane; 4 mL) was stirred at rt for 3 h. The reaction mixture was concentrated in vacuo to provide the title compound (58 mg). LCMS (Method 2): 0.81 min, 419.2 [M+H]$^+$ Intermediate 3.47: (S)-2-amino-N-(3-methoxy-4-(3-methoxypyridin-4-yl)phenyl)-3,3-diphenylpropanamide dihydrochloride A solution of Intermediate 2.47 (75 mg, 0.13 mmol) in HCl (3 M in 1,4-dioxane; 4 mL) was stirred at rt for 2 h. The reaction mixture was concentrated in vacuo to provide the title compound (66 mg). LCMS (Method 2): 0.80 min, 454.3 [M+H]$^+$ Intermediate 3.48: (S)-2-amino-N-(3-fluoro-4-(1-methyl-6-oxo-1,6-dihydropyridazin-3-yl)phenyl)-3,3-diphenylpropanamide hydrochloride A suspension of Intermediate 2.48 (0.21 g, 0.39 mmol) in HCl (3 M in CPME; 3.2 mL) stirred at rt for 1 h. HCl (3 M in 1,4-dioxane; 3 mL) was added and the reaction mixture stirred at rt for 19 h. The reaction mixture was concentrated in vacuo to provide the title compound (0.19 g). LCMS (Method 4): 0.79 min, 443.2 [M+H]$^+$ Intermediate 3.49: (S)-2-amino-N-(4-(6-oxo-1,6-dihydropyridin-3-yl)phenyl)-3,3-diphenylpropanamide hydrochloride A solution of Intermediate 2.49 (52 mg, 0.1 mmol) in HCl (3 M in 1,4-dioxane; 4 mL) was stirred at rt for 2 h. The reaction mixture was concentrated in vacuo to provide the title compound (45 mg). LCMS (Method 2): 0.66 min, 410.3 [M+H]$^+$ Intermediate 3.50: (S)-2-amino-N-(4-(4-methyl-6-oxo-1,6-dihydropyridin-3-yl)phenyl)-3,3-diphenylpropanamide hydrochloride A solution of Intermediate 2.50 (35 mg, 0.07 mmol) in HCl (3 M in 1,4-dioxane; 3 mL) was stirred at rt for 2 h. The reaction mixture was concentrated in vacuo to provide the title compound (31 mg). LCMS (Method 2): 0.69 min, 424.3 [M+H]$^+$ Intermediate 3.51: (S)-2-amino-N-(4-(1-methyl-6-oxo-1,6-dihydropyridin-3-yl)phenyl)-3,3-diphenylpropanamide hydrochloride A solution of Intermediate 2.51 (0.46 g, 0.89 mmol) in HCl (3 M in 1,4-dioxane; 10 mL) was stirred at rt for 2 h. The reaction mixture was concentrated in vacuo to provide the title compound (0.41 g). LCMS (Method 2): 0.70 min, 424.3 [M+H]$^+$ Intermediate 3.52: (S)-2-amino-N-(4-(7-oxo-6,7-dihydro-1H-pyrrolo[2,3-c]pyridin-4-yl)phenyl)-3,3-diphenylpropanamide dihydrochloride A suspension of Intermediate 2.52 (0.16 g, 0.29 mmol) in HCl (3 M in CPME; 20 mL) was stirred at rt for 18 h. The reaction mixture was filtered and washed with EtOAc.

The filtrates were concentrated in vacuo to provide the title compound (0.14 g). LCMS (Method 12): 1.78 min, 449.2 [M+H]$^+$ Intermediate 3.53: (S)-2-amino-N-(4-(3-(hydroxymethyl)pyridin-4-yl)-3-methoxyphenyl)-3,3-diphenylpropanamide dihydrochloride A suspension of Intermediate 2.53 (38 mg, 0.07 mmol) in HCl (3 M in CPME; 0.69 mL) was stirred at rt for 2 h. The reaction mixture was concentrated in vacuo to provide the title compound (36 mg, 0.07 mmol). LCMS (Method 2): 0.71 min, 454.2 [M+H]$^+$ Intermediate 3.54: (S)-2-amino-N-(4-(1,2-dimethyl-6-oxo-1,6-dihydropyridin-3-yl)-3-(trifluoromethyl)phenyl)-3,3-diphenylpropanamide hydrochloride A suspension of Intermediate 2.54 (56 mg, 0.09 mmol) in HCl (3 M in CPME; 0.62 mL) was stirred at rt for 2 h. The reaction mixture was concentrated in vacuo to provide the title compound (50 mg). LCMS (Method 4): 0.86 min, 506.2 [M+H]$^+$ Intermediate 3.55: (S)-2-amino-N-(3-chloro-4-(3,5-dimethylpyridin-4-yl)phenyl)-3,3-diphenylpropanamide dihydrochloride A suspension of Intermediate 2.55 (65 mg, 0.120 mmol) in HCl (4 M in 1,4-dioxane; 0.44 mL) and 1,4-dioxane (2 mL) was stirred at rt for 2 h. The reaction mixture was concentrated in vacuo to provide the title compound (69 mg). LCMS (Method 4): 0.94 min, 456.2 $[M+H]^+$ Intermediate 3.56: (S)-2-amino-N-(4-(2,5-dimethylpyridin-4-yl)-3-fluorophenyl)-3,3-diphenylpropanamide dihydrochloride A suspension of Intermediate 2.56 (0.1 g, 0.19 mmol) in HCl (3 M in CPME; 15 mL) was stirred at rt for 16 h. The reaction mixture was filtered and the filtrate concentrated in vacuo to provide the title compound (86 mg). LCMS (Method 12): 2.37 min, 440.2 $[M+H]^+$ Intermediate 3.57: (S)-2-amino-N-(4-(2,3-dimethylpyridin-4-yl)-3-fluorophenyl)-3,3-diphenylpropanamide dihydrochloride A suspension of Intermediate 2.57 (0.12 mg, 0.21 mmol) in HCl (3 M in CPME; 15 mL) was stirred at rt for 24 h. The reaction mixture was filtered and the filtrate concentrated in vacuo to provide the title compound (90 mg). LCMS (Method 4): 0.92 min, 440.2 $[M+H]^+$ Intermediate 3.59: (S)-2-amino-N-(4-(1-benzyl-3-methyl-1H-pyrazol-4-yl)-3-fluorophenyl)-3,3-diphenylpropanamide hydrochloride A solution of Intermediate 2.59 (0.37 g, 0.61 mmol) in HCl (3 M in 1,4-dioxane; 10 mL) was stirred at rt for 1 h. The reaction mixture was concentrated in vacuo to provide the title compound (0.33 mg) as a mixture of regioisomers with (S)-2-amino-N-(4-(1-benzyl-5-methyl-1H-pyrazol-4-yl)-3-fluorophenyl)-3,3-diphenylpropanamide hydrochloride. LCMS (Method 4): 1.01 min, 505.2 $[M+H]^+$ Intermediate 3.59a: (S)—N-(1-((4-(1-benzyl-3-methyl-1H-pyrazol-4-yl)-3-fluorophenyl)amino)-1-oxo-3,3-diphenylpropan-2-yl)-1-ethyl-1H-pyrazole-5-carboxamide To a solution of Intermediate 3.59 (0.11 g, 0.2 mmol), 1-ethyl-1H-pyrazole-5-carboxylic acid (28 mg, 0.2 mmol, CAS: 400755-43-3) and triethylamine (0.08 mL, 0.61 mmol) in EtOAc (8 mL) was added HATU (92 mg, 0.24 mmol) and the reaction stirred at rt for 16 h. The mixture was diluted with saturated aqueous $NaHCO_3$ and extracted into EtAOc. The combined organics were washed with water, dried over $MgSO_4$, filtered and concentrated in vacuo. The crude product was purified flash column chromatography on the Biotage Isolera One™ (30 g ZIP sphere silica column, eluting 40-100% EtOAc in heptanes) to provide the title compound (29 mg) as a mixture of regioisomers with (S)—N-(1-((4-(1-benzyl-5-methyl-1H-pyrazol-4-yl)-3-fluorophenyl)amino)-1-oxo-3,3-diphenylpropan-2-yl)-1-ethyl-1H-pyrazole-5-carboxamide. LCMS (Method 4): 1.04 min, 627.3 $[M+H]^+$ Intermediate 3.60: (S)-2-amino-N-(4-(3,5-dimethylisoxazol-4-yl)-3-fluorophenyl)-3,3-diphenylpropanamide hydrochloride A suspension of Intermediate 2.60 (0.22 g, 0.42 mmol) in HCl (4 M in 1,4-dioxane; 3.1 mL) was stirred at rt for 3 h. The reaction mixture was concentrated in vacuo to provide the title compound (0.21 g). LCMS (Method 4): 0.92 min, 430.2 $[M+H]^+$ Intermediate 3.62: (S)-2-amino-N-(4-(1-benzyl-1H-pyrazol-4-yl)-3-fluorophenyl)-3,3-diphenylpropanamide hydrochloride A solution of Intermediate 2.62 (0.12 g, 0.18 mmol) in HCl (4 M in 1,4-dioxane; 0.46 mL) was stirred at rt for 3 h. The reaction mixture was concentrated in vacuo to provide the title compound (0.11 g). LCMS (Method 4): 0.99 min, 491.2 $[M+H]^+$ Intermediate 3.62a: (S)—N-(1-((4-(1-benzyl-1H-pyrazol-4-yl)-3-fluorophenyl)amino)-1-oxo-3,3-diphenylpropan-2-yl)-1-methyl-1H-pyrazole-5-carboxamide The title compound (90 mg) was prepared from Intermediate 3.62 (0.11 mg, 0.19 mmol), 2-methylpyrazole-3-carboxylic acid (23 mg, 0.19 mmol, CAS: 16034-46-1), HATU (74 mg, 0.2 mmol) and triethylamine (0.08 mL, 0.56 mmol) in accordance with the procedure described for Intermediate 3.59a. The crude product was purified by reverse phase column chromatography on the Biotage Isolera One™ (25 g ZIP Sphere column, eluting 50-100% EtOAc in heptanes). LCMS (Method 12): 2.61 min, 599.3 $[M+H]^+$ Intermediate 3.63: (S)-2-amino-N-(3-fluoro-4-(1-methyl-2-oxo-1,2-dihydropyrimidin-5-yl)phenyl)-3,3-diphenylpropanamide hydrochloride A solution of Intermediate 2.63 (62 mg, 0.110 mmol) in HCl (4 M in 1,4-dioxane; 1.25 mL) and 1,4-dioxane (1 mL) was stirred at rt for 2 h. The reaction mixture was concentrated in vacuo to provide the title compound (55 mg). LCMS (Method 12): 1.72 min, 443.2 $[M+H]^+$ Intermediate 3.64: (S)-2-amino-N-(3-fluoro-4-(2-oxo-1,2-dihydropyrimidin-5-yl)phenyl)-3,3-diphenylpropanamide hydrochloride A solution of Intermediate 2.64 (0.13 g, 0.25 mmol) in HCl (4 M in 1,4-dioxane; 6 mL) and 1,4-dioxane (2 mL) was stirred at rt for 2 h. The reaction mixture was concentrated in vacuo to provide the title compound (0.13 g). LCMS (Method 12): 1.07 min, 429.2 $[M+H]^+$ Intermediate 3.65a: (S)—N-(1-((4-(1-benzyl-3-methyl-1H-pyrazol-4-yl)-3-fluorophenyl)amino)-1-oxo-3,3-diphenylpropan-2-yl)-1-methyl-1H-pyrazole-5-carboxamide The title compound (0.19 g) was prepared as a mixture of regioisomers with (S)—N-(1-((4-(1-benzyl-5-methyl-1H-pyrazol-4-yl)-3-fluorophenyl)amino)-1-oxo-3,3-diphenylpropan-2-yl)-1-methyl-1H-pyrazole-5-carboxamide from Intermediate 3.59 (218.7 mg, 0.400 mmol), 2-methylpyrazole-3-carboxylic acid (50.97 mg, 0.400 mmol, CAS: 16034-46-1), HATU (184.43 mg, 0.490 mmol) and triethylamine (0.17 mL, 1.21 mmol) in accordance with the procedure described for Intermediate 3.59a. The crude product was purified by flash column chromatography on the Biotage Isolera One™ (30 g ZIP sphere silica column, eluting 40-100% EtOAc in heptanes). LCMS (Method 12): 2.64 min, 613.3 [M+H]$^+$, 2.65 min, 613.3 [M+H]$^+$ Intermediate 3.66: (S)-2-amino-N-(3-fluoro-4-(5-oxo-5,6-dihydro-1,6-naphthyridin-8-yl)phenyl)-3,3-diphenylpropanamide dihydrochloride A solution of Intermediate 2.66 (88 mg, 0.14 mmol) in HCl (4 M in 1,4-dioxane; 1 mL) was stirred at rt for 2 h. The reaction mixture was concentrated in vacuo to provide the title compound (77 mg). LCMS (Method 4): 0.75 min, 479.1 [M+H]$^+$ Intermediate 3.67: (S)-2-amino-N-(3-fluoro-4-(6-oxo-1,6-dihydropyridazin-4-yl)phenyl)-3,3-diphenylpropanamide hydrochloride A solution of Intermediate 2.67 (0.23 g, 0.43 mmol) in HCl (4 M in 1,4-dioxane; 3.3 mL) was stirred at rt for 5 h. The reaction mixture was concentrated in vacuo to provide the title compound (0.25 g). LCMS (Method 4): 0.69 min, 429.2 [M+H]$^+$ Intermediate 3.68: (S)-2-amino-N-(3-fluoro-4-(7-methoxy-1H-pyrrolo[2,3-c]pyridin-4-yl)phenyl)-3,3-diphenylpropanamide dihydrochloride A solution of Intermediate 2.68 (430 mg, 0.74 mmol) in HCl (3 M in CPME; 10 mL) was stirred at rt for 18 h. The reaction mixture was concentrated in vacuo to provide the title compound 420 mg). LCMS (Method 4): 0.89 min, 481.19 [M+H]$^+$ Intermediate 3.68a: (S)—N-(1-((3-fluoro-4-(7-methoxy-1H-pyrrolo[2,3-c]pyridin-4-yl)phenyl)amino)-1-oxo-3,3-diphenylpropan-2-yl)-1-methyl-1H-pyrazole-5-carboxamide The title compound (338 mg) was prepared from Intermediate 3.68 (370 mg, 0.67 mmol), 2-methylpyrazole-3-carboxylic acid (93 mg, 0.74 mmol, CAS: 16034-46-1), HATU (280 mg, 0.74 mmol) and triethylamine (0.28 mL, 2 mmol) in accordance with the procedure described for Intermediate 3.59a. The crude product was purified by flash column chromatography (eluting 3% MeOH in DCM) LCMS (Method 3): 2.32 min, 589.3 [M+H]$^+$ Intermediate 3.69: (S)-2-amino-N-(3-fluoro-4-(4-oxo-4,5-dihydro-3H-imidazo[4,5-c]pyridin-7-yl)phenyl)-3,3-diphenylpropanamide dihydrochloride A solution of Intermediate 2.69 (0.14 g, 0.25 mmol) in HCl (4 M in 1,4-dioxane; 1.9 mL) was stirred at rt for 3 h. The reaction mixture was concentrated in vacuo to provide the title compound (0.142 g). LCMS (Method 13): 1.00 min, 468.1 [M+H]$^+$ Intermediate 3.71: (S)-2-amino-N-(3-fluoro-4-(1-methyl-6-oxo-1,6-dihydropyridin-2-yl)phenyl)-3,3-diphenylpropanamide hydrochloride A solution of Intermediate 2.71 (0.14 g, 0.17 mmol) in HCl (3 M in 1,4-dioxane; 6 mL) was stirred at rt for 1.5 h. The reaction mixture was concentrated in vacuo to provide the title compound (82 mg). LCMS (Method 4): 0.78 min, 442.2 [M+H]$^+$ Intermediate 3.72: (S)-2-amino-N-(1',2'-dimethyl-6'-oxo-1',6'-dihydro-[3,3'-bipyridin]-6-yl)-3,3-diphenylpropanamide dihydrochloride A solution of Intermediate 2.72 (20 mg, 0.03 mmol) in HCl (3 M in 1,4-dioxane; 3 mL) was stirred at rt for 1.5 h. The reaction mixture was concentrated in vacuo to provide the title compound (15 mg). LCMS (Method 4): 0.74 min, 439.2 [M+H]$^+$ Intermediate 3.73: (S)-2-amino-N-(3',5'-dimethyl-[3,4'-bipyridin]-6-yl)-3,3-diphenylpropanamide dihydrochloride A solution of Intermediate 2.73 (0.19 g, 0.36 mmol) in HCl (3 M in 1,4-dioxane; 8 mL) was stirred at rt for 1.5 h. The reaction mixture was concentrated in vacuo to provide the title compound (27 mg). LCMS (Method 4): 0.85 min, 423.2 [M+H]$^+$ Intermediate 3.74: (S)-2-amino-N-(4-(1-benzyl-5-methyl-1H-pyrazol-4-yl)phenyl)-3,3-diphenylpropanamide hydrochloride A solution of Intermediate 2.74 (0.67 g, 1.1 mmol) in HCl (3 M in 1,4-dioxane; 15 mL) was stirred at rt for 1.5 h. The reaction mixture was concentrated in vacuo to provide the title compound (0.56 g). LCMS (Method 4): 0.95 min, 487.3 [M+H]$^+$ Intermediate 3.74a: (S)—N-(1-((4-(1-benzyl-5-methyl-1H-pyrazol-4-yl)phenyl)amino)-1-oxo-3,3-diphenylpropan-2-yl)-1-methyl-1H-pyrazole-5-carboxamide The title compound (0.6 g) was prepared from Intermediate 3.74 (0.56 g, 1.1 mmol) 2-methylpyrazole-3-carboxylic acid (0.13 g, 1.1 mmol, CAS: 16034-46-1), HATU (0.4 g, 1.1 mmol) and triethylamine (0.15 mL, 1.1 mmol) in accordance with the procedure described for Intermediate 3.59a. The crude product was purified by flash column chromatography on the Biotage Isolera One™ (25 g SiliCycle silica column, eluting 30-100% EtOAc in heptanes). LCMS (Method 4): 0.96 min, 595.3 [M+H]$^+$ Intermediate 3.75: (S)-2-amino-N-(3-fluoro-4-(6-methyl-7-oxo-6,7-dihydro-1H-pyrazolo[3,4-c]pyridin-4-yl)phenyl)-3,3-diphenylpropanamide dihydrochloride A solution of Intermediate 2.75 (83 mg, 0.14 mmol) in HCl (4 M in 1,4-dioxane; 1.1 mL) was stirred at rt for 2 h. The reaction mixture was concentrated in vacuo to provide the title compound (79 mg). LCMS (Method 4): 0.76 min, 482.2 [M+H]$^+$ Intermediate 3.76: (S)-2-amino-N-(4-(7-methoxy-1H-pyrrolo[2,3-c]pyridin-4-yl)phenyl)-3,3-diphenylpropanamide dihydrochloride A solution of Intermediate 2.76 (0.2 g, 0.33 mmol) in HCl (3 M in CPME; 0.9 mL) was stirred at rt for 2 h. The reaction mixture was concentrated in vacuo to provide the title compound (0.15 g). LCMS (Method 4): 0.86 min, 463.2 [M+H]$^+$ Intermediate 3.77: (S)-2-amino-N-(4-(1-benzyl-6-oxo-1,6-dihydropyridin-2-yl)-3-fluorophenyl)-3,3-diphenylpropanamide hydrochloride A solution of Intermediate 2.77 (86 mg, 0.12 mmol) in HCl (3 M in 1,4-dioxane; 4 mL) was stirred at rt for 1 h. The reaction mixture was concentrated in vacuo to provide the title compound (66 mg). LCMS (Method 20): 0.82 min, 518.2 $[M+H]^+$ Intermediate 3.77a: (S)—N-(1-((4-(1-benzyl-6-oxo-1,6-dihydropyridin-2-yl)-3-fluorophenyl)amino)-1-oxo-3,3-diphenylpropan-2-yl)-1-methyl-1H-pyrazole-5-carboxamide The title compound (87 mg) was prepared from Intermediate 3.77 (66 mg, 0.12 mmol) 2-methylpyrazole-3-carboxylic acid (5 mg, 0.12 mmol, CAS: 16034-46-1), HATU (54 mg, 0.14 mmol) and triethylamine (0.04 mL, 0.3 mmol) in accordance with the procedure described for Intermediate 3.59a. The crude product was purified by flash column chromatography on the Biotage Isolera One™ (5 g ZIP sphere silica column, eluting 40-100% EtOAc in heptanes). LCMS (Method 4): 1.16 min, 626.3 $[M+H]^+$ Intermediate 3.78: (S)-2-amino-N-(4-(3-(2-oxo-2-(pyrrolidin-1-yl)ethyl)pyridin-4-yl)phenyl)-3,3-diphenylpropanamide dihydrochloride A solution of Intermediate 2.77 (61 mg, 0.1 mmol) in HCl (4 M in 1,4-dioxane; 5 mL) was stirred at rt for 18 h. The reaction mixture was concentrated in vacuo to provide the title compound (58 mg). LCMS (Method 4): 0.76 min, 505.2 $[M+H]^+$ Intermediate 3.80: (S)-2-amino-N-(3-fluoro-4-(6-oxo-1,6-dihydropyrimidin-4-yl)phenyl)-3,3-diphenylpropanamide hydrochloride A solution of Intermediate 2.80 (75 mg, 0.14 mmol) in HCl (4 M in 1,4-dioxane; 0.14 mL) and 1,4-dioxane (1 mL) was stirred at rt for 3 h. The reaction mixture was concentrated in vacuo to provide the title compound. LCMS (Method 12) 1.05 min, 429 $[M+H]^+$ Intermediate 3.81: (S)-2-amino-N-(4-(3,6-dihydro-2H-pyran-4-yl)phenyl)-3,3-diphenylpropanamide hydrochloride A suspension of Intermediate 2.81 (0.23 g, 0.46 mmol) in HCl (4 M in 1,4-dioxane; 1.2 mL) was stirred at rt for 35 min. The reaction mixture was concentrated in vacuo and co-evaporated with MeCN to provide the title compound (0.22 g). LCMS (Method 4): 0.88 min, 399.0 $[M+H]^+$ Intermediate 3.83: (S)-2-amino-N-(4-(1,2-dimethyl-6-oxo-1,6-dihydropyridin-3-yl)-3-fluorophenyl)-2-((1r,4S)-4-methylcyclohexyl)acetamide hydrochloride A solution of Intermediate 2.83 (60 mg, 0.12 mmol) in HCl (4 M in 1,4-dioxane; 3 mL) and 1,4-dioxane (2 mL) was stirred at rt for 2 h. The reaction mixture was concentrated in vacuo to provide the title compound (70 mg). LCMS (Method 3): 0.86 min, 384.2 $[M-H]^-$ Intermediate 3.84: (S)-2-amino-N-(4-(1-(4-methoxybenzyl)-3,5-dimethyl-1H-pyrazol-4-yl)phenyl)-2-((1r,4S)-4-methylcyclohexyl)acetamide A solution of Intermediate 2.84 (0.69 g, 1.2 mmol) in HCl (4 M in 1,4-dioxane; 3.1 mL) and 1,4-dioxane (2 mL) was stirred at rt for 16 h. The reaction mixture was concentrated in vacuo and the crude product purified by flash column chromatography on the Biotage Isolera™ (20 g silica column, eluting 30-100% EtOAc in heptanes) to provide the title compound (0.4 g). LCMS (Method 14): 1.57 min, 461.2 $[M+H]^+$ Intermediate 3.84a: (S)—N-(2-((4-(1-(4-methoxybenzyl)-3,5-dimethyl-1H-pyrazol-4-yl)phenyl)amino)-1-(4-methylcyclohexyl)-2-oxoethyl)-1-methyl-1H-pyrazole-5-carboxamide The title compound (0.4 g) was prepared from Intermediate 3.84 (0.37 mg, 0.8 mmol) 2-methylpyrazole-3-carboxylic acid (0.1 g, 0.8 mmol, CAS: 16034-46-1), HATU (0.37 g, 0.96 mmol) and triethylamine (0.34 mL, 2.4 mmol) in accordance with the procedure described for Intermediate 3.59a. The crude product was purified by flash column chromatography on the Biotage Isolera One™ (120 g silica column, eluting 30-100% EtOAc in heptanes). $^1H$ NMR (400 MHz, MeOD) δ: 7.67-7.60 (m, 2H), 7.47 (d, 1H), 7.22 (s, 2H), 7.12-7.04 (m, 2H), 6.92-6.84 (m, 3H), 5.22 (s, 2H), 4.44 (d, 1H), 4.08 (s, 3H), 3.77 (s, 3H), 2.21 (s, 3H), 2.18 (s, 3H), 1.94 (d, 1H), 1.88-1.84 (m, 1H), 1.77 (d, 3H), 1.35-1.27 (m, 2H), 1.17 (d, 1H), 0.98 (q, 2H), 0.90 (d, 3H).

Intermediate 3.85: (S)-2-amino-2-((1r,4S)-4-methylcyclohexyl)-N-(4-(7-oxo-6,7-dihydro-1H-pyrrolo[2,3-c]pyridin-4-yl)phenyl)acetamide hydrochloride A solution of Intermediate 2.85 (0.12 g, 0.25 mmol) in HCl (3 M in 1,4-dioxane; 15 mL) was stirred at rt for 18 h. The reaction mixture was concentrated in vacuo to provide the title compound (0.11 g). LCMS (Method 4): 0.73 min, 379.3 $[M+H]^+$ Intermediate 3.86: (S)-2-amino-2-((1r,4S)-4-methylcyclohexyl)-N-(4-(3-(2-oxo-2-(pyrrolidin-1-yl)ethyl)pyridin-4-yl)phenyl)acetamide dihydrochloride A solution of Intermediate 2.86 (98 mg, 0.18 mmol) in HCl (4 M in 1,4-dioxane; 1.4 mL) was stirred at rt for 3 h. The reaction mixture was concentrated in vacuo to provide the title compound (95 mg). LCMS (Method 4): 0.77 min, 435.3 $[M+H]^+$ Intermediate 3.87: (S)-2-amino-2-((1r,4S)-4-methylcyclohexyl)-N-(4-(2-oxo-1,2-dihydropyridin-4-yl)phenyl)acetamide hydrochloride A solution of Intermediate 2.87 (49 mg, 0.11 mmol) in HCl (3 M in 1,4-dioxane; 10 mL) was stirred at rt for 18 h. The reaction mixture was concentrated in vacuo to provide the title compound (40 mg). LCMS (Method 4): 0.68 min, 340.2 $[M+H]^+$ Intermediate 3.88: (S)-2-amino-N-(4-(imidazo[1,2-a]pyridin-5-yl)phenyl)-2-((1r,4S)-4-methylcyclohexyl)acetamide dihydrochloride A solution of Intermediate 2.88 (32 mg, 0.07 mmol) in HCl (3 M in 1,4-dioxane; 2 mL) was stirred at rt for 1.5 h.

The reaction mixture was concentrated in vacuo to provide the title compound (28 mg). LCMS (Method 4): 0.84 min, 363.2 [M+H]$^+$ Intermediate 3.89: (S)-2-amino-N-(1',2'-dimethyl-6'-oxo-1',6'-dihydro-[3,3'-bipyridin]-6-yl)-2-((1r,4S)-4-methylcyclohexyl)acetamide dihydrochloride A solution of Intermediate 2.89 (18 mg, 0.04 mmol) in HCl (3 M in 1,4-dioxane; 3 mL) was stirred at rt for 1.5 h. The reaction mixture was concentrated in vacuo to provide the title compound (16 mg). LCMS (Method 4): 0.75 min, 369.2 [M+H]$^+$ Intermediate 3.90: (S)-2-amino-N-(3',5'-dimethyl-[3,4'-bipyridin]-6-yl)-2-((1r,4S)-4-methylcyclohexyl)acetamide dihydrochloride A solution of Intermediate 2.90 (60 mg, 0.13 mmol) in HCl (3 M in 1,4-dioxane; 3 mL) and 1,4-dioxane (1 mL) was stirred at rt for 1 h. The reaction mixture was concentrated in vacuo to provide the title compound (57 mg). LCMS (Method 4): 0.90 min, 353.2 [M+H]$^+$ Intermediate 3.93: (S)-2-amino-2-((1r,4S)-4-methylcyclohexyl)-N-(4-(tetrahydro-2H-pyran-4-yl)phenyl)acetamide hydrochloride A solution of Intermediate 2.93 (0.13 g, 0.3 mmol) in HCl (4 M in 1,4-dioxane; 0.8 mL) and 1,4-dioxane (2 mL) was stirred at rt for 3 h. The reaction mixture was concentrated in vacuo and the residue triturated with diethyl ether (5 mL) to provide the title compound (75 mg). LCMS (Method 12) 2.20 min, 331 [M+H]$^+$ Intermediate 3.94: (S)-2-amino-N-(4-(4-hydroxytetrahydro-2H-pyran-4-yl)phenyl)-2-((1r,4S)-4-methylcyclohexyl)acetamide A suspension of Intermediate 2.94 (0.1 g, 0.22 mmol) in HCl (4 M in 1,4-dioxane; 0.56 mL) was stirred at rt for 35 min. The reaction mixture was diluted with water and purified by reverse phase column chromatography on the Biotage Isolera One™ (30 g 018 column, eluting 5-100% 0.1% ammonia MeCN in 0.1% ammonia/water) to provide the title compound (54 mg). LCMS (Method 4): 0.70 min, 347.2 [M+H]$^+$ Intermediate 3.95: (S)-2-amino-N-(4-(3,6-dihydro-2H-pyran-4-yl)phenyl)-2-((1r,4S)-4-methylcyclohexyl)acetamide A suspension of Intermediate 2.95 (0.23 g, 0.54 mmol) in HCl (4 M in 1,4-dioxane; 1.5 mL) was stirred at rt for 1 h. The reaction mixture was diluted with water and purified by reverse phase column chromatography on the Biotage Isolera One™ (30 g 018 column, eluting 5-100% 0.1% ammonia MeCN in 0.1% ammonia/water) to provide the title compound (0.11 g). LCMS (Method 4): 0.91 min, 329.0 [M+H]$^+$ Intermediate 3.96: (S)-2-amino-N-(4-(3,5-dimethylisoxazol-4-yl)phenyl)-2-((1r,4S)-4-methylcyclohexyl)acetamide hydrochloride A solution of Intermediate 2.96 (81 mg, 0.18 mmol) in HCl (4 M in 1,4-dioxane; 2 mL) was stirred at rt for 2 h. The reaction mixture was concentrated in vacuo to provide the title compound (70 mg). LCMS (Method 14): 1.44 min, 342.2 [M+H]$^+$ Intermediate 3.97: (S)-2-amino-N-(5-(3,5-dimethylisoxazol-4-yl)pyridin-2-yl)-2-((1r,4S)-4-methylcyclohexyl)acetamide A solution of Intermediate 2.97 (0.28 g, 0.62 mmol) in HCl (4 M in 1,4-dioxane; 5 mL) was stirred at rt for 1 h. The reaction mixture was concentrated in vacuo, the residue dissolved in MeOH (6 mL) and passed through an SCX cartridge (5 g, washed with MeOH and eluted with 2 M methanolic ammonia). The solvent was removed in vacuo to provide the title compound (0.19 mg). LCMS (Method 14): 1.40 min, 343.2 [M+H]$^+$ Intermediate 3.99: (S)-2-amino-N-(5-(1-(4-methoxybenzyl)-3,5-dimethyl-1H-pyrazol-4-yl)pyridin-2-yl)-2-((1r,4S)-4-methylcyclohexyl)acetamide dihydrochloride A solution of Intermediate 2.99 (37 mg, 0.07 mmol) in HCl (4 M in 1,4-dioxane; 0.17 mL) and 1,4-dioxane (1 mL) was stirred at rt for 2 h. The reaction mixture was concentrated in vacuo to provide the title compound (33 mg). $^1H$ NMR (400 MHz, DMSO-$d_6$) δ: 11.03 (s, 1H), 8.36-8.24 (m, 4H), 8.12 (d, 1H), 7.78 (dd, 1H), 7.20-7.14 (m, 2H), 6.95-6.88 (m, 2H), 5.21 (s, 2H), 3.95-3.86 (m, 1H), 3.73 (s, 3H), 2.22 (s, 3H), 2.17 (s, 3H), 1.84-1.61 (m, 5H), 1.30-1.04 (m, 3H), 0.94-0.83 (m, 5H).

Intermediate 3.99a: N—((S)-2-((5-(1-(4-methoxybenzyl)-3,5-dimethyl-1H-pyrazol-4-yl)pyridin-2-yl)amino)-1-((1r,4S)-4-methylcyclohexyl)-2-oxoethyl)-1-methyl-1H-pyrazole-5-carboxamide The title compound (24 mg) was prepared from Intermediate 3.99 (33 mg, 0.07 mmol) 2-methylpyrazole-3-carboxylic acid (9.2 mg, 0.07 mmol, CAS: 16034-46-1), HATU (28 mg, 0.07 mmol) and triethylamine (0.03 mL, 0.2 mmol) in accordance with the procedure described for Intermediate 3.59a. The crude product was purified by flash column chromatography (eluting 30-100% EtOAc in heptanes). LCMS (Method B): 2.78 min, 570.2 [M+H]$^+$ Intermediate 3.106: (S)-2-amino-N-(5-(1,4-dimethyl-1H-pyrazol-5-yl)pyridin-2-yl)-2-((1r,4S)-4-methylcyclohexyl)acetamide dihydrochloride A solution of Intermediate 2.106 (28 mg, 0.06 mmol) in HCl (4 M in 1,4-dioxane; 0.75 mL) was stirred at rt for 45 min. The reaction mixture was concentrated in vacuo to provide the title compound (24 mg). LCMS (Method 14): 1.38 min, 342.3 [M+H]$^+$ Intermediate 3.108: (S)-2-amino-2-cyclohexyl-N-(5-(3,5-dimethylisoxazol-4-yl)pyridin-2-yl)acetamide A solution of Intermediate 2.108 (0.6 g, 1.4 mmol) in HCl (4 M in 1,4-dioxane; 6 mL) was stirred at rt for 1.5 h. The reaction mixture was concentrated in vacuo, the residue dissolved in MeOH (6 mL) and passed through an SCX cartridge (5 g, washed with MeOH and eluted with 2 M methanolic ammonia). The solvent was removed in vacuo to provide the title compound (0.45 mg). LCMS (Method 14): 1.36 min, 329.2 [M+H]$^+$ Intermediate 3.115: (S)-2-amino-2-cycloheptyl-N-(5-(3,5-dimethylisoxazol-4-yl)pyridin-2-yl)acetamide A solution of Intermediate 2.115 (0.2 g, 0.38 mmol) in HCl (4 M in 1,4-dioxane; 4 mL) was stirred at rt for 1 h. The reaction mixture was concentrated in vacuo and the residue suspended in EtOAc and washed with saturated aqueous $NaHCO_3$. The aqueous layer was extracted twice with EtOAc and the combined organics dried over $Na_2SO_4$, filtered and concentrated in vacuo to provide the title compound (0.15 g). LCMS (Method 14): 1.35 min, 343.2 $[M+H]^+$ Intermediate 3.119: (S)-2-amino-2-cyclohexyl-N-(4-(1,2-dimethyl-6-oxo-1,6-dihydropyridin-3-yl)phenyl)acetamide hydrochloride A suspension of Intermediate 2.119 (0.26 g, 0.57 mmol) in HCl (4 M in 1,4-dioxane; 0.14 mL) was stirred at rt for 4 h. The reaction mixture was concentrated in vacuo to provide the title compound (0.28 g). LCMS (Method 14): 1.27 min, 354.2 $[M+H]^+$ Intermediate 3.125: (S)-2-amino-N-(5-(1,4-dimethyl-1H-1,2,3-triazol-5-yl)pyridin-2-yl)-2-((1r,4S)-4-methylcyclohexyl)acetamide dihydrochloride A solution of Intermediate 2.125 (35 mg, 0.08 mmol) in HCl (4 M in 1,4-dioxane; 1 mL) was stirred at rt for 1 h. The reaction mixture was concentrated in vacuo to provide the title compound (32 mg). LCMS (Method 14): 1.32 min, 343.3 $[M+H]^+$ Intermediate 3.130a: tert-butyl (S)-6-((1-cyclohexyl-2-((5-(3,5-dimethylisoxazol-4-yl)pyridin-2-yl)amino)-2-oxoethyl)carbamoyl)-3,4-dihydropyrrolo[1,2-a]pyrazine-2(1H)-carboxylate To 2-tert-butoxycarbonyl-3,4-dihydro-1H-pyrrolo[1,2-a]pyrazine-6-carboxylic acid (61 mg, 0.23 mmol, CAS: 1363380-86-2) in anhydrous DCM (1.5 mL) was added HATU (88 mg, 0.23 mmol) and DIPEA (0.1 mL, 0.58 mmol). The mixture was stirred for 5 min at rt before the addition of Intermediate 3.108 (70 mg, 0.19 mmol). The reaction was stirred for a further 20 h at rt under an argon atmosphere before diluting with DCM and washing with saturated aqueous $NaHCO_3$. The organics were washed with brine, passed through a hydrophobic fritted tube and concentrated in vacuo. The crude product was purified by flash column chromatography (12 g silica, eluting 0-80% EtOAc in heptanes) to afford the title compound (41 mg). LCMS (Method 14): 2.71 min, 577.4 $[M+H]^+$ Intermediate 3.132: (S)-2-amino-2-cycloheptyl-N-(5-(1,4-dimethyl-1H-pyrazol-5-yl)pyridin-2-yl)acetamide A suspension of Intermediate 2.132 (0.36 g, 0.81 mmol) in HCl (4 M in 1,4-dioxane; 7 mL) was stirred at rt for 1 h. The reaction was diluted with saturated aqueous $NaHCO_3$ and EtOAc and the phases separated. The aqueous phase was extracted with EtOAc and the combined organics were dried over $Na_2SO_4$, filtered and concentrated in vacuo to afford the title compound (0.3 g). LCMS (Method 14): 1.35 min, 342.2 $[M+H]^+$ Intermediate 3.135: (S)-2-amino-N-(2-(3,5-dimethylisoxazol-4-yl)pyrimidin-5-yl)-2-((1r,4S)-4-methylcyclohexyl)acetamide A solution of Intermediate 2.135 (0.24 g, 0.54 mmol) in HCl (4 M in 1,4-dioxane; 2 mL) was stirred at rt for 2 h. The reaction mixture was concentrated in vacuo, the residue dissolved in MeOH and passed through an SCX cartridge (washed with MeOH and eluted with 2 M methanolic ammonia). The solvent was removed in vacuo to provide the title compound (97 mg). LCMS (Method 14): 1.42 min, 344.2 $[M+H]^+$ Intermediate 3.138: (S)-2-amino-N-(6-(3,5-dimethylisoxazol-4-yl)pyridin-3-yl)-2-((1r,4S)-4-methylcyclohexyl)acetamide A solution of Intermediate 2.138 (0.13 g, 0.29 mmol) in HCl (4 M in 1,4-dioxane; 2 mL) was stirred at rt for 2 h. The reaction mixture was concentrated in vacuo, the residue dissolved in MeOH and passed through an SCX cartridge (washed with MeOH and eluted with 2 M methanolic ammonia). The solvent was removed in vacuo to provide the title compound (93 mg). LCMS (Method 14): 1.43 min, 343.2 $[M+H]^+$ Intermediate 3.140: (S)-2-amino-2-((1r,4S)-4-methylcyclohexyl)-N-(5-(5-methylpyrimidin-4-yl)pyridin-2-yl)acetamide A solution of Intermediate 2.140 (0.13 g, 0.3 mmol) in HCl (4 M in 1,4-dioxane; 0.08 mL) was stirred at rt for 1.5 h. The reaction mixture was concentrated in vacuo, the residue dissolved in MeOH and passed through an SCX cartridge (washed with MeOH and eluted with 2 M methanolic ammonia). The solvent was removed in vacuo to provide the title compound (93 mg). LCMS (Method 14): 1.32 min, 340.2 $[M+H]^+$ Intermediate 3.142: (S)-2-amino-N-(5-(3-(methoxymethyl)-5-methylisoxazol-4-yl)pyridin-2-yl)-2-((1r,4S)-4-methylcyclohexyl)acetamide A solution of Intermediate 2.142 (0.12 g, 0.25 mmol) in HCl (4 M in 1,4-dioxane; 0.08 mL) was stirred at rt for 1 h. The reaction mixture was concentrated in vacuo, and the residue diluted with saturated aqueous $NaHCO_3$ extracted into ethyl acetate. The aqueous phase was extracted with EtOAc and combined organics were washed with brine, dried over $Na_2SO_4$, filtered and concentrated in vacuo to provide the title compound (82 mg). LCMS (Method 14): 1.37 min, 373.2 $[M+H]^+$ Intermediate 3.143: (S)-2-amino-2-cycloheptyl-N-(5-(3,5-dimethyl-4H-1,2,4-triazol-4-yl)pyridin-2-yl)acetamide dihydrochloride A solution of Intermediate 2.143 (34 mg, 0.08 mmol) in HCl (4 M in 1,4-dioxane; 0.19 mL) was stirred at rt for 18 h. The reaction mixture was concentrated in vacuo, and the crude product was purified by flash column chromatography (eluting 2-100% MeOH in DCM) to provide the title compound (23 mg). $^1H$ NMR (400 MHz, MeOD) δ: 8.60 (s, 1H), 8.49 (d, 1H), 8.18-8.04 (m, 1H), 4.13-4.07 (m, 1H), 2.52 (d, 6H), 2.25 (s, 1H), 1.94-1.39 (m, 12H).

Intermediate 3.144: (S)-2-amino-2-(4,4-difluorocyclohexyl)-N-(5-(1,4-dimethyl-1H-pyrazol-5-yl)pyridin-2-yl)acetamide A solution of Intermediate 2.144 (0.29 g, 0.6 mmol) in HCl (4 M in 1,4-dioxane; 1.6 mL) and 1,4-dioxane (5 mL) was stirred at rt for 18 h. The reaction mixture was concentrated in vacuo, the residue dissolved in MeOH and passed through an SCX cartridge (washed with MeOH and eluted with 2 M methanolic ammonia). The solvent was removed in vacuo to provide the title compound (0.19 g). LCMS (Method 19): 1.63 min, 364.2 $[M+H]^+$ Intermediate 3.145: (S)-2-amino-N-(6-(1,4-dimethyl-1H-pyrazol-5-yl)pyridin-3-yl)-2-((1r,4S)-4-methylcyclohexyl)acetamide A solution of Intermediate 2.145 (0.34 g, 0.77 mmol) in HCl (4 M in 1,4-dioxane; 2 mL) was stirred at rt for 2 h. The reaction mixture was concentrated in vacuo, the residue dissolved in MeOH and passed through an SCX cartridge (washed with MeOH and eluted with 2 M methanolic ammonia). The solvent was removed in vacuo to provide the title compound (239 mg). LCMS (Method 19): 1.68 min, 342.2 $[M+H]^+$ Intermediate 3.146: (S)-2-amino-N-(4-methyl-5-(1-methyl-1H-pyrazol-5-yl)pyridin-2-yl)-2-((1r,4S)-4-methylcyclohexyl)acetamide A solution of Intermediate 2.146 (0.23 g, 0.51 mmol) in HCl (4 M in 1,4-dioxane; 1.3 mL) and 1,4-dioxane (10 mL) was stirred at rt for 19 h. The reaction mixture was concentrated in vacuo, the residue dissolved in MeOH and passed through an SCX cartridge (0.5 g, washed with MeOH and eluted with 2 M methanolic ammonia). The solvent was removed in vacuo to provide the title compound (0.12 g). LCMS (Method 14): 1.29 min, 342.2 $[M+H]^+$ Intermediate 3.147: (S)-2-amino-N-(2-(1,4-dimethyl-1H-pyrazol-5-yl)pyrimidin-5-yl)-2-((1r,4S)-4-methylcyclohexyl)acetamide A solution of Intermediate 2.147 (0.5 g, 0.89 mmol) in HCl (4 M in 1,4-dioxane; 2 mL) was stirred at rt for 3 h. The reaction mixture was concentrated in vacuo, the residue dissolved in MeOH and passed through an SCX cartridge (washed with MeOH and eluted with 2 M methanolic ammonia). The solvent was removed in vacuo to provide the title compound (0.27 g). LCMS (Method 14): 1.41 min, 343.2 $[M+H]^+$ Intermediate 3.148: (S)-2-amino-2-cycloheptyl-N-(5-(1,4-dimethyl-1H-1,2,3-triazol-5-yl)pyridin-2-yl)acetamide A solution of Intermediate 2.148 (0.14 g, 0.31 mmol) in HCl (4 M in 1,4-dioxane; 2.5 mL) was stirred at rt for 3 h. The reaction mixture was concentrated in vacuo, the residue dissolved in MeOH and passed through an SCX cartridge (2 g, washed with MeOH and eluted with 2 M methanolic ammonia). The solvent was removed in vacuo to provide the title compound (0.1 g). $^1H$ NMR (400 MHz, MeOD) δ: 8.41-8.33 (m, 2H), 7.89 (dd, 1H), 3.99 (s, 3H), 3.44 (d, 1H), 2.29 (s, 3H), 2.10-1.97 (m, 1H), 1.81-1.34 (m, 12H)

Intermediate 3.150: (S)-2-amino-2-cycloheptyl-N-(5-(5-(methoxymethyl)-3-methylisoxazol-4-yl)pyridin-2-yl)acetamide dihydrochloride A solution of Intermediate 2.150 (90 mg, 0.19 mmol) in HCl (4 M in 1,4-dioxane; 0.48 mL) and 1,4-dioxane (3 mL) was stirred at rt for 40 h. The reaction mixture was concentrated in vacuo to provide the title compound (0.1 g). LCMS (Method 19): 1.810 min, 373.2 $[M+H]^+$ Intermediate 3.151: (S)-2-amino-N-(3'-methoxy-2'-methyl-[3,4'-bipyridin]-6-yl)-2-((1r,4S)-4-methylcyclohexyl)acetamide A solution of Intermediate 2.151 (0.11 g, 0.24 mmol) in HCl (4 M in 1,4-dioxane; 0.6 mL) and 1,4-dioxane (2 mL) was stirred at rt for 18 h. The reaction mixture was concentrated in vacuo, the residue dissolved in MeOH and passed through an SCX cartridge (washed with MeOH and eluted with 2 M methanolic ammonia). The solvent was removed in vacuo to provide the title compound (86 mg). LCMS: (Method 19): 1.50 min, 369.2 $[M+H]^+$ Intermediate 3.152: (S)-2-amino-N-(2',3'-dimethyl-[3,4'-bipyridin]-6-yl)-2-((1r,4S)-4-methylcyclohexyl)acetamide A solution of Intermediate 2.152 (0.19 g, 0.43 mmol) in HCl (4 M in 1,4-dioxane; 1.1 mL) and 1,4-dioxane (3 mL) was stirred at rt for 4 h. The reaction mixture was concentrated in vacuo, the residue dissolved in MeOH and passed through an SCX cartridge (washed with MeOH and eluted with 2 M methanolic ammonia). The solvent was removed in vacuo to provide the title compound (0.13 g). $^1H$ NMR (400 MHz, $CDCl_3$) δ: 10.05 (s, 1H), 8.42-8.32 (m, 2H), 8.25 (dd, 1H), 7.66 (dd, 1H), 6.99 (d, 1H), 3.45 (d, 1H), 2.59 (s, 3H), 2.21 (s, 3H), 2.06-1.95 (m, 1H), 1.78-1.71 (m, 3H), 1.60 (m, 1H), 1.35-1.22 (m, 2H), 1.16 (m, 1H), 1.09-0.91 (m, 2H), 0.88 (d, 3H)

Intermediate 3.153: (S)-2-amino-N-(2',5'-dimethyl-[3,4'-bipyridin]-6-yl)-2-((1r,4S)-4-methylcyclohexyl)acetamide A solution of Intermediate 2.153 (0.1 g, 0.23 mmol) in HCl (4 M in 1,4-dioxane; 0.56 mL) and 1,4-dioxane (3 mL) was stirred at rt for 18 h. The reaction mixture was concentrated in vacuo, the residue dissolved in MeOH and passed through an SCX cartridge (washed with MeOH and eluted with 2 M methanolic ammonia). The solvent was removed in vacuo to provide the title compound (77 mg). LCMS (Method 14): 1.24 min, 353.2 $[M+H]^+$ Intermediate 3.157: (S)-2-amino-2-cycloheptyl-N-(5-(1-ethyl-4-methyl-1H-1,2,3-triazol-5-yl)pyridin-2-yl)acetamide A solution of Intermediate 2.157 (31 mg, 0.068 mmol) in HCl (4 M in 1,4-dioxane; 0.17 mL) and 1,4-dioxane (10 mL) was stirred at rt for 19 h. The reaction mixture was concentrated in vacuo, the residue dissolved in MeOH and passed through an SCX cartridge (0.5 g, washed with MeOH and eluted with 2 M methanolic ammonia). The solvent was removed in vacuo to provide the title compound (19 mg). LCMS (Method 19): 1.67 min, 357.2 $[M+H]^+$ Intermediate 3.158: (S)-2-amino-2-cycloheptyl-N-(5-(3,5-dimethylisoxazol-4-yl)pyrazin-2-yl)acetamide A solution of Intermediate 2.158 (20 mg, 0.05 mmol) in HCl (4 M in 1,4-dioxane; 0.17 mL), 1,4-dioxane (5 mL) and MeOH (5 mL) was stirred at rt for 19 h. The reaction mixture was concentrated in vacuo, the residue dissolved in MeOH and passed through an SCX cartridge (0.1 g, washed with MeOH and eluted with 2 M methanolic ammonia). The solvent was removed in vacuo to provide the title compound (16 mg). LCMS (Method 14): 1.36 min, 344.2 $[M+H]^+$ Intermediate 3.161: (S)-2-amino-2-cycloheptyl-N-(5-(1-cyclopropyl-4-methyl-1H-1,2,3-triazol-5-yl)pyridin-2-yl)acetamide A solution of Intermediate 2.161 (18 mg, 0.04 mmol) in HCl (4 M in 1,4-dioxane; 0.05 mL) and 1,4-dioxane (5 mL) was stirred at rt for 19 h. The reaction mixture was concentrated in vacuo, the residue dissolved in MeOH and passed through an SCX cartridge (0.1 g, washed with MeOH and eluted with 2 M methanolic ammonia). The solvent was removed in vacuo to provide the title compound (16 mg). LCMS (Method 14): 1.35 min, 369.2 $[M+H]^+$ Intermediate 3.162: (S)-2-amino-2-cycloheptyl-N-(5-(3,5-dimethylisoxazol-4-yl)-3-fluoropyridin-2-yl)acetamide A solution of Intermediate 2.162 (0.22 g, 0.49 mmol) in HCl (4 M in 1,4-dioxane; 1.2 mL) and 1,4-dioxane (3 mL) was stirred at rt for 18 h. The reaction mixture was concentrated in vacuo, the residue dissolved in MeOH and passed through an SCX cartridge (washed with MeOH and eluted with 2 M methanolic ammonia). The solvent was removed in vacuo to provide the title compound (99 mg). LCMS (Method 14): 1.36 min, 361.2 $[M+H]^+$ Intermediate 3.165: (S)-2-amino-2-cycloheptyl-N-(5-(1,4-dimethyl-1H-pyrazol-5-yl)pyrimidin-2-yl)acetamide A solution of Intermediate 2.165 (59 mg, 0.13 mmol) in HCl (4 M in 1,4-dioxane; 1 mL) was stirred at rt for 1 h. The reaction mixture was poured into saturated aqueous $NaHCO_3$ and extracted with EtOAc. The combined organics were dried over $Na_2SO_4$, filtered and concentrated in vacuo to provide the title compound (51 mg). LCMS (Method 14): 1.27 min, 343.2 $[M+H]^+$ Intermediate 3.166: (S)-2-amino-2-cycloheptyl-N-(5-(4-hydroxy-1-methyl-1H-pyrazol-5-yl)pyridin-2-yl)acetamide To a solution of Intermediate 2.166 (30 mg, 0.06 mmol) in DCM (10 mL) at 0° C. was added boron tribromide (1 M in DCM; 0.17 mL, 0.17 mmol). The mixture was allowed to warm to rt, then an additional portion of boron tribromide (0.56 mL, 0.56 mmol) was added and the mixture stirred at rt for 8 h. A further portion of boron tribromide (0.56 mL, 0.56 mmol) was added and the reaction mixture stirred at rt for 16 h. The mixture was quenched with water and neutralised using 1 M NaOH solution, extracted with DCM and the phases separated with a phase separation cartridge. The organic layers were concentrated in vacuo to provide the title compound (21 mg). LCMS (Method 14): 1.24 min, 344.2 $[M+H]^+$ Intermediate 3.169: (S)-2-amino-2-cycloheptyl-N-(6-(3,5-dimethylisoxazol-4-yl)pyridin-3-yl)acetamide A solution of Intermediate 2.169 (0.44 g, 0.99 mmol) in HCl (4 M in 1,4-dioxane; 5 mL) and 1,4-dioxane (5 mL) was stirred at rt for 2 h. The reaction mixture was concentrated in vacuo, the residue dissolved in MeOH and passed through an SCX cartridge (washed with MeOH and eluted with 2 M methanolic ammonia). The solvent was removed in vacuo to provide the title compound (0.3 g). LCMS (Method 14): 1.34 min, 343.2 $[M+H]^+$ Intermediate 3.173: (S)-2-amino-2-cycloheptyl-N-(5-(4-cyclopropyl-1-methyl-1H-1,2,3-triazol-5-yl)pyridin-2-yl)acetamide A solution of Intermediate 2.173 (53 mg, 0.09 mmol) in HCl (4 M in 1,4-dioxane; 1 mL) and 1,4-dioxane (5 mL) was stirred at rt for 2 h. The reaction was diluted with saturated aqueous $NaHCO_3$ and EtOAc and the phases separated. The aqueous phase was extracted with EtOAc and the combined organics were dried over $Na_2SO_4$, filtered and concentrated in vacuo to provide the title compound (46 mg). LCMS (Method 19): 1.70 min, 369.2 $[M+H]^+$ Intermediate 3.174: (S)-2-amino-N-(5-(4-chloro-1-methyl-1H-pyrazol-5-yl)pyridin-2-yl)-2-cycloheptylacetamide A solution of Intermediate 2.174 (0.58 g, 1.1 mmol) in HCl (4 M in 1,4-dioxane; 5.6 mL) was stirred at rt for 2 h. The reaction mixture was concentrated in vacuo, the residue dissolved in MeOH and passed through an SCX cartridge (10 g cartridge, washed with MeOH and eluted with 2 M methanolic ammonia). The solvent was removed in vacuo to provide the title compound (0.38 g). LCMS (Method 19): 1.78 min, 362.2 $[M+H]^+$ Intermediate 3.177: (S)-2-amino-2-cyclohexyl-N-(5-(1,4-dimethyl-1H-pyrazol-5-yl)pyridin-2-yl)acetamide A solution of Intermediate 2.177 (0.5 g, 1.2 mmol) in HCl (4 M in 1,4-dioxane; 2.9 mL) and 1,4-dioxane (2 mL) was stirred at rt for 18 h. The reaction was diluted with saturated aqueous $NaHCO_3$ and EtOAc and the phases separated. The aqueous phase was extracted with EtOAc and the combined organics were dried over $Na_2SO_4$, filtered and concentrated in vacuo to provide the title compound (0.38 g). $^1H$ NMR (400 MHz, MeOD) δ: 8.35-8.28 (m, 2H), 7.81 (dd, 1H), 7.38 (d, 1H), 3.74 (s, 3H), 3.36 (d, 1H), 2.01 (d, 3H), 1.81-1.65 (m, 6H), 1.45-1.11 (m, 5H).

Intermediate 3.179: (S)-2-amino-N-(6-(1,4-dimethyl-1H-pyrazol-5-yl)-5-fluoropyridin-3-yl)-2-(4-methylcyclohexyl)acetamide A solution of Intermediate 2.179 (0.49 g, 1.1 mmol) in HCl (4 M in 1,4-dioxane; 5.3 mL) and 1,4-dioxane (4 mL) was stirred at rt for 5 h. The reaction mixture was concentrated in vacuo, the residue dissolved in MeOH and passed through an SCX cartridge (10 g cartridge, washed with MeOH and eluted with 2 M methanolic ammonia). The solvent was removed in vacuo to provide the title compound (0.33 g). LCMS (Method 14): 1.35 min, 360.2 $[M+H]^+$ Intermediate 3.182: (S)-2-amino-2-cycloheptyl-N-(5-(4-(hydroxymethyl)-1-methyl-1H-pyrazol-5-yl)pyridin-2-yl)acetamide A solution of Intermediate 2.182 (70 mg, 0.12 mmol) in HCl (4 M in 1,4-dioxane; 0.15 mL) and 1,4-dioxane (2 mL) was stirred at rt for 3 h. An additional portion of HCl (4 M in 1,4-dioxane; 0.15 mL) was added and the mixture stirred at rt for 5 h. The reaction was diluted with saturated aqueous $NaHCO_3$ and extracted with DCM. The combined organics were dried over $Na_2SO_4$, filtered and concentrated in vacuo to provide the title compound (36 mg). LCMS (Method 15): 1.45 min, 358.2 $[M+H]^+$ Intermediate 3.183: (S)-2-amino-2-cyclopentyl-N-(5-(1,4-dimethyl-1H-pyrazol-5-yl)pyridin-2-yl)acetamide A solution of Intermediate 2.183 (48 mg, 0.12 mmol) in HCl (4 M in 1,4-dioxane; 0.3 mL) and 1,4-dioxane (1 mL) was stirred at rt for 18 h. The reaction mixture was concentrated in vacuo and the residue partitioned between saturated aqueous $NaHCO_3$ and DCM. The phases were separated, and the aqueous layer extracted with DCM. The combined organics were washed with water and brine, separated using a phase separating cartridge and concentrated in vacuo to provide the title compound (34 mg). LCMS (Method 26): 1.02 min, 314.2 $[M+H]^+$ Intermediate 3.184: 2-amino-2-(bicyclo[2.2.1]heptan-2-yl)-N-(5-(1,4-dimethyl-1H-pyrazol-5-yl)pyridin-2-yl)acetamide A solution of Intermediate 2.184 (60 mg, 0.13 mmol) in HCl (4 M in 1,4-dioxane; 0.33 mL) and 1,4-dioxane (1 mL) was stirred at rt for 18 h. The reaction mixture was concentrated in vacuo and the residue partitioned between saturated aqueous $NaHCO_3$ and DCM. The phases were separated, and the aqueous layer extracted with DCM. The combined organics were washed with brine, dried over $Na_2SO_4$, filtered and concentrated in vacuo to provide the title compound (30 mg). LCMS (Method 26): 1.30 min, 340.3 $[M+H]^+$ Intermediate 3.185: 2-amino-N-(5-(1,4-dimethyl-1H-pyrazol-5-yl)pyridin-2-yl)-2-((1r,4r)-4-(trifluoromethyl)cyclohexyl)acetamide A solution of Intermediate 2.185 (0.22 g, 0.44 mmol) in HCl (4 M in 1,4-dioxane; 2 mL) was stirred at rt for 1.5 h. The reaction mixture was quenched with saturated aqueous $NaHCO_3$ and extracted with EtOAc. The organics were dried over $Na_2SO_4$, filtered, and concentrated in vacuo provide the title compound (0.16 g). LCMS (Method 14): 1.30 min, 396.2 $[M+H]^+$ Intermediate 3.190: (S)-2-amino-2-cycloheptyl-N-(5-(1-(2-(dimethylamino)-2-oxoethyl)-4-methyl-1H-1,2,3-triazol-5-yl)pyridin-2-yl)acetamide A solution of Intermediate 2.190 (55 mg, 0.1 mmol) in HCl (4 M in 1,4-dioxane; 0.48 mL) and 1,4-dioxane (1.5 mL) was stirred at rt for 17 h. The reaction mixture was concentrated in vacuo, the residue dissolved in MeOH and passed through an SCX cartridge (2 g cartridge, washed with MeOH and eluted with 2 M methanolic ammonia). The solvent was removed in vacuo to provide the title compound (36 mg). LCMS (Method 14): 1.25 min, 414.2 $[M+H]^+$ Intermediate 3.193: (S)-2-amino-N-(5-(4-cyano-1-methyl-1H-pyrazol-5-yl)pyridin-2-yl)-2-((1r,4S)-4-methylcyclohexyl)acetamide A solution of Intermediate 2.193 (71 mg, 0.14 mmol) in HCl (4 M in 1,4-dioxane; 0.71 mL) and 1,4-dioxane (1 mL) was stirred at rt for 5 h. The reaction mixture was concentrated in vacuo, the residue dissolved in MeOH and passed through an SCX cartridge (2 g cartridge, washed with MeOH and eluted with 2 M methanolic ammonia). The solvent was removed in vacuo to provide the title compound (44 mg). LCMS (Method 14): 1.33 min, 353.2 $[M+H]^+$ Intermediate 3.195: (S)-2-amino-2-cycloheptyl-N-(5-(1,3,4-trimethyl-1H-pyrazol-5-yl)pyridin-2-yl)acetamide A solution of Intermediate 2.195 (0.36 g, 0.78 mmol) in HCl (4 M in 1,4-dioxane; 0.98 mL) was stirred at rt for 1 h. The reaction mixture was concentrated in vacuo, the residue dissolved in MeOH and passed through an SCX cartridge (10 g cartridge, washed with MeOH and eluted with 2 M methanolic ammonia). The solvent was removed in vacuo to provide the title compound (0.29 g). LCMS (Method 14): 1.35 min, 356.2 $[M+H]^+$ Intermediate 3.196: (S)-2-amino-N-(5-(3,5-dimethylisothiazol-4-yl)pyridin-2-yl)-2-((1r,4S)-4-methylcyclohexyl)acetamide A solution of Intermediate 2.196 (0.1 g, 0.23 mmol) in HCl (4 M in 1,4-dioxane; 2 mL) was stirred at rt for 5 h. The reaction mixture was quenched with saturated aqueous $NaHCO_3$ and extracted with DCM. The organics were dried over $Na_2SO_4$, filtered, and concentrated in vacuo provide the title compound (77 mg). LCMS (Method 15): 1.77 min, 359.2 $[M+H]^+$ Intermediate 3.199: (S)-2-amino-N-(5-(4-chloro-1-methyl-1H-pyrazol-5-yl)pyridin-2-yl)-2-((1r,4S)-4-methylcyclohexyl)acetamide A solution of Intermediate 2.199 (0.48 g, 0.93 mmol) in HCl (4 M in 1,4-dioxane; 2 mL) and 1,4-dioxane (2 mL) was stirred at rt for 3 h. The reaction mixture was concentrated in vacuo, the residue dissolved in MeOH and passed through an SCX cartridge (10 g cartridge, washed with MeOH and eluted with 2 M methanolic ammonia). The solvent was removed in vacuo. The crude compound was purified by flash column chromatography on the Biotage Isolera One™ (10 g silica column, eluting 0-5% 2 M methanolic ammonia in DCM) to provide the title compound (0.28 g). LCMS (Method 15): 1.77 min, 362.2 $[M+H]^+$ Intermediate 3.205: (S)-2-amino-N-(5-(4-(hydroxymethyl)-1-methyl-1H-pyrazol-5-yl)pyridin-2-yl)-2-((1r,4S)-4-methylcyclohexyl)acetamide A solution of Intermediate 2.205 (0.27 g, 0.47 mmol) in HCl (4 M in 1,4-dioxane; 0.59 mL) and 1,4-dioxane (11.5 mL) was stirred at rt for 3 h. A further portion of HCl (4 M in 1,4-dioxane; 0.59 mL) was added and the mixture stirred at rt for a further 2 h. The reaction mixture was quenched with saturated aqueous $NaHCO_3$ and extracted with DCM. The organics were dried over $Na_2SO_4$, filtered, and concentrated in vacuo to provide the title compound (0.17 g). LCMS (Method 15): 1.48 min, 358.2 $[M+H]^+$ Intermediate 3.207: (S)-2-amino-2-cyclohexyl-N-(6-(3,5-dimethyl-1H-pyrazol-4-yl)pyridin-3-yl)acetamide dihydrochloride A solution of Intermediate 2.207 (37 mg, 0.05 mmol) in HCl (4 M in 1,4-dioxane; 0.5 mL) 1,4-dioxane (0.5 mL) and MeOH (1 mL) was stirred at 40° C. for 3 h. The mixture was concentrated in vacuo to provide the title compound (30 mg). LCMS (Method 28): 1.03 min, 328.3 $[M+H]^+$ Intermediate 3.208: (S)-2-amino-2-cycloheptyl-N-(6-(3,5-dimethyl-1H-pyrazol-4-yl)pyridin-3-yl)acetamide dihydrochloride A solution of Intermediate 2.208 (0.9 g, 1.6 mmol) in HCl (4 M in 1,4-dioxane; 5 mL) 1,4-dioxane (5 mL) and MeOH (20 mL) was stirred at rt for 1 h. The mixture was concentrated in vacuo to provide the title compound (0.76 g). LCMS (Method 28): 1.14 min, 342.3 $[M+H]^+$ Intermediate 3.211: (S)-2-amino-N-(6-(3,5-dimethyl-1H-pyrazol-4-yl)pyridin-3-yl)-2-((1r,4S)-4-methylcyclohexyl)acetamide dihydrochloride A solution of Intermediate 2.211 (0.36 g, 0.62 mmol) in HCl (4 M in 1,4-dioxane; 2.2 mL) and MeOH (5 mL) was stirred at 40° C. for 20 h. The mixture was concentrated in vacuo to provide the title compound (0.34 g). LCMS (Method 28): 1.16 min, 342.3 $[M+H]^+$ Intermediate 3.214: (S)-2-amino-2-cycloheptyl-N-(1',2',4'-trimethyl-6'-oxo-1',6'-dihydro-[3,3'-bipyridin]-6-yl)acetamide A solution of Intermediate 2.214 (30 mg, 0.06 mmol) in HCl (4 M in 1,4-dioxane; 0.16 mL) and 1,4-dioxane (0.5 mL) was stirred at rt for 18 h. The reaction mixture was concentrated in vacuo, the residue dissolved in MeOH and passed through an SCX cartridge (1 g cartridge, washed with MeOH and eluted with 5% methanolic ammonia). The solvent was removed in vacuo to provide the title compound (25 mg). LCMS (Method 29): 1.27 min, 383.3 $[M+H]^+$ Intermediate 3.215: (S)-2-amino-2-((1r,4S)-4-methylcyclohexyl)-N-(1',2',4'-trimethyl-6'-oxo-1',6'-dihydro-[3,3'-bipyridin]-6-yl)acetamide A solution of Intermediate 2.215 (30 mg, 0.06 mmol) in HCl (4 M in 1,4-dioxane; 0.15 mL) and 1,4-dioxane (0.5 mL) was stirred at rt for 18 h. The reaction mixture was concentrated in vacuo, the residue dissolved in MeOH and passed through an SCX cartridge (1 g cartridge, washed with MeOH and eluted with 5% methanolic ammonia). The solvent was removed in vacuo to provide the title compound (16 mg). LCMS (Method 28): 1.23 min, 383.4 $[M+H]^+$ Intermediate 3.216: (S)-2-amino-2-cycloheptyl-N-(5-(1,3,5-trimethyl-1H-pyrazol-4-yl)pyridin-2-yl)acetamide A solution of Intermediate 2.216 (71 mg, 0.16 mmol) in HCl (4 M in 1,4-dioxane; 0.39 mL) and 1,4-dioxane (1 mL) was stirred at rt for 18 h. The reaction mixture was concentrated in vacuo and the residue partitioned between saturated aqueous $NaHCO_3$ and DCM. The phases separated with a phase separation cartridge, and the organics concentrated in vacuo to provide the title compound (65 mg). LCMS (Method 26): 1.30 min, 356.3 $[M+H]^+$ Intermediate 3.217: (S)-2-amino-2-((1r,4S)-4-methylcyclohexyl)-N-(5-(1,3,5-trimethyl-1H-pyrazol-4-yl)pyridin-2-yl)acetamide A solution of Intermediate 2.217 (80 mg, 0.16 mmol) in HCl (4 M in 1,4-dioxane; 0.4 mL) and 1,4-dioxane (1 mL) was stirred at rt for 18 h. The reaction mixture was concentrated in vacuo and the residue partitioned between saturated aqueous $NaHCO_3$ and DCM. The phases separated with a phase separation cartridge, and the organics concentrated in vacuo to provide the title compound (46 mg). LCMS (Method 28): 1.37 min, 356.3 $[M+H]^+$ Intermediate 3.219: (S)-2-amino-N-(5-(1-methyl-4-(trifluoromethyl)-1H-pyrazol-5-yl)pyridin-2-yl)-2-((1r,4S)-4-methylcyclohexyl)acetamide A solution of Intermediate 2.219 (0.11 g, 0.21 mmol) in HCl (4 M in 1,4-dioxane; 1 mL) and DCM (0.5 mL) was stirred at rt for 1 h. The reaction mixture was quenched with saturated aqueous $NaHCO_3$ and extracted with EtOAc. The organics were dried over $Na_2SO_4$, filtered, and concentrated in vacuo to provide the title compound (85 mg). LCMS (Method 14): 1.42 min, 396.2 $[M+H]^+$ Intermediate 3.220: 2-amino-N-(5-(1,4-dimethyl-1H-pyrazol-5-yl)pyridin-2-yl)-2-(dispiro[$2.1.2^5.2^3$]nonan-4-yl)acetamide A solution of Intermediate 2.220 (30 mg, 0.06 mmol) in HCl (4 M in 1,4-dioxane; 0.08 mL) and 1,4-dioxane (5 mL) was stirred at rt for 18 h. The reaction mixture was quenched with saturated aqueous $NaHCO_3$ and extracted with DCM. The organics were dried over $Na_2SO_4$, filtered, and concentrated in vacuo. The crude product was purified by flash column chromatography on the Biotage Isolera One™ (10 g silica column, eluting 0-10% MeOH in DCM) to provide the title compound (16 mg). LCMS (Method 14): 1.36 min, 366.2 $[M+H]^+$ Intermediate 4.1: (S)-2-(1-methyl-1H-pyrazole-5-carboxamido)-3,3-diphenylpropanoic acid Intermediate 4.1a: Allyl (S)-2-((tert-butoxycarbonyl)amino)-3,3-diphenylpropanoate To a stirred solution of (S)-2-((tert-butoxycarbonyl)amino)-3,3-diphenylpropanoic acid (8.0 g, 23 mmol, CAS: 138662-63-2) in acetone (300 mL) at rt was added potassium carbonate (6.5 g, 47 mmol) and allyl bromide (2.2 mL, 26 mmol) and the reaction mixture stirred at 65° C. for 20 h. The reaction mixture was diluted with water and the crude product extracted into EtOAc. The combined organics were washed with brine, dried over $Na_2SO_4$, filtered and concentrated in vacuo to provide the title compound (3.4 g), which was used without further purification. LCMS (Method 2): 1.07 min, 282.0 $[M-CO_2{}^tBu+H]^+$ Intermediate 4.1 b: Allyl (S)-2-amino-3,3-diphenylpropanoate hydrochloride A suspension of Intermediate 4.1a (8.9 g, 23 mmol) in HCl (4 M in 1,4-dioxane; 29 mL, 120 mmol) at rt was stirred for 30 h. The reaction mixture was concentrated in vacuo to provide the title compound (7.4 g) which was used without further purification. LCMS (Method 2): 0.88 min, 282.1 $[M+H]^+$ Intermediate 4.1c: Allyl (S)-2-(1-methyl-1H-pyrazole-5-carboxamido)-3,3-diphenylpropanoate To a stirred suspension of 2-methylpyrazole-3-carboxylic acid (3.2 g, 26 mmol) in EtOAc (110 mL) at rt was added Intermediate 4.1b (8.2 g, 23 mmol), HATU (9.8 g, 26 mmol) and triethylamine (9.8 mL, 70 mmol) and the reaction mixture stirred at rt for 2 h. The reaction mixture was diluted with saturated aqueous $NaHCO_3$ and the crude product extracted into EtOAc. The combined organics were washed with brine, dried over $Na_2SO_4$, filtered and concentrated in vacuo. The crude product was purified by flash column chromatography (eluting 20-40% EtOAc in heptanes) to provide the title compound (8.1 g). LCMS (Method 2): 0.91 min, 390.2 $[M+H]^+$ Intermediate 4.1: (S)-2-(1-methyl-1H-pyrazole-5-carboxamido)-3,3-diphenylpropanoic acid To a solution of Intermediate 4.1c (8.1 g, 21 mmol) and morpholine (4.6 mL, 52 mmol) in THF (90 mL) was added tetrakis(triphenylphosphine)palladium(0) (0.36 g, 0.31 mmol) and the reaction stirred at rt for 2 h. The reaction mixture was diluted with water and the mixture washed with EtOAc. The aqueous phase was acidified (~pH 4) with 0.5 M aqueous HCl and the crude product extracted into EtOAc. The combined organics were washed with water, brine, dried over $Na_2SO_4$, filtered and concentrated in vacuo to provide the title compound (5.9 g) which was used without further purification. LCMS (Method 8): 0.71 min, 349.9 $[M+H]^+$.

Intermediate 4.2: 2-(9H-fluoren-9-yl)-2-(1-methyl-1H-pyrazole-5-carboxamido)acetic acid Intermediate 4.2a: ethyl 2-amino-2-(9H-fluoren-9-yl)acetate To a stirred solution of ethyl 2-(benzhydrylideneamino) acetate (3 g, 11.2 mmol, CAS: 69555-14-2) in DMSO (6 mL) at 10° C. was added potassium hydroxide (1.9 g, 33.7 mmol) and 9-bromo-9H-fluorene (2.8 g, 11.2 mmol, CAS: 1940-57-4) and the reaction mixture stirred at 10° C. for 30 min. The reaction mixture was poured into HCl (2 M aqueous; 28 mL, 56.1 mmol) and tetrahydrofuran (5 mL) at rt and the reaction mixture stirred for 15 min. The reaction mixture was diluted with water and washed with EtOAc. The aqueous phase was basified with saturated aqueous $NaHCO_3$ and the crude product extracted into EtOAc. The combined organics were washed with water, brine, dried over $Na_2SO_4$, filtered and concentrated in vacuo to provide the title compound (1.150 g) which was used without further purification. LCMS (Method 2): 0.87 min, 268.1 $[M+H]^+$ Intermediate 4.2b: ethyl 2-(9H-fluoren-9-yl)-2-(1-methyl-1H-pyrazole-5-carboxamido)acetate To a stirred solution of Intermediate 4.2a (1 g, 3.7 mmol), 2-methylpyrazole-3-carboxylic acid (0.47 g, 3.7 mmol, CAS: 16034-46-1) and triethylamine (1 mL, 7.5 mmol) in ethyl acetate (3 mL) was T3P® (50% w/w solution in EtOAc; 7.1 mL, 11.2 mmol) and the reaction mixture stirred at rt for 18 h. The reaction mixture was diluted with water and the crude product extracted into EtOAc. The combined organics were washed with brine, dried over $Na_2SO_4$, filtered and concentrated in vacuo. The crude product was purified by flash column chromatography (eluting 40% EtOAc in heptanes) to provide the title compound (0.73 g). LCMS (Method 2): 0.93 min, 376.2 $[M+H]^+$ Intermediate 4.2: 2-(9H-fluoren-9-yl)-2-(1-methyl-1H-pyrazole-5-carboxamido)acetic acid To a stirred suspension of Intermediate 4.2b (0.73 g, 1.9 mmol) in 2-propanol (4 mL) and water (5 mL) was added potassium hydroxide (0.43 g, 7.7 mmol) and the reaction mixture stirred at rt for 1 h. The reaction mixture was diluted with water and washed with EtOAc. The aqueous phase was acidified with 2 M aqueous HCl and the crude product extracted into EtOAc. The combined organics were washed with brine, dried over $Na_2SO_4$, filtered and concentrated in vacuo to provide the racemic product. The racemate was purified by chiral separation. Chiral separation was performed using a Waters UV directed automated Fraction Lynx preparative HPLC system; 2525 binary pump, 2996 PDA detector, 2767 liquid sample handler. Column: ChiralPak IA 5 μm, 20 mm×250 mm (flow 18 mL/min). Run time: 16 min. gradient: heptane (80%), IPA (20%), TFA (0.1%) to give the title compound (165 mg) and the other enantiomer (172 mg). Chiral LC analysis: Waters Alliance 2695 with diode array (210-350 nm). Column: YMCSA 5 μm, 4.6 mm×250 mm (flow 1 mL/min). Run time: 30 min. gradient: heptane (80%), IPA (20%), TFA (0.1%). Enantiomer 1: 8.51 min (100% area); 100% ee. Enantiomer 2: 10.34 min (99.5% area); 99% ee. LCMS (Method 2): 0.46 min, 348.1 $[M+H]^+$ Intermediate 5.98: 4-(4,4-difluorocyclohexylidene)-2-(1-methyl-1H-pyrazol-5-yl)oxazol-5(4H)-one To a mixture of titanium (IV) chloride (1 M in DCM; 4.8 mL, 4.8 mmol) in THF (10 mL) under argon at −10° C. was added a solution of 2-(2-methylpyrazol-3-yl)-4H-oxazol-5-one (200 mg, 1.2 mmol CAS: 2256070-09-2) in THF (10 mL) followed by a solution of 4,4-difluorocyclohexanone (179 mg, 1.3 mmol, CAS: 22515-18-0) in THF (5 mL). The mixture was stirred at −10° C. for 30 min before addition of pyridine (0.59 mL, 7.3 mmol) dropwise, then the mixture was stirred at −10° C. to rt for 16 h. The mixture was quenched by the addition of saturated aqueous $NH_4Cl$ then extracted with EtOAc. The combined extracts were washed with brine, dried over $MgSO_4$, filtered and concentrated in vacuo. The crude product was purified by flash column chromatography on the Biotage Isolera™ (10 g silica column, eluting 0-30% EtOAc in heptanes) to afford the title compound (240 mg), $^1H$ NMR (400 MHz, $CDCl_3$) δ:7.55 (d, 1H), 6.90 (d, 1H), 4.28 (s, 3H), 3.30-3.19 (m, 2H), 3.08-2.97 (m, 2H), 2.22-2.05 (m, 4H)

Intermediate 5.100: 4-(4,4-dimethylcyclohexylidene)-2-(1-methyl-1H-pyrazol-5-yl)oxazol-5(4H)-one The title compound (0.17 g) was prepared from 2-(2-methylpyrazol-3-yl)-4H-oxazol-5-one (0.19 g, 1.1 mmol, CAS: 22515-18-0) and 4,4-dimethylcyclohexanone (0.13 g, 1 mmol, CAS: 4255-62-3) in accordance with the procedure described for Intermediate 5.98. LCMS (Method 14): 2.07 min, 274.2 $[M+H]^+$ Intermediate 5.101: 4-(4,4-difluorocyclohexyl)-2-(1-methyl-1H-pyrazol-5-yl)oxazol-5(4H)-one A mixture of Intermediate 5.98 (60 mg, 0.21 mmol) in THF (10 mL) was hydrogenated in an H-Cube® using a 10% Pd/C cartridge at 50 bar and 70° C. The crude product was purified by flash column chromatography on the Biotage Isolera One™ (4 g silica column, eluting 0-10% MeOH in DCM) to afford the title compound (45 mg). $^1$H NMR (400 MHz, $CDCl_3$) δ: 7.57 (d, 1H), 6.84 (d, 1H), 4.35 (d, 1H), 4.26 (s, 3H), 2.30-2.00 (m, 4H), 1.91-1.64 (m, 4H), 1.62-1.58 (m, 1H).

Intermediate 5.103: 4-cyclooctylidene-2-(1-methyl-1H-pyrazol-5-yl)oxazol-5(4H)-one The title compound (0.14 g) was prepared from 2-(2-methylpyrazol-3-yl)-4H-oxazol-5-one (0.13 g, 0.76 mmol, CAS: 22515-18-0) and cyclooctanone (96 mg, 0.76 mmol, CAS: 696-71-9) in accordance with the procedure described for Intermediate 5.98. $^1$H NMR (400 MHz, $CDCl_3$) δ:7.53 (d, 1H), 6.86 (d, 1H), 4.29 (s, 3H), 3.02-2.95 (m, 2H), 2.91-2.83 (m, 2H), 1.92 (tdd, 4H), 1.45-1.31 (m, 2H), 1.26 (s, 2H), 0.85 (d, 2H).

Intermediate 6.98: N-(1-(4,4-difluorocyclohexylidene)-2-((4-(3,5-dimethylpyridin-4-yl)phenyl) amino)-2-oxoethyl)-1-methyl-1H-pyrazole-5-carboxamide To a mixture of Intermediate 5.98 (50 mg, 0.18 mmol) and Intermediate 1.6 (41 mg, 0.21 mmol) in THF (10 mL) under argon, was added acetic acid (0.1 mL, 1.8 mmol). The reaction mixture was heated by microwave irradiation at 100° C. for 30 min. The reaction mixture was concentrated in vacuo and purified by flash column chromatography (50% EtOAc in heptanes) to afford the title compound (80 mg), $^1$H NMR (400 MHz, MeOD) δ: 8.28 (s, 2H), 7.78 (d, 2H), 7.52 (d, 1H), 7.20-7.13 (m, 2H), 6.99 (d, 1H), 4.12 (s, 3H), 2.77 (t, 2H), 2.54 (t, 2H), 2.17-2.10 (m, 4H), 2.08 (s, 6H).

Intermediate 6.100: (N-(1-(4,4-dimethylcyclohexylidene)-2-((4-(3,5-dimethylpyridin-4-yl)phenyl) amino)-2-oxoethyl)-1-methyl-1H-pyrazole-5-carboxamide The title compound (30 mg) was prepared from Intermediate 5.100 (51 mg, 0.19 mmol) and Intermediate 1.6 (41 mg, 0.21 mmol) in accordance with the procedure described for Intermediate 6.98. LCMS (Method 14): 1.50 min, 472.2 $[M+H]^+$ Intermediate 6.102: N-(2-((4-(1,2-dimethyl-6-oxo-1,6-dihydropyridin-3-yl)phenyl)amino)-1-(4,4-dimethylcyclohexylidene)-2-oxoethyl)-1-methyl-1H-pyrazole-5-carboxamide The title compound (75 mg) was prepared from Intermediate 5.100 (50 mg, 0.18 mmol) and Intermediate 1.13 (43 mg, 0.20 mmol) in accordance with the procedure described for Intermediate 6.98. LCMS (Method 14): 1.72 min, 488.2 $[M+H]^+$ Intermediate 6.103: N-(1-cyclooctylidene-2-((4-(3,5-dimethylpyridin-4-yl)phenyl)amino)-2-oxoethyl)-1-methyl-1H-pyrazole-5-carboxamide The title compound (50 mg) was prepared from Intermediate 5.103 (41 mg, 0.15 mmol) and Intermediate 1.6 (30 mg, 0.15 mmol) in accordance with the procedure described for Intermediate 6.98. LCMS (Method 14): 1.51 min, 472.2 $[M+H]^+$ Intermediate 6.104: N-(1-cyclooctylidene-2-((4-(3,5-dimethyl-1H-pyrazol-4-yl)phenyl)amino)-2-oxoethyl)-1-methyl-1H-pyrazole-5-carboxamide The title compound (14 mg) was prepared from Intermediate 5.103 (51 mg, 0.19 mmol) and Intermediate 1.104 (54 mg, 0.11 mmol) in accordance with the procedure described for Intermediate 6.98. $^1$H NMR (400 MHz, MeOD) δ: 7.66-7.57 (m, 2H), 7.49 (dd, 1H), 7.28-7.20 (m, 2H), 6.95 (d, 1H), 4.10 (d, 3H), 2.71-2.64 (m, 2H), 2.47-2.39 (m, 2H), 2.23 (s, 6H), 1.85 (s, 2H), 1.77 (s, 2H), 1.59 (s, 6H).

SYNTHESIS OF EXAMPLES

Example 1: (S)—N-(1-((4-(2,3-dimethylpyridin-4-yl)phenyl)amino)-1-oxo-3,3-diphenylpropan-2-yl)-1-methyl-1H-pyrazole-5-carboxamide

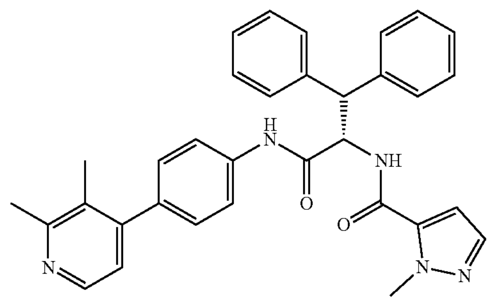 [SMILES: Cc1nccc(-c2ccc(NC(=O)[C@@H](NC(=O)c3ccnn3C)C(c3ccccc3)c3ccccc3)cc2)c1C]

To a stirred suspension of Intermediate 3.1 (0.14 g, 0.28 mmol), 2-methylpyrazole-3-carboxylic acid (37 mg, 0.30 mmol, CAS: 16034-46-1) and triethylamine (0.16 mL, 1.1 mmol) in EtOAc (4 mL) and MeCN (1 mL) at rt was added HATU (0.11 g, 0.30 mmol) and the reaction mixture stirred for 17 h. The reaction mixture was diluted with saturated aqueous $NaHCO_3$ and the crude product extracted into EtOAc. The combined organics were washed with water, brine, dried over $Na_2SO_4$, filtered and concentrated in vacuo. The crude product was purified by reverse phase column chromatography on the Biotage Isolera One™ (30 g C18 column, eluting 10-70% MeCN in pH10 0.1 M $NH_4HCO_3$ buffer solution) to afford the title compound (0.10 g). LCMS (Method 5): 2.23 min, 530.3 $[M+H]^+$; $^1$H NMR (400 MHz, DMSO-$d_6$) δ: 10.40 (s, 1H), 8.90 (d, 1H), 8.24 (d, 1H), 7.52 (d, 2H), 7.47 (d, 2H), 7.43 (d, 2H), 7.37 (d, 1H), 7.31-7.18 (m, 6H), 7.18-7.07 (m, 2H), 6.98 (d, 1H), 6.77 (d, 1H), 5.63 (dd, 1H), 4.64 (d, 1H), 3.91 (s, 3H), 2.47 (bs, 3H), 2.12 (s, 3H).

Example 2: (S)—N-(1-((4-(3-chloropyridin-4-yl)phenyl)amino)-1-oxo-3,3-diphenylpropan-2-yl)-1-methyl-1H-pyrazole-5-carboxamide

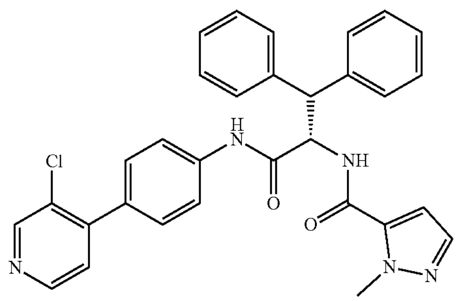 [SMILES: Cn1nccc1C(=O)N[C@H](C(=O)Nc1ccc(-c2ccncc2Cl)cc1)C(c1ccccc1)c1ccccc1]

The title compound (75 mg) was prepared from Intermediate 3.2 (0.41 g, 0.89 mmol), 2-methylpyrazole-3-carboxylic acid (0.11 g, 0.89 mmol, CAS: 16034-46-1), HATU (0.40 g, 1.07 mmol) and triethylamine (0.31 mL, 2.2 mmol) in accordance with the procedure described for Example 1. The crude product was purified by reverse phase column chromatography on the Biotage Isolera One™ (30 g C18 column, eluting 30-70% MeCN in pH10 0.1 M $NH_4HCO_3$ buffer solution). LCMS (Method 6): 2.34 min, 536.2 $[M+H]^+$; $^1$H NMR (400 MHz, DMSO-$d_6$) δ: 10.51 (s, 1H), 8.94 (d, 1H), 8.68 (s, 1H), 8.54 (d, 1H), 7.56 (d, 2H), 7.47 (bd, 2H), 7.45-7.39 (m, 5H), 7.37 (d, 1H), 7.31-7.19 (m, 4H), 7.17-7.07 (m, 2H), 6.78 (d, 1H), 5.63 (dd, 1H), 4.65 (d, 1H), 3.91 (s, 3H).

Example 3: (S)—N-(1-((4-(3-methoxypyridin-4-yl)phenyl)amino)-1-oxo-3,3-diphenylpropan-2-yl)-1-methyl-1H-pyrazole-5-carboxamide

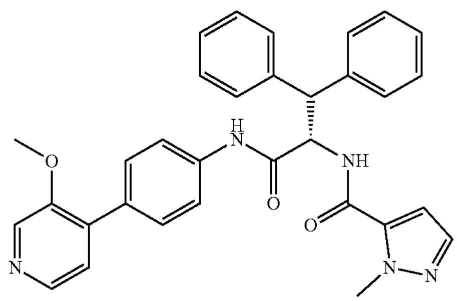 [SMILES: COc1cnccc1-c1ccc(NC(=O)[C@@H](NC(=O)c2ccnn2C)C(c2ccccc2)c2ccccc2)cc1]

The title compound (0.11 g) was prepared from Intermediate 3.3 (0.15 g, 0.30 mmol), 2-methylpyrazole-3-carboxylic acid (40 mg, 0.32 mmol, CAS: 16034-46-1), HATU (0.12 g, 0.32 mmol) and triethylamine (0.17 mL, 1.2 mmol) in accordance with the procedure described for Example 1. The crude product was purified by reverse phase column chromatography on the Biotage Isolera One™ (30 g C18 column, eluting 10-70% MeCN in pH10 0.1 M $NH_4HCO_3$ buffer solution). LCMS (Method 7): 2.42 min, 532.2 $[M+H]^+$; $^1$H NMR (400 MHz, DMSO-$d_6$) δ: 10.40 (s, 1H), 8.92 (d, 1H), 8.41 (s, 1H), 8.23 (d, 1H), 7.53-7.39 (m, 8H), 7.37 (d, 1H), 7.31-7.19 (m, 5H), 7.18-7.06 (m, 2H), 6.78 (d, 1H), 5.63 (dd, 1H), 4.63 (d, 1H), 3.91 (s, 3H), 3.86 (s, 3H).

Example 4: (S)-1-methyl-N-(1-((4-(3-methylpyridin-4-yl)phenyl)amino)-1-oxo-3,3-diphenylpropan-2-yl)-1H-pyrazole-5-carboxamide

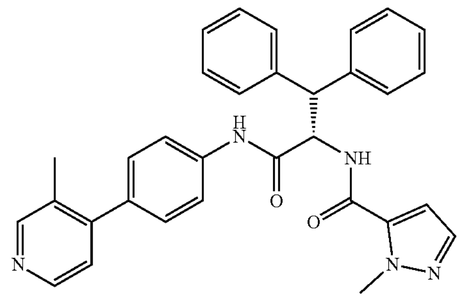 [SMILES: Cc1cnccc1-c1ccc(NC(=O)[C@@H](NC(=O)c2ccnn2C)C(c2ccccc2)c2ccccc2)cc1]

The title compound (26 mg) was prepared from Intermediate 3.4 (0.15 g, 0.33 mmol), 2-methylpyrazole-3-carboxylic acid (41 mg, 0.33 mmol, CAS: 16034-46-1), HATU (0.15 g, 0.39 mmol) and triethylamine (0.11 mL, 0.82 mmol) in accordance with the procedure described for Example 1. The crude product was purified by reverse phase column chromatography on the Biotage Isolera One™ (30 g C18 column, eluting 30-70% MeCN in pH10 0.1 M $NH_4HCO_3$ buffer solution). LCMS (Method 6): 1.43 min, 516.3 $[M+H]^+$; $^1$H NMR (400 MHz, DMSO-$d_6$) δ: 10.44 (s, 1H), 8.93 (d, 1H), 8.46 (m, 1H), 8.40 (bd, 1H), 7.54 (m, 2H), 7.51-7.40 (m, 4H), 7.38 (d, 1H), 7.34-7.20 (m, 6H), 7.20-7.07 (m, 3H), 6.78 (d, 1H), 5.64 (dd, 1H), 4.65 (d, 1H), 3.91 (s, 3H), 2.22 (s, 3H).

Example 5: (S)-1-methyl-N-(1-oxo-3,3-diphenyl-1-((4-(3-(trifluoromethyl)pyridin-4-yl)phenyl)amino)propan-2-yl)-1H-pyrazole-5-carboxamide

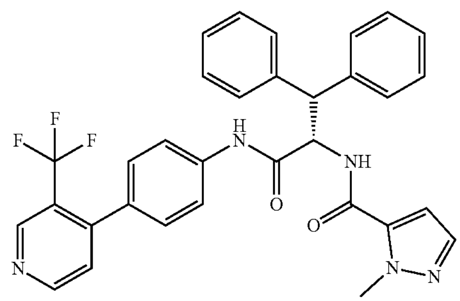 [SMILES: Cn1nccc1C(=O)N[C@H](C(=O)Nc1ccc(-c2ccncc2C(F)(F)F)cc1)C(c1ccccc1)c1ccccc1]

The title compound (22 mg) was prepared from Intermediate 3.5 (0.12 g, 0.16 mmol), 2-methylpyrazole-3-carboxylic acid (22 mg, 0.18 mmol, CAS: 16034-46-1), HATU (67 mg, 0.18 mmol) and triethylamine (0.09 mL, 0.65 mmol) in accordance with the procedure described for Example 1. The crude product was purified by MDAP (Method 1: 50-60% MeCN in 0.1% $NH_4OH$). LCMS (Method 7): 2.68 min, 570.1 $[M+H]^+$; $^1$H NMR (400 MHz, DMSO-$d_6$) δ: 10.46 (s, 1H), 8.98 (s, 1H), 8.91 (d, 1H), 8.85 (d, 1H), 7.53 (m, 2H), 7.49-7.39 (m, 5H), 7.37 (d, 1H), 7.31-7.19 (m, 6H), 7.17-7.07 (m, 2H), 6.77 (d, 1H), 5.63 (dd, 1H), 4.63 (d, 1H), 3.90 (s, 3H).

Example 6: (S)—N-(1-((4-(3,5-dimethylpyridin-4-yl)phenyl)amino)-1-oxo-3,3-diphenylpropan-2-yl)-1-methyl-1H-pyrazole-5-carboxamide

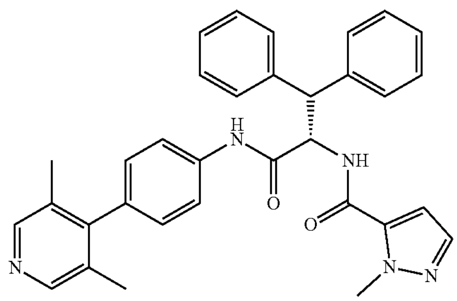 [SMILES: Cc1cncc(C)c1-c1ccc(NC(=O)[C@@H](NC(=O)c2ccnn2C)C(c2ccccc2)c2ccccc2)cc1]

The title compound (154 mg) was prepared from Intermediate 3.6 (0.25 g, 0.51 mmol), 2-methylpyrazole-3-carboxylic acid (70 mg, 0.56 mmol, CAS: 16034-46-1), HATU (0.21 g, 0.56 mmol) and triethylamine (0.28 mL, 2.0 mmol) in accordance with the procedure described for Example 1. The crude product was purified by reverse phase column chromatography on the Biotage Isolera One™ (30 g C18 column, eluting 10-80% 0.1% ammonia/MeCN in pH11 0.1% ammonia/$H_2O$). LCMS (Method 3): 2.30 min, 530.3 $[M+H]^+$; $^1H$ NMR (400 MHz, DMSO-$d_6$) δ: 10.40 (s, 1H), 8.91 (d, 1H), 8.29 (s, 2H), 7.54 (d, 2H), 7.48 (d, 2H), 7.43 (d, 2H), 7.37 (d, 1H), 7.29-7.21 (m, 4H), 7.17-7.08 (m, 2H), 7.06 (d, 2H), 6.77 (d, 1H), 5.64 (dd, 1H), 4.65 (d, 1H), 3.91 (s, 3H), 1.94 (s, 6H).

Example 7: (S)-1-methyl-N-(1-((4-(3-(methylamino)pyridin-4-yl)phenyl)amino)-1-oxo-3,3-diphenylpropan-2-yl)-1H-pyrazole-5-carboxamide

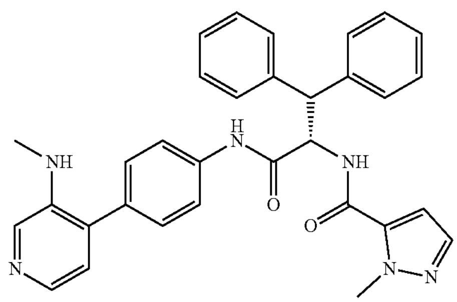 [SMILES: CNc1cnccc1-c1ccc(NC(=O)[C@@H](NC(=O)c2ccnn2C)C(c2ccccc2)c2ccccc2)cc1]

The title compound (70 mg) was prepared from Intermediate 3.7 (0.15 g, 0.28 mmol), 2-methylpyrazole-3-carboxylic acid (37 mg, 0.30 mmol, CAS: 16034-46-1), HATU (0.11 g, 0.30 mmol) and triethylamine (0.20 mL, 1.4 mmol) in accordance with the procedure described for Example 1. The crude product was purified by reverse phase column chromatography on the Biotage Isolera One™ (30 g C18 column, eluting 25-70% MeCN in pH10 0.1 M $NH_4HCO_3$ buffer solution). LCMS (Method 5): 2.06 min, 531.3 $[M+H]^+$; $^1H$ NMR (400 MHz, DMSO-$d_6$) δ: 10.42 (s, 1H), 8.90 (d, 1H), 7.92 (s, 1H), 7.87 (d, 1H), 7.55 (d, 2H), 7.48 (d, 2H), 7.43 (d, 2H), 7.37 (d, 1H), 7.33-7.19 (m, 6H), 7.16-7.07 (m, 2H), 6.90 (d, 1H), 6.76 (d, 1H), 5.64 (dd, 1H), 4.99 (m, 1H), 4.63 (d, 1H), 3.90 (s, 3H), 2.69 (d, 3H).

Example 8: (S)—N-(1-((4-(3-(dimethylamino)pyridin-4-yl)phenyl)amino)-1-oxo-3,3-diphenylpropan-2-yl)-1-methyl-1H-pyrazole-5-carboxamide

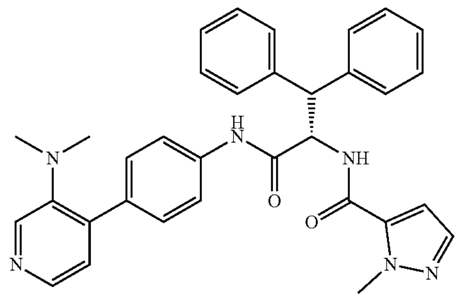 [SMILES: CN(C)c1cnccc1-c1ccc(NC(=O)[C@@H](NC(=O)c2ccnn2C)C(c2ccccc2)c2ccccc2)cc1]

The title compound (0.10 g) was prepared from Intermediate 3.8 (0.14 g, 0.25 mmol), 2-methylpyrazole-3-carboxylic acid (38 mg, 0.31 mmol, CAS: 16034-46-1), HATU (0.12 g, 0.31 mmol) and triethylamine (0.18 mL, 1.3 mmol) in accordance with the procedure described for Example 1. The crude product was purified by reverse phase column chromatography on the Biotage Isolera One™ (30 g C18 column, eluting 25-70% MeCN in pH10 0.1 M $NH_4HCO_3$ buffer solution). LCMS (Method 5): 2.21 min, 545.3 $[M+H]^+$; $^1H$ NMR (400 MHz, DMSO-$d_6$) δ: 10.37 (s, 1H), 8.89 (d, 1H), 8.27 (s, 1H), 8.15 (d, 1H), 7.55-7.39 (m, 8H), 7.37 (d, 1H), 7.30-7.18 (m, 4H), 7.17-7.06 (m, 3H), 6.77 (d, 1H), 5.63 (dd, 1H), 4.63 (d, 1H), 3.91 (s, 3H), 2.51 (s, 6H).

Example 9: (S)—N-(1-((4-(3,5-dimethoxypyridin-4-yl)phenyl)amino)-1-oxo-3,3-diphenylpropan-2-yl)-1-methyl-1H-pyrazole-5-carboxamide

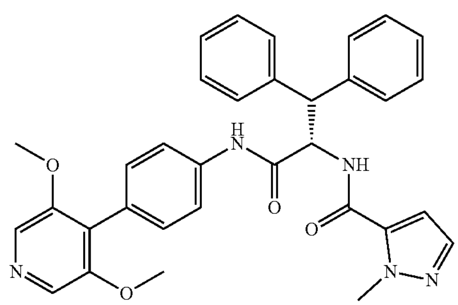 [SMILES: COc1cncc(OC)c1-c1ccc(NC(=O)[C@@H](NC(=O)c2ccnn2C)C(c2ccccc2)c2ccccc2)cc1]

The title compound (92 mg) was prepared from Intermediate 3.9 (0.16 g, 0.30 mmol), 2-methylpyrazole-3-carboxylic acid (46 mg, 0.36 mmol, CAS: 16034-46-1), HATU (0.14 g, 0.36 mmol) and triethylamine (0.17 mL, 1.2 mmol) in accordance with the procedure described for Example 1. The crude product was purified by reverse phase column chromatography on the Biotage Isolera One™ (30 g C18 column, eluting 40-60% MeCN in pH10 0.1 M $NH_4HCO_3$ buffer solution). LCMS (Method 5): 2.10 min, 562.3 $[M+H]^+$; $^1H$ NMR (400 MHz, DMSO-$d_6$) δ: 10.34 (s, 1H), 8.89 (d, 1H), 8.14 (s, 2H), 7.48 (d, 2H), 7.45-7.40 (m, 4H), 7.37 (d, 1H), 7.29-7.21 (m, 4H), 7.16-7.09 (m, 4H), 6.77 (d, 1H), 5.63 (dd, 1H), 4.63 (d, 1H), 3.90 (s, 3H), 3.76 (s, 6H).

Example 10: (S)—N-(1-((4-(3-fluoro-5-methoxypyridin-4-yl)phenyl)amino)-1-oxo-3,3-diphenylpropan-2-yl)-1-methyl-1H-pyrazole-5-carboxamide

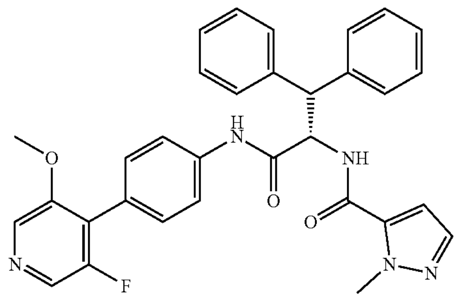 [SMILES: COc1cncc(F)c1-c1ccc(NC(=O)[C@@H](NC(=O)c2ccnn2C)C(c2ccccc2)c2ccccc2)cc1]

The title compound (58 mg) was prepared from Intermediate 3.10 (80 mg, 0.16 mmol), 2-methylpyrazole-3-carboxylic acid (23 mg, 0.62 mmol, CAS: 16034-46-1), HATU (71 mg, 0.19 mmol) and triethylamine (0.09 mL, 0.62 mmol) in accordance with the procedure described for Example 1. The crude product was purified by reverse phase column chromatography on the Biotage Isolera One™ (30 g C18 column, eluting 25-70% MeCN in pH10 0.1 M $NH_4HCO_3$ buffer solution). LCMS (Method 5): 2.18 min, 550.3 $[M+H]^+$; $^1H$ NMR (400 MHz, DMSO-$d_6$) δ: 10.42 (s, 1H), 8.90 (d, 1H), 8.34 (s, 1H), 8.31 (s, 1H), 7.54-7.41 (m, 6H), 7.37 (d, 1H), 7.32-7.21 (m, 6H), 7.17-7.08 (m, 2H), 6.77 (d, 1H), 5.63 (dd, 1H), 4.63 (d, 1H), 3.91 (s, 3H), 3.85 (s, 3H).

Example 11: (S)-1-methyl-N-(1-((4-(2-methyl-6-oxo-1,6-dihydropyridin-3-yl)phenyl)amino)-1-oxo-3,3-diphenylpropan-2-yl)-1H-pyrazole-5-carboxamide

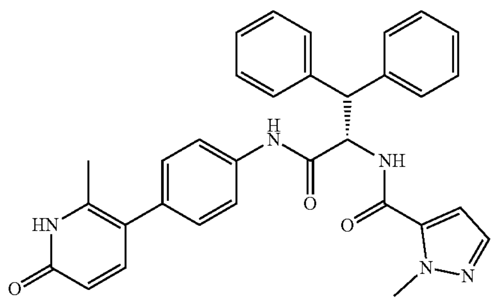

The title compound (55 mg) was prepared from Intermediate 3.11 (89 mg, 0.19 mmol), 2-methylpyrazole-3-carboxylic acid (25 mg, 0.20 mmol, CAS: 16034-46-1), HATU (76 mg, 0.20 mmol) and triethylamine (0.10 mL, 0.73 mmol) in accordance with the procedure described for Example 1. The crude product was purified by reverse phase column chromatography on the Biotage Isolera One™ (30 g C18 column, eluting 10-60% MeCN in pH10 0.1 M $NH_4HCO_3$ buffer solution). LCMS (Method 5): 1.79 min, 532.3 $[M+H]^+$; $^1H$ NMR (400 MHz, DMSO-$d_6$) δ: 11.63 (s, 1H), 10.32 (s, 1H), 8.88 (d, 1H), 7.49-7.40 (m, 6H), 7.36 (d, 1H), 7.32-7.20 (m, 5H), 7.18-7.07 (m, 4H), 6.76 (d, 1H), 6.19 (d, 1H), 5.61 (dd, 1H), 4.62 (d, 1H), 3.90 (s, 3H), 2.12 (s, 3H).

Example 12: (S)—N-(1-((4-(1,4-dimethyl-6-oxo-1,6-dihydropyridin-3-yl)phenyl)amino)-1-oxo-3,3-diphenylpropan-2-yl)-1-methyl-1H-pyrazole-5-carboxamide

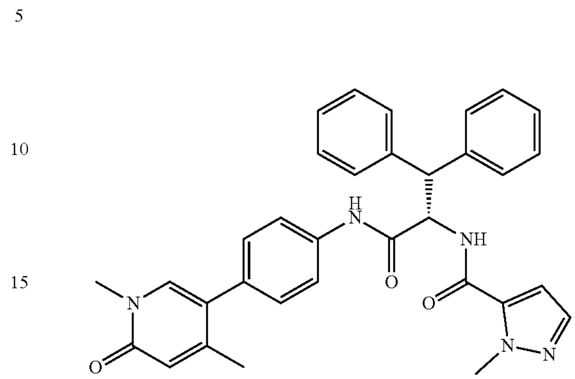

The title compound (38 mg) was prepared from Intermediate 3.12 (0.25 g, 0.53 mmol), 2-methylpyrazole-3-carboxylic acid (67 mg, 0.53 mmol, CAS: 16034-46-1), HATU (0.24 g, 0.63 mmol) and triethylamine (0.18 mL, 1.3 mmol) in accordance with the procedure described for Example 1. The crude product was purified by reverse phase column chromatography on the Biotage Isolera One™ (30 g C18 column, eluting 10-70% MeCN in pH10 0.1 M $NH_4HCO_3$ buffer solution). LCMS (Method 3): 1.96 min, 546.3 $[M+H]^+$; $^1H$ NMR (400 MHz, DMSO-$d_6$) δ: 10.41 (s, 1H), 8.95 (d, 1H), 7.50 (s, 1H), 7.48-7.40 (dd, 6H), 7.39 (dd, 1H), 7.28-7.07 (m, 8H), 6.78 (d, 1H), 6.29 (s, 1H), 5.61 (dd, 1H), 4.64 (d, 1H), 3.90 (s, 3H), 3.39 (s, 3H), 2.01 (s, 3H).

Example 13: (S)—N-(1-((4-(1,2-dimethyl-6-oxo-1,6-dihydropyridin-3-yl)phenyl)amino)-1-oxo-3,3-diphenylpropan-2-yl)-1-methyl-1H-pyrazole-5-carboxamide

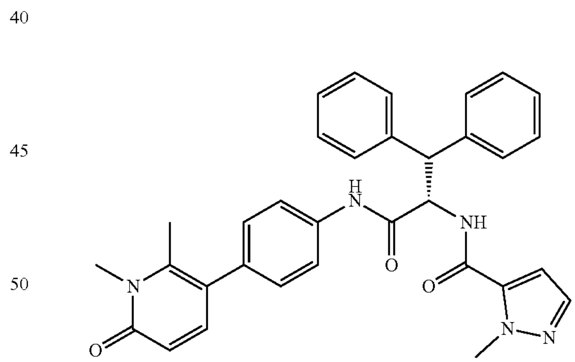

The title compound (97 mg) was prepared from Intermediate 3.13 (0.26 g, 0.55 mmol), 2-methylpyrazole-3-carboxylic acid (69 mg, 0.55 mmol, CAS: 16034-46-1), HATU (0.25 g, 0.66 mmol) and triethylamine (0.19 mL, 1.4 mmol) in accordance with the procedure described for Example 1. The crude product was purified by reverse phase column chromatography on the Biotage Isolera One™ (30 g C18 column, eluting 10-70% MeCN in pH10 0.1 M $NH_4HCO_3$ buffer solution). LCMS (Method 3): 2.06 min, 546.3 $[M+H]^+$; $^1H$ NMR (400 MHz, DMSO-$d_6$) δ: 10.34 (s, 1H), 8.89 (d, 1H), 7.51-7.40 (m, 6H), 7.36 (d, 1H), 7.29-7.20 (m, 5H), 7.16-7.11 (m, 4H), 6.77 (d, 1H), 6.31 (d, 1H), 5.62 (dd, 1H), 4.63 (d, 1H), 3.90 (s, 3H), 3.48 (s, 3H), 2.25 (s, 3H).

Example 14: (S)—N-(1-((4-(3,5-dimethylpyridin-4-yl)-3-fluorophenyl)amino)-1-oxo-3,3-diphenylpropan-2-yl)-1-methyl-1H-pyrazole-5-carboxamide

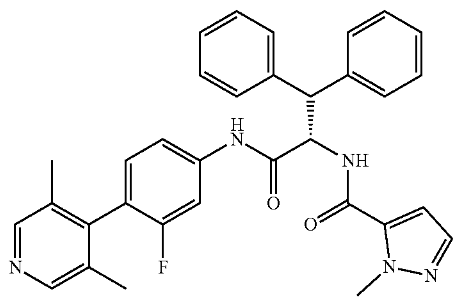 [SMILES: Cc1cncc(C)c1-c1ccc(NC(=O)[C@@H](NC(=O)c2ccnn2C)C(c2ccccc2)c2ccccc2)cc1F]

The title compound (59 mg) was prepared from Intermediate 3.14 (0.10 g, 0.19 mmol), 2-methylpyrazole-3-carboxylic acid (26 mg, 0.21 mmol, CAS: 16034-46-1), HATU (78 mg, 0.21 mmol) and triethylamine (0.07 mL, 0.21 mmol) in accordance with the procedure described for Example 1. The crude product was purified by reverse phase column chromatography on the Biotage Isolera One™ (30 g C18 column, eluting 20-80% 0.1% ammonia/MeCN in 0.1% ammonia/$H_2O$). LCMS (Method 3): 2.40 min, 548.2 $[M+H]^+$; $^1H$ NMR (400 MHz, DMSO-$d_6$) δ: 10.62 (s, 1H), 8.95 (d, 1H), 8.33 (s, 2H), 7.54 (dd, 1H), 7.45 (d, 2H), 7.42 (d, 2H), 7.37 (d, 1H), 7.31-7.22 (m, 5H), 7.17-7.09 (m, 3H), 6.77 (d, 1H), 5.61 (dd, 1H), 4.65 (d, 1H), 3.91 (s, 3H), 1.95 (s, 6H).

Example 15: (S)—N-(1-((3-fluoro-4-(3-methylpyridin-4-yl)phenyl)amino)-1-oxo-3,3-diphenylpropan-2-yl)-1-methyl-1H-pyrazole-5-carboxamide

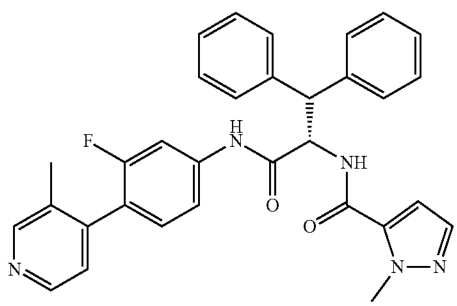 [SMILES: Cc1cnccc1-c1ccc(NC(=O)[C@@H](NC(=O)c2ccnn2C)C(c2ccccc2)c2ccccc2)cc1F]

The title compound (0.11 g) was prepared from Intermediate 3.15 (0.19 g, 0.38 mmol), 2-methylpyrazole-3-carboxylic acid (53 mg, 0.42 mmol, CAS: 16034-46-1), HATU (0.16 g, 0.42 mmol) and triethylamine (0.21 mL, 1.5 mmol) in accordance with the procedure described for Example 1. The crude product was purified by reverse phase column chromatography on the Biotage Isolera One™ (30 g C18 column, eluting 10-60% 0.1% ammonia/MeCN in pH11 0.1% ammonia/$H_2O$). LCMS (Method 3): 2.27 min, 534.3 $[M+H]^+$; $^1H$ NMR (400 MHz, DMSO-$d_6$) δ: 10.63 (s, 1H), 8.96 (d, 1H), 8.50 (s, 1H), 8.42 (d, 1H), 7.52 (dd, 1H), 7.47-7.40 (m, 4H), 7.37 (d, 1H), 7.30-7.21 (m, 6H), 7.19-7.09 (m, 3H), 6.77 (d, 1H), 5.61 (dd, 1H), 4.64 (d, 1H), 3.91 (s, 3H), 2.10 (s, 3H).

Example 16: (S)—N-(1-((4-(1,2-dimethyl-6-oxo-1,6-dihydropyridin-3-yl)-3-fluorophenyl)amino)-1-oxo-3,3-diphenylpropan-2-yl)-1-methyl-1H-pyrazole-5-carboxamide

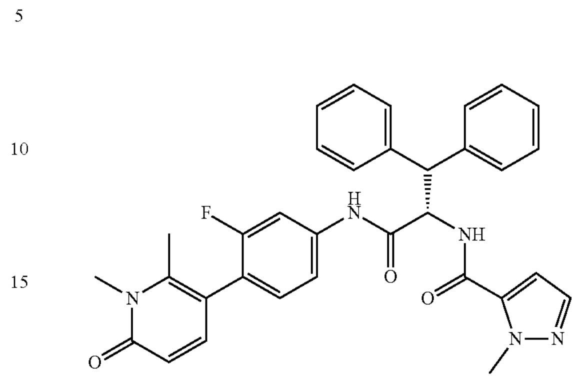

The title compound (50 mg) was prepared from Intermediate 3.16 (0.10 g, 0.21 mmol), 2-methylpyrazole-3-carboxylic acid (29 mg, 0.23 mmol, CAS: 16034-46-1), HATU (88 mg, 0.23 mmol) and triethylamine (0.12 mL, 0.85 mmol) in accordance with the procedure described for Example 1. The crude product was purified by flash column chromatography (eluting 4% MeOH in DCM) and by reverse phase column chromatography on the Biotage Isolera One™ (30 g C18 column, eluting 20-60% 0.1% ammonia/MeCN in pH11 0.1% ammonia/$H_2O$). LCMS (Method 3): 2.12 min, 564.2 $[M+H]^+$; $^1H$ NMR (400 MHz, DMSO-$d_6$) δ: 10.56 (bs, 1H), 8.93 (d, 1H), 7.52-7.39 (m, 5H), 7.37 (d, 1H), 7.30-7.08 (m, 9H), 6.76 (d, 1H), 6.32 (d, 1H), 5.60 (dd, 1H), 4.63 (d, 1H), 3.90 (s, 3H), 3.48 (s, 3H), 2.15 (s, 3H).

Example 17: (S)—N-(1-((4-(1,4-dimethyl-6-oxo-1,6-dihydropyridin-3-yl)-3-fluorophenyl)amino)-1-oxo-3,3-diphenylpropan-2-yl)-1-methyl-1H-pyrazole-5-carboxamide

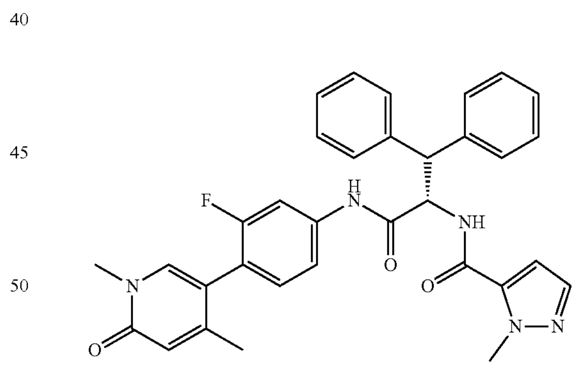

The title compound (60 mg) was prepared from Intermediate 3.17 (0.14 g, 0.29 mmol), 2-methylpyrazole-3-carboxylic acid (40 mg, 0.32 mmol, CAS: 16034-46-1), HATU (0.12 g, 0.32 mmol) and triethylamine (0.16 mL, 1.1 mmol) in accordance with the procedure described for Example 1. The crude product was purified by reverse phase column chromatography on the Biotage Isolera One™ (30 g C18 column, eluting 10-50% 0.1% ammonia/MeCN in pH11 0.1% ammonia/$H_2O$). LCMS (Method 3): 2.11 min, 564.3 $[M+H]^+$; $^1H$ NMR (400 MHz, DMSO-$d_6$) δ: 10.57 (s, 1H), 8.95 (d, 1H), 7.55 (s, 1H), 7.48-7.39 (m, 5H), 7.37 (d, 1H), 7.30-7.07 (m, 8H), 6.77 (d, 1H), 6.31 (s, 1H), 5.59 (dd, 1H), 4.63 (d, 1H), 3.89 (s, 3H), 3.39 (s, 3H), 1.89 (s, 3H).

Example 18: N-((2S)-1-((3-fluoro-4-(3-fluoro-5-methoxypyridin-4-yl)phenyl)amino)-1-oxo-3,3-diphenylpropan-2-yl)-1-methyl-1H-pyrazole-5-carboxamide

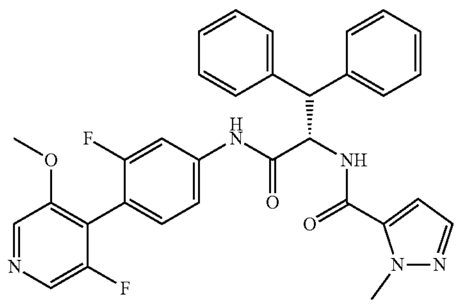 [SMILES: COc1cncc(F)c1-c1ccc(NC(=O)[C@@H](NC(=O)c2ccnn2C)C(c2ccccc2)c2ccccc2)cc1F]

The title compound (47 mg) was prepared from Intermediate 3.18 (95 mg, 0.18 mmol), 2-methylpyrazole-3-carboxylic acid (25 mg, 0.20 mmol, CAS: 16034-46-1), HATU (75 mg, 0.20 mmol) and triethylamine (0.10 mL, 0.71 mmol) in accordance with the procedure described for Example 1. The crude product was purified by reverse phase column chromatography on the Biotage Isolera One™ (30 g C18 column, eluting 10-70% 0.1% ammonia/MeCN in pH11 0.1% ammonia/$H_2O$). LCMS (Method 3): 2.44 min, 568.2 $[M+H]^+$; $^1H$ NMR (400 MHz, DMSO-$d_6$) δ: 10.67 (s, 1H), 8.97 (d, 1H), 8.39 (s, 1H), 8.35 (s, 1H), 7.51 (bd, 1H), 7.48-7.40 (m, 4H), 7.38 (d, 1H), 7.34-7.21 (m, 6H), 7.18-7.08 (m, 2H), 6.81 (d, 1H), 5.61 (dd, 1H), 4.64 (d, 1H), 3.91 (s, 3H), 3.87 (s, 3H).

Example 19: (S)—N-(1,1-bis(4-fluorophenyl)-3-((4-(3-methoxypyridin-4-yl)phenyl)amino)-3-oxopropan-2-yl)-1-methyl-1H-pyrazole-5-carboxamide

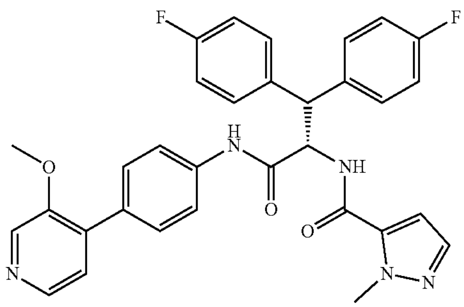 [SMILES: COc1cnccc1-c1ccc(NC(=O)[C@@H](NC(=O)c2ccnn2C)C(c2ccc(F)cc2)c2ccc(F)cc2)cc1]

The title compound (0.12 g) was prepared from Intermediate 3.19 (0.24 g, 0.44 mmol), 2-methylpyrazole-3-carboxylic acid (62 mg, 0.49 mmol, CAS: 16034-46-1), HATU (0.19 g, 0.49 mmol) and triethylamine (0.19 mL, 1.34 mmol) in accordance with the procedure described for Example 1. The crude product was purified by flash column chromatography (eluting with 100% EtOAc) and by reverse phase column chromatography on the Biotage Isolera One™ (30 g C18 column, eluting 40-70% MeCN in pH10 0.1 M $NH_4HCO_3$ buffer solution). LCMS (Method 5): 2.15 min, 568.3 $[M+H]^+$; $^1H$ NMR (400 MHz, DMSO-$d_6$) δ: 10.39 (s, 1H), 8.93 (s, 1H), 8.41 (s, 1H), 8.23 (d, 1H), 7.56-7.41 (m, 8H), 7.39 (d, 1H), 7.29 (d, 1H), 7.19-6.99 (m, 4H), 6.79 (d, 1H), 5.57 (dd, 1H), 4.65 (d, 1H), 3.93 (s, 3H), 3.86 (s, 3H).

Example 20: (S)—N-(1-((4-(3-methoxypyridin-4-yl)-3-methylphenyl)amino)-1-oxo-3,3-diphenylpropan-2-yl)-1-methyl-1H-pyrazole-5-carboxamide

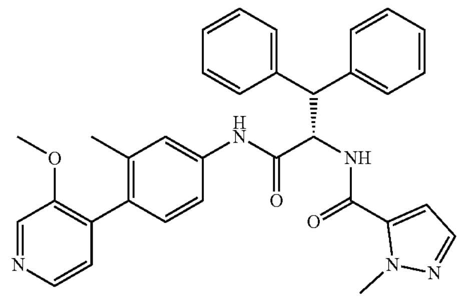 [SMILES: COc1cnccc1-c1ccc(NC(=O)[C@@H](NC(=O)c2ccnn2C)C(c2ccccc2)c2ccccc2)cc1C]

To a solution of Intermediate 4.1 (0.19 g, 0.56 mmol), Intermediate 1.20 (0.13 g, 0.56 mmol) and 2,4,6-collidine (0.18 mL, 1.4 mmol) in EtOAc (8 mL) and MeCN (2 mL) was added T3P® (50% w/w solution in EtOAc; 1 mL, 1.7 mmol) and the reaction stirred at rt for 16 h. The reaction was diluted with saturated aqueous $NaHCO_3$ and extracted into EtOAc. The combined organics were washed with water, dried over $MgSO_4$, filtered and concentrated in vacuo. The crude product was purified by reverse phase column chromatography on the Biotage Isolera One™ (30 g C18 column, eluting 30-70% MeCN in pH10 0.1 M $NH_4HCO_3$ buffer solution) to afford the title compound (98 mg). LCMS (Method 6): 1.63 min, 545.9 $[M+H]^+$; $^1H$ NMR (400 MHz, DMSO-$d_6$) δ: 10.27 (s, 1H), 8.87 (d, 1H), 8.38 (s, 1H), 8.21 (d, 1H), 7.43 (dd, 4H), 7.34 (d, 1H), 7.20-7.28 (m, 6H), 7.05-7.13 (m, 3H), 6.95 (d, 1H), 6.75 (d, 1H), 5.60 (dd, 1H), 4.60 (d, 1H), 3.82-4.01 (m, 3H), 3.75 (d, 3H), 2.00 (t, 3H).

Example 21: (S)—N-(1-((4-(1H-pyrrolo[2,3-b]pyridin-4-yl)phenyl)amino)-1-oxo-3,3-diphenylpropan-2-yl)-1-methyl-1H-pyrazole-5-carboxamide

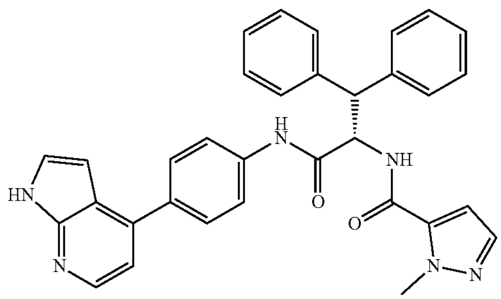 [SMILES: Cn1nccc1C(=O)N[C@H](C(=O)Nc1ccc(-c2ccnc3[nH]ccc23)cc1)C(c1ccccc1)c1ccccc1]

To a stirred solution of Intermediate 4.1 (0.10 g, 0.29 mmol) and Intermediate 1.21 (60 mg, 0.29 mmol) in MeCN (10 mL) at rt was added DIPEA (0.1 mL, 0.57 mmol) and T3P® (50% w/w solution in EtOAc; 0.55 mL, 0.86 mmol) and the reaction mixture stirred at rt for 20 h. The reaction mixture was diluted with saturated aqueous $NaHCO_3$ and the crude product was extracted into EtOAc. The combined organics were washed with brine, dried over $Na_2SO_4$, filtered and concentrated in vacuo. The crude product was purified by reverse phase column chromatography on the Biotage Isolera One™ (30 g 018 column, eluting 30-70% MeCN in pH10 0.1 M $NH_4HCO_3$ buffer solution) and by MDAP (Method 1: 40-50% MeCN in 0.1% $NH_4OH$) to afford the title compound (8.1 mg). LCMS (Method 6): 1.80 min, 540.8 $[M+H]^+$; $^1H$ NMR (400 MHz, DMSO-$d_6$) δ: 11.73 (bs, 1H), 10.43 (s, 1H), 8.91 (d, 1H), 8.23 (d, 1H), 7.66 (d, 2H), 7.60 (d, 2H), 7.53-7.40 (m, 5H), 7.37 (d, 1H), 7.32-7.19 (m, 4H), 7.18-7.06 (m, 3H), 6.78 (d, 1H), 6.59 (m, 1H), 5.65 (dd, 1H), 4.64 (d, 1H), 3.91 (s, 3H).

Example 22: (S)—N-(1-((4-(2,3-dihydro-1H-pyrrolo[2,3-b]pyridin-4-yl)phenyl)amino)-1-oxo-3,3-diphenylpropan-2-yl)-1-methyl-1H-pyrazole-5-carboxamide

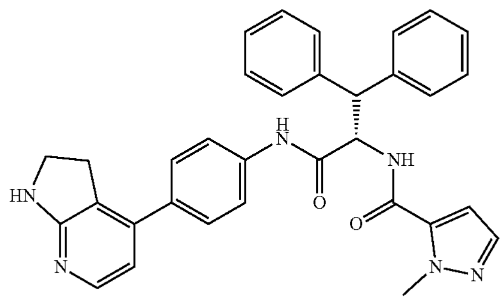 [SMILES: Cn1nccc1C(=O)N[C@H](C(=O)Nc1ccc(-c2ccnc3c2CCN3)cc1)C(c1ccccc1)c1ccccc1]

The title compound (14 mg) was prepared from Intermediate 1.22 (35 mg, 0.17 mmol), Intermediate 4.1 (58 mg, 0.17 mmol), T3P® (50% w/w solution in EtOAc; 0.32 mL, 0.50 mmol) and DIPEA (0.06 mL, 0.33 mmol) in accordance with the procedure described for Example 21. The crude product was purified by reverse phase column chromatography on the Biotage Isolera One™ (30 g C18 column, eluting 30-70% MeCN in pH10 0.1 M $NH_4HCO_3$ buffer solution) and MDAP (Method 1: 40% MeCN in 10 mM $NH_4HCO_3$ pH10). LCMS (Method 5): 2.02 min, 543.3 $[M+H]^+$; $^1H$ NMR (400 MHz, DMSO-$d_6$): δ 10.38 (s, 1H), 8.89 (d, 1H), 7.71 (d, 1H), 7.51 (d, 2H), 7.48-7.39 (m, 6H), 7.37 (d, 1H), 7.30-7.18 (m, 4H), 7.18-7.04 (m, 2H), 6.77 (d, 1H), 6.47 (d, 1H), 6.35 (s, 1H), 5.62 (dd, 1H), 4.63 (d, 1H), 3.90 (s, 3H), 3.42 (t, 2H), 3.06 (t, 2H).

Example 23: (S)—N-(1-((2-fluoro-4-(3-methoxypyridin-4-yl)phenyl)amino)-1-oxo-3,3-diphenylpropan-2-yl)-1-methyl-1H-pyrazole-5-carboxamide

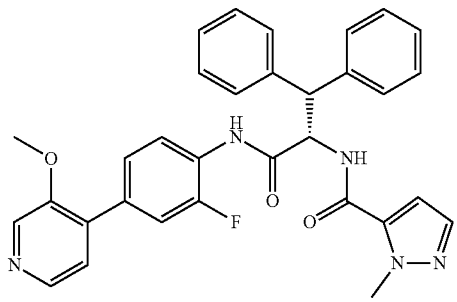 [SMILES: COc1cnccc1-c1ccc(NC(=O)[C@@H](NC(=O)c2ccnn2C)C(c2ccccc2)c2ccccc2)c(F)c1]

The title compound (61 mg) was prepared from Intermediate 1.23 (80 mg, 0.37 mmol), Intermediate 4.1 (0.14 g, 0.40 mmol), T3P® (50% w/w solution in EtOAc; 0.65 mL, 1.1 mmol) and triethylamine (0.15 mL, 1.1 mmol) in accordance with the procedure described for Example 21. An additional portion of T3P® (50% w/w solution in EtOAc; 0.30 mL, 0.51 mmol) was added after 2 h. The crude product was purified by reverse phase column chromatography on the Biotage Isolera One™ (30 g C18 column, eluting 25-70% MeCN in pH10 0.1 M $NH_4HCO_3$ buffer solution). LCMS (Method 9): 2.30 min, 550.3 $[M+H]^+$; $^1H$ NMR (400 MHz, DMSO-$d_6$) δ: 10.09 (d, 1H), 8.85 (d, 1H), 8.44 (s, 1H), 8.25 (d, 1H), 7.57-7.41 (m, 6H), 7.37 (d, 1H), 7.33 (d, 1H), 7.30-7.20 (m, 5H), 7.17-7.10 (m, 2H), 6.76 (d, 1H), 5.83 (dd, 1H), 4.62 (d, 1H), 3.92 (s, 3H), 3.88 (s, 3H).

Example 24: (S)—N-(1-((3-fluoro-4-(3-methoxypyridin-4-yl)phenyl)amino)-1-oxo-3,3-diphenylpropan-2-yl)-1-methyl-1H-pyrazole-5-carboxamide

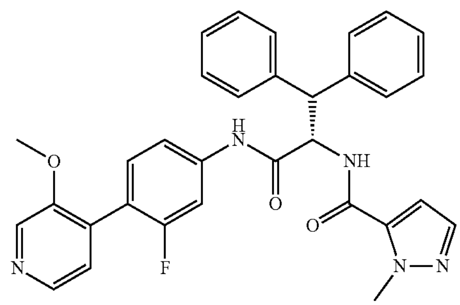 [SMILES: COc1cnccc1-c1ccc(NC(=O)[C@@H](NC(=O)c2ccnn2C)C(c2ccccc2)c2ccccc2)cc1F]

The title compound (38 mg) was prepared from Intermediate 1.24 (80 mg, 0.37 mmol), Intermediate 4.1 (0.14 g, 0.40 mmol) T3P® (50% w/w solution in EtOAc; 0.70 mL, 1.1 mmol) and triethylamine (0.15 mL, 1.1 mmol) in accordance with the procedure described for Example 21. The crude product was purified by reverse phase column chromatography on the Biotage Isolera One™ (30 g C18 column, eluting 25-70% MeCN in pH10 0.1 M $NH_4HCO_3$ buffer solution). LCMS (Method 5): 2.14 min, 550.2 $[M+H]^+$; $^1H$ NMR (400 MHz, DMSO-$d_6$) δ: 10.58 (s, 1H), 8.93 (s, 1H), 8.44 (s, 1H), 8.25 (d, 1H), 7.49-7.40 (m, 5H), 7.37 (d, 1H), 7.32-7.19 (m, 7H), 7.19-7.08 (m, 2H), 6.77 (d, 1H), 5.61 (dd, 1H), 4.63 (d, 1H), 3.91 (s, 3H), 3.84 (s, 3H).

Example 25: (S)-3-methoxy-4-(4-(2-(1-methyl-1H-pyrazole-5-carboxamido)-3,3-diphenylpropanamido)phenyl)pyridine 1-oxide

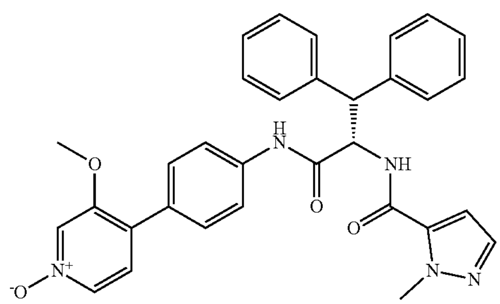

To a stirred solution of Example 3 (0.15 g, 0.27 mmol) in EtOAc (12 mL) at rt was added mCPBA (98 mg, 0.40 mmol) and the reaction mixture stirred for 2 h. The reaction mixture was diluted with 10% aqueous sodium thiosulfate and the crude product extracted into EtOAc. The combined organics were washed with brine, dried over $Na_2SO_4$, filtered and concentrated in vacuo. The crude product was purified by reverse phase column chromatography on the Biotage Isolera One™ (30 g C18 column, eluting 20-60% MeCN in pH10 0.1 M $NH_4HCO_3$ buffer solution) to afford the title compound (86 mg). LCMS (Method 5): 1.76 min, 548.3 $[M+H]^+$; $^1H$ NMR (400 MHz, DMSO-$d_6$) δ: 10.37 (s, 1H), 8.89 (d, 1H), 8.14 (d, 1H), 7.92 (dd, 1H), 7.50-7.40 (m, 8H), 7.37 (d, 1H), 7.30 (d, 1H), 7.29-7.19 (m, 4H), 7.17-7.06 (m, 2H), 6.77 (d, 1H), 5.62 (dd, 1H), 4.62 (d, 1H), 3.90 (s, 3H), 3.82 (s, 3H).

Example 26: (S)-3,5-dimethyl-4-(4-(2-(1-methyl-1H-pyrazole-5-carboxamido)-3,3-diphenylpropanamido)phenyl)pyridine 1-oxide

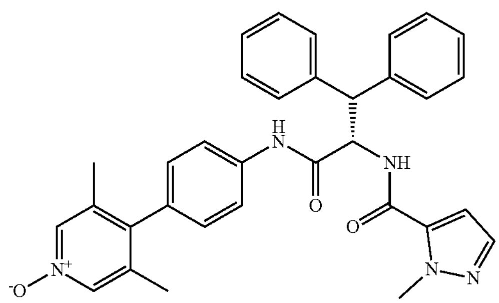

The title compound (13 mg) was prepared from Example 6 (40 mg, 0.07 mmol) and mCPBA (27 mg, 0.11 mmol) in accordance with the procedure described for Example 25. The crude product was purified by reverse phase column chromatography on the Biotage Isolera One™ (12 g C18 column, eluting 10-70% MeCN in pH10 0.1 M $NH_4HCO_3$ buffer solution). LCMS (Method 3): 1.81 min, 546.3 $[M+H]^+$; $^1H$ NMR (400 MHz, DMSO-$d_6$) δ: 10.47 (s, 1H), 8.97 (s, 1H), 8.07 (s, 2H), 7.54 (d, 2H), 7.47 (d, 2H), 7.42 (d, 2H), 7.36 (d, 1H), 7.29-7.21 (m, 4H), 7.16-7.04 (m, 4H), 6.78 (d, 1H), 5.62 (dd, 1H), 4.67 (d, 1H), 3.90 (s, 3H), 1.89 (s, 6H).

Example 27: (S)-3,5-dimethoxy-4-(4-(2-(1-methyl-1H-pyrazole-5-carboxamido)-3,3-diphenylpropanamido)phenyl)pyridine 1-oxide

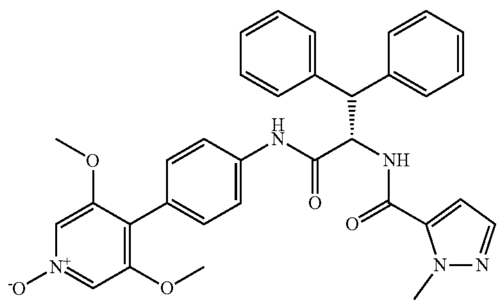

The title compound (38 mg) was prepared from Example 9 (40 mg, 0.07 mmol) and mCPBA (26 mg, 0.11 mmol) in accordance with the procedure described for Example 25. The crude product was purified by reverse phase column chromatography on the Biotage Isolera One™ (30 g C18 column, eluting 10-60% MeCN in pH10 0.1 M $NH_4HCO_3$ buffer solution). LCMS (Method 5): 1.81 min, 578.3 $[M+H]^+$; $^1H$ NMR (400 MHz, DMSO-$d_6$) δ: 10.34 (s, 1H), 8.89 (d, 1H), 7.92 (s, 2H), 7.47 (d, 2H), 7.44-7.39 (m, 4H), 7.37 (d, 1H), 7.29-7.21 (m, 4H), 7.17-7.09 (m, 4H), 6.76 (d, 1H), 5.62 (dd, 1H), 4.63 (d, 1H), 3.90 (s, 3H), 3.71 (s, 6H).

Example 28: (S)-3-fluoro-5-methoxy-4-(4-(2-(1-methyl-1H-pyrazole-5-carboxamido)-3,3-diphenylpropanamido)phenyl)pyridine 1-oxide

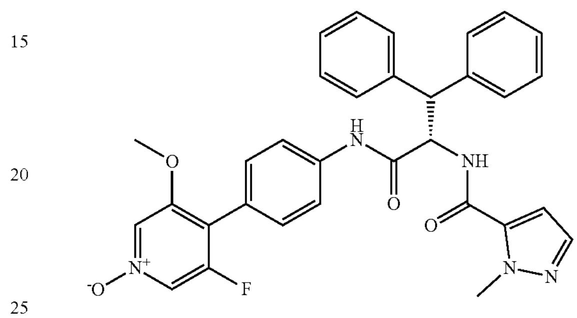

The title compound (7 mg) was prepared from Example 10 (18 mg, 0.03 mmol) and mCPBA (12 mg, 0.05 mmol) in accordance with the procedure described for Example 25. The crude product was purified by reverse phase column chromatography on the Biotage Isolera One™ (30 g C18 column, eluting 0-80% 0.1% ammonia/MeCN in pH11 0.1% ammonia/$H_2O$). LCMS (Method 3): 1.93 min, 566.3 $[M+H]^+$; $^1H$ NMR (400 MHz, DMSO-$d_6$) δ: 10.41 (s, 1H), 8.90 (d, 1H), 8.29 (dd, 1H), 8.11 (s, 1H), 7.51-7.41 (m, 6H), 7.37 (d, 1H), 7.30-7.21 (m, 6H), 7.16-7.08 (m, 2H), 6.77 (d, 1H), 5.62 (dd, 1H), 4.62 (d, 1H), 3.90 (s, 3H), 3.79 (s, 3H).

Example 29: (S)—N-(1-((4-(1,2-dimethyl-6-oxo-1,6-dihydropyridin-3-yl)-3,5-difluorophenyl)amino)-1-oxo-3,3-diphenylpropan-2-yl)-1-methyl-1H-pyrazole-5-carboxamide

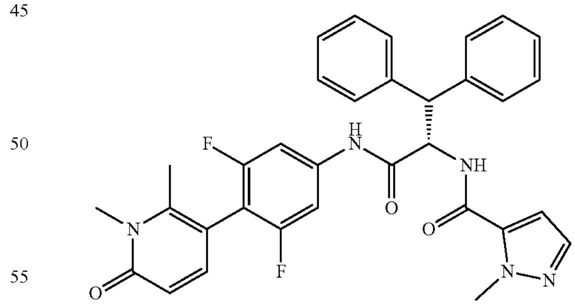

The title compound (10 mg) was prepared from Intermediate 3.29 (32 mg, 0.06 mmol), 2-methylpyrazole-3-carboxylic acid (12 mg, 0.09 mmol, CAS: 16034-46-1), HATU (36 mg, 0.09 mmol) and triethylamine (0.20 mL, 1.4 mmol) in accordance with the procedure described for Example 1. The crude product was purified by reverse phase column chromatography on the Biotage Isolera One™ (12 g C18 column, eluting 15-65% 0.1% ammonia/MeCN in pH11 0.1% ammonia/$H_2O$). LCMS (Method 3): 2.16 min, 582.2 $[M+H]^+$; $^1H$ NMR (400 MHz, DMSO-$d_6$) δ: 10.73 (s, 1H), 8.97 (d, 1H), 7.38-7.44 (m, 5H), 7.11-7.31 (m, 9H), 6.77 (d, 1H), 6.35 (d, 1H), 5.57 (dd, 1H), 4.64 (d, 1H), 3.92 (s, 3H), 3.50 (s, 3H), 2.16 (d, 3H).

Example 30: (S)—N-(1-((3,5-difluoro-4-(3-methoxypyridin-4-yl)phenyl)amino)-1-oxo-3,3-diphenylpropan-2-yl)-1-methyl-1H-pyrazole-5-carboxamide

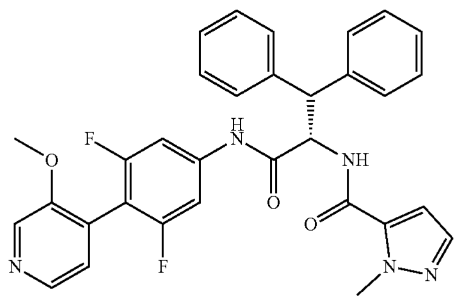 [SMILES: COc1cnccc1-c1c(F)cc(NC(=O)[C@@H](NC(=O)c2ccnn2C)C(c2ccccc2)c2ccccc2)cc1F]

The title compound (35 mg) was prepared from Intermediate 3.30 (0.12 g, 0.23 mmol), 2-methylpyrazole-3-carboxylic acid (35 mg, 0.28 mmol, CAS: 16034-46-1), HATU (0.11 g, 0.28 mmol) and DIPEA (0.16 mL, 0.92 mmol) in accordance with the procedure described for Example 1. The crude product was purified by reverse phase column chromatography on the Biotage Isolera One™ (30 g C18 column, eluting 0-80% 0.1% ammonia/MeCN in pH11 0.1% ammonia/$H_2O$). LCMS (Method 3): 2.30 min, 568.3 $[M+H]^+$; $^1H$ NMR (300 MHz, DMSO-$d_6$) δ: 10.73 (s, 1H), 8.95 (d, 1H), 8.47 (s, 1H), 8.25 (d, 1H), 7.38-7.42 (m, 4H), 7.35 (d, 1H), 7.18-7.27 (m, 7H), 7.08-7.14 (m, 2H), 6.74 (d, 1H), 5.50-5.57 (m, 1H), 4.60 (d, 1H), 3.89 (s, 3H), 3.82 (s, 3H).

Example 31: (S)—N-(1-((4-(1-benzyl-3,5-dimethyl-1H-pyrazol-4-yl)phenyl)amino)-1-oxo-3,3-diphenylpropan-2-yl)-1-methyl-1H-pyrazole-5-carboxamide

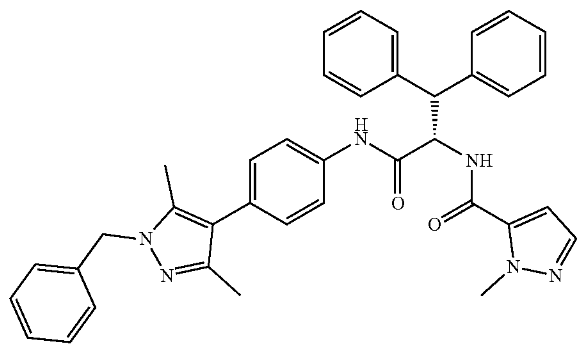 [SMILES: Cc1nn(Cc2ccccc2)c(C)c1-c1ccc(NC(=O)[C@@H](NC(=O)c2ccnn2C)C(c2ccccc2)c2ccccc2)cc1]

The title compound (0.16 g) was prepared from Intermediate 3.31 (0.13 g, 0.24 mmol), 2-methylpyrazole-3-carboxylic acid (30 mg, 0.24 mmol, CAS: 16034-46-1), HATU (0.11 g, 0.29 mmol) and triethylamine (0.08 mL, 0.60 mmol) in accordance with the procedure described for Example 1. The crude product was purified by flash column chromatography on the Biotage Isolera One™ (10 g ZIP sphere silica column, eluting 30-100% EtOAc in heptanes). LCMS (Method 3): 2.65 min, 609.3 $[M+H]^+$; $^1H$ NMR (400 MHz, DMSO-$d_6$) δ: 10.27 (s, 1H), 8.86 (d, 1H), 7.42 (q, 6H), 7.28-7.33 (m, 3H), 7.21 (q, 5H), 7.05-7.13 (m, 6H), 6.73 (d, 1H), 5.59 (dd, 1H), 5.18 (d, 2H), 4.60 (d, 1H), 3.78-3.93 (m, 3H), 2.03-2.17 (m, 6H).

Example 32: (S)—N-(1-((4-(3,5-dimethyl-1H-pyrazol-4-yl)phenyl)amino)-1-oxo-3,3-diphenylpropan-2-yl)-1-methyl-1H-pyrazole-5-carboxamide

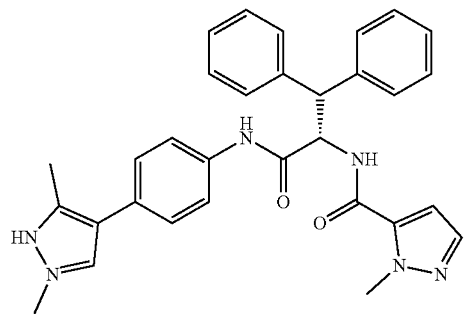

To a solution of Example 31 (0.16 g, 0.17 mmol) in ethanol (8 mL) and THF (4 mL) was added 20% palladium hydroxide on carbon (25 mg, 0.17 mmol) and the reaction stirred at rt under an atmosphere of hydrogen for 5 d. The reaction mixture was filtered through a pad of Celite*, washed with EtOAc and concentrated in vacuo. The crude product was purified by reverse phase column chromatography on the Biotage Isolera One™ (30 g C18 column, eluting 10-70% MeCN in pH10 0.1 M $NH_4HCO_3$ buffer solution) to afford the title compound (23 mg). LCMS (Method 3): 2.11 min, 519.3 $[M+H]^+$; $^1H$ NMR (400 MHz, DMSO-$d_6$) δ: 12.16 (s, 1H), 10.26 (s, 1H), 8.86 (d, 1H), 7.44 (d, 2H), 7.38-7.41 (m, 4H), 7.33 (d, 1H), 7.22 (q, 4H), 7.06-7.11 (m, 4H), 6.73 (d, 1H), 5.59 (dd, 1H), 4.60 (d, 1H), 3.84 (d, 3H), 2.13 (d, 6H).

Example 33: N—((S)-2-((4-(1,2-dimethyl-6-oxo-1,6-dihydropyridin-3-yl)phenyl)amino)-1-((1r,4S)-4-methylcyclohexyl)-2-oxoethyl)-1-methyl-1H-pyrazole-5-carboxamide

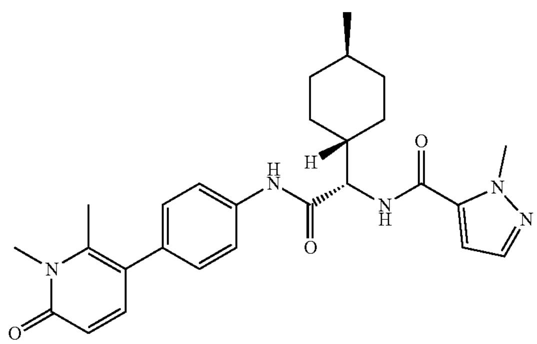 [SMILES: Cc1c(-c2ccc(NC(=O)[C@@H](NC(=O)c3ccnn3C)[C@H]3CC[C@H](C)CC3)cc2)ccc(=O)n1C]

The title compound (37 mg) was prepared from Intermediate 3.33 (0.11 g, 0.27 mmol), 2-methylpyrazole-3-carboxylic acid (41 mg, 0.33 mmol, CAS: 16034-46-1), HATU (0.13 g, 0.33 mmol) and triethylamine (0.15 mL, 1.1 mmol) in accordance with the procedure described for Example 1.

The crude product was purified by reverse phase column chromatography on the Biotage Isolera One™ (30 g C18 column, eluting 10-80% 0.1% ammonia/MeCN in 0.1% ammonia/$H_2O$). LCMS (Method 3): 2.05 min, 476.3 $[M+H]^+$; $^1H$ NMR (400 MHz, DMSO-$d_6$) δ: 10.29 (s, 1H), 8.52 (d, 1H), 7.69 (d, 2H), 7.46 (d, 1H), 7.29 (d, 1H), 7.21 (d, 2H), 7.07 (d, 1H), 6.34 (d, 1H), 4.38 (t, 1H), 4.03 (s, 3H), 3.50 (s, 3H), 2.30 (s, 3H), 1.90-1.54 (m, 5H), 1.37-0.98 (m, 3H), 0.94-0.81 (m, 5H).

Example 34: (S)-1-ethyl-N-(1-((3-fluoro-4-(6-oxo-1,6-dihydropyridazin-3-yl)phenyl)amino)-1-oxo-3,3-diphenylpropan-2-yl)-1H-pyrazole-5-carboxamide

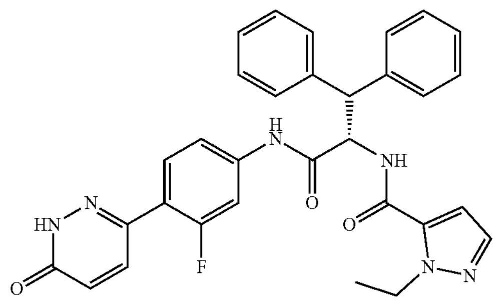 [SMILES: CCn1nccc1C(=O)N[C@H](C(=O)Nc1ccc(-c2ccc(=O)[nH]n2)c(F)c1)C(c1ccccc1)c1ccccc1]

The title compound (23 mg) was prepared from Intermediate 3.34 (60 mg, 0.1 mmol), 2-ethylpyrazole-3-carboxylic acid (16 mg, 0.12 mmol, CAS: 400755-43-3), HATU (45 mg, 0.12 mmol) and DIPEA (0.07 mL, 0.39 mmol) in accordance with the procedure described for Example 1. The crude product was purified by flash column chromatography (eluting 0-2% MeOH in EtOAc) and automated reverse phase column chromatography on the Biotage Isolera One™ (30 g C18 column, eluting 0-80% 0.1% ammonia/MeCN in pH11 0.1% ammonia/$H_2O$). LCMS (Method 3): 1.88 min, 551.2 $[M+H]^+$; $^1H$ NMR (400 MHz, DMSO-$d_6$) δ: 10.62 (s, 1H), 8.97 (d, 1H), 7.67 (dd, 1H), 7.57-7.50 (m, 2H), 7.43-7.38 (m, 5H), 7.29-7.20 (m, 5H), 7.12 (td, 2H), 6.94 (d, 1H), 6.73 (d, 1H), 5.61 (dd, 1H), 4.62 (d, 1H), 4.43-4.25 (m, 2H), 1.15 (t, 3H).

Example 35: (S)—N-(1-((3-fluoro-4-(2-oxo-1,2-dihydropyridin-4-yl)phenyl)amino)-1-oxo-3,3-diphenylpropan-2-yl)-1-methyl-1H-pyrazole-5-carboxamide

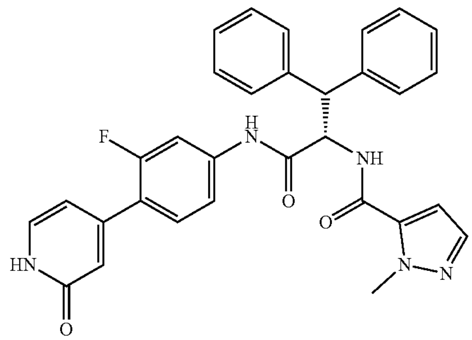 [SMILES: Cn1nccc1C(=O)N[C@H](C(=O)Nc1ccc(-c2cc[nH]c(=O)c2)c(F)c1)C(c1ccccc1)c1ccccc1]

The title compound (70 mg) was prepared from Intermediate 3.35 (0.15 g, 0.33 mmol), 2-methylpyrazole-3-carboxylic acid (46 mg, 0.36 mmol, CAS: 16034-46-1), HATU (0.14 g, 0.36 mmol) and triethylamine (0.14 mL, 0.990 mmol) in accordance with the procedure described for Example 1. The crude product was purified by reverse phase column chromatography on the Biotage Isolera One™ (30 g C18 column, eluting 10-50% 0.1% ammonia/MeCN in pH11 0.1% ammonia/$H_2O$). LCMS (Method 3): 1.90 min, 536.2 $[M+H]^+$; $^1H$ NMR (300 MHz, DMSO-$d_6$) δ: 11.56 (s, 1H), 10.59 (s, 1H), 8.92 (d, 1H), 7.04-7.48 (m, 15H), 6.74 (d, 1H), 6.36 (s, 1H), 6.26 (d, 1H), 5.53-5.59 (m, 1H), 4.59 (d, 1H), 3.88 (s, 3H).

Example 36: (S)—N-(1-((4-(3-fluoropyridin-4-yl)phenyl)amino)-1-oxo-3,3-diphenylpropan-2-yl)-1-methyl-1H-pyrazole-5-carboxamide

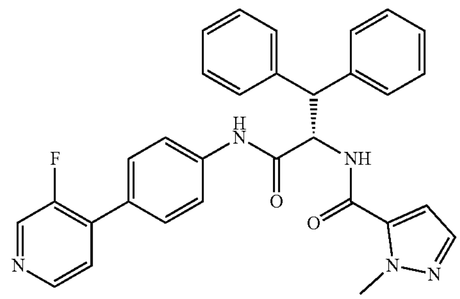

The title compound (42 mg) was prepared from Intermediate 3.36 (0.18 g, 0.24 mmol), 2-methylpyrazole-3-carboxylic acid (31 mg, 0.24 mmol, CAS: 16034-46-1), HATU (0.11 g, 0.29 mmol) and triethylamine (0.1 mL, 0.73 mmol) in accordance with the procedure described for Example 1. The crude product was purified by reverse phase column chromatography on the Biotage Isolera One™ (12 g C18 column, eluting 10-80% MeCN in pH10 0.1 M $NH_4HCO_3$ buffer solution). LCMS (Method 10): 2.19 min, 520.2 $[M+H]^+$; $^1H$ NMR (300 MHz, DMSO-$d_6$) δ: 10.45 (s, 1H), 8.89 (d, 1H), 8.58 (d, 1H), 8.43 (d, 1H), 7.54 (t, 5H), 7.42 (t, 4H), 7.35 (d, 1H), 7.17-7.27 (m, 4H), 7.04-7.14 (m, 2H), 6.75 (d, 1H), 5.61 (dd, 1H), 4.60 (d, 1H), 3.88 (s, 3H).

Example 37: (S)—N-(1-((4-(2,5-dimethylpyrimidin-4-yl)phenyl)amino)-1-oxo-3,3-diphenylpropan-2-yl)-1-methyl-1H-pyrazole-5-carboxamide

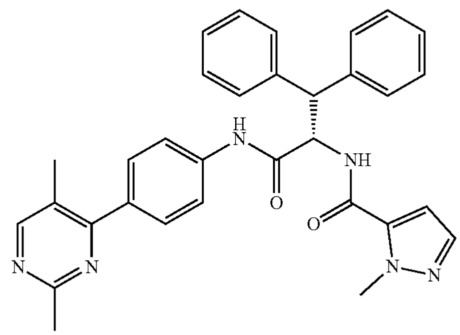 [SMILES: Cc1ncc(C)c(-c2ccc(NC(=O)[C@@H](NC(=O)c3ccnn3C)C(c3ccccc3)c3ccccc3)cc2)n1]

The title compound (36 mg) was prepared from Intermediate 3.37 (0.25 g, 0.5 mmol), 2-methylpyrazole-3-carboxylic acid (63 mg, 0.5 mmol CAS: 16034-46-1), HATU (0.23 g, 0.6 mmol) and triethylamine (0.17 mL, 1.3 mmol) in accordance with the procedure described for Example 1. The crude product was purified by reverse phase column chromatography on the Biotage Isolera One™ (30 g C18 column, eluting 30-70% MeCN in pH10 0.1 M $NH_4HCO_3$ buffer solution). LCMS (Method 6): 2.06 min, 530.8 $[M+H]^+$; $^1H$ NMR (400 MHz, DMSO-$d_6$) δ: 10.47 (s, 1H), 8.93 (d, 1H), 8.51 (s, 1H), 7.52 (s, 4H), 7.42 (dd, 4H), 7.34 (d, 1H), 7.22 (dt, 4H), 7.05-7.13 (m, 2H), 6.75 (d, 1H), 5.60 (dd, 1H), 4.62 (d, 1H), 3.85 (d, 3H), 2.56 (d, 3H), 2.21 (d, 3H)

Example 38: (S)—N-(1-((4-(2,5-dimethylpyridin-4-yl)phenyl)amino)-1-oxo-3,3-diphenylpropan-2-yl)-1-methyl-1H-pyrazole-5-carboxamide

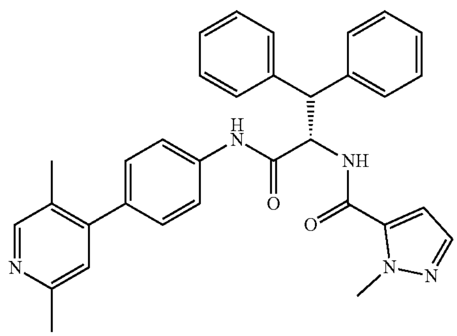 [SMILES: Cc1cc(-c2ccc(NC(=O)[C@@H](NC(=O)c3ccnn3C)C(c3ccccc3)c3ccccc3)cc2)c(C)cn1]

The title compound (9.2 mg) was prepared from Intermediate 3.38 (35 mg, 0.07 mmol), 2-methylpyrazole-3-carboxylic acid (9.4 mg, 0.07 mmol CAS: 16034-46-1), HATU (34 mg, 0.09 mmol) and triethylamine (0.03 mL, 0.19 mmol) in accordance with the procedure described for Example 1. The crude product was purified by reverse phase column chromatography on the Biotage Isolera One™ (12 g C18 column, eluting 30-70 MeCN in pH10 0.1 M $NH_4HCO_3$ buffer solution). LCMS (Method 6): 1.42 min, 529.8 $[M+H]^+$; $^1H$ NMR (400 MHz, DMSO-$d_6$) δ: 10.38 (s, 1H), 8.88 (d, 1H), 8.27 (s, 1H), 7.39-7.50 (m, 6H), 7.34 (d, 1H), 7.18-7.29 (m, 6H), 7.06-7.12 (m, 2H), 7.00 (s, 1H), 6.74 (d, 1H), 5.60 (dd, 1H), 4.61 (d, 1H), 3.88-3.94 (m, 3H), 2.39 (s, 3H), 2.13 (t, 3H).

Example 39: (S)—N-(1-((4-(imidazo[1,2-a]pyridin-3-yl)phenyl)amino)-1-oxo-3,3-diphenylpropan-2-yl)-1-methyl-1H-pyrazole-5-carboxamide

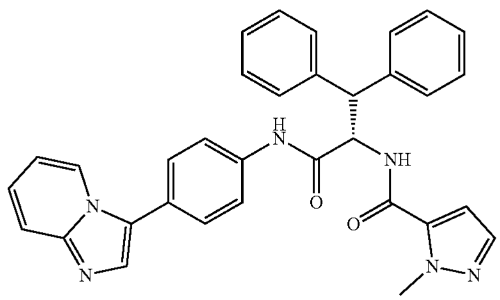 [SMILES: Cn1nccc1C(=O)N[C@H](C(=O)Nc1ccc(-c2cnc3ccccn23)cc1)C(c1ccccc1)c1ccccc1]

The title compound (13 mg) was prepared from 4-(imidazo[1,2-a]pyridin-3-yl)aniline (92 mg, 0.44 mmol), Intermediate 4.1 (0.15 g, 0.44 mmol), T3P® (50% w/w solution in EtOAc; 0.84 mL, 1.3 mmol) and triethylamine (0.15 mL, 1.1 mmol) in accordance with the procedure described for Example 21. The crude product was purified by reverse phase column chromatography on the Biotage Isolera One™ (30 g C18 column, eluting 30-70% MeCN in pH10 0.1 M $NH_4HCO_3$ buffer solution). LCMS (Method 9): 1.70 min, 541.2 $[M+H]^+$; $^1H$ NMR (400 MHz, DMSO-$d_6$) δ: 10.41 (s, 1H), 8.89 (d, 1H), 8.45 (d, 1H), 7.65 (d, 1H), 7.58 (dd, 3H), 7.40-7.50 (m, 6H), 7.34 (d, 1H), 7.19-7.26 (m, 5H), 7.06-7.13 (m, 2H), 6.89 (t, 1H), 6.75 (d, 1H), 5.61 (dd, 1H), 4.61 (d, 1H), 3.88 (s, 3H).

Example 40: (S)—N-(1-((4-(6,7-dihydro-5H-pyrrolo[2,3-d]pyrimidin-4-yl)phenyl)amino)-1-oxo-3,3-diphenylpropan-2-yl)-1-methyl-1H-pyrazole-5-carboxamide

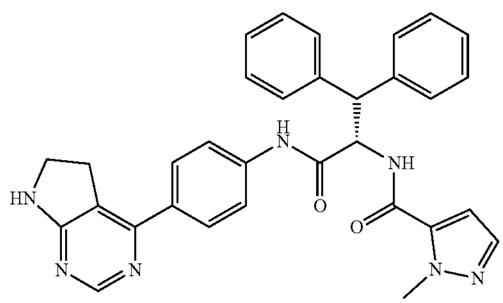 [SMILES: Cn1nccc1C(=O)N[C@H](C(=O)Nc1ccc(-c2ncnc3c2CCN3)cc1)C(c1ccccc1)c1ccccc1]

The title compound (74 mg) was prepared from Intermediate 1.40 (0.31 g, 0.9 mmol), Intermediate 4.1 (0.19 mg, 0.9 mmol), T3P® (50% w/w solution in EtOAc; 1.7 mL, 2.7 mmol) and 2,4,6-collidine (0.29 mL, 2.24 mmol) in accordance with the procedure described for Example 21. The crude product was purified by reverse phase column chromatography on the Biotage Isolera One™ (30 g C18 column, eluting 30-70% MeCN in pH10 0.1 M $NH_4HCO_3$ buffer solution). LCMS (Method 6): 1.30 min, 544.3 $[M+H]^+$; $^1H$ NMR (400 MHz, DMSO-$d_6$) δ: 10.44 (s, 1H), 8.87-8.93 (m, 1H), 8.19 (s, 1H), 7.75 (d, 2H), 7.50 (d, 2H), 7.41 (t, 5H), 7.33 (d, 1H), 7.21 (dt, 4H), 7.08 (dt, 2H), 6.75 (d, 1H), 5.59 (dd, 1H), 4.61 (d, 1H), 3.83-3.87 (m, 3H), 3.50 (q, 2H), 3.22 (t, 2H).

Example 41: (S)—N-(1-((4-(imidazo[1,2-a]pyrimidin-3-yl)phenyl)amino)-1-oxo-3,3-diphenylpropan-2-yl)-1-methyl-1H-pyrazole-5-carboxamide

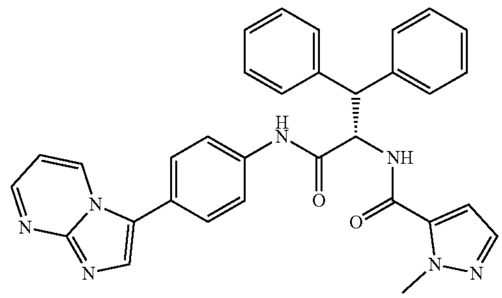

The title compound (0.15 g) was prepared from Intermediate 1.41 (0.1 g, 0.48 mmol), Intermediate 4.1 (0.17 mg, 0.48 mmol), T3P® (50% w/w solution in EtOAc; 0.91 mL, 1.4 mmol) and 2,4-6-collidine (0.16 mL, 1.2 mmol) in accordance with the procedure described for Example 21. The crude product was purified by reverse phase column chromatography on the Biotage Isolera One™ (30 g C18 column, eluting 30-50% MeCN in pH10 0.1 M $NH_4HCO_3$ buffer solution). LCMS (Method 5): 1.82 min, 542.2 $[M+H]^+$; $^1H$ NMR (400 MHz, DMSO-$d_6$) δ: 10.36 (d, 1H), 8.85-8.92 (m, 2H), 8.49 (dq, 1H), 8.22 (s, 0.5H), 7.84 (s, 1H), 7.81 (s, 0.5H), 7.54 (dd, 2H), 7.39-7.48 (m, 5H), 7.34 (t, 1H), 7.18-7.28 (m, 4H), 6.98-7.13 (m, 3H), 6.75 (d, 1H), 5.58-5.63 (m, 1H), 4.60 (dd, 1H), 3.88 (s, 3H).

Example 42: (S)—N-(1-((4-(3-(hydroxymethyl)pyridin-4-yl)phenyl)amino)-1-oxo-3,3-diphenylpropan-2-yl)-1-methyl-1H-pyrazole-5-carboxamide

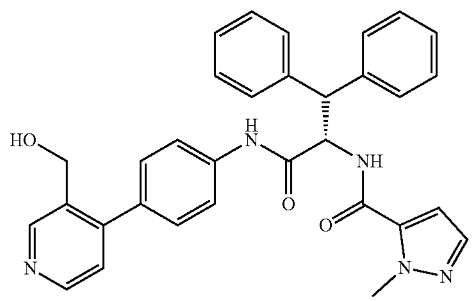

The title compound (38 mg) was prepared from Intermediate 3.42 (0.28 g, 0.56 mmol), 2-methylpyrazole-3-carboxylic acid (82 mg, 0.65 mmol, CAS: 16034-46-1), HATU (0.3 g, 0.78 mmol) and triethylamine (0.23 mL, 1.6 mmol) in accordance with the procedure described for Example 1. The crude product was purified by reverse phase column chromatography on the Biotage Isolera One™ (30 g C18 column, eluting 30-70% MeCN in pH10 0.1 M $NH_4HCO_3$ buffer solution). LCMS (Method 9): 1.82 min, 532.3 $[M+H]^+$; $^1H$ NMR (400 MHz, DMSO-$d_6$) δ: 10.42 (s, 1H), 8.85-8.92 (m, 1H), 8.64 (d, 1H), 8.40-8.45 (m, 1H), 7.50 (d, 2H), 7.42 (q, 4H), 7.33-7.35 (m, 3H), 7.18-7.26 (m, 5H), 7.06-7.12 (m, 2H), 6.75 (d, 1H), 5.61 (dd, 1H), 5.30 (s, 1H), 4.58-4.69 (m, 1H), 4.43 (d, 2H), 3.88-3.96 (m, 3H).

Example 43: (S)—N-(1-((4-(3-cyanopyridin-4-yl)phenyl)amino)-1-oxo-3,3-diphenylpropan-2-yl)-1-methyl-1H-pyrazole-5-carboxamide

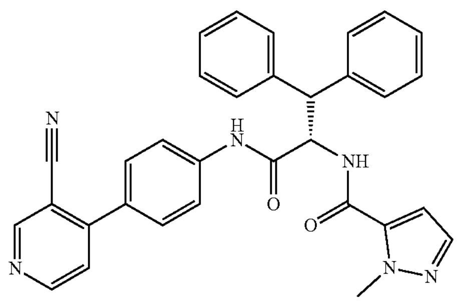 [SMILES: Cn1nccc1C(=O)N[C@H](C(=O)Nc1ccc(-c2ccncc2C#N)cc1)C(c1ccccc1)c1ccccc1]

The title compound (2.5 mg) was prepared from Intermediate 3.43 (58 mg, 0.12 mmol), 2-methylpyrazole-3-carboxylic acid (16 mg, 0.13 mmol, CAS: 16034-46-1), HATU (58 mg, 0.15 mmol) and triethylamine (0.04 mL, 0.32 mmol) in accordance with the procedure described for Example 1. The crude product was purified by flash column chromatography on the Biotage Isolera One™ (30 g ZIP sphere silica column, eluting 40-100% EtOAc in heptanes) and reverse phase column chromatography on the Biotage Isolera One™ (30 g C18 column, eluting 30-70% MeCN in pH10 0.1 M $NH_4HCO_3$ buffer solution). LCMS (Method 6): 2.19 min, 526.8 $[M+H]^+$; $^1H$ NMR (400 MHz, DMSO-$d_6$) δ: 10.51 (s, 1H), 9.02 (s, 1H), 8.90 (d, 1H), 8.81 (d, 1H), 7.55-7.62 (m, 5H), 7.39-7.44 (m, 4H), 7.34 (s, 1H), 7.18-7.26 (m, 4H), 7.05-7.13 (m, 2H), 6.74 (s, 1H), 5.58-5.63 (m, 1H), 4.61 (d, 1H), 3.88 (s, 3H).

Example 44: (S)—N-(1-((4-(6,7-dihydro-5H-cyclopenta[b]pyridin-4-yl)phenyl)amino)-1-oxo-3,3-diphenylpropan-2-yl)-1-methyl-1H-pyrazole-5-carboxamide

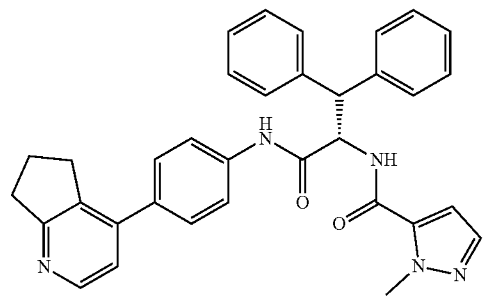 [SMILES: Cn1nccc1C(=O)N[C@H](C(=O)Nc1ccc(-c2ccnc3c2CCC3)cc1)C(c1ccccc1)c1ccccc1]

The title compound (24 mg) was prepared from Intermediate 1.44 (65 mg, 0.28 mmo), Intermediate 4.1 (99 mg, 0.28 mmol), T3P® (50% w/w solution in EtOAc; 0.5 mL, 0.84 mmol) and pyridine (0.06 mL, 0.7 mmol) in accordance with the procedure described for Example 21. The crude product was purified by reverse phase column chromatography on the Biotage Isolera One™ (30 g C18 column, eluting 45-70% MeCN in pH10 0.1 M $NH_4HCO_3$ buffer solution). LCMS (Method 5): 2.22 min, 542.3 $[M+H]^+$; $^1H$ NMR (400 MHz, DMSO-$d_6$) δ: 10.39 (s, 1H), 8.87 (d, 1H), 8.27 (d, 1H), 7.51 (d, 2H), 7.41 (dd, 6H), 7.34 (d, 1H), 7.18-7.25 (m, 4H), 7.05-7.12 (m, 3H), 6.74 (d, 1H), 5.60 (dd, 1H), 4.60 (d, 1H), 3.87 (s, 3H), 2.88-2.96 (m, 4H), 1.94-2.01 (m, 2H).

Example 45: (S)-1-methyl-N-(1-((3-methyl-4-(pyridin-4-yl)phenyl)amino)-1-oxo-3,3-diphenylpropan-2-yl)-1H-pyrazole-5-carboxamide

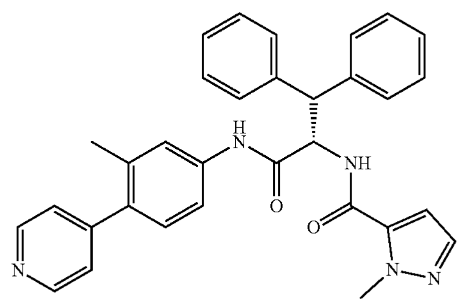 [SMILES: Cc1cc(NC(=O)[C@@H](NC(=O)c2ccnn2C)C(c2ccccc2)c2ccccc2)ccc1-c1ccncc1]

The title compound (0.1 g) was prepared from 3-methyl-4-(pyridin-4-yl)aniline (0.15 g, 0.79 mmol, CAS: 82160-27-8), Intermediate 4.1 (0.28 g, 0.79 mmol), T3P® (50% w/w solution in EtOAc; 1.5 mL, 2.4 mmol) and pyridine (0.16 mL, 2.0 mmol) in accordance with the procedure described for Example 21. The crude product was purified by reverse phase column chromatography on the Biotage Isolera One™ (30 g C18 column, eluting 40-70% MeCN in pH10 0.1 M $NH_4HCO_3$ buffer solution). LCMS (Method 5): 2.11 min, 516.3 $[M+H]^+$; $^1H$ NMR (400 MHz, DMSO-$d_6$) δ: 10.27 (s, 1H), 8.84 (d, 1H), 8.55 (dd, 2H), 7.41 (q, 4H), 7.28-7.34 (m, 5H), 7.18-7.25 (m, 4H), 7.06-7.12 (m, 3H), 6.74 (d, 1H), 5.59 (dd, 1H), 4.59 (d, 1H), 3.87 (s, 3H), 2.15 (s, 3H).

Example 46: (S)-1-(difluoromethyl)-N-(1-((4-(3-methoxypyridin-4-yl)phenyl)amino)-1-oxo-3,3-diphenylpropan-2-yl)-1H-pyrazole-5-carboxamide

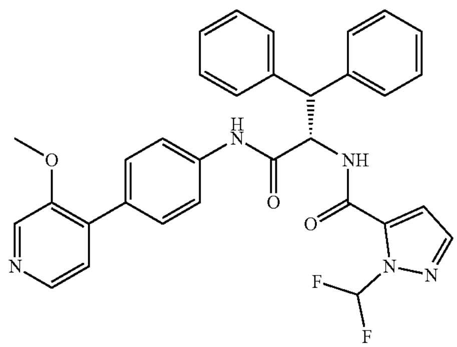 [SMILES: COc1cnccc1-c1ccc(NC(=O)[C@@H](NC(=O)c2ccnn2C(F)F)C(c2ccccc2)c2ccccc2)cc1]

The title compound (72 mg) was prepared from Intermediate 3.3 (95 mg, 0.19 mmol), 2-(difluoromethyl)pyrazole-3-carboxylic acid (30 mg, 0.19 mmol, CAS: 925199-97-9), HATU (74 mg, 0.19 mmol) and triethylamine (0.1 mL, 0.74 mmol) in accordance with the procedure described for Example 1. The crude product was purified by reverse phase column chromatography on the Biotage Isolera One™ (30 g C18 column, eluting 40-70% MeCN in pH10 0.1 M $NH_4HCO_3$ buffer solution). LCMS (Method 5): 2.26 min, 568.2 $[M+H]^+$; $^1H$ NMR (400 MHz, DMSO-$d_6$) δ: 10.39 (s, 1H), 9.33 (d, 1H), 8.38 (s, 1H), 8.20 (d, 1H), 8.07 (t, 1H), 7.76 (s, 1H), 7.38-7.47 (m, 8H), 7.19-7.26 (m, 5H), 7.06-7.13 (m, 2H), 7.00 (s, 1H), 5.61 (dd, 1H), 4.59 (d, 1H), 3.83 (s, 3H).

Example 47: (S)—N-(1-((3-methoxy-4-(3-methoxypyridin-4-yl)phenyl)amino)-1-oxo-3,3-diphenylpropan-2-yl)-1-methyl-1H-pyrazole-5-carboxamide

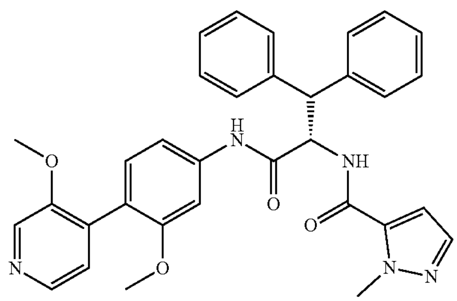 [SMILES: COc1cnccc1-c1ccc(NC(=O)[C@@H](NC(=O)c2ccnn2C)C(c2ccccc2)c2ccccc2)cc1OC]

The title compound (39 mg) was prepared from Intermediate 3.47 (66 mg, 0.13 mmol), 2-methylpyrazole-3-carboxylic acid (17 mg, 0.13 mmol, CAS: 16034-46-1), HATU (62 mg, 0.16 mmol) and triethylamine (0.05 mL, 0.34 mmol) in accordance with the procedure described for Example 1. The crude product was purified by reverse phase column chromatography on the Biotage Isolera One™ (30 g C18 column, eluting 30-70% MeCN in pH10 0.1 M $NH_4HCO_3$ buffer solution). LCMS (Method 6): 1.60 min, 561.8 $[M+H]^+$; $^1H$ NMR (400 MHz, DMSO-$d_6$) δ: 10.32 (s, 1H), 8.83 (s, 1H), 8.33 (s, 1H), 8.15 (d, 1H), 7.42 (q, 4H), 7.32 (d, 1H), 7.19-7.25 (m, 5H), 7.08-7.13 (m, 3H), 7.01 (dd, 2H), 6.72 (s, 1H), 5.54-5.59 (m, 1H), 4.67 (d, 1H), 3.87 (s, 3H), 3.76 (s, 3H), 3.60 (d, 3H).

Example 48: (S)—N-(1-((3-fluoro-4-(1-methyl-6-oxo-1,6-dihydropyridazin-3-yl)phenyl)amino)-1-oxo-3,3-diphenylpropan-2-yl)-1-methyl-1H-pyrazole-5-carboxamide

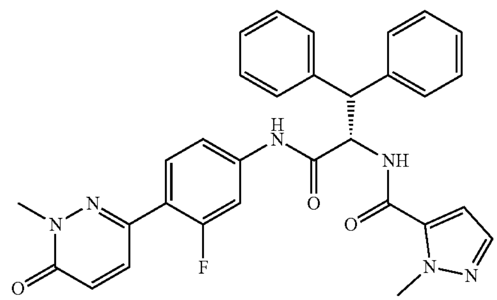 [SMILES: Cn1nccc1C(=O)N[C@H](C(=O)Nc1ccc(-c2ccc(=O)n(C)n2)c(F)c1)C(c1ccccc1)c1ccccc1]

The title compound (77 mg) was prepared from Intermediate 3.48 (0.19 g, 0.39 mmol), 2-methylpyrazole-3-carboxylic acid (59 mg, 0.47 mmol, CAS: 16034-46-1), HATU (0.18 g, 0.47 mmol) and DIPEA (0.27 mL, 1.6 mmol) in accordance with the procedure described for Example 1. The crude product was purified by reverse phase column chromatography on the Biotage Isolera One™ (30 g C18 column, eluting 0-100% 0.1% ammonia/MeCN in pH11 0.1% ammonia/$H_2O$) and flash column chromatography (eluting 75-100% EtOAc in heptanes). LCMS (Method 3): 2.16 min, 551.6 $[M+H]^+$; $^1H$ NMR (300 MHz, DMSO-$d_6$) δ: 10.58 (s, 1H), 8.90 (d, 1H), 7.66 (dd, 1H), 7.47-7.58 (m, 2H), 7.38-7.41 (m, 4H), 7.34 (d, 1H), 7.04-7.27 (m, 7H), 6.97 (d, 1H), 6.75 (d, 1H), 5.57 (dd, 1H), 4.59 (d, 1H), 3.88 (s, 3H), 3.68 (s, 3H).

Example 49: (S)-1-methyl-N-(1-oxo-1-((4-(6-oxo-1,6-dihydropyridin-3-yl)phenyl)amino)-3,3-diphenylpropan-2-yl)-1H-pyrazole-5-carboxamide

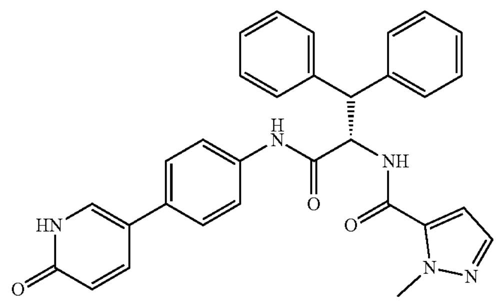 [SMILES: Cn1nccc1C(=O)N[C@H](C(=O)Nc1ccc(-c2ccc(=O)[nH]c2)cc1)C(c1ccccc1)c1ccccc1]

The title compound (4 mg was prepare from Intermediate 3.49 (46 mg, 0.1 mmol), 2-methylpyrazole-3-carboxylic acid (13 mg, 0.1 mmol, CAS: 16034-46-1), HATU (47 mg, 0.12 mmol) and triethylamine (0.04 mL, 0.26 mmol) in accordance with the procedure described for Example 1. The crude product was purified by reverse phase column chromatography on the Biotage Isolera One™ (12 g 18 column, eluting 30-70% MeCN in pH10 0.1 M $NH_4HCO_3$ buffer solution) and reverse phase column chromatography on the Biotage Isolera One™ (12 g C18 column, eluting 45-60% MeCN in pH10 0.1 M $NH_4HCO_3$ buffer solution). LCMS (Method 9): 2.46 min, 518.4 $[M+H]^+$; $^1$H NMR (400 MHz, DMSO-$d_6$) δ: 10.25 (s, 1H), 8.86 (d, 1H), 7.72 (dd, 1H), 7.56 (s, 1H), 7.35-7.42 (m, 9H), 7.33 (d, 1H), 7.21 (dt, 4H), 7.04-7.12 (m, 2H), 6.74 (d, 1H), 6.36 (d, 1H), 5.57 (dd1H), 4.58 (d, 1H), 3.87 (s, 3H).

Example 50: (S)-1-methyl-N-(1-((4-(4-methyl-6-oxo-1,6-dihydropyridin-3-yl)phenyl)amino)-1-oxo-3,3-diphenylpropan-2-yl)-1H-pyrazole-5-carboxamide

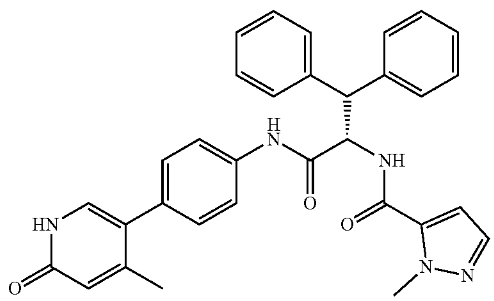 [SMILES: Cc1cc(=O)[nH]cc1-c1ccc(NC(=O)[C@@H](NC(=O)c2ccnn2C)C(c2ccccc2)c2ccccc2)cc1]

The title compound (5 mg) was prepared from Intermediate 3.50 (31 mg, 0.07 mmol), 2-methylpyrazole-3-carboxylic acid (8.4 mg, 0.07 mmol, CAS: 16034-46-1), HATU (30 mg, 0.08 mmol) and triethylamine (0.02 mL, 0.17 mmol) in accordance with the procedure described for Example 1. The crude product was purified by reverse phase column chromatography on the Biotage Isolera One™ (12 g C18 column, eluting 30-70% MeCN in pH10 0.1 M $NH_4HCO_3$ buffer solution). LCMS (Method 17): 1.91 min, 531.8 $[M+H]^+$; $^1$H NMR (400 MHz, DMSO-$d_6$) δ: 10.37 (s, 1H), 8.91 (s, 1H), 7.38-7.44 (m, 6H), 7.33 (d, 1H), 7.18-7.24 (m, 5H), 7.06-7.13 (m, 5H), 6.75 (d, 1H), 6.19 (s, 1H), 5.55-5.60 (m, 1H), 4.62 (d, 1H), 3.87 (s, 3H), 1.97 (s, 3H).

Example 51: (S)-1-methyl-N-(1-((4-(1-methyl-6-oxo-1,6-dihydropyridin-3-yl)phenyl)amino)-1-oxo-3,3-diphenylpropan-2-yl)-1H-pyrazole-5-carboxamide

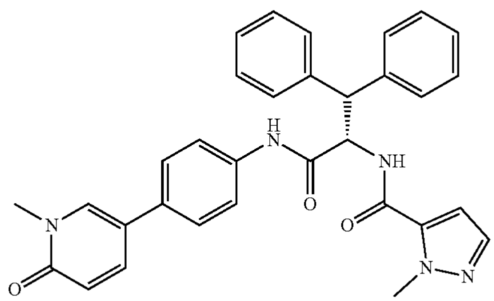 [SMILES: Cn1nccc1C(=O)N[C@H](C(=O)Nc1ccc(-c2ccc(=O)n(C)c2)cc1)C(c1ccccc1)c1ccccc1]

The title compound (67 mg) was prepared from Intermediate 3.51 (0.41 g, 0.88 mmol), 2-methylpyrazole-3-carboxylic acid (0.11 g, 0.88 mmol, CAS: 16034-46-1), HATU (0.4 g, 1.1 mmol) and triethylamine (0.31 mL, 2.2 mmol) in accordance with the procedure described for Example 1. The crude product was purified by reverse phase column chromatography on the Biotage Isolera One™ (30 g C18 column, eluting 30-70% MeCN in pH10 0.1 M $NH_4HCO_3$ buffer solution). LCMS (Method 17): 1.96 min, 532.3 $[M+H]^+$; $^1$H NMR (400 MHz, DMSO-$d_6$) δ: 10.29 (s, 1H), 8.89 (d, 1H), 7.99 (d, 1H), 7.71 (dd, 1H), 7.37-7.42 (m, 8H), 7.33 (d, 1H), 7.21 (dt, 4H), 7.08 (dt, 2H), 6.75 (d, 1H), 6.41 (d, 1H), 5.57 (dd, 1H), 4.60 (d, 1H), 3.90 (d, 3H), 3.45 (d, 3H).

Example 52: (S)-1-methyl-N-(1-oxo-1-((4-(7-oxo-6,7-dihydro-1H-pyrrolo[2,3-c]pyridin-4-yl)phenyl)amino)-3,3-diphenylpropan-2-yl)-1H-pyrazole-5-carboxamide

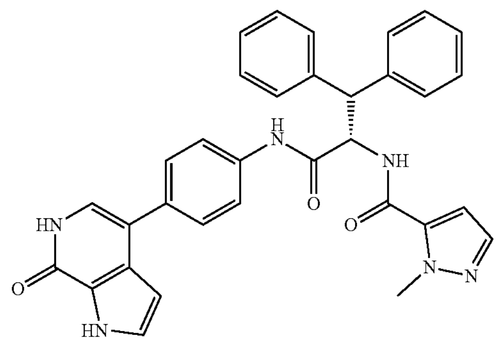 [SMILES: Cn1nccc1C(=O)N[C@H](C(=O)Nc1ccc(-c2c[nH]c(=O)c3[nH]ccc23)cc1)C(c1ccccc1)c1ccccc1]

The title compound (62 mg) was prepared from Intermediate 3.52 (0.14 g, 0.27 mmol), 2-methylpyrazole-3-carboxylic acid (34 mg, 0.27 mmol, CAS: 16034-46-1), HATU (0.1 g, 0.27 mmol) and triethylamine (0.11 mL, 0.81 mmol) in accordance with the procedure described for Example 1. The crude product was purified by reverse phase column chromatography on the Biotage Isolera One™ (30 g C18 column, eluting 15-60% 0.1% ammonia/MeCN in pH11 0.1% ammonia/$H_2O$). LCMS (Method 3): 1.96 min, 557.2 [M+H] 1; $^1$H NMR (400 MHz, DMSO-$d_6$) δ: 12.03 (s, 1H), 11.01 (d, 1H), 10.27 (s, 1H), 8.84 (d, 1H), 7.44-7.19 (m, 14H), 7.10 (dd, 2H), 6.86 (d, 1H), 6.74 (s, 1H), 6.37 (s, 1H), 5.60 (t, 1H), 4.61 (d, 1H), 3.88 (d, 3H).

Example 53: (S)—N-(1-((4-(3-(hydroxymethyl)pyridin-4-yl)-3-methoxyphenyl)amino)-1-oxo-3,3-diphenylpropan-2-yl)-1-methyl-1H-pyrazole-5-carboxamide

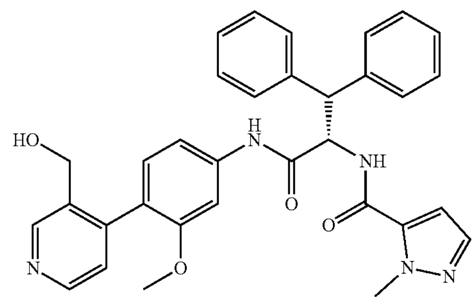 [SMILES: COc1cc(NC(=O)[C@@H](NC(=O)c2ccnn2C)C(c2ccccc2)c2ccccc2)ccc1-c1ccncc1CO]

The title compound (13 mg) was prepared from Intermediate 3.53 (36 mg, 0.07 mmol), 2-methylpyrazole-3-carboxylic acid (10 mg, 0.08 mmol, CAS: 16034-46-1), HATU (32 mg, 0.08 mmol) and DIPEA (0.05 mL, 0.28 mmol) in accordance with the procedure described for Example 1. The crude product was purified by reverse phase column chromatography on the Biotage Isolera One™ (30 g C18 column, eluting 0-100% MeCN in pH10 0.1 M $NH_4HCO_3$ buffer solution). LCMS (Method 5): 1.85 min, 562.3 $[M+H]^+$; $^1H$ NMR (400 MHz, DMSO-$d_6$) δ: 10.37 (s, 1H), 8.86 (d, 1H), 8.61 (s, 1H), 8.38 (d, 1H), 7.42 (dd, 4H), 7.34 (d, 1H), 7.23 (td, 5H), 7.03-7.12 (m, 4H), 6.99 (d, 1H), 6.74 (d, 1H), 5.60 (dd, 1H), 5.09 (t, 1H), 4.60 (d, 1H), 4.24 (d, 2H), 3.87 (s, 3H), 3.61 (s, 3H).

Example 54: (S)—N-(1-((4-(1,2-dimethyl-6-oxo-1,6-dihydropyridin-3-yl)-3-(trifluoromethyl)phenyl)amino)-1-oxo-3,3-diphenylpropan-2-yl)-1-methyl-1H-pyrazole-5-carboxamide

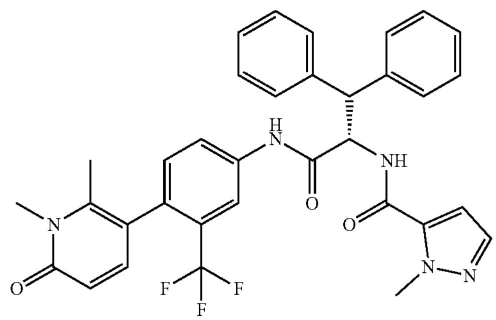 [SMILES: Cc1c(-c2ccc(NC(=O)[C@@H](NC(=O)c3ccnn3C)C(c3ccccc3)c3ccccc3)cc2C(F)(F)F)ccc(=O)n1C]

The title compound (22 mg) was prepared from Intermediate 3.54 (50 mg, 0.09 mmol), 2-methylpyrazole-3-carboxylic acid (14 mg, 0.11 mmol, CAS: 16034-46-1), HATU (42 mg, 0.11 mmol) and DIPEA (0.06 mL, 0.37 mmol) in accordance with the procedure described for Example 1. The crude product was purified by reverse phase column chromatography on the Biotage Isolera One™ (30 g C18 column, eluting 0-100% 0.1% ammonia/MeCN in pH11 0.1% ammonia/$H_2O$). LCMS (Method 3): 2.23 min, 614.3 $[M+H]^+$; $^1H$ NMR (400 MHz, DMSO-$d_6$) δ: 10.67 (s, 1H), 8.95 (d, 1H), 7.92 (d, 1H), 7.64-7.73 (m, 1H), 7.43 (t, 4H), 7.38 (d, 1H), 7.25 (td, 5H), 7.09-7.17 (m, 3H), 6.77 (s, 1H), 6.28 (d, 1H), 5.58-5.63 (m, 1H), 4.64 (d, 1H), 3.91 (s, 3H), 3.47 (s, 3H), 1.98 (s, 3H).

Example 55: (S)—N-(1-((3-chloro-4-(3,5-dimethylpyridin-4-yl)phenyl)amino)-1-oxo-3,3-diphenylpropan-2-yl)-1-methyl-1H-pyrazole-5-carboxamide

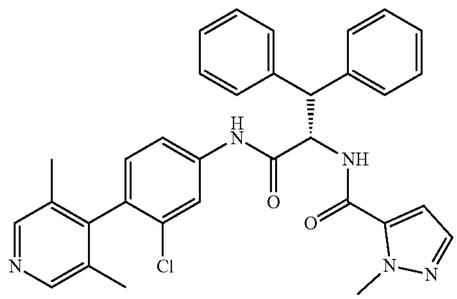

The title compound (20 mg) was prepared from Intermediate 3.55 (69 mg, 0.13 mmol), 2-methylpyrazole-3-carboxylic acid (18 mg, 0.14 mmol, CAS: 16034-46-1), HATU (55 mg, 0.14 mmol) and triethylamine (0.04 mL, 0.26 mmol) in accordance with the procedure described for Example 1. The crude product was purified by reverse phase column chromatography on the Biotage Isolera One™ (30 g C18 column, eluting 40-80% 0.1% ammonia/MeCN in pH11 0.1% ammonia/$H_2O$) and MDAP (Method 1: 30-50% MeCN in 0.1% formic acid). LCMS (Method 3): 2.50 min, 564.2 $[M+H]^+$; $^1H$ NMR (400 MHz, DMSO-$d_6$) δ: 1.93 (s, 6H), 3.96 (s, 3H), 4.69 (d, 1H), 5.64 (t, 1H), 6.81 (s, 1H), 7.11-7.22 (m, 3H), 7.25-7.35 (m, 4H), 7.41 (s, 1H), 7.43-7.53 (m, 5H), 7.83 (s, 1H), 8.38 (s, 2H), 8.99 (d, 1H), 10.63 (s, 1H).

Example 56: (S)—N-(1-((4-(2,5-dimethylpyridin-4-yl)-3-fluorophenyl)amino)-1-oxo-3,3-diphenylpropan-2-yl)-1-methyl-1H-pyrazole-5-carboxamide

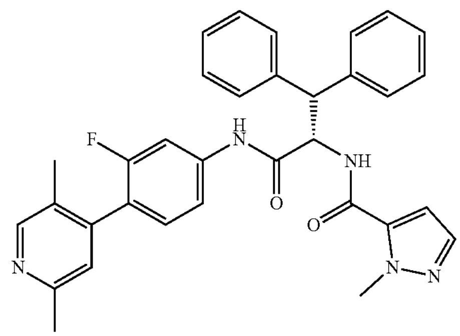 [SMILES: Cc1cc(-c2ccc(NC(=O)[C@@H](NC(=O)c3ccnn3C)C(c3ccccc3)c3ccccc3)cc2F)c(C)cn1]

The title compound (54 mg) was prepared from Intermediate 3.56 (86 mg, 0.17 mmol), 2-methylpyrazole-3-carboxylic acid (23 mg, 0.18 mmol, CAS: 16034-46-1), HATU (70 mg, 0.18 mmol) and triethylamine (0.09 mL, 0.67 mmol) in accordance with the procedure described for Example 1. The crude product was purified by reverse phase column chromatography on the Biotage Isolera One™ (30 g C18 column, eluting 10-60% 0.1% ammonia/MeCN in pH11 0.1% ammonia/$H_2O$). LCMS (Method 3): 2.45 min, 548.3 $[M+H]^+$; $^1H$ NMR (400 MHz, DMSO-$d_6$) δ: 10.61 (s, 1H), 8.95 (d, 1H), 8.31 (s, 1H), 6.95-7.49 (m, 15H), 6.70-6.75 (m, 1H), 5.57 (dd, 1H), 4.62 (d, 1H), 3.84-4.05 (m, 3H), 2.40 (s, 3H), 2.02 (d, 3H).

Example 57: (S)—N-(1-((4-(2,3-dimethylpyridin-4-yl)-3-fluorophenyl)amino)-1-oxo-3,3-diphenylpropan-2-yl)-1-methyl-1H-pyrazole-5-carboxamide

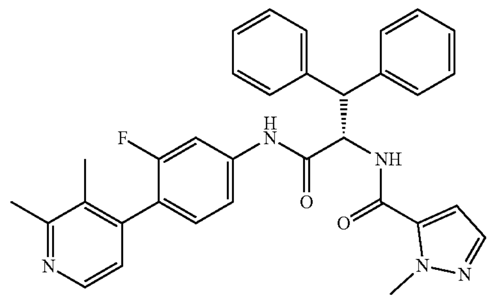 [SMILES: Cc1nccc(-c2ccc(NC(=O)[C@@H](NC(=O)c3ccnn3C)C(c3ccccc3)c3ccccc3)cc2F)c1C]

The title compound (35 mg) was prepared from Intermediate 3.57 (90 mg, 0.18 mmol), 2-methylpyrazole-3-carboxylic acid (24 mg, 0.19 mmol, CAS: 16034-46-1), HATU (74 mg, 0.19 mmol) and triethylamine (0.1 mL, 0.7 mmol) in accordance with the procedure described for Example 1. The crude product was purified by reverse phase column chromatography on the Biotage Isolera One™ (30 g C18 column, eluting 10-60% 0.1% ammonia/MeCN in pH11 0.1% ammonia/$H_2O$). LCMS (Method 3): 2.46 min, 548.3 $[M+H]^+$; $^1H$ NMR (400 MHz, DMSO-$d_6$) δ: 10.60 (s, 1H), 8.93 (d, 1H), 8.24 (d, 1H), 6.96-7.49 (m, 15H), 6.74 (d, 1H), 5.58 (dd, 1H), 4.61 (d, 1H), 3.85-4.05 (m, 3H), 2.45 (s, 3H), 1.95-2.14 (m, 3H).

Example 58: (S)—N-(1-((3-fluoro-4-(6-oxo-1,6-dihydropyridazin-3-yl)phenyl)amino)-1-oxo-3,3-diphenylpropan-2-yl)-1-methyl-1H-pyrazole-5-carboxamide

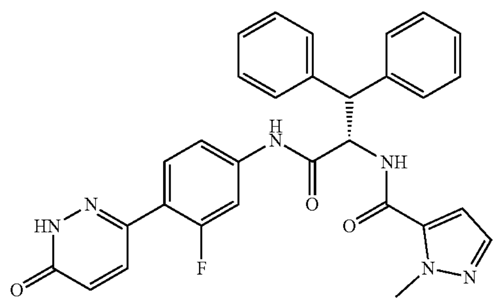 [SMILES: Cn1nccc1C(=O)N[C@H](C(=O)Nc1ccc(-c2ccc(=O)[nH]n2)c(F)c1)C(c1ccccc1)c1ccccc1]

The title compound (37 mg) was prepared from Intermediate 3.34 (0.15 g, 0.26 mmol), 2-methylpyrazole-3-carboxylic acid (40 mg, 0.31 mmol, CAS: 16034-46-1), HATU (119 mg, 0.31 mmol) and DIPEA (0.18 mL, 1.1 mmol) in accordance with the procedure described for Example 1. The crude product was purified by flash column chromatography (eluting 0-2% MeOH in EtOAc) and reverse phase column chromatography on the Biotage Isolera One™ (30 g C18 column, eluting 0-80% 0.1% ammonia/MeCN in pH11 0.1% ammonia/$H_2O$). LCMS (Method 3): 1.79 min, 537.2 $[M+H]^+$; $^1H$ NMR (400 MHz, DMSO-$d_6$) δ: 10.61 (s, 1H), 8.95 (d, 1H), 7.67 (dd, 1H), 7.57-7.49 (m, 2H), 7.42 (dd, 4H), 7.37 (d, 1H), 7.29-7.20 (m, 5H), 7.12 (td, 2H), 6.94 (d, 1H), 6.78 (d, 1H), 5.59 (dd, 1H), 4.62 (d, 1H), 3.91 (s, 3H).

Example 59: (S)-1-ethyl-N-(1-((3-fluoro-4-(3-methyl-1H-pyrazol-4-yl)phenyl)amino)-1-oxo-3,3-diphenylpropan-2-yl)-1H-pyrazole-5-carboxamide

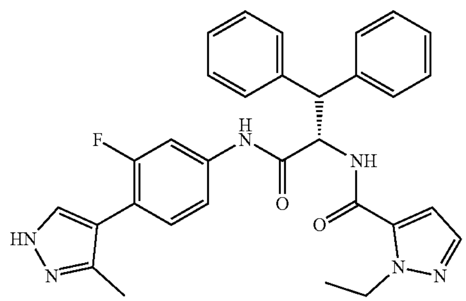 [SMILES: CCn1nccc1C(=O)N[C@H](C(=O)Nc1ccc(-c2c[nH]nc2C)c(F)c1)C(c1ccccc1)c1ccccc1]

To a solution of Intermediate 3.59a (29 mg, 0.05 mmol) in ethanol (0.8 mL) and THF (0.4 mL) and HCl (6M aq; 2 drops) was added 20% palladium hydroxide on carbon (6.5 mg, 0.05 mmol) and the reaction stirred at rt for 48 h in 200 psi hydrogen in an autoclave. The reaction mixture was filtered through a plug of celite washed with EtOAc and concentrated in vacuo. The crude product was purified by automated reverse phase column chromatography on the Biotage Isolera One™ (12 g C18 column, eluting 10-65% 0.1% ammonia/MeCN in pH11 0.1% ammonia/$H_2O$) and flash column chromatography on the Biotage Isolera One™ (5 g ZIP sphere silica column, eluting 60-100% EtOAc in heptanes) to afford the title compound (4.8 mg). LCMS (Method 3): 2.15 min, 537.2 $[M+H]^+$; $^1H$ NMR (400 MHz, DMSO-$d_6$) δ: 12.65 (s, 1H), 10.45 (s, 1H), 8.93 (d, 1H), 7.46-7.40 (m, 5H), 7.38 (d, 1H), 7.30-7.20 (m, 6H), 7.19-7.08 (m, 3H), 6.72 (d, 1H), 5.61 (dd, 1H), 4.62 (d, 1H), 4.43-4.24 (m, 2H), 2.21 (s, 3H), 1.15 (t, 3H).

Example 60: (S)—N-(1-((4-(3,5-dimethylisoxazol-4-yl)-3-fluorophenyl)amino)-1-oxo-3,3-diphenylpropan-2-yl)-1-methyl-1H-pyrazole-5-carboxamide

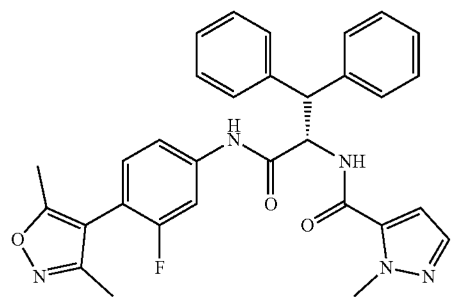 [SMILES: Cc1noc(C)c1-c1ccc(NC(=O)[C@@H](NC(=O)c2ccnn2C)C(c2ccccc2)c2ccccc2)cc1F]

The title compound (22 mg) was prepared from Intermediate 3.60 (0.3 g, 0.27 mmol), 2-methylpyrazole-3-carboxylic acid (41 mg, 0.32 mmol, CAS: 16034-46-1), HATU (0.12 g, 0.32 mmol) and triethylamine (0.15 mL, 1.1 mmol) in accordance with the procedure described for Example 1. The crude product was purified by flash column chromatography (eluting 33-66% EtOAc in heptanes) and reverse phase column chromatography on the Biotage Isolera One™ (30 g C18 column, eluting 40-80% 0.1% ammonia/MeCN in pH11 0.1% ammonia/$H_2O$). LCMS (Method 3): 2.18 min, 538.2 $[M+H]^+$; $^1H$ NMR (400 MHz, DMSO-$d_6$) δ: 10.61 (s, 1H), 8.93 (d, 1H), 7.56-7.50 (m, 1H), 7.48-7.40 (m, 4H), 7.37 (d, 1H), 7.31-7.21 (m, 6H), 7.17-7.09 (m, 2H), 6.77 (d, 1H), 5.61 (dd, 1H), 4.63 (d, 1H), 3.90 (s, 3H), 2.27 (s, 3H), 2.09 (s, 3H).

Example 61: (S)—N-(1-((4-(3,5-dimethylisoxazol-4-yl)-3-fluorophenyl)amino)-1-oxo-3,3-diphenylpropan-2-yl)-1-ethyl-1H-pyrazole-5-carboxamide

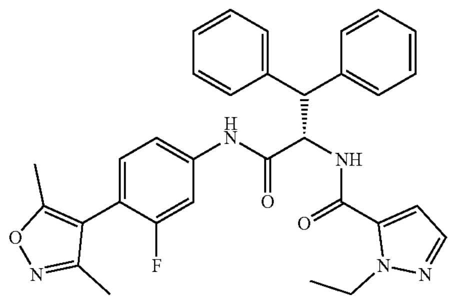 [SMILES: CCn1nccc1C(=O)N[C@H](C(=O)Nc1ccc(-c2c(C)noc2C)c(F)c1)C(c1ccccc1)c1ccccc1]

The title compound (3.9 mg) was prepared from Intermediate 3.60 (75 mg, 0.16 mmol), 2-ethylpyrazole-3-carboxylic acid (27 mg, 0.19 mmol, CAS: 400755-43-3), HATU (73 mg, 0.19 mmol) and triethylamine (0.09 mL, 0.64 mmol) in accordance with the procedure described for Example 1. The crude product was purified by flash column chromatography (eluting 33-66% EtOAc in heptanes), reverse phase column chromatography on the Biotage Isolera One™ (30 g C18 column, eluting 40-80% 0.1% ammonia/MeCN in pH11 0.1% ammonia/$H_2O$) and MDAP (Method 1: 48% MeCN in 0.1% formic acid). LCMS (Method 3): 2.60 min, 552.2 $[M+H]^+$; $^1H$ NMR (400 MHz, DMSO-$d_6$) δ: 10.60 (s, 1H), 8.95 (d, 1H), 7.53 (d, 1H), 7.48-7.36 (m, 5H), 7.32-7.20 (m, 6H), 7.13 (m, 2H), 6.72 (m, 1H), 5.63 (dd, 1H), 4.63 (d, 1H), 4.43-4.24 (m, 2H), 2.27 (s, 3H), 2.09 (s, 3H), 1.16 (t, 3H).

Example 62: (S)—N-(1-((3-fluoro-4-(1H-pyrazol-4-yl)phenyl)amino)-1-oxo-3,3-diphenylpropan-2-yl)-1-methyl-1H-pyrazole-5-carboxamide

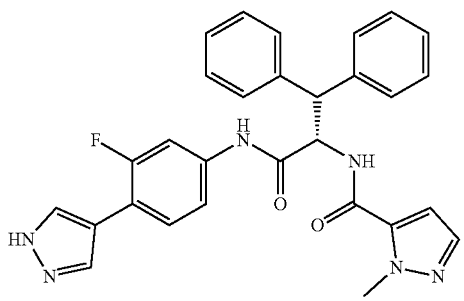 [SMILES: Cn1nccc1C(=O)N[C@H](C(=O)Nc1ccc(-c2cn[nH]c2)c(F)c1)C(c1ccccc1)c1ccccc1]

The title compound (29 mg) was prepared from Intermediate 3.62a (85 mg, 0.13 mmol), HCl (2 M aq; 0.07 mL, 0.13 mmol), 20% palladium hydroxide on carbon (9.5 mg, 0.01 mmol) and 200 psi hydrogen in an autoclave in accordance with the procedure described for Example 59. The crude product was purified by reverse phase column chromatography on the Biotage Isolera One™ (12 g C18 column, eluting 40-70% 0.1% ammonia/MeCN in pH11 0.1% ammonia/$H_2O$). LCMS (Method 3): 2.10 min, 509.2 $[M+H]^+$; $^1H$ NMR (400 MHz, DMSO-$d_6$) δ: 13.01 (s, 1H), 10.42 (s, 1H), 8.91 (d, 1H), 8.03 (s, 1H), 7.85 (s, 1H), 7.57 (t, 1H), 7.45-7.39 (m, 5H), 7.37 (d, 1H), 7.30-7.19 (m, 4H), 7.17-7.06 (m, 3H), 6.78 (d, 1H), 5.58 (dd, 1H), 4.61 (d, 1H), 3.91 (s, 3H).

Example 63: (S)—N-(1-((3-fluoro-4-(1-methyl-2-oxo-1,2-dihydropyrimidin-5-yl)phenyl)amino)-1-oxo-3,3-diphenylpropan-2-yl)-1-methyl-1H-pyrazole-5-carboxamide

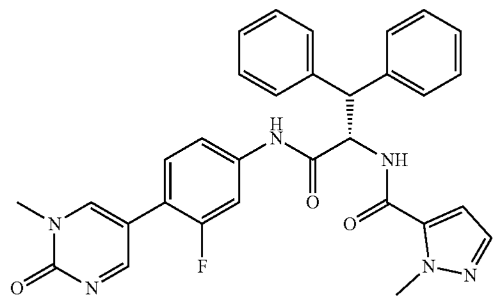 [SMILES: Cn1nccc1C(=O)N[C@H](C(=O)Nc1ccc(-c2cnc(=O)n(C)c2)c(F)c1)C(c1ccccc1)c1ccccc1]

The title compound (8.4 mg) was prepared from Intermediate 3.63 (27 mg, 0.06 mmol), 2-methylpyrazole-3-carboxylic acid (11 mg, 0.08 mmol, CAS: 16034-46-1), HATU (32 mg, 0.08 mmol) and triethylamine (0.02 mL, 0.17 mmol) in accordance with the procedure described for Example 1. The crude product was purified by reverse phase column chromatography on the Biotage Isolera One™ (30 g C18 column, eluting 25-65% 0.1% ammonia/MeCN in pH11 0.1% ammonia/$H_2O$). LCMS (Method 3): 1.93 min, 551.2 $[M+H]^+$; $^1H$ NMR (400 MHz, DMSO-$d_6$) δ: 10.53 (s, 1H), 8.93 (d, 1H), 8.70 (m, 1H), 8.41 (d, 1H), 7.51-7.45 (m, 1H), 7.45-7.39 (m, 5H), 7.39-7.36 (m, 1H), 7.30-7.19 (m, 5H), 7.17-7.07 (m, 2H), 6.78 (d, 1H), 5.58 (dd, 1H), 4.61 (d, 1H), 3.91 (s, 3H), 3.49 (s, 3H).

Example 64: (S)—N-(1-((3-fluoro-4-(2-oxo-1,2-dihydropyrimidin-5-yl)phenyl)amino)-1-oxo-3,3-diphenylpropan-2-yl)-1-methyl-1H-pyrazole-5-carboxamide

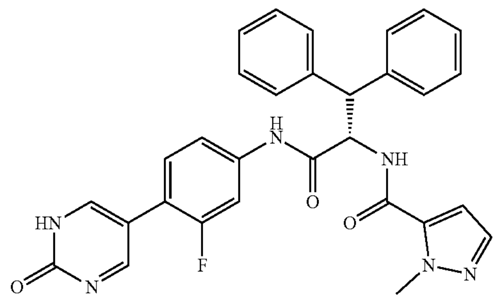 [SMILES: Cn1nccc1C(=O)N[C@H](C(=O)Nc1ccc(-c2cnc(=O)[nH]c2)c(F)c1)C(c1ccccc1)c1ccccc1]

The title compound (14 mg) was prepared from Intermediate 3.64 (91 mg, 0.2 mmol), 2-methylpyrazole-3-carboxylic acid (37 mg, 0.29 mmol, CAS: 16034-46-1), HATU (0.11 mg, 0.29 mmol) and triethylamine (0.08 mL, 0.59 mmol) in accordance with the procedure described for Example 1. The crude product was purified by reverse phase column chromatography on the Biotage Isolera One™ (30 g C18 column, eluting 5-40% 0.1% ammonia/MeCN in pH11 0.1% ammonia/$H_2O$). LCMS (Method 3): 1.23 min, 537.2

[M+H]$^+$; $^1$H NMR (400 MHz, DMSO-$d_6$) δ: 10.52 (s, 1H), 8.95 (d, 1H), 8.29 (s, 2H), 7.46-7.39 (m, 5H), 7.39-7.31 (m, 2H), 7.30-7.07 (m, 7H), 6.78 (d, 1H), 5.58 (dd, 1H), 4.62 (d, 1H), 3.91 (s, 3H).

Example 65: (S)—N-(1-((3-fluoro-4-(3-methyl-1H-pyrazol-4-yl)phenyl)amino)-1-oxo-3,3-diphenylpropan-2-yl)-1-methyl-1H-pyrazole-5-carboxamide

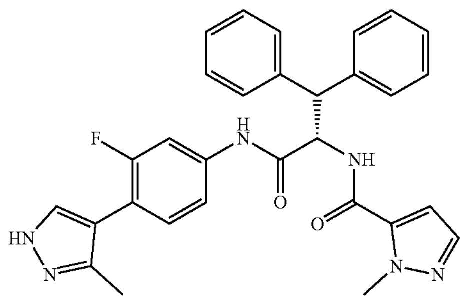 [SMILES: Cc1n[nH]cc1-c1ccc(NC(=O)[C@@H](NC(=O)c2ccnn2C)C(c2ccccc2)c2ccccc2)cc1F]

The title compound (12 mg) was prepared from Intermediate 3.65a (133.5 mg, 0.220 mmol), HCl (6 M aq; 3 drops), 20% palladium hydroxide on carbon (30.6 mg, 0.220 mmol) and 200 psi hydrogen in an autoclave in accordance with the procedure described for Example 59. The crude product was purified by reverse phase column chromatography on the Biotage Isolera One™ (30 g C18 column, eluting 10-65% 0.1% ammonia/MeCN in pH11 0.1% ammonia/$H_2O$), flash column chromatography on the Biotage Isolera One™ (5 g ZIP sphere silica column, eluting 60-100% EtOAc in heptanes) and reverse phase preparative HPLC (Method 1: 40% MeCN in 0.1% $NH_4OH$). LCMS (Method 3): 2.04 min, 523.2 [M+H]$^+$; $^1$H NMR (400 MHz, DMSO-$d_6$) δ: 12.63 (s, 1H), 10.44 (s, 1H), 8.89 (d, 1H), 7.44-7.37 (m, 5H), 7.34 (d, 1H), 7.27-7.18 (m, 5H), 7.17-7.05 (m, 3H), 6.76 (d, 1H), 5.57 (dd, 1H), 5.25 (s, 1H), 4.62 (d, 1H), 3.90 (s, 3H), 2.21 (s, 3H).

Example 66: (S)—N-(1-((3-fluoro-4-(5-oxo-5,6-dihydro-1,6-naphthyridin-8-yl)phenyl)amino)-1-oxo-3,3-diphenylpropan-2-yl)-1-methyl-1H-pyrazole-5-carboxamide

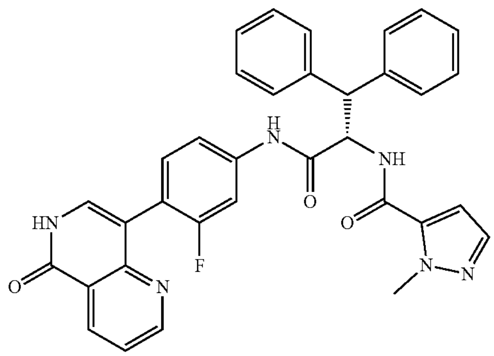 [SMILES: Cn1nccc1C(=O)N[C@H](C(=O)Nc1ccc(-c2c[nH]c(=O)c3cccnc23)c(F)c1)C(c1ccccc1)c1ccccc1]

The title compound (30 mg) was prepared from Intermediate 3.66 (77 mg, 0.14 mmol), 2-methylpyrazole-3-carboxylic acid (23 mg, 0.18 mmol, CAS: 16034-46-1), HATU (68 mg, 0.18 mmol) and triethylamine (0.08 mL, 0.6 mmol) in accordance with the procedure described for Example 1. The crude product was purified by flash column chromatography (eluting 5-10% MeOH in EtOAc) and reverse phase column chromatography on the Biotage Isolera One™ (30 g C18 column, eluting 10-80% 0.1% ammonia/MeCN in pH11 0.1% ammonia/$H_2O$). LCMS (Method 3): 1.97 min, 587.2 [M+H]$^+$; $^1$H NMR (400 MHz, DMSO-$d_6$) δ: 11.75 (s, 1H), 10.56 (s, 1H), 8.96 (d, 1H), 8.85 (dd, 1H), 8.54 (dd, 1H), 7.51 (dd, 1H), 7.49-7.45 (m, 2H), 7.45-7.39 (m, 4H), 7.38 (dd, 1H), 7.32-7.23 (m, 5H), 7.19 (dd, 1H), 7.17-7.10 (m, 2H), 5.62 (dd, 1H), 4.64 (d, 1H), 3.92 (s, 3H).

Example 67: (S)-1-ethyl-N-(1-((3-fluoro-4-(6-oxo-1,6-dihydropyridazin-4-yl)phenyl)amino)-1-oxo-3,3-diphenylpropan-2-yl)-1H-pyrazole-5-carboxamide

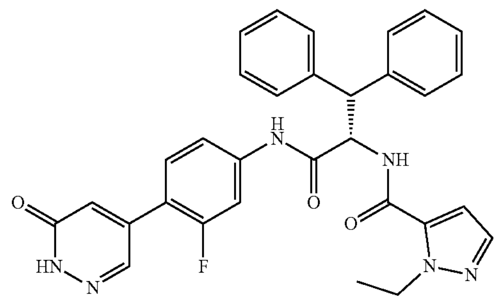 [SMILES: CCn1nccc1C(=O)N[C@H](C(=O)Nc1ccc(-c2cn[nH]c(=O)c2)c(F)c1)C(c1ccccc1)c1ccccc1]

The title compound (17 mg) was prepared from Intermediate 3.67 (0.13 g, 0.25 mmol), 2-ethylpyrazole-3-carboxylic acid (42 mg, 0.3 mmol, CAS: 400755-43-3), HATU (0.11 g, 0.300 mmol) and triethylamine (0.14 mL, 1 mmol) in accordance with the procedure described for Example 1. The crude product was purified by flash column chromatography (eluting 50-100% EtOAc in heptanes, then 5% MeOH in EtOAc), reverse phase column chromatography on the Biotage Isolera One™ (30 g C18 column, eluting 10-50% 0.1% ammonia/MeCN in pH11 0.1% ammonia/$H_2O$) and MDAP (Method 1: 30-60% MeCN in 0.1% $NH_4OH$). LCMS (Method 3): 1.94 min, 551.3 [M+H]$^+$; $^1$H NMR (400 MHz, DMSO-$d_6$) δ: 13.08 (s, 1H), 10.67 (s, 1H), 8.97 (d, 1H), 8.04 (t, 1H), 7.61-7.50 (m, 2H), 7.45-7.37 (m, 5H), 7.31-7.18 (m, 5H), 7.18-7.06 (m, 2H), 6.95 (m, 1H), 6.72 (d, 1H), 5.61 (dd, 1H), 4.62 (d, 1H), 4.34 (m, 2H), 1.15 (t, 3H).

Example 68: (S)—N-(1-((3-fluoro-4-(7-oxo-6,7-dihydro-1H-pyrrolo[2,3-c]pyridin-4-yl)phenyl)amino)-1-oxo-3,3-diphenylpropan-2-yl)-1-methyl-1H-pyrazole-5-carboxamide

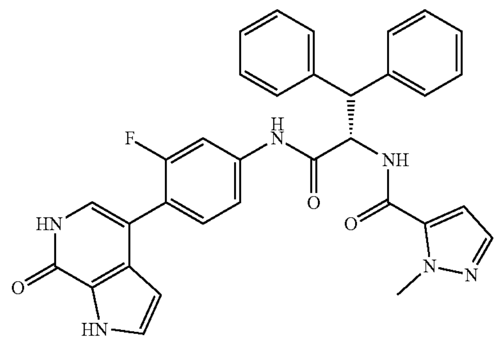 [SMILES: Cn1nccc1C(=O)N[C@H](C(=O)Nc1ccc(-c2c[nH]c(=O)c3[nH]ccc23)c(F)c1)C(c1ccccc1)c1ccccc1]

A suspension of Intermediate 3.68a (0.1 g, 0.17 mmol) in glacial acetic acid (2 mL, 35 mmol) and water (1 mL) was heated by microwave irradiation at 140° C. for 2 h. The mixture was concentrated in vacuo. The residue was partitioned between water and EtOAc and neutralised with a saturated aqueous $NaHCO_3$ at 0° C., then extracted into EtOAc, dried over $MgSO_4$, filtered and concentrated in vacuo. The crude product was purified by flash column chromatography on silica gel (eluting 5% MeOH in DCM) and reverse phase column chromatography on the Biotage Isolera One™ (30 g C18 column, eluting 10-60% 0.1% ammonia/MeCN in pH11 0.1% ammonia/$H_2O$) to afford the title compound (57 mg). LCMS (Method 3): 1.99 min, 575.2 $[M+H]^+$; $^1H$ NMR (400 MHz, DMSO-$d_6$) δ: 12.07 (s, 1H), 11.11 (d, 1H), 10.54 (s, 1H), 8.94 (d, 1H), 7.53-7.41 (m, 5H), 7.39 (d, 1H), 7.37 (d, 1H), 7.31-7.22 (m, 6H), 7.18-7.10 (m, 2H), 6.88 (d, 1H), 6.78 (d, 1H), 6.17-6.14 (m, 1H), 5.62 (dd, 1H), 4.64 (d, 1H), 3.91 (s, 3H).

Example 69: (S)—N-(1-((3-fluoro-4-(4-oxo-4,5-dihydro-3H-imidazo[4,5-c]pyridin-7-yl)phenyl)amino)-1-oxo-3,3-diphenylpropan-2-yl)-1-methyl-1H-pyrazole-5-carboxamide

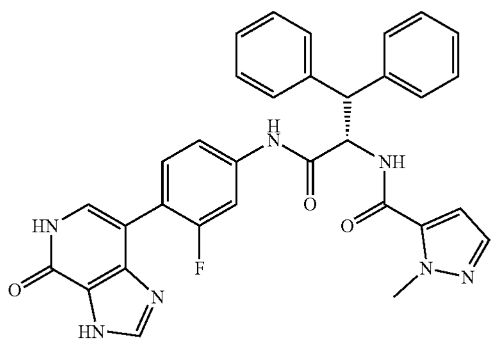 [SMILES: Cn1nccc1C(=O)N[C@H](C(=O)Nc1ccc(-c2c[nH]c(=O)c3[nH]cnc23)c(F)c1)C(c1ccccc1)c1ccccc1]

The title compound (12 mg) was prepared from Intermediate 3.69 (0.14 g, 0.26 mmol), 2-methylpyrazole-3-carboxylic acid (40 mg, 0.31 mmol, CAS: 16034-46-1), HATU (0.12 g, 0.31 mmol) and triethylamine (0.16 mL, 1.2 mmol) in accordance with the procedure described for Example 1. The crude product was purified by reverse phase column chromatography on the Biotage Isolera One™ (30 g C18 column, eluting 20-50% 0.1% ammonia/MeCN in pH11 0.1% ammonia/$H_2O$), flash column chromatography (eluting 20% MeOH in EtOAc) and MDAP (Method 1: 20-50% MeCN in 0.1% $NH_4OH$). LCMS (Method 3): 1.60 min, 576.2 $[M+H]^+$; $^1H$ NMR (400 MHz, DMSO-$d_6$) δ: 11.27 (s, 1H), 10.53 (s, 1H), 8.94 (d, 1H), 8.01 (s, 1H), 7.68 (s, 1H), 7.51-7.35 (m, 6H), 7.31-7.06 (m, 9H), 6.78 (s, 1H), 5.61 (dd, 1H), 4.63 (d, 1H), 3.91 (s, 3H).

Example 70: (S)—N-(1-((3-fluoro-4-(6-oxo-1,6-dihydropyridazin-4-yl)phenyl)amino)-1-oxo-3,3-diphenylpropan-2-yl)-1-methyl-1H-pyrazole-5-carboxamide

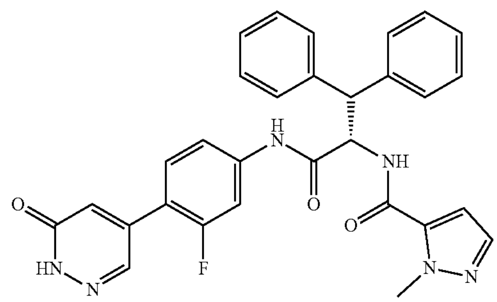 [SMILES: Cn1nccc1C(=O)N[C@H](C(=O)Nc1ccc(-c2cn[nH]c(=O)c2)c(F)c1)C(c1ccccc1)c1ccccc1]

The title compound (24 mg) was prepared from Intermediate 3.67 (0.13 g, 0.25 mmol), 2-methylpyrazole-3-carboxylic acid (38 mg, 0.3 mmol, CAS: 16034-46-1), HATU (0.11 g, 0.3 mmol) and triethylamine (0.14 mL, 1 mmol) in accordance with the procedure described for Example 1. The crude product was purified by flash column chromatography (eluting 50-100% EtOAc in heptanes, then 5% MeOH in EtOAc), reverse phase column chromatography on the Biotage Isolera One™ (30 g C18 column, eluting 10-50% 0.1% ammonia/MeCN in pH11 0.1% ammonia/$H_2O$) and MDAP (Method 1: 20-60% MeCN in 0.1% $NH_4OH$). LCMS (Method 3): 1.74 min, 537.2 $[M+H]^+$; $^1H$ NMR (400 MHz, DMSO-$d_6$) δ: 13.08 (s, 1H), 10.69 (s, 1H), 8.97 (d, 1H), 8.04 (t, 1H), 7.60-7.50 (m, 2H), 7.45-7.40 (m, 4H), 7.37 (d, 1H), 7.31-7.19 (m, 5H), 7.15 (m, 1H), 7.10 (m, 1H), 6.95 (m, 1H), 6.78 (d, 1H), 5.59 (dd, 1H), 4.62 (d, 1H), 3.91 (s, 3H).

Example 71: (S)—N-(1-((3-fluoro-4-(1-methyl-6-oxo-1,6-dihydropyridin-2-yl)phenyl)amino)-1-oxo-3,3-diphenylpropan-2-yl)-1-methyl-1H-pyrazole-5-carboxamide

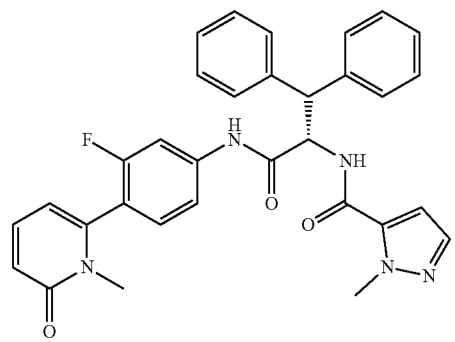 [SMILES: Cn1nccc1C(=O)N[C@H](C(=O)Nc1ccc(-c2cccc(=O)n2C)c(F)c1)C(c1ccccc1)c1ccccc1]

The title compound (22 mg) was prepared from Intermediate 3.71 (82 mg, 0.17 mmol), 2-methylpyrazole-3-carboxylic acid (22 mg, 0.17 mmol, CAS: 16034-46-1), HATU (78 mg, 0.2 mmol) and triethylamine (0.06 mL, 0.43 mmol) in accordance with the procedure described for Example 1. The crude product was purified by reverse phase column chromatography on the Biotage Isolera One™ (30 g C18 column, eluting 10-70% 0.1% ammonia/MeCN in pH11 0.1% ammonia/$H_2O$). LCMS (Method 3): 2.02 min, 550.2

[M+H]$^+$; $^1$H NMR (400 MHz, DMSO-$d_6$) δ: 10.69 (s, 1H), 8.96 (d, 1H), 7.47-7.39 (m, 5H), 7.39-7.20 (m, 8H), 7.18-7.07 (m, 2H), 6.77 (d, 1H), 6.45 (d, 1H), 6.14 (d, 1H), 5.61 (dd, 1H), 4.63 (d, 1H), 3.91 (s, 3H), 3.15 (s, 3H).

Example 72: (S)—N-(1-((1',2'-dimethyl-6'-oxo-1',6'-dihydro-[3,3'-bipyridin]-6-yl)amino)-1-oxo-3,3-diphenylpropan-2-yl)-1-methyl-1H-pyrazole-5-carboxamide

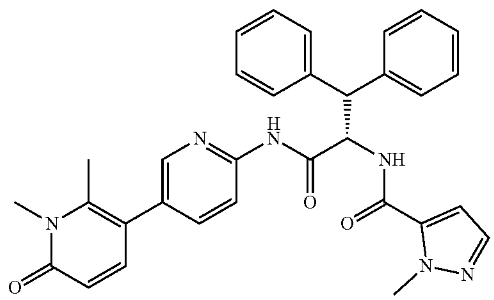 [SMILES: Cc1c(-c2ccc(NC(=O)[C@@H](NC(=O)c3ccnn3C)C(c3ccccc3)c3ccccc3)nc2)ccc(=O)n1C]

The title compound (8 mg) was prepared from Intermediate 3.72 (27 mg, 0.05 mmol), 2-methylpyrazole-3-carboxylic acid (7.3 mg, 0.06 mmol, CAS: 16034-46-1), HATU (26 mg, 0.07 mmol) and triethylamine (0.02 mL, 0.14 mmol) in accordance with the procedure described for Example 1. The crude product was purified by reverse phase column chromatography on the Biotage Isolera One™ (12 g C18 column, eluting 10-70% 0.1% ammonia/MeCN in pH11 0.1% ammonia/$H_2O$). LCMS (Method 3): 1.91 min, 547.2 [M+H]$^+$; $^1$H NMR (400 MHz, DMSO-$d_6$) δ: 10.73 (s, 1H), 8.79 (d, 1H), 8.19 (d, 1H), 7.88 (d, 1H), 7.61 (dd, 1H), 7.53-7.48 (m, 2H), 7.47-7.43 (m, 2H), 7.37 (d, 1H), 7.30 (d, 1H), 7.29-7.24 (m, 2H), 7.24-7.19 (m, 2H), 7.16-7.07 (m, 2H), 6.73 (d, 1H), 6.35 (d, 1H), 5.81 (dd, 1H), 4.63 (d, 1H), 3.90 (s, 3H), 3.50 (s, 3H), 2.26 (s, 3H).

Example 73: (S)—N-(1-((3',5'-dimethyl-[3,4'-bipyridin]-6-yl)amino)-1-oxo-3,3-diphenylpropan-2-yl)-1-methyl-1H-pyrazole-5-carboxamide

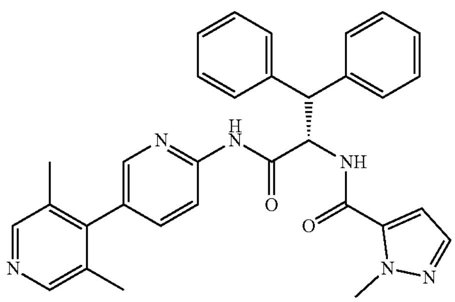

The title compound (9.6 mg) was prepared from Intermediate 3.73 (0.17 g, 0.33 mmol), 2-methylpyrazole-3-carboxylic acid (45 mg, 0.36 mmol, CAS: 16034-46-1), HATU (0.16 g, 0.43 mmol) and triethylamine (0.13 mL, 0.9 mmol) in accordance with the procedure described for Example 1. The crude product was purified by flash column chromatography on the Biotage Isolera One™ (25 g SiliCycle silica column, eluting 40-100% EtOAc in heptanes), reverse phase column chromatography on the Biotage Isolera One™ (30 g C18 column, eluting 10-70% 0.1% ammonia/MeCN in pH11 0.1% ammonia/$H_2O$) and MDAP (Method 1: 30-60% MeCN in 0.1% $NH_4OH$). LCMS (Method 3): 2.17 min, 531.2 [M+H]$^+$; $^1$H NMR (400 MHz, DMSO-$d_6$) δ: 10.78 (s, 1H), 8.82 (d, 1H), 8.34 (s, 2H), 8.15 (m, 1H), 7.95 (d, 1H), 7.59 (dd, 1H), 7.52 (d, 2H), 7.46 (d, 2H), 7.37 (d, 1H), 7.30-7.20 (m, 4H), 7.17-7.08 (m, 2H), 6.74 (d, 1H), 5.83 (dd, 1H), 4.65 (d, 1H), 3.90 (s, 3H), 1.98 (s, 6H).

Example 74: (S)-1-methyl-N-(1-((4-(5-methyl-1H-pyrazol-4-yl)phenyl)amino)-1-oxo-3,3-diphenylpropan-2-yl)-1H-pyrazole-5-carboxamide

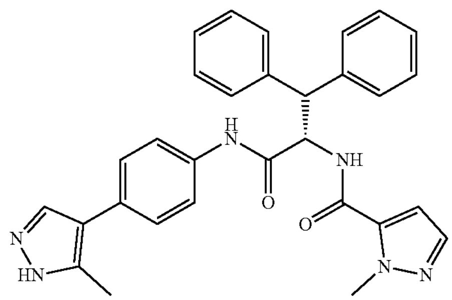 [SMILES: Cc1[nH]ncc1-c1ccc(NC(=O)[C@@H](NC(=O)c2ccnn2C)C(c2ccccc2)c2ccccc2)cc1]

The title compound (0.13 g) was prepared from Intermediate 3.74a (0.6 g, 1 mmol), HCl (6 M aqueous; 3 drops), 20% palladium hydroxide on carbon (0.14 g, 1 mmol) and 200 psi hydrogen in an autoclave in accordance with the procedure described for Example 59. The crude product was purified by reverse phase column chromatography on the Biotage Isolera One™ (30 g C18 column, eluting 10-70% 0.1% ammonia/MeCN in pH11 0.1% ammonia/$H_2O$). LCMS (Method 3): 1.97 min, 505.2 [M+H]$^+$; $^1$H NMR (400 MHz, DMSO-$d_6$) δ: 12.29 (s, 1H), 10.02 (s, 1H), 8.70 (d, 1H), 7.47 (s, 1H), 7.35-7.25 (m, 6H), 7.23 (d, 1H), 7.18-7.06 (m, 6H), 7.03-6.94 (m, 2H), 6.66 (d, 1H), 5.54 (dd, 1H), 4.57 (d, 1H), 3.87 (s, 3H), 2.31 (s, 3H).

Example 75: (S)—N-(1-((3-fluoro-4-(6-methyl-7-oxo-6,7-dihydro-1H-pyrazolo[3,4-c]pyridin-4-yl)phenyl)amino)-1-oxo-3,3-diphenylpropan-2-yl)-1-methyl-1H-pyrazole-5-carboxamide

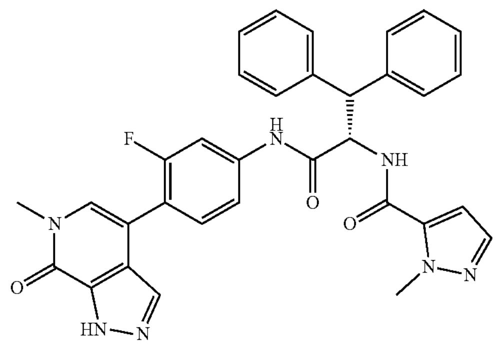 [SMILES: Cn1nccc1C(=O)N[C@H](C(=O)Nc1ccc(-c2cn(C)c(=O)c3[nH]ncc23)c(F)c1)C(c1ccccc1)c1ccccc1]

The title compound (13 mg) was prepared from Intermediate 3.75 (79 mg, 0.14 mmol), 2-methylpyrazole-3-carboxylic acid (22 mg, 0.170 mmol, CAS: 16034-46-1), HATU (65 mg, 0.17 mmol) and triethylamine (0.08 mL, 0.57 mmol) in accordance with the procedure described for Example 1. The crude product was purified by flash column chromatography (eluting 10% MeOH in EtOAc), reverse phase column chromatography on the Biotage Isolera One™ (30 g C18 column, eluting 10-80% 0.1% ammonia/MeCN in pH11 0.1% ammonia/$H_2O$) and MDAP (Method 1: 31-45% MeCN in 0.1% $NH_4OH$). LCMS (Method 3): 1.94 min, 590.3 $[M+H]^+$; $^1H$ NMR (400 MHz, DMSO-$d_6$) δ: 10.57 (s, 1H), 8.93 (s, 1H), 7.77 (s, 1H), 7.53 (dd, 1H), 7.49-7.39 (m, 5H), 7.38 (d, 1H), 7.36-7.20 (m, 6H), 7.13 (dd, 2H), 6.78 (d, 1H), 5.61 (dd, 1H), 4.63 (d, 1H), 3.91 (s, 3H), 3.56 (s, 3H).

Example 76: (S)—N-(1-((4-(7-methoxy-1H-pyrrolo[2,3-c]pyridin-4-yl)phenyl)amino)-1-oxo-3,3-diphenylpropan-2-yl)-1-methyl-1H-pyrazole-5-carboxamide

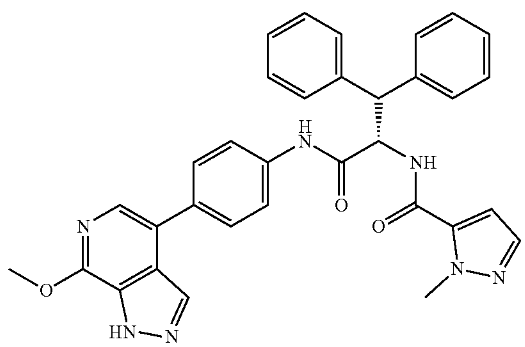 [SMILES: COc1ncc(-c2ccc(NC(=O)[C@@H](NC(=O)c3ccnn3C)C(c3ccccc3)c3ccccc3)cc2)c2cn[nH]c12]

The title compound (0.1 g) was prepared from Intermediate 3.76 (0.15 g, 0.27 mmol), 2-methylpyrazole-3-carboxylic acid (34 mg, 0.27 mmol, CAS: 16034-46-1), HATU (0.11 mg, 0.28 mmol) and triethylamine (0.11 mL, 0.81 mmol) in accordance with the procedure described for Example 1. The crude product was purified by reverse phase column chromatography on the Biotage Isolera One™ (30 g C18 column, eluting 45-70% 0.1% ammonia/MeCN in pH11 0.1% ammonia/$H_2O$). LCMS (Method 13): 2.13 min, 571.2 [M+H]1; $^1H$ NMR (400 MHz, DMSO-$d_6$) δ: 11.85 (s, 1H), 10.37 (s, 1H), 8.92 (d, 1H), 7.67 (s, 1H), 7.56-7.46 (m, 7H), 7.46-7.42 (m, 2H), 7.37 (d, 1H), 7.30-7.21 (m, 4H), 7.17-7.08 (m, 2H), 6.79 (d, 1H), 6.55 (dd, 1H), 5.65 (dd, 1H), 4.65 (d, 1H), 4.03 (s, 3H), 3.91 (s, 3H).

Example 77: (S)—N-(1-((3-fluoro-4-(6-oxo-1,6-dihydropyridin-2-yl)phenyl)amino)-1-oxo-3,3-diphenylpropan-2-yl)-1-methyl-1H-pyrazole-5-carboxamide

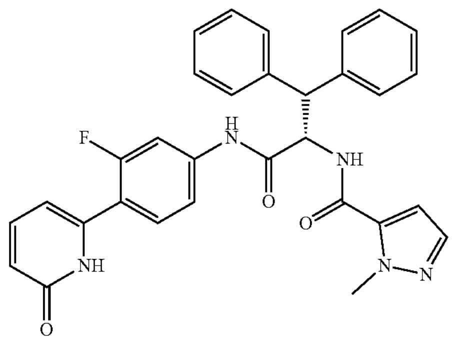 [SMILES: Cn1nccc1C(=O)N[C@H](C(=O)Nc1ccc(-c2cccc(=O)[nH]2)c(F)c1)C(c1ccccc1)c1ccccc1]

The title compound (9.6 mg) was prepared from Intermediate 3.77a (87 mg, 0.1 mmol), HCl (6 M aqueous; 2 drops), palladium on carbon (10 mg, 0.1 mmol) and an atmosphere of hydrogen in accordance with the procedure described for Example 59. The crude product was purified by reverse phase column chromatography on the Biotage Isolera One™ (12 g C18 column, eluting 10-70% 0.1% ammonia/MeCN in pH11 0.1% ammonia/$H_2O$). LCMS (Method 13): 1.99 min, 536.2 $[M+H]^+$; $^1H$ NMR (400 MHz, DMSO-$d_6$) δ: 10.62 (s, 1H), 8.94 (d, 1H), 7.54-7.45 (m, 3H), 7.45-7.40 (m, 5H), 7.37 (d, 1H), 7.30-7.20 (m, 6H), 7.17-7.07 (m, 2H), 6.77 (d, 1H), 6.35 (s, 1H), 5.59 (dd, 1H), 4.62 (d, 1H), 3.91 (s, 3H).

Example 78: (S)-1-methyl-N-(1-oxo-1-((4-(3-(2-oxo-2-(pyrrolidin-1-yl)ethyl)pyridin-4-yl)phenyl)amino)-3,3-diphenylpropan-2-yl)-1H-pyrazole-5-carboxamide

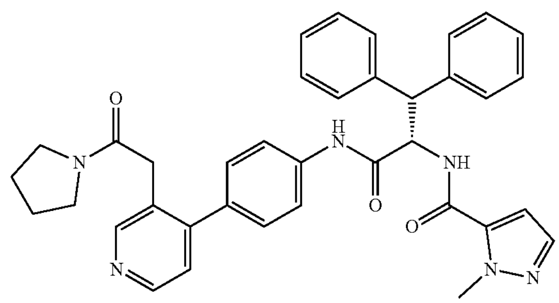 [SMILES: Cn1nccc1C(=O)N[C@H](C(=O)Nc1ccc(-c2ccncc2CC(=O)N2CCCC2)cc1)C(c1ccccc1)c1ccccc1]

The title compound (31 mg) was prepared from Intermediate 3.78 (58 mg, 0.1 mmol), 2-methylpyrazole-3-carboxylic acid (13 mg, 0.1 mmol, CAS: 16034-46-1), HATU (46 mg, 0.12 mmol) and triethylamine (0.04 mL, 0.3 mmol) in accordance with the procedure described for Example 1. The crude product was purified by reverse phase column chromatography on the Biotage Isolera One™ (30 g C18 column, eluting 10-70% 0.1% ammonia/MeCN in pH11 0.1% ammonia/$H_2O$). LCMS (Method 11): 2.22 min, 613.3 $[M+H]^+$; $^1H$ NMR (400 MHz, DMSO-$d_6$) δ: 10.40 (s, 1H), 8.90 (d, 1H), 8.43 (d, 1H), 8.41 (s, 1H), 7.51-7.40 (m, 6H), 7.37 (d, 1H), 7.30-7.08 (m, 9H), 6.77 (d, 1H), 5.63 (dd, 1H), 4.63 (d, 1H), 3.91 (s, 3H), 3.53 (s, 2H), 3.18 (m, 4H), 1.80-1.63 (m, 4H).

Example 79: (S)-4-(4-(2-(1-methyl-1H-pyrazole-5-carboxamido)-3,3-diphenylpropanamido)phenyl)-3-(2-oxo-2-(pyrrolidin-1-yl)ethyl)pyridine 1-oxide

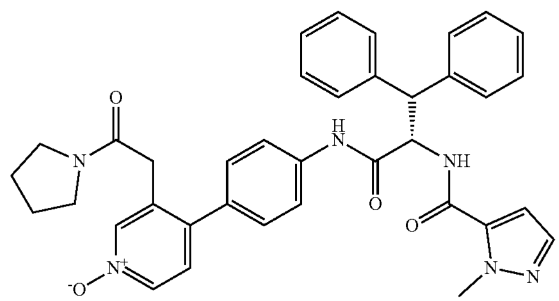

The title compound (2.6 mg) was prepared from Example 78 (14 mg, 0.02 mmol) and mCPBA (7.9 mg, 0.03 mmol) in accordance with the procedure described for Example 25. The crude product was purified by reverse phase column chromatography on the Biotage Isolera One™ (12 g C18 column, eluting 10-70% MeCN in pH10 0.1 M $NH_4HCO_3$ buffer solution). LCMS (Method 11): 2.00 min, 629.4 $[M+H]^+$; $^1H$ NMR (400 MHz, DMSO-$d_6$) δ: 10.41 (s, 1H), 8.91 (s, 1H), 8.16-8.10 (m, 2H), 7.50-7.39 (m, 6H), 7.37 (d, 1H), 7.29-7.20 (m, 5H), 7.17 (d, 2H), 7.16-7.07 (m, 2H), 6.77 (d, 1H), 5.62 (dd, 1H), 4.63 (d, 1H), 3.90 (s, 3H), 3.50 (s, 2H), 3.22-3.13 (m, 4H), 1.80-1.64 (m, 4H).

Example 80: (S)—N-(1-((3-fluoro-4-(6-oxo-1,6-dihydropyrimidin-4-yl)phenyl)amino)-1-oxo-3,3-diphenylpropan-2-yl)-1-methyl-1H-pyrazole-5-carboxamide

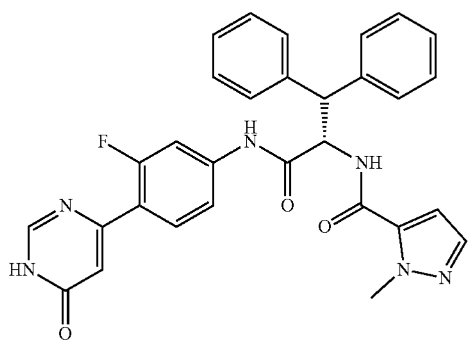 [SMILES: Cn1nccc1C(=O)N[C@H](C(=O)Nc1ccc(-c2cc(=O)[nH]cn2)c(F)c1)C(c1ccccc1)c1ccccc1]

The title compound (15 mg) was prepared from Intermediate 3.80 (41 mg, 0.09 mmol), 2-methylpyrazole-3-carboxylic acid (11 mg, 0.09 mmol, CAS: 16034-46-1), HATU (34 mg, 0.09 mmol) and triethylamine (0.04 mL, 0.26 mmol) in accordance with the procedure described for Example 1. The crude product was purified by reverse phase column chromatography on the Biotage Isolera One™ (25 g C18 column, eluting 5-40% MeCN in pH10 0.1 M $NH_4HCO_3$ buffer solution). LCMS (Method 12): 1.35 min, 537.2 $[M+H]^+$; $^1H$ NMR (400 MHz, MeOD) δ: 8.26 (d, 1H), 7.92 (t, 1H), 7.50-7.41 (m, 3H), 7.41-7.27 (m, 5H), 7.26-7.18 (m, 3H), 7.16-7.08 (m, 2H), 6.84 (s, 1H), 6.54 (d, 1H), 5.57 (d, 1H), 4.64 (d, 1H), 3.96 (s, 3H).

Example 81: (S)—N-(1-((4-(3,6-dihydro-2H-pyran-4-yl)phenyl)amino)-1-oxo-3,3-diphenylpropan-2-yl)-1-methyl-1H-pyrazole-5-carboxamide

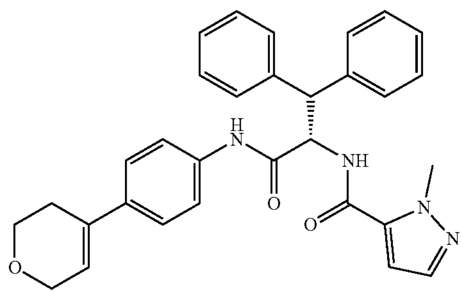 [SMILES: Cn1nccc1C(=O)N[C@H](C(=O)Nc1ccc(C2=CCOCC2)cc1)C(c1ccccc1)c1ccccc1]

The title compound (15 mg) was prepared from Intermediate 3.81 (0.22 g, 0.51 mmol), 2-methylpyrazole-3-carboxylic acid (64 mg, 0.51 mmol, CAS: 16034-46-1), HATU (0.23 g, 0.61 mmol) and triethylamine (0.21 mL, 1.5 mmol) in accordance with the procedure described for Example 1. The crude product was purified by flash column chromatography on the Biotage Isolera One™ (25 g SiliCycle silica column, eluting 5-90% EtOAc in heptanes) and reverse phase column chromatography on the Biotage Isolera One™ (25 g C18 column, eluting 5-80% 0.1% ammonia/MeCN in pH11 0.1% ammonia/$H_2O$). LCMS (Method 3): 2.28 min, 504.8 $[M-H]^-$; $^1H$ NMR (400 MHz, DMSO-$d_6$) δ: 10.24 (s, 1H), 8.86 (d, 1H), 7.46-7.34 (m, 7H), 7.33-7.17 (m, 6H), 7.13 (m, 1H), 7.08 (m, 1H), 6.76 (d, 1H), 6.14 (m, 1H), 5.59 (dd, 1H), 4.60 (d, 1H), 4.18 (m, 2H), 3.90 (s, 3H), 3.78 (m, 2H), 1.40-1.13 (m, 2H).

Example 82: N-(1-(9H-fluoren-9-yl)-2-((4-(3-methoxypyridin-4-yl)phenyl)amino)-2-oxoethyl)-1-methyl-1H-pyrazole-5-carboxamide

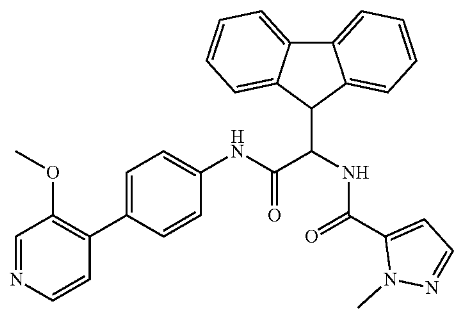 [SMILES: COc1cnccc1-c1ccc(NC(=O)C(NC(=O)c2ccnn2C)C2c3ccccc3-c3ccccc32)cc1]

The title compound (22 mg) was prepared from Intermediate 1.3 (95 mg, 0.47 mmol), Intermediate 4.2 (0.17 g, 0.47 mmol), T3P® (50% w/w solution in EtOAc; 0.91 mL, 1.4 mmol) and triethylamine (0.17 mL, 1.2 mmol) in accordance with the procedure described for Example 21. The crude product was purified by reverse phase column chromatography on the Biotage Isolera One™ (30 g C18 column, eluting 30-70% MeCN in pH10 0.1 M $NH_4HCO_3$ buffer solution). LCMS (Method 6): 1.64 min, 529.8 $[M+H]^+$; $^1H$ NMR (400 MHz, DMSO-$d_6$) δ: 10.32 (s, 1H), 9.16 (d, 1H), 8.45 (s, 1H), 8.27 (d, 1H), 7.92 (d, 2H), 7.74 (d, 2H), 7.62-7.58 (m, 3H), 7.51 (d, 1H), 7.45-7.35 (m, 4H), 7.25 (t, 1H), 7.20 (t, 1H), 7.09 (d, 1H), 4.72-4.62 (m, 2H), 3.95 (s, 3H), 3.91 (s, 3H). Chiral analysis undertaken on Waters Alliance 2996 with diode array (336 nm). Column: YMC SB 5 μm, 4.6 mm×250 mm (flow 0.5 mL/min). Run time 15 min. Conditions: EtOH (100%), TFA (0.1%). Column temp: 25° C. Enantiomer 1: 5.64 min (28.43% area); Enantiomer 2: 6.48 min (71.57% area). 43% ee.

Example 83: N—((S)-2-((4-(1,2-Dimethyl-6-oxo-1,6-dihydropyridin-3-yl)-3-fluorophenyl)amino)-1-((1r,4S)-4-methylcyclohexyl)-2-oxoethyl)-1-methyl-1H-pyrazole-5-carboxamide

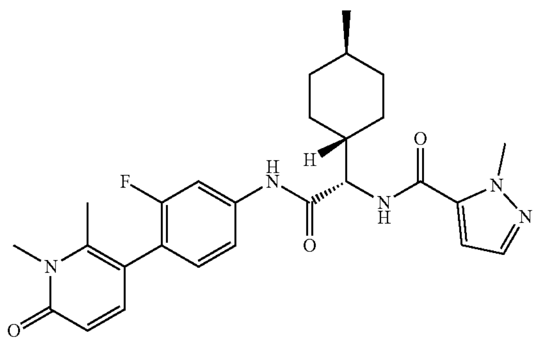 [SMILES: Cc1c(-c2ccc(NC(=O)[C@@H](NC(=O)c3ccnn3C)[C@H]3CC[C@H](C)CC3)cc2F)ccc(=O)n1C]

The title compound (23 mg) was prepared from Intermediate 3.83 (52 mg, 0.12 mmol) and 2-methylpyrazole-3-carboxylic acid (23 mg, 0.19 mmol, CAS: 16034-46-1), HATU (71 mg, 0.19 mmol) and triethylamine (0.1 mL, 0.74 mmol) in accordance with the procedure described for Example 1 in MeCN/DMF. The crude product was purified by flash column chromatography on the Biotage Isolera One™ (25 g SiliCycle silica column, eluting 10-60% EtOAc in heptanes). The compound was dissolved in a mixture of DCM/MeOH (95:5) and washed with 10% LiCl solution then $H_2O$. The organic layer was concentrated in vacuo, the residue dissolved in hot EtOAc then washed with $H_2O$. The organic layer was filtered through a phase-separating cartridge, and the organics concentrated in vacuo. LCMS (Method 3): 2.14 min, 494.2 $[M+H]^+$; $^1H$ NMR (400 MHz, DMSO-$d_6$) δ: 10.51 (s, 1H), 8.57 (d, 1H), 7.72 (dd, 1H), 7.46 (d, 1H), 7.42 (dd, 1H), 7.27-7.21 (m, 2H), 7.07 (d, 1H), 6.35 (d, 1H), 4.36 (dd, 1H), 4.03 (s, 3H), 3.51 (s, 3H), 2.21 (d, 3H), 2.12-1.75 (m, 2H), 1.75-1.65 (m, 2H), 1.62-1.54 (m, 1H), 1.37-1.13 (m, 2H), 1.10-0.98 (m, 1H), 0.95-0.79 (m, 5H).

Example 84: N—((S)-2-((4-(3,5-Dimethyl-1H-pyrazol-4-yl)phenyl)amino)-1-((1r,4S)-4-methylcyclohexyl)-2-oxoethyl)-1-methyl-1H-pyrazole-5-carboxamide

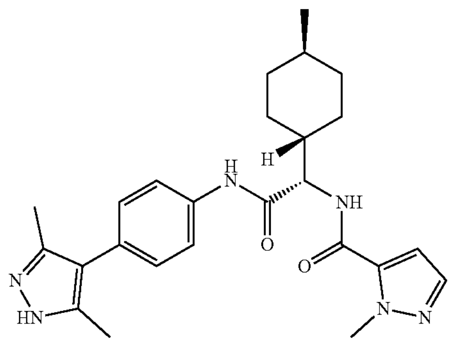 [SMILES: Cc1n[nH]c(C)c1-c1ccc(NC(=O)[C@@H](NC(=O)c2ccnn2C)[C@H]2CC[C@H](C)CC2)cc1]

A solution of Intermediate 3.84a (0.2 g, 0.35 mmol) in MeOH (80 mL) was hydrogenated in an H-Cube® using a $Pd(OH)_2/C$ cartridge at 60 bar and 60° C. for 14 runs. The mixture was concentrated in vacuo then purified by automated reverse phase column chromatography on the Biotage Isolera One™ (10 g C18 column, 5-100% 0.1% ammonia/MeCN in pH11 0.1% ammonia/$H_2O$) to afford the title compound (25 mg). LCMS (Method 15): 2.32 min, 448.2 $[M+H]^+$; $^1H$ NMR (400 MHz, DMSO-$d_6$) δ: 12.20 (s, 1H), 10.21 (s, 1H), 8.51 (d, 1H), 7.70-7.62 (m, 2H), 7.46 (d, 1H), 7.25-7.17 (m, 2H), 7.07 (d, 1H), 4.38 (t, 1H), 4.03 (s, 3H), 2.17 (s, 6H), 1.90-1.56 (m, 5H), 1.32-0.79 (m, 8H).

Example 85: 1-Methyl-N—((S)-1-((1r,4S)-4-methylcyclohexyl)-2-oxo-2-((4-(7-oxo-6,7-dihydro-1H-pyrrolo[2,3-c]pyridin-4-yl)phenyl)amino)ethyl)-1H-pyrazole-5-carboxamide

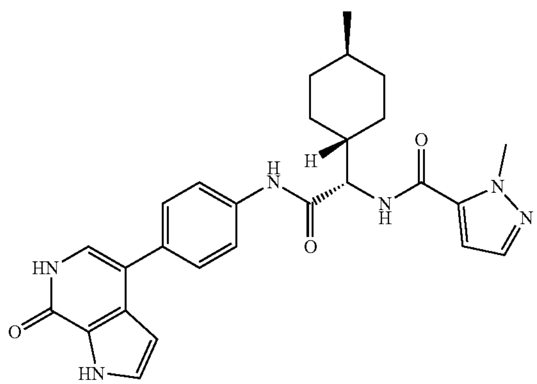 [SMILES: Cn1nccc1C(=O)N[C@H](C(=O)Nc1ccc(-c2c[nH]c(=O)c3[nH]ccc23)cc1)[C@H]1CC[C@H](C)CC1]

The title compound (50 mg) was prepare from Intermediate 3.85 (0.1 g, 0.22 mmol), 2-methylpyrazole-3-carboxylic acid (28 mg, 0.22 mmol, CAS: 16034-46-1) HATU (84 mg, 0.22 mmol) and triethylamine (0.12 mL, 0.89 mmol) in accordance with the procedure described for Example 1 in MeCN/DMF. The crude product was purified by reverse phase column chromatography on the Biotage Isolera One™ (25 g C18 column, eluting 10-50% 0.1% ammonia/MeCN in pH11 0.1% ammonia/$H_2O$). LCMS (Method 18) 2.19 min, 487.4 $[M+H]^+$; $^1H$ NMR (400 MHz, DMSO-$d_6$) δ: 12.24 (s, 1H), 11.21 (d, 1H), 10.38 (s, 1H), 8.61 (d, 1H), 7.80 (d, 2H), 7.58 (d, 2H), 7.54 (d, 1H), 7.42 (dd, 1H), 7.14 (d, 1H), 7.00 (d, 1H), 6.51 (dd, 1H), 4.42 (t, 1H), 4.06 (s, 3H), 1.91-1.55 (m, 5H), 1.34-1.13 (m, 2H), 1.02 (m, 1H), 0.93-0.78 (m, 5H).

Example 86: 1-Methyl-N—((S)-1-((1r,4S)-4-methylcyclohexyl)-2-oxo-2-((4-(3-(2-oxo-2-(pyrrolidin-1-yl)ethyl)pyridin-4-yl)phenyl)amino)ethyl)-1H-pyrazole-5-carboxamide

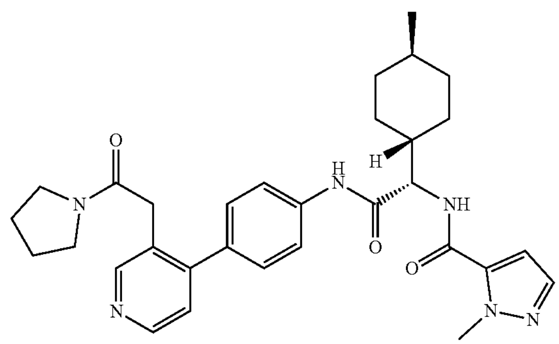 [SMILES: Cn1nccc1C(=O)N[C@H](C(=O)Nc1ccc(-c2ccncc2CC(=O)N2CCCC2)cc1)[C@H]1CC[C@H](C)CC1]

The title compound (47 mg) was prepared from Intermediate 3.86 (93 mg, 0.18 mmol), 2-methylpyrazole-3-carboxylic acid (28 mg, 0.22 mmol, CAS: 16034-46-1), HATU (84 mg, 0.22 mmol) and triethylamine (0.1 mL, 0.73 mmol) in accordance with the procedure described for Example 1. The crude product was purified by flash column chromatography (eluting 25% MeOH in EtOAc) and MDAP (Method 1: 38% MeCN in 0.1% $NH_4OH$). LCMS (Method 3): 2.05 min, 543.3 $[M+H]^+$; $^1H$ NMR (400 MHz, DMSO-$d_6$) δ: 10.36 (s, 1H), 8.55 (d, 1H), 8.46 (d, 1H), 8.43 (s, 1H), 7.72 (d, 2H), 7.46 (d, 1H), 7.28 (d, 2H), 7.22 (d, 1H), 7.07 (d, 1H), 4.38 (t, 1H), 4.03 (s, 3H), 3.58 (s, 2H), 3.26-3.17 (m, 4H), 1.91-1.54 (m, 9H), 1.37-1.15 (m, 2H), 1.04 (m, 1H), 0.94-0.81 (m, 5H).

Example 87: 1-Methyl-N—((S)-1-((1r,4S)-4-methylcyclohexyl)-2-oxo-2-((4-(2-oxo-1,2-dihydropyridin-4-yl)phenyl)amino)ethyl)-1H-pyrazole-5-carboxamide

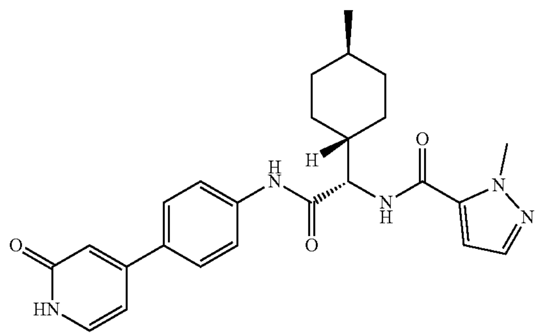 [SMILES: Cn1nccc1C(=O)N[C@H](C(=O)Nc1ccc(-c2cc[nH]c(=O)c2)cc1)[C@H]1CC[C@H](C)CC1]

The title compound (13 mg) was prepared from Intermediate 3.87 (30 mg, 0.08 mmol), 2-methylpyrazole-3-carboxylic acid (10 mg, 0.08 mmol, CAS: 16034-46-1) HATU (30 mg, 0.08 mmol) and triethylamine (0.03 mL, 0.24 mmol) in accordance with the procedure described for Example 1 in MeCN/DMF. The crude product was purified by reverse phase column chromatography on the Biotage Isolera One™ (25 g C18 column, eluting 10-50% 0.1% ammonia/MeCN in pH11 0.1% ammonia/$H_2O$) and flash column chromatography on the Biotage Isolera One™ (5 g ZIP silica column, eluting 0-10% MeOH in DCM). LCMS (Method 3): 1.84 min, 448.3 $[M+H]^+$; $^1H$ NMR (400 MHz, DMSO-$d_6$) δ: 11.66 (s, 1H), 10.51 (s, 1H), 8.63 (d, 1H), 7.82 (d, 2H), 7.75 (d, 2H), 7.54 (d, 1H), 7.49 (d, 1H), 7.14 (d, 1H), 6.62 (d, 1H), 6.55 (d, 1H), 4.42 (t, 1H), 4.05 (s, 3H), 1.90-1.51 (m, 5H), 1.35-1.11 (m, 2H), 1.02 (m, 1H), 0.92-0.77 (m, 5H).

Example 88: N—((S)-2-((4-(Imidazo[1,2-a]pyridin-5-yl)phenyl)amino)-1-((1r,4S)-4-methylcyclohexyl)-2-oxoethyl)-1-methyl-1H-pyrazole-5-carboxamide

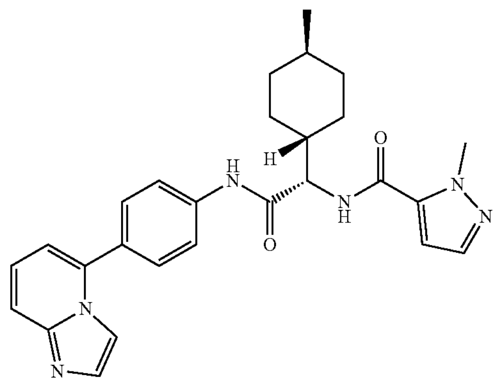 [SMILES: Cn1nccc1C(=O)N[C@H](C(=O)Nc1ccc(-c2cccc3nccn23)cc1)[C@H]1CC[C@H](C)CC1]

The title compound (14 mg) was prepared from Intermediate 3.88 (28 mg, 0.07 mmol), 2-methylpyrazole-3-carboxylic acid (8.7 mg, 0.07 mmol, CAS: 16034-46-1), HATU (32 mg, 0.08 mmol) and triethylamine (0.02 mL, 0.17 mmol) in accordance with the procedure described for Example 1. The crude product was purified by reverse phase column chromatography on the Biotage Isolera One™ (30 g C18 column, eluting 30-70% 0.1% ammonia/MeCN in pH11 0.1% ammonia/$H_2O$). LCMS (Method 12): 2.23 min, 471.3 $[M+H]^+$; $^1H$ NMR (400 MHz, DMSO-$d_6$) δ: 10.50 (d, 1H), 8.58 (dd, 1H), 7.91-7.79 (m, 3H), 7.73-7.54 (m, 4H), 7.50-7.44 (m, 1H), 7.39-7.28 (m, 1H), 7.11-7.04 (m, 1H), 6.88 (dd, 1H), 4.41 (dd, 1H), 4.08-4.00 (m, 3H), 1.96-1.52 (m, 5H), 1.38-1.18 (m, 2H), 1.13-1.01 (m, 1H), 0.93-0.80 (m, 5H).

Example 89: N—((S)-2-((1',2'-Dimethyl-6'-oxo-1',6'-dihydro-[3,3'-bipyridin]-6-yl)amino)-1-((1r,4S)-4-methylcyclohexyl)-2-oxoethyl)-1-methyl-1H-pyrazole-5-carboxamide

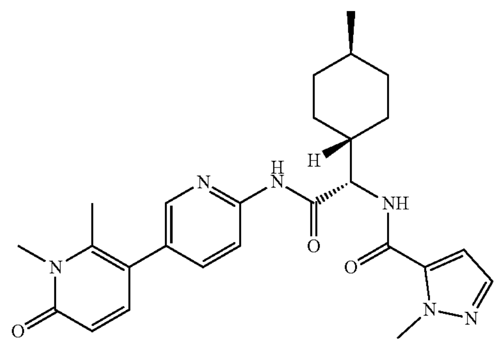 [SMILES: Cc1c(-c2ccc(NC(=O)[C@@H](NC(=O)c3ccnn3C)[C@H]3CC[C@H](C)CC3)nc2)ccc(=O)n1C]

The title compound (3.2 mg) was prepared from Intermediate 3.89 (16 mg, 0.04 mmol), 2-methylpyrazole-3-carboxylic acid (16 mg, 0.04 mmol, CAS: 16034-46-1), HATU (18 mg, 0.05 mmol) and triethylamine (0.01 mL, 0.1 mmol) in accordance with the procedure described for Example 1. The crude product was purified by reverse phase column chromatography on the Biotage Isolera One™ (12 g C18 column, eluting 10-70% 0.1% ammonia/MeCN in pH11 0.1% ammonia/$H_2O$). LCMS (Method 12): 1.96 min, 477.3 $[M+H]^+$; $^1H$ NMR (400 MHz, DMSO-$d_6$) δ: 10.71 (s, 1H), 8.48 (s, 1H), 8.24 (s, 1H), 8.14 (s, 1H), 7.71 (dd, 1H), 7.47 (d, 1H), 7.35 (d, 1H), 7.04 (d, 1H), 6.38 (d, 1H), 4.53 (dd, 1H), 4.02 (s, 3H), 3.52 (s, 3H), 2.31 (s, 3H), 1.88-1.54 (m, 5H), 1.36-1.19 (m, 2H), 1.17-1.00 (m, 1H), 0.88-0.81 (m, 5H).

Example 90: N—((S)-2-((3',5'-Dimethyl-[3,4'-bipyridin]-6-yl)amino)-1-((1r,4S)-4-methylcyclohexyl)-2-oxoethyl)-1-methyl-1H-pyrazole-5-carboxamide

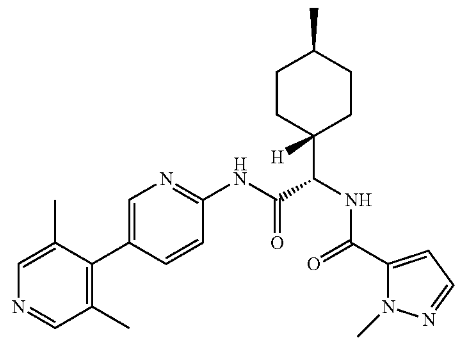 [SMILES: Cc1cncc(C)c1-c1ccc(NC(=O)[C@@H](NC(=O)c2ccnn2C)[C@H]2CC[C@H](C)CC2)nc1]

The title compound (33 mg) was prepared from Intermediate 3.90 (57 mg, 0.13 mmol), 2-methylpyrazole-3-carboxylic acid (17 mg, 0.13 mmol, CAS: 16034-46-1), HATU (61 mg, 0.16 mmol) and triethylamine (0.05 mL, 0.33 mmol) in accordance with the procedure described for Example 1. The crude product was purified by MDAP (Method 1: 40-70% MeCN in 0.1% $NH_4OH$). LCMS (Method 12): 2.29 min, 461.3 $[M+H]^+$; $^1H$ NMR (400 MHz, DMSO-$d_6$) δ: 10.77 (s, 1H), 8.50 (d, 1H), 8.36 (s, 2H), 8.22-8.19 (m, 2H), 7.69 (dd, 1H), 7.47 (d, 1H), 7.04 (d, 1H), 4.54 (t, 1H), 4.02 (s, 3H), 2.03 (s, 6H), 1.90-1.75 (m, 2H), 1.75-1.55 (m, 3H), 1.37-1.19 (m, 2H), 1.08 (m, 1H), 0.95-0.80 (m, 5H).

Example 91: N—((S)-2-((1',2'-Dimethyl-6'-oxo-1',6'-dihydro-[3,3'-bipyridin]-6-yl)amino)-1-((1r,4S)-4-methylcyclohexyl)-2-oxoethyl)-1-ethyl-1H-pyrazole-5-carboxamide

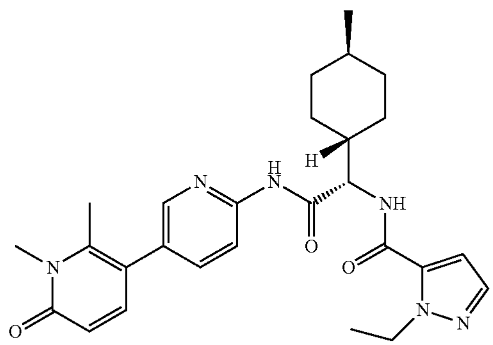 [SMILES: CCn1nccc1C(=O)N[C@H](C(=O)Nc1ccc(-c2ccc(=O)n(C)c2C)cn1)[C@H]1CC[C@H](C)CC1]

The title compound (2 mg) was prepared from Intermediate 3.89 (11 mg, 0.03 mmol), 2-ethylpyrazole-3-carboxylic acid (3.9 mg, 0.03 mmol, CAS: 400755-43-3), HATU (13 mg, 0.03 mmol) and triethylamine (0.01 mL, 0.070 mmol) in accordance with the procedure described for Example 1. The crude product was purified by reverse phase column chromatography on the Biotage Isolera One™ (12 g C18 column, eluting 10-70% 0.1% ammonia/MeCN in pH11 0.1% ammonia/$H_2O$). LCMS (Method 12): 2.07 min, 491.3 $[M+H]^+$; $^1H$ NMR (400 MHz, DMSO-$d_6$) δ: 10.71 (s, 1H), 8.49 (d, 1H), 8.24 (d, 1H), 8.14 (d, 1H), 7.71 (dd, 1H), 7.48 (d, 1H), 7.35 (d, 1H), 7.00 (d, 1H), 6.38 (d, 1H), 4.52 (dd, 1H), 4.45 (m, 2H), 3.52 (s, 3H), 2.31 (s, 3H), 1.88-1.78 (m, 2H), 1.73-1.65 (m, 2H), 1.63-1.55 (m, 1H), 1.38-1.20 (m, 5H), 1.16-1.02 (m, 1H), 0.93-0.81 (m, 5H).

Example 92: N—((S)-2-((3',5'-Dimethyl-[3,4'-bipyridin]-6-yl)amino)-1-((1r,4S)-4-methylcyclohexyl)-2-oxoethyl)-1-ethyl-1H-pyrazole-5-carboxamide

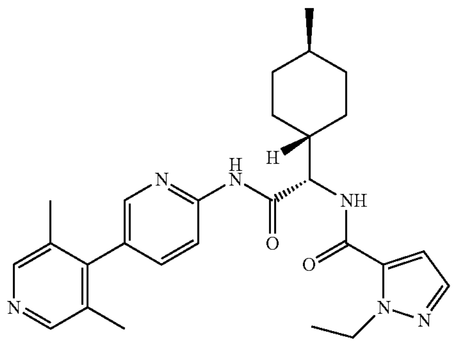 [SMILES: CCn1nccc1C(=O)N[C@H](C(=O)Nc1ccc(-c2c(C)cncc2C)cn1)[C@H]1CC[C@H](C)CC1]

The title compound (25 mg) was prepared from Intermediate 3.90 (42 mg, 0.1 mmol), 2-ethylpyrazole-3-carboxylic acid (17 mg, 0.12 mmol, CAS: 400755-43-3), HATU (5.1 mg, 0.12 mmol) and triethylamine (0.05 mL, 0.35 mmol) in accordance with the procedure described for Example 1 in DCM. The crude product was purified by MDAP (Method 1: 40-80% MeCN in 0.1% $NH_4OH$). LCMS (Method 12): 2.42 min, 475.3 $[M+H]^+$; $^1H$ NMR (400 MHz, DMSO-$d_6$) δ: 10.76 (s, 1H), 8.50 (d, 1H), 8.36 (s, 2H), 8.23-8.18 (m, 2H), 7.69 (dd, 1H), 7.49 (d, 1H), 7.01 (d, 1H), 4.54 (t, 1H), 4.46 (m, 2H), 2.03 (s, 6H), 1.90-1.76 (m, 2H), 1.76-1.57 (m, 3H), 1.37-1.20 (m, 5H), 1.09 (m, 1H), 0.90-0.80 (m, 5H).

Example 93: 1-Methyl-N—((S)-1-((1r,4S)-4-methylcyclohexyl)-2-oxo-2-((4-(tetrahydro-2H-pyran-4-yl)phenyl)amino)ethyl)-1H-pyrazole-5-carboxamide

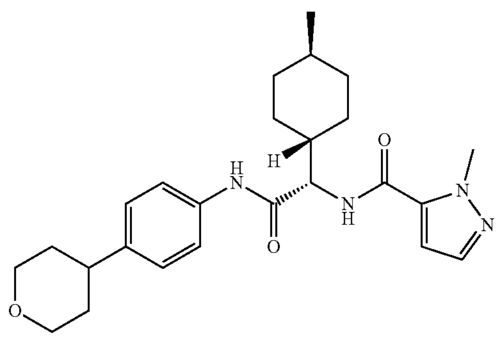 [SMILES: Cn1nccc1C(=O)N[C@H](C(=O)Nc1ccc(C2CCOCC2)cc1)[C@H]1CC[C@H](C)CC1]

The title compound (20 mg) was prepared from Intermediate 3.93 (65 mg, 0.18 mmol), 2-methylpyrazole-3-carboxylic acid (22 mg, 0.18 mmol, CAS: 16034-46-1), HATU (67 mg, 0.18 mmol) and triethylamine (0.05 mL, 0.35 mmol) in accordance with the procedure described for Example 1. The crude product was purified by reverse phase column chromatography on the Biotage Isolera One™ (30 g C18 column, eluting 10-70% MeCN in pH10 0.1 M $NH_4HCO_3$ buffer solution). LCMS (Method 12): 2.38 min, 439.3 $[M+H]^+$; $^1H$ NMR (300 MHz, $CDCl_3$) δ: 7.60 (s, 1H), 7.47-7.41 (m, 3H), 7.18 (d, 2H), 6.65 (d, 1H), 6.58 (d, 1H), 4.40 (t, 1H), 4.14 (s, 3H), 4.07 (m, 1H), 4.03 (m, 1H), 3.56-3.44 (m, 2H), 2.78-2.64 (m, 1H), 1.90-1.66 (m, 9H), 1.35-1.05 (m, 3H), 1.02-0.82 (m, 5H).

Example 94: N—((S)-2-((4-(4-Hydroxytetrahydro-2H-pyran-4-yl)phenyl)amino)-1-((1r,4S)-4-methylcyclohexyl)-2-oxoethyl)-1-methyl-1H-pyrazole-5-carboxamide

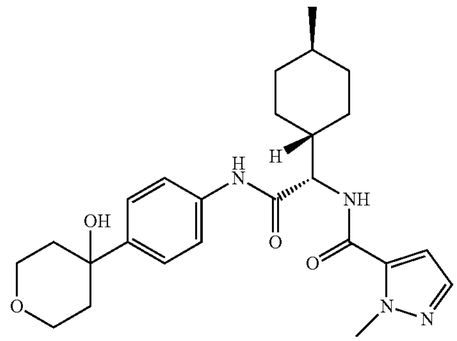 [SMILES: Cn1nccc1C(=O)N[C@H](C(=O)Nc1ccc(C2(O)CCOCC2)cc1)[C@H]1CC[C@H](C)CC1]

The title compound (29 mg) was prepared from Intermediate 3.94 (54 mg, 0.16 mmol), 2-methylpyrazole-3-carboxylic acid (20 mg, 0.16 mmol, CAS: 16034-46-1), HATU (71 mg, 0.19 mmol) and triethylamine (0.07 mL, 0.47 mmol) in accordance with the procedure described for Example 1. The crude product was purified by reverse phase column chromatography on the Biotage Isolera One™ (25 g C18 column, eluting 10-70% 0.1% ammonia/MeCN in pH11 0.1% ammonia/$H_2O$). LCMS (Method 12): 1.90 min, 452.8 $[M-H]^-$; $^1H$ NMR (400 MHz, DMSO-$d_6$) δ: 10.15 (s, 1H), 8.48 (d, 1H), 7.57 (d, 2H), 7.45 (d, 1H), 7.40 (d, 2H), 7.05 (d, 1H), 4.95 (s, 1H), 4.37 (t, 1H), 4.02 (s, 3H), 3.80-3.72 (m, 2H), 3.72-3.65 (m, 2H), 2.00-1.73 (m, 4H), 1.72-1.63 (m, 2H), 1.57 (m, 1H), 1.53-1.46 (m, 1H), 1.24-1.12 (m, 2H), 1.03 (m, 1H), 0.92-0.80 (m, 5H).

Example 95: N—((S)-2-((4-(3,6-Dihydro-2H-pyran-4-yl)phenyl)amino)-1-((1r,4S)-4-methylcyclohexyl)-2-oxoethyl)-1-methyl-1H-pyrazole-5-carboxamide

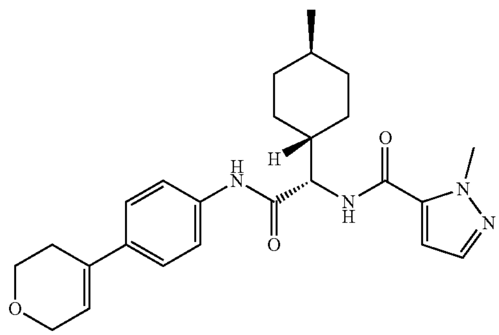 [SMILES: Cn1nccc1C(=O)N[C@H](C(=O)Nc1ccc(C2=CCOCC2)cc1)[C@H]1CC[C@H](C)CC1]

The title compound (5.2 mg) was prepared from Intermediate 3.95 (0.11 g, 0.3 mmol), 2-methylpyrazole-3-carboxylic acid (38 mg, 0.3 mmol, CAS: 16034-46-1), HATU (0.14 g, 0.36 mmol) and triethylamine (0.13 mL, 0.9 mmol) in accordance with the procedure described for Example 1. The crude product was purified by reverse phase column chromatography on the Biotage Isolera One™ (25 g C18 column, eluting 5-80% 0.1% ammonia/MeCN in pH11 0.1% ammonia/$H_2O$). LCMS (Method 3): 2.39 min, 435.2 $[M-H]^-$; $^1H$ NMR (400 MHz, DMSO-$d_6$) δ: 10.24 (s, 1H), 8.52 (d, 1H), 7.62 (d, 2H), 7.46 (d, 1H), 7.40 (d, 2H), 7.07 (d, 1H), 6.19 (m, 1H), 4.37 (t, 1H), 4.21 (m, 2H), 4.02 (s, 3H), 3.81 (t, 2H), 1.90-1.53 (m, 6H), 1.33-0.95 (m, 4H), 0.93-0.78 (m, 5H).

Example 96: N—((S)-2-((4-(3,5-Dimethylisoxazol-4-yl)phenyl)amino)-1-((1r,4S)-4-methylcyclohexyl)-2-oxoethyl)-1-methyl-1H-pyrazole-5-carboxamide

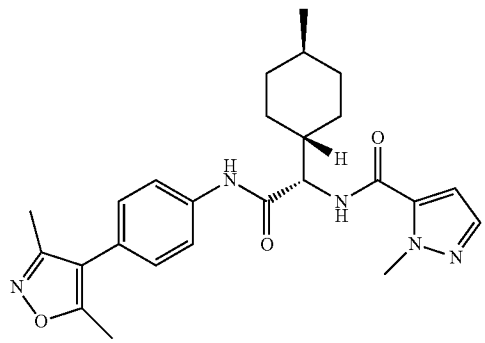 [SMILES: Cc1noc(C)c1-c1ccc(NC(=O)[C@@H](NC(=O)c2ccnn2C)[C@H]2CC[C@H](C)CC2)cc1]

The title compound (38 mg) was prepared from Intermediate 3.96 (69 mg, 0.2 mmol), 2-methylpyrazole-3-carboxylic acid (28 mg, 0.22 mmol, CAS: 16034-46-1), HATU (85 mg, 0.22 mmol) and triethylamine (0.1 mL, 0.71 mmol) in accordance with the procedure described for Example 1. The crude product was purified by flash column chromatography on the Biotage Isolera One™ (12 g silica column, 0-2% MeOH in DCM) and reverse phase preparative HPLC (Method 2). LCMS (Method 10): 2.68 min, 450.2 $[M+H]^+$; $^1H$ NMR (400 MHz, $CDCl_3$) δ: 7.91 (s, 1H), 7.58 (d, 2H), 7.44 (d, 1H), 7.20 (d, 2H), 6.68 (d, 1H), 6.60 (d, 1H), 4.44 (t, 1H), 4.14 (s, 3H), 2.36 (s, 3H), 2.23 (s, 3H), 1.96-1.81 (m, 3H), 1.81-1.69 (m, 2H), 1.31 (m, 1H), 1.16 (m, 2H), 1.03-0.90 (m, 2H), 0.87 (d, 3H).

Example 97: N—((S)-2-((5-(3,5-Dimethylisoxazol-4-yl)pyridin-2-yl)amino)-1-((1r,4S)-4-methylcyclohexyl)-2-oxoethyl)-1-methyl-1H-pyrazole-5-carboxamide

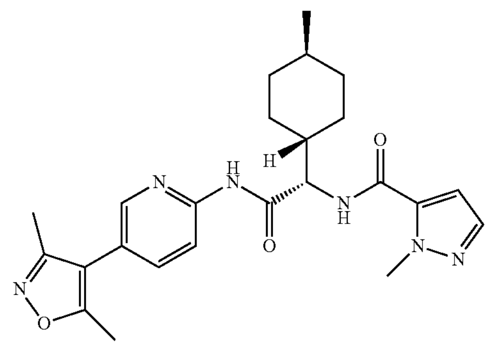 [SMILES: Cc1noc(C)c1-c1ccc(NC(=O)[C@@H](NC(=O)c2ccnn2C)[C@H]2CC[C@H](C)CC2)nc1]

The title compound (8.5 mg) was prepared from Intermediate 3.97 (19 g, 0.05 mmol), 2-methylpyrazole-3-carboxylic acid (7.1 mg, 0.06 mmol, CAS: 16034-46-1), HATU (22 mg, 0.06 mmol) and triethylamine (0.01 mL, 0.18 mmol) in accordance with the procedure described for Example 1. The crude product was purified by flash column chromatography on the Biotage Isolera One™ (4 g silica column, eluting 0-2% MeOH in DCM) and reverse phase preparative HPLC (Method 2). LCMS (Method 10): 2.61 min, 451.2 $[M+H]^+$; $^1H$ NMR (400 MHz, DMSO-$d_6$) δ: 10.75 (s, 1H), 8.48 (d, 1H), 8.36 (m, 1H), 8.18 (m, 1H), 7.83 (m, 1H), 7.47 (d, 1H), 7.04 (d, 1H), 4.54 (t, 1H), 3.33 (s, 3H), 2.41 (s, 3H), 2.23 (s, 3H), 1.90-1.54 (m, 5H), 1.35-1.17 (m, 2H), 1.07 (m, 1H), 0.95-0.80 (m, 5H).

Example 98: (S)—N-(1-(4,4-Difluorocyclohexyl)-2-((4-(3,5-dimethylpyridin-4-yl)phenyl)amino)-2-oxoethyl)-1-methyl-1H-pyrazole-5-carboxamide

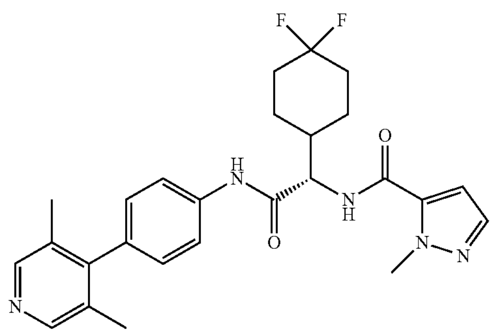 [SMILES: Cc1cncc(C)c1-c1ccc(NC(=O)[C@@H](NC(=O)c2ccnn2C)C2CCC(F)(F)CC2)cc1]

A solution of Intermediate 6.98 (80 mg, 0.17 mmol) in MeOH (10 mL) was hydrogenated in an H-Cube® using a 10% Pd/C cartridge at 50 bar and 60° C. The mixture was concentrated in vacuo and the crude compound was purified by preparative SFC (Chiralpak® AD-H, 5 μM, 10 mm×250 mm i.d. column, 15 ml/min, 20% IPA+1% diethylamine and $CO_2$ as eluant) to afford the title compound (2.3 mg), stereochemistry assumed based on activity data. LCMS (Method 14): 1.84 min, 482.2 $[M+H]^+$; $^1H$ NMR (400 MHz, MeOD) δ: 8.30 (s, 2H), 7.79 (d, 2H), 7.52 (d, 1H), 7.18 (d, 2H), 6.95 (d, 1H), 4.60 (d, 1H), 4.13 (s, 3H), 2.21-1.98 (m, 10H), 1.94-1.75 (m, 3H), 1.67-1.46 (m, 2H). The other inactive enantiomer was also isolated (3.7 mg).

Example 99: N—((S)-2-((5-(3,5-Dimethyl-1H-pyrazol-4-yl)pyridin-2-yl)amino)-1-((1r,4S)-4-methylcyclohexyl)-2-oxoethyl)-1-methyl-1H-pyrazole-5-carboxamide

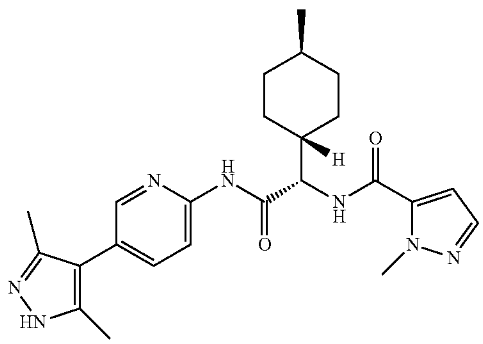 [SMILES: Cc1n[nH]c(C)c1-c1ccc(NC(=O)[C@@H](NC(=O)c2ccnn2C)[C@H]2CC[C@H](C)CC2)nc1]

The title compound (3.9 mg) was prepared from Intermediate 3.99a (20 mg, 0.04 mmol) and hydrogenated in an H-Cube® using a 10% Pd/C cartridge in accordance with the procedure described for Example 84. The crude product was purified by reverse phase preparative HPLC (Method 2). LCMS (Method 15): 2.31 min, 450.2 $[M+H]^+$; $^1H$ NMR (400 MHz, MeOD) δ: 8.27 (dd, 1H), 8.19 (d, 1H), 7.75 (dd, 1H), 7.51 (d, 1H), 6.94 (d, 1H), 4.57 (d, 1H), 4.12 (s, 3H), 2.29 (s, 6H), 1.99-1.88 (m, 2H), 1.88-1.77 (m, 3H), 1.46-1.17 (m, 3H), 1.09-0.96 (m, 2H), 0.94 (d, 3H).

Example 100: (S)—N-(1-(4,4-Dimethylcyclohexyl)-2-((4-(3,5-dimethylpyridin-4-yl)phenyl)amino)-2-oxoethyl)-1-methyl-1H-pyrazole-5-carboxamide

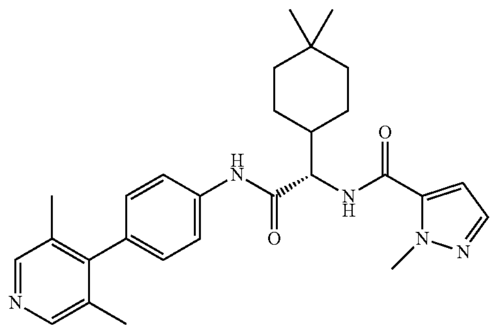 [SMILES: Cc1cncc(C)c1-c1ccc(NC(=O)[C@@H](NC(=O)c2ccnn2C)C2CCC(C)(C)CC2)cc1]

A solution of Intermediate 6.100 (30 mg, 0.06 mmol) in MeOH (5 mL) was hydrogenated in an H-Cube® using a 10% Pd/C cartridge at 50 bar and 60° C. The mixture was concentrated in vacuo and the crude compound was purified by flash column chromatography (eluting 5% MeOH in DCM) and preparative SFC (Chiralpak® AD-H, 5 μM, 10 mm×250 mm i.d. column, 15 ml/min, 17% IPA+1% diethylamine and $CO_2$ as eluant) to afford the title compound (5.3 mg), stereochemistry assumed based on activity data. LCMS (Method 14): 1.54 min, 474.2 $[M+H]^+$; $^1H$ NMR (400 MHz, $CDCl_3$) δ: 8.32 (s, 2H), 7.86 (s, 1H), 7.62 (d, 2H), 7.45 (d, 1H), 7.08 (d, 2H), 6.63 (d, 1H), 6.59 (d, 1H), 4.47 (t, 1H), 4.16 (s, 3H), 2.00 (s, 6H), 1.93-1.82 (m, 1H), 1.74-1.64 (m, 2H), 1.40-1.30 (m, 2H), 1.30-1.15 (m, 4H), 0.91 (s, 3H), 0.88 (s, 3H). The other inactive enantiomer was also isolated (3.6 mg).

Example 101: (S)—N-(1-(4,4-Difluorocyclohexyl)-2-((4-(1,2-dimethyl-6-oxo-1,6-dihydropyridin-3-yl)phenyl)amino)-2-oxoethyl)-1-methyl-1H-pyrazole-5-carboxamide

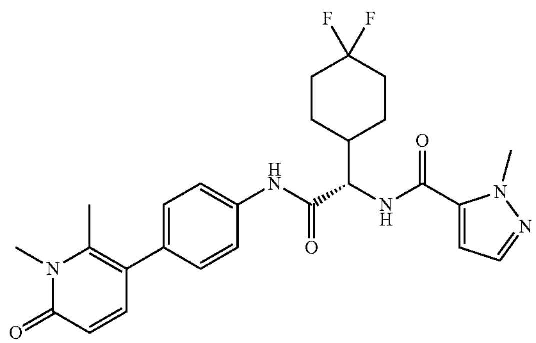 [SMILES: Cc1c(-c2ccc(NC(=O)[C@@H](NC(=O)c3ccnn3C)C3CCC(F)(F)CC3)cc2)ccc(=O)n1C]

To a mixture of Intermediate 5.101 (45 mg, 0.16 mmol) and Intermediate 1.13 (37 mg, 0.17 mmol) in THF (3 mL) under argon was added acetic acid (0.09 mL, 1.6 mmol) and the mixture was heated by microwave irradiation at 100° C. for 1 h. The mixture was concentrated in vacuo and purified directly by flash column chromatography (0-10% MeOH in DCM) and preparative SFC (Chiralpak® AD-H, 5 μM, 10 mm×250 mm i.d. column, 15 ml/min, 40% IPA+1% diethylamine and $CO_2$ as eluant) to afford the title compound (16 mg), stereochemistry assumed based on activity data. LCMS (Method 14): 2.22 min, 498.2 $[M+H]^+$; $^1H$ NMR (400 MHz, MeOD) δ: 7.71 (d, 2H), 7.51 (d, 1H), 7.46 (d, 1H), 7.29 (d, 2H), 6.94 (d, 1H), 6.54 (d, 1H), 4.59 (d, 1H), 4.13 (s, 3H), 3.69 (s, 3H), 2.41 (s, 3H), 2.21-1.97 (m, 4H), 1.94-1.73 (m, 3H), 1.66-1.43 (m, 2H). The other inactive enantiomer was also isolated (15 mg).

Example 102: (S)—N-(2-((4-(1,2-Dimethyl-6-oxo-1,6-dihydropyridin-3-yl)phenyl)amino)-1-(4,4-dimethylcyclohexyl)-2-oxoethyl)-1-methyl-1H-pyrazole-5-carboxamide

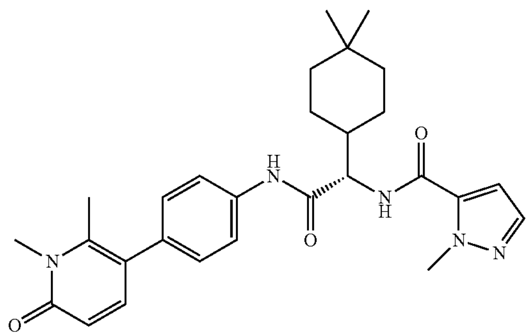 [SMILES: Cc1c(-c2ccc(NC(=O)[C@@H](NC(=O)c3ccnn3C)C3CCC(C)(C)CC3)cc2)ccc(=O)n1C]

A solution of Intermediate 6.102 (75 mg, 0.14 mmol) in MeOH (5 mL) was hydrogenated in an H-Cube® using a 10% Pd/C cartridge at 30 bar and 60° C. The mixture was concentrated in vacuo and the crude compound was purified by flash column chromatography (eluting 5% MeOH in DCM) and preparative SFC (Daicel Chiralpak AS-H, 5 μM, 10 mm×250 mm i.d. column, 15 mL/min, 40% IPA+1% diethylamine and $CO_2$ as eluant) to afford the title compound (2.9 mg), stereochemistry assumed based on activity data. LCMS (Method 14): 1.79 min, 490.2 $[M+H]^+$; $^1$H NMR (400 MHz, MeOD) δ: 7.71 (d, 2H), 7.51 (d, 1H), 7.46 (d, 1H), 7.28 (d, 2H), 6.93 (d, 1H), 6.54 (d, 1H), 4.53 (d, 1H), 4.12 (s, 3H), 3.69 (s, 3H), 2.41 (s, 3H), 1.95-1.75 (m, 2H), 1.65-1.22 (m, 7H), 0.97 (s, 3H), 0.96 (s, 3H). The other inactive enantiomer was also isolated (3.3 mg).

Example 103: N-(1-Cyclooctyl-2-((4-(3,5-dimethylpyridin-4-yl)phenyl)amino)-2-oxoethyl)-1-methyl-1H-pyrazole-5-carboxamide

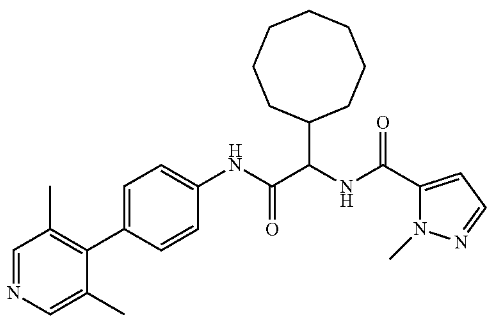 [SMILES: Cc1cncc(C)c1-c1ccc(NC(=O)C(NC(=O)c2ccnn2C)C2CCCCCCC2)cc1]

A solution of Intermediate 6.103 (50 mg, 0.11 mmol) in THF (10 mL) was hydrogenated in an H-Cube® using a 10% Pd/C cartridge at 70 bar and 60° C. The mixture was concentrated in vacuo and the crude compound was purified by reverse phase preparative HPLC (Method 3) to afford the title compound (2 mg). LCMS (Method 16): 2.09 min, 474.2 $[M+H]^+$; $^1$H NMR (400 MHz, MeOD) δ: 8.29-8.24 (m, 2H), 7.78-7.71 (m, 2H), 7.47 (d, 1H), 7.18-7.11 (m, 2H), 6.88 (d, 1H), 4.55 (d, 1H), 4.09 (s, 3H), 2.26 (s, 1H), 2.06 (d, 6H), 1.91-1.42 (m, 14H).

Example 104: N-(1-Cyclooctyl-2-((4-(3,5-dimethyl-1H-pyrazol-4-yl)phenyl)amino)-2-oxoethyl)-1-methyl-1H-pyrazole-5-carboxamide

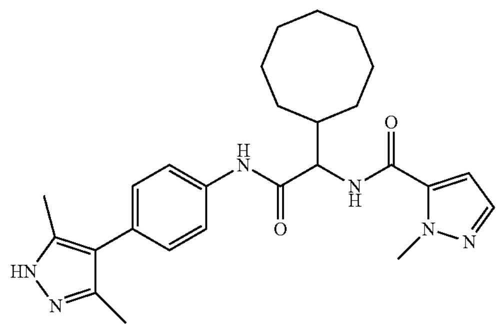 [SMILES: Cc1n[nH]c(C)c1-c1ccc(NC(=O)C(NC(=O)c2ccnn2C)C2CCCCCCC2)cc1]

A solution of Intermediate 6.104 (14 mg, 0.03 mmol) in MeOH (5 mL) was hydrogenated in an H-Cube® using a 10% Pd/C cartridge at 50 bar and 70° C. The mixture was concentrated in vacuo to afford the title compound (12 mg). LCMS (Method 16): 2.41 min, 463.2 $[M+H]^+$; $^1$H NMR (400 MHz, MeOD) δ: 7.66-7.59 (m, 2H), 7.47 (d, 1H), 7.29-7.21 (m, 2H), 6.88 (d, 1H), 4.54 (d, 1H), 4.09 (s, 3H), 2.26-2.21 (br m, 1H), 2.23 (s, 6H), 1.82-1.70 (m, 4H), 1.70-1.51 (m, 7H), 1.29 (m, 3H).

Example 105: N-(1-Cyclooctyl-2-((5-(3,5-dimethylisoxazol-4-yl)pyridin-2-yl)amino)-2-oxoethyl)-1-methyl-1H-pyrazole-5-carboxamide To a mixture of 2-cyclooctyl-2-[(2-methylpyrazole-3-carbonyl)amino]acetic acid (70 mg, 0.24 mmol, CAS: 2256069-75-5) in THF (6 mL) was added 5-(3,5-dimethylisoxazol-4-yl)pyridin-2-amine (68 mg, 0.36 mmol, CAS: 1177269-12-3) and EEDQ (89 mg, 0.36 mmol) and the mixture was stirred at rt for 16 h. The mixture was concentrated in vacuo then purified by automated reverse phase chromatography on the Biotage Isolera™ (10 g C18 column, eluting 10-80% 0.1% ammonia/MeCN in pH11 0.1% ammonia/$H_2O$) to afford the title compound (9.2 mg). LCMS (Method 16): 2.69 min, 465.2 $[M+H]^+$; $^1$H NMR (400 MHz, MeOD) δ: 8.30 (dd, 1H), 8.23 (d, 1H), 7.78 (dd, 1H), 7.48 (d, 1H), 6.88 (d, 1H), 4.62 (d, 1H), 4.09 (s, 3H), 2.42 (s, 3H), 2.29 (s, 1H), 2.26 (s, 3H), 1.77 (s, 2H), 1.68-1.45 (m, 11H), 1.32-1.27 (m, 1H).

Example 106: N—((S)-2-((5-(1,4-Dimethyl-1H-pyrazol-5-yl)pyridin-2-yl)amino)-1-((1r,4S)-4-methylcyclohexyl)-2-oxoethyl)-1-methyl-1H-pyrazole-5-carboxamide

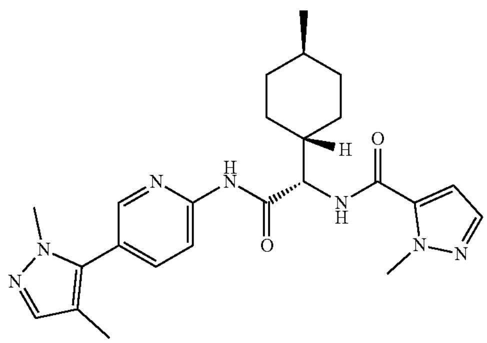 [SMILES: Cc1cnn(C)c1-c1ccc(NC(=O)[C@@H](NC(=O)c2ccnn2C)[C@H]2CC[C@H](C)CC2)nc1]

The title compound (15 mg) was prepared from Intermediate 3.106 (24 mg, 0.07 mmol), 2-methylpyrazole-3-carboxylic acid (9.6 mg, 0.08 mmol, CAS: 16034-46-1), HATU (29 mg, 0.08 mmol) and triethylamine (0.03 mL, 0.21 mmol) in accordance with the procedure described for Example 1. The crude product was purified by reverse phase preparative HPLC (Method 2) and flash column chromatography on the Biotage Isolera One™ (2 g silica column, eluting 33% EtOAc in heptanes. LCMS (Method 15): 2.52 min, 450.2 $[M+H]^+$; $^1H$ NMR (400 MHz, MeOD) δ: 8.33 (dd, 1H), 8.29 (dd, 1H), 7.81 (dd, 1H), 7.48 (d, 1H), 7.38 (d, 1H), 6.91 (d, 1H), 4.55 (d, 1H), 4.09 (s, 3H), 3.74 (s, 3H), 2.02 (s, 3H), 1.97-1.84 (m, 2H), 1.77 (d, 3H), 1.42-1.31 (m, 2H), 1.26-1.14 (m, 1H), 1.02 (d, 1H), 0.96 (d, 1H), 0.90 (d, 3H).

Example 107: N-(1-Cyclooctyl-2-((4-(1,2-dimethyl-6-oxo-1,6-dihydropyridin-3-yl)phenyl)amino)-2-oxoethyl)-1-methyl-1H-pyrazole-5-carboxamide

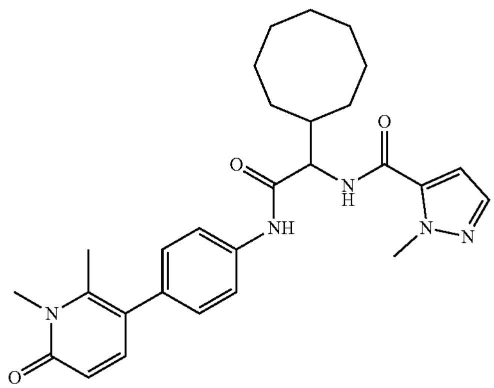 [SMILES: Cc1c(-c2ccc(NC(=O)C(NC(=O)c3ccnn3C)C3CCCCCCC3)cc2)ccc(=O)n1C]

To a mixture of 2-cyclooctyl-2-[(2-methylpyrazole-3-carbonyl)amino]acetic acid (40 mg, 0.14 mmol, CAS: 2256069-75-5) in acetonitrile (8 mL) was added Intermediate 1.13 (29 mg, 0.14 mmol) followed by TCFH (134 mg, 0.48 mmol) and the mixture was stirred at rt for 16 h. The mixture was concentrated in vacuo and purified by automated reverse phase chromatography on the Biotage Isolera® (10 g C18 column, eluting 5-100% 0.1% ammonia/MeCN in pH 110.1% ammonia/$H_2O$) then reverse phase preparative HPLC (Method 3) to afford the title compound (6.4 mg). LCMS (Method 15): 2.53 min, 490.2 $[M+H]^+$; $^1H$ NMR (400 MHz, MeOD) δ: 7.71-7.63 (m, 2H), 7.47 (d, 1H), 7.43 (d, 1H), 7.29-7.21 (m, 2H), 6.88 (d, 1H), 6.54-6.47 (m, 1H), 4.54 (d, 1H), 4.09 (s, 3H), 3.65 (s, 3H), 2.38 (s, 3H), 2.28-2.21 (m, 1H), 1.79-1.48 (m, 14H).

Example 108: (S)—N-(1-Cyclohexyl-2-((5-(3,5-dimethylisoxazol-4-yl)pyridin-2-yl)amino)-2-oxoethyl)-1-isopropyl-1H-pyrazole-5-carboxamide

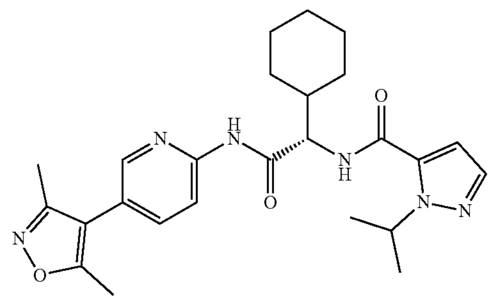 [SMILES: Cc1noc(C)c1-c1ccc(NC(=O)[C@@H](NC(=O)c2ccnn2C(C)C)C2CCCCC2)nc1]

The title compound (25 mg) was prepared from Intermediate 3.108 (62 mg, 0.17 mmol), 2-isopropylpyrazole-3-carboxylic acid (31 mg, 0.20 mmol, CAS: 920006-32-2), HATU (78 mg, 0.20 mmol) and DIPEA (0.12 mL, 0.68 mmol) in accordance with the procedure described for Example 1. The crude product was purified by flash column chromatography on the Biotage Isolera One™ (5 g silica column, eluting 0-1.5% MeOH in DCM) and reverse preparative HPLC (Method 2). LCMS (Method 15): 2.72 min, 465.2 $[M+H]^+$; $^1H$ NMR (400 MHz, $CDCl_3$) δ: 8.56 (s, 1H), 8.32 (d, 1H), 8.27 (dd, 1H), 7.65 (dd, 1H), 7.54 (d, 1H), 6.66 (d, 1H), 6.61 (d, 1H), 5.49 (hept, 1H), 4.65-4.57 (m, 1H), 2.44 (s, 3H), 2.29 (s, 3H), 2.06-1.92 (m, 1H), 1.85 (t, 4H), 1.73 (s, 1H), 1.51 (dd, 6H), 1.38-1.09 (m, 5H).

Example 109: N—((S)-2-((5-(3,5-Dimethylisoxazol-4-yl)pyridin-2-yl)amino)-1-((1r,4S)-4-methylcyclohexyl)-2-oxoethyl)-1-ethyl-1H-pyrazole-5-carboxamide

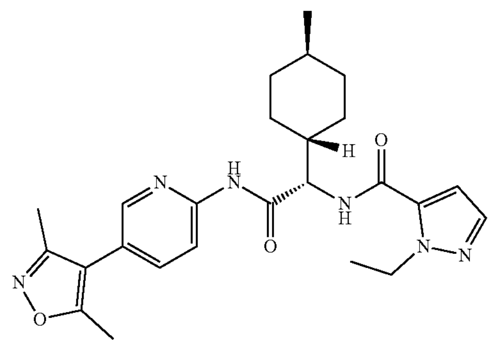 [SMILES: CCn1nccc1C(=O)N[C@H](C(=O)Nc1ccc(-c2c(C)noc2C)cn1)[C@H]1CC[C@H](C)CC1]

To a solution of 2-ethylpyrazole-3-carboxylic acid (18 mg, 0.13 mmol, CAS: 400755-43-3) in DCM (1 mL) was added DIPEA (0.06 mL, 0.32 mmol) and HATU (48 mg, 0.13 mmol). The reaction was stirred at rt for 5 min then Intermediate 3.97 (40 mg, 0.11 mmol) was added. The reaction was stirred at rt for 20 h, then diluted with DCM and washed with saturated aqueous $NaHCO_3$. The combined organics were washed with brine and the phases separated with a phase separation cartridge. The organics were concentrated in vacuo and the crude product purified by flash column chromatography on the Biotage Isolera One™ (5 g silica column, eluting 20-100% EtOAc in heptanes) to afford the title compound (15 mg). LCMS (Method 15): 2.72 min, 465.3 $[M+H]^+$; $^1H$ NMR (400 MHz, MeOD) δ: 8.30 (dd, 1H), 8.23 (dd, 1H), 7.78 (dd, 1H), 7.51 (dd, 1H), 6.81 (d, 1H), 5.44-5.31 (m, 1H), 4.53 (d, 1H), 2.42 (s, 3H), 2.26 (s, 3H), 1.95-1.85 (m, 2H), 1.77 (d, 3H), 1.44 (t, 3H), 1.38-1.14 (m, 4H), 1.06-0.93 (m, 2H), 0.90 (d, 3H).

Example 110: N—((S)-2-((5-(3,5-dimethylisoxazol-4-yl)pyridin-2-yl)amino)-1-((1r,4S)-4-methylcyclohexyl)-2-oxoethyl)-1-isopropyl-1H-pyrazole-5-carboxamide

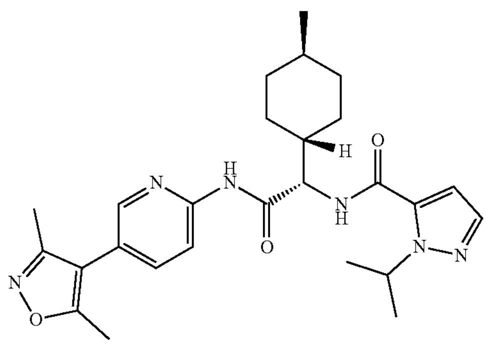 [SMILES: Cc1noc(C)c1-c1ccc(NC(=O)[C@@H](NC(=O)c2ccnn2C(C)C)[C@H]2CC[C@H](C)CC2)nc1]

The title compound (21 mg) was prepared from Intermediate 3.97 (40 mg, 0.11 mmol), 2-isopropylpyrazole-3-carboxylic acid (20 mg, 0.13 mmol, CAS: 920006-32-2), HATU (48 mg, 0.13 mmol) and DIPEA (0.06 mL, 0.32 mmol) in accordance with the procedure described for Example 109. The crude product was purified by flash column chromatography on the Biotage Isolera One™ (5 g silica column, eluting 0-80% EtOAc in heptanes). LCMS (Method 15): 2.81 min, 479.3 $[M+H]^+$; $^1H$ NMR (400 MHz, MeOD) δ: 8.30 (dd, 1H), 8.23 (dd, 1H), 7.78 (dd, 1H), 7.51 (dd, 1H), 6.81 (d, 1H), 5.44-5.31 (m, 1H), 4.53 (d, 1H), 2.42 (s, 3H), 2.26 (s, 3H), 1.95-1.85 (m, 2H), 1.77 (d, 3H), 1.44 (t, 6H), 1.38-1.14 (m, 3H), 1.06-0.93 (m, 2H), 0.90 (d, 3H).

Example 111: N—((S)-2-((5-(3,5-dimethylisoxazol-4-yl)pyridin-2-yl)amino)-1-((1r,4S)-4-methylcyclohexyl)-2-oxoethyl)-3-ethylisoxazole-4-carboxamide

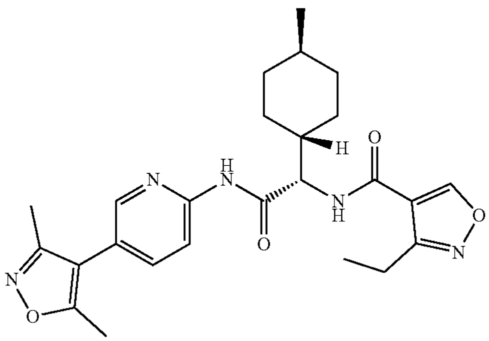 [SMILES: CCc1nocc1C(=O)N[C@H](C(=O)Nc1ccc(-c2c(C)noc2C)cn1)[C@H]1CC[C@H](C)CC1]

The title compound (22 mg) was prepared from Intermediate 3.97 (40 mg, 0.11 mmol), 3-ethylisoxazole-4-carboxylic acid (18 mg, 0.13 mmol, CAS: 639523-12-9), HATU (48 mg, 0.13 mmol) and DIPEA (0.06 mL, 0.32 mmol) in accordance with the procedure described for Example 109. The crude product was purified by flash column chromatography on the Biotage Isolera One™ (5 g silica column, eluting 0-80% EtOAc in heptanes). LCMS (Method 15): 2.7 min, 466.3 $[M+H]^+$; $^1H$ NMR (400 MHz, MeOD) δ: 9.13 (d, 1H), 8.30 (dd, 1H), 8.22 (dd, 1H), 7.78 (dd, 1H), 4.53 (d, 1H), 2.91 (q, 2H), 2.42 (s, 3H), 2.26 (s, 3H), 1.96-1.83 (m, 2H), 1.76 (d, 3H), 1.35-1.20 (m, 6H), 1.03-0.94 (m, 3H), 0.90 (d, 2H).

Example 112: N—((S)-2-((5-(3,5-dimethylisoxazol-4-yl)pyridin-2-yl)amino)-1-((1r,4S)-4-methylcyclohexyl)-2-oxoethyl)-3-methylisoxazole-4-carboxamide

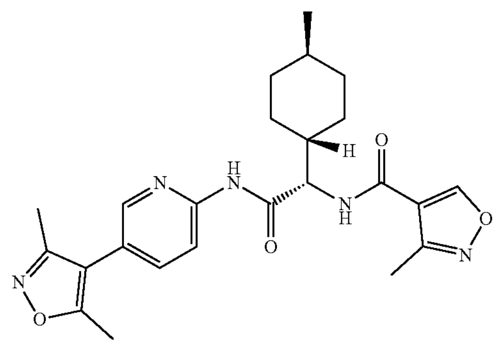 [SMILES: Cc1nocc1C(=O)N[C@H](C(=O)Nc1ccc(-c2c(C)noc2C)cn1)[C@H]1CC[C@H](C)CC1]

The title compound (8.3 mg) was prepared from Intermediate 3.97 (40 mg, 0.11 mmol), 3-methylisoxazole-4-carboxylic acid (16 mg, 0.13 mmol, CAS: 17153-20-7), HATU (48 mg, 0.13 mmol) and DIPEA (0.06 mL, 0.32 mmol) in accordance with the procedure described for Example 109. The crude product was purified by flash column chromatography on the Biotage Isolera One™ (5 g silica column, eluting 0-80% EtOAc in heptanes) and reverse phase preparative HPLC (Method 2). LCMS (Method 15): 2.65 min, 452.2 $[M+H]^+$; $^1H$ NMR (400 MHz, MeOD) δ: 9.15 (d, 1H), 8.30 (dd, 1H), 8.22 (dd, 1H), 7.78 (dd, 1H), 4.52 (s, 1H), 2.43 (s, 6H), 2.26 (s, 3H), 1.95-1.72 (m, 5H), 1.40-1.14 (m, 3H), 1.05-0.95 (m, 2H), 0.90 (d, 3H).

Example 113: N-(1-Cyclooctyl-2-((5-(1,4-dimethyl-1H-pyrazol-5-yl)pyridin-2-yl)amino)-2-oxoethyl)-1-methyl-1H-pyrazole-5-carboxamide

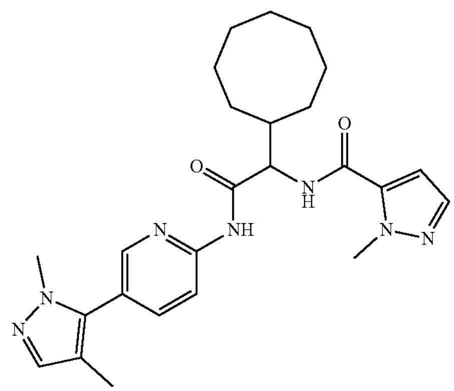 [SMILES: Cc1cnn(C)c1-c1ccc(NC(=O)C(NC(=O)c2ccnn2C)C2CCCCCCC2)nc1]

The title compound (0.7 mg) was prepared from 2-cyclooctyl-2-[(2-methylpyrazole-3-carbonyl)amino]acetic acid (10 mg, 0.03 mmol, CAS: 2256069-75-5), Intermediate 1.106 (6.4 mg, 0.03 mmol), 1-methylimidazole (0.01 mL, 0.1 mmol) and TCFH (12 mg, 0.04 mmol) in accordance with the procedure described for Example 107. The crude product was purified by flash column chromatography on the Biotage Isolera One™ (5 g silica column, 0-100% EtOAc in heptanes). LCMS (Method 15): 2.61 min, 464.2 $[M+H]^+$; $^1H$ NMR (400 MHz, MeOD) δ: 8.33 (dd, 1H), 8.28 (d, 1H), 7.81 (dd, 1H), 7.48 (d, 1H), 7.38 (d, 1H), 6.89 (d, 1H), 4.63 (d, 1H), 4.09 (s, 3H), 3.74 (s, 3H), 2.30 (br s, 1H), 2.02 (d, 3H), 1.81-1.49 (m, 14H).

Example 114: (S)—N-(1-Cyclohexyl-2-((5-(3,5-dimethylisoxazol-4-yl)pyridin-2-yl)amino)-2-oxoethyl)-3-ethylisoxazole-4-carboxamide

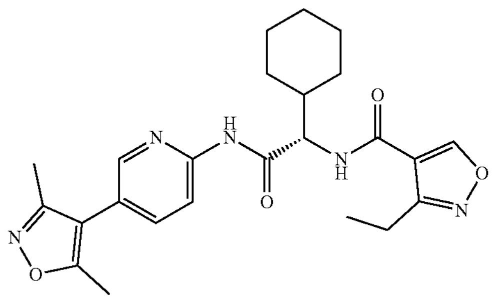 [SMILES: CCc1nocc1C(=O)N[C@H](C(=O)Nc1ccc(-c2c(C)noc2C)cn1)C1CCCCC1]

The title compound (22 mg) was prepared from Intermediate 3.108 (40 mg, 0.11 mmol), 3-ethylisoxazole-4-carboxylic acid (19 mg, 0.13 mmol, CAS: 639523-12-9), HATU (50 mg, 0.130 mmol) and DIPEA (0.06 mL, 0.33 mmol) in accordance with the procedure described for Example 109. The crude product was purified by flash column chromatography on the Biotage Isolera One™ (5 g silica column, eluting 0-20% EtOAc in heptanes). LCMS (Method 15): 2.59 min, 452.2 $[M+H]^+$; $^1H$ NMR (400 MHz, MeOD) δ: 9.13 (d, 1H), 8.30 (dd, 1H), 8.23 (dd, 1H), 7.78 (dd, 1H), 4.55 (d, 1H), 2.90 (q, 2H), 2.42 (s, 3H), 2.26 (s, 3H), 1.99-1.87 (m, 2H), 1.85-1.66 (m, 4H), 1.37-1.13 (m, 8H).

Example 115: (S)—N-(1-Cycloheptyl-2-((5-(3,5-dimethylisoxazol-4-yl)pyridin-2-yl)amino)-2-oxoethyl)-1-methyl-1H-pyrazole-5-carboxamide

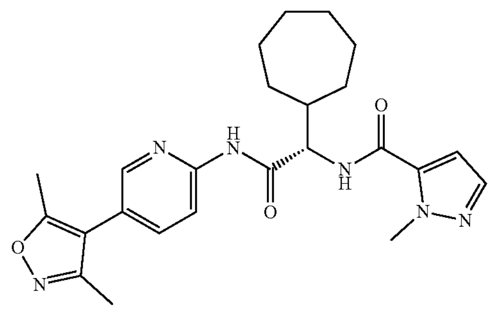 [SMILES: Cc1noc(C)c1-c1ccc(NC(=O)[C@@H](NC(=O)c2ccnn2C)C2CCCCCC2)nc1]

The title compound (32 mg) was prepared from Intermediate 3.115 (50 mg, 0.15 mmol), 2-methylpyrazole-3-carboxylic acid (22 mg, 0.18 mmol, CAS: 16034-46-1), HATU (111 mg, 0.29 mmol) and DIPEA (0.08 mL, 0.44 mmol) in accordance with the procedure described for Example 109. The crude product was purified by flash column chromatography on the Biotage Isolera One™ (5 g silica column, eluting 0-2.5% MeOH in DCM) and reverse phase preparative HPLC (Method 2). LCMS (Method 15): 2.62 min, 451.2 $[M+H]^+$; $^1H$ NMR (400 MHz, $CDCl_3$) δ: 8.56 (s, 1H), 8.29 (dd, 1H), 8.24 (dd, 1H), 7.63 (dd, 2.4 Hz, 1H), 7.47 (d, 1H), 6.68-6.59 (m, 2H), 4.66 (dd, 1H), 4.18 (s, 3H), 2.41 (s, 3H), 2.26 (s, 3H), 2.25-2.13 (m, 1H), 1.92-1.79 (m, 2H), 1.77-1.65 (m, 2H), 1.65-1.55 (m, 2H), 1.55-1.33 (m, 6H).

Example 116: (S)—N-(1-Cycloheptyl-2-((5-(3,5-dimethylisoxazol-4-yl)pyridin-2-yl)amino)-2-oxoethyl)-3-methylisoxazole-4-carboxamide

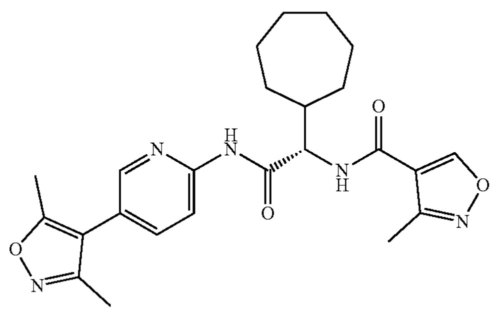 [SMILES: Cc1nocc1C(=O)N[C@H](C(=O)Nc1ccc(-c2c(C)noc2C)cn1)C1CCCCCC1]

The title compound (33 mg) was prepared from Intermediate 3.115 (50 mg, 0.15 mmol), 3-methylisoxazole-4-carboxylic acid (22 mg, 0.18 mmol, CAS: 17153-20-7), HATU (0.11 g, 0.29 mmol) and DIPEA (0.08 mL, 0.44 mmol) in accordance with the procedure described for Example 109. The crude product was triturated with diethyl ether. LCMS (Method 15): 2.62 min, 452.2 $[M+H]^+$; $^1H$ NMR (400 MHz, DMSO-$d_6$) δ: 10.78 (s, 1H), 9.44 (d, 1H), 8.40 (d, 1H), 8.36 (dd, 1H), 8.18 (dd, 1H), 7.83 (dd, 1H), 4.66 (t, 1H), 2.41 (s, 3H), 2.37 (d, 3H), 2.23 (s, 3H), 2.12-1.98 (m, 1H), 1.79-1.61 (m, 4H), 1.61-1.48 (m, 3H), 1.48-1.31 (m, 5H).

Example 117: (S)—N-(1-Cycloheptyl-2-((5-(3,5-dimethylisoxazol-4-yl)pyridin-2-yl)amino)-2-oxoethyl)-1-methyl-1H-1,2,3-triazole-5-carboxamide

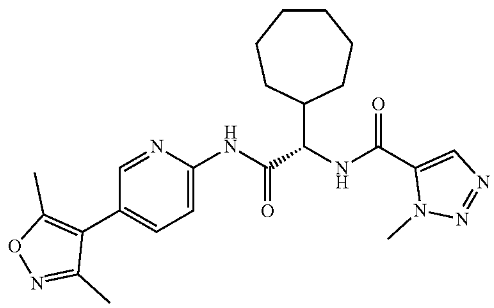 [SMILES: Cc1noc(C)c1-c1ccc(NC(=O)[C@@H](NC(=O)c2cnnn2C)C2CCCCCC2)nc1]

The title compound (38 mg) was prepared from Intermediate 3.115 (50 mg, 0.15 mmol), 3-methyltriazole-4-carboxylic acid (22 mg, 0.18 mmol, CAS: 716361-91-0), HATU (0.11 g, 0.29 mmol) and DIPEA (0.08 mL, 0.44 mmol) in accordance with the procedure described for Example 109.

The crude product was purified by flash column chromatography on the Biotage Isolera One™ (5 g silica column, eluting 0-2.5% MeOH in DCM) and reverse phase preparative HPLC (Method 2). LCMS (Method 15): 2.51 min, 452.2 $[M+H]^+$; $^1$H NMR (400 MHz, $CDCl_3$) δ: 8.59 (s, 1H), 8.28 (d, 1H), 8.24 (dd, 1H), 8.02 (s, 1H), 7.64 (dd, 1H), 6.88 (d, 1H), 4.69 (dd, 1H), 4.32 (s, 3H), 2.41 (s, 3H), 2.27 (s, 3H), 2.22-2.11 (m, 1H), 1.92-1.80 (m, 2H), 1.78-1.65 (m, 2H), 1.64-1.56 (m, 2H), 1.56-1.32 (m, 6H).

Example 118: (S)—N-(1-Cyclohexyl-2-((5-(3,5-dimethylisoxazol-4-yl)pyridin-2-yl)amino)-2-oxo-ethyl)-1-ethyl-1H-pyrazole-5-carboxamide

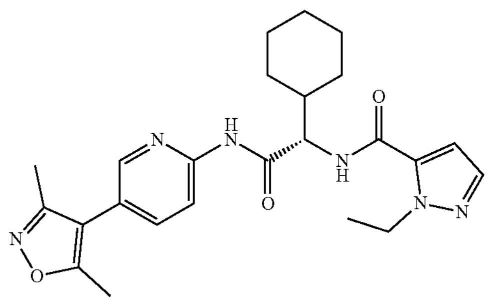 [SMILES: CCn1nccc1C(=O)N[C@H](C(=O)Nc1ccc(-c2c(C)noc2C)cn1)C1CCCCC1]

The title compound (13 mg) was prepared from Intermediate 3.108 (40 mg, 0.11 mmol), 2-ethylpyrazole-3-carboxylic acid (18 mg, 0.13 mmol, CAS: 400755-43-3), HATU (50 mg, 0.13 mmol) and DIPEA (0.06 mL, 0.33 mmol) in accordance with the procedure described for Example 109. The crude product was purified by flash column chromatography on the Biotage Isolera One™ (5 g silica column, eluting 20-80% EtOAc in heptanes) and reverse phase preparative HPLC (Method 2). LCMS (Method 15): 2.56 min, 451.3 $[M+H]^+$; $^1$H NMR (400 MHz, MeOD) δ: 8.30 (dd, 1H), 8.26-8.19 (m, 1H), 7.78 (ddd, 1H), 7.49 (t, 1H), 6.88 (d, 1H), 4.60-4.45 (m, 3H), 2.42 (d, 3H), 2.25 (d, 3H), 2.03-1.86 (m, 2H), 1.76 (d, 3H), 1.73-1.66 (m, 1H), 1.41-1.10 (m, 8H).

Example 119: (S)—N-(1-Cyclohexyl-2-((4-(1,2-dimethyl-6-oxo-1,6-dihydropyridin-3-yl)phenyl)amino)-2-oxoethyl)-1-methyl-1H-pyrazole-5-carboxamide

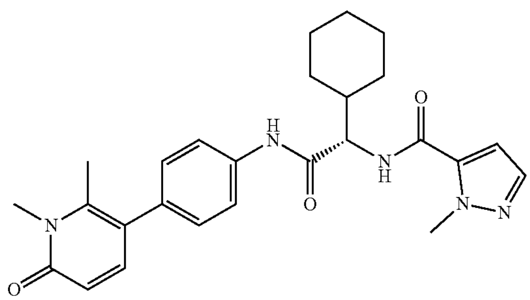 [SMILES: Cc1c(-c2ccc(NC(=O)[C@@H](NC(=O)c3ccnn3C)C3CCCCC3)cc2)ccc(=O)n1C]

The title compound (89 mg) was prepared from Intermediate 3.119 (95 mg, 0.231 mmol), 2-methylpyrazole-3-carboxylic acid (35.027 mg, 0.278 mmol, CAS: 16034-46-1), HATU (176.01 mg, 0.463 mmol) and DIPEA (119.66 mg, 0.926 mmol) in accordance with the procedure described for Example 109. The crude product was purified by flash column chromatography on the Biotage Isolera One™ (12 g silica column, eluting 0-5% 2 M methanoic ammonia in DCM). LCMS (Method 15): 2.19 min, 462.2 $[M+H]^+$; $^1$H NMR (400 MHz, $CDCl_3$) δ: 8.15 (s, 1H), 7.64-7.56 (m, 2H), 7.48 (d, 1H), 7.25 (d, 1H), 7.22-7.16 (m, 2H), 6.78 (d, 1H), 6.65 (d, 1H), 6.56 (d, 1H), 4.52 (t, 1H), 4.19 (s, 3H), 3.64 (s, 3H), 2.32 (s, 3H), 2.06-1.95 (m, 1H), 1.95-1.77 (m, 4H), 1.77-1.69 (m, 1H), 1.37-1.08 (m, 5H).

Example 120: N—((S)-2-((5-(3,5-Dimethylisoxazol-4-yl)pyridin-2-yl)amino)-1-((1r,4S)-4-methylcyclohexyl)-2-oxoethyl)-4-methyl-1,2,5-oxadiazole-3-carboxamide

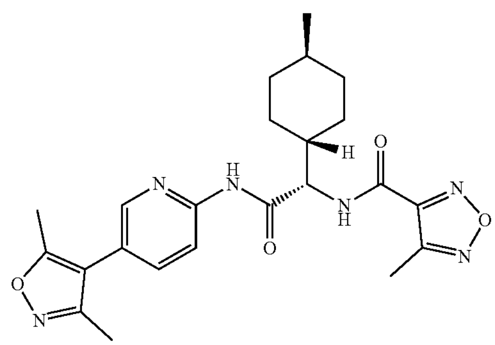 [SMILES: Cc1nonc1C(=O)N[C@H](C(=O)Nc1ccc(-c2c(C)noc2C)cn1)[C@H]1CC[C@H](C)CC1]

The title compound (17 mg) was prepared from Intermediate 3.97 (38 mg, 0.11 mmol), 4-methyl-1,2,5-oxadiazole-3-carboxylic acid (17 mg, 0.14 mmol, CAS: 58677-34-2), HATU (0.13 g, 0.34 mmol) and DIPEA (29 mg, 0.22 mmol) in accordance with the procedure described for Example 109. The crude product was purified by flash column chromatography on the Biotage Isolera One™ (10 g silica column, eluting 0-30% EtOAc in heptanes) and an SCX cartridge (5 g, washed with MeOH and eluted with 2 M methanolic ammonia). LCMS (Method 15): 2.63 min, 453.2 $[M+H]^+$; $^1$H NMR (400 MHz, DMSO-$d_6$) δ: 10.84 (s, 1H), 9.13 (d, 1H), 8.37 (dd, 1H), 8.18 (dd, 1H), 7.85 (dd, 1H), 4.63 (t, 1H), 2.47 (s, 3H), 2.41 (s, 3H), 2.23 (s, 3H), 1.82 (d, 2H), 1.69 (d, 2H), 1.61 (d, 1H), 1.27 (t, 2H), 1.10 (q, 1H), 0.92-0.85 (m, 5H).

Example 121: (S)—N-(1-Cyclohexyl-2-((5-(3,5-dimethylisoxazol-4-yl)pyridin-2-yl)amino)-2-oxo-ethyl)-3-methylisoxazole-4-carboxamide

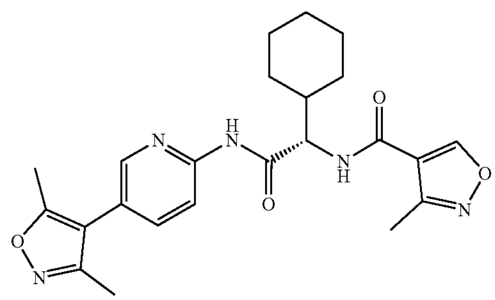 [SMILES: Cc1nocc1C(=O)N[C@H](C(=O)Nc1ccc(-c2c(C)noc2C)cn1)C1CCCCC1]

The title compound (21 mg) was prepared from Intermediate 3.108 (50 mg, 0.14 mmol), 3-methylisoxazole-4-carboxylic acid (21 mg, 0.15, CAS: 17153-20-7), HATU (63 mg, 0.16 mmol) and DIPEA (71 mg, 0.55 mmol) in accordance with the procedure described for Example 109. The crude product was purified by flash column chromatography on the Biotage Isolera One™ (5 g silica column, eluting 0-2% MeOH in DCM). LCMS (Method 15): 2.40 min, 438.2 $[M+H]^+$; $^1H$ NMR (400 MHz, MeOD) δ: 9.15 (d, 1H), 8.30 (dd, 1H), 8.22 (dd, 1H), 7.77 (dd, 1H), 4.54 (d, 1H), 2.46-2.39 (m, 6H), 2.25 (s, 3H), 1.98-1.66 (m, 6H), 1.39-1.12 (m, 5H).

Example 122: (S)—N-(1-Cycloheptyl-2-((5-(3,5-dimethylisoxazol-4-yl)pyridin-2-yl)amino)-2-oxoethyl)-1-ethyl-1H-pyrazole-5-carboxamide

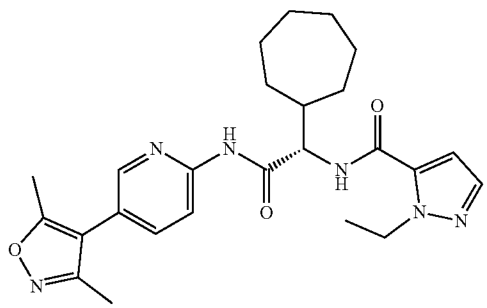 [SMILES: CCn1nccc1C(=O)N[C@H](C(=O)Nc1ccc(-c2c(C)noc2C)cn1)C1CCCCCC1]

The title compound (14 mg) was prepared from Intermediate 3.115 (50 mg, 0.13 mmol), 2-ethylpyrazole-3-carboxylic acid (22 mg, 0.16 mmol, CAS: 400755-43-3), HATU (0.1 g, 0.26 mmol) and DIPEA (68 mg, 0.53 mmol) in accordance with the procedure described for Example 109. The crude product was purified by flash column chromatography on the Biotage Isolera One™ (12 g silica column, eluting 0-2% MeOH in DCM) and reverse phase preparative HPLC (Method 2). LCMS (Method 15): 2.44 min, 465.2 $[M+H]^+$; $^1H$ NMR (400 MHz, $CDCl_3$) δ: 8.50 (s, 1H), 8.29 (dd, 1H), 8.23 (dd, 1H), 7.63 (dd, 1H), 7.49 (d, 1H), 6.67-6.57 (m, 2H), 4.65 (dd, 1H), 4.60 (q, 2H), 2.41 (s, 3H), 2.26 (s, 3H), 2.24-2.14 (m, 1H), 1.92-1.68 (m, 4H), 1.64-1.56 (m, 2H*), 1.54-1.34 (m, 9H).

Example 123: (S)—N-(1-Cycloheptyl-2-((5-(3,5-dimethylisoxazol-4-yl)pyridin-2-yl)amino)-2-oxoethyl)-1-isopropyl-1H-pyrazole-5-carboxamide

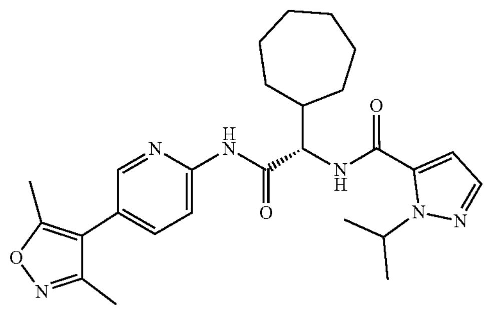 [SMILES: Cc1noc(C)c1-c1ccc(NC(=O)[C@@H](NC(=O)c2ccnn2C(C)C)C2CCCCCC2)nc1]

The title compound (31 mg) was prepared from Intermediate 3.115 (50 mg, 0.13 mmol), 2-isopropylpyrazole-3-carboxylic acid (24 mg, 0.16 mmol, CAS: 920006-32-2), HATU (0.1 g, 0.26 mmol) and DIPEA (68 g, 0.53 mmol) in accordance with the procedure described for Example 109. The crude product was purified by flash column chromatography on the Biotage Isolera One™ (12 g silica column, eluting 0-1% MeOH in DCM) and reverse phase preparative HPLC (Method 2). LCMS (Method 15): 2.58 min, 479.2 $[M+H]^+$; $^1H$ NMR (400 MHz, $CDCl_3$) δ: 8.50 (s, 1H), 8.22 (d, 1H), 8.17 (dd, 1H), 7.56 (dd, 1H), 7.45 (dd, 1H), 6.56 (d, 1H), 6.51 (d, 1H), 5.39 (m, 1H), 4.59 (dd, 1H), 2.34 (s, 3H), 2.20 (s, 3H), 2.17-2.07 (m, 1H), 1.85-1.73 (m, 2H), 1.71-1.59 (m, 2H), 1.57-1.50 (m, 2H*), 1.49-1.27 (m, 12H).

Example 124: (S)—N-(1-Cycloheptyl-2-((5-(3,5-dimethylisoxazol-4-yl)pyridin-2-yl)amino)-2-oxoethyl)-3-ethylisoxazole-4-carboxamide

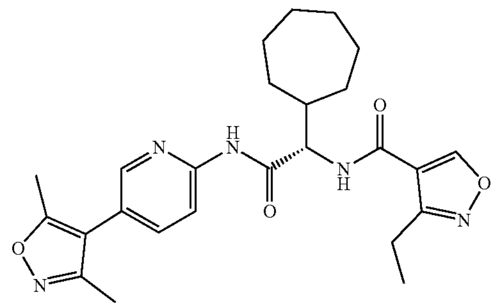 [SMILES: CCc1nocc1C(=O)N[C@H](C(=O)Nc1ccc(-c2c(C)noc2C)cn1)C1CCCCCC1]

The title compound (31 mg) was prepared from Intermediate 3.115 (50 mg, 0.13 mmol), 3-ethylisoxazole-4-carboxylic acid (22 mg, 0.6 mmol, CAS: 639523-12-9), HATU (0.1 g, 0.26 mmol) and DIPEA (68 mg, 0.53 mmol) in accordance with the procedure described for Example 109. The crude product was purified by flash column chromatography on the Biotage Isolera One™ (12 g silica column, eluting 0-1% MeOH in DCM) and reverse phase preparative HPLC (Method 2). LCMS (Method 15): 2.50 min, 466.2 $[M+H]^+$; $^1H$ NMR (400 MHz, DMSO-$d_6$) δ: 10.78 (s, 1H), 9.41 (s, 1H), 8.43 (d, 1H), 8.36 (dd, 1H), 8.18 (dd, 1H), 7.84 (dd, 1H), 4.67 (t, 1H), 2.83 (q, 2H), 2.42 (s, 3H), 2.24 (s, 3H), 2.05 (s, 1H), 1.78-1.33 (m, 12H), 1.17 (t, 3H).

Example 125: N—((S)-2-((5-(1,4-Dimethyl-1H-1,2,3-triazol-5-yl)pyridin-2-yl)amino)-1-((1r,4S)-4-methylcyclohexyl)-2-oxoethyl)-1-methyl-1H-pyrazole-5-carboxamide

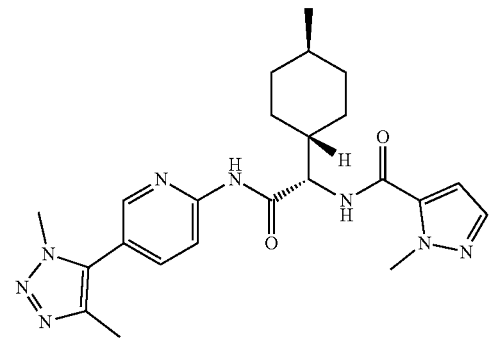

The title compound (14 mg) was prepared from Intermediate 3.125 (32 mg, 0.08 mmol), 2-methylpyrazole-3-carboxylic acid (13 mg, 0.1 mmol, CAS: 16034-46-1), HATU (39 mg, 0.1 mmol) and DIPEA (33 mg, 0.25 mmol) in accordance with the procedure described for Example 109. The crude product was purified by flash column chromatography on the Biotage Isolera One™ (12 g silica column, eluting 0-10% MeOH in DCM) and reverse phase preparative HPLC (Method 2). LCMS (Method 15): 2.2 min, 451.3 $[M+H]^+$; $^1H$ NMR (400 MHz, MeOD) δ: 8.40 (dd, 1H), 8.33 (dd, 1H), 7.88 (dd, 1H), 7.47 (d, 1H), 6.91 (d, 1H), 4.60-4.52 (m, 1H), 4.09 (d, 3H), 3.99 (d, 3H), 2.29 (s, 3H), 1.97-1.84 (m, 2H), 1.76 (d, 3H), 1.30 (ddd, 2H), 1.18 (td, 1H), 1.05-0.87 (m, 5H).

Example 126: N—((S)-2-((5-(1,4-Dimethyl-1H-pyrazol-5-yl)pyridin-2-yl)amino)-1-((1r,4S)-4-methylcyclohexyl)-2-oxoethyl)-1-ethyl-1H-pyrazole-5-carboxamide

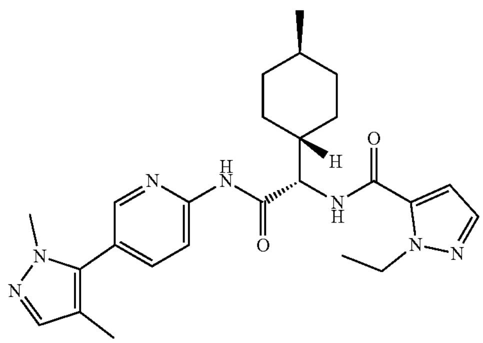 [SMILES: CCn1nccc1C(=O)N[C@H](C(=O)Nc1ccc(-c2c(C)cnn2C)cn1)[C@H]1CC[C@H](C)CC1]

The title compound (15 mg) was prepared from Intermediate 3.106 (50 mg, 0.13 mmol), 2-ethylpyrazole-3-carboxylic acid (22 mg, 0.16 mmol, CAS: 400755-43-3), HATU (61 mg, 0.16 mmol) and DIPEA (51 mg, 0.4 mmol) in accordance with the procedure described for Example 109. The crude product was purified by flash column chromatography on the Biotage Isolera One™ (12 g silica column, eluting 0-10% MeOH in DCM) and reverse phase preparative HPLC (Method 2). LCMS (Method 15): 2.39 min, 464.3 $[M+H]^+$; $^1H$ NMR (400 MHz, MeOD) δ: 8.36-8.26 (m, 2H), 7.84-7.76 (m, 1H), 7.49 (t, 1H), 7.38 (d, 1H), 6.89 (d, 1H), 4.62-4.45 (m, 3H), 3.74 (s, 3H), 2.01 (d, 3H), 1.97-1.85 (m, 2H), 1.82-1.71 (m, 3H), 1.41-1.26 (m, 5H), 1.24-1.13 (m, 1H), 1.04-0.86 (m, 5H).

Example 127: N—((S)-2-((5-(1,4-Dimethyl-1H-pyrazol-5-yl)pyridin-2-yl)amino)-1-((1r,4S)-4-methylcyclohexyl)-2-oxoethyl)-3-ethylisoxazole-4-carboxamide

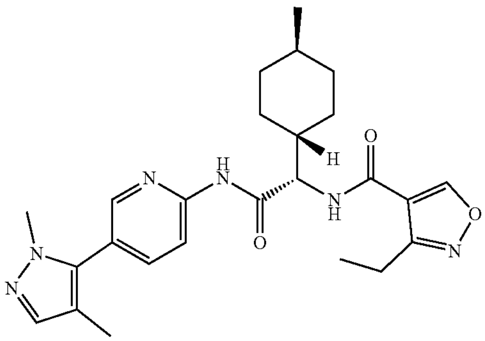 [SMILES: CCc1nocc1C(=O)N[C@H](C(=O)Nc1ccc(-c2c(C)cnn2C)cn1)[C@H]1CC[C@H](C)CC1]

The title compound (26 mg) was prepared from Intermediate 3.106 (50 mg, 0.13 mmol), 3-ethylisoxazole-4-carboxylic acid (22 mg, 0.16 mmol, CAS: 639523-12-9), HATU (61 mg, 0.16 mmol) and DIPEA (51 mg, 0.4 mmol) in accordance with the procedure described for Example 109. The crude product was purified by flash column chromatography on the Biotage Isolera One™ (12 g silica column, eluting 0-10% MeOH in DCM). LCMS (Method 15): 2.43 min, 465.3 $[M+H]^+$; $^1H$ NMR (400 MHz, MeOD) δ: 9.13 (s, 1H), 8.32 (dd, 1H), 8.28 (dd, 1H), 7.81 (dd, 1H), 7.38 (d, 1H), 4.54 (d, 1H), 3.74 (s, 3H), 2.96-2.86 (m, 2H), 2.02 (d, 3H), 1.95-1.72 (m, 5H), 1.25 (t, 6H), 1.05-0.87 (m, 5H).

Example 128: (S)—N-(1-Cycloheptyl-2-((5-(3,5-dimethylisoxazol-4-yl)pyridin-2-yl)amino)-2-oxoethyl)-4-methyl-1,2,5-oxadiazole-3-carboxamide

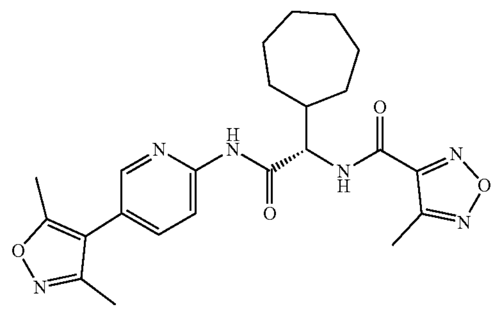 [SMILES: Cc1nonc1C(=O)N[C@H](C(=O)Nc1ccc(-c2c(C)noc2C)cn1)C1CCCCCC1]

The title compound (21 mg) was prepared from Intermediate 3.115 (50 mg, 0.13 mmol), 4-methyl-1,2,5-oxadiazole-3-carboxylic acid (20 mg, 0.16 mmol, CAS: 58677-34-2), HATU (0.1 mg, 0.26 mmol) and DIPEA (68 mg, 0.53 mmol) in accordance with the procedure described for Example 109. The crude product was purified by flash column chromatography on the Biotage Isolera One™ (12 g silica column, eluting 0-50% EtOAc in heptanes) and recrystallised from hot EtOAc/Heptanes (1:1). LCMS (Method 15): 2.69 min, 453.2 $[M+H]^+$; $^1H$ NMR (400 MHz, $CDCl_3$) δ: 8.44 (s, 1H), 8.30 (d, 1H), 8.23 (dd, 1H), 7.63 (dd, 1H), 7.43 (d, 1H), 4.66 (dd, 1H), 2.62 (s, 3H), 2.41 (s, 3H), 2.26 (m, 4H), 1.89-1.82 (m, 2H), 1.77-1.58 (m, 4H), 1.56-1.34 (m, 6H).

Example 129: (S)—N-(1-Cyclohexyl-2-((5-(3,5-dimethylisoxazol-4-yl)pyridin-2-yl)amino)-2-oxoethyl)-1-methyl-1H-pyrazole-5-carboxamide

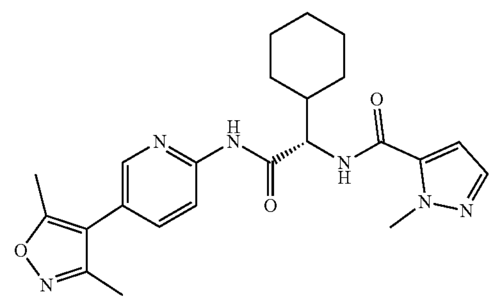 [SMILES: Cc1noc(C)c1-c1ccc(NC(=O)[C@@H](NC(=O)c2ccnn2C)C2CCCCC2)nc1]

The title compound (33 mg) was prepared from Intermediate 3.108 (50 mg, 0.14 mmol), 2-methylpyrazole-3-carboxylic acid (19 mg, 0.15 mmol, CAS: 16034-46-1), HATU (63 mg, 0.16 mmol) and DIPEA (53 mg, 0.41 mmol) in accordance with the procedure described for Example 109. The crude product was purified by flash column chromatography on the Biotage Isolera One™ (5 g silica column, eluting 0-2% MeOH in DCM). LCMS (Method 15): 2.26 min, 437.2 $[M+H]^+$; $^1H$ NMR (400 MHz, DMSO-$d_6$) δ: 10.75 (s, 1H), 8.47 (d, 1H), 8.36 (dd, 1H), 8.18 (dd, 1H), 7.83 (dd, 1H), 7.47 (d, 1H), 7.04 (d, 1H), 4.56 (t, 1H), 4.02 (s, 3H), 2.41 (s, 3H), 2.23 (s, 3H), 1.71 (td, 6H), 1.12 (dq, 5H).

Example 130: (S)—N-(1-Cyclohexyl-2-((5-(3,5-dimethylisoxazol-4-yl)pyridin-2-yl)amino)-2-oxo-ethyl)-1,2,3,4-tetrahydropyrrolo[1,2-a]pyrazine-6-carboxamide

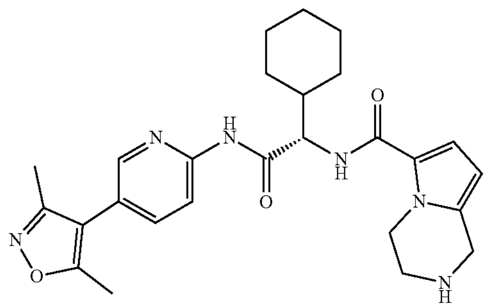 [SMILES: Cc1noc(C)c1-c1ccc(NC(=O)[C@@H](NC(=O)c2ccc3n2CCNC3)C2CCCCC2)nc1]

To Intermediate 3.130a (40 mg, 0.07 mmol) in 1,4-dioxane (0.34 mL) was added HCl (4 M in 1,4-dioxane; 0.34 ml, 1.37 mmol). The reaction was stirred for 1.5 h at rt. The solvent was removed in vacuo and the residue dissolved in DMSO (0.75 mL) and purified by reverse phase preparative HPLC (Method 2) to afford the title compound (19 mg). LCMS (Method 15): 1.80 min, 477.3 $[M+H]^+$; $^1H$ NMR (400 MHz, MeOD) δ: 8.29 (dd, 1H), 8.23 (dd, 1H), 7.77 (dd, 1H), 6.89 (d, 1H), 5.90 (dt, 1H), 4.48 (d, 1H), 4.38-4.21 (m, 2H), 4.00 (s, 2H), 3.18-3.09 (m, 2H), 2.41 (s, 3H), 2.25 (s, 3H), 1.98-1.85 (m, 2H), 1.84-1.64 (m, 4H), 1.39-1.10 (m, 5H).

Example 131: N—((S)-2-((5-(1,4-Dimethyl-1H-pyrazol-5-yl)pyridin-2-yl)amino)-1-((1r,4S)-4-methylcyclohexyl)-2-oxoethyl)-3-methylisoxazole-4-carboxamide

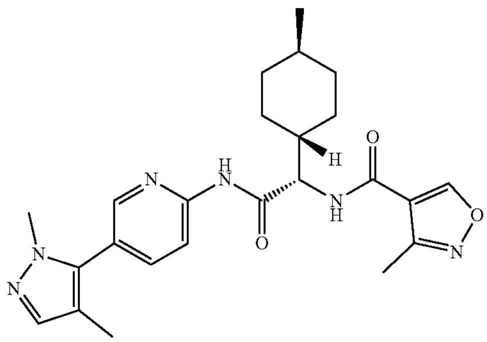 [SMILES: Cc1cnn(C)c1-c1ccc(NC(=O)[C@@H](NC(=O)c2conc2C)[C@H]2CC[C@H](C)CC2)nc1]

The title compound (15 mg) was prepared from Intermediate 3.106 (50 mg, 0.13 mmol), 3-methylisoxazole-4-carboxylic acid (22 mg, 0.16 mmol, CAS: 17153-20-7), HATU (61 mg, 0.16 mmol) and DIPEA (0.07 mL, 0.4 mmol) in accordance with the procedure described for Example 109. The crude product was purified by flash column chromatography on the Biotage Isolera One™ (12 g silica column, eluting 0-10% MeOH in DCM), reverse phase preparative HPLC (Method 2) and an SCX cartridge (5 g, washed with MeOH and eluted with 2 M methanolic ammonia). LCMS (Method 15): 2.42 min, 451.2 $[M+H]^+$; $^1H$ NMR (400 MHz, MeOD) δ: 9.15 (t, 1H), 8.33 (dd, 1H), 8.29 (dd, 1H), 7.81 (dd, 1H), 7.39 (d, 1H), 4.54 (d, 1H), 3.75 (s, 3H), 2.44 (d, 3H), 2.02 (d, 3H), 1.96-1.73 (m, 5H), 1.41-1.16 (m, 3H), 1.06-0.86 (m, 5H).

Example 132: (S)—N-(1-Cycloheptyl-2-((5-(1,4-dimethyl-1H-pyrazol-5-yl)pyridin-2-yl)amino)-2-oxoethyl)-1-methyl-1H-pyrazole-5-carboxamide

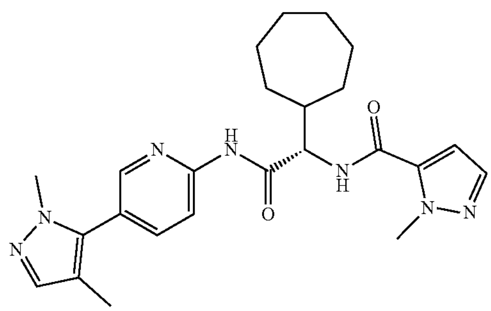 [SMILES: Cc1cnn(C)c1-c1ccc(NC(=O)[C@@H](NC(=O)c2ccnn2C)C2CCCCCC2)nc1]

The title compound (29 mg) was prepared from Intermediate 3.132 (40 mg, 0.12 mmol), 2-methylpyrazole-3-carboxylic acid (18 mg, 0.14 mmol, CAS: 16034-46-1), HATU (89 mg, 0.23 mmol) and DIPEA (45 mg, 0.35 mmol) in accordance with the procedure described for Example 109. The crude product was purified by flash column chromatography on the Biotage Isolera One™ (10 g silica column, eluting 0-3% MeOH in DCM) and reverse phase preparative HPLC (Method 2). LCMS (Method 15): 2.42 min, 450.2 $[M+H]^+$; $^1H$ NMR (400 MHz, $CDCl_3$) δ: 8.50 (s, 1H), 8.25 (dd, 1H), 8.21 (dd, 1H), 7.65-7.58 (m, 1H), 7.41 (d, 1H), 7.33 (d, 1H), 6.61-6.53 (m, 2H), 4.60 (dd, 1H), 4.11 (s, 3H), 3.70 (s, 3H), 2.13 (dtt, 1H), 1.94 (s, 3H), 1.86-1.74 (m, 2H), 1.71-1.59 (m, 2H), 1.54 (s, 2H), 1.49-1.27 (m, 6H).

Example 133: (S)—N-(1-Cycloheptyl-2-((5-(1,4-dimethyl-1H-pyrazol-5-yl)pyridin-2-yl)amino)-2-oxoethyl)-1-methyl-1H-1,2,3-triazole-5-carboxamide

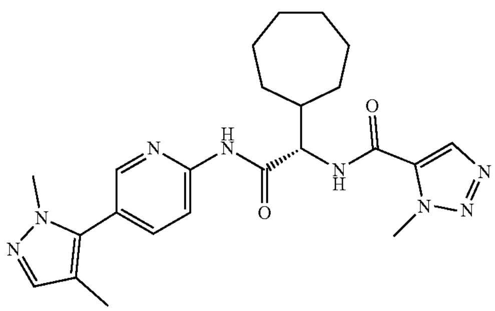 [SMILES: Cc1cnn(C)c1-c1ccc(NC(=O)[C@@H](NC(=O)c2cnnn2C)C2CCCCCC2)nc1]

The title compound (29 mg) was prepared from Intermediate 3.132 (40 mg, 0.12 mmol), 3-methyltriazole-4-carboxylic acid (18 mg, 0.14 mmol, CAS: 716361-91-0), HATU (89 mg, 0.23 mmol) and DIPEA (0.06 mL, 0.35 mmol) in accordance with the procedure described for Example 109. The crude product was purified by flash column chromatography on the Biotage Isolera One™ (10 g silica column, eluting 0-3% MeOH in DCM) and reverse phase preparative HPLC (Method 2). LCMS (Method 14): 2.25 min, 451.2 $[M+H]^+$; $^1H$ NMR (400 MHz, $CDCl_3$) δ: 8.57 (s, 1H), 8.32 (d, 1H), 8.28 (dd, 1H), 8.02 (s, 1H), 7.70 (dd, 1H), 7.40 (d, 1H), 6.88 (d, 1H), 4.74-4.65 (m, 1H), 4.33 (s, 3H), 3.77 (s, 3H), 2.22-2.13 (m, 1H), 2.01 (s, 3H), 1.93-1.80 (m, 2H), 1.79-1.66 (m, 2H), 1.66-1.55 (m, 2H), 1.55-1.35 (m, 6H).

Example 134: (S)—N-(1-Cycloheptyl-2-((5-(1,4-dimethyl-1H-pyrazol-5-yl)pyridin-2-yl)amino)-2-oxoethyl)-4-methyl-1,2,5-oxadiazole-3-carboxamide

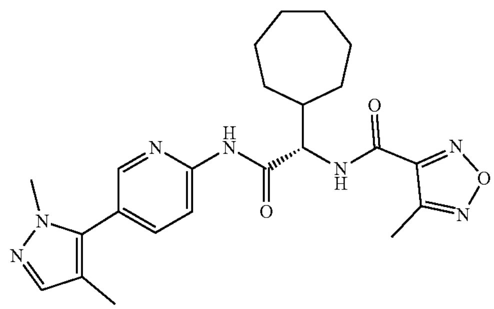 [SMILES: Cc1cnn(C)c1-c1ccc(NC(=O)[C@@H](NC(=O)c2nonc2C)C2CCCCCC2)nc1]

The title compound (40 mg) was prepared from Intermediate 3.132 (40 mg, 0.117 mmol), 4-methyl-1,2,5-oxadiazole-3-carboxylic acid (18 mg, 0.14 mmol, CAS: 58677-34-2), HATU (89 mg, 0.23 mmol) and DIPEA (0.06 mL, 0.35 mmol) in accordance with the procedure described for Example 109. The crude product was purified by flash column chromatography on the Biotage Isolera One™ (10 g silica column, eluting 0-2% MeOH in DCM) and an SCX cartridge (2 g, washed with MeOH and eluted with 2 M methanolic ammonia). LCMS (Method 15): 2.59 min, 452.2 $[M+H]^+$; $^1H$ NMR (400 MHz, $CDCl_3$) δ: 8.46 (s, 1H), 8.26 (d, 1H), 8.20 (dd, 1H), 7.62 (dd, 1H), 7.39 (d, 1H), 7.33 (d, 1H), 4.61 (dd, 1H), 3.70 (s, 3H), 2.56 (s, 3H), 2.24-2.12 (m, 1H), 1.94 (s, 3H), 1.86-1.76 (m, 2H), 1.73-1.61 (m, 2H), 1.59-1.51 (m, 2H*), 1.50-1.29 (m, 6H).

Example 135: N—((S)-2-((2-(3,5-dimethylisoxazol-4-yl)pyrimidin-5-yl)amino)-1-((1r,4S)-4-methylcyclohexyl)-2-oxoethyl)-1-methyl-1H-pyrazole-5-carboxamide

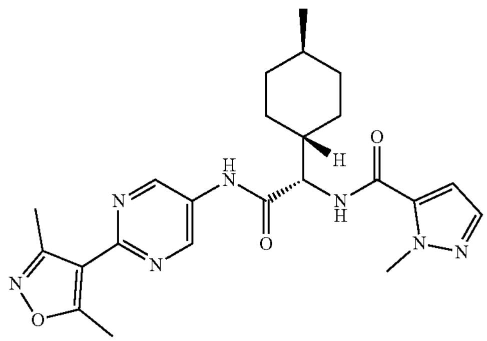 [SMILES: Cc1noc(C)c1-c1ncc(NC(=O)[C@@H](NC(=O)c2ccnn2C)[C@H]2CC[C@H](C)CC2)cn1]

The title compound (42 mg) was prepared from Intermediate 3.135 (97 mg, 0.28 mmol), 2-methylpyrazole-3-carboxylic acid (43 mg, 0.34 mmol, CAS: 16034-46-1), HATU (0.22 mg, 0.57 mmol) and DIPEA (0.2 mL, 1.1 mmol) in accordance with the procedure described for Example 109. The crude product was triturated with acetone. LCMS (Method 15): 2.46 min, 452.2 $[M+H]^+$; $^1H$ NMR (400 MHz, DMSO-$d_6$) δ: 10.72 (s, 1H), 9.11 (s, 2H), 8.62 (d, 1H), 7.47 (d, 1H), 7.08 (d, 1H), 4.41 (t, 1H), 4.03 (s, 3H), 2.71 (s, 3H), 2.48 (s, 3H), 1.84 (q, 2H), 1.70 (d, 2H), 1.60 (d, 1H), 1.36-1.26 (m, 1H), 1.25 (d, 1H), 1.12-0.99 (m, 1H), 0.86 (d, 5H).

Example 136: (S)—N-(1-Cycloheptyl-2-((5-(1,4-dimethyl-1H-pyrazol-5-yl)pyridin-2-yl)amino)-2-oxoethyl)-3-methylisoxazole-4-carboxamide

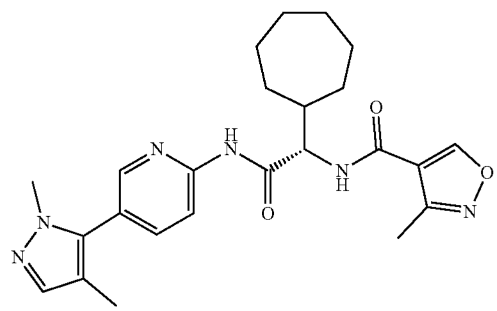 [SMILES: Cc1cnn(C)c1-c1ccc(NC(=O)[C@@H](NC(=O)c2conc2C)C2CCCCCC2)nc1]

The title compound (18 mg) was prepared from Intermediate 3.132 (40 mg, 0.12 mmol), 3-methylisoxazole-4-carboxylic acid (20 mg, 0.14 mmol, CAS: 17153-20-7), HATU (89 mg, 0.23 mmol) and DIPEA (0.06 mL, 0.35 mmol) in accordance with the procedure described for Example 109. The crude product was purified by flash column chromatography on the Biotage Isolera One™ (10 g silica column, eluting 0-3% MeOH in DCM), reverse phase preparative HPLC (Method 2) and flash column chromatography on the Biotage Isolera One™ (10 g silica column, eluting 0-3% MeOH in DCM). LCMS (Method 15): 2.40 min, 451.2 $[M+H]^+$; $^1H$ NMR (400 MHz, $CDCl_3$) δ: 9.05-8.85 (m, 2H), 8.35 (d, 1H), 8.29 (dd, 1H), 7.73 (dd, 1H), 7.42 (d, 1H), 6.65 (d, 1H), 4.82 (dd, 1H), 3.79 (s, 3H), 2.57 (d, 3H), 2.24-2.14 (m, 1H), 2.04 (d, 3H), 1.96-1.85 (m, 2H*), 1.81-1.73 (m, 2H), 1.64-1.61 (m, 2H), 1.54-1.37 (m, 6H).

Example 137: (S)—N-(1-Cycloheptyl-2-((5-(1,4-dimethyl-1H-pyrazol-5-yl)pyridin-2-yl)amino)-2-oxoethyl)-3-(methoxymethyl)isoxazole-4-carboxamide

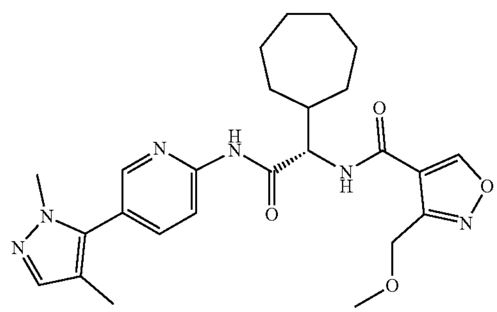 [SMILES: COCc1nocc1C(=O)N[C@H](C(=O)Nc1ccc(-c2c(C)cnn2C)cn1)C1CCCCCC1]

The title compound (28 mg) was prepared from Intermediate 3.132 (40 mg, 0.117 mmol), 3-(methoxymethyl)isoxazole-4-carboxylic acid (22.087 mg, 0.141 mmol, CAS: 1076245-90-3), HATU (89.086 mg, 0.234 mmol) and DIPEA (0.06 mL, 0.351 mmol) in accordance with the procedure described for Example 109. The crude product was purified by flash column chromatography on the Biotage Isolera One™ (10 g silica column eluting 0-2% MeOH in DCM) and reverse phase preparative HPLC (Method 2). LCMS (Method 15): 2.49 min, 481.2 $[M+H]^+$; $^1H$ NMR (400 MHz, DMSO-$d_6$) δ: 10.90 (s, 1H), 9.49 (d, 1H), 8.46 (d, 1H), 8.38 (dd, 1H), 8.21 (dd, 1H), 7.87 (dd, 1H), 7.35 (d, 1H), 4.78-4.69 (m, 3H), 3.72 (s, 3H), 3.36 (s, 3H), 2.04 (s, 1H), 1.97 (s, 3H), 1.70 (dq, 4H), 1.61-1.29 (m, 8H).

Example 138: N—((S)-2-((6-(3,5-dimethylisoxazol-4-yl)pyridin-3-yl)amino)-1-((1r,4S)-4-methylcyclohexyl)-2-oxoethyl)-1-methyl-1H-pyrazole-5-carboxamide

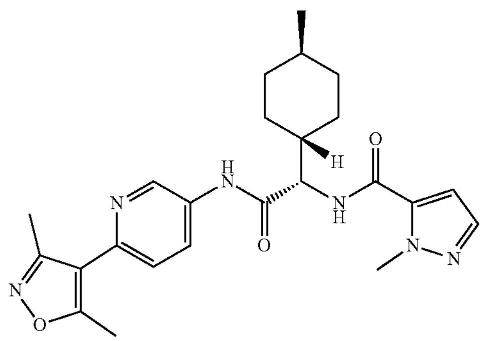 [SMILES: Cc1noc(C)c1-c1ccc(NC(=O)[C@@H](NC(=O)c2ccnn2C)[C@H]2CC[C@H](C)CC2)cn1]

The title compound (23 mg) was prepared from Intermediate 3.138 (93 mg, 0.27 mmol), 2-methylpyrazole-3-carboxylic acid (41 mg, 0.33 mmol, CAS: 16034-46-1), HATU (0.21 g, 0.54 mmol) and DIPEA (0.19 mL, 1.1 mmol) in accordance with the procedure described for Example 109. The crude product was triturated with acetone. LCMS (Method 14): 1.76 min, 451.2 $[M+H]^+$; $^1H$ NMR (400 MHz, DMSO-$d_6$): δ: 10.54 (s, 1H), 8.87 (dd, 1H), 8.58 (d, 1H), 8.17 (dd, 1H), 7.52 (dd, 1H), 7.46 (d, 1H), 7.07 (d, 1H), 4.40 (t, 1H), 4.03 (s, 3H), 2.53 (s, 3H), 2.34 (s, 3H), 1.85 (t, 2H), 1.70 (d, 2H), 1.60 (d, 1H), 1.30 (s, 1H), 1.18 (dd, 1H), 1.04 (t, 1H), 0.94-0.84 (m, 5H).

Example 139: 6-((S)-2-(1-Ethyl-1H-pyrazole-5-carboxamido)-2-((1r,4S)-4-methylcyclohexyl)acetamido)-3',5'-dimethyl-[3,4'-bipyridine]1'-oxide

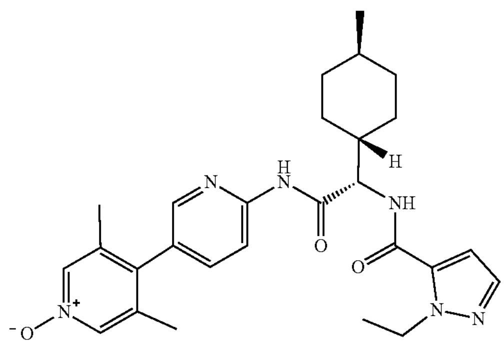 [SMILES: CCn1nccc1C(=O)N[C@H](C(=O)Nc1ccc(-c2c(C)c[n+]([O-])cc2C)cn1)[C@H]1CC[C@H](C)CC1]

The title compound (3.7 mg) was prepared from Example 92 (33 mg, 0.07 mmol) and mCPBA (24 mg, 0.07 mmol) in accordance with the procedure described for Example 25. The crude product was purified by reverse phase preparative HPLC (Method 2) to afford the title compound (3.7 mg). LCMS (Method 15): 2.24 min, 491.3 $[M+H]^+$; $^1H$ NMR (400 MHz, MeOD) δ: 8.29 (dd, 1H), 8.20 (dt, 3H), 7.69 (dd, 1H), 7.49 (d, 1H), 6.88 (d, 1H), 4.57-4.47 (m, 3H), 2.09 (s, 6H), 1.92 (s, 2H), 1.78 (d, 3H), 1.39-1.14 (m, 6H), 0.99 (q, 2H), 0.91 (d, 3H).

Example 140: 3-Ethyl-N—((S)-1-((1r,4S)-4-methylcyclohexyl)-2-((5-(5-methylpyrimidin-4-yl)pyridin-2-yl)amino)-2-oxoethyl)isoxazole-4-carboxamide

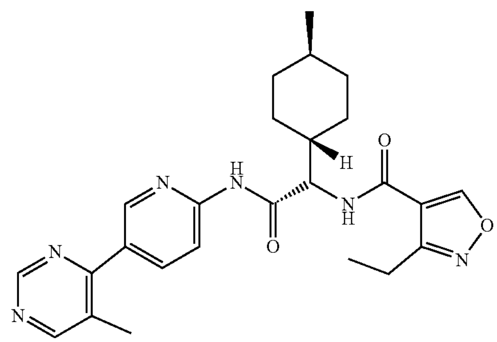

The title compound (50 mg) was prepared from Intermediate 3.140 (46 mg, 0.14 mmol), 3-ethyl-4-isoxazolecarboxylic acid (23 mg, 0.16 mmol, CAS: 639523-12-9), HATU (103 mg, 0.27 mmol) and DIPEA (53 mg, 0.41 mmol) in accordance with the procedure described for Example 109. The crude product was purified by flash column chromatography on the Biotage Isolera One™ (10 g silica column, eluting 0-4% MeOH in DCM). LCMS (Method 15): 2.33 min, 463.2 $[M+H]^+$; $^1H$ NMR (400 MHz, DMSO-$d_6$) δ: 10.89 (s, 1H), 9.41 (s, 1H), 9.10 (s, 1H), 8.75 (d, 1H), 8.69 (dd, 1H), 8.46 (d, 1H), 8.24 (dd, 1H), 8.17 (dd, 1H), 4.58 (t, 1H), 2.82 (d, 2H), 2.41 (t, 3H), 1.88-1.79 (m, 1H), 1.76-1.65 (m, 2H), 1.65-1.56 (m, 1H), 1.35-1.05 (m, 7H), 0.95-0.83 (m, 5H).

Example 141: (S)—N-(1-Cycloheptyl-2-((5-(1,4-dimethyl-1H-pyrazol-5-yl)pyridin-2-yl)amino)-2-oxoethyl)-1-ethyl-1H-1,2,3-triazole-5-carboxamide

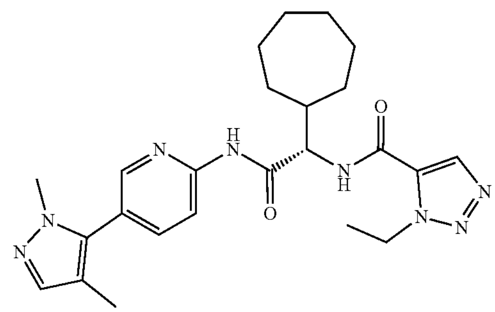 [SMILES: CCn1nncc1C(=O)N[C@H](C(=O)Nc1ccc(-c2c(C)cnn2C)cn1)C1CCCCCC1]

The title compound (53 mg) was prepared from Intermediate 3.132 (48 mg, 0.14 mmol), 1-ethyl-1H-1,2,3-triazole- 5-carboxylic acid (22 mg, 0.16 mmol, CAS: 860751-24-2) HATU (70 mg, 0.18 mmol) and DIPEA (45 mg, 0.35 mmol) in accordance with the procedure described for Example 109. The crude product was purified by flash column chromatography on the Biotage Isolera One™ (10 g silica column, eluting 0-3% MeOH in DCM). LCMS (Method 15): 2.41 min, 465.2 $[M+H]^+$; $^1$H NMR (400 MHz, DMSO-$d_6$) δ: 10.92 (s, 1H), 8.87 (d, 1H), 8.39 (dd, 1H), 8.37 (s, 1H), 8.23 (dd, 1H), 7.88 (dd, 1H), 7.36 (d, 1H), 4.75-4.60 (m, 3H), 3.73 (s, 3H), 2.14 (s, 1H), 1.98 (s, 3H), 1.77-1.33 (m, 15H).

Example 142: N—((S)-2-((5-(3-(methoxymethyl)-5-methylisoxazol-4-yl)pyridin-2-yl)amino)-1-((1r,4S)-4-methylcyclohexyl)-2-oxoethyl)-1-methyl-1H-pyrazole-5-carboxamide

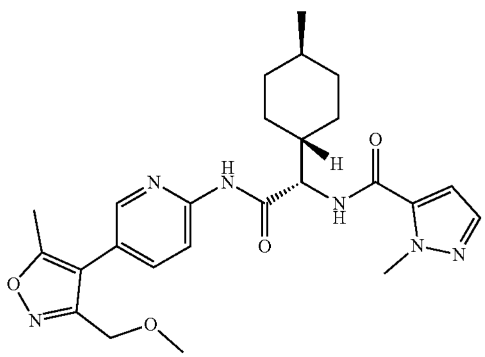 [SMILES: COCc1noc(C)c1-c1ccc(NC(=O)[C@@H](NC(=O)c2ccnn2C)[C@H]2CC[C@H](C)CC2)nc1]

The title compound (38 mg) was prepared from Intermediate 3.142 (41 mg, 0.11 mmol), 2-methylpyrazole-3-carboxylic acid (17 mg, 0.13 mmol, CAS: 16034-46-1), HATU (84 mg, 0.22 mmol) and DIPEA (19 mg, 0.11 mmol) in accordance with the procedure described for Example 109. The crude product was purified by flash column chromatography on the Biotage Isolera One™ (10 g silica column, eluting 0-70% EtOAc in heptanes). LCMS (Method 19): 2.58 min, 481.2 $[M+H]^+$; $^1$H NMR (400 MHz, DMSO-$d_6$) δ: 10.75 (s, 1H), 8.49 (d, 1H), 8.40 (dd, 1H), 8.18 (dd, 1H), 7.86 (dd, 1H), 7.47 (d, 1H), 7.04 (d, 1H), 4.53 (t, 1H), 4.47 (s, 2H), 4.02 (s, 3H), 3.23 (s, 3H), 2.46 (s, 3H), 1.89-1.76 (m, 2H), 1.74-1.64 (m, 2H), 1.63-1.56 (m, 1H), 1.34-1.20 (m, 2H), 1.16-1.00 (m, 1H), 0.95-0.83 (m, 5H).

Example 143: (S)—N-(1-cycloheptyl-2-((5-(3,5-dimethyl-4H-1,2,4-triazol-4-yl)pyridin-2-yl)amino)-2-oxoethyl)-1-methyl-1H-pyrazole-5-carboxamide

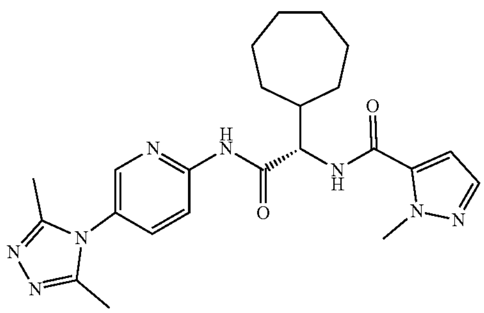 [SMILES: Cc1nnc(C)n1-c1ccc(NC(=O)[C@@H](NC(=O)c2ccnn2C)C2CCCCCC2)nc1]

The title compound (8 mg) was prepared from Intermediate 3.143 (23 mg, 0.06 mmol), 2-methylpyrazole-3-carboxylic acid (11 mg, 0.08 mmol, CAS: 16034-46-1), HATU (46 mg, 0.12 mmol) and DIPEA (0.04 mL, 0.24 mmol) in accordance with the procedure described for Example 109. The crude product was purified by reverse phase preparative HPLC (Method 2). LCMS (Method 19): 2.04 min, 451.2 $[M+H]^+$; $^1$H NMR (400 MHz, MeOD) δ: 8.40 (dd, 2H), 7.88 (dd, 1H), 7.49 (d, 1H), 6.90 (d, 1H), 4.66 (d, 1H), 4.09 (s, 3H), 2.29 (s, 6H), 2.21 (tt, 1H), 1.95-1.39 (m, 12H).

Example 144: (S)—N-(1-(4,4-difluorocyclohexyl)-2-((5-(1,4-dimethyl-1H-pyrazol-5-yl)pyridin-2-yl)amino)-2-oxoethyl)-3-ethylisoxazole-4-carboxamide

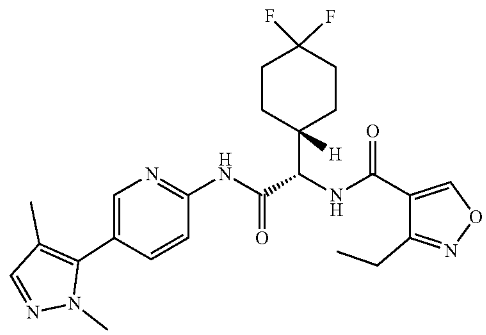

The title compound (25 mg) was prepared from Intermediate 3.144 (40 mg, 0.11 mmol), 3-ethyl-4-isoxazolecarboxylic acid (19 mg, 0.13 mmol, CAS: 639523-12-9), HATU (59 mg, 0.15 mmol) and DIPEA (0.06 mL, 0.33 mmol) in accordance with the procedure described for Example 109. The crude product was purified by flash column chromatography on the Biotage Isolera One™ (10 g silica column, eluting 0-10% MeOH in DCM), an SCX cartridge (5 g, washed with MeOH and eluted with 2 M methanolic ammonia) and reverse phase preparative HPLC (Method 2). LCMS (Method 15): 2.36 min, 487.2 $[M+H]^+$; $^1$H NMR (400 MHz, DMSO-$d_6$) δ: 10.92 (s, 1H), 9.41 (s, 1H), 8.59 (d, 1H), 8.39 (dd, 1H), 8.23 (dd, 1H), 7.88 (dd, 1H), 7.35 (d, 1H), 4.71 (t, 1H), 3.72 (s, 3H), 2.83 (q, 2H), 2.13-2.01 (m, 2H), 1.97 (s, 3H), 1.95-1.65 (m, 5H), 1.51 (m, 1H), 1.38 (m, 1H), 1.17 (t, 3H).

Example 145: N—((S)-2-((6-(1,4-dimethyl-1H-pyrazol-5-yl)pyridin-3-yl)amino)-1-((1r,4S)-4-methylcyclohexyl)-2-oxoethyl)-1-methyl-1H-pyrazole-5-carboxamide

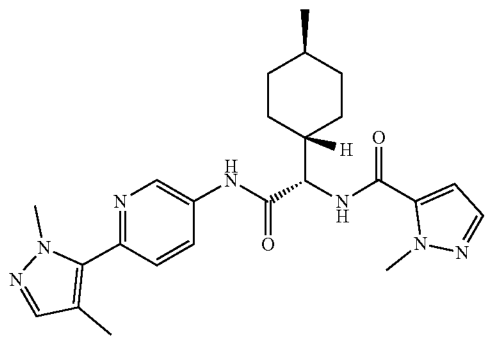 [SMILES: Cc1cnn(C)c1-c1ccc(NC(=O)[C@@H](NC(=O)c2ccnn2C)[C@H]2CC[C@H](C)CC2)cn1]

The title compound (15 mg) was prepared from Intermediate 3.145 (80 mg, 0.23 mmol), 2-methylpyrazole-3-carboxylic acid (44 mg, 0.35 mmol, CAS: 16034-46-1), HATU (0.18 g, 0.47 mmol) and DIPEA (0.12 g, 0.94 mmol) in accordance with the procedure described for Example 109. The crude product was purified by flash column chromatography on the Biotage Isolera One™ (10 g silica column, eluting 5% MeOH in DCM) and trituration in diethyl ether/acetone (9:1). LCMS (Method 19): 2.40 min, 450.2 $[M+H]^+$; $^1H$ NMR (400 MHz, DMSO-$d_6$) δ: 10.62 (s, 1H), 8.93 (dd, 1H), 8.60 (d, 1H), 8.23 (dd, 1H), 7.53 (dd, 1H), 7.47 (d, 1H), 7.32 (d, 1H), 7.08 (d, 1H), 4.40 (t, 1H), 4.03 (s, 3H), 3.85 (s, 3H), 2.06 (d, 3H), 1.86 (t, 2H), 1.71 (d, 2H), 1.61 (d, 1H), 1.29 (d, 1H), 1.20 (t, 1H), 1.06 (d, 1H), 0.88 (t, 5H).

Example 146: 1-methyl-N—((S)-2-((4-methyl-5-(1-methyl-1H-pyrazol-5-yl)pyridin-2-yl)amino)-1-((1r,4S)-4-methylcyclohexyl)-2-oxoethyl)-1H-pyrazole-5-carboxamide

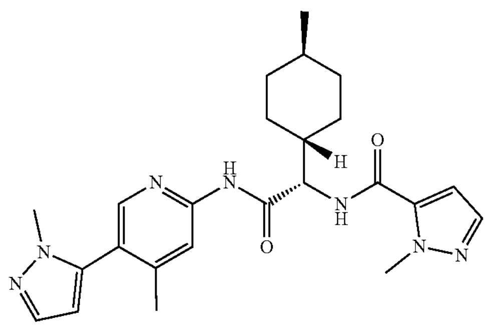 [SMILES: Cc1cc(NC(=O)[C@@H](NC(=O)c2ccnn2C)[C@H]2CC[C@H](C)CC2)ncc1-c1ccnn1C]

The title compound (26 mg) was prepared from Intermediate 3.146 (58 mg, 0.17 mmol), 2-methylpyrazole-3-carboxylic acid (24 mg, 0.19 mmol, CAS: 16034-46-1), HATU (71 mg, 0.19 mmol) and DIPEA (0.09 mL, 0.51 mmol) in accordance with the procedure described for Example 109. The crude product was purified by flash column chromatography on the Biotage Isolera One™ (12 g silica column, eluting 0-10% MeOH in DCM). LCMS (Method 19): 2.46 min, 450.2 $[M+H]^+$; $^1H$ NMR (400 MHz, DMSO-$d_6$) δ: 10.72 (s, 1H), 8.48 (d, 1H), 8.19 (s, 1H), 8.12 (s, 1H), 7.53 (d, 1H), 7.47 (d, 1H), 7.04 (d, 1H), 6.33 (d, 1H), 4.52 (t, 1H), 4.02 (s, 3H), 3.63 (s, 3H), 2.15 (s, 3H), 1.84 (t, 2H), 1.70 (d, 2H), 1.60 (d, 1H), 1.33-1.23 (m, 2H), 1.08 (q, 1H), 0.87 (d, 5H).

Example 147: N—((S)-2-((2-(1,4-dimethyl-1H-pyrazol-5-yl)pyrimidin-5-yl)amino)-1-((1r,4S)-4-methylcyclohexyl)-2-oxoethyl)-1-ethyl-1H-pyrazole-5-carboxamide

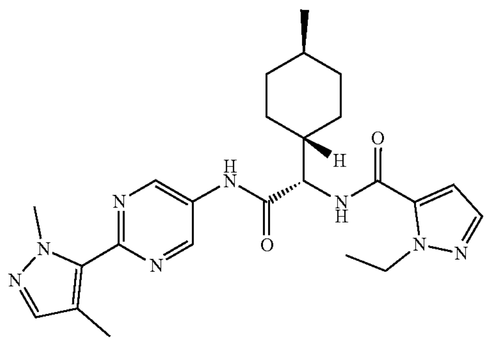 [SMILES: CCn1nccc1C(=O)N[C@H](C(=O)Nc1cnc(-c2c(C)cnn2C)nc1)[C@H]1CC[C@H](C)CC1]

The title compound (6 mg) was prepared from Intermediate 3.147 (70 mg, 0.20 mmol), 2-ethylpyrazole-3-carboxylic acid (43 mg, 0.31 mmol, CAS: 400755-43-3), HATU (0.16 g, 0.41 mmol) and DIPEA (0.14 mL, 0.82 mmol) in accordance with the procedure described for Example 109. The crude product was purified by flash column chromatography on the Biotage Isolera One™ (12 g silica column, eluting 10% MeOH in DCM) and reverse phase preparative HPLC (Method 3). LCMS (Method 14): 1.79 min, 465.2 $[M+H]^{+1}H$ NMR (400 MHz, MeOD) δ: 9.17 (d, 2H), 7.50 (d, 1H), 7.35 (s, 1H), 6.89 (d, 1H), 4.52 (qd, 2H), 4.47 (d, 1H), 4.12 (s, 3H), 2.29 (s, 3H), 1.99-1.87 (m, 2H), 1.83-1.71 (m, 3H), 1.37 (t, 4H), 1.29 (d, 1H), 1.20 (q, 1H), 1.00 (q, 2H), 0.91 (d, 3H).

Example 148: (S)—N-(1-cycloheptyl-2-((5-(1,4-dimethyl-1H-1,2,3-triazol-5-yl)pyridin-2-yl)amino)-2-oxoethyl)-1-methyl-1H-pyrazole-5-carboxamide

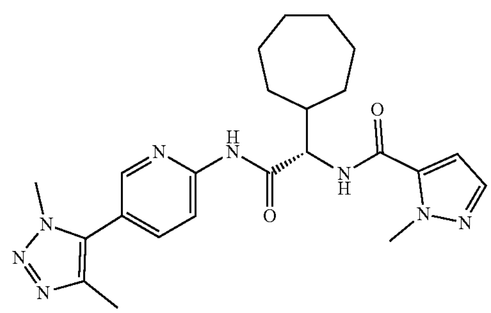 [SMILES: Cc1nnn(C)c1-c1ccc(NC(=O)[C@@H](NC(=O)c2ccnn2C)C2CCCCCC2)nc1]

The title compound (40 mg) was prepared from Intermediate 3.148 (50 mg, 0.14 mmol), 2-methylpyrazole-3-carboxylic acid (22 mg, 0.17 mmol, CAS: 16034-46-1), HATU (65 mg, 0.17 mmol) and DIPEA (0.07 mL, 0.43 mmol) in accordance with the procedure described for Example 109. The crude product was purified by flash column chromatography on the Biotage Isolera One™ (12 g silica column, eluting 50-100% EtOAc in heptanes) and reverse phase preparative HPLC (Method 2). LCMS (Method 15): 2.22 min, 451.3 $[M+H]^+$; $^1H$ NMR (400 MHz, MeOD) δ: 8.40 (dd, 1H), 8.33 (dd, 1H), 7.89 (dd, 1H), 7.48 (d, 1H), 6.90 (d, 1H), 4.66 (d, 1H), 4.09 (s, 3H), 3.99 (s, 3H), 2.30 (s, 3H), 2.26-2.15 (m, 1H), 1.92-1.71 (m, 4H), 1.70-1.43 (m, 8H).

Example 149: (S)—N-(1-cycloheptyl-2-((5-(1,4-dimethyl-1H-1,2,3-triazol-5-yl)pyridin-2-yl)amino)-2-oxoethyl)-1-ethyl-1H-pyrazole-5-carboxamide

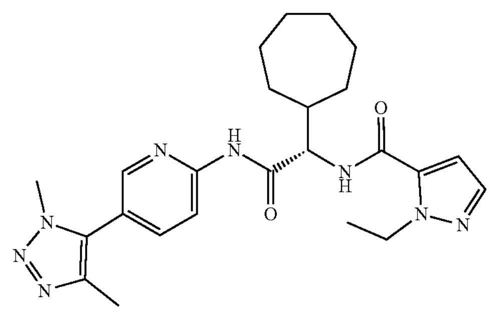 [SMILES: CCn1nccc1C(=O)N[C@H](C(=O)Nc1ccc(-c2c(C)nnn2C)cn1)C1CCCCCC1]

The title compound (18 mg) was prepared from Intermediate 3.148 (50 mg, 0.14 mmol) 2-ethylpyrazole-3-carboxylic acid (24 mg, 0.17 mmol, CAS: 400755-43-3), HATU (65 mg, 0.17 mmol) and DIPEA (0.07 mL, 0.43 mmol) in accordance with the procedure described for Example 109. The crude product was purified by flash column chromatography on the Biotage Isolera One™ (12 g silica column, eluting 50-100% EtOAc in heptanes) and reverse phase preparative HPLC (Method 2). LCMS (Method 15): 2.18 min, 465.3 $[M+H]^+$; $^1H$ NMR (400 MHz, MeOD) δ: 8.40 (dd, 1H), 8.33 (dd, 1H), 7.88 (dd, 1H), 7.50 (d, 1H), 6.87 (d, 1H), 4.65 (d, 1H), 4.52 (q, 2H), 3.99 (s, 3H), 2.29 (s, 3H), 2.23-2.15 (m, 1H), 1.88-1.42 (m, 12H), 1.37 (t, 3H).

Example 150: (S)—N-(1-cycloheptyl-2-((5-(5-(methoxymethyl)-3-methylisoxazol-4-yl)pyridin-2-yl)amino)-2-oxoethyl)-1-methyl-1H-pyrazole-5-carboxamide

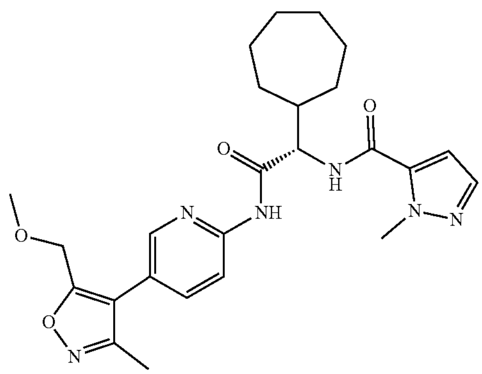 [SMILES: COCc1onc(C)c1-c1ccc(NC(=O)[C@@H](NC(=O)c2ccnn2C)C2CCCCCC2)nc1]

The title compound (31 mg) was prepared from Intermediate 3.150 (80 mg, 0.18 mmol), 2-methylpyrazole-3-carboxylic acid (35 mg, 0.27 mmol, CAS: 16034-46-1), HATU (0.15 g, 0.39 mmol) and DIPEA (0.14 mL, 0.78 mmol) in accordance with the procedure described for Example 109. The crude product was purified by flash column chromatography on the Biotage Isolera One™ (4 g silica column, eluting 0-100% EtOAc in heptanes). LCMS (Method 15): 2.25 min, 481.2 $[M+H]^+$; $^1H$ NMR (400 MHz, MeOD) δ: 8.36 (dd, 1H), 8.23 (dd, 1H), 7.83 (dd, 1H), 7.48 (d, 1H), 6.89 (d, 1H), 4.64 (d, 1H), 4.49 (s, 2H), 4.09 (s, 3H), 3.37 (s, 3H), 2.31 (s, 3H), 2.20 (t, 1H), 1.92-1.71 (m, 4H), 1.68-1.40 (m, 8H).

Example 151: N—((S)-2-((3'-methoxy-2'-methyl-[3,4'-bipyridin]-6-yl)amino)-1-((1r,4S)-4-methylcyclohexyl)-2-oxoethyl)-1-methyl-1H-pyrazole-5-carboxamide

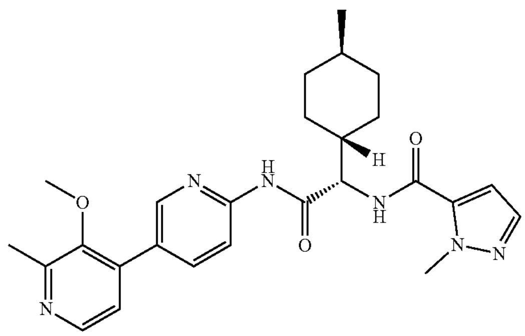 [SMILES: COc1c(-c2ccc(NC(=O)[C@@H](NC(=O)c3ccnn3C)[C@H]3CC[C@H](C)CC3)nc2)ccnc1C]

The title compound (11 mg) was prepared from Intermediate 3.151 (40 mg, 0.11 mmol), 2-methylpyrazole-3-carboxylic acid (16 mg, 0.13 mmol, CAS: 16034-46-1), HATU (58 mg, 0.15 mmol) and DIPEA (0.02 mL, 0.11 mmol) in accordance with the procedure described for Example 109. The crude product was purified by flash column chromatography on the Biotage Isolera One™ (4 g silica column, eluting 0-2% MeOH in DCM) and reverse phase preparative HPLC (Method 2). LCMS (Method 19): 2.08 min, 477.2 $[M+H]^+$; $^1H$ NMR (400 MHz, $CDCl_3$) δ: 8.59 (dd, 2H), 8.35-8.28 (m, 2H), 8.05 (dd, 1H), 7.47 (d, 1H), 7.16 (d, 1H), 6.69 (d, 1H), 6.63 (d, 1H), 4.64-4.58 (t, 1H), 4.18 (s, 3H), 3.47 (s, 3H), 2.61 (s, 3H), 1.95-1.89 (m, 1H), 1.83 (m, 2H), 1.78-1.73 (m, 2H), 1.31 (m, 1H), 1.26-1.12 (m, 2H), 1.03-0.91 (m, 2H), 0.88 (d, 3H).

Example 152: N—((S)-2-((2',3'-dimethyl-[3,4'-bipyridin]-6-yl)amino)-1-((1r,4S)-4-methylcyclohexyl)-2-oxoethyl)-1-methyl-1H-pyrazole-5-carboxamide

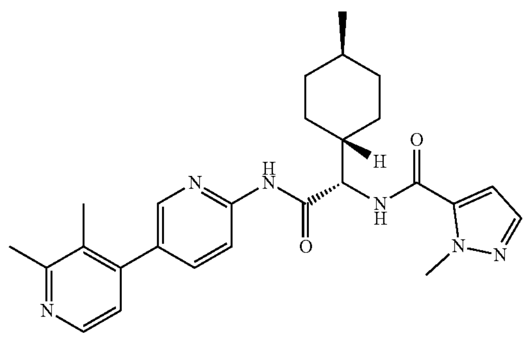 [SMILES: Cc1nccc(-c2ccc(NC(=O)[C@@H](NC(=O)c3ccnn3C)[C@H]3CC[C@H](C)CC3)nc2)c1C]

The title compound (26 mg) was prepared from Intermediate 3.152 (50 mg, 0.14 mmol), 2-methylpyrazole-3-carboxylic acid (22 mg, 0.17 mmol, CAS: 16034-46-1), HATU (0.11 g, 0.28 mmol) and DIPEA (55 mg, 0.43 mmol) in accordance with the procedure described for Example 109. The crude product was purified by flash column chromatography on the Biotage Isolera One™ (4 g silica column, eluting 0-2% MeOH in DCM) and reverse phase preparative HPLC (Method 2). LCMS (Method 19): 1.04 min, 461.2 $[M+H]^+$; $^1H$ NMR (400 MHz, DMSO-$d_6$) δ: 10.79 (s, 1H), 8.49 (d, 1H), 8.34 (dd, 1H), 8.31 (d, 1H), 8.19 (dd, 1H), 7.82 (dd, 1H), 7.47 (d, 1H), 7.11 (d, 1H), 7.05 (d, 1H), 4.55 (t, 1H), 4.02 (s, 3H), 2.51 (s, 3H), 2.18 (s, 3H), 1.83 (m, 2H), 1.70 (m, 2H), 1.60 (m, 1H), 1.26 (m, 2H), 1.08 (m, 1H), 0.86 (m, 5H).

Example 153: N—((S)-2-((2',5'-dimethyl-[3,4'-bipyridin]-6-yl)amino)-1-((1r,4S)-4-methylcyclohexyl)-2-oxoethyl)-1-methyl-1H-pyrazole-5-carboxamide

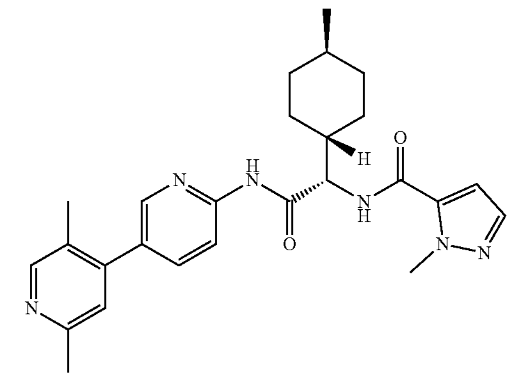 [SMILES: Cc1cc(-c2ccc(NC(=O)[C@@H](NC(=O)c3ccnn3C)[C@H]3CC[C@H](C)CC3)nc2)c(C)cn1]

The title compound (21 mg) was prepared from Intermediate 3.153 (77 mg, 0.22 mmol), 2-methylpyrazole-3-carboxylic acid (33 mg, 0.26 mmol, CAS: 16034-46-1), HATU (0.12 g, 0.31 mmol) and DIPEA (0.11 mL, 0.66 mmol) in accordance with the procedure described for Example 109. The crude product was purified by flash column chromatography on the Biotage Isolera One™ (4 g silica column, eluting 0-5% MeOH in DCM) and reverse phase preparative HPLC (Method 2). LCMS (Method 15): 1.91 min, 461.4 $[M+H]^+$; $^1H$ NMR (400 MHz, DMSO-$d_6$) δ: 10.80 (s, 1H), 8.49 (d, 1H), 8.41-8.36 (m, 2H), 8.19 (dd, 1H), 7.88 (dd, 1H), 7.47 (d, 1H), 7.17 (s, 1H), 7.05 (d, 1H), 4.55 (t, 1H), 4.02 (s, 3H), 2.46 (s, 3H), 2.23 (s, 3H), 1.83 (m, 2H), 1.70 (m, 2H), 1.60 (m, 1H), 1.26 (m, 2H), 1.08 (m, 1H), 0.87 (m, 5H).

Example 154: N—((S)-2-((6-(1,4-dimethyl-1H-pyrazol-5-yl)pyridin-3-yl)amino)-1-((1r,4S)-4-methylcyclohexyl)-2-oxoethyl)-1-ethyl-1H-pyrazole-5-carboxamide

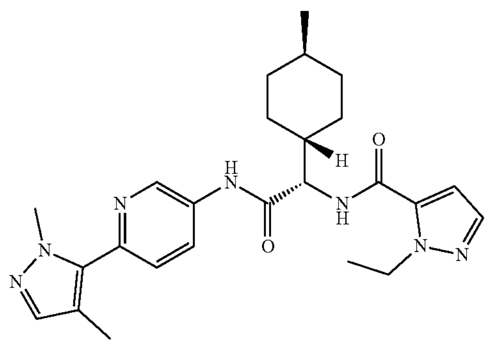 [SMILES: CCn1nccc1C(=O)N[C@H](C(=O)Nc1ccc(-c2c(C)cnn2C)nc1)[C@H]1CC[C@H](C)CC1]

The title compound (12 mg) was prepared from Intermediate 3.145 (75 mg, 0.19 mmol), 2-ethylpyrazole-3-carboxylic acid (39 mg, 0.28 mmol, CAS: 400755-43-3), HATU (0.14 g, 0.37 mmol) and DIPEA (0.13 mL, 0.75 mmol) in accordance with the procedure described for Example 109. The crude product was purified by flash column chromatography on the Biotage Isolera One™ (4 g silica column, eluting 0-100% EtOAc in heptanes). LCMS (Method 15): 2.36 min, 464.2 $[M+H]^+$; $^1H$ NMR (400 MHz, MeOD) δ: 8.93 (dd, 1H), 8.29 (dd, 1H), 7.54 (dd, 1H), 7.50 (d, 1H), 7.36 (t, 1H), 6.89 (d, 1H), 4.59-4.44 (m, 3H), 3.87 (s, 3H), 2.11 (d, 3H), 2.00-1.86 (m, 2H), 1.83-1.72 (m, 3H), 1.41-1.33 (m, 4H), 1.23 (ddd, 2H), 1.00 (q, 2H), 0.91 (d, 3H).

Example 155: N—((S)-2-((6-(1,4-dimethyl-1H-pyrazol-5-yl)pyridin-3-yl)amino)-1-((1r,4S)-4-methylcyclohexyl)-2-oxoethyl)-3-ethylisoxazole-4-carboxamide

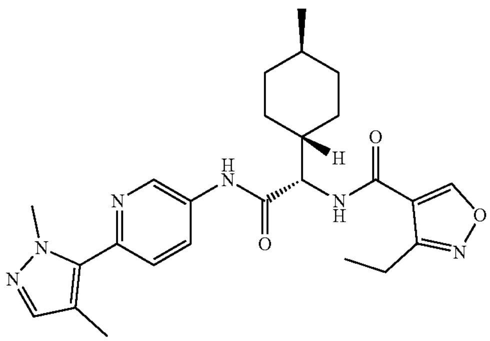 [SMILES: CCc1nocc1C(=O)N[C@H](C(=O)Nc1ccc(-c2c(C)cnn2C)nc1)[C@H]1CC[C@H](C)CC1]

The title compound (23 mg) was prepared from Intermediate 3.145 (75 mg, 0.19 mmol), 3-ethyl-4-isoxazolecarboxylic acid (40 mg, 0.28 mmol, CAS: 639523-12-9), HATU (142 mg, 0.37 mmol) and DIPEA (0.13 mL, 0.75 mmol) in accordance with the procedure described for Example 109. The crude product was purified by flash column chromatography Biotage Isolera One™ (4 g silica column, eluting 0-100% EtOAc in heptanes). LCMS (Method 19): 2.56 min, 463.2 $[M-H]^-$, $^1H$ NMR (400 MHz, MeOD) δ: 9.13 (d, 1H), 8.92 (dd, 1H), 8.28 (dd, 1H), 7.54 (dd, 1H), 7.36 (d, 1H), 4.45 (d, 1H), 3.86 (s, 3H), 2.91 (q, 2H), 2.10 (d, 3H), 1.99-1.71 (m, 5H), 1.44-1.13 (m, 6H), 1.06-0.93 (m, 2H), 0.91 (d, 3H).

Example 156: N—((S)-2-((2-(1,4-dimethyl-1H-pyrazol-5-yl)pyrimidin-5-yl)amino)-1-((1r,4S)-4-methylcyclohexyl)-2-oxoethyl)-1-methyl-1H-pyrazole-5-carboxamide

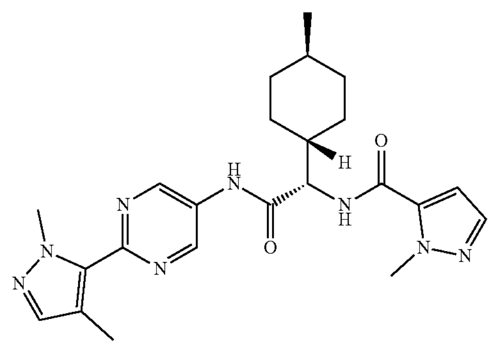 [SMILES: Cc1cnn(C)c1-c1ncc(NC(=O)[C@@H](NC(=O)c2ccnn2C)[C@H]2CC[C@H](C)CC2)cn1]

The title compound (12 mg) was prepared from Intermediate 3.147 (0.1 g, 0.29 mmol), 2-methylpyrazole-3-carboxylic acid (56 mg, 0.44 mmol, CAS: 16034-46-1), HATU (0.22 g, 0.59 mmol) and DIPEA (0.21 mL, 1.2 mmol) in accordance with the procedure described for Example 109. The crude product was purified by flash column chromatography on the Biotage Isolera One™ (10 g silica column, eluting 80% EtOAc in Heptanes), trituration in diethyl ether/MeOH (9:1) and reverse phase preparative HPLC (Method 3). LCMS (Method 19): 2.47 min, 451.2 $[M+H]^+$; $^1H$ NMR (400 MHz, DMSO-$d_6$) δ: 10.85-10.79 (m, 1H), 9.17 (s, 2H), 8.67 (d, 1H), 7.47 (d, 1H), 7.35 (d, 1H), 7.08 (d, 1H), 4.41 (t, 1H), 4.05 (s, 3H), 4.03 (s, 3H), 2.23 (d, 3H), 1.85 (q, 2H), 1.71 (d, 2H), 1.62 (d, 1H), 1.36-1.26 (m, 1H), 1.21 (q, 1H), 1.06 (q, 1H), 0.88 (t, 5H).

Example 157: (S)—N-(1-cycloheptyl-2-((5-(1-ethyl-4-methyl-1H-1,2,3-triazol-5-yl)pyridin-2-yl)amino)-2-oxoethyl)-1-methyl-1H-pyrazole-5-carboxamide

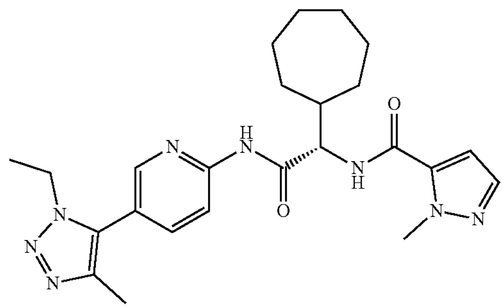 [SMILES: CCn1nnc(C)c1-c1ccc(NC(=O)[C@@H](NC(=O)c2ccnn2C)C2CCCCCC2)nc1]

The title compound (20 mg) was prepared from Intermediate 3.157 (19 mg, 0.05 mmol), 2-methylpyrazole-3-carboxylic acid (7 mg, 0.06 mmol, CAS: 16034-46-1), HATU (22 mg, 0.06 mmol) and DIPEA (0.03 mL, 0.16 mmol) in accordance with the procedure described for Example 109. The crude product was purified by flash column chromatography on the Biotage Isolera One™ (12 g silica column, eluting 0-100% EtOAc in Heptanes). LCMS (Method 19): 2.37 min, 465.2 $[M+H]^+$; $^1H$ NMR (400 MHz, DMSO-$d_6$) δ: 10.92 (s, 1H), 8.50 (d, 1H), 8.43 (dd, 1H), 8.26 (dd, 1H), 7.92 (dd, 1H), 7.48 (d, 1H), 7.05 (d, 1H), 4.65 (t, 1H), 4.28 (q, 2H), 4.03 (s, 3H), 2.21 (s, 3H), 2.13 (s, 1H), 1.67 (d, 3H), 1.53 (s, 3H), 1.41 (d, 4H), 1.33-1.22 (m, 5H).

Example 158: (S)—N-(1-cycloheptyl-2-((5-(3,5-dimethylisoxazol-4-yl)pyrazin-2-yl)amino)-2-oxoethyl)-1-methyl-1H-pyrazole-5-carboxamide

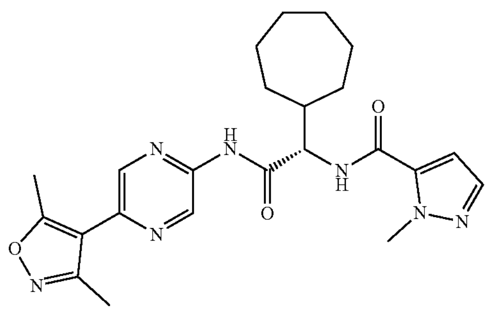 [SMILES: Cc1noc(C)c1-c1cnc(NC(=O)[C@@H](NC(=O)c2ccnn2C)C2CCCCCC2)cn1]

The title compound (2 mg) was prepared from Intermediate 3.158 (16 mg, 0.05 mmol), 2-methylpyrazole-3-carboxylic acid (7 mg, 0.05 mmol, CAS: 16034-46-1), HATU (20 mg, 0.05 mmol) and DIPEA (0.02 mL, 0.14 mmol) in accordance with the procedure described for Example 109. The crude product was purified by flash column chromatography on the Biotage Isolera One™ (12 g silica column, eluting 0-100% EtOAc in Heptanes) and reverse phase preparative HPLC (Method 2). LCMS (Method 14): 2.58 min, 452.2 $[M+H]^+$; $^1H$ NMR (400 MHz, DMSO-$d_6$) δ: 11.12 (s, 1H), 9.41 (d, 1H), 8.60 (d, 1H), 8.53 (d, 1H), 7.48 (d, 1H), 7.06 (d, 1H), 4.68 (t, 1H), 4.03 (s, 3H), 2.58 (s, 3H), 2.38 (s, 3H), 2.14 (s, 1H), 1.78-1.64 (m, 4H), 1.53 (s, 3H), 1.42 (d, 4H), 1.24 (s, 1H).

Example 159: N—((S)-2-((5-(1,4-dimethyl-1H-1,2,3-triazol-5-yl)pyridin-2-yl)amino)-1-((1r,4S)-4-methylcyclohexyl)-2-oxoethyl)-1-ethyl-1H-pyrazole-5-carboxamide

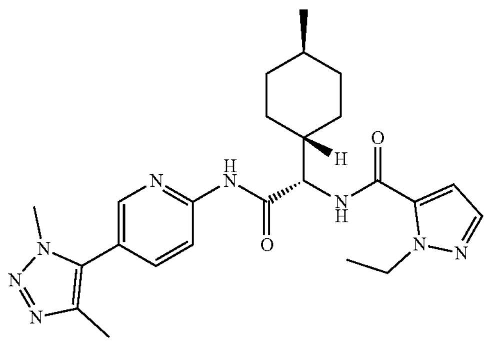 [SMILES: CCn1nccc1C(=O)N[C@H](C(=O)Nc1ccc(-c2c(C)nnn2C)cn1)[C@H]1CC[C@H](C)CC1]

The title compound (49 mg) was prepared from Intermediate 3.125 (63 mg, 0.18 mmol), 2-ethylpyrazole-3-carboxylic acid (31 mg, 0.22 mmol, CAS: 400755-43-3), HATU (90 mg, 0.24 mmol) and DIPEA (0.1 mL, 0.55 mmol) in accordance with the procedure described for Example 109. The crude product was purified by reverse phase chromatography on the Biotage Isolera One™ (30 g Biotage SNAP KP-C18-HS, eluting 5-100% MeCN in water buffer with 0.005 M $NH_4OH$) and an SCX cartridge (2 g, washed with MeOH and eluted with 2 M methanolic ammonia). LCMS (Method 15): 2.47 min, 465.3 $[M+H]^+$; $^1H$ NMR (400 MHz, DMSO-$d_6$) δ: 10.88 (s, 1H), 8.51 (d, 1H), 8.47 (dd, 1H), 8.26 (dd, 1H), 7.96 (dd, 1H), 7.49 (d, 1H), 7.01 (d, 1H), 4.55 (t, 1H), 4.46 (q, 2H), 3.95 (s, 3H), 2.24 (s, 3H), 1.90-1.76 (m, 2H), 1.74-1.67 (m, 2H), 1.64-1.57 (m, 1H), 1.34-1.23 (m, 5H), 1.18-1.03 (m, 1H), 0.96-0.84 (m, 5H).

Example 160: N—((S)-2-((5-(1,4-dimethyl-1H-1,2,3-triazol-5-yl)pyridin-2-yl)amino)-1-((1r,4S)-4-methylcyclohexyl)-2-oxoethyl)-3-methylisoxazole-4-carboxamide

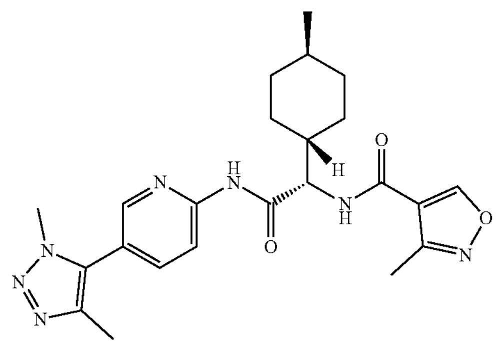 [SMILES: Cc1nocc1C(=O)N[C@H](C(=O)Nc1ccc(-c2c(C)nnn2C)cn1)[C@H]1CC[C@H](C)CC1]

The title compound (35 mg) was prepared from Intermediate 3.125 (63 mg, 0.18 mmol), 3-methylisoxazole-4-carboxylic acid (28 mg, 0.22 mmol, CAS: 17153-20-7), HATU (90 mg, 0.24 mmol) and DIPEA (0.1 mL, 0.55 mmol) in accordance with the procedure described for Example 109. The crude product was purified by flash column chromatography on the Biotage Isolera One™ (10 g silica column, eluting 0-80% MeOH in DCM) and reverse phase chromatography on the Biotage Isolera One™ (30 g Biotage SNAP KP-C18-HS, eluting 5-100% MeCN in water buffer with 0.005 M $NH_4OH$). LCMS (Method 19): 2.35 min, 452.2 $[M+H]^+$; $^1H$ NMR (400 MHz, DMSO-$d_6$) δ: 10.90 (s, 1H), 9.45 (d, 1H), 8.55-8.38 (m, 2H), 8.26 (dd, 1H), 7.95 (dd, 1H), 4.58 (t, 1H), 3.95 (s, 3H), 2.37 (d, 3H), 2.24 (s, 3H), 1.89-1.82 (m, 1H), 1.82-1.66 (m, 3H), 1.64-1.57 (m, 1H), 1.33-1.19 (m, 2H), 1.18-1.03 (m, 1H), 0.95-0.81 (m, 5H).

Example 161: (S)—N-(1-cycloheptyl-2-((5-(1-cyclopropyl-4-methyl-1H-1,2,3-triazol-5-yl)pyridin-2-yl)amino)-2-oxoethyl)-1-methyl-1H-pyrazole-5-carboxamide

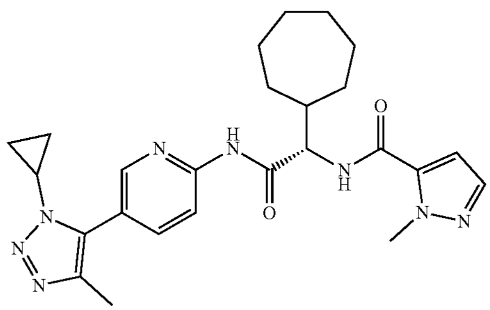 [SMILES: Cc1nnn(C2CC2)c1-c1ccc(NC(=O)[C@@H](NC(=O)c2ccnn2C)C2CCCCCC2)nc1]

The title compound (11 mg) was prepared from Intermediate 3.161 (12 mg, 0.03 mmol), 2-methylpyrazole-3-carboxylic acid (5 mg, 0.04 mmol, CAS: 16034-46-1), HATU (14 mg, 0.04 mmol) and DIPEA (0.02 mL, 0.10 mmol) in accordance with the procedure described for Example 109. The crude product was purified by flash column chromatography on the Biotage Isolera One™ (10 g silica column, eluting 0-100% EtOAc in heptanes) and reverse phase preparative HPLC (Method 2). LCMS (Method 15): 2.47 min, 477.2 $[M+H]^+$; $^1$H NMR (400 MHz, DMSO-$d_6$) δ: 10.91 (s, 1H), 8.55-8.47 (m, 2H), 8.26 (dd, 1H), 8.02 (dd, 1H), 7.48 (d, 1H), 7.05 (d, 1H), 4.65 (t, 1H), 4.03 (s, 3H), 3.80 (tt, 1H), 2.24 (s, 3H), 2.13 (s, 1H), 1.80-1.64 (m, 4H), 1.53 (s, 3H), 1.42 (d, 5H), 1.09-0.96 (m, 4H).

Example 162: (S)—N-(1-cycloheptyl-2-((5-(3,5-dimethylisoxazol-4-yl)-3-fluoropyridin-2-yl)amino)-2-oxoethyl)-1-methyl-1H-pyrazole-5-carboxamide

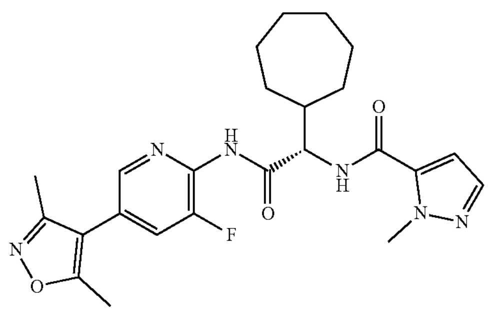 [SMILES: Cc1noc(C)c1-c1cnc(NC(=O)[C@@H](NC(=O)c2ccnn2C)C2CCCCCC2)c(F)c1]

The title compound (15 mg) was prepared from Intermediate 3.162 (30 mg, 0.08 mmol), 2-methylpyrazole-3-carboxylic acid (13 mg, 0.1 mmol, CAS: 16034-46-1), HATU (44 mg, 0.12 mmol) and DIPEA (0.04 mL, 0.25 mmol) in accordance with the procedure described for Example 109. The crude product was purified by flash column chromatography on the Biotage Isolera One™ (5 g silica column, eluting 0-2% MeOH in DCM) and reverse phase preparative HPLC (Method 2). LCMS (Method 15): 2.48 min, 469.2 $[M+H]^+$; $^1$H NMR (400 MHz, DMSO-$d_6$) δ: 10.62 (br s, 1H), 8.46 (d, 1H), 8.31 (dd, 1H), 7.90 (dd, 1H), 7.46 (d 1H), 7.04 (d, 1H), 4.65 (t, 1H), 4.04 (s, 3H), 2.44 (s, 3H), 2.26 (s, 3H), 2.12 (m, 1H), 1.82-1.73 (m, 2H), 1.72-1.62 (m, 2H), 1.60-1.38 (m, 8H).

Example 163: (S)—N-(1-cycloheptyl-2-((5-(3,5-dimethylisoxazol-4-yl)-3-fluoropyridin-2-yl)amino)-2-oxoethyl)-1-ethyl-1H-pyrazole-5-carboxamide

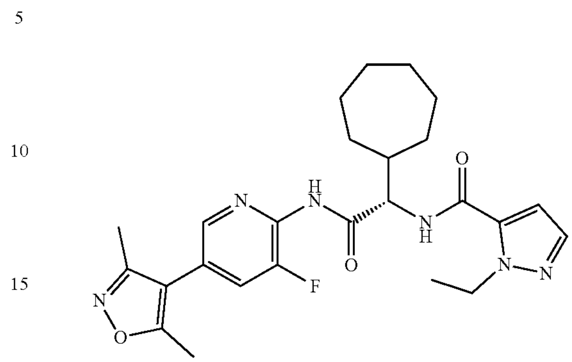

The title compound (5 mg) was prepared from Intermediate 3.162 (30 mg, 0.08 mmol), 2-ethylpyrazole-3-carboxylic acid (13 mg, 0.09 mmol, CAS: 400755-43-3), HATU (44 mg, 0.12 mmol) and DIPEA (0.04 mL, 0.25 mmol) in accordance with the procedure described for Example 109. The crude product was purified by flash column chromatography on the Biotage Isolera One™ (4 g silica column, eluting 0-2% MeOH in DCM) and reverse phase preparative HPLC (Method 2). LCMS (Method 15): 2.60 min, 483.2 $[M+H]^+$; $^1$H NMR (400 MHz, DMSO-$d_6$) δ: 10.61 (br s, 1H), 8.46 (d, 1H), 8.30 (dd, 1H), 7.90 (dd, 1H), 7.48 (d, 1H), 6.99 (d, 1H), 4.65 (t, 1H), 4.47 (q, 2H), 2.44 (s, 3H), 2.26 (s, 3H), 2.14 (s, 1H), 1.76 (m, 2H), 1.68 (m, 2H), 1.58-1.38 (m, 8H), 1.29 (t, 3H).

Example 164: (S)—N-(1-cycloheptyl-2-((5-(3,5-dimethylisoxazol-4-yl)-3-fluoropyridin-2-yl)amino)-2-oxoethyl)-3-ethylisoxazole-4-carboxamide

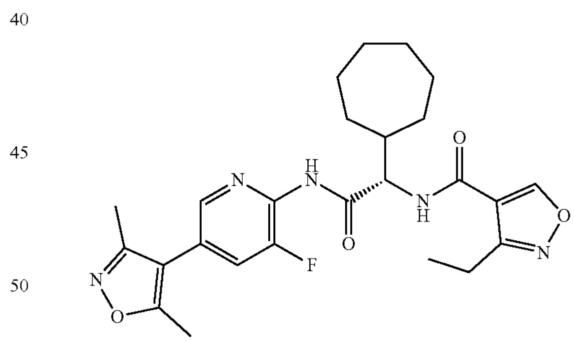

The title compound (16 mg) was prepared from Intermediate 3.162 (30 mg, 0.08 mmol), 3-ethylisoxazole-4-carboxylic acid (13 mg, 0.09 mmol, CAS: 639523-12-9), HATU (44 mg, 0.12 mmol) and DIPEA (0.04 mL, 0.25 mmol) in accordance with the procedure described for Example 109. The crude product was purified by flash column chromatography on the Biotage Isolera One™ (4 g silica column, eluting 0-2% MeOH in DCM) and reverse phase preparative HPLC (Method 2). LCMS (Method 15): 2.65 min, 484.2 $[M+H]^+$; $^1$H NMR (400 MHz, DMSO-$d_6$) δ: 10.61 (brs, 1H), 9.40 (d, 1H), 8.43 (d, 1H), 8.31 (dd, 1H), 7.90 (dd, 1H), 4.68 (t, 1H), 2.85 (q, 2H), 2.44 (s, 3H), 2.26 (s, 3H), 2.10 (m, 1H), 1.82-1.73 (m, 2H), 1.67 (s, 2H), 1.58-1.37 (m, 8H), 1.18 (t, 3H).

Example 165: (S)—N-(1-cycloheptyl-2-((5-(1,4-dimethyl-1H-pyrazol-5-yl)pyrimidin-2-yl)amino)-2-oxoethyl)-1-methyl-1H-pyrazole-5-carboxamide

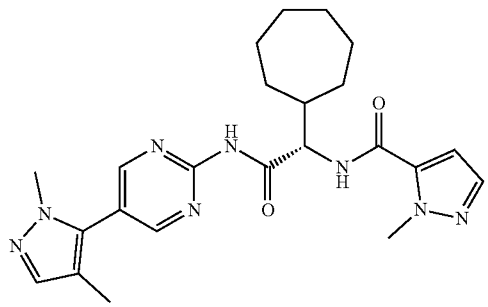 [SMILES: Cc1cnn(C)c1-c1cnc(NC(=O)[C@@H](NC(=O)c2ccnn2C)C2CCCCCC2)nc1]

To a stirred solution of Intermediate 3.165 (52 mg, 0.15 mmol) and 2-methylpyrazole-3-carboxylic acid (24 mg, 0.19 mmol, CAS: 16034-46-1) in DCM (2 mL) at rt was added DIPEA (0.1 mL, 0.57 mmol) and T3P® (50% w/w solution in EtOAc; 0.13 mL, 0.21 mmol) and the reaction mixture stirred at rt for 1.5 h. The reaction mixture was diluted with saturated aqueous $NaHCO_3$ and the crude product was extracted into EtOAc. The combined organics were washed with brine, dried over $Na_2SO_4$, filtered and concentrated in vacuo. The crude product was purified by reverse phase column chromatography on the Biotage Isolera One™ (12 g silica column, eluting 0-3% 2 M methanolic ammonia in DCM) to afford the title compound (34 mg). LCMS (Method 15): 2.29 min, 451.2 $[M+H]^+$; 1H NMR (400 MHz, DMSO-$d_6$) δ: 11.01 (s, 1H), 8.77 (s, 2H), 8.47 (d, 1H), 7.47 (d, 1H), 7.38 (d, 1H), 7.03 (d, 1H), 4.69 (t, 1H), 4.02 (s, 3H), 3.76 (s, 3H), 2.14 (d, 1H), 1.99 (d, 3H), 1.80-1.60 (m, 4H), 1.60-1.31 (m, 8H).

Example 166: (S)—N-(1-cycloheptyl-2-((5-(4-hydroxy-1-methyl-1H-pyrazol-5-yl)pyridin-2-yl)amino)-2-oxoethyl)-1-methyl-1H-pyrazole-5-carboxamide

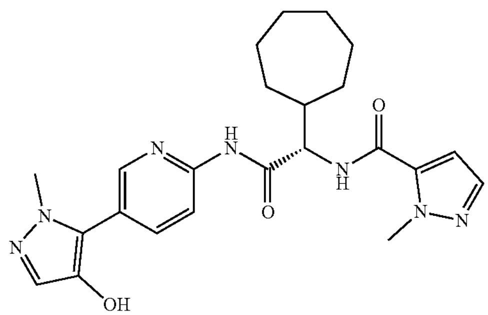 [SMILES: Cn1nccc1C(=O)N[C@H](C(=O)Nc1ccc(-c2c(O)cnn2C)cn1)C1CCCCCC1]

The title compound (3.1 mg) was prepared from Intermediate 3.166 (21 mg, 0.06 mmol), 2-methylpyrazole-3-carboxylic acid (8.5 mg, 0.075 mmol, CAS16034-46-1), HATU (26 mg, 0.07 mmol) and DIPEA (0.03 mL, 0.18 mmol) in accordance with the procedure described for Example 109. The crude product was purified by flash column chromatography on the Biotage Isolera One™ (10 g silica column, eluting 0-100% EtOAc in heptanes). The product was dissolved in EtOH and NaOH (0.5 mL, 1 mmol) was added, and the mixture stirred at rt for 1 h. The product was extracted with EtOAc, and the organics dried over $Na_2SO_4$, filtered and concentrated in vacuo. The product was further purified by reverse phase preparative HPLC (Method 2). LCMS (Method 15): 2.23 min, 452.2 $[M+H]^+$; $^1H$ NMR (400 MHz, DMSO-$d_6$) δ: 10.78 (s, 1H), 8.64 (d, 1H), 8.52-8.43 (m, 2H), 8.19 (d, 1H), 7.91 (dd, 1H), 7.48 (d, 1H), 7.13 (d, 1H), 7.05 (d, 1H), 4.64 (t, 1H), 4.03 (d, 3H), 3.75 (d, 3H), 2.13 (s, 1H), 1.70 (d, 4H), 1.52 (s, 4H), 1.41 (d, 4H).

Example 167: N—((S)-2-((5-(1,4-dimethyl-1H-pyrazol-5-yl)pyridin-2-yl)amino)-1-((1r,4S)-4-methylcyclohexyl)-2-oxoethyl)-1-methyl-1H-1,2,3-triazole-5-carboxamide

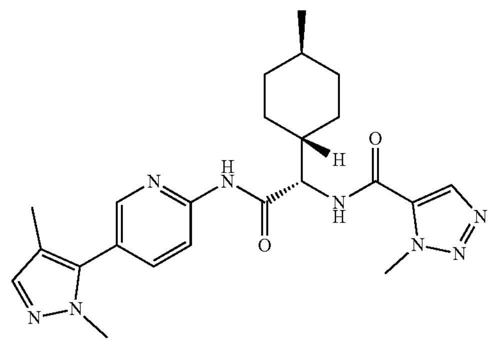 [SMILES: Cc1cnn(C)c1-c1ccc(NC(=O)[C@@H](NC(=O)c2cnnn2C)[C@H]2CC[C@H](C)CC2)nc1]

The title compound (43 mg) was prepared from Intermediate 3.106 (58 mg, 0.17 mmol) 3-methyltriazole-4-carboxylic acid (27 mg, 0.21 mmol, CAS: 716361-91-0), T3P® (50% w/w solution in EtOAc; 0.14 mL, 0.24 mmol) and DIPEA (0.09 mL, 0.51 mmol) in accordance with the procedure described for Example 165. The crude product was purified by reverse phase preparative HPLC (Method 2), further purification by reverse phase preparative HPLC (Method 3), an SCX cartridge (1 g, washed with MeOH and eluted with 2 M methanolic ammonia) and reverse phase preparative HPLC (Method 2). LCMS (Method 19): 2.40 min, 451.2 $[M+H]^+$; $^1H$ NMR (400 MHz, DMSO-$d_6$) δ: 10.89 (s, 1H), 8.85 (d, 1H), 8.43-8.36 (m, 2H), 8.22 (dd, 1H), 7.86 (dd, 1H), 7.35 (d, 1H), 4.61 (t, 1H), 4.19 (s, 3H), 3.72 (s, 3H), 1.97 (d, 3H), 1.89-1.75 (m, 2H), 1.75-1.66 (m, 2H), 1.61 (d, 1H), 1.36-1.21 (m, 2H), 1.10 (q, 1H), 0.87 (t, 5H).

Example 168: N—((S)-2-((5-(1,4-dimethyl-1H-pyrazol-5-yl)pyridin-2-yl)amino)-1-((1r,4S)-4-methylcyclohexyl)-2-oxoethyl)-1-ethyl-1H-1,2,3-triazole-5-carboxamide

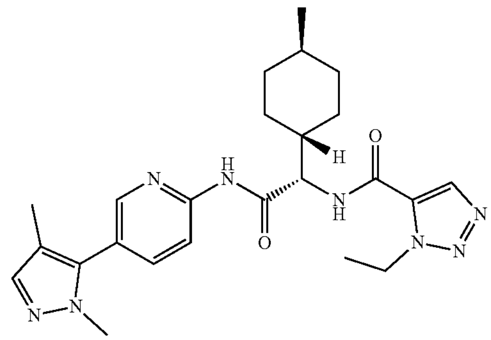 [SMILES: CCn1nncc1C(=O)N[C@H](C(=O)Nc1ccc(-c2c(C)cnn2C)cn1)[C@H]1CC[C@H](C)CC1]

The title compound (43 mg) was prepared from Intermediate 3.106 (58 mg, 0.17 mmol), 3-ethyltriazole-4-carboxylic acid (30 mg, 0.21 mmol, CAS: 860751-24-2), T3P® (50% w/w solution in EtOAc; 0.14 mL, 0.24 mmol) and DIPEA (0.09 mL, 0.51 mmol) in accordance with the procedure described for Example 165. The crude product was purified by reverse phase preparative HPLC (Method 2). LCMS (Method 15): 2.53 min, 465.2 $[M+H]^+$; $^1H$ NMR (400 MHz, DMSO-$d_6$) δ: 10.89 (s, 1H), 8.88 (d, 1H), 8.41-8.36 (m, 2H), 8.22 (dd, 1H), 7.87 (dd, 1H), 7.35 (d, 1H), 4.69-4.56 (m, 3H), 3.72 (s, 3H), 1.97 (d, 3H), 1.89-1.75 (m, 2H), 1.70 (d, 2H), 1.61 (d, 1H), 1.36 (t, 3H), 1.29 (s, 2H), 1.10 (q, 1H), 0.86 (d, 5H).

Example 169: (S)—N-(1-cycloheptyl-2-((6-(3,5-dimethylisoxazol-4-yl)pyridin-3-yl)amino)-2-oxoethyl)-1-ethyl-1H-pyrazole-5-carboxamide

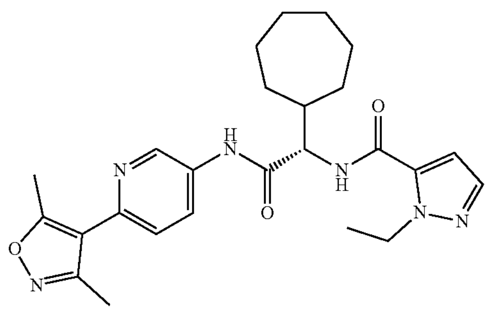 [SMILES: CCn1nccc1C(=O)N[C@H](C(=O)Nc1ccc(-c2c(C)noc2C)nc1)C1CCCCCC1]

The title compound (22 mg) was prepared from Intermediate 3.169 (77 mg, 0.22 mmol), 2-ethylpyrazole-3-carboxylic acid (40 mg, 0.28 mmol, CAS: 400755-43-3), T3P® (50% w/w solution in EtOAc; 0.19 mL, 0.31 mmol) and DIPEA (0.12 mL, 0.67 mmol) in accordance with the procedure described for Example 165. Further portions of 2-ethylpyrazole-3-carboxylic acid (20 mg, 0.14 mmol, CAS: 400755-43-3) and T3P® (50% w/w solution in EtOAc; 0.09 mL, 0.15 mmol) were added, and the reaction stirred at rt for a further 4 h. The crude product was purified by flash column chromatography on the Biotage Isolera One™ (5 g silica column, eluting 0-5% MeOH in DCM). LCMS (Method 19): 2.56 min, 465.2 $[M+H]^+$; $^1H$ NMR (400 MHz, MeOD) δ: 8.86 (dd, 1H), 8.22 (dd, 1H), 7.53-7.46 (m, 2H), 6.87 (d, 1H), 4.61-4.44 (m, 3H), 2.52 (s, 3H), 2.36 (s, 3H), 2.24-2.10 (m, 1H), 1.93-1.72 (m, 4H), 1.70-1.43 (m, 8H), 1.43-1.33 (m, 3H).

Example 170: (S)—N-(1-cycloheptyl-2-((6-(3,5-dimethylisoxazol-4-yl)pyridin-3-yl)amino)-2-oxoethyl)-3-methylisoxazole-4-carboxamide

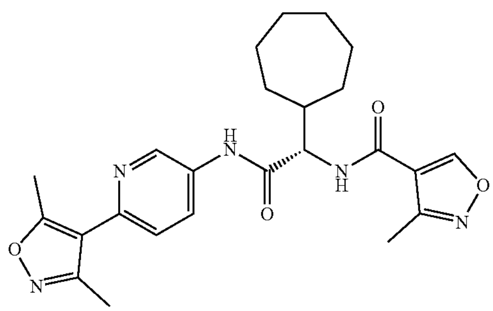 [SMILES: Cc1nocc1C(=O)N[C@H](C(=O)Nc1ccc(-c2c(C)noc2C)nc1)C1CCCCCC1]

The title compound (26 mg) was prepared from Intermediate 3.169 (77 mg, 0.22 mmol), 3-methylisoxazole-4-carboxylic acid (40 mg, 0.28 mmol, CAS: 17153-20-7), T3P® (50% w/w solution in EtOAc; 0.19 mL, 0.31 mmol) and DIPEA (0.12 mL, 0.67 mmol) in accordance with the procedure described for Example 165. The crude product was purified by flash column chromatography on the Biotage Isolera One™ (5 g silica column, eluting 0-5% MeOH in DCM) and trituration in MeOH. LCMS (Method 19): 2.49 min, 452.2 $[M+H]^+$; $^1H$ NMR (400 MHz, MeOD) δ: 9.15 (q, 1H), 8.86 (dd, 1H), 8.21 (dd, 1H), 7.49 (dd, 1H), 4.56 (d, 1H), 2.52 (s, 3H), 2.44 (d, 3H), 2.36 (s, 3H), 2.21-2.09 (m, 1H), 1.91-1.40 (m, 12H).

Example 171: (S)—N-(1-cycloheptyl-2-((6-(3,5-dimethylisoxazol-4-yl)pyridin-3-yl)amino)-2-oxoethyl)-3-ethylisoxazole-4-carboxamide

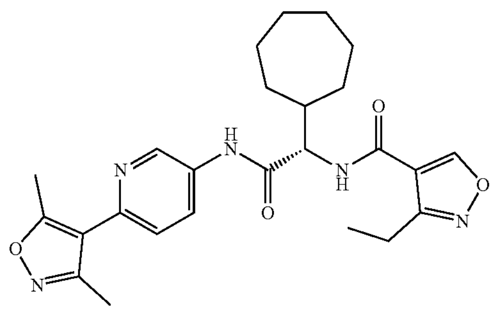 [SMILES: CCc1nocc1C(=O)N[C@H](C(=O)Nc1ccc(-c2c(C)noc2C)nc1)C1CCCCCC1]

The title compound (13 mg) was prepared from Intermediate 3.169 (67 mg, 0.2 mmol), 3-ethylisoxazole-4-carboxylic acid (35 mg, 0.24 mmol, CAS: 639523-12-9), T3P® (50% w/w solution in EtOAc; 0.16 mL, 0.27 mmol) and DIPEA (0.1 mL, 0.59 mmol) in accordance with the procedure described for Example 165. The crude product was purified by flash column chromatography on the Biotage Isolera One™ (5 g silica column, eluting 0-5% MeOH in DCM) and trituration in MeOH. LCMS (Method 19): 2.61 min, 466.2 $[M+H]^+$; $^1H$ NMR (400 MHz, MeOD) δ: 9.12 (d, 1H), 8.86 (dd, 1H), 8.21 (dd, 1H), 7.49 (dd, 1H), 4.56 (d, 1H), 2.92 (qt, 2H), 2.52 (s, 3H), 2.36 (s, 3H), 2.21-2.13 (m, 1H), 1.90-1.84 (m, 1H), 1.78 (dd, 3H), 1.69-1.42 (m, 8H), 1.26 (t, 3H).

Example 172: (S)—N-(1-cycloheptyl-2-((6-(3,5-dimethylisoxazol-4-yl)pyridin-3-yl)amino)-2-oxoethyl)-1-methyl-1H-pyrazole-5-carboxamide

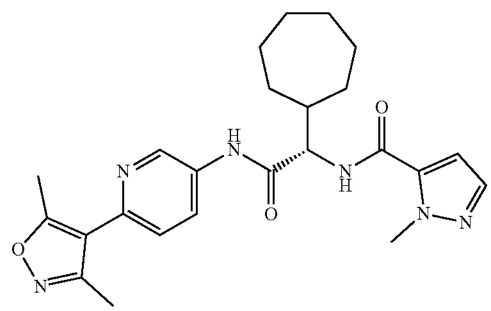 [SMILES: Cc1noc(C)c1-c1ccc(NC(=O)[C@@H](NC(=O)c2ccnn2C)C2CCCCCC2)cn1]

The title compound (13 mg) was prepared from Intermediate 3.169 (77 mg, 0.22 mmol), 2-methylpyrazole-3-carboxylic acid (36 mg, 0.28 mmol, CAS: 16034-46-1), T3P® (50% w/w solution in EtOAc; 0.19 mL, 0.31 mmol) and DIPEA (0.12 mL, 0.67 mmol) in accordance with the procedure described for Example 165. The crude product was purified by flash column chromatography on the Biotage Isolera One™ (5 g silica column, eluting 0-5% MeOH in DCM) and trituration in MeOH. LCMS (Method 19): 2.46 min, 451.2 $[M+H]^+$; $^1H$ NMR (400 MHz, MeOD) δ: 8.86 (dd, 1H), 8.22 (dd, 1H), 7.53-7.45 (m, 2H), 6.90 (d, 1H), 4.57 (d, 1H), 4.09 (s, 3H), 2.52 (s, 3H), 2.36 (s, 3H), 2.22-2.13 (m, 1H), 1.92-1.72 (m, 4H), 1.70-1.40 (m, 8H).

Example 173: (S)—N-(1-cycloheptyl-2-((5-(4-cyclopropyl-1-methyl-1H-1,2,3-triazol-5-yl)pyridin-2-yl)amino)-2-oxoethyl)-1-methyl-1H-pyrazole-5-carboxamide

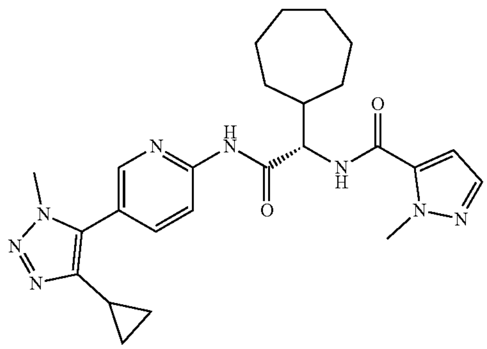 [SMILES: Cn1nccc1C(=O)N[C@H](C(=O)Nc1ccc(-c2c(C3CC3)nnn2C)cn1)C1CCCCCC1]

The title compound (12 mg) was prepared from Intermediate 3.173 (46 mg, 0.12 mmol), 2-methylpyrazole-3-carboxylic acid (19 mg, 0.15 mmol, CAS: 16034-46-1), HATU (57 mg, 0.15 mmol) and DIPEA (0.06 mL, 0.37 mmol) in accordance with the procedure described for Example 109. The crude product was purified by flash column chromatography on the Biotage Isolera One™ (12 g silica column, eluting 2-100% EtOAc in heptanes) and reverse phase preparative HPLC (Method 2). LCMS (Method 15): 2.48 min, 477.2 $[M+H]^+$; $^1H$ NMR (400 MHz, MeOD) δ: 8.47 (dd, 1H), 8.34 (dd, 1H), 7.94 (dd, 1H), 7.48 (d, 1H), 6.90 (d, 1H), 4.66 (d, 1H), 4.09 (s, 3H), 3.98 (s, 3H), 2.20 (td, 1H), 1.90-1.42 (m, 13H), 0.98-0.83 (m, 4H).

Example 174: (S)—N-(2-((5-(4-chloro-1-methyl-1H-pyrazol-5-yl)pyridin-2-yl)amino)-1-cycloheptyl-2-oxoethyl)-1-methyl-1H-pyrazole-5-carboxamide

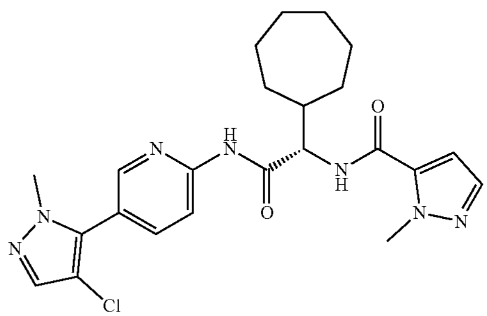 [SMILES: Cn1nccc1C(=O)N[C@H](C(=O)Nc1ccc(-c2c(Cl)cnn2C)cn1)C1CCCCCC1]

The title compound (29 mg) was prepared from Intermediate 3.174 (70 mg, 0.16 mmol), 2-methylpyrazole-3-carboxylic acid (25 mg, 0.2 mmol, CAS: 16034-46-1), T3P® (50% w/w solution in EtOAc; 0.13 mL, 0.22 mmol) and DIPEA (0.08 mL, 0.48 mmol) in accordance with the procedure described for Example 165. The crude product was purified by reverse phase preparative HPLC (Method 3) and further purification by reverse phase preparative HPLC (Method 2). LCMS (Method 15): 2.65 min, 470.2 $[M+H]^+$; $^1H$ NMR (400 MHz, MeOD) δ: 8.42 (dd, 1H), 8.31 (dd, 1H), 7.90 (dd, 1H), 7.56 (s, 1H), 7.48 (d, 1H), 6.90 (d, 1H), 4.66 (d, 1H), 4.09 (s, 3H), 3.82 (s, 3H), 2.25-2.15 (m, 1H), 1.92-1.72 (m, 4H), 1.69-1.41 (m, 8H).

Example 175: (S)—N-(2-((5-(4-chloro-1-methyl-1H-pyrazol-5-yl)pyridin-2-yl)amino)-1-cycloheptyl-2-oxoethyl)-3-ethylisoxazole-4-carboxamide

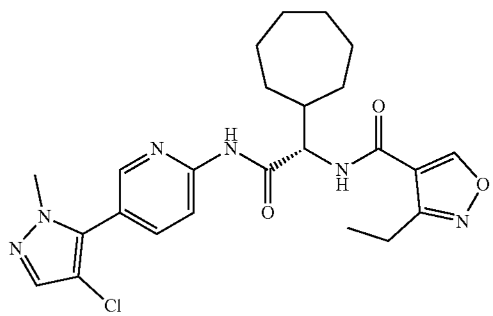 [SMILES: CCc1nocc1C(=O)N[C@H](C(=O)Nc1ccc(-c2c(Cl)cnn2C)cn1)C1CCCCCC1]

The title compound (16 mg) was prepared from Intermediate 3.174 (70 mg, 0.16 mmol), 3-ethylisoxazole-4-carboxylic acid (28 mg, 0.2 mmol, CAS: 639523-12-9), T3P® (50% w/w solution in EtOAc; 0.13 mL, 0.22 mmol) and DIPEA (0.08 mL, 0.48 mmol) in accordance with the procedure described for Example 165. The crude product was purified by reverse phase preparative HPLC (Method 3) and further purification by reverse phase preparative HPLC (Method 2). LCMS (Method 15): 2.81 min, 485.2 $[M+H]^+$; $^1H$ NMR (400 MHz, MeOD) δ: 9.13 (s, 1H), 8.42 (dd, 1H), 8.31 (dd, 1H), 7.90 (dd, 1H), 7.56 (s, 1H), 4.65 (d, 1H), 3.82 (s, 3H), 2.91 (q, 2H), 2.25-2.10 (m, 1H), 1.91-1.70 (m, 4H), 1.68-1.41 (m, 8H), 1.26 (t, 3H).

Example 176: (S)—N-(2-((5-(4-chloro-1-methyl-1H-pyrazol-5-yl)pyridin-2-yl)amino)-1-cycloheptyl-2-oxoethyl)-1-ethyl-1H-pyrazole-5-carboxamide

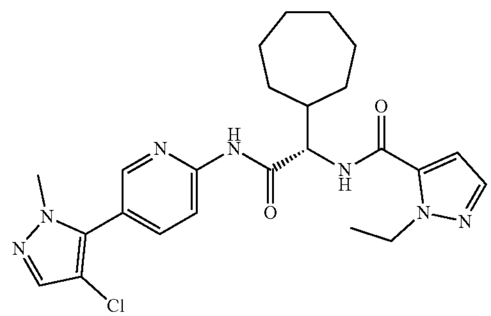 [SMILES: CCn1nccc1C(=O)N[C@H](C(=O)Nc1ccc(-c2c(Cl)cnn2C)cn1)C1CCCCCC1]

The title compound (22 mg) was prepared from Intermediate 3.174 (70 mg, 0.16 mmol), 2-ethylpyrazole-3-carboxylic acid (28 mg, 0.2 mmol, CAS: 400755-43-3), T3P® (50% w/w solution in EtOAc; 0.13 mL, 0.22 mmol) and DIPEA (0.08 mL, 0.48 mmol) in accordance with the procedure described for Example 165. The crude product was purified by reverse phase preparative HPLC (Method 2). LCMS (Method 15): 2.77 min, 484.2 $[M+H]^+$; $^1$H NMR (400 MHz, MeOD) δ: 8.43 (dd, 1H), 8.32 (dd, 1H), 7.90 (dd, 1H), 7.57 (s, 1H), 7.50 (d, 1H), 6.88 (d, 1H), 4.66 (d, 1H), 4.53 (qd, 2H), 3.82 (s, 3H), 2.27-2.15 (m, 1H), 1.92-1.70 (m, 4H), 1.68-1.44 (m, 8H), 1.37 (t, 3H).

Example 177: (S)—N-(1-cyclohexyl-2-((5-(1,4-dimethyl-1H-pyrazol-5-yl)pyridin-2-yl)amino)-2-oxoethyl)-1-methyl-1H-pyrazole-5-carboxamide

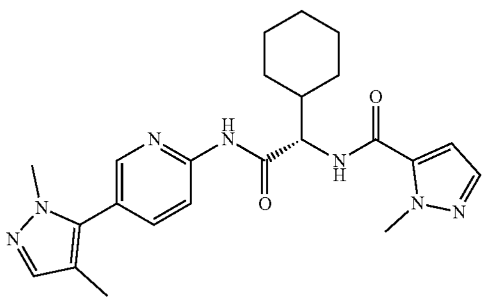 [SMILES: Cc1cnn(C)c1-c1ccc(NC(=O)[C@@H](NC(=O)c2ccnn2C)C2CCCCC2)nc1]

The title compound (47 mg) was prepared from Intermediate 3.177 (65 mg, 0.2 mmol), 2-methylpyrazole-3-carboxylic acid (31 mg, 0.25 mmol, CAS: 16034-46-1), T3P® (50% w/w solution in EtOAc; 0.24 mL, 0.4 mmol) and DIPEA (0.1 mL, 0.6 mmol) in accordance with the procedure described for Example 165. The crude product was purified by flash column chromatography on the Biotage Isolera One™ (4 g silica column eluting 0-70% EtOAc in heptanes). LCMS (Method 15): 2.39 min, 436.2 $[M+H]^+$; $^1$H NMR (400 MHz, MeOD) δ: 8.36-8.26 (m, 2H), 7.81 (dd, 1H), 7.48 (d, 1H), 7.39 (d, 1H), 6.91 (d, 1H), 4.57 (d, 1H), 4.09 (s, 3H), 3.75 (s, 3H), 2.02 (d, 3H), 2.00-1.67 (m, 6H), 1.41-1.13 (m, 5H).

Example 178: (S)—N-(1-cyclohexyl-2-((5-(1,4-dimethyl-1H-pyrazol-5-yl)pyridin-2-yl)amino)-2-oxoethyl)-3-ethylisoxazole-4-carboxamide

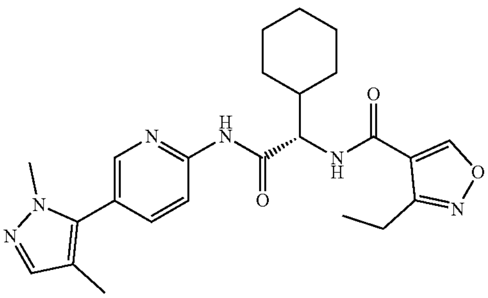 [SMILES: CCc1nocc1C(=O)N[C@H](C(=O)Nc1ccc(-c2c(C)cnn2C)cn1)C1CCCCC1]

The title compound (43 mg) was prepared from Intermediate 3.177 (65 mg, 0.2 mmol), 3-ethylisoxazole-4-carboxylic acid (35 mg, 0.25 mmol, CAS: 639523-12-9), T3P® (50% w/w solution in EtOAc; 0.24 mL, 0.4 mmol) and DIPEA (0.1 mL, 0.6 mmol) in accordance with the procedure described for Example 165. The crude product was purified by flash column chromatography on the Biotage Isolera One™ (4 g silica column eluting 0-60% EtOAc in heptanes). LCMS (Method 15): 2.55 min, 451.2 $[M+H]^+$; $^1$H NMR (400 MHz, MeOD) δ: 9.14 (s, 1H), 8.33 (dd, 1H), 8.29 (dd, 1H), 7.81 (dd, 1H), 7.39 (d, 1H), 4.56 (d, 1H), 3.75 (s, 3H), 2.97-2.86 (m, 2H), 2.02 (d, 3H), 1.96-1.67 (m, 6H), 1.26 (t, 8H).

Example 179: N—((S)-2-((6-(1,4-dimethyl-1H-pyrazol-5-yl)-5-fluoropyridin-3-yl)amino)-1-((1r, 4S)-4-methylcyclohexyl)-2-oxoethyl)-1-methyl-1H-pyrazole-5-carboxamide

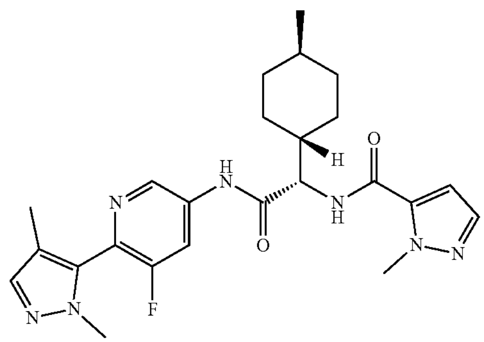 [SMILES: Cc1cnn(C)c1-c1ncc(NC(=O)[C@@H](NC(=O)c2ccnn2C)[C@H]2CC[C@H](C)CC2)cc1F]

The title compound (24 mg) was prepared from Intermediate 3.179 (80 mg, 0.22 mmol), 2-methylpyrazole-3-carboxylic acid (34 mg, 0.27 mmol, CAS: 16034-46-1), T3P® (50% w/w solution in EtOAc; 0.18 mL, 0.3 mmol) and DIPEA (0.11 mL, 0.65 mmol) in accordance with the procedure described for Example 165. The crude product was purified by flash column chromatography on the Biotage Isolera One™ (4 g silica column eluting 0-5% MeOH in DCM) and reverse phase preparative HPLC (Method 2). LCMS (Method 15): 2.57 min, 468.2 $[M+H]^+$; $^1$H NMR (400 MHz, DMSO-$d_6$) δ: 10.91 (s, 1H), 8.73 (t, 1H), 8.64 (d, 1H), 8.26 (dd, 1H), 7.47 (d, 1H), 7.35 (d, 1H), 7.07 (d, 1H), 4.38 (t, 1H), 4.03 (s, 3H), 3.72 (s, 3H), 1.94 (dd, 3H), 1.87 (t, 2H), 1.71 (d, 2H), 1.61 (d, 1H), 1.30 (s, 1H), 1.22 (d, 1H), 1.06 (d, 1H), 0.87 (d, 5H).

Example 180: N—((S)-2-((6-(1,4-dimethyl-1H-pyrazol-5-yl)-5-fluoropyridin-3-yl)amino)-1-((1r, 4S)-4-methylcyclohexyl)-2-oxoethyl)-3-ethylisoxazole-4-carboxamide

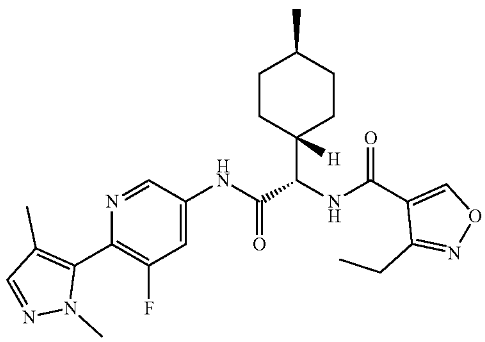 [SMILES: CCc1nocc1C(=O)N[C@H](C(=O)Nc1cnc(-c2c(C)cnn2C)c(F)c1)[C@H]1CC[C@H](C)CC1]

The title compound (39 mg) was prepared from Intermediate 3.179 (80 mg, 0.22 mmol), 3-ethylisoxazole-4-carboxylic acid (38 mg, 0.27 mmol, CAS: 639523-12-9), T3P® (50% w/w solution in EtOAc; 0.18 mL, 0.3 mmol) and DIPEA (0.11 mL, 0.65 mmol) in accordance with the procedure described for Example 165. The crude product was purified by flash column chromatography on the Biotage Isolera One™ (4 g silica column eluting 0-5% MeOH in DCM) and reverse phase preparative HPLC (Method 2). LCMS (Method 15): 2.72 min, 483.2 $[M+H]^+$; $^1H$ NMR (400 MHz, DMSO-$d_6$) δ: 10.89 (s, 1H), 9.42 (s, 1H), 8.73 (t, 1H), 8.61 (d, 1H), 8.25 (dd, 1H), 7.35 (d, 1H), 4.41 (s, 1H), 3.72 (s, 3H), 2.83 (q, 2H), 1.94 (d, 3H), 1.88 (d, 1H), 1.72 (s, 3H), 1.61 (d, 1H), 1.31 (s, 1H), 1.17 (t, 4H), 1.08 (d, 1H), 0.96-0.83 (m, 5H).

Example 181: (S)—N-(1-cyclohexyl-2-((5-(1,4-dimethyl-1H-pyrazol-5-yl)pyridin-2-yl)amino)-2-oxoethyl)-3-methylisoxazole-4-carboxamide

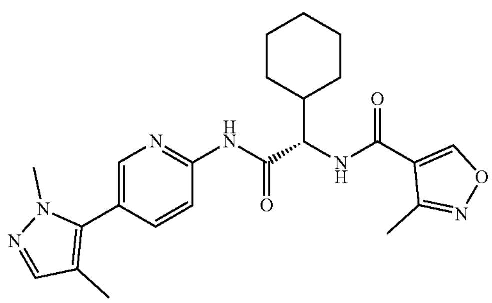 [SMILES: Cc1cnn(C)c1-c1ccc(NC(=O)[C@@H](NC(=O)c2conc2C)C2CCCCC2)nc1]

The title compound (42 mg) was prepared from Intermediate 3.177 (65 mg, 0.2 mmol), 3-methylisoxazole-4-carboxylic acid (35 mg, 0.25 mmol, CAS: 17153-20-7), T3P® (50% w/w solution in EtOAc; 0.24 mL, 0.4 mmol) and DIPEA (0.1 mL, 0.6 mmol) in accordance with the procedure described for Example 165. The crude product was purified by flash column chromatography on the Biotage Isolera One™ (4 g silica column eluting 0-60% EtOAc in heptanes). LCMS (Method 15): 2.45 min, 437.2 $[M+H]^+$; $^1H$ NMR (400 MHz, MeOD) δ: 9.16 (q, 1H), 8.33 (dd, 1H), 8.29 (dd, 1H), 7.81 (dd, 1H), 7.39 (d, 1H), 4.56 (d, 1H), 3.75 (s, 3H), 2.44 (d, 3H), 2.02 (d, 3H), 1.96-1.66 (m, 6H), 1.37-1.17 (m, 5H).

Example 182: (S)—N-(1-cycloheptyl-2-((5-(4-(hydroxymethyl)-1-methyl-1H-pyrazol-5-yl)pyridin-2-yl)amino)-2-oxoethyl)-1-methyl-1H-pyrazole-5-carboxamide

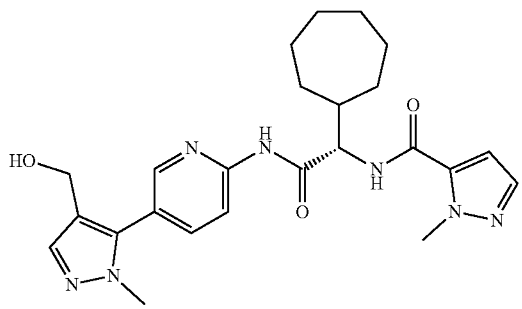 [SMILES: Cn1nccc1C(=O)N[C@H](C(=O)Nc1ccc(-c2c(CO)cnn2C)cn1)C1CCCCCC1]

The title compound (17 mg) was prepared from Intermediate 3.182 (36 mg, 0.1 mmol), 2-methylpyrazole-3-carboxylic acid (15 mg, 0.12 mmol, CAS: 16034-46-1), HATU (46 mg, 0.12 mmol) and DIPEA (0.05 mL, 0.3 mmol) in accordance with the procedure described for Example 109. The crude product was purified by flash column chromatography on the Biotage Isolera One™ (12 g silica column, eluting 0-10% MeOH in DCM) and reverse phase preparative HPLC (Method 2). LCMS (Method 15): 2.19 min, 466.4 $[M+H]^+$; $^1H$ NMR (400 MHz, MeOD) δ: 8.43 (dd, 1H), 8.30 (dd, 1H), 7.90 (dd, 1H), 7.59 (s, 1H), 7.48 (d, 1H), 6.90 (d, 1H), 4.66 (d, 1H), 4.38 (s, 2H), 4.10 (s, 3H), 3.80 (s, 3H), 2.20 (td, 1H), 1.90-1.41 (m, 12H).

Example 183: (S)—N-(1-cyclopentyl-2-((5-(1,4-dimethyl-1H-pyrazol-5-yl)pyridin-2-yl)amino)-2-oxoethyl)-1-methyl-1H-pyrazole-5-carboxamide

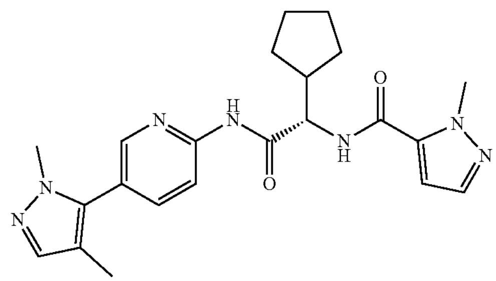 [SMILES: Cc1cnn(C)c1-c1ccc(NC(=O)[C@@H](NC(=O)c2ccnn2C)C2CCCC2)nc1]

The title compound (27 mg) was prepared from Intermediate 3.183 (34 mg, 0.11 mmol), 2-methylpyrazole-3-carboxylic acid (15 mg, 0.12 mmol, CAS: 16034-46-1), HATU (46 mg, 0.12 mmol) and DIPEA (0.04 mL, 0.23 mmol) in accordance with the procedure described for Example 109. The crude product was purified by flash column chromatography on the Teledyne ISCO CombiFlash® (12 g silica column, eluting 0-100% EtOAc in isohexane) and an SCX cartridge (1 g, washed with MeOH and eluted with 0.7 M methanolic ammonia). LCMS (Method 25): 1.90 min, 422.3 $[M+H]^+$; $^1H$ NMR (400 MHz, DMSO-$d_6$) δ: 10.81 (s, 1H), 8.60 (d, 1H), 8.38 (dd, 1H), 8.22 (dd, 1H), 7.87 (dd, 1H), 7.47 (d, 1H), 7.35 (d, 1H), 7.03 (d, 1H), 4.55 (dd, 1H), 4.02 (s, 3H), 3.72 (s, 3H), 2.40-2.31 (m, 1H), 1.97 (s, 3H), 1.90-1.81 (m, 1H), 1.68-1.58 (m, 3H), 1.56-1.47 (m, 3H), 1.35-1.27 (m, 1H).

Example 184: N-(1-(bicyclo[2.2.1]heptan-2-yl)-2-((5-(1,4-dimethyl-1H-pyrazol-5-yl)pyridin-2-yl)amino)-2-oxoethyl)-1-methyl-1H-pyrazole-5-carboxamide

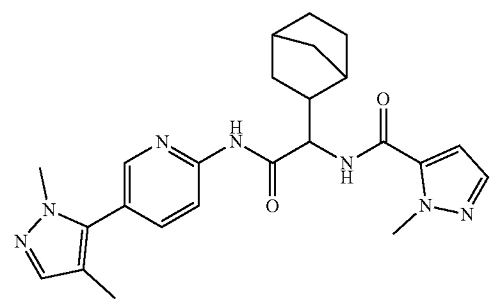 [SMILES: Cc1cnn(C)c1-c1ccc(NC(=O)C(NC(=O)c2ccnn2C)C2CC3CCC2C3)nc1]

The title compound (11 mg) was prepared from Intermediate 3.184 (30 mg, 0.09 mmol), 2-methylpyrazole-3-carboxylic acid (12 mg, 0.1 mmol, CAS: 16034-46-1), HATU (50 mg, 0.13 mmol) and DIPEA (0.03 mL, 0.18 mmol) in accordance with the procedure described for Example 109 in DMF. The crude product was purified by flash column chromatography on the Teledyne ISCO CombiFlash® (12 g silica column, eluting 0-100% EtOAc in isohexane) and an SCX cartridge (1 g, washed with MeOH and eluted with 0.7 M methanolic ammonia). LCMS (Method 27): 1.84 min, 448.3 $[M+H]^+$; $^1H$ NMR (400 MHz, DMSO-$d_6$) δ: 10.91 (s, 1H), 8.73-8.48 (m, 1H), 8.38 (d, 1H), 8.21 (d, 1H), 7.85 (dd, 1H), 7.47 (d, 1H), 7.35 (s, 1H), 7.05 (d, 1H), 4.56 (d, 1H), 4.03 (q, 3H), 3.72 (d, 3H), 2.19 (s, 5H), 1.59-1.03 (m, 9H).

Example 185: N-(2-((5-(1,4-dimethyl-1H-pyrazol-5-yl)pyridin-2-yl)amino)-2-oxo-1-((1r,4r)-4-(trifluoromethyl)cyclohexyl)ethyl)-1-methyl-1H-pyrazole-5-carboxamide

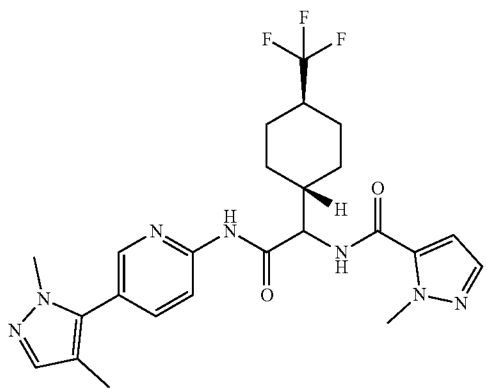 [SMILES: Cc1cnn(C)c1-c1ccc(NC(=O)C(NC(=O)c2ccnn2C)[C@H]2CC[C@H](C(F)(F)F)CC2)nc1]

The title compound (37 mg) was prepared from Intermediate 3.185 (53 mg, 0.13 mmol), 2-methylpyrazole-3-carboxylic acid (21 mg, 0.17 mmol, CAS: 16034-46-1), T3P® (50% w/w solution in EtOAc; 0.11 mL, 0.19 mmol) and DIPEA (0.07 mL, 0.4 mmol) in accordance with the procedure described for Example 165. The crude product was purified by flash column chromatography on the Biotage Isolera One™ (4 g silica column eluting 0-2.5% MeOH in DCM). LCMS (Method 19): 2.45 min, 504.2 $[M+H]^+$; $^1H$ NMR (400 MHz, DMSO-$d_6$) δ: 10.88 (s, 1H), 8.52 (d, 1H), 8.39 (dd, 1H), 8.24 (dd, 1H), 7.88 (dd, 1H), 7.48 (d, 1H), 7.36 (d, 1H), 7.06 (d, 1H), 4.60 (t, 1H), 4.03 (s, 3H), 3.72 (s, 3H), 2.31-2.17 (m, 1H), 2.02-1.82 (m, 7H), 1.79-1.70 (m, 1H), 1.42-1.10 (m, 4H).

Example 186: N-(2-((5-(1,4-dimethyl-1H-pyrazol-5-yl)pyridin-2-yl)amino)-2-oxo-1-((1r,4r)-4-(trifluoromethyl)cyclohexyl)ethyl)-1-ethyl-1H-pyrazole-5-carboxamide

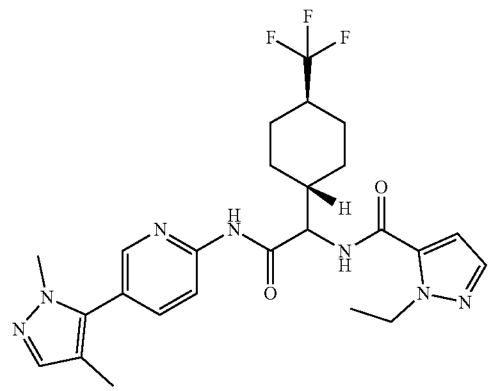 [SMILES: CCn1nccc1C(=O)NC(C(=O)Nc1ccc(-c2c(C)cnn2C)cn1)[C@H]1CC[C@H](C(F)(F)F)CC1]

The title compound (49 mg) was prepared from Intermediate 3.185 (53 mg, 0.13 mmol), 2-ethylpyrazole-3-carboxylic acid (24 mg, 0.17 mmol, CAS: 400755-43-3), T3P® (50% w/w solution in EtOAc; 0.11 mL, 0.19 mmol) and DIPEA (0.07 mL, 0.4 mmol) in accordance with the procedure described for Example 165. The crude product was purified by flash column chromatography on the Biotage Isolera One™ (4 g silica column eluting 0-2.5% MeOH in DCM). LCMS (Method 19): 2.54 min, 518.2 [M+H]1; $^1H$ NMR (400 MHz, DMSO-$d_6$) δ: 10.87 (s, 1H), 8.53 (d, 1H), 8.39 (dd, 1H), 8.24 (dd, 1H), 7.88 (dd, 1H), 7.50 (d, 1H), 7.36 (d, 1H), 7.02 (d, 1H), 4.60 (t, 1H), 4.46 (q, 2H), 3.73 (s, 3H), 2.32-2.15 (m, 1H), 2.00-1.86 (m, 7H), 1.80-1.70 (m, 1H), 1.41-1.14 (m, 7H).

Example 187: N-(2-((5-(1,4-dimethyl-1H-pyrazol-5-yl)pyridin-2-yl)amino)-2-oxo-1-((1r,4r)-4-(trifluoromethyl)cyclohexyl)ethyl)-3-ethylisoxazole-4-carboxamide

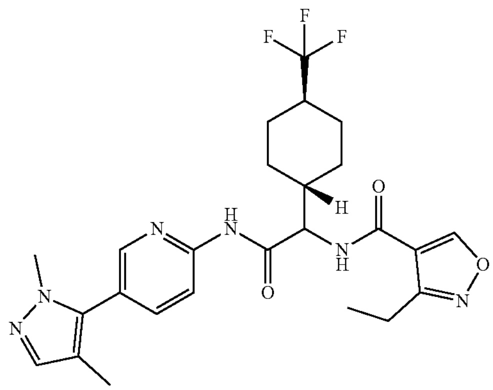 [SMILES: CCc1nocc1C(=O)NC(C(=O)Nc1ccc(-c2c(C)cnn2C)cn1)[C@H]1CC[C@H](C(F)(F)F)CC1]

The title compound (46 mg) was prepared from Intermediate 3.185 (53 mg, 0.13 mmol), 2 3-ethylisoxazole-4-carboxylic acid (24 mg, 0.17 mmol, CAS: 639523-12-9), T3P® (50% w/w solution in EtOAc; 0.11 mL, 0.19 mmol) and DIPEA (0.07 mL, 0.4 mmol) in accordance with the procedure described for Example 165. The crude product was purified by flash column chromatography on the Biotage Isolera One™ (4 g silica column eluting 0-2% MeOH in DCM). LCMS (Method 19): 2.59 min, 519.2 $[M+H]^+$; $^1$H NMR (400 MHz, DMSO-$d_6$) δ: 10.88 (s, 1H), 9.42 (s, 1H), 8.50 (d, 1H), 8.38 (dd, 1H), 8.23 (dd, 1H), 7.87 (dd, 1H), 7.35 (d, 1H), 4.63 (t, 1H), 3.72 (s, 3H), 2.83 (q, 2H), 2.31-2.13 (m, 1H), 2.03-1.68 (m, 8H), 1.39-1.10 (m, 7H).

Example 188: N—((S)-2-((5-(1,4-dimethyl-1H-1,2,3-triazol-5-yl)pyridin-2-yl)amino)-1-((1r,4S)-4-methylcyclohexyl)-2-oxoethyl)-3-ethylisoxazole-4-carboxamide

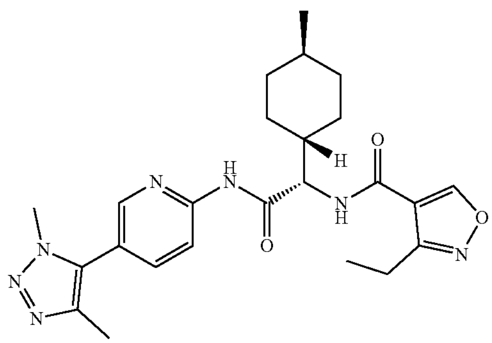 [SMILES: CCc1nocc1C(=O)N[C@H](C(=O)Nc1ccc(-c2c(C)nnn2C)cn1)[C@H]1CC[C@H](C)CC1]

The title compound (46 mg) was prepared from Intermediate 3.125 (50 mg, 0.14 mmol), 3-ethylisoxazole-4-carboxylic acid (25 mg, 0.18 mmol, CAS: 639523-12-9), T3P® (50% w/w solution in EtOAc; 0.12 mL, 0.2 mmol) and DIPEA (0.07 mL, 0.43 mmol) in accordance with the procedure described for Example 165. The crude product was purified by flash column chromatography on the Biotage Isolera One™ (4 g silica column eluting 0-2% MeOH in DCM). LCMS (Method 19): 2.45 min, 466.2 $[M+H]^+$; $^1$H NMR (400 MHz, DMSO-$d_6$) δ: 10.89 (s, 1H), 9.42 (s, 1H), 8.50-8.43 (m, 2H), 8.25 (dd, 1H), 7.95 (dd, 1H), 4.58 (t, 1H), 3.95 (s, 3H), 2.84 (q, 2H), 2.24 (s, 3H), 1.94-1.52 (m, 5H), 1.37-1.04 (m, 6H), 0.96-0.81 (m, 5H).

Example 189: N—((S)-2-((6-(1,4-dimethyl-1H-pyrazol-5-yl)-5-fluoropyridin-3-yl)amino)-1-((1r,4S)-4-methylcyclohexyl)-2-oxoethyl)-1-ethyl-1H-pyrazole-5-carboxamide

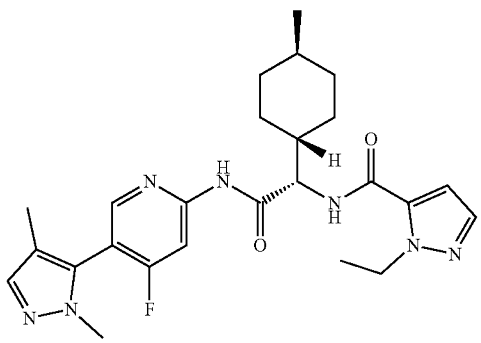 [SMILES: CCn1nccc1C(=O)N[C@H](C(=O)Nc1cc(F)c(-c2c(C)cnn2C)cn1)[C@H]1CC[C@H](C)CC1]

The title compound (21 mg) was prepared from Intermediate 3.179 (80 mg, 0.22 mmol), 2-ethylpyrazole-3-carboxylic acid (38 mg, 0.27 mmol, CAS: 400755-43-3), T3P® (50% w/w solution in EtOAc; 0.18 mL, 0.3 mmol) and DIPEA (0.11 mL, 0.65 mmol) in accordance with the procedure described for Example 165. The crude product was purified by flash column chromatography on the Biotage Isolera One™ (5 g silica column, eluting 0-100% EtOAc in heptanes) and reverse phase preparative HPLC (Method 2). LCMS (Method 15): 2.67 min, 482.2 $[M+H]^+$; $^1$H NMR (400 MHz, DMSO-$d_6$) δ: 10.90 (s, 1H), 8.73 (s, 1H), 8.65 (s, 1H), 8.26 (dd, 1H), 7.49 (d, 1H), 7.35 (d, 1H), 7.03 (d, 1H), 4.46 (q, 2H), 4.38 (s, 1H), 3.72 (s, 3H), 1.94 (dd, 3H), 1.86 (t, 2H), 1.71 (d, 2H), 1.61 (d, 1H), 1.28 (t, 4H), 1.14 (dd, 2H), 0.87 (d, 5H).

Example 190: (S)—N-(1-cycloheptyl-2-((5-(1-(2-(dimethylamino)-2-oxoethyl)-4-methyl-1H-1,2,3-triazol-5-yl)pyridin-2-yl)amino)-2-oxoethyl)-1-methyl-1H-pyrazole-5-carboxamide

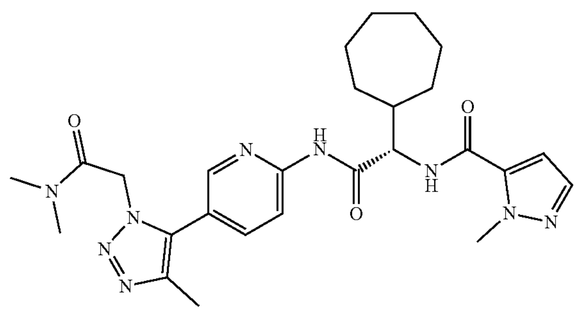 [SMILES: Cc1nnn(CC(=O)N(C)C)c1-c1ccc(NC(=O)[C@@H](NC(=O)c2ccnn2C)C2CCCCCC2)nc1]

The title compound (21 mg) was prepared from Intermediate 3.190 (39 mg, 0.08 mmol), 2-methylpyrazole-3-carboxylic acid (12 mg, 0.1 mmol, CAS: 16034-46-1), T3P® (50% w/w solution in EtOAc; 0.07 mL, 0.11 mmol) and DIPEA (0.04 mL, 0.24 mmol) in accordance with the procedure described for Example 165. The crude product was purified by reverse phase preparative HPLC (Method 2). LCMS (Method 15): 2.26 min, 522.2 $[M+H]^+$; $^1$H NMR (400 MHz, DMSO-$d_6$) δ: 10.88 (s, 1H), 8.49 (s, 1H), 8.33 (d, 1H), 8.19 (d, 1H), 7.80 (d, 1H), 7.47 (d, 1H), 7.03 (d, 1H), 5.32 (s, 2H), 4.61 (d, 1H), 4.03 (s, 3H), 2.99 (s, 3H), 2.81 (s, 3H), 2.23 (s, 3H), 2.12 (s, 1H), 1.78-1.61 (m, 4H), 1.60-1.48 (m, 3H), 1.40 (t, 5H).

Example 191: N—((S)-2-((5-(1,4-dimethyl-1H-pyrazol-5-yl)pyridin-2-yl)amino)-1-((1r,4S)-4-methylcyclohexyl)-2-oxoethyl)-3-isopropylisoxazole-4-carboxamide

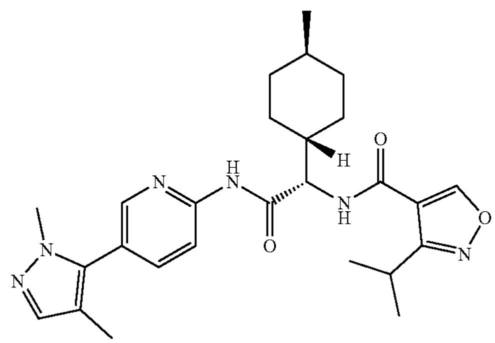 [SMILES: Cc1cnn(C)c1-c1ccc(NC(=O)[C@@H](NC(=O)c2conc2C(C)C)[C@H]2CC[C@H](C)CC2)nc1]

The title compound (21 mg) was prepared from Intermediate 3.106 (50 mg, 0.15 mmol), 3-isopropylisoxazole-4-carboxylic acid (28 mg, 0.18 mmol, CAS: 1368177-31-4), T3P® (50% w/w solution in EtOAc; 0.12 mL, 0.21 mmol) and DIPEA (0.08 mL, 0.44 mmol) in accordance with the procedure described for Example 165. The crude product was purified by reverse phase preparative HPLC (Method 2) and flash column chromatography on the Biotage Isolera One™ (10 g silica column, eluting 0-10% MeOH in DCM). LCMS (Method 15): 2.80 min, 479.2 $[M+H]^+$; $^1$H NMR (400 MHz, DMSO-$d_6$) δ: 10.82 (s, 1H), 9.36 (s, 1H), 8.49 (d, 1H), 8.38 (dd, 1H), 8.23 (dd, 1H), 7.87 (dd, 1H), 7.36 (d, 1H), 4.58 (t, 1H), 3.72 (s, 3H), 3.48-3.40 (m, 1H), 2.00-1.96 (m, 3H), 1.85 (d, 1H), 1.72 (s, 2H), 1.61 (d, 1H), 1.30 (d, 2H), 1.23 (dd, 6H), 1.18-1.04 (m, 2H), 0.88 (t, 5H).

Example 192: 3-(tert-butyl)-N—((S)-2-((5-(1,4-dimethyl-1H-pyrazol-5-yl)pyridin-2-yl)amino)-1-((1r,4S)-4-methylcyclohexyl)-2-oxoethyl)isoxazole-4-carboxamide

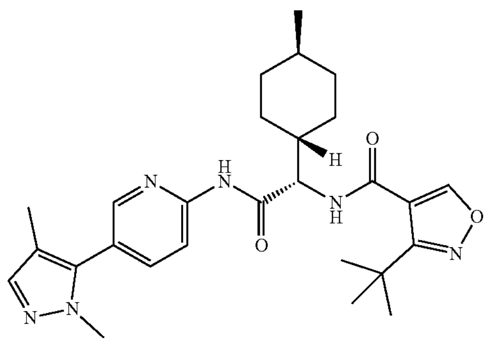 [SMILES: Cc1cnn(C)c1-c1ccc(NC(=O)[C@@H](NC(=O)c2conc2C(C)(C)C)[C@H]2CC[C@H](C)CC2)nc1]

The title compound (21 mg) was prepared from Intermediate 3.106 (70 mg, 0.2 mmol), 3-tert-butylisoxazole-4-carboxylic acid (43 mg, 0.26 mmol, CAS: 1217047-14-7), T3P® (50% w/w solution in EtOAc; 0.17 mL, 0.29 mmol) and DIPEA (0.11 mL, 0.62 mmol) in accordance with the procedure described for Example 165. The crude product was purified by flash column chromatography on the Biotage Isolera One™ (5 g silica column, eluting 0-100% EtOAc in heptanes) and reverse phase preparative HPLC (Method 2). LCMS (Method 15): 2.88 min, 493.2 $[M+H]^+$; $^1$H NMR (400 MHz, DMSO-$d_6$) δ: 10.78 (s, 1H), 9.17 (s, 1H), 8.59 (d, 1H), 8.38 (dd, 1H), 8.22 (dd, 1H), 7.87 (dd, 1H), 7.36 (d, 1H), 4.55 (t, 1H), 3.73 (s, 3H), 1.98 (d, 3H), 1.86 (d, 1H), 1.72 (t, 3H), 1.60 (d, 1H), 1.34 (s, 9H), 1.28 (d, 2H), 1.11 (q, 1H), 0.87 (t, 5H).

Example 193: N—((S)-2-((5-(4-cyano-1-methyl-1H-pyrazol-5-yl)pyridin-2-yl)amino)-1-((1r,4S)-4-methylcyclohexyl)-2-oxoethyl)-1-methyl-1H-pyrazole-5-carboxamide

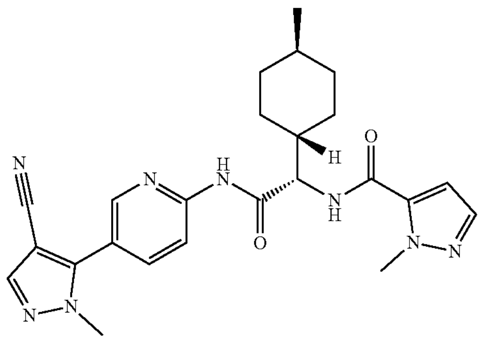 [SMILES: Cn1nccc1C(=O)N[C@H](C(=O)Nc1ccc(-c2c(C#N)cnn2C)cn1)[C@H]1CC[C@H](C)CC1]

The title compound (13 mg) was prepared from Intermediate 3.193 (44 mg, 0.11 mmol), 2-methylpyrazole-3-carboxylic acid (18 mg, 0.14 mmol, CAS: 16034-46-1), T3P® (50% w/w solution in EtOAc; 0.09 mL, 0.16 mmol) and DIPEA (0.06 mL, 0.34 mmol) in accordance with the procedure described for Example 165. The crude product was purified by flash column chromatography on the Biotage Isolera One™ (5 g silica column, eluting 0-100% EtOAc in heptanes) and reverse phase preparative HPLC (Method 2). LCMS (Method 15): 2.54 min, 461.2 $[M+H]^+$; $^1$H NMR (400 MHz, DMSO-$d_6$) δ: 10.99 (s, 1H), 8.59 (dd, 1H), 8.51 (d, 1H), 8.30 (dd, 1H), 8.17 (s, 1H), 8.08 (dd, 1H), 7.47 (d, 1H), 7.05 (d, 1H), 4.56 (t, 1H), 4.02 (s, 3H), 3.88 (s, 3H), 1.84 (t, 2H), 1.70 (d, 2H), 1.60 (d, 1H), 1.34-1.23 (m, 2H), 1.09 (d, 1H), 0.86 (d, 5H).

Example 194: N—((S)-2-((5-(1,4-dimethyl-1H-pyrazol-5-yl)pyridin-2-yl)amino)-1-((1r,4S)-4-methylcyclohexyl)-2-oxoethyl)-3-(trifluoromethyl)isoxazole-4-carboxamide

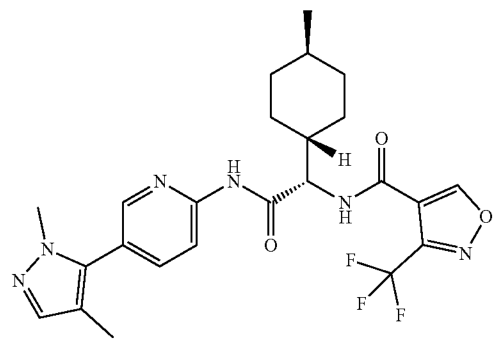 [SMILES: Cc1cnn(C)c1-c1ccc(NC(=O)[C@@H](NC(=O)c2conc2C(F)(F)F)[C@H]2CC[C@H](C)CC2)nc1]

The title compound (64 mg) was prepared from Intermediate 3.106 (70 mg, 0.21 mmol), 3-(trifluoromethyl)isoxazole-4-carboxylic acid (46 mg, 0.26 mmol, CAS: 1076245-98-1), T3P® (50% w/w solution in EtOAc; 0.24 mL, 0.41 mmol) and DIPEA (0.11 mL, 0.62 mmol) in accordance with the procedure described for Example 165. The crude product was purified by flash column chromatography on the Biotage Isolera One™ (4 g silica column, eluting 0-100% EtOAc in heptanes). LCMS (Method 15): 2.80 min, 505.2 $[M+H]^+$; $^1$H NMR (400 MHz, DMSO-$d_6$) δ: 10.87 (s, 1H), 9.79 (q, 1H), 8.83 (d, 1H), 8.36 (dd, 1H), 8.20 (dd, 1H), 7.85 (dd, 1H), 7.33 (d, 1H), 4.60 (t, 1H), 3.70 (s, 3H), 1.95 (d, 3H), 1.85-1.60- (m, 5H), 1.32-1.03 (m, 3H), 0.93-0.81 (m, 5H).

Example 195: (S)—N-(1-cycloheptyl-2-oxo-2-((5-(1,3,4-trimethyl-1H-pyrazol-5-yl)pyridin-2-yl)amino)ethyl)-1-methyl-1H-pyrazole-5-carboxamide

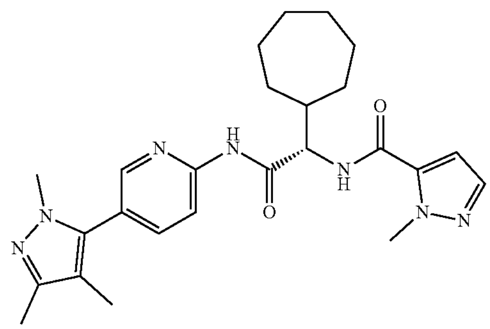 [SMILES: Cc1nn(C)c(-c2ccc(NC(=O)[C@@H](NC(=O)c3ccnn3C)C3CCCCCC3)nc2)c1C]

The title compound (53 mg) was prepared from Intermediate 3.195 (73 mg, 0.2 mmol), 2-methylpyrazole-3-carboxylic acid (32 mg, 0.26 mmol, CAS: 16034-46-1), T3P® (50% w/w solution in EtOAc; 0.17 mL, 0.29 mmol) and DIPEA (0.11 mL, 0.61 mmol) in accordance with the procedure described for Example 165. The crude product was purified by reverse phase preparative HPLC (Method 3) and an SCX cartridge (2 g, washed with MeOH and eluted with 2 M methanolic ammonia). LCMS (Method 15): 2.59 min, 464.3 [M+H]$^+$; $^1$H NMR (400 MHz, DMSO-$d_6$) δ: 10.83 (s, 1H), 8.48 (d, 1H), 8.35 (dd, 1H), 8.22 (dd, 1H), 7.84 (dd, 1H), 7.48 (d, 1H), 7.05 (d, 1H), 4.65 (t, 1H), 4.03 (s, 3H), 3.64 (s, 3H), 2.19-2.07 (m, 4H), 1.89 (s, 3H), 1.77-1.34 (m, 12H).

Example 196: N—((S)-2-((5-(3,5-dimethylisothiazol-4-yl)pyridin-2-yl)amino)-1-((1r,4S)-4-methylcyclohexyl)-2-oxoethyl)-1-methyl-1H-pyrazole-5-carboxamide

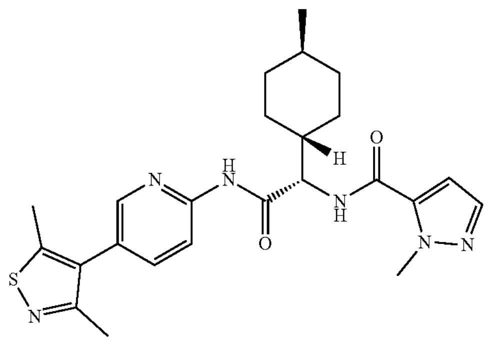 [SMILES: Cc1nsc(C)c1-c1ccc(NC(=O)[C@@H](NC(=O)c2ccnn2C)[C@H]2CC[C@H](C)CC2)nc1]

The title compound (25 mg) was prepared from Intermediate 3.196 (77 mg, 0.22 mmol), 2-methylpyrazole-3-carboxylic acid (32 mg, 0.26 mmol, CAS: 16034-46-1), HATU (98 mg, 0.26 mmol) and DIPEA (0.11 mL, 0.64 mmol) in accordance with the procedure described for Example 109. The crude product was purified by reverse phase preparative HPLC (Method 3) and an SCX cartridge (1 g, washed with MeOH and eluted with 2 M methanolic ammonia). LCMS (Method 15): 2.74 min, 467.2 [M+H]$^+$; $^1$H NMR (400 MHz, MeOD) δ: 8.29-8.22 (m, 2H), 7.77-7.70 (m, 1H), 7.48 (d, 1H), 6.91 (d, 1H), 4.55 (d, 1H), 4.09 (s, 3H), 2.43 (s, 3H), 2.32 (s, 3H), 1.99-1.85 (m, 2H), 1.83-1.75 (m, 3H), 1.40-1.24 (m, 2H), 1.25-1.10 (m, 1H), 1.07-0.93 (m, 2H), 0.91 (d, 3H).

Example 197: N—((S)-2-((5-(3,5-dimethylisothiazol-4-yl)pyridin-2-yl)amino)-1-((1r,4S)-4-methylcyclohexyl)-2-oxoethyl)-1-methyl-1H-1,2,3-triazole-5-carboxamide

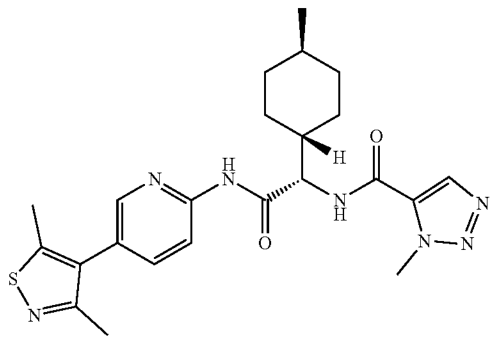 [SMILES: Cc1nsc(C)c1-c1ccc(NC(=O)[C@@H](NC(=O)c2cnnn2C)[C@H]2CC[C@H](C)CC2)nc1]

The title compound (36 mg) was prepared from Intermediate 3.196 (97 mg, 0.27 mmol), 3-methyltriazole-4-carboxylic acid (41 mg, 0.33 mmol, CAS: 716361-91-0), HATU (0.12 g, 0.33 mmol) and DIPEA (0.14 mL, 0.81 mmol) in accordance with the procedure described for Example 109. The crude product was purified by flash column chromatography on the Biotage Isolera One™ (20 g silica column, eluting 2-100% EtOAc in heptanes) and reverse phase preparative HPLC (Method 2). LCMS (Method 15): 2.62 min, 468.2 [M+H]$^+$; $^1$H NMR (400 MHz, MeOD) δ: 8.29-8.22 (m, 3H), 7.73 (dd, 1H), 4.57 (d, 1H), 4.28 (s, 3H), 2.43 (s, 3H), 2.32 (s, 3H), 1.98-1.85 (m, 2H), 1.83-1.75 (m, 3H), 1.46-1.16 (m, 3H), 1.07-0.94 (m, 2H), 0.91 (d, 3H).

Example 198: (S)—N-(1-cycloheptyl-2-((5-(4-(hydroxymethyl)-1-methyl-1H-pyrazol-5-yl)pyridin-2-yl)amino)-2-oxoethyl)-1-ethyl-1H-pyrazole-5-carboxamide

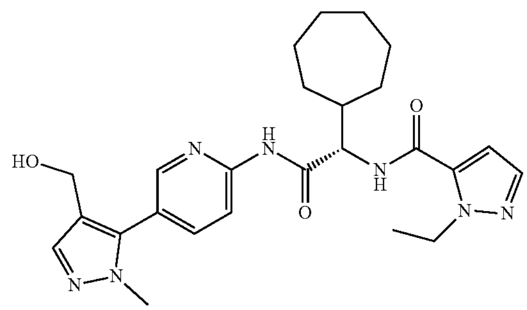 [SMILES: CCn1nccc1C(=O)N[C@H](C(=O)Nc1ccc(-c2c(CO)cnn2C)cn1)C1CCCCCC1]

The title compound (11 mg) was prepared from Intermediate 3.182 (45 mg, 0.13 mmol), 2-ethylpyrazole-3-carboxylic acid (21 mg, 0.15 mmol, CAS: 400755-43-3), HATU (57 mg, 0.33 mmol) and DIPEA (0.07 mL, 0.38 mmol) in accordance with the procedure described for Example 109. The crude product was purified by flash column chromatography on the Biotage Isolera One™ (12 g silica column, eluting 0-10% MeOH in DCM) and reverse phase preparative HPLC (Method 2). LCMS (Method 15): 2.30 min, 480.2 [M+H]$^+$; $^1$H NMR (400 MHz, MeOD) δ: 8.43 (dd, 1H), 8.30 (dd, 1H), 7.90 (dd, 1H), 7.59 (s, 1H), 7.50 (d, 1H), 6.87 (d, 1H), 4.66 (d, 1H), 4.53 (qd, 2H), 4.38 (s, 2H), 3.80 (s, 3H), 2.21 (td, 1H), 1.92-1.71 (m, 4H), 1.70-1.42 (m, 8H), 1.38 (t, 3H).

Example 199: N—((S)-2-((5-(4-chloro-1-methyl-1H-pyrazol-5-yl)pyridin-2-yl)amino)-1-((1r,4S)-4-methylcyclohexyl)-2-oxoethyl)-1-ethyl-1H-pyrazole-5-carboxamide

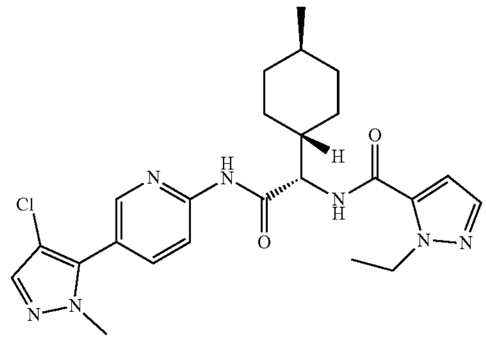 [SMILES: CCn1nccc1C(=O)N[C@H](C(=O)Nc1ccc(-c2c(Cl)cnn2C)cn1)[C@H]1CC[C@H](C)CC1]

The title compound (58 mg) was prepared from Intermediate 3.199 (93 mg, 0.23 mmol), 2-ethylpyrazole-3-carboxylic acid (41 mg, 0.29 mmol, CAS: 400755-43-3), T3P® (50% w/w solution in EtOAc; 0.19 mL, 0.32 mmol) and DIPEA (0.12 mL, 0.69 mmol) in accordance with the procedure described for Example 165. The crude product was purified by flash column chromatography on the Biotage Isolera One™ (10 g silica column eluting 20-80% EtOAc in heptanes) and reverse phase preparative HPLC (Method 2). LCMS (Method 15): 2.79 min, 484.2 $[M+H]^+$; $^1$H NMR (400 MHz, DMSO-$d_6$) δ: 10.86 (s, 1H), 8.51-8.42 (m, 2H), 8.24 (dd, 1H), 7.94 (dd, 1H), 7.66 (s, 1H), 7.46 (d, 1H), 6.98 (d, 1H), 4.52 (t, 1H), 4.43 (q, 2H), 3.77 (s, 3H), 1.87-1.74 (m, 2H), 1.67 (d, 2H), 1.58 (d, 1H), 1.32-1.20 (m, 2H), 1.25 (t, 3H), 1.14-1.00 (m, 1H), 0.93-0.78 (m, 2H), 0.83 (d, 3H).

Example 200: N—((S)-2-((5-(4-chloro-1-methyl-1H-pyrazol-5-yl)pyridin-2-yl)amino)-1-((1r,4S)-4-methylcyclohexyl)-2-oxoethyl)-1-methyl-1H-1,2,3-triazole-5-carboxamide

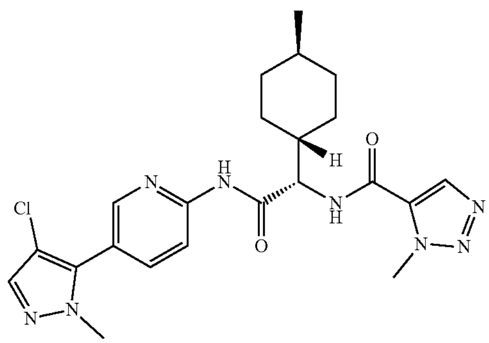 [SMILES: Cn1nncc1C(=O)N[C@H](C(=O)Nc1ccc(-c2c(Cl)cnn2C)cn1)[C@H]1CC[C@H](C)CC1]

The title compound (58 mg) was prepared from Intermediate 3.199 (35 mg, 0.09 mmol), 3-methyltriazole-4-carboxylic acid (12 mg, 0.09 mmol, CAS: 716361-91-0), T3P® (50% w/w solution in EtOAc; 0.07 mL, 0.12 mmol) and DIPEA (0.05 mL, 0.26 mmol) in accordance with the procedure described for Example 165. The crude product was purified by flash column chromatography on the Biotage Isolera One™ (10 g silica column eluting 20-80% EtOAc in heptanes) and reverse phase preparative HPLC (Method 3). LCMS (Method 15): 2.60 min, 471.2 $[M+H]^+$; $^1$H NMR (400 MHz, DMSO-$d_6$) δ: 10.95 (s, 1H), 8.83 (s, 1H), 8.45 (dd, 1H), 8.38 (s, 1H), 8.23 (dd, 1H), 7.94 (dd, 1H), 7.66 (s, 1H), 4.59 (d, 1H), 4.16 (s, 3H), 3.77 (s, 3H), 1.87-1.73 (m, 2H), 1.73-1.63 (m, 2H), 1.59 (d, 1H), 1.32-1.19 (m, 2H), 1.08 (q, 1H), 0.89 (d, 2H), 0.84 (d, 3H).

Example 201: N—((S)-2-((5-(4-chloro-1-methyl-1H-pyrazol-5-yl)pyridin-2-yl)amino)-1-((1r,4S)-4-methylcyclohexyl)-2-oxoethyl)-3-ethylisoxazole-4-carboxamide

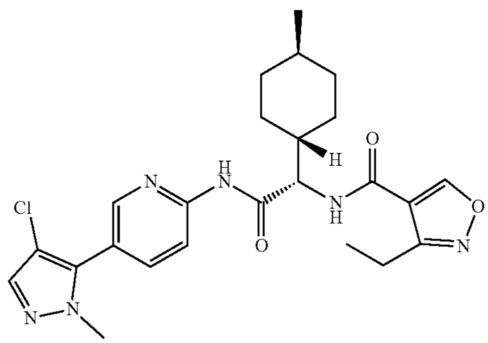 [SMILES: CCc1nocc1C(=O)N[C@H](C(=O)Nc1ccc(-c2c(Cl)cnn2C)cn1)[C@H]1CC[C@H](C)CC1]

The title compound (21 mg) was prepared from Intermediate 3.199 (93 mg, 0.23 mmol), 3-ethylisoxazole-4-carboxylic acid (40 mg, 0.29 mmol, CAS: 639523-12-9), T3P® (50% w/w solution in EtOAc; 0.19 mL, 0.32 mmol) and DIPEA (0.12 mL, 0.69 mmol) in accordance with the procedure described for Example 165. The crude product was purified by flash column chromatography on the Biotage Isolera One™ (10 g silica column eluting 10-80% EtOAc in heptanes) and reverse phase preparative HPLC (Method 3). The residue was partitioned between saturated aqueous $NaHCO_3$ and EtOAc. The layers were separated, and the organics concentrated in vacuo. The reside was further purified by reverse phase preparative HPLC (Method 2). LCMS (Method 15): 2.83 min, 485.2 $[M+H]^+$; $^1$H NMR (400 MHz, DMSO-$d_6$) δ: 10.90 (s, 1H), 9.41 (s, 1H), 8.50-8.43 (m, 2H), 8.25 (dd, 1H), 7.96 (dd, 1H), 7.69 (s, 1H), 4.58 (t, 1H), 3.79 (s, 3H), 2.88-2.78 (m, 2H), 1.88-1.81 (m, 1H), 1.79-1.65 (m, 3H), 1.64-1.57 (m, 1H), 1.36-1.22 (m, 2H), 1.16 (t, 3H), 1.09 (td, 1H), 0.95-0.80 (m, 2H), 0.86 (d, 3H).

Example 202: (S)—N-(1-cycloheptyl-2-((5-(4-(hydroxymethyl)-1-methyl-1H-pyrazol-5-yl)pyridin-2-yl)amino)-2-oxoethyl)-3-ethylisoxazole-4-carboxamide

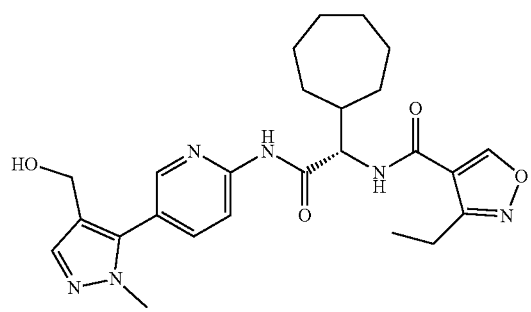 [SMILES: CCc1nocc1C(=O)N[C@H](C(=O)Nc1ccc(-c2c(CO)cnn2C)cn1)C1CCCCCC1]

The title compound (18 mg) was prepared from Intermediate 3.182 (45 mg, 0.13 mmol), 3-ethylisoxazole-4-carboxylic acid (32 mg, 0.22 mmol, CAS: 639523-12-9), HATU (85 mg, 0.22 mmol) and DIPEA (0.1 mL, 0.56 mmol) in accordance with the procedure described for Example 109. The crude product was purified by flash column chromatography on the Biotage Isolera One™ (12 g silica column, eluting 0-10% MeOH in DCM) and reverse phase preparative HPLC (Method 2). LCMS (Method 15): 2.36 min, 481.3 $[M+H]^+$; $^1$H NMR (400 MHz, DMSO-$d_6$) δ: 10.85 (s, 1H), 9.41 (s, 1H), 8.49-8.40 (m, 2H), 8.21 (dd, 1H), 7.93 (dd, 1H), 7.49 (s, 1H), 4.85 (t, 1H), 4.68 (t, 1H), 4.23 (d, 2H), 3.76 (s, 3H), 2.84 (q, 2H), 2.14-1.99 (m, 1H), 1.79-1.61 (m, 4H), 1.60-1.34 (m, 8H), 1.17 (t, 3H).

Example 203: N—((S)-2-((6-(3,5-dimethylisoxazol-4-yl)pyridin-3-yl)amino)-1-((1r,4S)-4-methylcyclohexyl)-2-oxoethyl)-3-ethylisoxazole-4-carboxamide

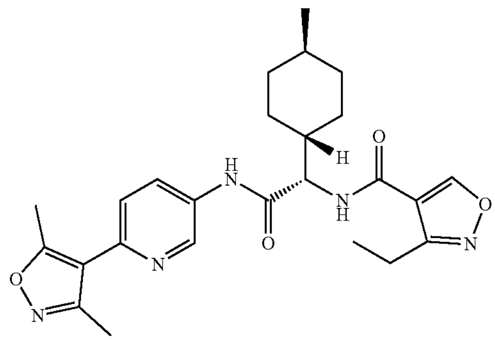 [SMILES: CCc1nocc1C(=O)N[C@H](C(=O)Nc1ccc(-c2c(C)noc2C)nc1)[C@H]1CC[C@H](C)CC1]

The title compound (43 mg) was prepared from Intermediate 3.138 (50 mg, 0.14 mmol), 3-ethylisoxazole-4-carboxylic acid (20 mg, 0.14 mmol, CAS: 639523-12-9), T3P® (50% w/w solution in EtOAc; 0.06 mL, 0.2 mmol) and DIPEA (0.08 mL, 0.43 mmol) in accordance with the procedure described for Example 165. The crude product was purified by flash column chromatography on the Biotage Isolera One™ (4 g silica column eluting 0-100% EtOAc in heptanes). LCMS (Method 15): 2.70 min, 466.2 $[M+H]^+$; $^1H$ NMR (400 MHz, DMSO-$d_6$) δ: 10.53 (s, 1H), 9.42 (s, 1H), 8.87 (dd, 1H), 8.56 (d, 1H), 8.17 (dd, 1H), 7.52 (dd, 1H), 4.42 (t, 1H), 2.89-2.79 (m, 2H), 2.53 (s, 3H), 2.34 (s, 3H), 1.95-1.50 (m, 5H), 1.38-0.80 (m, 11H).

Example 204: N—((S)-2-((6-(1,4-dimethyl-1H-pyrazol-5-yl)pyridin-3-yl)amino)-1-((1r,4S)-4-methylcyclohexyl)-2-oxoethyl)-1-isopropyl-1H-pyrazole-5-carboxamide

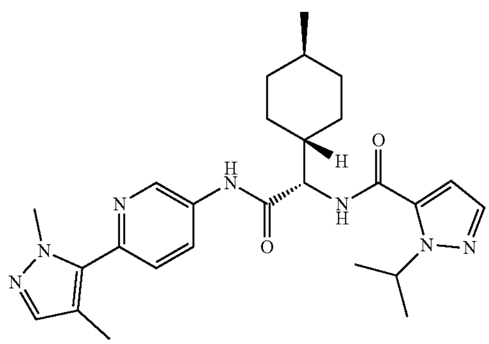 [SMILES: Cc1cnn(C)c1-c1ccc(NC(=O)[C@@H](NC(=O)c2ccnn2C(C)C)[C@H]2CC[C@H](C)CC2)cn1]

The title compound (22 mg) was prepared from Intermediate 3.145 (75 mg, 0.22 mmol), 2-isopropylpyrazole-3-carboxylic acid (51 mg, 0.33 mmol, CAS: 920006-32-2), T3P® (50% w/w solution in EtOAc; 0.2 mL, 0.33 mmol) and DIPEA (0.11 mL, 0.66 mmol) in accordance with the procedure described for Example 165. The crude product was purified by flash column chromatography on the Biotage Isolera One™ (10 g silica column eluting 0-6% MeOH in DCM) and reverse phase preparative HPLC (Method 4). LCMS (Method 15): 2.67 min, 478.2 $[M+H]^+$; $^1H$ NMR (400 MHz, $CDCl_3$) δ: 8.86 (s, 2H), 8.38 (dd, 1H), 7.54 (d, 1H), 7.51 (d, 1H), 7.43 (d, 1H), 6.77 (d, 1H), 6.62 (d, 1H), 5.49-5.37 (m, 1H), 4.51 (t, 1H), 3.96 (s, 3H), 2.11 (s, 3H), 1.99-1.74 (m, 5H), 1.48 (dd, 6H), 1.34 (dd, 1H), 1.26-1.09 (m, 2H), 1.04-0.93 (m, 2H), 0.90 (d, 3H).

Example 205: 1-ethyl-N—((S)-2-((5-(4-(hydroxymethyl)-1-methyl-1H-pyrazol-5-yl)pyridin-2-yl)amino)-1-((1r,4S)-4-methylcyclohexyl)-2-oxoethyl)-1H-pyrazole-5-carboxamide

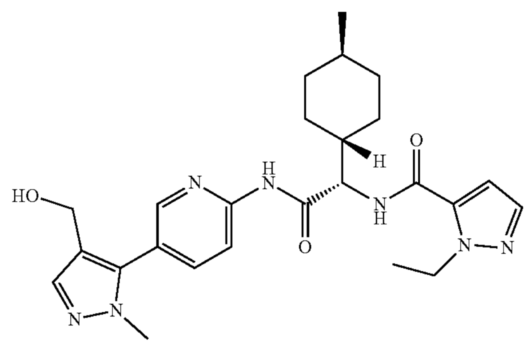 [SMILES: CCn1nccc1C(=O)N[C@H](C(=O)Nc1ccc(-c2c(CO)cnn2C)cn1)[C@H]1CC[C@H](C)CC1]

The title compound (31 mg) was prepared from Intermediate 3.205 (65 mg, 0.18 mmol), 2-ethylpyrazole-3-carboxylic acid (31 mg, 0.22 mmol, CAS: 400755-43-3), HATU (83 mg, 0.22 mmol) and DIPEA (0.1 mL, 0.55 mmol) in accordance with the procedure described for Example 109. The crude product was purified by flash column chromatography on the Biotage Isolera One™ (12 g silica column, eluting 0-10% MeOH in DCM) and reverse phase preparative HPLC (Method 2). LCMS (Method 15): 2.32 min, 480.2 $[M+H]^+$; $^1H$ NMR (400 MHz, DMSO-$d_6$) δ: 10.82 (s, 1H), 8.50 (d, 1H), 8.46 (dd, 1H), 8.22 (dd, 1H), 7.93 (dd, 1H), 7.52-7.46 (m, 2H), 7.01 (d, 1H), 4.85 (t, 1H), 4.54 (t, 1H), 4.45 (q, 2H), 4.23 (d, 2H), 3.76 (s, 3H), 1.82 (q, 2H), 1.70 (d, 2H), 1.61 (d, 1H), 1.27 (t, 5H), 1.16-1.02 (m, 1H), 0.86 (d, 5H).

Example 206: N—((S)-2-((6-(3,5-dimethylisoxazol-4-yl)pyridin-3-yl)amino)-1-((1r,4S)-4-methylcyclohexyl)-2-oxoethyl)-1-isopropyl-1H-pyrazole-5-carboxamide

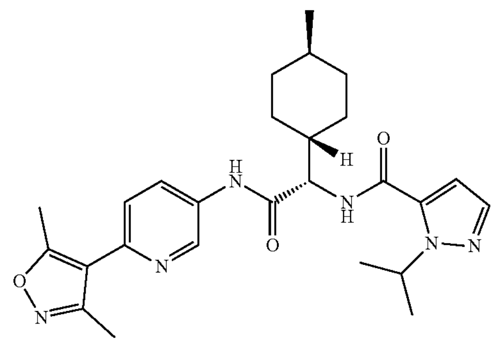 [SMILES: Cc1noc(C)c1-c1ccc(NC(=O)[C@@H](NC(=O)c2ccnn2C(C)C)[C@H]2CC[C@H](C)CC2)cn1]

The title compound (45 mg) was prepared from Intermediate 3.138 (50 mg, 0.14 mmol), 2-isopropylpyrazole-3-carboxylic acid (29 mg, 0.19 mmol, CAS: 920006-32-2), T3P® (50% w/w solution in EtOAc; 0.06 mL, 0.2 mmol) and DIPEA (0.08 mL, 0.43 mmol) in accordance with the procedure described for Example 165. The crude product was purified by flash column chromatography on the Biotage Isolera One™ (4 g silica column eluting 0-100% EtOAc in heptanes). LCMS (Method 15): 2.75 min, 479.2 $[M+H]^+$; $^1$H NMR (400 MHz, DMSO-$d_6$) δ: 10.55 (s, 1H), 8.86 (d, 1H), 8.58 (s, 1H), 8.17 (dd, 1H), 7.55-7.47 (m, 2H), 6.96 (d, 1H), 5.48-5.30 (m, 1H), 4.37 (d, 1H), 2.53 (s, 3H), 2.34 (s, 3H), 1.91-1.56 (m, 5H), 1.40-0.81 (m, 14H).

Example 207: (S)—N-(1-cyclohexyl-2-((6-(3,5-dimethyl-1H-pyrazol-4-yl)pyridin-3-yl)amino)-2-oxoethyl)-1-methyl-1H-pyrazole-5-carboxamide

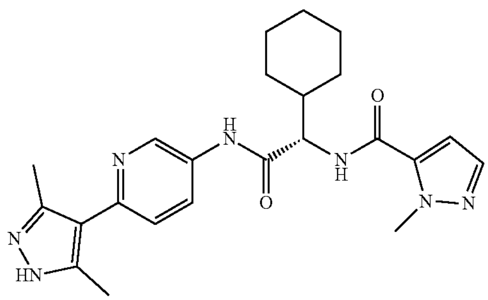 [SMILES: Cc1n[nH]c(C)c1-c1ccc(NC(=O)[C@@H](NC(=O)c2ccnn2C)C2CCCCC2)cn1]

The title compound (5 mg) was prepared from Intermediate 3.207 (30 mg, 0.06 mmol), 2-methylpyrazole-3-carboxylic acid (11 mg, 0.07 mmol, CAS: 16034-46-1), HATU (33 mg, 0.09 mmol) and DIPEA (0.07 mL, 0.4 mmol) in accordance with the procedure described for Example 109 in DMF. The crude product was purified by flash column chromatography on the Teledyne ISCO CombiFlash® (4 g silica column, eluting 0-100% 3:1 EtOAc:EtOH in isohexane). LCMS (Method 25): 1.44 min, 436.3 $[M+H]^+$; $^1$H NMR (400 MHz, DMSO-$d_6$) δ: 12.32 (s, 1H), 10.42 (s, 1H), 8.80 (d, 1H), 8.55 (d, 1H), 8.07 (dd, 1H), 7.46 (d, 1H), 7.36 (d, 1H), 7.08 (d, 1H), 4.42 (t, 1H), 4.03 (s, 3H), 2.30 (d, 6H), 1.85 (d, 2H), 1.72 (s, 2H), 1.61 (s, 2H), 1.17 (t, 4H), 1.04 (s, 1H).

Example 208: (S)—N-(1-cycloheptyl-2-((6-(3,5-dimethyl-1H-pyrazol-4-yl)pyridin-3-yl)amino)-2-oxoethyl)-1-ethyl-1H-pyrazole-5-carboxamide

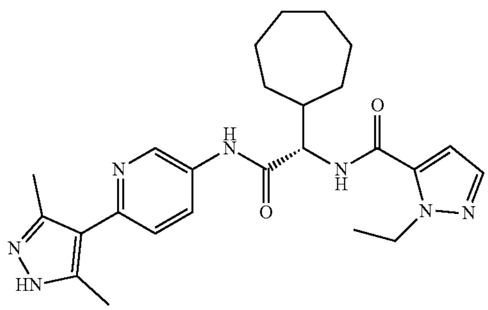 [SMILES: CCn1nccc1C(=O)N[C@H](C(=O)Nc1ccc(-c2c(C)n[nH]c2C)nc1)C1CCCCCC1]

The title compound (61 mg) was prepared from Intermediate 3.208 (0.1 g, 0.21 mmol), 2-ethylpyrazole-3-carboxylic acid (35 mg, 0.25 mmol, CAS: 400755-43-1), HATU (95 mg, 0.25 mmol) and DIPEA (0.2 mL, 1.2 mmol) in accordance with the procedure described for Example 109 in DMF. The crude product was purified by an SCX cartridge (1 g, washed with MeOH and eluted with 0.7 M methanolic ammonia) and flash column chromatography on the Teledyne ISCO CombiFlash® (4 g silica column, eluting 0-100% 3:1 EtOAc:EtOH in isohexane). LCMS (Method 28): 1.35 min, 464.3 $[M+H]^+$; $^1$H NMR (400 MHz, DMSO-$d_6$) δ: 12.32 (s, 1H), 10.41 (s, 1H), 8.80 (d, 1H), 8.56 (d, 1H), 8.07 (dd, 1H), 7.48 (d, 1H), 7.37 (d, 1H), 7.03 (d, 1H), 4.52-4.43 (m, 3H), 2.33 (s, 3H), 2.28 (s, 3H), 2.17-2.07 (m, 1H), 1.78-1.31 (m, 12H), 1.28 (t, 3H).

Example 209: (S)—N-(1-cycloheptyl-2-((6-(3,5-dimethyl-1H-pyrazol-4-yl)pyridin-3-yl)amino)-2-oxoethyl)-1-methyl-1H-1,2,3-triazole-5-carboxamide

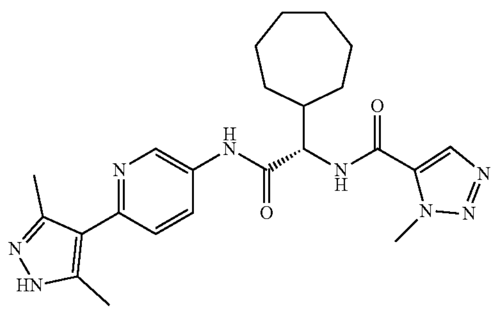 [SMILES: Cc1n[nH]c(C)c1-c1ccc(NC(=O)[C@@H](NC(=O)c2cnnn2C)C2CCCCCC2)cn1]

The title compound (52 mg) was prepared from Intermediate 3.208 (0.1 g, 0.21 mmol), 3-methyltriazole-4-carboxylic acid (36 mg, 0.28 mmol, CAS: 716361-91-0), HATU (95 mg, 0.25 mmol) and DIPEA (0.2 mL, 1.2 mmol) in accordance with the procedure described for Example 109 in DMF. The crude product was purified by an SCX cartridge (1 g, washed with MeOH and eluted with 0.7 M methanolic ammonia) and flash column chromatography on the Teledyne ISCO CombiFlash® (4 g silica column, eluting 0-100% 3:1 EtOAc:EtOH in isohexane). LCMS (Method 28): 1.19 min, 451.3 $[M+H]^+$; $^1$H NMR (400 MHz, DMSO-$d_6$) δ: 12.32 (s, 1H), 10.46 (s, 1H), 8.94 (d, 1H), 8.79 (dd, 1H), 8.42 (s, 1H), 8.07 (dd, 1H), 7.37 (d, 1H), 4.54 (t, 1H), 4.20 (s, 3H), 2.33 (s, 3H), 2.28 (s, 3H), 2.16-2.05 (m, 1H), 1.80-1.30 (m, 12H).

Example 210: (S)—N-(1-cycloheptyl-2-((6-(3,5-dimethyl-1H-pyrazol-4-yl)pyridin-3-yl)amino)-2-oxoethyl)-3-ethylisoxazole-4-carboxamide

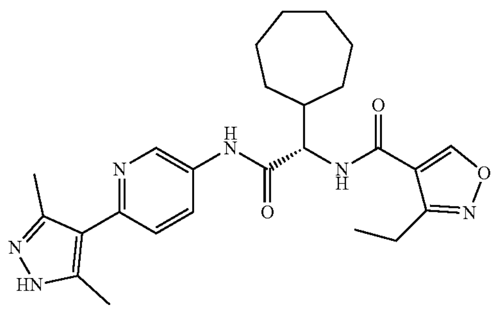 [SMILES: CCc1nocc1C(=O)N[C@H](C(=O)Nc1ccc(-c2c(C)n[nH]c2C)nc1)C1CCCCCC1]

The title compound (52 mg) was prepared from Intermediate 3.208 (0.1 g, 0.21 mmol), 3-ethylisoxazole-4-carboxylic acid (36 mg, 0.26 mmol, CAS: 639523-12-9), HATU (95 mg, 0.25 mmol) and DIPEA (0.2 mL, 1.2 mmol) in accordance with the procedure described for Example 109 in DMF. The crude product was purified by an SCX cartridge (1 g, washed with MeOH and eluted with 0.7 M methanolic ammonia) and flash column chromatography on the Teledyne ISCO CombiFlash® (4 g silica column, eluting 0-100% 3:1 EtOAc:EtOH in isohexane). LCMS (Method 28): 1.39 min, 465.3 $[M+H]^+$; $^1H$ NMR (400 MHz, DMSO-$d_6$) δ: 12.32 (s, 1H), 10.41 (s, 1H), 9.42 (s, 1H), 8.79 (d, 1H), 8.54 (d, 1H), 8.06 (dd, 1H), 7.36 (d, 1H), 4.56-4.47 (m, 1H), 2.84 (q, 2H), 2.34 (s, 3H), 2.27 (s, 3H), 2.10-1.99 (m, 1H), 1.80-1.30 (m, 12H), 1.17 (t, 3H).

Example 211: N—((S)-2-((6-(3,5-dimethyl-1H-pyrazol-4-yl)pyridin-3-yl)amino)-1-((1r,4S)-4-methylcyclohexyl)-2-oxoethyl)-1-methyl-1H-pyrazole-5-carboxamide

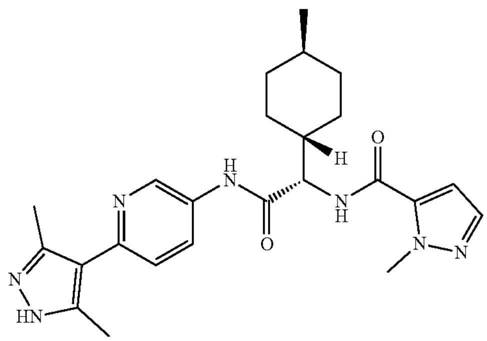 [SMILES: Cc1n[nH]c(C)c1-c1ccc(NC(=O)[C@@H](NC(=O)c2ccnn2C)[C@H]2CC[C@H](C)CC2)cn1]

The title compound (26 mg) was prepared from Intermediate 3.211 (50 mg, 0.09 mmol), 2-methylpyrazole-3-carboxylic acid (14 mg, 0.11 mmol, CAS: 16034-46-1), HATU (42 mg, 0.11 mmol) and DIPEA (0.08 mL, 0.46 mmol) in accordance with the procedure described for Example 109 in DMF. The crude product was purified by an SCX cartridge (1 g, washed with MeOH and eluted with 0.7 M methanolic ammonia) and flash column chromatography on the Teledyne ISCO CombiFlash® (4 g silica column, eluting 0-100% 3:1 EtOAc:EtOH in isohexane). LCMS (Method 28): 1.29 min, 450.3 $[M+H]^+$; $^1H$ NMR (400 MHz, DMSO-$d_6$) δ: 12.31 (s, 1H), 10.41 (s, 1H), 8.79 (d, 1H), 8.56 (d, 1H), 8.07 (dd, 1H), 7.46 (d, 1H), 7.36 (d, 1H), 7.07 (d, 1H), 4.39 (app. t, 1H), 4.03 (s, 3H), 2.33 (s, 3H), 2.28 (s, 3H), 1.91-1.77 (m, 2H), 1.75-1.66 (m, 2H), 1.63-1.56 (m, 1H), 1.21 (dd, 2H), 1.05 (q, 1H), 0.86 (d, 5H).

Example 212: N—((S)-2-((6-(3,5-dimethyl-1H-pyrazol-4-yl)pyridin-3-yl)amino)-1-((1r,4S)-4-methylcyclohexyl)-2-oxoethyl)-1-ethyl-1H-pyrazole-5-carboxamide

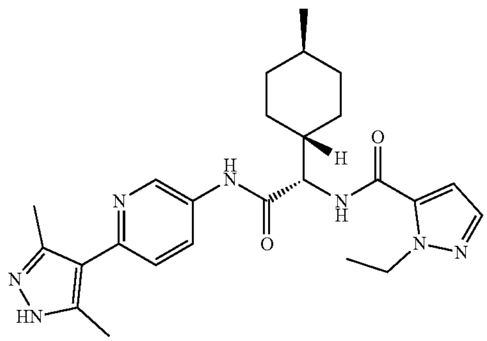 [SMILES: CCn1nccc1C(=O)N[C@H](C(=O)Nc1ccc(-c2c(C)n[nH]c2C)nc1)[C@H]1CC[C@H](C)CC1]

The title compound (27 mg) was prepared from Intermediate 3.211 (50 mg, 0.09 mmol), 2-ethylpyrazole-3-carboxylic acid (14 mg, 0.11 mmol, CAS: 400755-43-1), HATU (42 mg, 0.11 mmol) and DIPEA (0.08 mL, 0.46 mmol) in accordance with the procedure described for Example 109 in DMF. The crude product was purified by an SCX cartridge (1 g, washed with MeOH and eluted with 0.7 M methanolic ammonia) and flash column chromatography on the Teledyne ISCO CombiFlash® (4 g silica column, eluting 0-100% 3:1 EtOAc:EtOH in isohexane). LCMS (Method 28): 1.37 min, 464.4 $[M+H]^+$; $^1H$ NMR (400 MHz, DMSO-$d_6$) δ: 12.27 (s, 1H), 10.40 (s, 1H), 8.79 (d, 1H), 8.56 (d, 1H), 8.07 (dd, 1H), 7.48 (d, 1H), 7.36 (d, 1H), 7.03 (d, 1H), 4.46 (q, 2H), 4.39 (app. t, 1H), 2.31 (s, 6H), 1.90-1.76 (m, 2H), 1.74-1.66 (m, 2H), 1.64-1.56 (m, 1H), 1.36-1.13 (m, 5H), 1.12-0.99 (m, 1H), 0.95-0.81 (m, 5H).

Example 213: N—((S)-2-((6-(3,5-dimethyl-1H-pyrazol-4-yl)pyridin-3-yl)amino)-1-((1r,4S)-4-methylcyclohexyl)-2-oxoethyl)-3-ethylisoxazole-4-carboxamide

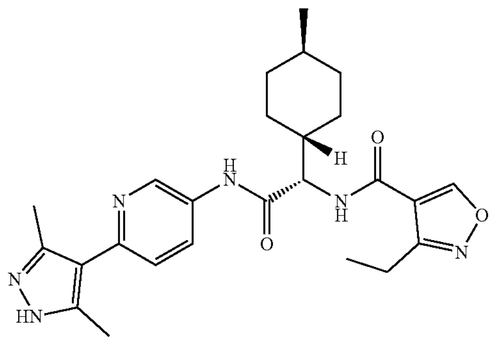 [SMILES: CCc1nocc1C(=O)N[C@H](C(=O)Nc1ccc(-c2c(C)n[nH]c2C)nc1)[C@H]1CC[C@H](C)CC1]

The title compound (25 mg) was prepared from Intermediate 3.211 (50 mg, 0.09 mmol), 3-ethylisoxazole-4-carboxylic acid (16 mg, 0.11 mmol, CAS: 639523-12-9), HATU (42 mg, 0.11 mmol) and DIPEA (0.08 mL, 0.46 mmol) in accordance with the procedure described for Example 109 in DMF. The crude product was purified by an SCX cartridge (1 g, washed with MeOH and eluted with 0.7 M methanolic ammonia) and flash column chromatography on the Teledyne ISCO CombiFlash® (4 g silica column, eluting 0-100% 3:1 EtOAc:EtOH in isohexane). LCMS (Method 28): 1.41 min, 465.2 $[M+H]^+$; $^1H$ NMR (400 MHz, DMSO-$d_6$) δ: 12.32 (s, 1H), 10.40 (s, 1H), 9.42 (s, 1H), 8.79 (d, 1H), 8.55 (d, 1H), 8.06 (dd, 1H), 7.36 (d, 1H), 4.42 (app. t, 1H), 2.84 (q, 2H), 2.33 (s, 3H), 2.28 (s, 3H), 1.89-1.81 (m, 1H), 1.79-1.66 (m, 3H), 1.64-1.56 (m, 1H), 1.36-1.14 (m, 5H), 1.12-0.99 (m, 1H), 0.94-0.81 (m, 5H).

Example 214: (S)—N-(1-cycloheptyl-2-oxo-2-((1',2',4'-trimethyl-6'-oxo-1',6'-dihydro-[3,3'-bipyridin]-6-yl)amino)ethyl)-1-methyl-1H-pyrazole-5-carboxamide

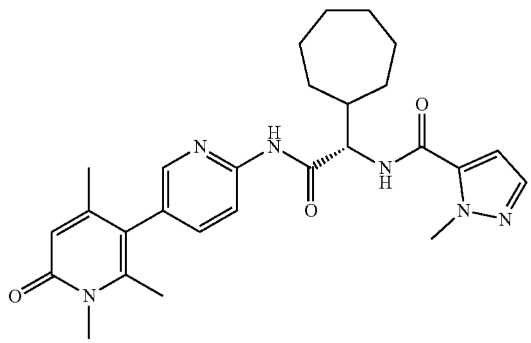 [SMILES: Cc1cc(=O)n(C)c(C)c1-c1ccc(NC(=O)[C@@H](NC(=O)c2ccnn2C)C2CCCCCC2)nc1]

The title compound (3 mg) was prepared from Intermediate 3.214 (25 mg, 0.07 mmol), 2-methylpyrazole-3-carboxylic acid (10 mg, 0.08 mmol, CAS: 16034-46-1), HATU (38 mg, 0.1 mmol) and DIPEA (0.03 mL, 0.17 mmol) in accordance with the procedure described for Example 109 in DMF. The crude product was purified by an SCX cartridge (1 g, washed with MeOH and eluted with 0.7 M methanolic ammonia), flash column chromatography on the Teledyne ISCO CombiFlash® (4 g silica column, eluting 0-100% 3:1 EtOAc:EtOH in isohexane) and reverse phase preparative HPLC (Method 5). LCMS (Method 25): 1.19 min, 491.20 $[M+H]^+$ $^1H$ NMR (400 MHz, DMSO-$d_6$) δ 10.31 (s, 1H), 8.18-8.09 (m, 3H), 7.60 (dd, 1H), 7.45 (d, 1H), 6.95 (d, 1H), 6.25 (s, 1H), 4.70-4.65 (m, 1H), 4.04 (s, 3H), 3.48 (s, 3H), 2.17 (s, 1H), 2.10 (s, 3H), 1.82 (s, 3H), 1.76-1.40 (m, 12H).

Example 215: 1-methyl-N—((S)-1-((1r,4S)-4-methylcyclohexyl)-2-oxo-2-((1',2',4'-trimethyl-6'-oxo-1',6'-dihydro-[3,3'-bipyridin]-6-yl)amino)ethyl)-1H-pyrazole-5-carboxamide

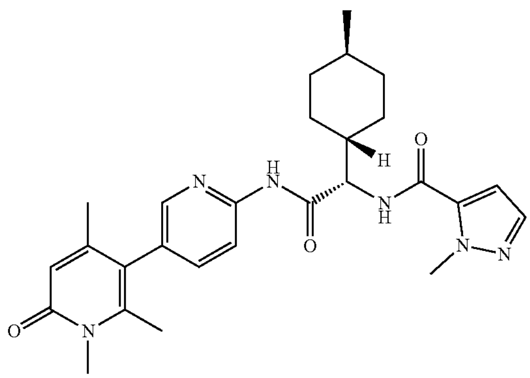 [SMILES: Cc1cc(=O)n(C)c(C)c1-c1ccc(NC(=O)[C@@H](NC(=O)c2ccnn2C)[C@H]2CC[C@H](C)CC2)nc1]

The title compound (3 mg) was prepared from Intermediate 3.215 (16 mg, 0.04 mmol), 2-methylpyrazole-3-carboxylic acid (6 mg, 0.05 mmol, CAS: 16034-46-1), HATU (24 mg, 0.06 mmol) and DIPEA (0.01 mL, 0.08 mmol) in accordance with the procedure described for Example 109 in DMF. The crude product was purified by an SCX cartridge (1 g, washed with MeOH and eluted with 0.7 M methanolic ammonia), flash column chromatography on the Teledyne ISCO CombiFlash® (4 g silica column, eluting 0-100% 3:1 EtOAc:EtOH in isohexane) and reverse phase preparative HPLC (Method 5). LCMS (Method 28): 1.34 min, 491.18 $[M+H]^+$; $^1H$ NMR (400 MHz, DMSO-$d_6$) δ: 10.31 (s, 1H), 8.20-8.10 (m, 3H), 7.59 (d, 1H), 7.45 (d, 1H), 6.96 (d, 1H), 6.25 (s, 1H), 4.62-4.56 (m, 1H), 4.04 (s, 3H), 3.48 (s, 3H), 2.10 (s, 3H), 1.89-1.80 (m, 5H), 1.78-1.68 (m, 3H), 1.37-1.23 (m, 2H), 1.19-1.14 (m, 1H), 0.96-0.85 (m, 5H).

Example 216: (S)—N-(1-cycloheptyl-2-oxo-2-((5-(1,3,5-trimethyl-1H-pyrazol-4-yl)pyridin-2-yl)amino)ethyl)-1-methyl-1H-pyrazole-5-carboxamide

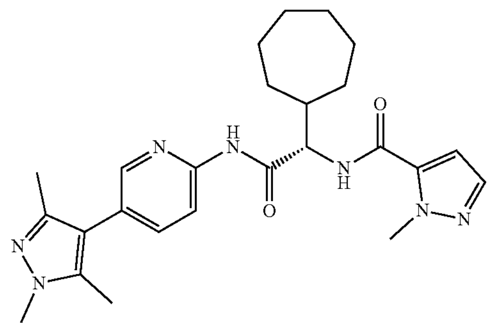 [SMILES: Cc1nn(C)c(C)c1-c1ccc(NC(=O)[C@@H](NC(=O)c2ccnn2C)C2CCCCCC2)nc1]

The title compound (29 mg) was prepared from Intermediate 3.216 (67 mg, 0.19 mmol), 2-methylpyrazole-3-carboxylic acid (24 mg, 0.19 mmol, CAS: 16034-46-1), HATU (79 mg, 0.21 mmol) and DIPEA (0.05 mL, 0.29 mmol) in accordance with the procedure described for Example 109 in DMF. The crude product was purified by flash column chromatography on the Teledyne ISCO CombiFlash® (12 g silica column, eluting 0-100% EtOAc in isohexane). LCMS (Method 27): 1.84 min, 464.3 $[M+H]^+$; $^1H$ NMR (400 MHz, DMSO-$d_6$) δ: 10.64 (s, 1H), 8.46 (d, 1H), 8.21 (dd, 1H), 8.13 (d, 1H), 7.68 (dd, 1H), 7.47 (d, 1H), 7.04 (d, 1H), 4.62 (t, 1H), 4.02 (s, 3H), 3.70 (s, 3H), 2.21 (s, 3H), 2.12 (s, 4H), 1.73-1.37 (m, 12H).

Example 217: 1-methyl-N—((S)-1-((1r,4S)-4-methylcyclohexyl)-2-oxo-2-((5-(1,3,5-trimethyl-1H-pyrazol-4-yl)pyridin-2-yl)amino)ethyl)-1H-pyrazole-5-carboxamide

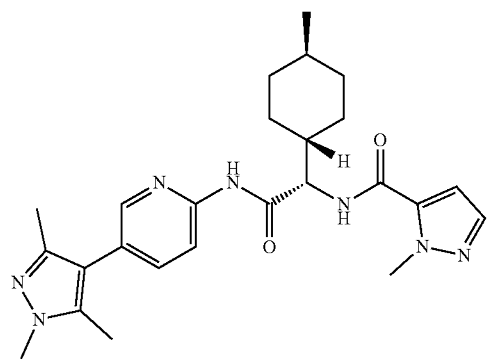 [SMILES: Cc1nn(C)c(C)c1-c1ccc(NC(=O)[C@@H](NC(=O)c2ccnn2C)[C@H]2CC[C@H](C)CC2)nc1]

The title compound (19 mg) was prepared from Intermediate 3.217 (46 mg, 0.1 mmol), 2-methylpyrazole-3-carboxylic acid (13 mg, 0.1 mmol, CAS: 16034-46-1), HATU (39 mg, 0.1 mmol) and DIPEA (0.02 mL, 0.11 mmol) in accordance with the procedure described for Example 109 in DMF. The crude product was purified by flash column chromatography on the Teledyne ISCO CombiFlash® (12 g silica column, eluting 0-100% EtOAc in isohexane) and reverse phase preparative HPLC (Method 6). LCMS (Method 28): 1.45 min, 464.2 $[M+H]^+$; $^1H$ NMR (400 MHz, DMSO-$d_6$) δ: 10.62 (s, 1H), 8.47 (d, 1H), 8.21 (d, 1H), 8.13 (d, 1H), 7.68 (dd, 1H), 7.47 (d, 1H), 7.04 (d, 1H), 4.53 (t, 1H), 4.02 (s, 3H), 3.70 (s, 3H), 2.21 (s, 3H), 2.12 (s, 3H), 1.87-1.75 (m, 2H), 1.73-1.65 (m, 2H), 1.63-1.53 (m, 1H), 1.34-1.20 (m, 2H), 1.13-1.01 (m, 1H), 0.94-0.83 (m, 5H).

Example 218: (S)—N-(1-cycloheptyl-2-((6-(3,5-dimethyl-1H-pyrazol-4-yl)pyridin-3-yl)amino)-2-oxoethyl)-1-methyl-1H-pyrazole-5-carboxamide The title compound (59 mg) was prepared from Intermediate 3.208 (0.1 g, 0.21 mmol), 2-methylpyrazole-3-carboxylic acid (32 mg, 0.25 mmol, CAS: 16034-46-1), HATU (95 mg, 0.25 mmol) and DIPEA (0.2 mL, 1.2 mmol) in accordance with the procedure described for Example 109 in DMF. The crude product was purified by an SCX cartridge (1 g, washed with MeOH and eluted with 0.7 M methanolic ammonia) and flash column chromatography on the Teledyne ISCO CombiFlash® (4 g silica column, eluting 0-100% 3:1 EtOAc:EtOH in isohexane). LCMS (Method 28): 1.27 min, 450.3 $[M+H]^+$; $^1$H NMR (400 MHz, DMSO-$d_6$) δ: 12.32 (s, 1H), 10.42 (s, 1H), 8.80 (d, 1H), 8.56 (d, 1H), 8.07 (dd, 1H), 7.46 (d, 1H), 7.36 (d, 1H), 7.07 (d, 1H), 4.55-4.45 (m, 1H), 4.04 (s, 3H), 2.33 (s, 3H), 2.28 (s, 3H), 2.17-2.07 (m, 1H), 1.79-1.30 (m, 12H).

Example 219: 1-methyl-N—((S)-2-((5-(1-methyl-4-(trifluoromethyl)-1H-pyrazol-5-yl)pyridin-2-yl)amino)-1-((1r,4S)-4-methylcyclohexyl)-2-oxoethyl)-1H-pyrazole-5-carboxamide

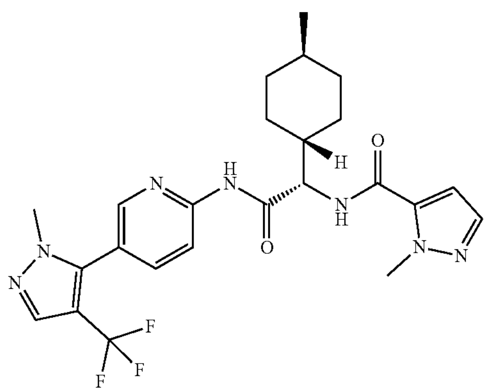 [SMILES: Cn1nccc1C(=O)N[C@H](C(=O)Nc1ccc(-c2c(C(F)(F)F)cnn2C)cn1)[C@H]1CC[C@H](C)CC1]

The title compound (27 mg) was prepared from Intermediate 3.219 (85 mg, 0.22 mmol), 2-methylpyrazole-3-carboxylic acid (34 mg, 0.27 mmol, CAS: 16034-46-1), T3P® (50% w/w solution in EtOAc; 0.18 mL, 0.3 mmol) and DIPEA (0.11 mL, 0.65 mmol) in accordance with the procedure described for Example 165. The crude product was purified by flash column chromatography on the Biotage Isolera One™ (10 g silica column eluting 0-2.5% MeOH in DCM), reverse phase preparative HPLC (Method 2) and flash column chromatography on the Biotage Isolera One™ (5 g silica column, eluting 0-75% EtOAc in heptanes). LCMS (Method 15): 2.79 min, 504.2 $[M+H]^+$; $^1$H NMR (400 MHz, MeOD) δ: 8.31-8.25 (m, 1H), 8.22 (dd, 1H), 7.76 (dd, 1H), 7.75-7.73 (m, 1H), 7.38 (d, 1H), 6.81 (d, 1H), 4.46 (d, 1H), 3.99 (s, 3H), 3.68 (s, 3H), 1.87-1.75 (m, 2H), 1.73-1.64 (m, 3H), 1.37-1.03 (m, 3H), 0.89 (q, 2H), 0.81 (d, 3H).

Example 220: N-(2-((5-(1,4-dimethyl-1H-pyrazol-5-yl)pyridin-2-yl)amino)-1-(dispiro[2.1.2$^5$.2$^3$]nonan-4-yl)-2-oxoethyl)-1-methyl-1H-pyrazole-5-carboxamide

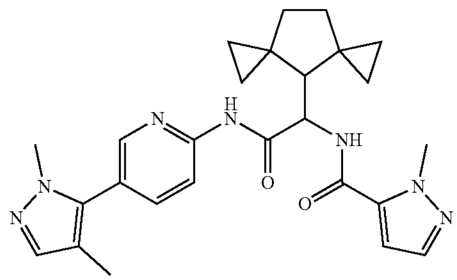 [SMILES: Cc1cnn(C)c1-c1ccc(NC(=O)C(NC(=O)c2ccnn2C)C2C3(CC3)CCC23CC3)nc1]

The title compound (1 mg) was prepared from Intermediate 3.220 (16 mg, 0.04 mmol), 2-methylpyrazole-3-carboxylic acid (6.9 mg, 0.06 mmol, CAS: 16034-46-1), T3P® (50% w/w solution in EtOAc; 0.04 mL, 0.06 mmol) and DIPEA (0.02 mL, 0.13 mmol) in accordance with the procedure described for Example 165. An additional portion of HATU (25.0 mg, 0.07 mmol) and DIPEA (0.01 mL, 0.07 mmol) were added after 16 h and the mixture stirred at rt for a further 2 h. The crude product was purified by preparative reverse phase HPLC (Method 2), followed by further purification by preparative reverse phase HPLC (2×Method 4). The product was further purified by flash column chromatography on the Biotage Isolera One™ (10 g silica column, eluting 0-100% EtOAc in heptanes). LCMS (Method B): 2.55 min, 474.2 $[M+H]^+$; $^1$H NMR (400 MHz, DMSO-$d_6$) δ: 11.03 (s, 1H), 8.43-8.35 (m, 2H), 8.22 (dd, 1H), 7.89 (dd, 1H), 7.48 (d, 1H), 7.36 (d, 1H), 6.98 (d, 1H), 5.02 (dd, 1H), 4.06 (s, 3H), 3.73 (s, 3H), 2.44 (td, 1H), 2.20 (td, 1H), 1.99 (d, 3H), 1.41-1.33 (m, 2H), 1.27 (dd, 2H), 1.00-0.92 (m, 1H), 0.62 (dd, 1H), 0.47-0.35 (m, 5H).

Biological Assays

The biological activity of the compounds of the present disclosure was determined utilising the assays described herein. Activity is reported as a $pK_D$, where $pK_D=-Log_{10}(K_D)$, or a $pIC_{50}$, where $pIC_{50}=-Log_{10}(IC_{50})$. These values may fluctuate depending on the daily assay performance, fluctuations of this kind are known to those skilled in the art. These results show that the compounds of the present disclosure are capable of inhibiting the biological action of IL-17A.

Surface Plasmon Resonance (SPR) Analysis of Compound Interactions with IL-17A

SPR analysis was carried out using a multi-cycle kinetics (MCK) method on a Biacore T200 or 8K instrument (GE Healthcare). The Biacore NTA chip (Series S sensor chip, GE Healthcare) was primed with HBS-N buffer (GE Healthcare) containing 10 μM EDTA and 0.005% (v/v) Tween-20 and was then conditioned with 350 mM EDTA for 60 seconds (s). The chip was washed with 500 μM nickel chloride for 60 s to form a nickel chelate on the chip followed by a 1:1 mixture of NHS:EDC (5.8 mg/mL and 37.5 mg/mL) for 420 s to activate the surface of the chip for amine coupling by modification of the carboxymethyl groups to N-hydroxysuccinimide (NHS) esters. In one flow cell of the NTA chip, the recombinant human IL-17A protein (C-6×His-tag, Speed Biosystems YSP6965) at a concentration of 1072 nM was then injected onto the chip until the immobilisation level reached approximately 4000 RU (Resonance Units). Therefore, the IL-17A protein was immobilised onto the chip via its 6-His-tag and through amine coupling. A blank flow cell was also prepared by activation of the surface with NHS:EDC but no nickel chloride or protein injections. Following protein immobilisation, the chip was washed with 1 M ethanolamine for 420 s to deactivate any remaining NHS-esters and with 350 mM EDTA for 60s to remove any non-covalently bound protein.

Compounds were diluted from 10 mM stocks in DMSO to give a 7-point dose response curve in HBS-N buffer containing 10 M EDTA, 0.005% (v/v) Tween-20 and 1% DMSO with 3.16 M as the highest concentration. Prior to compound testing, the NTA chip was primed with HBS-N buffer containing 10 M EDTA, 0.005% (v/v) Tween-20 and 1% DMSO. A single injection of 10 mM glycine, pH1.5 was passed across the chip for 60 s to aid equilibration of the chip surface and this was also used to regenerate the chip following injection of each compound concentration. Compounds were injected onto the chip for 240 s at a flow rate of 30 μL per min followed by a dissociation step for 540 s.

Analysis of kinetic parameters was conducted using the Biacore Evaluation Software (GE Healthcare). Blank-subtracted data were fitted using a 1:1 binding model and the on rate ($k_a$) and off rate ($k_d$) were determined.

A negative control to assess specificity of compound binding to IL-17A was conducted by immobilising his-tagged human IL-17E protein and conducting the same analysis as for IL-17 Å.

The dissociation constant ($K_D$) was calculated using the equation $K_D=k_a/k_d$ and is reported as a $pK_D$ value.

Selected example compounds tested in the SPR assay were found to have $pK_D$ values >7.0.

IL-17A AlphaLISA Assay

The ability of the compounds to block binding of IL-17A to its receptor, IL-17RA, was analysed in a competition assay using AlphaLISA technology (Perkin Elmer). The assay is a bead based AlphaLISA where the IL-17RA is captured on the acceptor bead via an Fc tag and IL-17A is captured on the streptavidin donor bead via a biotinylated anti-IL17A antibody.

Assay buffer was prepared by adding 0.05% Tween-20 (v/v) and 0.1% BSA to Phosphate Buffered Saline (PBS). The assay was carried out in 384-well white low volume plates (Corning 4512). 10 L of a 7.5 nM stock of human recombinant IL-17A (R&D Systems 7955-IL/CF) diluted in assay buffer was dispensed into the assay plate and compounds or DMSO vehicle control were added in a volume of 75 nL using a D300 dispenser (Hewlett Packard). The compounds were pre-incubated with the IL-17A for 24 h at room temperature (or for 30 min, where indicated by * in Table A below) prior to addition of 5 μL of a 5 nM stock of human recombinant IL-17RA/Fc chimera (R&D Systems 177-IR-100) diluted in assay buffer. The IL-17A was incubated with the receptor for a further 90 minutes at room temperature before addition of 5 μL of a mixture of anti-human Fc IgG acceptor beads (75 μg/mL, Perkin Elmer AL103C) and anti-IL-17A biotin conjugated antibody (5 nM, Enzo Life Sciences, ENZ-ABS278-0100) in assay buffer. After a further 30 min incubation at room temperature, 5 μL of streptavidin donor beads (75 g/mL, Perkin Elmer 6760002S) were added and the plate was incubated for 3 h in the dark.

The luminescence signal was measured using an Enspire plate reader (Perkin Elmer) with excitation at 680 nm and emission at 615 nm. Data were analysed using GraphPad Prism and fitted to a 4-parameter logistic equation. The $IC_{50}$ values were calculated using the DMSO vehicle as the negative control and a high concentration (6 μM) of a reference IL-17A inhibitor as the positive control.

Activity of the Example compounds is reported as a $PIC_{50}$ value in Table A.

TABLE A

| Ex. | AlphaLISA $pIC_{50}$ | Ex. | AlphaLISA $pIC_{50}$ | Ex. | AlphaLISA $pIC_{50}$ | Ex. | AlphaLISA $pIC_{50}$ |
|---|---|---|---|---|---|---|---|
| 1 | 7.3 | 2 | 7.5 | 3 | 7.9 | 4 | 7.7 |
| 5 | 7.2 | 6 | 7.9 | 7 | 7.9 | 8 | 7.8 |
| 9 | 8.2 | 10 | 8.1 | 11 | 7.8 | 12 | 8.0 |
| 13 | 8.1 | 14 | 7.4 | 15 | 7.3 | 16 | 7.8 |
| 17 | 7.8 | 18 | 7.5 | 19 | 7.2 | 20 | 7.5 |
| 21 | 7.4 | 22 | 7.6 | 23 | 7.4 | 24 | 7.5 |
| 25 | 8.3 | 26 | 8.1 | 27 | 8.3 | 28 | 8.1 |
| 29 | 7.7 | 30 | 7.4 | 31 | 6.2 | 32 | 7.9 |
| 33 | 7.1 | 34 | 6.7 | 35 | 7.6 | 36 | 7.1 |
| 37 | 7.4 | 38 | 7.0 | 39 | 6.7 | 40 | 7.2 |
| 41 | 6.7 | 42 | 7.3 | 43 | 6.9 | 44 | 6.6 |
| 45 | 7.0 | 46 | 7.0 | 47 | 7.6 | 48 | 6.8 |
| 49 | 7.0 | 50 | 7.4 | 51 | 7.6 | 52 | 7.9 |
| 53 | 6.6 | 54 | 6.5 | 55 | 7.0 | 56 | 7.0 |
| 57 | 6.9 | 58 | 6.5 | 59 | 7.0 | 60 | 7.4 |
| 61 | 7.4 | 62 | 6.1 | 63 | 6.8 | 64 | 6.4 |
| 65 | 7.3 | 66 | 7.6 | 67 | 6.4 | 68 | 8.1 |
| 69 | 7.1 | 70 | 6.5 | 71 | 7.8 | 72 | 7.1 |
| 73 | 7.6 | 74 | 7.5 | 75 | 7.5 | 76 | 6.2 |
| 77 | 6.9 | 78 | 7.6 | 79 | 6.6 | 80 | 6.5 |
| 81 | 7.9 | 82 | 7.6 | 83 | 7.2 | 84 | 7.5 |
| 85 | 7.2 | 86 | 6.6 | 87 | 6.3 | 88 | 6.4 |
| 89 | 6.0 | 90 | 7.2 | 91 | 6.6 | 92 | 7.7 |
| 93 | 7.3 | 94 | 6.9 | 95 | 7.0 | 96 | 7.3 |
| 97 | 7.1 | 98 | 6.6* | 99 | 6.7* | 100 | 6.7* |
| 101 | 6.0* | 102 | 6.0* | 103 | 6.9* | 104 | 7.1* |
| 105 | 6.8* | 106 | 7.0* | 107 | 6.8* | 108 | 6.9* |
| 109 | 7.0* | 110 | 7.1* | 111 | 7.1* | 112 | 7.0* |
| 113 | 6.8* | 114 | 6.8* | 115 | 6.9* | 116 | 7.2* |
| 117 | 6.3* | 118 | 6.8* | 119 | 6.3* | 120 | 6.6* |
| 121 | 6.6* | 122 | 7.4* | 123 | 7.4* | 124 | 7.4* |
| 125 | 6.8* | 126 | 7.3* | 127 | 7.4* | 128 | 6.6* |
| 129 | 6.5* | 130 | 6.5* | 131 | 7.2* | 132 | 7.1* |
| 133 | 6.6* | 134 | 6.7* | 135 | 6.4* | 136 | 7.2* |
| 137 | 6.7* | 138 | 6.6* | 139 | 6.9* | 140 | 6.2* |
| 141 | 6.8* | 142 | 6.4* | 143 | 6.1* | 144 | 6.1* |
| 145 | 6.4* | 146 | 6.3* | 147 | 6.4* | 148 | 6.7* |
| 149 | 7.1* | 150 | 6.4* | 151 | 6.1* | 152 | 6.1* |
| 153 | 6.4* | 154 | 6.6* | 155 | 7.0* | 156 | 6.4* |
| 157 | 6.6* | 158 | 6.2* | 159 | 7.0* | 160 | 6.7* |
| 161 | 6.7* | 162 | 6.7* | 163 | 7.2* | 164 | 7.2* |
| 165 | 6.2* | 166 | 6.2* | 167 | 6.5* | 168 | 6.8* |
| 169 | 7.0* | 170 | 6.8* | 171 | 7.1* | 172 | 6.7* |
| 173 | 6.8* | 174 | 6.8* | 175 | 7.5* | 176 | 7.4* |
| 177 | 6.7* | 178 | 7.1* | 179 | 6.3* | 180 | 6.8* |
| 181 | 6.8* | 182 | 7.5* | 183 | 6.1* | 184 | 6.6* |
| 185 | 6.2* | 186 | 6.4* | 187 | 6.4* | 188 | 7.0* |
| 189 | 6.8* | 190 | 6.1* | 191 | 7.4* | 192 | 6.7* |
| 193 | 6.6* | 194 | 6.8* | 195 | 6.3* | 196 | 6.6* |
| 197 | 6.0* | 198 | 6.7* | 199 | 7.0* | 200 | 6.4* |
| 201 | 7.1* | 202 | 6.8* | 203 | 7.1* | 204 | 6.7* |
| 205 | 6.6* | 206 | 6.9* | 207 | 6.3* | 208 | 7.2* |
| 209 | 6.1* | 210 | 7.2* | 211 | 6.8* | 212 | 7.0* |
| 213 | 7.0* | 214 | 6.8* | 215 | 6.9* | 216 | 6.3* |
| 217 | 6.3* | 218 | 6.8* | 219 | 6.9* | 220 | 7.5* |

Inhibition of IL-17A Induced Secretion of IL-8 in Primary Human Epidermal Keratinocytes This assay was used to determine the ability of compounds to inhibit IL-17A induced stimulation of IL-8 secretion in normal human epidermal keratinocytes (NHEK). It is known that IL-17A in combination with other cytokines found in psoriatic skin including TNF-αL and Oncostatin M can stimulate IL-8 production by human epidermal keratinocytes (Guilloteau et al., J Immunol 2010, 184, 5263-5270).

NHEK were isolated from skin samples from plastic surgery procedures and were cryopreserved. NHEK were seeded in 96-well plates (20,000 cells per well) and cultured for 48 hours at 37°, 5% $CO_2$ in medium (Keratinocyte-SFM (Gibco™) supplemented with 0.25 ng/mL EGF, 25 μg/mL pituitary extract and 25 μg/mL gentamycin) with medium replaced after 24 h of incubation. The compounds were prepared from 10 mM stocks in DMSO and were diluted in culture medium containing a mixture of cytokines (3 ng/mL each of recombinant human IL-17A (R&D Systems 7955-IL), recombinant human TNF-α (R&D Systems 210-TA) and recombinant human Oncostatin M (R&D Systems 295-OM)) and were left for 30 min before being added to the cells. The medium was replaced by culture medium containing the mix of cytokines with test compounds or vehicle control and the cells were incubated for a further 48 h. The final concentration of DMSO in the assay was 0.1% for all conditions tested. At the end of the incubation, the culture supernatants were collected for quantification of IL-8 release which was measured using a Duoset IL-8 ELISA kit (R&D Systems DY208) according to the manufacturer's instructions. The viability of the NHEK cell layers was then evaluated using a standard MTT (tetrazolium salt) reduction assay.

Data were analysed using GraphPad Prism software and fitted to a 4-parameter logistic equation to determine the $IC_{50}$ values. For this analysis, as the compounds only inhibit the IL-17A stimulated response, the maximum inhibition was calculated using the level of IL-8 secreted by the NHEK after stimulation with TNF-α and Oncostatin M in the absence of IL-17A and this value was constrained to 100% inhibition. The minimum inhibition was calculated using the level of IL-8 secreted by NHEK after stimulation with the cytokine mix (IL-17 Å, TNF-α and Oncostatin M) with no compound present.

Selected example compounds tested in the NHEK assay were found to have $pIC_{50}$ values>5.0.

While particular embodiments of the present disclosure have been shown and described herein, it will be obvious to those skilled in the art that such embodiments are provided by way of example only. Numerous variations, changes, and substitutions will occur to those skilled in the art without departing from the disclosure. It should be understood that various alternatives to the embodiments of the disclosure described herein may be employed in practising the disclosure. It is intended that the following claims define the scope of the disclosure and that methods and structures within the scope of these claims and their equivalents be covered thereby. The disclosures of all patent and scientific literature cited herein are expressly incorporated herein in their entirety by reference. To the extent that any incorporated material is inconsistent with the express content of this disclosure, the express content controls.

The invention claimed is:

1. A compound of Formula I

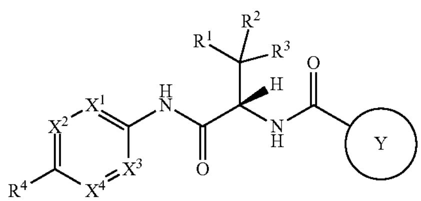

wherein:

two of $X^1$, $X^2$, $X^3$, and $X^4$ are $CR^5$, and two are N; or three of $X^1$, $X^2$, $X^3$, and $X^4$ are $CR^5$, and the other is N;

Y is heteroaryl optionally substituted by one or more substituents independently selected from the group consisting of halo, $C_{1-4}$alkyl, $C_{1-4}$alkoxy, and $C_{1-4}$haloalkyl;

$R^1$ and $R^2$:

(A) are both phenyl optionally substituted with one or more substituents independently selected from the group consisting of halo, $C_{1-4}$alkyl, $C_{1-4}$alkoxy, and $C_{1-4}$haloalkyl, and wherein the phenyl groups are optionally linked by a bond or a $C_{1-2}$alkylene moiety; OR (B) together with the carbon atom to which they are attached form a 4- to 10-membered cycloalkyl or a 4- to 10-membered heterocyclyl ring, wherein the cycloalkyl or heterocyclyl ring:

a. is optionally substituted with one or more substituents independently selected from the group consisting of halo, $C_{1-4}$alkyl, $C_{1-4}$alkoxy, $C_{1-4}$haloalkyl, and $C_{1-4}$haloalkoxy;

b. optionally comprises one or two C═C double bonds;

c. is optionally bridged by a $C_{1-3}$alkylene group connecting two carbon atoms of the ring; and d. is optionally spiro-attached to a $C_{3-5}$cycloalkyl group;

$R^3$ is hydrogen, fluoro, or $C_{1-4}$alkyl;

$R^4$ is:

(A) a 5- to 10-membered heteroaryl optionally substituted by one or more substituents independently selected from the group consisting of hydroxy, halo, $C_{1-4}$alkyl, $C_{1-4}$alkoxy, $C_{1-4}$haloalkyl, cyano, $NR^6R^7$, C (O) $NR^8R^9$, $CO_2R^{10}$, and $C_{1-3}$alkylene-$R^{11}$;

(B) 5- to 6-membered heteroaryl ring, said ring being fused to a 5- or 6-membered cycloalkyl or heterocyclyl ring, each of which is optionally substituted by one or more substituents independently selected from the group consisting of hydroxy, halo, oxo, $C_{1-4}$alkyl, $C_{1-4}$alkoxy, $C_{1-4}$haloalkyl, cyano $NR^6R^7$, $C(O)NR^8R^9$, $CO_2R^{10}$, and $C_{1-3}$alkylene-$R^{11}$;

(C) a 5- or 6-membered cycloalkyl or a 5- or 6-membered heterocyclyl ring, said ring being fused to a phenyl or 5- to 6-membered heteroaryl ring, each of which rings is optionally substituted by one or more substituents independently selected from the group consisting of hydroxy, halo, oxo, $C_{1-4}$alkyl, $C_{1-4}$alkoxy, $C_{1-4}$haloalkyl, cyano, $NR^6R^7$, C(O) $NR^8R^9$, $CO_2R^{10}$, and $C_{1-3}$alkylene-$R^{11}$; or (D) a partially unsaturated heterocyclic ring, optionally fused to a 5- to 6-membered heteroaryl ring and optionally substituted with one or more substituents independently selected from the group consisting of hydroxy, halo, oxo, $C_{1-4}$alkyl, $C_{1-4}$alkoxy, $C_{1-4}$haloalkyl, cyano, $NR^6R^7$, $C(O)NR^8R^9$, and $CO_2R^{10}$;

$R^5$ is hydrogen, fluoro, chloro, methyl, methoxy, or trifluoromethyl;

$R^{11}$ is hydroxy, halo, $C_{1-4}$alkoxy, cyano, $NR^{12}R^{13}$, C(O) $R^{14}$, aryl or heteroaryl;

$R^{14}$ is hydroxy, $C_{1-4}$alkyl, $C_{1-4}$alkoxy or $NR^{15}R^{16}$;

$R^6$, $R^7$, $R^8$, $R^9$, $R^{10}$, $R^{12}$, and $R^{13}$ are independently hydrogen or $C_{1-4}$alkyl;

$R^{15}$ and $R^{16}$ are independently hydrogen or $C_{1-4}$alkyl; or $R^{15}$ and $R^{16}$, taken together with the nitrogen atom to which they are attached, form a 3- to 7-membered heterocyclyl ring, the ring optionally containing a further heteroatom selected from the group consisting of O, S, and N and the ring being optionally substituted with $C_{1-4}$alkyl;

or a pharmaceutically acceptable salt thereof.

2. The compound according to claim 1, wherein $X^1$ is N and $X^2$, $X^3$, and $X^4$ are CH.

3. The compound according claim 1, wherein Y is:

(i) a 5- or 6-membered heteroaryl ring, said ring being optionally fused to a 5- or 6-membered cycloalkyl or heterocyclyl ring, each of which is optionally substituted by one or more substituents independently selected from the group consisting of halo, $C_{1-4}$alkyl, $C_{1-4}$alkoxy, and $C_{1-4}$haloalkyl;

(ii) a heteroaryl ring optionally substituted by one or more substituents independently selected from the group consisting of halo, $C_{1-3}$alkyl, $C_{1-2}$alkoxy, and $C_{1-2}$haloalkyl;

(iii) a 5- to 6-membered heteroaryl optionally substituted by one or more substituents independently selected from the group consisting of halo and methyl;

(iv) a 5- to 6-membered heteroaryl ring substituted in a position ortho to the NHC(O)-moiety by methyl or ethyl; or (v) selected from the group consisting of

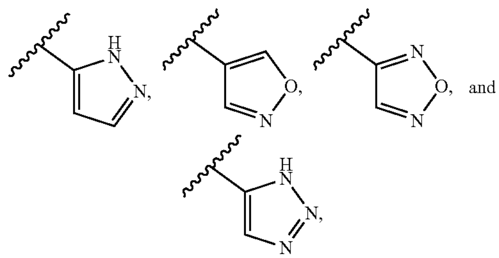

and ∿∿∿ is the point of attachment to the rest of the wherein compound of Formula I and Y is optionally substituted by one or more substituents independently selected from the group consisting of halo, $C_{1-3}$alkyl, $C_{1-2}$alkoxy, and $C_{1-2}$haloalkyl.

4. The compound according to claim 1, wherein $R^1$ and $R^2$ are both phenyl optionally substituted with one or more substituents independently selected from the group consisting of fluoro and methyl.

5. The compound according to claim 1, wherein $R^1$ and $R^2$ together with the carbon atom to which they are attached form:

(i) a 5- to 8-membered cycloalkyl ring, wherein the cycloalkyl ring:

a. is optionally substituted with one or more substituents independently selected from the group consisting of halo, $C_{1-2}$alkyl, $C_{1-2}$alkoxy, and $C_{1-2}$haloalkyl;

b. optionally comprises one or two C═C double bonds;

c. is optionally bridged by a $C_{1-3}$alkylene group connecting two carbon atoms of the ring; and d. is optionally spiro-attached to a $C_{3-5}$cycloalkyl group;

(ii) a ring selected from the group consisting of:

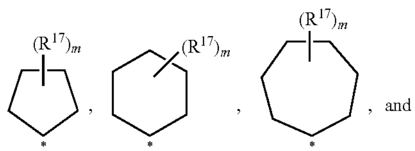

-continued

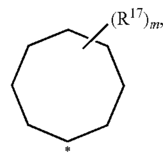

wherein * is the carbon atom to which $R^1$ and $R^2$ are attached, each occurrence of $R^{17}$ is independently selected from the group consisting of halo, $C_{1-2}$alkyl, $C_{1-2}$alkoxy, and $C_{1-2}$haloalkyl, and m is 0, 1, 2 or 3; or (iii)

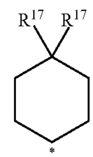

wherein* is the carbon atom to which $R^1$ and $R^2$ are attached, and each $R^{17}$ is independently selected from the group consisting of hydrogen, fluoro, methyl, and trifluoromethyl.

6. The compound according to claim 1, wherein $R^3$ is hydrogen.

7. The compound according to claim 1, wherein $R^4$ is:

(i) a 5- to 10-membered heteroaryl ring, optionally substituted by one or more substituents independently selected from the group consisting of hydroxy, halo, $C_{1-4}$alkyl, $C_{1-4}$alkoxy, $C_{1-2}$fluoroalkyl, cyano, $NR^6R^7$, $C(O)NR^8R^9$, and $C_{1-3}$alkylene-$R^{11}$;

(ii) a 5- to 6-membered monocyclic heteroaryl ring, or a 9- to 10-membered bi cyclic heteroaryl ring, optionally substituted by one or more substituents independently selected from the group consisting of fluoro, chloro, methyl, methoxy, cyano, $NR^6R^7$, and $CH_2$—$R^{11}$; or (iii) a partially unsaturated heterocyclic ring, optionally fused to a 5- to 6-membered heteroaryl ring and optionally substituted with one or more substituents independently selected from the group consisting of hydroxy, halo, oxo, $C_{1-2}$alkyl, $C_{1-2}$alkoxy, $C_{1-2}$haloalkyl, and cyano.

8. The compound according to claim 1, wherein $R^4$ is selected from the group consisting of:

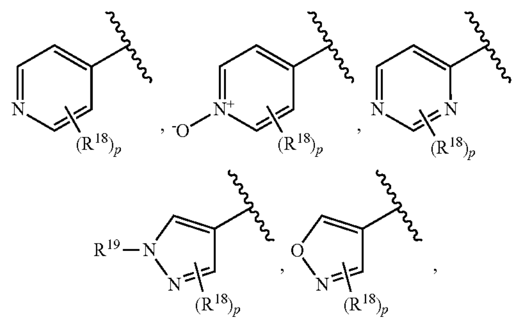

-continued

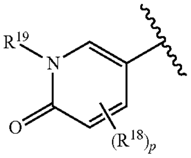, 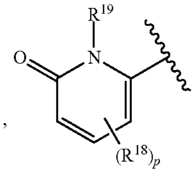,

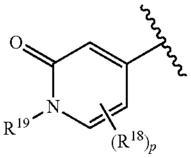, 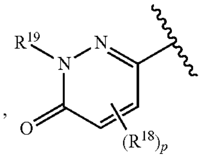,

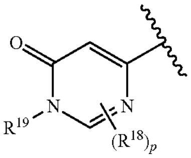, 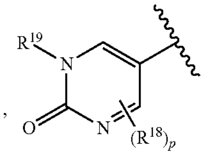,

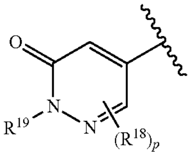, 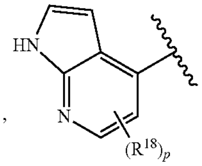,

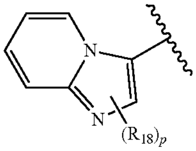, 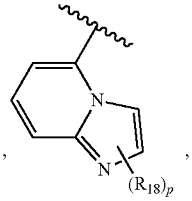,

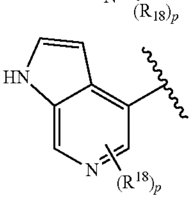, 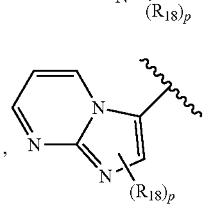,

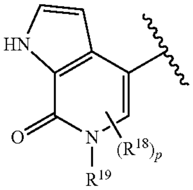, 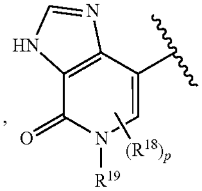,

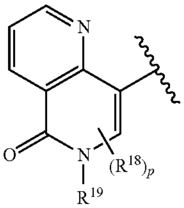, 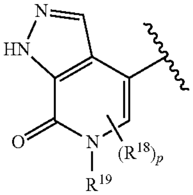,

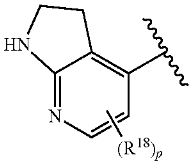, 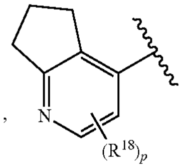,

-continued

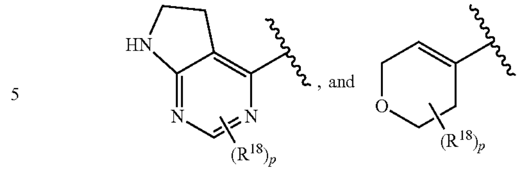

wherein:

∿∿∿ is the point of attachment to the rest of the compound of Formula I;

$R^{18}$ is independently selected from the group consisting of hydroxy, halo, $C_{1-4}$alkyl, $C_{1-4}$alkoxy, $C_{1-4}$haloalkyl, cyano, $NR^6R^7$, and $C_{1-3}$alkylene-$R^{11}$;

$R^{19}$ is independently selected from the group consisting of hydrogen, $C_{1-4}$alkyl, and $C_{1-3}$alkylene-$R^{11}$; and p is 0, 1 or 2;

wherein when $R^4$ is a bicyclic group and p is 1 or 2, then each $R^{18}$ substituent may be present on either ring of the bicyclic group.

9. The compound according to claim 8, wherein $R^{18}$ is independently selected from the group consisting of hydroxy, fluoro, chloro, methyl, methoxy, $CF_3$, $NR^6R^7$, and $C_{1-3}$alkylene-$R^{11}$; and $R^{19}$ is independently selected from the group consisting of hydrogen and methyl.

10. The compound according to claim 1, wherein the compound is of Formula IA, IB, IC or ID:

(IA)

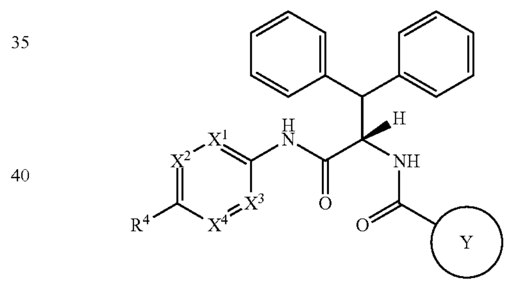

(IB)

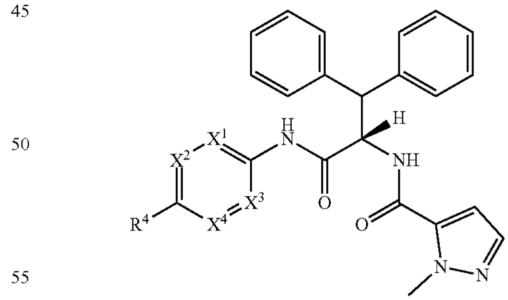

(IC)

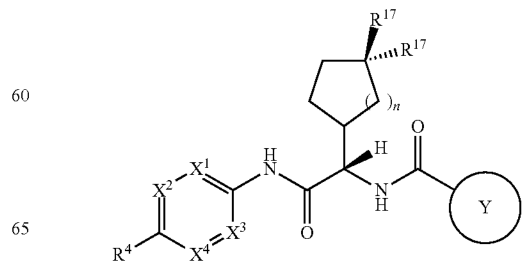

-continued (ID)

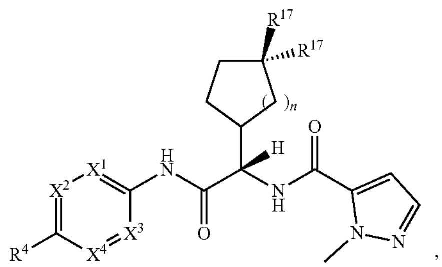

, wherein $X^1$ to $X^4$, Y and $R^4$ are as defined in claim 1; each $R^{17}$ is independently selected from the group consisting of hydrogen, halo, $C_{1-2}$alkyl, $C_{1-2}$alkoxy, and $C_{1-2}$haloalkyl; and n is 1, 2, 3 or 4.

11. The compound according to claim 1, wherein the compound is of Formula IE, IF, IG, IH, IJ, IK, IL or IM:

(IE)

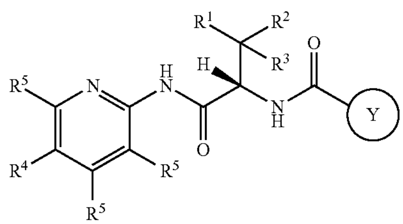

(IF)

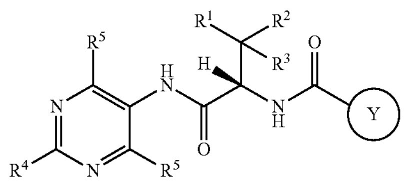

(IG)

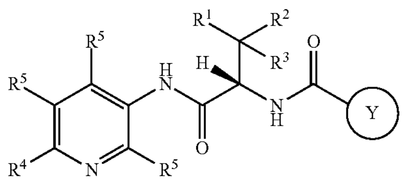

(IH)

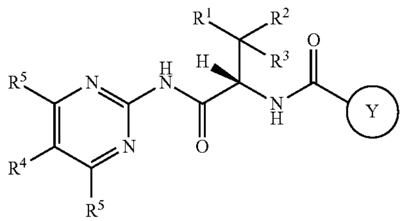

(IJ)

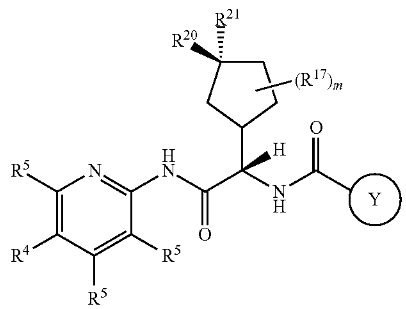

-continued (IK)

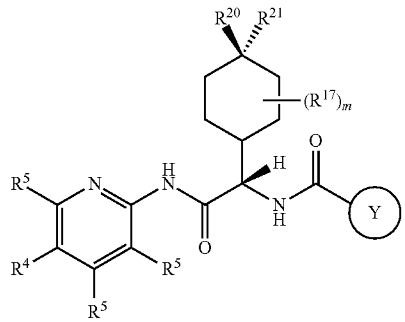

(IL)

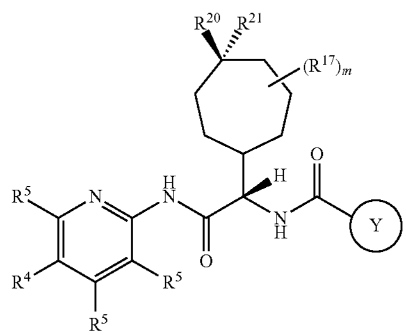

(IM)

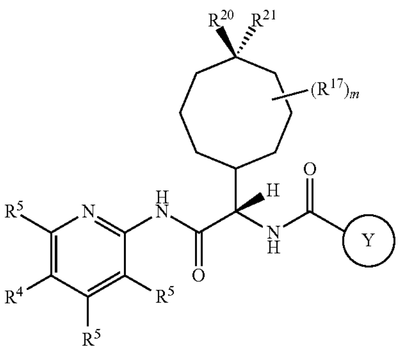

, wherein Y, $R^1$, $R^2$, $R^3$, $R^4$ and $R^5$ are as defined in claim 1; each $R^{17}$ is independently selected from the group consisting of halo, $C_{1-4}$alkyl, $C_{1-4}$alkoxy, $C_{1-4}$haloalkyl, and $C_{1-4}$haloalkoxy;

$R^{20}$ and $R^{21}$ are independently selected from the group consisting of hydrogen, halo, $C_{1-4}$alkyl, $C_{1-4}$alkoxy, $C_{1-4}$haloalkyl, and $C_{1-4}$haloalkoxy; and m is 0 to 4.

12. The compound according to claim 11, wherein $R^{20}$ and $R^{21}$ are independently selected from the group consisting of hydrogen, fluoro, methyl, trifluoromethyl, and methoxy; and m is 0.

13. The compound according to claim 11, wherein each $R^5$ is hydrogen.

14. A compound selected from the group consisting of:

(S)—N-(1-((1',2'-dimethyl-6'-oxo-1',6'-dihydro-[3,3'-bipyridin]-6-yl)amino)-1-oxo-3,3-diphenylpropan-2-yl)-1-methyl-1H-pyrazole-5-carboxamide;

(S)—N-(1-((3',5'-dimethyl-[3,4'-bipyridin]-6-yl)amino)-1-oxo-3,3-diphenylpropan-2-yl)-1-methyl-1H-pyrazole-5-carboxamide;

N—((S)-2-((1',2'-dimethyl-6'-oxo-1',6'-dihydro-[3,3'-bipyridin]-6-yl)amino)-1-((1r,4S)-4-methylcyclohexyl)-2-oxoethyl)-1-methyl-1H-pyrazole-5-carboxamide;

N—((S)-2-((3',5'-dimethyl-[3,4'-bipyridin]-6-yl)amino)-1-((1r,4S)-4-methylcyclohexyl)-2-oxoethyl)-1-methyl-1H-pyrazole-5-carboxamide;

N—((S)-2-((1',2'-dimethyl-6'-oxo-1',6'-dihydro-[3,3'-bipyridin]-6-yl)amino)-1-((1r,4S)-4-methylcyclohexyl)-2-oxoethyl)-1-ethyl-1H-pyrazole-5-carboxamide;

N—((S)-2-((3',5'-dimethyl-[3,4'-bipyridin]-6-yl)amino)-1-((1r,4S)-4-methylcyclohexyl)-2-oxoethyl)-1-ethyl-1H-pyrazole-5-carboxamide;

N—((S)-2-((5-(3,5-dimethylisoxazol-4-yl) pyridin-2-yl)amino)-1-((1r,4S)-4-methylcyclohexyl)-2-oxoethyl)-1-methyl-1H-pyrazole-5-carboxamide;

N—((S)-2-((5-(3,5-dimethyl-1H-pyrazol-4-yl) pyridin-2-yl)amino)-1-((1r,4S)-4-methylcyclohexyl)-2-oxoethyl)-1-methyl-1H-pyrazole-5-carboxamide;

N-(1-Cyclooctyl-2-((5-(3,5-dimethylisoxazol-4-yl) pyridin-2-yl)amino)-2-oxoethyl)-1-methyl-1H-pyrazole-5-carboxamide;

N—((S)-2-((5-(1,4-dimethyl-1H-pyrazol-5-yl) pyridin-2-yl)amino)-1-((1r,4S)-4-methylcyclohexyl)-2-oxoethyl)-1-methyl-1H-pyrazole-5-carboxamide;

(S)—N-(1-Cyclohexyl-2-((5-(3,5-dimethylisoxazol-4-yl) pyridin-2-yl)amino)-2-oxoethyl)-1-isopropyl-1H-pyrazole-5-carboxamide;

N—((S)-2-((5-(3,5-Dimethylisoxazol-4-yl) pyridin-2-yl) amino)-1-((1r,4S)-4-methylcyclohexyl)-2-oxoethyl)-1-ethyl-1H-pyrazole-5-carboxamide;

N—((S)-2-((5-(3,5-dimethylisoxazol-4-yl) pyridin-2-yl) amino)-1-((1r,4S)-4-methylcyclohexyl)-2-oxoethyl)-1-isopropyl-1H-pyrazole-5-carboxamide;

N—((S)-2-((5-(3,5-dimethylisoxazol-4-yl) pyridin-2-yl) amino)-1-((1r,4S)-4-methylcyclohexyl)-2-oxoethyl)-3-ethylisoxazole-4-carboxamide;

N—((S)-2-((5-(3,5-dimethylisoxazol-4-yl) pyridin-2-yl) amino)-1-((1r,4S)-4-methylcyclohexyl)-2-oxoethyl)-3-methylisoxazole-4-carboxamide;

N-(1-Cyclooctyl-2-((5-(1,4-dimethyl-1H-pyrazol-5-yl) pyridin-2-yl)amino)-2-oxoethyl)-1-methyl-1H-pyrazole-5-carboxamide;

(S)—N-(1-Cyclohexyl-2-((5-(3,5-dimethylisoxazol-4-yl) pyridin-2-yl)amino)-2-oxoethyl)-3-ethylisoxazole-4-carboxamide;

(S)—N-(1-Cycloheptyl-2-((5-(3,5-dimethylisoxazol-4-yl) pyridin-2-yl)amino)-2-oxoethyl)-1-methyl-1H-pyrazole-5-carboxamide;

(S)—N-(1-Cycloheptyl-2-((5-(3,5-dimethylisoxazol-4-yl) pyridin-2-yl)amino)-2-oxoethyl)-3-methylisoxazole-4-carboxamide;

(S)—N-(1-Cycloheptyl-2-((5-(3,5-dimethylisoxazol-4-yl) pyridin-2-yl)amino)-2-oxoethyl)-1-methyl-1H-1,2,3-triazole-5-carboxamide;

(S)—N-(1-Cyclohexyl-2-((5-(3,5-dimethylisoxazol-4-yl) pyridin-2-yl)amino)-2-oxoethyl)-1-ethyl-1H-pyrazole-5-carboxamide;

N—((S)-2-((5-(3,5-Dimethylisoxazol-4-yl) pyridin-2-yl) amino)-1-((1r,4S)-4-methylcyclohexyl)-2-oxoethyl)-4-methyl-1,2,5-oxadiazole-3-carboxamide;

(S)—N-(1-Cyclohexyl-2-((5-(3,5-dimethylisoxazol-4-yl) pyridin-2-yl)amino)-2-oxoethyl)-3-methylisoxazole-4-carboxamide;

(S)—N-(1-Cycloheptyl-2-((5-(3,5-dimethylisoxazol-4-yl) pyridin-2-yl)amino)-2-oxoethyl)-1-ethyl-1H-pyrazole-5-carboxamide;

(S)—N-(1-Cycloheptyl-2-((5-(3,5-dimethylisoxazol-4-yl) pyridin-2-yl)amino)-2-oxoethyl)-1-isopropyl-1H-pyrazole-5-carboxamide;

(S)—N-(1-Cycloheptyl-2-((5-(3,5-dimethylisoxazol-4-yl) pyridin-2-yl)amino)-2-oxoethyl)-3-ethylisoxazole-4-carboxamide;

N—((S)-2-((5-(1,4-dimethyl-1H-1,2,3-triazol-5-yl) pyridin-2-yl)amino)-1-((1r,4S)-4-methylcyclohexyl)-2-oxoethyl)-1-methyl-1H-pyrazole-5-carboxamide;

N—((S)-2-((5-(1,4-Dimethyl-1H-pyrazol-5-yl) pyridin-2-yl)amino)-1-((1r,4S)-4-methylcyclohexyl)-2-oxoethyl)-1-ethyl-1H-pyrazole-5-carboxamide;

N—((S)-2-((5-(1,4-Dimethyl-1H-pyrazol-5-yl) pyridin-2-yl)amino)-1-((1r,4S)-4-methylcyclohexyl)-2-oxoethyl)-3-ethylisoxazole-4-carboxamide;

(S)—N-(1-Cycloheptyl-2-((5-(3,5-dimethylisoxazol-4-yl) pyridin-2-yl)amino)-2-oxoethyl)-4-methyl-1,2,5-oxadiazole-3-carboxamide;

(S)—N-(1-Cyclohexyl-2-((5-(3,5-dimethylisoxazol-4-yl) pyridin-2-yl)amino)-2-oxoethyl)-1-methyl-1H-pyrazole-5-carboxamide;

(S)—N-(1-Cyclohexyl-2-((5-(3,5-dimethylisoxazol-4-yl) pyridin-2-yl)amino)-2-oxoethyl)-1,2,3,4-tetrahydropyrrolo [1,2-a]pyrazine-6-carboxamide;

N—((S)-2-((5-(1,4-Dimethyl-1H-pyrazol-5-yl) pyridin-2-yl)amino)-1-((1r,4S)-4-methylcyclohexyl)-2-oxoethyl)-3-methylisoxazole-4-carboxamide;

(S)—N-(1-Cycloheptyl-2-((5-(1,4-dimethyl-1H-pyrazol-5-yl) pyridin-2-yl)amino)-2-oxoethyl)-1-methyl-1H-pyrazole-5-carboxamide;

(S)—N-(1-Cycloheptyl-2-((5-(1,4-dimethyl-1H-pyrazol-5-yl) pyridin-2-yl)amino)-2-oxoethyl)-1-methyl-1H-1,2,3-triazole-5-carboxamide;

(S)—N-(1-Cycloheptyl-2-((5-(1,4-dimethyl-1H-pyrazol-5-yl) pyridin-2-yl)amino)-2-oxoethyl)-4-methyl-1,2,5-oxadiazole-3-carboxamide;

N—((S)-2-((2-(3,5-dimethylisoxazol-4-yl)pyrimidin-5-yl)amino)-1-((1r,4S)-4-methylcyclohexyl)-2-oxoethyl)-1-methyl-1H-pyrazole-5-carboxamide;

(S)—N-(1-Cycloheptyl-2-((5-(1,4-dimethyl-1H-pyrazol-5-yl) pyridin-2-yl)amino)-2-oxoethyl)-3-methylisoxazole-4-carboxamide;

(S)—N-(1-Cycloheptyl-2-((5-(1,4-dimethyl-1H-pyrazol-5-yl) pyridin-2-yl)amino)-2-oxoethyl)-3-(methoxymethyl) isoxazole-4-carboxamide;

N—((S)-2-((6-(3,5-dimethylisoxazol-4-yl) pyridin-3-yl) amino)-1-((1r,4S)-4-methylcyclohexyl)-2-oxoethyl)-1-methyl-1H-pyrazole-5-carboxamide;

6-((S)-2-(1-Ethyl-1H-pyrazole-5-carboxamido)-2-((1r,4S)-4-methylcyclohexyl) acetamido)-3',5'-dimethyl-[3,4'-bipyridine] 1'-oxide;

3-ethyl-N—((S)-1-((1r,4S)-4-methylcyclohexyl)-2-((5-(5-methylpyrimidin-4-yl) pyridin-2-yl)amino)-2-oxoethyl) isoxazole-4-carboxamide;

(S)—N-(1-cycloheptyl-2-((5-(1,4-dimethyl-1H-pyrazol-5-yl) pyridin-2-yl)amino)-2-oxoethyl)-1-ethyl-1H-1,2,3-triazole-5-carboxamide;

N—((S)-2-((5-(3-(methoxymethyl)-5-methylisoxazol-4-yl) pyridin-2-yl)amino)-1-((1r,4S)-4-methylcyclohexyl)-2-oxoethyl)-1-methyl-1H-pyrazole-5-carboxamide;

(S)—N-(1-cycloheptyl-2-((5-(3,5-dimethyl-4H-1,2,4-triazol-4-yl) pyridin-2-yl)amino)-2-oxoethyl)-1-methyl-1H-pyrazole-5-carboxamide;

(S)—N-(1-(4,4-difluorocyclohexyl)-2-((5-(1,4-dimethyl-1H-pyrazol-5-yl) pyridin-2-yl)amino)-2-oxoethyl)-3-ethylisoxazole-4-carboxamide;

N—((S)-2-((6-(1,4-dimethyl-1H-pyrazol-5-yl) pyridin-3-yl)amino)-1-((1r,4S)-4-methylcyclohexyl)-2-oxoethyl)-1-methyl-1H-pyrazole-5-carboxamide;

1-methyl-N—((S)-2-((4-methyl-5-(1-methyl-1H-pyrazol-5-yl) pyridin-2-yl)amino)-1-((1r,4S)-4-methylcyclohexyl)-2-oxoethyl)-1H-pyrazole-5-carboxamide;

N—((S)-2-((2-(1,4-dimethyl-1H-pyrazol-5-yl)pyrimidin-5-yl)amino)-1-((1r,4S)-4-methylcyclohexyl)-2-oxoethyl)-1-ethyl-1H-pyrazole-5-carboxamide;

(S)—N-(1-cycloheptyl-2-((5-(1,4-dimethyl-1H-1,2,3-triazol-5-yl) pyridin-2-yl)amino)-2-oxoethyl)-1-methyl-1H-pyrazole-5-carboxamide;

(S)—N-(1-cycloheptyl-2-((5-(1,4-dimethyl-1H-1,2,3-triazol-5-yl) pyridin-2-yl)amino)-2-oxoethyl)-1-ethyl-1H-pyrazole-5-carboxamide;

(S)—N-(1-cycloheptyl-2-((5-(5-(methoxymethyl)-3-methylisoxazol-4-yl) pyridin-2-yl)amino)-2-oxoethyl)-1-methyl-1H-pyrazole-5-carboxamide;

N—((S)-2-((3'-methoxy-2'-methyl-[3,4'-bipyridin]-6-yl) amino)-1-((1r,4S)-4-methylcyclohexyl)-2-oxoethyl)-1-methyl-1H-pyrazole-5-carboxamide;

N—((S)-2-((2',3'-dimethyl-[3,4'-bipyridin]-6-yl)amino)-1-((1r,4S)-4-methylcyclohexyl)-2-oxoethyl)-1-methyl-1H-pyrazole-5-carboxamide;

N—((S)-2-((2',5'-dimethyl-[3,4'-bipyridin]-6-yl)amino)-1-((1r,4S)-4-methylcyclohexyl)-2-oxoethyl)-1-methyl-1H-pyrazole-5-carboxamide;

N—((S)-2-((6-(1,4-dimethyl-1H-pyrazol-5-yl) pyridin-3-yl)amino)-1-((1r,4S)-4-methylcyclohexyl)-2-oxoethyl)-1-ethyl-1H-pyrazole-5-carboxamide;

N—((S)-2-((6-(1,4-dimethyl-1H-pyrazol-5-yl) pyridin-3-yl)amino)-1-((1,4S)-4-methylcyclohexyl)-2-oxoethyl)-3-ethylisoxazole-4-carboxamide;

N—((S)-2-((2-(1,4-dimethyl-1H-pyrazol-5-yl)pyrimidin-5-yl)amino)-1-((1r,4S)-4-methylcyclohexyl)-2-oxoethyl)-1-methyl-1H-pyrazole-5-carboxamide;

(S)—N-(1-cycloheptyl-2-((5-(1-ethyl-4-methyl-1H-1,2,3-triazol-5-yl) pyridin-2-yl)amino)-2-oxoethyl)-1-methyl-1H-pyrazole-5-carboxamide;

(S)—N-(1-cycloheptyl-2-((5-(3,5-dimethylisoxazol-4-yl) pyrazin-2-yl)amino)-2-oxoethyl)-1-methyl-1H-pyrazole-5-carboxamide;

N—((S)-2-((5-(1,4-dimethyl-1H-1,2,3-triazol-5-yl) pyridin-2-yl)amino)-1-((1r,4S)-4-methylcyclohexyl)-2-oxoethyl)-1-ethyl-1H-pyrazole-5-carboxamide;

N—((S)-2-((5-(1,4-dimethyl-1H-1,2,3-triazol-5-yl) pyridin-2-yl)amino)-1-((1r,4S)-4-methylcyclohexyl)-2-oxoethyl)-3-methylisoxazole-4-carboxamide;

(S)—N-(1-cycloheptyl-2-((5-(1-cyclopropyl-4-methyl-1H-1,2,3-triazol-5-yl) pyridin-2-yl)amino)-2-oxoethyl)-1-methyl-1H-pyrazole-5-carboxamide;

(S)—N-(1-cycloheptyl-2-((5-(3,5-dimethylisoxazol-4-yl)-3-fluoropyridin-2-yl)amino)-2-oxoethyl)-1-methyl-1H-pyrazole-5-carboxamide;

(S)—N-(1-cycloheptyl-2-((5-(3,5-dimethylisoxazol-4-yl)-3-fluoropyridin-2-yl)amino)-2-oxoethyl)-1-ethyl-1H-pyrazole-5-carboxamide;

(S)—N-(1-cycloheptyl-2-((5-(3,5-dimethylisoxazol-4-yl)-3-fluoropyridin-2-yl)amino)-2-oxoethyl)-3-ethylisoxazole-4-carboxamide;

(S)—N-(1-cycloheptyl-2-((5-(1,4-dimethyl-1H-pyrazol-5-yl)pyrimidin-2-yl)amino)-2-oxoethyl)-1-methyl-1H-pyrazole-5-carboxamide;

(S)—N-(1-cycloheptyl-2-((5-(4-hydroxy-1-methyl-1H-pyrazol-5-yl) pyridin-2-yl)amino)-2-oxoethyl)-1-methyl-1H-pyrazole-5-carboxamide;

N—((S)-2-((5-(1,4-dimethyl-1H-pyrazol-5-yl) pyridin-2-yl)amino)-1-((1r,4S)-4-methylcyclohexyl)-2-oxoethyl)-1-methyl-1H-1,2,3-triazole-5-carboxamide;

N—((S)-2-((5-(1,4-dimethyl-1H-pyrazol-5-yl) pyridin-2-yl)amino)-1-((1r,4S)-4-methylcyclohexyl)-2-oxoethyl)-1-ethyl-1H-1,2,3-triazole-5-carboxamide;

(S)—N-(1-cycloheptyl-2-((6-(3,5-dimethylisoxazol-4-yl) pyridin-3-yl)amino)-2-oxoethyl)-1-ethyl-1H-pyrazole-5-carboxamide;

(S)—N-(1-cycloheptyl-2-((6-(3,5-dimethylisoxazol-4-yl) pyridin-3-yl)amino)-2-oxoethyl)-3-methylisoxazole-4-carboxamide;

(S)—N-(1-cycloheptyl-2-((6-(3,5-dimethylisoxazol-4-yl) pyridin-3-yl)amino)-2-oxoethyl)-3-ethylisoxazole-4-carboxamide;

(S)—N-(1-cycloheptyl-2-((6-(3,5-dimethylisoxazol-4-yl) pyridin-3-yl)amino)-2-oxoethyl)-1-methyl-1H-pyrazole-5-carboxamide;

(S)—N-(1-cycloheptyl-2-((5-(4-cyclopropyl-1-methyl-1H-1,2,3-triazol-5-yl) pyridin-2-yl)amino)-2-oxoethyl)-1-methyl-1H-pyrazole-5-carboxamide;

(S)—N-(2-((5-(4-chloro-1-methyl-1H-pyrazol-5-yl) pyridin-2-yl)amino)-1-cycloheptyl-2-oxoethyl)-1-methyl-1H-pyrazole-5-carboxamide;

(S)—N-(2-((5-(4-chloro-1-methyl-1H-pyrazol-5-yl) pyridin-2-yl)amino)-1-cycloheptyl-2-oxoethyl)-3-ethylisoxazole-4-carboxamide;

(S)—N-(2-((5-(4-chloro-1-methyl-1H-pyrazol-5-yl) pyridin-2-yl)amino)-1-cycloheptyl-2-oxoethyl)-1-ethyl-1H-pyrazole-5-carboxamide;

(S)—N-(1-cyclohexyl-2-((5-(1,4-dimethyl-1H-pyrazol-5-yl) pyridin-2-yl)amino)-2-oxoethyl)-1-methyl-1H-pyrazole-5-carboxamide;

(S)—N-(1-cyclohexyl-2-((5-(1,4-dimethyl-1H-pyrazol-5-yl) pyridin-2-yl)amino)-2-oxoethyl)-3-ethylisoxazole-4-carboxamide;

N—((S)-2-((6-(1,4-dimethyl-1H-pyrazol-5-yl)-5-fluoropyridin-3-yl)amino)-1-((1r,4S)-4-methylcyclohexyl)-2-oxoethyl)-1-methyl-1H-pyrazole-5-carboxamide;

N—((S)-2-((6-(1,4-dimethyl-1H-pyrazol-5-yl)-5-fluoropyridin-3-yl)amino)-1-((1r,4S)-4-methylcyclohexyl)-2-oxoethyl)-3-ethylisoxazole-4-carboxamide;

(S)—N-(1-cyclohexyl-2-((5-(1,4-dimethyl-1H-pyrazol-5-yl) pyridin-2-yl)amino)-2-oxoethyl)-3-methylisoxazole-4-carboxamide;

(S)—N-(1-cycloheptyl-2-((5-(4-(hydroxymethyl)-1-methyl-1H-pyrazol-5-yl) pyridin-2-yl)amino)-2-oxoethyl)-1-methyl-1H-pyrazole-5-carboxamide;

(S)—N-(1-cyclopentyl-2-((5-(1,4-dimethyl-1H-pyrazol-5-yl) pyridin-2-yl)amino)-2-oxoethyl)-1-methyl-1H-pyrazole-5-carboxamide;

N-(1-(bicyclo[2.2.1]heptan-2-yl)-2-((5-(1,4-dimethyl-1H-pyrazol-5-yl) pyridin-2-yl)amino)-2-oxoethyl)-1-methyl-1H-pyrazole-5-carboxamide;

N-(2-((5-(1,4-dimethyl-1H-pyrazol-5-yl) pyridin-2-yl) amino)-2-oxo-1-((1r,4r)-4-(trifluoromethyl)cyclohexyl) ethyl)-1-methyl-1H-pyrazole-5-carboxamide;

N-(2-((5-(1,4-dimethyl-1H-pyrazol-5-yl) pyridin-2-yl) amino)-2-oxo-1-((1r,4r)-4-(trifluoromethyl)cyclohexyl) ethyl)-1-ethyl-1H-pyrazole-5-carboxamide;

N-(2-((5-(1,4-dimethyl-1H-pyrazol-5-yl) pyridin-2-yl) amino)-2-oxo-1-((1r,4r)-4-(trifluoromethyl)cyclohexyl) ethyl)-3-ethylisoxazole-4-carboxamide;

N—((S)-2-((5-(1,4-dimethyl-1H-1,2,3-triazol-5-yl) pyridin-2-yl)amino)-1-((1r,4S)-4-methylcyclohexyl)-2-oxoethyl)-3-ethylisoxazole-4-carboxamide;

N—((S)-2-((6-(1,4-dimethyl-1H-pyrazol-5-yl)-5-fluoropyridin-3-yl)amino)-1-((1r,4S)-4-methylcyclohexyl)-2-oxoethyl)-1-ethyl-1H-pyrazole-5-carboxamide;

(S)—N-(1-cycloheptyl-2-((5-(1-(2-(dimethylamino)-2-oxoethyl)-4-methyl-1H-1,2,3-triazol-5-yl) pyridin-2-yl)amino)-2-oxoethyl)-1-methyl-1H-pyrazole-5-carboxamide;

N—((S)-2-((5-(1,4-dimethyl-1H-pyrazol-5-yl) pyridin-2-yl)amino)-1-((1r,4S)-4-methylcyclohexyl)-2-oxoethyl)-3-isopropylisoxazole-4-carboxamide;

3-(tert-butyl)-N—((S)-2-((5-(1,4-dimethyl-1H-pyrazol-5-yl) pyridin-2-yl)amino)-1-((1r,4S)-4-methylcyclohexyl)-2-oxoethyl) isoxazole-4-carboxamide;

N—((S)-2-((5-(4-cyano-1-methyl-1H-pyrazol-5-yl) pyridin-2-yl)amino)-1-((1r,4S)-4-methylcyclohexyl)-2-oxoethyl)-1-methyl-1H-pyrazole-5-carboxamide;

N—((S)-2-((5-(1,4-dimethyl-1H-pyrazol-5-yl) pyridin-2-yl)amino)-1-((1r,4S)-4-methylcyclohexyl)-2-oxoethyl)-3-(trifluoromethyl) isoxazole-4-carboxamide;

(S)—N-(1-cycloheptyl-2-oxo-2-((5-(1,3,4-trimethyl-1H-pyrazol-5-yl) pyridin-2-yl)amino)ethyl)-1-methyl-1H-pyrazole-5-carboxamide;

N—((S)-2-((5-(3,5-dimethylisothiazol-4-yl) pyridin-2-yl) amino)-1-((1r,4S)-4-methylcyclohexyl)-2-oxoethyl)-1-methyl-1H-pyrazole-5-carboxamide;

N—((S)-2-((5-(3,5-dimethylisothiazol-4-yl) pyridin-2-yl) amino)-1-((1r,4S)-4-methylcyclohexyl)-2-oxoethyl)-1-methyl-1H-1,2,3-triazole-5-carboxamide;

(S)—N-(1-cycloheptyl-2-((5-(4-(hydroxymethyl)-1-methyl-1H-pyrazol-5-yl) pyridin-2-yl)amino)-2-oxoethyl)-1-ethyl-1H-pyrazole-5-carboxamide;

N—((S)-2-((5-(4-chloro-1-methyl-1H-pyrazol-5-yl) pyridin-2-yl)amino)-1-((1r,4S)-4-methylcyclohexyl)-2-oxoethyl)-1-ethyl-1H-pyrazole-5-carboxamide;

N—((S)-2-((5-(4-chloro-1-methyl-1H-pyrazol-5-yl) pyridin-2-yl)amino)-1-((1r,4S)-4-methylcyclohexyl)-2-oxoethyl)-1-methyl-1H-1,2,3-triazole-5-carboxamide;

N—((S)-2-((5-(4-chloro-1-methyl-1H-pyrazol-5-yl) pyridin-2-yl)amino)-1-((1r,4S)-4-methylcyclohexyl)-2-oxoethyl)-3-ethylisoxazole-4-carboxamide;

(S)—N-(1-cycloheptyl-2-((5-(4-(hydroxymethyl)-1-methyl-1H-pyrazol-5-yl) pyridin-2-yl)amino)-2-oxoethyl)-3-ethylisoxazole-4-carboxamide;

N—((S)-2-((6-(3,5-dimethylisoxazol-4-yl) pyridin-3-yl) amino)-1-((1r,4S)-4-methylcyclohexyl)-2-oxoethyl)-3-ethylisoxazole-4-carboxamide;

N—((S)-2-((6-(1,4-dimethyl-1H-pyrazol-5-yl) pyridin-3-yl)amino)-1-((1r,4S)-4-methylcyclohexyl)-2-oxoethyl)-1-isopropyl-1H-pyrazole-5-carboxamide;

1-ethyl-N—((S)-2-((5-(4-(hydroxymethyl)-1-methyl-1H-pyrazol-5-yl) pyridin-2-yl)amino)-1-((1r,4S)-4-methylcyclohexyl)-2-oxoethyl)-1H-pyrazole-5-carboxamide;

N—((S)-2-((6-(3,5-dimethylisoxazol-4-yl) pyridin-3-yl) amino)-1-((1r,4S)-4-methylcyclohexyl)-2-oxoethyl)-1-isopropyl-1H-pyrazole-5-carboxamide;

(S)—N-(1-cyclohexyl-2-((6-(3,5-dimethyl-1H-pyrazol-4-yl) pyridin-3-yl)amino)-2-oxoethyl)-1-methyl-1H-pyrazole-5-carboxamide;

(S)—N-(1-cycloheptyl-2-((6-(3,5-dimethyl-1H-pyrazol-4-yl) pyridin-3-yl)amino)-2-oxoethyl)-1-ethyl-1H-pyrazole-5-carboxamide;

(S)—N-(1-cycloheptyl-2-((6-(3,5-dimethyl-1H-pyrazol-4-yl) pyridin-3-yl)amino)-2-oxoethyl)-1-methyl-1H-1,2,3-triazole-5-carboxamide;

(S)—N-(1-cycloheptyl-2-((6-(3,5-dimethyl-1H-pyrazol-4-yl) pyridin-3-yl)amino)-2-oxoethyl)-3-ethylisoxazole-4-carboxamide;

N—((S)-2-((6-(3,5-dimethyl-1H-pyrazol-4-yl) pyridin-3-yl)amino)-1-((1r,4S)-4-methylcyclohexyl)-2-oxoethyl)-1-methyl-1H-pyrazole-5-carboxamide;

N—((S)-2-((6-(3,5-dimethyl-1H-pyrazol-4-yl) pyridin-3-yl)amino)-1-((1r,4S)-4-methylcyclohexyl)-2-oxoethyl)-1-ethyl-1H-pyrazole-5-carboxamide;

N—((S)-2-((6-(3,5-dimethyl-1H-pyrazol-4-yl) pyridin-3-yl)amino)-1-((1r,4S)-4-methylcyclohexyl)-2-oxoethyl)-3-ethylisoxazole-4-carboxamide;

(S)—N-(1-cycloheptyl-2-oxo-2-((1',2',4'-trimethyl-6'-oxo-1',6'-dihydro-[3,3'-bipyridin]-6-yl)amino)ethyl)-1-methyl-1H-pyrazole-5-carboxamide;

1-methyl-N—((S)-1-((1r,4S)-4-methylcyclohexyl)-2-oxo-2-((1',2',4'-trimethyl-6'-oxo-1',6'-dihydro-[3,3'-bipyridin]-6-yl)amino)ethyl)-1H-pyrazole-5-carboxamide;

(S)—N-(1-cycloheptyl-2-oxo-2-((5-(1,3,5-trimethyl-1H-pyrazol-4-yl) pyridin-2-yl)amino)ethyl)-1-methyl-1H-pyrazole-5-carboxamide;

1-methyl-N—((S)-1-((1r,4S)-4-methylcyclohexyl)-2-oxo-2-((5-(1,3,5-trimethyl-1H-pyrazol-4-yl) pyridin-2-yl)amino)ethyl)-1H-pyrazole-5-carboxamide;

(S)—N-(1-cycloheptyl-2-((6-(3,5-dimethyl-1H-pyrazol-4-yl) pyridin-3-yl)amino)-2-oxoethyl)-1-methyl-1H-pyrazole-5-carboxamide;

1-methyl-N—((S)-2-((5-(1-methyl-4-(trifluoromethyl)-1H-pyrazol-5-yl) pyridin-2-yl)amino)-1-((1r,4S)-4-methylcyclohexyl)-2-oxoethyl)-1H-pyrazole-5-carboxamide; and N-(2-((5-(1,4-dimethyl-1H-pyrazol-5-yl) pyridin-2-yl) amino)-1-(dispiro $[2.1.2^5.2^3]$nonan-4-yl)-2-oxoethyl)-1-methyl-1H-pyrazole-5-carboxamide;

or a pharmaceutically acceptable salt thereof.

15. A pharmaceutical composition comprising a compound according to claim 1, or a pharmaceutically acceptable salt thereof, and one or more pharmaceutically acceptable excipients.

* * * * *